US012521428B2

(12) United States Patent
Amino et al.

(10) Patent No.: US 12,521,428 B2
(45) Date of Patent: Jan. 13, 2026

(54) MALARIA PRE-ERYTHROCYTIC ANTIGENS AS A FUSION POLYPEPTIDE AND THEIR USE IN THE ELICITATION OF A PROTECTIVE IMMUNE RESPONSE IN A HOST

(71) Applicant: INSTITUT PASTEUR, Paris (FR)

(72) Inventors: Rogerio Amino, Bagneux (FR); Pierre Charneau, Paris (FR); Catherine Blanc, Chantilly (FR); Vanessa Lagal, Fontenay sous Bois (FR)

(73) Assignee: INSTITUT PASTEUR, Paris (FR)

( * ) Notice: Subject to any disclaimer, the term of this patent is extended or adjusted under 35 U.S.C. 154(b) by 0 days.

(21) Appl. No.: 17/057,095

(22) PCT Filed: May 23, 2019

(86) PCT No.: PCT/IB2019/000702

§ 371 (c)(1),
(2) Date: Nov. 19, 2020

(87) PCT Pub. No.: WO2019/224606

PCT Pub. Date: Nov. 28, 2019

(65) Prior Publication Data

US 2021/0187089 A1 Jun. 24, 2021

Related U.S. Application Data

(60) Provisional application No. 62/675,277, filed on May 23, 2018.

(51) Int. Cl.

*A61K 39/015* (2006.01)
*C07K 14/445* (2006.01)
*C12N 15/86* (2006.01)

(52) U.S. Cl.

CPC .......... *A61K 39/015* (2013.01); *C07K 14/445* (2013.01); *C12N 15/86* (2013.01); *C07K 2319/00* (2013.01); *C12N 2740/15034* (2013.01)

(58) Field of Classification Search

CPC ................ A61K 39/015; C07K 14/445; C07K 2319/00; C12N 15/36; C12N 2740/15034

See application file for complete search history.

(56) References Cited

FOREIGN PATENT DOCUMENTS

| | | | |
|---|---|---|---|
| WO | 2011/138251 | A1 | 11/2011 |
| WO | 2018/141864 | A1 | 8/2018 |
| WO | 2018/141874 | A2 | 8/2018 |

OTHER PUBLICATIONS

Skolnick et al. (Trends in Biotechnology 18: 34-39, 2000).*

Bauza K, Atcheson E, Malinauskas T, Blagborough AM, Reyes-Sandoval A. 2016. Tailoring a combination breerythrocytic malaria vaccine. Infect Immun 84:622-634.

Coutant F, Sanchez David RY, Fe' lix T, Boulay A, Caleechum L, et al. (2012) A Nonintegrative Lentiviral Vector-Based Vaccine Provides Long-Term Sterile Protection against Malaria. PLoS ONE 7(11): e48644.

Lei Li & Nikolai Petrovsky (2016) Molecular mechanisms for enhanced DNA vaccine immunogenicity, Expert Review of Vaccines, 15:3, 313-329.

Nagata, T., et al., "Codon Optimization Effect on Translational Efficiency of DNA Vaccine in Mammalian Cells: Analysis of Plasmid DNA Encoding a CTL Epitope Derived from Microorganisms," Biochemical and Biophysical Research Communications 261, 445-451 (1999).

Speake C, Pichugin A, Sahu T, Malkov V, Morrison R, Pei Y, et al. (2016) Identification of Novel Pre-Erythrocytic Malaria Antigen Candidates for Combination Vaccines with Circumsporozoite Protein. PLoS ONE 11(7): e0159449.

Collins, K. A. et al. Enhancing protective immunity to malaria with a highly immunogenic virus-like particle vaccine. Sci. Rep. 7, 46621.

* cited by examiner

*Primary Examiner* — Robert A Zeman

(74) *Attorney, Agent, or Firm* — Arrigo, Lee, Guttman & Mouta-Bellum LLP

(57) ABSTRACT

The invention relates to chimeric *Plasmodium* antigenic polypeptides derived from pre-erythrocytic (PE) antigens and associated in a fusion polypeptide. In particular, the invention relates to antigenic fusion polypeptides of malaria parasites wherein said antigenic polypeptides exhibit a protective effect, especially that of eliciting a protective immune response in a host against challenge by *Plasmodium* sporozoites or a sterile response. Such identified antigenic fusion polypeptides may thus constitute active ingredients suitable for the design of a vaccine candidate, in particular a vaccine suitable for a human host.

10 Claims, 35 Drawing Sheets

Figure 1:
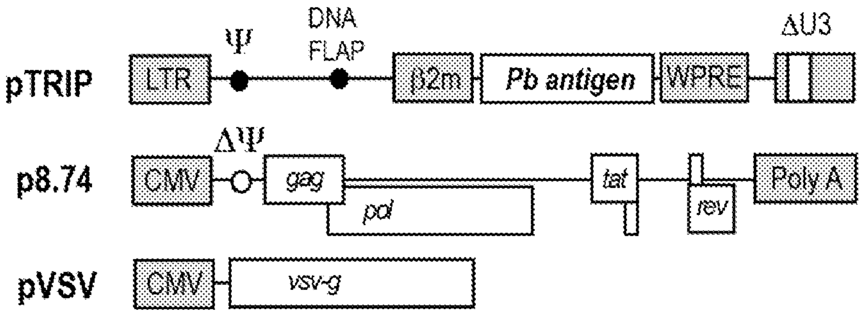

Specification includes a Sequence Listing.

a.

b.

c.

d.

e.

95- DNA sequence of PD *Plasmodium berghei* ANKA 18-10NT – mouse codon optimized, with adaptors and Kozak sequence (372 bp)

GGATCC – 5′ restriction site BamHI
GCCACCATGG – Kozak sequence (first methionine codon underlined)
CTCGAG – 3′ restriction site XhoI
Bold – sequence added leading to extra amino acid(s)

GGATCCGCCACCATGGACAATGACATCTACAGCTTCGACATTGTCAATGAGACAAATTGGCTGAAGAT
CGCCAAGAACATCTTCAAAGGCAAGTCTCCTAGCAATTTCACGATCATACCGTTTAACAATACCGGTA
GTTCTAACGATAACGAGTCAAACAAGGAGGAATCAGTACTGCTGATCAGAAAGAAGATCAAAAGCAAC
AAGAATCACGATAGTTCCATCATTAGTGGTGACACTGTTAACGGGGACATTAGTGACCTGAATTATAC
GGCTAGCAACTTTTCCGATAACTCTGAGGACATAGAAGATAACCAGAAATATCCCACAACCAGCTACA
ATAGTTTCAACCATCTCAATTCCTGACTCGAG (SEQ ID NO:95)

96- Amino acid sequence of PD *Plasmodium berghei* ANKA 18-10NT (117 aa)

MDNDIYSFDIVNETNWLKIAKNIFKGKSPSNFTIIPFNNTGSSNDNESNKEESVLLIRKKIKSNKNHD
SSIISGDTVNGDISDLNYTASNFSDNSEDIEDNQKYPTTSYNSFNHLNS (SEQ ID NO:96)

Figure 27

97- DNA sequence of PD *Plasmodium berghei* ANKA 18-10CT – mouse codon optimized, with adaptors and Kozak sequence (528 bp).

GGATCC – 5′ restriction site BamHI
GCCACCATGG – Kozak sequence (first methionine codon underlined)
CTCGAG – 3′ restriction site XhoI
Bold – sequence added leading to extra amino acid(s)

GGATCCGCCACCATGGCTCTCACTGGGGACGAGAAATGTGGTAAAAGCCTGAAGCTCGGCAACATCAG
CAATCAGACAAACCAGGAAACCATAACCCAAAGCCTGTCAGTTGGAGAGATTCTGTGCATTGACCTCG
AAGGGAATGCAGGAACAGGCTATCTGTGGGTGTTGCTGGGCATACACAAGGATGAGCCAATCATAAAC
CCCGAGAACTTCCCAACCAAACTGACAAAGAAGTCTTTCTTTTCCGAGGAAATAAGTGTGACTCAGCC
AAAGAAGTACAAGATCGATGAGCATGATTCTTCAAAGAATGTGAATCGCGAAATCGAAAGCCCTGAAC
AGAAGGAGTCCGACTCAAAGCCCAAGAAACCTCAGATGCAACTTCTTGGAGGACCAGATCGGATGAGG
TCAGTCATCAAAGGACACAAACCTGGCAAATATTACATTGTGTACTCTTACTATCGACCGTTTTCTCC
CACTTCTGGGGCGAACACTAAAATCATTTACGTCACAGTACAGTGACTCGAG (SEQ ID NO:97)

98-Amino acid sequence of PD *Plasmodium berghei* ANKA 18-10CT (169 aa)

MALTGDEKCGKSLKLGNISNQTNQETITQSLSVGEILCIDLEGNAGTGYLWVLLGIHKDEPIINPENF
PTKLTKKSFFSEEISVTQPKKYKIDEHDSSKNVNREIESPEQKESDSKPKKPQMQLLGGPDRMRSVIK
GHKPGKYYIVYSYYRPFSPTSGANTKIIYVTVQ (SEQ ID NO:98)

Figure 28

**99- DNA sequence of PD *Plasmodium falciparum 3D7* 18-10 minus Signal Peptide (SP-), human codon optimized, with adaptors and Kozak sequence (1197 bp).**

GGATCC – 5′ restriction site BamHI

GCCACCATGG – Kozak sequence (first methionine codon underlined)

CTCGAG – 3′ restriction site XhoI

Bold – sequence added leading to extra amino acid(s)

GGATCCGCCACCATGGACAACAACAGCTACAGCTTCGAGATCGTGAACCGCAGCACCTGGCTGAACAT
CGCCGAGCGCATCTTCAAGGGCAACGCCCCCTTCAACTTCACCATCATCCCCTACAACTACGTGAACA
ACAGCACCGAGGAGAACAACAACAAGGACAGCGTGCTGCTGATCAGCAAGAACCTGAAGAACAGCAGC
AACCCCGTGGACGAGAACAACCACATCATCGACAGCACCAAGAAGAACACCAGCAACAACAACAACAA
CAACAGCAACATCGTGGGCATCTACGAGAGCCAGGTGCACGAGGAGAAGATCAAGGAGGACAACACCC
GCCAGGACAACATCAACAAGAAGGAGAACGAGATCATCAACAACAACCACCAGATCCCCGTGAGCAAC
ATCTTCAGCGAGAACATCGACAACAACAAGAACTACATCGAGAGCAACTACAAGAGCACCTACAACAA
CAACCCCGAGCTGATCCACAGCACCGACTTCATCGGCAGCAACAACAACCACACCTTCAACTTCCTGA
GCCGCTACAACAACAGCGTGCTGAACAACATGCAGGGCAACACCAAGGTGCCCGGCAACGTGCCCGAG
CTGAAGGCCCGCATCTTCAGCGAGGAGGAGAACACCGAGGTGGAGAGCGCCGAGAACAACCACACCAA
CAGCCTGAACCCCAACGAGAGCTGCGACCAGATCATCAAGCTGGGCGACATCATCAACAGCGTGAACG
AGAAGATCATCAGCATCAACAGCACCGTGAACAACGTGCTGTGCATCAACCTGGACAGCGTGAACGGC
AACGGCTTCGTGTGGACCCTGCTGGGCGTGCACAAGAAGAAGCCCCTGATCGACCCCAGCAACTTCCC
CACCAAGCGCGTGACCCAGAGCTACGTGAGCCCCGACATCAGCGTGACCAACCCCGTGCCCATCCCCA
AGAACAGCAACACCAACAAGGACGACAGCATCAACAACAAGCAGGACGGCAGCCAGAACAACACCACC
ACCAACCACTTCCCCAAGCCCCGCGAGCAGCTGGTGGGCGGCAGCAGCATGCTGATCAGCAAGATCAA
GCCCCACAAGCCCGGCAAGTACTTCATCGTGTACAGCTACTACCGCCCCTTCGACCCCACCCGCGACA
CCAACACCCGCATCGTGGAGCTGAACGTGCAGTGACTCGAG (SEQ ID NO:99)

**100-Amino acid sequence of PD *Plasmodium falciparum 3D7* 18-10 -SP (392 aa)**

MDNNSYSFEIVNRSTWLNIAERIFKGNAPFNFTIIPYNYVNNSTEENNNKDSVLLISKNLKNSSNPVD
ENNHIIDSTKKNTSNNNNNNSNIVGIYESQVHEEKIKEDNTRQDNINKKENEIINNNHQIPVSNIFSE
NIDNNKNYIESNYKSTYNNNPELIHSTDFIGSNNNHTFNFLSRYNNSVLNNMQGNTKVPGNVPELKAR
IFSEEENTEVESAENNHTNSLNPNESCDQIIKLGDIINSVNEKIISINSTVNNVLCINLDSVNGNGFV
WTLLGVHKKKPLIDPSNFPTKRVTQSYVSPDISVTNPVPIPKNSNTNKDDSINNKQDGSQNNTTTNHF
PKPREQLVGGSSMLISKIKPHKPGKYFIVYSYYRPFDPTRDTNTRIVELNVQ (SEQ ID NO:100)

Figure 29

**101-DNA sequence of PD *Plasmodium berghei* ANKA 11-10CT – mouse codon optimized, with adaptors and Kozak sequence (528 bp).**

GGATCC – 5′ restriction site BamHI

GCCACCATGG – Kozak sequence (first methionine codon underlined)

CTCGAG – 3′ restriction site XhoI

Bold – sequence added leading to extra amino acid(s)

GGATCCGCCACCATGGCTCTGATCGAAGAGAAAGAGGAAATCACCCCTGAGAACAAAACCCTCATAAT
GCCCTCTAAAACTCTGATGAAGGGCATTAAGACCAACATTTACTTCCTGTCAAACAAGGAAAAGATCC
AAGTGCTTATGTGCTATAACTACAAGTGTGATGCCGTTGTGTTCGAGAAAGACACCTTTCTGCGCTAT
CTCTACATCAAGAGCATCAATAATATCATCCTGAACGAAAGAATGATTGAACAGTTGTGCAAGAACGA
AAACCTGAAGTACATCCTTGCCTGCAACAGCATAGTGGTTGAATCAAGCGACTTCATCAAACCCCTGA
TCATTGAGTTTGAGTCATCCACTTCCAAGAACATCTTCGTAAAGCACATTAAGCACAATAGCCAGAAA
GAAATGGACATCAACAAGTTCAACGAGTATATGCGGGATCTCAAAAGCAATGAGAAGCTCAGACTGAA
GAAAGTCGAGCGATTCCACTCTATTAATCTGGCAGCCAAGAAATGACTCGAG (SEQ ID NO:101)

**102-Amino acid sequence of PD *Plasmodium berghei* ANKA 11-10CT (169 aa)**

MALIEEKEEITPENKTLIMPSKTLMKGIKTNIYFLSNKEKIQVLMCYNYKCDAVVFEKDTFLRYLYIK
SINNIILNERMIEQLCKNENLKYILACNSIVVESSDFIKPLIIEFESSTSKNIFVKHIKHNSQKEMDI
NKFNEYMRDLKSNEKLRLKKVERFHSINLAAKK (SEQ ID NO:102)

Figure 30

103-DNA sequence of PD *Plasmodium falciparum 3D7* 11-10CT – human codon optimized, with adaptors and Kozak sequence (561 bp).

GGATCC – 5′ restriction site BamHI

GCCACCATGG – Kozak sequence (first methionine codon underlined)

CTCGAG – 3′ restriction site XhoI

Bold – sequence added leading to extra amino acid(s)

GGATCCGCCACCATGGAGGAGGACGACAAGGAGGTGGAGCCCGAGGAGGAGAAGGAGAACGAGCAGAA
GAAGGAGGAGCAGGAGGAGAACAACCTGGAGGCCCCCAGCAAGACCCTGATGAAGGGCGTGAAGACCA
ACATCTACTTCCTGAGCACCAAGGAGCGCATCGAGGCCCTGATGTGCTACAACTACATCAGCAACGCC
ATCATCTTCGAGAAGGGCAAGTTCCTGCGCTACATCTTCATGAACAACGTGAACAACATCATCGTGAA
CGAGCACATGATCAACATGCTGTGCAAGAAGGAGAAGATCAAGTACATCCTGAGCAGCAACAGCATCA
TCATCGAGAGCAACGACTTCATCAAGCCCCTGATCATCGAGTTCGACAGCAACATCAGCAAGAAGATC
TTCGTGAAGCACCTGAAGATGGTGGACAGCTTCAAGCTGGACGACAAGCTGTACCGCGAGTACCTGAA
CGACCTGAGCGAGCACGAGCGCGACCGCCTGAAGCACGTGGAGAGCTTCTACAGCAACGCCATCAAGG
TGCACAACtgaCTCGAG (SEQ ID NO:103)

104-Amino acid sequence of PD *Plasmodium falciparum 3D7* 11-10CT (180 aa)

MEEDDKEVEPEEEKENEQKKEEQEENNLEAPSKTLMKGVKTNIYFLSTKERIEALMCYNYISNAIIFE
KGKFLRYIFMNNVNNIIVNEHMINMLCKKEKIKYILSSNSIIIESNDFIKPLIIEFDSNISKKIFVKH
LKMVDSFKLDDKLYREYLNDLSEHERDRLKHVESFYSNAIKVHN (SEQ ID NO:104)

Figure 31

105- DNA sequence of PD *Plasmodium berghei* ANKA TRAP NT – mouse codon optimized, with adaptors and Kozak sequence (747 bp).

GGATCC – 5′ restriction site BamHI

GCCACCATGG – Kozak sequence (first methionine codon underlined)

CTCGAG – 3′ restriction site XhoI

Bold – sequence added leading to extra amino acid(s)

GGATCCGCCACC<u>ATG</u>GCTAACGGTCAGGAGATTCTGGACGAAATCAAGTACTCTGAGGAGGTCTGCAA
CGAACAAATCGATCTCCACATTCTGCTGGATGGGAGTGGCAGCATAGGTCACTCTAACTGGATCAGTC
ACGTGATACCCATGCTGACAACCCTTGTGGACAATTTGAACATCAGCCGCGATGAGATCAATATCTCC
ATGACCTTGTTCTCCACTTATGCCAGGGAACTTGTGAGACTTAAGAGATATGGGTCTACAAGCAAAGC
CAGTCTGAGGTTCATCATCGCGCAACTCCAGAATAACTATTCTCCTCATGGAACGACAAATCTGACTA
GCGCCCTGTTGAATGTGGACAATCTCATTCAGAAGAAAATGAATCGCCCTAATGCCATTCAGCTCGTG
ATTATCCTTACTGACGGCATCCCTAACAATCTGAAGAAGTCCACTACTGTTGTCAACCAGCTGAAGAA
GAAGGACGTCAATGTCGCTATTATTGGTGTTGGCGCCGGAGTAAACAATATGTTTAACCGTATATTGG
TAGGATGTGGAAAACTTGGGCCTTGTCCCTACTACTCTTATGGCTCTTGGGATCAAGCACAAACCATG
ATCAAACCATTTCTCTCAAAGGTCTGTCAGGAAGTGGAGAAAGTGGCACTGTGCGGTAAGTGGGAGGA
GTGGAGTGAGTGTTCAACCACTTGCGACAACGGAACGAAAATAAGGAAGCGAAAGGTTTGACTCGAG (SEQ ID NO:105)

106-Amino acid sequence of PD *Plasmodium berghei* ANKA TRAP NT (242 aa)

<u>MA</u>NGQEILDEIKYSEEVCNEQIDLHILLDGSGSIGHSNWISHVIPMLTTLVDNLNISRDEINISMTLF
STYARELVRLKRYGSTSKASLRFIIAQLQNNYSPHGTTNLTSALLNVDNLIQKKMNRPNAIQLVIILT
DGIPNNLKKSTTVVNQLKKKDVNVAIIGVGAGVNNMFNRILVGCGKLGPCPYYSYGSWDQAQTMIKPF
LSKVCQEVEKVALCGKWEEWSECSTTCDNGTKIRKRKV (SEQ ID NO:106)

Figure 32

107- DNA sequence of PD *Plasmodium falciparum 3D7* TRAP NT – human codon optimized, with adaptors and Kozak sequence (903 bp).

GGATCC – 5′ restriction site BamHI

GCCACCATGG – Kozak sequence (first methionine codon underlined)

CTCGAG – 3′ restriction site XhoI

Bold – sequence added leading to extra amino acid(s)

GGATCCGCCACCATGGACGTGCAGAACAACATCGTGGACGAGATCAAGTACCGCGAGGAGGTGTGCAA
CGACGAGGTGGACCTGTACCTGCTGATGGACTGCAGCGGCAGCATCCGCCGCCACAACTGGGTGAACC
ACGCCGTGCCCCTGGCCATGAAGCTGATCCAGCAGCTGAACCTGAACGACAACGCCATCCACCTGTAC
GCCAGCGTGTTCAGCAACAACGCCCGCGAGATCATCCGCCTGCACAGCGACGCCAGCAAGAACAAGGA
GAAGGCCCTGATCATCATCAAGAGCCTGCTGAGCACCAACCTGCCCTACGGCAAGACCAACCTGACCG
ACGCCCTGCTGCAGGTGCGCAAGCACCTGAACGACCGCATCAACCGCGAGAACGCCAACCAGCTGGTG
GTGATCCTGACCGACGGCATCCCCGACAGCATCCAGGACAGCCTGAAGGAGAGCCGCAAGCTGAGCGA
CCGCGGCGTGAAGATCGCCGTGTTCGGCATCGGCCAGGGCATCAACGTGGCCTTCAACCGCTTCCTGG
TGGGCTGCCACCCCAGCGACGGCAAGTGCAACCTGTACGCCGACAGCGCCTGGGAGAACGTGAAGAAC
GTGATCGGCCCCTTCATGAAGGCCGTGTGCGTGGAGGTGGAGAAGACCGCCAGCTGCGGCGTGTGGGA
CGAGTGGAGCCCCTGCAGCGTGACCTGCGGCAAGGGCACCCGCAGCCGCAAGCGCGAGATCCTGCACG
AGGGCTGCACCAGCGAGCTGCAGGAGCAGTGCGAGGAGGAGCGCTGCCTGCCCAAGCGCGAGCCCCTG
GACGTGCCCGACGAGCCCGAGGACGACCAGCCCCGCCCCCGCGGCGACAACTTCGCCGTGGAGAAGCC
CAACGAGAACtgaCTCGAG (SEQ ID NO:107)

108-Amino acid sequence of PD *Plasmodium falciparum 3D7* TRAP NT ( 294 aa)

MDVQNNIVDEIKYREEVCNDEVDLYLLMDCSGSIRRHNWVNHAVPLAMKLIQQLNLNDNAIHLYASVF
SNNAREIIRLHSDASKNKEKALIIIKSLLSTNLPYGKTNLTDALLQVRKHLNDRINRENANQLVVILT
DGIPDSIQDSLKESRKLSDRGVKIAVFGIGQGINVAFNRFLVGCHPSDGKCNLYADSAWENVKNVIGP
FMKAVCVEVEKTASCGVWDEWSPCSVTCGKGTRSRKREILHEGCTSELQEQCEEERCLPKREPLDVPD
EPEDDQPRPRGDNFAVEKPNEN (SEQ ID NO:108)

Figure 33

**109- DNA sequence of PD *Plasmodium berghei* ANKA 11-09 – mouse codon optimized, with adaptors and Kozak sequence (654 bp).**

GGATCC – 5′ restriction site BamHI

GCCACCATGG – Kozak sequence (first methionine codon underlined)

CTCGAG – 3′ restriction site XhoI

Bold – sequence added leading to extra amino acid(s)

GGATCCGCCACCATGGCTGGGGCGAGTATGAGCCACTTGCAGTGTCTGACATCTGTTGCTGGTCTGTC
CTCTATCGTCATGTCAATGTTCCCCAAACTCATTGCCAATAATCCTTCCCTGTTTAGACCACTGCTCA
ACATTTCCTGGGGATATCTGTTCGGAAGCACTGTATGGCTGTGCTTCTTCAGTGAGATTGGGTTGGTC
AGGAGAATCAATGCTCCTAAACGGAAGAATCTGCCAGAGAATGCAGAACAAGCCAAAGAACAGCTGAA
GGAGATCAAGAACAACGAAGGCGATTTTAACCGACGCAATATCGACTTCAAGTACTTCTTTAGCCTTT
CCACAATCTTCTCTAGCATACTGCTGCTTAGCACAGTGAAACTCGCCAACAACAATCTGCAGTTGAGG
ATCTGTTCCACCATTGTGTCACTGAGTTGCATACTGAACAATATGTACTTTCAGAACAAGATACACTC
ACTTGCACTGAAGAAAGAGAGTCTCTTTAAGGACATGATCGATCGTCCGAAAGATACCACTATTCTGG
TGAACCTGAAGAAGAACAAGACCGACTTTCACATCCATCATGGCCTTTCTCTGCTCTTGCTCTATAGC
AGCTTCTTTGGCCTCACTCCCTACATTTTCACGTGACTCGAG (SEQ ID NO:109)

**110-Amino acid sequence of PD *Plasmodium berghei* ANKA 11-09 (211 aa)**

MAGASMSHLQCLTSVAGLSSIVMSMFPKLIANNPSLFRPLLNISWGYLFGSTVWLCFFSEIGLVRRIN
APKRKNLPENAEQAKEQLKEIKNNEGDFNRRNIDFKYFFSLSTIFSSILLLSTVKLANNNLQLRICST
IVSLSCILNNMYFQNKIHSLALKKESLFKDMIDRPKDTTILVNLKKNKTDFHIHHGLSLLLLYSSFFG
LTPYIFT (SEQ ID NO:110)

Figure 34

**111- DNA sequence of PD *Plasmodium falciparum* 3D7 11-09 – human codon optimized, with adaptors and Kozak sequence (642 bp).**

GGATCC – 5′ restriction site BamHI

GCCACCATGG – Kozak sequence (first methionine codon underlined)

CTCGAG – 3′ restriction site XhoI

Bold – sequence added leading to extra amino acid(s)

GGATCCGCCACCATGGCTAGCAACCTGAAGTGCGTGACCAACGTGGCCGGCCTGGCCAGCCTGGTGAT
CAGCCTGTTCCCCAAGCTGATCATCAAGAACCCCCAGGTGCTGCGCCCCCTGCTGAACGTGAGCTGGG
GCTACCTGTTCGGCAGCACCTTCTGGCTGTGCTTCTTCAGCGAGGTGGGCCTGCTGCGCAGCCTGAAG
AACATGAAGGGCGTGCCCCTGCCCGAGAGCGCCAGCGAGGCCAAGAAGCTGCTGGAGGAGATGAAGAA
CAGCGAGGGCGACTTCAACCGCCGCAGCCTGGACTTCCAGTACTTCTTCAGCCTGGCCACCCTGTTCA
GCGGCATCCTGCTGCTGAGCACCGTGAAGCTGGCCAACCACAACCTGCAGCTGCGCCTGAGCAGCAGC
GTGGTGGTGATCACCAGCCTGCTGAACAGCCTGTACCTGCACAACAAGGTGCACAACCTGAAGAGCAA
GAAGGAGAGCCTGTACAACGACTTCATCGCCAACCCCAAGAACGAGAAGACCGTGGCCGACCTGAAGA
AGAACAAGAAGGAGTTCCACATCTTCCACGGCCTGAGCGTGCTGAGCCTGTACGTGAGCTTCTTCGGC
CTGACCCCCTACATCTTCACCtgaCTCGAG (SEQ ID NO:111)

**112-Amino acid sequence of PD *Plasmodium falciparum 3D7* 11-09 (207 aa)**

MASNLKCVTNVAGLASLVISLFPKLIIKNPQVLRPLLNVSWGYLFGSTFWLCFFSEVGLLRSLKNMKG
VPLPESASEAKKLLEEMKNSEGDFNRRSLDFQYFFSLATLFSGILLLSTVKLANHNLQLRLSSSVVVI
TSLLNSLYLHNKVHNLKSKKESLYNDFIANPKNEKTVADLKKNKKEFHIFHGLSVLSLYVSFFGLTPY
IFT (SEQ ID NO:112)

Figure 35

**113- DNA sequence of *Plasmodium berghei* ANKA Fusion of PD Pb18-10NT and PD Pb18-10CT – mouse codon optimized + ATG**

ATGGACAATGACATCTACAGCTTCGACATTGTCAATGAGACAAATTGGCTGAAGATCGCCAAGAACAT
CTTCAAAGGCAAGTCTCCTAGCAATTTCACGATCATACCGTTTAACAATACCGGTAGTTCTAACGATAACGAGTCAAACA
AGGAGGAATCAGTACTGCTGATCAGAAAGAAGATCAAAAGCAACAAGAATCACGATAGTTCCATCATTAGTGGTGACACT
GTTAACGGGGACATTAGTGACCTGAATTATACGGCTAGCAACTTTTCCGATAACTCTGAGGACATAGAAGATAACCAGAA
ATATCCCACAACCAGCTACAATAGTTTCAACCATCTCAATTCCCTCACTGGGGACGAGAAATGTGGTAAAAGCCTGAAGC
TCGGCAACATCAGCAATCAGACAAACCAGGAAACCATAACCCAAAGCCTGTCAGTTGGAGAGATTCTGTGCATTGACCTC
GAAGGGAATGCAGGAACAGGCTATCTGTGGGTGTTGCTGGGCATACACAAGGATGAGCCAATCATAAACCCCGAGAACTT
CCCAACCAAACTGACAAAGAAGTCTTTCTTTTCCGAGGAAATAAGTGTGACTCAGCCAAAGAAGTACAAGATCGATGAGC
ATGATTCTTCAAAGAATGTGAATCGCGAAATCGAAAGCCCTGAACAGAAGGAGTCCGACTCAAAGCCCAAGAAACCTCAG
ATGCAACTTCTTGGAGGACCAGATCGGATGAGGTCAGTCATCAAAGGACACAAACCTGGCAAATATTACATTGTGTACTC
TTACTATCGACCGTTTTCTCCCACTTCTGGGGCGAACACTAAAATCATTTACGTCACAGTACAG (SEQ ID NO:113)

**114- Amino acid sequence of *Plasmodium berghei* ANKA Fusion of PD Pb18-10NT and PD Pb18-10CT**

MDNDIYSFDIVNETNWLKIAKNIFKGKSPSNFTIIPFNNTGSSNDNESNKEESVLLIRKKIKSNKNHD
SSIISGDTVNGDISDLNYTASNFSDNSEDIEDNQKYPTTSYNSFNHLNSLTGDEKCGKSLKLGNISNQ
TNQETITQSLSVGEILCIDLEGNAGTGYLWVLLGIHKDEPIINPENFPTKLTKKSFFSEEISVTQPKK
YKIDEHDSSKNVNREIESPEQKESDSKPKKPQMQLLGGPDRMRSVIKGHKPGKYYIVYSYYRPFSPTS
GANTKIIYVTVQ (SEQ ID NO:114)

Figure 36

115- DNA sequence of *Plasmodium berghei* ANKA Fusion 4cPEAg – mouse codon optimized, with adaptors and Kozak sequence (2715 bp).

GGATCC – 5′ restriction site BamHI

GCCACCATGG – Kozak sequence (first methionine codon underlined)

CTCGAG – 3′ restriction site XhoI

Bold – sequence added leading to extra amino acid(s)

GGATCCGCCACCATGGACAATGACATCTACAGCTTCGACATTGTCAATGAGACAAATTGGCTGAAGATCGCCAAGAACAT
CTTCAAAGGCAAGTCTCCTAGCAATTTCACGATCATACCGTTTAACAATACCGGTAGTTCTAACGATAACGAGTCAAACA
AGGAGGAATCAGTACTGCTGATCAGAAAGAAGATCAAAAGCAACAAGAATCACGATAGTTCCATCATTAGTGGTGACACT
GTTAACGGGGACATTAGTGACCTGAATTATACGGCTAGCAACTTTTCCGATAACTCTGAGGACATAGAAGATAACCAGAA
ATATCCCACAACCAGCTACAATAGTTTCAACCATCTCAATTCCCTCACTGGGGACGAGAAATGTGGTAAAAGCCTGAAGC
TCGGCAACATCAGCAATCAGACAAACCAGGAAACCATAACCCAAAGCCTGTCAGTTGGAGAGATTCTGTGCATTGACCTC
GAAGGGAATGCAGGAACAGGCTATCTGTGGGTGTTGCTGGGCATACACAAGGATGAGCCAATCATAAACCCCGAGAACTT
CCCAACCAAACTGACAAAGAAGTCTTTCTTTTCCGAGGAAATAAGTGTGACTCAGCCAAAGAAGTACAAGATCGATGAGC
ATGATTCTTCAAAGAATGTGAATCGCGAAATCGAAAGCCCTGAACAGAAGGAGTCCGACTCAAAGCCCAAGAAACCTCAG
ATGCAACTTCTTGGAGGACCAGATCGGATGAGGTCAGTCATCAAAGGACACAAACCTGGCAAATATTACATTGTGTACTC
TTACTATCGACCGTTTTCTCCCACTTCTGGGGCGAACACTAAAATCATTTACGTCACAGTACAGCTGATCGAAGAGAAAG
AGGAAATCACCCCTGAGAACAAAACCCTCATAATGCCCTCTAAAACTCTGATGAAGGGCATTAAGACCAACATTTACTTC
CTGTCAAACAAGGAAAAGATCCAAGTGCTTATGTGCTATAACTACAAGTGTGATGCCGTTGTGTTCGAGAAAGACACCTT
TCTGCGCTATCTCTACATCAAGAGCATCAATAATATCATCCTGAACGAAAGAATGATTGAACAGTTGTGCAAGAACGAAA
ACCTGAAGTACATCCTTGCCTGCAACAGCATAGTGGTTGAATCAAGCGACTTCATCAAACCCCTGATCATTGAGTTTGAG
TCATCCACTTCCAAGAACATCTTCGTAAAGCACATTAAGCACAATAGCCAGAAAGAAATGGACATCAACAAGTTCAACGA
GTATATGCGGGATCTCAAAAGCAATGAGAAGCTCAGACTGAAGAAAGTCGAGCGATTCCACTCTATTAATCTGGCAGCCA
AGAAACAGGAGATTCTGGACGAAATCAAGTACTCTGAGGAGGTCTGCAACGAACAAATCGATCTCCACATTCTGCTGGAT
GGGAGTGGCAGCATAGGTCACTCTAACTGGATCAGTCACGTGATACCCATGCTGACAACCCTTGTGGACAATTTGAACAT
CAGCCGCGATGAGATCAATATCTCCATGACCTTGTTCTCCACTTATGCCAGGGAACTTGTGAGACTTAAGAGATATGGGT
CTACAAGCAAAGCCAGTCTGAGGTTCATCATCGCGCAACTCCAGAATAACTATTCTCCTCATGGAACGACAAATCTGACT
AGCGCCCTGTTGAATGTGGACAATCTCATTCAGAAGAAAATGAATCGCCCTAATGCCATTCAGCTCGTGATTATCCTTAC
TGACGGCATCCCTAACAATCTGAAGAAGTCCACTACTGTTGTCAACCAGCTGAAGAAGAAGGACGTCAATGTCGCTATTA
TTGGTGTTGGCGCCGGAGTAAACAATATGTTTAACCGTATATTGGTAGGATGTGGAAAACTTGGGCCTTGTCCCTACTAC
TCTTATGGCTCTTGGGATCAAGCACAAACCATGATCAAACCATTTCTCTCAAAGGTCTGTCAGGAAGTGGAGAAAGTGGC
ACTGTGCGGTAAGTGGGAGGAGTGGAGTGAGTGTTCAACCACTTGCGACAACGGAACGAAAATAAGGAAGCGAAAGGTTG
GGGCGAGTATGAGCCACTTGCAGTGTCTGACATCTGTTGCTGGTCTGTCCTCTATCGTCATGTCAATGTTCCCCAAACTC
ATTGCCAATAATCCTTCCCTGTTTAGACCACTGCTCAACATTTCCTGGGGATATCTGTTCGGAAGCACTGTATGGCTGTG
CTTCTTCAGTGAGATTGGGTTGGTCAGGAGAATCAATGCTCCTAAACGGAAGAATCTGCCAGAGAATGCAGAACAAGCCA
AAGAACAGCTGAAGGAGATCAAGAACAACGAAGGCGATTTTAACCGACGCAATATCGACTTCAAGTACTTCTTTAGCCTT
TCCACAATCTTCTCTAGCATACTGCTGCTTAGCACAGTGAAACTCGCCAACAACAATCTGCAGTTGAGGATCTGTTCCAC
CATTGTGTCACTGAGTTGCATACTGAACAATATGTACTTTCAGAACAAGATACACTCACTTGCACTGAAGAAAGAGAGTC
TCTTTAAGGACATGATCGATCGTCCGAAAGATACCACTATTCTGGTGAACCTGAAGAAGAACAAGACCGACTTTCACATC
CATCATGGCCTTTCTCTGCTCTTGCTCTATAGCAGCTTCTTTGGCCTCACTCCCTACATTTTCACGTGACTCGAG (SEQ ID NO:115)

Figure 37(1)

**116- Amino acid sequence of *Plasmodium berghei* ANKA Fusion 4cPEAg (898 aa).**

PD Pb18-10NT + PD Pb18-10CT + (-MA)PD Pb11-10CT + (-MANG)PD PbbTRAPNT + (-MA)PD Pb11-09

MDNDIYSFDIVNETNWLKIAKNIFKGKSPSNFTIIPFNNTGSSNDNESNKEESVLLIRKKIKSNKNHD
SSIISGDTVNGDISDLNYTASNFSDNSEDIEDNQKYPTTSYNSFNHLNSLTGDEKCGKSLKLGNISNQ
TNQETITQSLSVGEILCIDLEGNAGTGYLWVLLGIHNDEPIINPENFPTKLTKKSFFSEEISVTQPKK
YKIDEHDSSKNVNREIESPEQKESDSKPKKPQMQLLGGPDRMRSVIKGHKPGKYYIVYSYYRPFSPTS
GANTKIIYVTVQLIEEKEEITPENKTLIMPSKTLMKGIKTNIYFLSNKEKIQVLMCYNYKCDAVVFEK
DTFLRYLYIKSINNIILNERMIEQLCKNENLKYILACNSIVVESSDFIKPLIIEFESSTSKNIFVKHI
KHNSQKEMDINKFNEYMRDLKSNEKLRLKKVERFHSINLAAKKQEILDEIKYSEEVCNEQIDLHILLD
GSGSIGHSNWISHVIPMLTTLVDNLNISRDEINISMTLFSTYARELVRLKRYGSTSKASLRPIIAQLQ
NNYSPHGTTNLTSALLNVDNLIQKKMNRPNAIQLVIILTDGIPNNLKKSTTVVNQLKKKDVNVAIIGV
GAGVNNMFNRILVGCGKLGPCPYYSYGSWDQAQTMIKPFLSKVCQEVEKVALCGKWEEWSECSTTCDN
GTKIRKRKVGASMSHLQCLTSVAGLSSIVMSMFPKLIANNPSLFFPLLNISWGYLFGSTVWLCFFSEI
SLVRRINAPKRKNLFENAEQAKEQLKEIKNNEGDPNKRNIDFKYFFSLSTIFSSILLLSTVKLANNE
QLRICSTIVSLSCILNNMYFQNKIHSLALKKESLFKQMIDRPKIDTTILVNLKKNNTDFHIHHGLSLLE
LYSSPFGLTPYIFT (SEQ ID NO:116)

Figure 37(2)

**117- DNA sequence of *Plasmodium falciparum 3D7* Fusion 4cPEAg – human codon optimized, with adaptors and Kozak sequence (3231 bp).**

GGATCC - 5′ restriction site BamHI

GCCACCATGG - Kozak sequence (first methionine codon underlined)

CTCGAG - 3′ restriction site XhoI

Bold - sequence added leading to extra amino acid(s)

GGATCCGCCACCATGGACAACAACAGCTACAGCTTCGAGATCGTGAACCGCAGCACCTGGCTGAACATCGCCGAGCG
CATCTTCAAGGGCAACGCCCCCTTCAACTTCACCATCATCCCCTACAACTACGTGAACAACAGCACCGAGGAGAACAACA
ACAAGGACAGCGTGCTGCTGATCAGCAAGAACCTGAAGAACAGCAGCAACCCCGTGGACGAGAACAACCACATCATCGAC
AGCACCAAGAAGAACACCAGCAACAACAACAACAACAACAGCAACATCGTGGGCATCTACGAGAGCCAGGTGCACGAGGA
GAAGATCAAGGAGGACAACACCCGCCAGGACAACATCAACAAGAAGGAGAACGAGATCATCAACAACAACCACCAGATCC
CCGTGAGCAACATCTTCAGCGAGAACATCGACAACAACAAGAACTACATCGAGAGCAACTACAAGAGCACCTACAACAAC
AACCCCGAGCTGATCCACAGCACCGACTTCATCGGCAGCAACAACAACCACACCTTCAACTTCCTGAGCCGCTACAACAA
CAGCGTGCTGAACAACATGCAGGGCAACACCAAGGTGCCCGGCAACGTGCCCGAGCTGAAGGCCCGCATCTTCAGCGAGG
AGGAGAACACCGAGGTGGAGAGCGCCGAGAACAACCACACCAACAGCCTGAACCCCAACGAGAGCTGCGACCAGATCATC
AAGCTGGGCGACATCATCAACAGCGTGAACGAGAAGATCATCAGCATCAACAGCACCGTGAACAACGTGCTGTGCATCAA
CCTGGACAGCGTGAACGGCAACGGCTTCGTGTGGACCCTGCTGGGCGTGCACAAGAAGAAGCCCCTGATCGACCCCAGCA
ACTTCCCCACCAAGCGCGTGACCCAGAGCTACGTGAGCCCCGACATCAGCGTGACCAACCCCGTGCCCATCCCCAAGAAC
AGCAACACCAACAAGGACGACAGCATCAACAACAAGCAGGACGGCAGCCAGAACAACACCACCACCAACCACTTCCCCAA
GCCCCGCGAGCAGCTGGTGGGCGGCAGCAGCATGCTGATCAGCAAGATCAAGCCCCACAAGCCCGGCAAGTACTTCATCG
TGTACAGCTACTACCGCCCCTTCGACCCCACCCGCGACACCAACACCCGCATCGTGGAGCTGAACGTGCAGGAGGAGGAC
GACAAGGAGGTGGAGCCCGAGGAGGAGAAGGAGAACGAGCAGAAGAAGGAGGAGCAGGAGGAGAACAACCTGGAGGCCCC
CAGCAAGACCCTGATGAAGGGCGTGAAGACCAACATCTACTTCCTGAGCACCAAGGAGCGCATCGAGGCCCTGATGTGCT
ACAACTACATCAGCAACGCCATCATCTTCGAGAAGGGCAAGTTCCTGCGCTACATCTTCATGAACAACGTGAACAACATC
ATCGTGAACGAGCACATGATCAACATGCTGTGCAAGAAGGAGAAGATCAAGTACATCCTGAGCAGCAACAGCATCATCAT
CGAGAGCAACGACTTCATCAAGCCCCTGATCATCGAGTTCGACAGCAACATCAGCAAGAAGATCTTCGTGAAGCACCTGA
AGATGGTGGACAGCTTCAAGCTGGACGACAAGCTGTACCGCGAGTACCTGAACGACCTGAGCGAGCACGAGCGCGACCGC
CTGAAGCACGTGGAGAGCTTCTACAGCAACGCCATCAAGGTGCACAACGAGGACGTGCAGAACAACATCGTGGACGAGAT
CAAGTACCGCGAGGAGGTGTGCAACGACGAGGTGGACCTGTACCTGCTGATGGACTGCAGCGGCAGCATCCGCCGCCACA
ACTGGGTGAACCACGCCGTGCCCCTGGCCATGAAGCTGATCCAGCAGCTGAACCTGAACGACAACGCCATCCACCTGTAC
GCCAGCGTGTTCAGCAACAACGCCCGCGAGATCATCCGCCTGCACAGCGACGCCAGCAAGAACAAGGAGAAGGCCCTGAT
CATCATCAAGAGCCTGCTGAGCACCAACCTGCCCTACGGCAAGACCAACCTGACCGACGCCCTGCTGCAGGTGCGCAAGC
ACCTGAACGACCGCATCAACCGCGAGAACGCCAACCAGCTGGTGGTGATCCTGACCGACGGCATCCCCGACAGCATCCAG
GACAGCCTGAAGGAGAGCCGCAAGCTGAGCGACCGCGGCGTGAAGATCGCCGTGTTCGGCATCGGCCAGGGCATCAACGT
GGCCTTCAACCGCTTCCTGGTGGGCTGCCACCCCAGCGACGGCAAGTGCAACCTGTACGCCGACAGCGCCTGGGAGAACG
TGAAGAACGTGATCGGCCCCTTCATGAAGGCCGTGTGCGTGGAGGTGGAGAAGACCGCCAGCTGCGGCGTGTGGGACGAG
TGGAGCCCCTGCAGCGTGACCTGCGGCAAGGGCACCCGCAGCCGCAAGCGCGAGATCCTGCACGAGGGCTGCACCAGCGA
GCTGCAGGAGCAGTGCGAGGAGGAGCGCTGCCTGCCCAAGCGCGAGCCCCTGGACGTGCCCGACGAGCCCGAGGACGACC
AGCCCCGCCCCCGCGGCGACAACTTCGCCGTGGAGAAGCCCAACGAGAACAGCAACCTGAAGTGCGTGACCAACGTGGCC
GGCCTGGCCAGCCTGGTGATCAGCCTGTTCCCCAAGCTGATCATCAAGAACCCCCAGGTGCTGCGCCCCCTGCTGAACGT
GAGCTGGGGCTACCTGTTCGGCAGCACCTTCTGGCTGTGCTTCTTCAGCGAGGTGGGCCTGCTGCGCAGCCTGAAGAACA
TGAAGGGCGTGCCCCTGCCCGAGAGCGCCAGCGAGGCCAAGAAGCTGCTGGAGGAGATGAAGAACAGCGAGGGCGACTTC
AACCGCCGCAGCCTGGACTTCCAGTACTTCTTCAGCCTGGCCACCCTGTTCAGCGGCATCCTGCTGCTGAGCACCGTGAA
GCTGGCCAACCACAACCTGCAGCTGCGCCTGAGCAGCAGCGTGGTGGTGATCACCAGCCTGCTGAACAGCCTGTACCTGC
ACAACAAGGTGCACAACCTGAAGAGCAAGAAGGAGAGCCTGTACAACGACTTCATCGCCAACCCCAAGAACGAGAAGACC
GTGGCCGACCTGAAGAAGAACAAGAAGGAGTTCCACATCTTCCACGGCCTGAGCGTGCTGAGCCTGTACGTGAGCTTCTT
CGGCCTGACCCCCTACATCTTCACCTGACTCGAG (SEQ ID NO:117)

Figure 38(1)

**118- Amino acid sequence of *Plasmodium falciparum 3D7* Fusion 4cPEAg (1070 aa)**

PD Pf18-10 -SP + (-M) PD Pf11-10CT + E + (-M) PD Pf TRAPNT + (-MA) Pf11-09

<u>M</u>DNNSYSFEIVNRSTWLNIAERIFKGNAPFNFTIIPYNYVNNSTEENNNKDSVLLISKNLKNSSNPVD
ENNHIIDSTKKNTSNNNNNNSNIVGIYESQVHEEKIKEDNTRQDNINKKENEIINNNHQIPVSNIFSE
NIDNNKNYIESNYKSTYNNNPELIHSTDFIGSNNNHTFNFLSRYNNSVLNNMQGNTKVPGNVPELKAR
IFSEEENTEVESAENNHTNSLNPNESCDQIIKLGDIINSVNEKIISINSTVNNVLCINLDSVNGNGFV
WTLLGVHKKKPLIDPSNFPTKRVTQSYVSPDISVTNPVPIPKNSNTNKDDSINNKQDGSQNNTTTNHF
PKPREQLVGGSSMLISKIKPHKPGKYFIVYSYYRPFDPTRDTNTRIVELNVQEEDDKEVEPEEEKENE
QKKEEQEENNLEAPSKTLMKGVKTNIYFLSTKERIEALMCYNYISNAIIFEKGKFLRYIFMNNVNNII
VNEHMINMLCKKEKIKYILSSNSIIIESNDFIKPLIIEFDSNISKKIFVKHLKMVDSFKLDDKLYREY
LNDLSEHERDRLKHVESFYSNAIKVHNEDVQNNIVDEIKYREEVCNDEVDLYLLMDCSGSIRRHNWVN
HAVPLAMKLIQQLNLNDNAIHLYASVFSNNAREIIRLHSDASKNKEKALIIIKSLLSTNLPYGKTNLT
DALLQVRKHLNDRINRENANQLVVILTDGIPDSIQDSLKESRKLSDRGVKIAVFGIGQGINVAFNRFL
VGCHPSDGKCNLYADSAWENVKNVIGPFMKAVCVEVEKTASCGVWDEWSPCSVTCGKGTRSRKREILH
EGCTSELQEQCEEERCLPKREPLDVPDEPEDDQPRPRGDNFAVEKPNENSNLKCVTNVAGLASLVISL
FPKLIIKNFQVLRPFLLNVSRGYLPGSTFWLCFPNEVGLLRSLKNNKGVPLPKSASEAKKILEKNKSE
GEFNRRSLDFQKFFSLATLFSGILLLSTVKLANHNLQLRLSSSVVVITSLLNSLYLLHNKVHNLKSKKE
SLYNDFIANFKNEKTVADLKKNKKEPHIFHGLSVLSLYVSFPGLTPYIET (SEQ ID NO:118)

Figure 38(2)

**119- DNA sequence of *Plasmodium berghei* Fusion 5cPEAg – mouse codon optimized, with adaptors and Kozak sequence (3597 bp).**

GGATCC – 5′ restriction site BamHI

GCCACCATGG – Kozak sequence (first methionine codon underlined)

CTCGAG – 3′ restriction site XhoI

Bold – sequence added leading to extra amino acid(s)

GGATCCGCCACC<u>ATG</u>GCCCAGAACAAATCCATTCAGGCACAGAGGAACCTCAACGAACTCTGCTACAATGAAGGGAA
TGACAATAAGCTGTATCACGTGCTGAATTCCAAGAACGGCAAAATCTACAATCGCAACACAGTAAATCGGTTGCT
TGCCGATGCACCCGAGGGTAAGAAGAATGAAAAGAAGAATGAGAAAATCGAGCGCAACAACAAGCTTAAACAGCC
ACCGCCTCCTCCTAACCCAAATGACCCACCGCCACCCAATCCAAACGACCCACCGCCTCCCAACCCTAACGATCC
TCCACCGCCCAACCCTAATGACCCACCACCTCCCAATGCAAACGATCCACCCCCTCCTAACGCTAACGACCCTGC
TCCACCCAACGCTAACGATCCCGCGCCCCCCAATGCCAACGACCCCGCACCACCTAATGCCAACGATCCCGCCCC
GCCCAATGCTAATGATCCTCCACCACCCAACCCAAACGACCCTGCCCCTCCTAATGCTAACGATCCACCACCTCC
CAATCCGAATGATCCCGCTCCACCTCAGGGGAACAACAACCCTCAGCCCCAACCTAGACCACAGCCGCAGCCCCA
ACCCCAACCCCAGCCCCAGCCTCAACCCCAGCCCCAGCCACGTCCGCAGCCTCAGCCTCAACCTGGAGGCAACAA
TAACAACAAGAATAACAACAACGACGACAGCTACATTCCAAGTGCCGAGAAAATTCTGGAGTTTGTTAAGCAGAT
CCGAGACAGCATAACCGAAGAATGGTCACAGTGTAACGTGACGTGTGGATCTGGCATCAGAGTGAGGAAACGGAA
GGGTTCCAATAAGAAAGCAGAGGATCTGACTCTGGAGGACATTGATACAGAGATCTGCAAAATGGACAAAGACAA
TGACATCTACAGCTTCGACATTGTCAATGAGACAAATTGGCTGAAGATCGCCAAGAACATCTTCAAAGGCAAGTC
TCCTAGCAATTTCACGATCATACCGTTTAACAATACCGGTAGTTCTAACGATAACGAGTCAAACAAGGAGGAATC
AGTACTGCTGATCAGAAAGAAGATCAAAAGCAACAAGAATCACGATAGTTCCATCATTAGTGGTGACACTGTTAA
CGGGGACATTAGTGACCTGAATTATACGGCTAGCAACTTTTCCGATAACTCTGAGGACATAGAAGATAACCAGAA
ATATCCCACAACCAGCTACAATAGTTTCAACCATCTCAATTCCCTCACTGGGGACGAGAAATGTGGTAAAAGCCT
GAAGCTCGGCAACATCAGCAATCAGACAAACCAGGAAACCATAACCCAAAGCCTGTCAGTTGGAGAGATTCTGTG
CATTGACCTCGAAGGGAATGCAGGAACAGGCTATCTGTGGGTGTTGCTGGGCATACACAAGGATGAGCCAATCAT
AAACCCCGAGAACTTCCCAACCAAACTGACAAAGAAGTCTTTCTTTTCCGAGGAAATAAGTGTGACTCAGCCAAA
GAAGTACAAGATCGATGAGCATGATTCTTCAAAGAATGTGAATCGCGAAATCGAAAGCCCTGAACAGAAGGAGTC
CGACTCAAAGCCCAAGAAACCTCAGATGCAACTTCTTGGAGGACCAGATCGGATGAGGTCAGTCATCAAAGGACA
CAAACCTGGCAAATATTACATTGTGTACTCTTACTATCGACCGTTTTCTCCCACTTCTGGGGCGAACACTAAAAT
CATTTACGTCACAGTACAGCTGATCGAAGAGAAAGAGGAAATCACCCCTGAGAACAAAACCCTCATAATGCCCTC
TAAAACTCTGATGAAGGGCATTAAGACCAACATTTACTTCCTGTCAAACAAGGAAAAGATCCAAGTGCTTATGTG
CTATAACTACAAGTGTGATGCCGTTGTGTTCGAGAAAGACACCTTTCTGCGCTATCTCTACATCAAGAGCATCAA
TAATATCATCCTGAACGAAAGAATGATTGAACAGTTGTGCAAGAACGAAAACCTGAAGTACATCCTTGCCTGCAA
CAGCATAGTGGTTGAATCAAGCGACTTCATCAAACCCCTGATCATTGAGTTTGAGTCATCCACTTCCAAGAACAT
CTTCGTAAAGCACATTAAGCACAATAGCCAGAAAGAAATGGACATCAACAAGTTCAACGAGTATATGCGGGATCT
CAAAAGCAATGAGAAGCTCAGACTGAAGAAAGTCGAGCGATTCCACTCTATTAATCTGGCAGCCAAGAAACAGGA
GATTCTGGACGAAATCAAGTACTCTGAGGAGGTCTGCAACGAACAAATCGATCTCCACATTCTGCTGGATGGGAG
TGGCAGCATAGGTCACTCTAACTGGATCAGTCACGTGATACCCATGCTGACAACCCTTGTGGACAATTTGAACAT
CAGCCGCGATGAGATCAATATCTCCATGACCTTGTTCTCCACTTATGCCAGGGAACTTGTGAGACTTAAGAGATA
TGGGTCTACAAGCAAAGCCAGTCTGAGGTTCATCATCGCGCAACTCCAGAATAACTATTCTCCTCATGGAACGAC
AAATCTGACTAGCGCCCTGTTGAATGTGGACAATCTCATTCAGAAGAAAATGAATCGCCCTAATGCCATTCAGCT
CGTGATTATCCTTACTGACGGCATCCCTAACAATCTGAAGAAGTCCACTACTGTTGTCAACCAGCTGAAGAAGAA
GGACGTCAATGTCGCTATTATTGGTGTTGGCGCCGGAGTAAACAATATGTTTAACCGTATATTGGTAGGATGTGG
AAAACTTGGGCCTTGTCCCTACTACTCTTATGGCTCTTGGGATCAAGCACAAACCATGATCAAACCATTTCTCTC
AAAGGTCTGTCAGGAAGTGGAGAAAGTGGCACTGTGCGGTAAGTGGGAGGAGTGGAGTGAGTGTTCAACCACTTG
CGACAACGGAACGAAAATAAGGAAGCGAAAGGTTGGGGCGAGTATGAGCCACTTGCAGTGTCTGACATCTGTTGC
TGGTCTGTCCTCTATCGTCATGTCAATGTTCCCCAAACTCATTGCCAATAATCCTTCCCTGTTTAGACCACTGCT
CAACATTTCCTGGGGATATCTGTTCGGAAGCACTGTATGGCTGTGCTTCTTCAGTGAGATTGGGTTGGTCAGGAG
AATCAATGCTCCTAAACGGAAGAATCTGCCAGAGAATGCAGAACAAGCCAAAGAACAGCTGAAGGAGATCAAGAA
CAACGAAGGCGATTTTAACCGACGCAATATCGACTTCAAGTACTTCTTTAGCCTTTCCACAATCTTCTCTAGCAT
ACTGCTGCTTAGCACAGTGAAACTCGCCAACAACAATCTGCAGTTGAGGATCTGTTCCACCATTGTGTCACTGAG
TTGCATACTGAACAATATGTACTTTCAGAACAAGATACACTCACTTGCACTGAAGAAAGAGAGTCTCTTTAAGGA
CATGATCGATCGTCCGAAAGATACCACTATTCTGGTGAACCTGAAGAAGAACAAGACCGACTTTCACATCCATCA
TGGCCTTTCTCTGCTCTTGCTCTATAGCAGCTTCTTTGGCCTCACTCCCTACATTTTCACGTGACTCGAG (SEQ ID NO:119)

Figure 39(1)

**120- Amino acid sequence of *Plasmodium berghei* Fusion 5cPEAg SP- (1192 aa)**

PbCSP SP- GPI- + PD Pb18-10NT + PD Pb18-10CT + (-MA) PD Pb11-10CT + (-MANG) PD PbbTRAPNT + (-MA) PD Pb11-09

MAQNKSIQAQRNLNELCYNEGNDNKLYHVLNSKNGKIYNRNTVNRLLADAPEGKKNEKKNEKIERNNK
LKQPPPPPNPNDPPPPNPNDPPPPNPNDPPPPNPNDPPPPNANDPPPPNANDPAPPNANDPAPPNAND
PAPPNANDPAPPNANDPPPPNPNDPAPPNANDPPPPNPNDPAPPQGNNNPQPQPRPQPQPQPQPQPQP
QPQPQPRPQPQPQPGGNNNNKNNNNDDSYIPSAEKILEFVKQIRDSITEEWSQCNVTCGSGIRVRKRK
GSNKKAEDLTLEDIDTEICKMDKDNDIYSFDIVNETNWLKIAKNIFKGKSPSNFTIIPFNNTGSSNDN
ESNKEESVLLIRKKIKSNKNHDSSIISGDTVNGDISDLNYTASNFSDNSEDIEDNQKYPTTSYNSFNH
LNSLTGDEKCGKSLKLGNISNQTNQETITQSLSVGEILCIDLEGNAGTGYLWVLLGIHKDEPIINPEN
FPTKLTKKSFFSEEISVTQPKKYKIDEHDSSKNVNREIESPEQKESDSKPKKPQMQLLGGPDRMRSVI
KGHKPGKYYIVYSYYRPFSPTSGANTKIIYVTVQLIEEKEEITPENKTLIMPSKTLMKGLKTNIYELS
NKEKIQVLMGYNYKCDAVVFEKDTFLRYLYIKSINNIILNERMIEQLCKNENLKYILACNSIVVESSD
FIKPLIIEFESSTSKNIFVKHIKHNSQKEMDINKFNEYNRDLKSNEKLKLKKVERFHSINLAAKKQEI
LDEIKYSEEVCNEQIDLHILLDGSGSIGHSNWISHVIPMLTTLVDNLNISRDEINISMTLFSTYAREL
VRLKRYGSTSKASLRFIIAQLQNNYSPHGTTNLTSALLNVDNLIQKKMNRPNAIQLVIILTDGIPNNL
KKSTTVVNQLKKKDVNVAIIGVGAGVNNMFNRILVGCGKLGPCPYYSYGSWDQAQTMIKPFLSKVCQE
VEKVALCGKWEEWSECSTTCDNGTKIRKRKVSASMSHLQCIFSVAGLSSTVNSMFPKLIANFSLFRF
LLNISWGILPGSTVWLCPFSEIGLVRRINAPKRKNLPENAEQALEQLKEIKNNEGDFNRANIDFKIFF
SLSTIFSSILLLSTVKLANNNLQLRICSTIVSLSCILNNMYFQNKIHSLALKKESLFKQMIDRPKDTT
ILVNLKKNKTDFHIIHGLSLLLLYSSFFGLTPYIFT (SEQ ID NO:120)

Figure 39(2)

121- DNA sequence of *Plasmodium berghei* Fusion 5cPEAg SP+ – mouse codon optimized, with adaptors and Kozak sequence (3663 bp).

GGATCC – 5′ restriction site BamHI

GCCACCATGG – Kozak sequence (first methionine codon underlined)

CTCGAG – 3′ restriction site XhoI

Bold – sequence added leading to extra amino acid(s)

GGATCCGCCACCATGGCCAAGAAGTGTACCATACTGGTCGTTGCGTCACTTCTGTTGGTCAATTCTCTGCTCCCAGG
CTATGGACAGAACAAATCCATTCAGGCACAGAGGAACCTCAACGAACTCTGCTACAATGAAGGGAATGACAATAA
GCTGTATCACGTGCTGAATTCCAAGAACGGCAAAATCTACAATCGCAACACAGTAAATCGGTTGCTTGCCGATGC
ACCCGAGGGTAAGAAGAATGAAAAGAAGAATGAGAAAATCGAGCGCAACAACAAGCTTAAACAGCCACCGCCTCC
TCCTAACCCAAATGACCCACCGCCACCCAATCCAAACGACCCACCGCCTCCCAACCCTAACGATCCTCCACCGCC
CAACCCTAATGACCCACCACCTCCCAATGCAAACGATCCACCCCCTCCTAACGCTAACGACCCTGCTCCACCCAA
CGCTAACGATCCCGCGCCCCCCAATGCCAACGACCCCGCACCACCTAATGCCAACGATCCCGCCCCGCCCAATGC
TAATGATCCTCCACCACCCAACCCAAACGACCCTGCCCCTCCTAATGCTAACGATCCACCACCTCCCAATCCGAA
TGATCCCGCTCCACCTCAGGGGAACAACAACCCTCAGCCCCAACCTAGACCACAGCCGCAGCCCCAACCCCAACC
CCAGCCCCAGCCTCAACCCCAGCCCCAGCCACGTCCGCAGCCTCAGCCTCAACCTGGAGGCAACAATAACAACAA
GAATAACAACAACGACGACAGCTACATTCCAAGTGCCGAGAAAATTCTGGAGTTTGTTAAGCAGATCCGAGACAG
CATAACCGAAGAATGGTCACAGTGTAACGTGACGTGTGGATCTGGCATCAGAGTGAGGAAACGGAAGGGTTCCAA
TAAGAAAGCAGAGGATCTGACTCTGGAGGACATTGATACAGAGATCTGCAAAATGGACAAAGACAATGACATCTA
CAGCTTCGACATTGTCAATGAGACAAATTGGCTGAAGATCGCCAAGAACATCTTCAAAGGCAAGTCTCCTAGCAA
TTTCACGATCATACCGTTTAACAATACCGGTAGTTCTAACGATAACGAGTCAAACAAGGAGGAATCAGTACTGCT
GATCAGAAAGAAGATCAAAAGCAACAAGAATCACGATAGTTCCATCATTAGTGGTGACACTGTTAACGGGGACAT
TAGTGACCTGAATTATACGGCTAGCAACTTTTCCGATAACTCTGAGGACATAGAAGATAACCAGAAATATCCCAC
AACCAGCTACAATAGTTTCAACCATCTCAATTCCCTCACTGGGGACGAGAAATGTGGTAAAAGCCTGAAGCTCGG
CAACATCAGCAATCAGACAAACCAGGAAACCATAACCCAAAGCCTGTCAGTTGGAGAGATTCTGTGCATTGACCT
CGAAGGGAATGCAGGAACAGGCTATCTGTGGGTGTTGCTGGGCATACACAAGGATGAGCCAATCATAAACCCCGA
GAACTTCCCAACCAAACTGACAAAGAAGTCTTTCTTTTCCGAGGAAATAAGTGTGACTCAGCCAAAGAAGTACAA
GATCGATGAGCATGATTCTTCAAAGAATGTGAATCGCGAAATCGAAAGCCCTGAACAGAAGGAGTCCGACTCAAA
GCCCAAGAAACCTCAGATGCAACTTCTTGGAGGACCAGATCGGATGAGGTCAGTCATCAAAGGACACAAACCTGG
CAAATATTACATTGTGTACTCTTACTATCGACCGTTTTCTCCCACTTCTGGGGCGAACACTAAAATCATTTACGT
CACAGTACAGCTGATCGAAGAGAAAGAGGAAATCACCCCTGAGAACAAAACCCTCATAATGCCCTCTAAAACTCT
GATGAAGGGCATTAAGACCAACATTTACTTCCTGTCAAACAAGGAAAAGATCCAAGTGCTTATGTGCTATAACTA
CAAGTGTGATGCCGTTGTGTTCGAGAAAGACACCTTTCTGCGCTATCTCTACATCAAGAGCATCAATAATATCAT
CCTGAACGAAAGAATGATTGAACAGTTGTGCAAGAACGAAAACCTGAAGTACATCCTTGCCTGCAACAGCATAGT
GGTTGAATCAAGCGACTTCATCAAACCCCTGATCATTGAGTTTGAGTCATCCACTTCCAAGAACATCTTCGTAAA
GCACATTAAGCACAATAGCCAGAAAGAAATGGACATCAACAAGTTCAACGAGTATATGCGGGATCTCAAAAGCAA
TGAGAAGCTCAGACTGAAGAAAGTCGAGCGATTCCACTCTATTAATCTGGCAGCCAAGAAACAGGAGATTCTGGA
CGAAATCAAGTACTCTGAGGAGGTCTGCAACGAACAAATCGATCTCCACATTCTGCTGGATGGGAGTGGCAGCAT
AGGTCACTCTAACTGGATCAGTCACGTGATACCCATGCTGACAACCCTTGTGGACAATTTGAACATCAGCCGCGA
TGAGATCAATATCTCCATGACCTTGTTCTCCACTTATGCCAGGGAACTTGTGAGACTTAAGAGATATGGGTCTAC
AAGCAAAGCCAGTCTGAGGTTCATCATCGCGCAACTCCAGAATAACTATTCTCCTCATGGAACGACAAATCTGAC
TAGCGCCCTGTTGAATGTGGACAATCTCATTCAGAAGAAAATGAATCGCCCTAATGCCATTCAGCTCGTGATTAT
CCTTACTGACGGCATCCCTAACAATCTGAAGAAGTCCACTACTGTTGTCAACCAGCTGAAGAAGAAGGACGTCAA
TGTCGCTATTATTGGTGTTGGCGCCGGAGTAAACAATATGTTTAACCGTATATTGGTAGGATGTGGAAAACTTGG
GCCTTGTCCCTACTACTCTTATGGCTCTTGGGATCAAGCACAAACCATGATCAAACCATTTCTCTCAAAGGTCTG
TCAGGAAGTGGAGAAAGTGGCACTGTGCGGTAAGTGGGAGGAGTGGAGTGAGTGTTCAACCACTTGCGACAACGG
AACGAAAATAAGGAAGCGAAAGGTTGGGGCGAGTATGAGCCACTTGCAGTGTCTGACATCTGTTGCTGGTCTGTC
CTCTATCGTCATGTCAATGTTCCCCAAACTCATTGCCAATAATCCTTCCCTGTTTAGACCACTGCTCAACATTTC
CTGGGGATATCTGTTCGGAAGCACTGTATGGCTGTGCTTCTTCAGTGAGATTGGGTTGGTCAGGAGAATCAATGC
TCCTAAACGGAAGAATCTGCCAGAGAATGCAGAACAAGCCAAAGAACAGCTGAAGGAGATCAAGAACAACGAAGG
CGATTTTAACCGACGCAATATCGACTTCAAGTACTTCTTTAGCCTTTCCACAATCTTCTCTAGCATACTGCTGCT
TAGCACAGTGAAACTCGCCAACAACAATCTGCAGTTGAGGATCTGTTCCACCATTGTGTCACTGAGTTGCATACT
GAACAATATGTACTTTCAGAACAAGATACACTCACTTGCACTGAAGAAAGAGAGTCTCTTTAAGGACATGATCGA
TCGTCCGAAAGATACCACTATTCTGGTGAACCTGAAGAAGAACAAGACCGACTTTCACATCCATCATGGCCTTTC
TCTGCTCTTGCTCTATAGCAGCTTCTTTGGCCTCACTCCCTACATTTTCACGTGACTCGAG (SEQ ID NO:121)

Figure 40(1)

**122- Amino acid sequence of *Plasmodium berghei* Fusion 5cPEAg SP⁺ (1214 aa)**

PbCSP SP⁺ GPI⁻ + PD Pb18-10NT + PD Pb18-10CT + (-MA)[redacted] + (-MANG)PD PbbTRAPNT + (-MA)[redacted]

MAKKCTILVVASLLLVNSLLPGYGQNKSIQAQRNLNELCYNEGNDNKLYHVLNSKNGKIYNRNTVNRL
LADAPEGKKNEKKNEKIERNNKLKQPPPPPNPNDPPPPNPNDPPPPNPNDPPPPNPNDPPPPNANDPP
PPNANDPAPPNANDPAPPNANDPAPPNANDPPPPNPNDPAPPNANDPPPPNPNDPAPPQG
NNNPQPQPRPQPQPQPQPQPQPQPQPQPRPQPQPQPGGNNNNKNNNNDDSYIPSAEKILEFVKQIRDS
ITEEWSQCNVTCGSGIRVRKRKGSNKKAEDLTLEDIDTEICKMDKDNDIYSFDIVNETNWLKIAKNIF
KGKSPSNFTIIPFNNTGSSNDNESNKEESVLLIRKKIKSNKNHDSSIISGDTVNGDISDLNYTASNFS
DNSEDIEDNQKYPTTSYNSFNHLNSLTGDEKCGKSLKLGNISNQTNQETITQSLSVGEILCIDLEGNA
GTGYLWVLLGIHKDEPIINPENFPTKLTKKSFFSEEISVTQPKKYKIDEHDSSKNVNREIESPEQKES
DSKPKKPQMQLLGGPDRMRSVIKGHKPGKYYIVYSYYRPFSPTSGANTKIIYVTVQ[redacted]QEILDEIKYSEEVCNEQIDLHILLDGSGSIGHSNWISHVIPMLTTLVDN
LNISRDEINISMTLFSTYARELVRLKRYGSTSKASLRFIIAQLQNNYSPHGTTNLTSALLNVDNLIQK
KMNRPNAIQLVIILTDGIPNNLKKSTTVVNQLKKKDVNVAIIGVGAGVNNMFNRILVGCGKLGPCPYY
SYGSWDQAQTMIKPFLSKVCQEVEKVALCGKWEEWSECSTTCDNGTKIRKRKV[redacted]

(SEQ ID NO:122)

Figure 40(2)

**123- DNA sequence of *Plasmodium berghei* ANKA CSP – mouse codon optimized, with adaptors and Kozak sequence (1044 bp).**

GGATCC - 5′ restriction site BamHI

GCCACCATGG - Kozak sequence (first methionine codon underlined)

CTCGAG - 3′ restriction site XhoI

Bold - sequence added leading to extra amino acid(s)

GGATCCGCCACCATGGCCAAGAAGTGTACCATACTGGTCGTTGCGTCACTTCTGTTGGTCAATTCTCT
GCTCCCAGGCTATGGACAGAACAAATCCATTCAGGCACAGAGGAACCTCAACGAACTCTGCTACAATG
AAGGGAATGACAATAAGCTGTATCACGTGCTGAATTCCAAGAACGGCAAAATCTACAATCGCAACACA
GTAAATCGGTTGCTTGCCGATGCACCCGAGGGTAAGAAGAATGAAAAGAAGAATGAGAAAATCGAGCG
CAACAACAAGCTTAAACAGCCACCGCCTCCTCCTAACCCAAATGACCCACCGCCACCCAATCCAAACG
ACCCACCGCCTCCCAACCCTAACGATCCTCCACCGCCCAACCCTAATGACCCACCACCTCCCAATGCA
AACGATCCACCCCCTCCTAACGCTAACGACCCTGCTCCACCCAACGCTAACGATCCCGCGCCCCCCAA
TGCCAACGACCCCGCACCACCTAATGCCAACGATCCCGCCCCGCCCAATGCTAATGATCCTCCACCAC
CCAACCCAAACGACCCTGCCCCTCCTAATGCTAACGATCCACCACCTCCCAATCCGAATGATCCCGCT
CCACCTCAGGGGAACAACAACCCTCAGCCCCAACCTAGACCACAGCCGCAGCCCCAACCCCAACCCCA
GCCCCAGCCTCAACCCCAGCCCCAGCCACGTCCGCAGCCTCAGCCTCAACCTGGAGGCAACAATAACA
ACAAGAATAACAACAACGACGACAGCTACATTCCAAGTGCCGAGAAAATTCTGGAGTTTGTTAAGCAG
ATCCGAGACAGCATAACCGAAGAATGGTCACAGTGTAACGTGACGTGTGGATCTGGCATCAGAGTGAG
GAAACGGAAGGGTTCCAATAAGAAAGCAGAGGATCTGACTCTGGAGGACATTGATACAGAGATCTGCA
AAATGGACAAATGCAGCTCTATCTTCAACATCGTGAGTAATAGCCTCGGGTTTGTGATTCTGCTGGTC
CTGGTGTTCTTCAATTGACTCGAG (SEQ ID NO:123)

**124- Amino acid sequence of *Plasmodium berghei* ANKA CSP (341 aa)**

MAKKCTILVVASLLLVNSLLPGYGQNKSIQAQRNLNELCYNEGNDNKLYHVLNSKNGKIYNRNTVNRL
LADAPEGKKNEKKNEKIERNNKLKQPPPPPNPNDPPPPNPNDPPPPNPNDPPPPNPNDPPPPNANDPP
PPNANDPAPPNANDPAPPNANDPAPPNANDPAPPNANDPPPPNPNDPAPPNANDPPPPNPNDPAPPQG
NNNPQPQPRPQPQPQPQPQPQPQPQPQPRPQPQPQPGGNNNNKNNNNDDSYIPSAEKILEFVKQIRDS
ITEEWSQCNVTCGSGIRVRKRKGSNKKAEDLTLEDIDTEICKMDKCSSIFNIVSNSLGFVILLVLVFF
N (SEQ ID NO:124)

Figure 41

MALARIA PRE-ERYTHROCYTIC ANTIGENS AS A FUSION POLYPEPTIDE AND THEIR USE IN THE ELICITATION OF A PROTECTIVE IMMUNE RESPONSE IN A HOST

FIELD OF THE INVENTION

The invention relates to chimeric *Plasmodium* antigenic polypeptides derived from pre-erythrocytic (PE) antigens and associated in a fusion polypeptide. In particular, the invention relates to antigenic fusion polypeptides of malaria parasites wherein said antigenic polypeptides exhibit a protective effect, especially that of eliciting a protective immune response in a host against challenge by *Plasmodium* sporozoites or a sterile response. Such identified antigenic fusion polypeptides may thus constitute active ingredients suitable for the design of a vaccine candidate, in particular a vaccine suitable for a human host.

BACKGROUND OF THE INVENTION

In the last 15 years, malaria control measures reduced by 48% the global deaths caused by this mosquito-borne disease. Despite this significant decrease in mortality, the WHO estimated ~215 millions of malaria clinical episodes, resulting in more than 400,000 deaths in 2015. Actual malaria control programs rely mainly on the use of insecticides and antiplasmodial medicines, but the emergence and spreading of resistant mosquitos and parasites put the efficacy of these interventions at risk[1]. In this scenario, an efficient malaria vaccine could be an important additional tool to control and eventually eliminate malaria.

Since the 60's, it has been known that multiple immunizations using, irradiated sporozoites can elicit sterile protection against malaria infection. However, during the last 50 years only a few protective antigens were identified, but none of them, individually or in combination, could match the robust protection induced by irradiated parasites.

The most advanced malaria vaccine, RTS,S (Mosquirix, GSK), targets the *Plasmodium falciparum* circumsporozoite protein (CSP), the major surface protein of sporozoites, the motile stage inoculated in the skin during an infective mosquito bite. This subunit vaccine reduced the clinical cases of malaria in African infants and children by 26-36%[2]. This partial protection is mainly associated with high titers of anti-CSP antibodies[3], and albeit significant, it is far from achieving the standards established by the WHO malaria vaccine road map, which preconizes the development of a vaccine with at least 75% of efficacy against clinical malaria, and ideally targeting morbidity, mortality and parasite transmission[4].

On the other hand, live irradiated sporozoites can invade but are arrested as early liver-stages inside hepatocytes, conferring sterile immunity against a homologous sporozoite challenge[5]. Unfortunately, technical and economical impediments associated with the production, storage and delivery of these live parasites still hinder their use for mass vaccination in poor tropical countries. This sterile protection seems to be mainly dependent on CD8+ T cells, since their depletion abolishes sterile immunity in several experimental models, however, the identity of the antigens conferring such robust protection is still elusive[6]. So far, the number of known protective antigens among the thousands of possible proteins expressed by pre-erythrocytic (PE) stages, sporozoite and the ensuing liver-stage, is extremely limited, and these antigens only confer weaker protection than CSP alone or in multi-antigenic formulations in humans[7]. To date the attempts to identify new protective antigens from live attenuated sporozoites have not yielded suitable candidates, despite the screening of thousands of PE peptides, minigenes and genes[8-10].

DESCRIPTION OF THE INVENTION

The invention concerns a chimeric antigen obtained as a fusion polypeptide of distinct antigens and/or antigenic fragments thereof suitable for the elicitation of an immunogenic response, in particular a protective immunogenic response or advantageously a sterile protection against *Plasmodium* parasite. Such chimeric antigen is suitable as an active ingredient in an immunogenic or in a vaccine composition or as the expression product of an active ingredient (such as a nucleic acid or a lentiviral vector) from which it is expressed.

Sterile protection when assessed in mice model immunized with the antigens, nucleic acids (either with DNA or RNA), or vectors constructs of the invention in particular lentiviral vectors as disclosed herein may be acknowledged if infected red blood cells are not detected after 10 days post inoculation of sporozoites.

Accordingly the invention relates to a chimeric antigenic polypeptide or a nucleic acid encoding such a chimeric antigenic polypeptide or a vector encoding same wherein the chimeric antigenic polypeptide is a fusion of antigens of *Plasmodium* parasite or antigenic domains or fragments of *Plasmodium* parasite antigens, in particular of protective domains of such antigens or where the antigens provide at least 2, in particular at least 3 or at least 4 or at least 5 and in particular are especially 2, 3, 4 or 5, and accordingly encompass at least 2, at least 3 or at least 4 antigens (and/or antigenic fragments thereof) or are from the group of antigens (and/or antigenic fragments thereof) designated as 18-10 (ICP), 11-10 (Ag45), TRAP, and 11-09 (Ag40). In a particular embodiment the chimeric antigenic polypeptide (also designated chimeric antigen) comprises or consist of a fusion of the above 4 antigens or antigenic fragments thereof or a combination of antigens within the above group and fragments thereof.

According to another embodiment, the invention relates the chimeric antigenic polypeptide (also designated chimeric antigen) or a nucleic acid encoding such a chimeric antigenic polypeptide or a vector encoding same wherein the chimeric antigenic polypeptide comprises or consists of a fusion of the 5 antigens or antigenic fragments thereof as defined herein wherein such fusion encompasses or consists of antigens or antigenic fragments thereof which are CSP, 18-10 (ICP), 11-10 (Ag45), TRAP, and 11-09 (Ag40).

According to another embodiment said 2, 3, 4 or at least 2, at least 3 or at least 4 antigens or antigenic fragments thereof are comprised in a combination or in a composition of antigens wherein the chimeric antigenic polypeptide is present in the combination or in the composition which additionally comprises as a separate antigen, the CSP antigen or an antigenic fragment thereof of a *Plasmodium* parasite.

In a particular embodiment a chimeric antigenic polypeptide comprising 5 antigens or antigenic fragment(s) of antigens as a fusion polypeptide is provided wherein the CSP or fragment thereof is fused, in particular in the N-terminal end of the chimeric polypeptide.

The invention accordingly also relates to a nucleic acid molecule encoding a chimeric polypeptide defined herein. The nucleic acid may be DNA, in particular cDNA or may be RNA, in particular stabilized RNA. The RNA sequences are deducted from the DNA sequences wherein the Thymine (T) nucleobase is replaced by an Uracile (U) nucleobase. RNA polynucleotides may be obtained by transcription of DNA or cDNA or may be synthesized.

The invention accordingly relates to a combination (i.e., an assembly of separated compounds or alternatively of mixed compounds) of compounds, or a composition of compounds (in admixture), comprising at least 2 distinct active ingredients wherein each active ingredient consists of one of the following types of compound: (i) an antigenic polypeptide, in particular a chimeric antigenic polypeptide as defined herein, of a *Plasmodium* parasite, (ii) a polynucleotide, e.g. a DNA or a RNA, encoding the antigenic polypeptide, in particular the chimeric antigenic polypeptide or, (iii) a vector, in particular a viral vector, especially a lentiviral vector wherein such vector expresses such antigenic polypeptide of a *Plasmodium* parasite.

A combination or a composition of compounds comprises or consists in particular of a chimeric antigen defined herein comprising or consisting of at least 2, or at least 3 or at least 4 or at least 5 antigens or antigenic fragment(s) thereof, its nucleic acid or a vector comprising such nucleic acid, especially a viral or a lentiviral vector comprising such nucleic acid in its genome.

In a combination of compounds, additional *Plasmodium* antigen(s), or antigenic fragments thereof, their nucleic acid or a vector, in particular a viral or lentiviral expressing the same may also be present. Such additional antigenic polypeptides are in particular PE antigens or fragments thereof, such as CSP antigen or a fragment thereof. Such additional antigens, their nucleic acid or a vector, in particular a viral or lentiviral expressing the same, may also be chimeric antigenic polypeptide(s) as defined herein which are different from other chimeric antigenic polypeptides contained in the combination or composition.

In a particular embodiment, the invention accordingly relates to a combination or to a composition of compounds, comprising at least 2 distinct active ingredients wherein each active ingredient consists of an antigenic polypeptide of a *Plasmodium* parasite, a polynucleotide encoding the antigenic polypeptide, or a vector, in particular a viral vector, especially a lentiviral vector wherein such vector expresses such antigenic polypeptide of a *Plasmodium* parasite, wherein one antigenic polypeptide is the circumsporozoite protein (CSP) or a polypeptidic derivative thereof.

According to a particular embodiment, a combination or a composition of compounds of the invention thus comprises at least a chimeric antigenic polypeptide which is a fusion of at least 2, in particular at least 3 or at least 4 antigens selected from the group of following antigens: thrombospondin related anonymous protein (TRAP) characterized by the sequence of SEQ ID No.20, 21, 23, 24, 26 or 27, the inhibitor of cysteine protease (ICP) characterized by the sequence of SEQ ID No.29, 30, 32, 33, 35 or 36, protein Ag40(11-09) having one of the sequences of SEQ ID No. 67, 68, 70, 71, 73 or 74 and Ag45 (11-10) having one of the sequences of SEQ ID No. 76, 77, 79, 80, 82 or 83 or independently of each other, a polypeptidic derivatives thereof in particular fragments thereof as defined herein comprising or consisting of the Protective Domain, provided each polypeptidic derivative keeps protective properties of the antigen from which it derives in the combination of compounds.

Optionally circumsporozoite protein (CSP) characterized by the sequence of SEQ ID No.11, 12, 14, 15, 17, 18 or 124 or a fragment thereof is also present in the chimeric antigen or is also present as an additional separate antigen in the combination or composition of compounds, A polypeptidic derivative is defined herein as an antigenic fragment of a native antigen.

It may alternatively or in combination be defined as a polypeptide whose amino acid sequence consists of an amino acid sequence with at least 70%, in particular at least 86% of identity in amino acids, preferably at least 95% amino acid identity with the antigenic polypeptide from which it derives (especially from *P. falciparum* or *P. vivax*) and which keeps the protective properties of the polypeptide from which it derives when it is encompassed in the chimeric antigenic polypeptide or in the composition or combination of compounds of the invention. The threshold of 86% amino acid identity corresponds to the average identity of the three most dissimilar Pf protective antigens (PfCSP; Query cover of 100%, and amino acid identity of 86%) obtained when comparing the 8 *P. falciparum* pre-erythrocytic antigens of the reference strain known as 3D7 strain (the amino acid sequence of its relevant antigens are those provided herein) with sequences of other *P. falciparum* parasites in the Genbank database identified herein. In a particular embodiment the circumsporozoite protein (CSP) used for determination of the variation threshold is a representative of the worldwide distributed variants of the protein such as CSP VK210 (reference in GenBank: AAKM01000017.1 and protein IDXP_001613068) or CSP VK247 (reference in GenBank: GU339076.1 and Protein ID: ADB92545.1).

DETAILED DESCRIPTION OF THE INVENTION

The invention thus relates to a chimeric antigenic polypeptide which comprises or consists of a fusion of a fusion of at least2, in particular of 2, 3, or 4 antigens of a *Plasmodium* parasite infecting human or antigenic fragments:

(a) wherein said antigens are antigens of a *Plasmodium* parasite, and are selected from the group of antigens designated as TRAP, 18-10 (ICP), 11-10 (Ag45) and 11-09 (Ag40) and, (b) when the chimeric antigenic polypeptide comprises antigenic fragments of antigens instead of such antigens as defined in (a), such antigenic fragments comprise T cell epitopes in particular CD8+ T cell epitopes and are either truncated antigens or antigenic fragments with amino acid deletion(s) in particular said antigenic fragments contain respectively:

i. the 18-10 antigen devoid of its signal peptide, and/or or devoid of 1 to 15, in particular 1 to 10 or 1 to 3 amino acid residues, ii. the C-terminal fragment of the 11-10 antigen, and/or a fragment thereof deleted from 1 to 3 amino acid residues in its N-terminal end and/or in the C-terminal end, iii. the N-terminal fragment of the TRAP antigen, and/or a fragment thereof deleted from 1 to 3 amino acid residues in its N-terminal end, iv. a fragment of the 11-09 antigen deleted from 1 to 6 amino acid residues, in particular at its N-terminal end.

The primary structure of the chimeric antigenic polypeptide comprises antigens as defined above and/or antigenic fragments in any order. In a particular embodiment the order of the antigens or antigenic fragments thereof in the fusion may be the following: 18-10 (ICP), 11-10 (Ag45), TRAP and 11-09 (Ag40).

In a particular embodiment, the chimeric antigenic polypeptide does not contain neo-epitopes in the junction of antigen partners in the fusion that would significantly negatively impact the immune response in a host.

In a particular embodiment of the invention, the chimeric antigenic polypeptide above defined comprises or consists of a fusion of antigens or antigenic fragments thereof wherein the antigens and the antigens suitable to provide such fragments are as follows:

a. at least 3, in particular 3 antigens of *Plasmodium* parasite wherein at least 2 of such antigens are selected from the group of antigens designated as TRAP, 18-10 (ICP), 11-10 (Ag45) and 11-09 (Ag40) and the antigens further include CSP, in particular wherein the antigens include CSP and TRAP or b. at least 4, in particular 4 antigens of *Plasmodium* parasite wherein at least 3 of such antigens are selected from the group of antigens designated as TRAP, 18-10 (ICP), 11-10 (Ag45) and 11-09 (Ag40) and the antigens further include CSP, in particular wherein the antigens include CSP and TRAP or c. at least 5, in particular of 5 antigens of *Plasmodium* parasite which are TRAP, 18-10 (ICP), 11-10 (Ag45), 11-09 (Ag40) and CSP In a particular embodiment the CPS antigen is devoid of its signal peptide or is devoid of its GPI fragment or both. In an embodiment, the CSP antigen or an antigenic fragment thereof is fused in the N-terminal end of the chimeric polypeptide.

Hence, in an embodiment of the invention, the primary structure of the chimeric antigenic polypeptide results from the junction, in particular a fusion of the following antigens of fragments thereof:

a. at least 2, or at least 3 or at least 4 of the TRAP antigen, the 18-10 antigen devoid of its signal peptide, the C-terminal fragment of the 11-10 antigen, and antigen 11-09 (Ag40) or b. at least 2, at least 3, at least 4 or at least 5 of the CSP antigen, the TRAP antigen, the 18-10 antigen devoid of its signal peptide, the C-terminal fragment of the 11-10 antigen, and antigen 11-09 (Ag40).

In a particular embodiment, in order to achieve the said junction, in particular to avoid the creation of neo-epitopes that could be significantly recognized by the HLA system in a human host, amino acid residue(s) may be introduced in the chimeric antigenic polypeptide at the junction of two antigens or antigenic fragments thereof such as illustrated in the Example at the junction of antigens/antigenic fragments of 11-10 and TRAP. The number of added residues is preferably minimized and in particular may be 1, 2 or 3 and especially less than 5 contiguous residues.

In a particular embodiment, the chimeric antigenic polypeptide of the invention comprises a fusion of antigenic fragments wherein one fragment is selected from each of each of the following lists:

antigenic fragment of antigen 18-10 wherein the amino acid sequence of such fragment is SEQ ID No. 96 or SEQ ID No.98 or SEQ ID No.114 or SEQ ID No; 100 or is a fragment thereof after deletion of 1 to 10, in particular 1 to 3 amino acid residues, especially in the N-terminal end and/or antigenic fragment of antigen 11-10 wherein the amino acid sequence of such fragment is SEQ ID No. 102 or SEQ ID No.104 or is a fragment thereof after deletion of 1 to 10, in particular 1 to 3 amino acid residues, especially in the N-terminal end and/or antigenic fragment of antigen TRAP (11-05) wherein the amino acid sequence of such fragment is SEQ ID No. 106 or SEQ ID No.108 or is a fragment thereof after deletion of 1 to 10, in particular 1 to 3 amino acid residues, especially in the N-terminal end and/or antigenic fragment of antigen 11-09 wherein the amino acid sequence of such fragment is SEQ ID No. 110 or SEQ ID No.112 or is a fragment thereof after deletion of 1 to 10, in particular 1 to 3 amino acid residues, especially in the N-terminal end and/or optionally, antigenic fragment of antigen CSP wherein the amino acid sequence of such fragment is SEQ ID No. 124 or is a fragment thereof after deletion of 1 to 10, in particular 1 to 3 amino acid residues, especially in the N-terminal end.

In a particular embodiment, the chimeric antigenic polypeptide arising from the fusion of antigenic fragments as disclosed herein is obtained by fusion of antigenic fragments of the same type of *Plasmodium* parasite such as fragments of *Plasmodium falciparum.*

As an example, the chimeric antigenic polypeptide is such that its amino acid sequence consists of:

i. the amino acid sequence of SEQ ID No.96 or SEQ ID No.98 or SEQ ID No. 100, or SEQ ID No.114 or the fusion of the amino acid sequences SEQ ID No. 96 and 98 for the 18-10 antigenic fragment fused to, ii. the amino acid sequence of SEQ ID No.102 or SEQ ID No.104 for the 11-10 antigenic fragment fused to, iii. the amino acid sequence of SEQ ID No.106 or SEQ ID No.108 for the TRAP antigenic fragment fused to, iv. the amino acid sequence of SEQ ID No.110 or SEQ ID No.112 for the 11-09 antigen, wherein said fragments are devoid or an initial Methionine residue when they feature an internal fusion partner and optionally are devoid of the 1 to 6 of the 1 to 5, in particular the 1 to 3 N-terminal residues of the original antigen and further optionally wherein said fragments contain 1 to 3 additional amino acid residues and/or are deleted for 1 to 3 amino acid residues in their N- and/or C-terminal end(s) to enable the junction with the contiguous antigen or antigenic fragment.

In a particular embodiment of this example, the amino acid sequence of the chimeric antigenic polypeptide is such that it:

a. contains 1 to 3 additional junctional amino acid residues at the junction of SEQ ID No.104 for the 11-10 antigenic fragment and SEQ ID No.108 for the TRAP antigen, in particular contains one amino acid residue such as the Glutamic acid residue at said junction or, b. contains a deletion of 1 to 6 or 1 to 5 amino acid residues present in the N-terminal end of the original antigen or antigenic fragment thereof present in the fusion such as the deletion of MA contiguous amino acid residues or MANG contiguous amino acid residues it is pointed out that the illustrated amino acid sequences of the antigens, fragments thereof and fusion thereof may contain an initial "M" amino acid residue. Such residue is kept in the used sequence as long as it is necessary for the construct. Accordingly, when the amino acid sequence is contained as an internal fusion partner in the chimeric antigenic polypeptide, the disclosed "M" residue may not be present as an initial residue in the final polypeptide.

In a particular embodiment all the antigens or antigenic fragments thereof provided in the chimeric antigenic polypeptide are from *Plasmodium falciparum* or from *Plasmodium vivax*

The invention thus concerns a chimeric antigenic polypeptide whose amino acid sequence is SEQ ID No. 116 or SEQ ID No.120, or SEQ ID No.122 (for *Plasmodium Berghei*) or SEQ ID No.118 (for *Plasmodium falciparum*).

The invention also relates to a nucleic acid that encodes a chimeric polypeptide as defined herein. A nucleic acid is thus a DNA, in particular a cDNA, or a RNA. It is the polynucleotide counterpart of the amino acid sequence of the chimeric antigenic polypeptide defined herein and accordingly encodes the same. It may further comprise control nucleotide sequences for the transcription or for the expression of the chimeric antigenic polypeptide. It may also be modified, in order to be operably ligated to a distinct polynucleotide such as a plasmid or a vector genome, in particular a lentiviral vector genome. It may also be modified, in particular to be rendered more stable such as for use as RNA. In a further embodiment, the nucleic acid is a mammalian codon-optimized, in particular a human codon-optimized sequence for expression in mammalian, respectively human cells. The DNA or RNA may be used as such as an active ingredient to elicit an immune response in a host.

In a particular embodiment, the nucleic acid encodes a chimeric antigenic polypeptide of the invention that comprises a fusion of antigenic fragments; accordingly the nucleic acid construct comprises or contains polynucleotide fragments wherein one fragment is selected from each of each of the following lists:

- a polynucleotide fragment that encodes an antigenic fragment of antigen 18-10 wherein the amino acid sequence of such fragment is SEQ ID No. 96 or SEQ ID No.98 or SEQ ID No.114 or SEQ ID No; 100 or is a fragment thereof after deletion of 1 to 10, in particular 1 to 3 amino acid residues, especially in the N-terminal end, in particular a polynucleotide fragment of SEQ ID No 95. SEQ ID No. 97 or SEQ ID No. 113 and/or
- a polynucleotide fragment that encodes an antigenic fragment of antigen 11-10 wherein the amino acid sequence of such fragment is SEQ ID No. 102 or SEQ ID No.104 or is a fragment thereof after deletion of 1 to 10, in particular 1 to 3 amino acid residues, especially in the N-terminal end in particular a polynucleotide fragment of SEQ ID No 101. SEQ ID No. 103 and/or
- a polynucleotide fragment that encodes an antigenic fragment of antigen TRAP (11-05) wherein the amino acid sequence of such fragment is SEQ ID No. 106 or SEQ ID No.108 or is a fragment thereof after deletion of 1 to 10, in particular 1 to 3 amino acid residues, especially in the N-terminal end in particular a polynucleotide fragment of SEQ ID No 105. SEQ ID No. 107 and/or
- a polynucleotide fragment that encodes an antigenic fragment of antigen 11-09 wherein the amino acid sequence of such fragment is SEQ ID No. 110 or SEQ ID No.112 or is a fragment thereof after deletion of 1 to 10, in particular 1 to 3 amino acid residues, especially in the N-terminal end in particular a polynucleotide fragment of SEQ ID No 109. SEQ ID No.111 and/or optionally,
- a polynucleotide fragment that encodes an antigenic fragment of antigen CSP wherein the amino acid sequence of such fragment is SEQ ID No. 124 or is a fragment thereof after deletion of 1 to 10, in particular 1 to 3 amino acid residues, especially in the N-terminal end in particular a polynucleotide fragment of SEQ ID No 123..

In a particular embodiment all the nucleic acid are derived from nucleotide sequence of *Plasmodium falciparum* or *Plasmodium vivax.*

In a particular embodiment of the nucleic acid, the polynucleotide encodes a chimeric antigenic polypeptide whose amino acid sequence consists of:

i. the amino acid sequence of SEQ ID No.96 or SEQ ID No.98 or SEQ ID No. 100, or SEQ ID No.114 or the fusion of the amino acid sequences SEQ ID No. 96 and 98 for the 18-10 antigenic fragment fused to,
ii. the amino acid sequence of SEQ ID No.102 or SEQ ID No.104 for the 11-10 antigenic fragment fused to,
iii. the amino acid sequence of SEQ ID No.106 or SEQ ID No.108 for the TRAP antigenic fragment fused to,
iv. the amino acid sequence of SEQ ID No.110 or SEQ ID No.112 for the 11-09 antigen, Accordingly, the nucleic acid may be the product of the fusion of the following polynucleotides:

i. sequence of SEQ ID No.95 or SEQ ID No.97 or SEQ ID No. 99, or SEQ ID No.113 or the fusion of the amino acid sequences SEQ ID No. 95 and 97 for the 18-10 antigenic fragment fused to,
ii. the amino acid sequence of SEQ ID No.101 or SEQ ID No.103 for the 11-10 antigenic fragment fused to,
iii. the amino acid sequence of SEQ ID No.105 or SEQ ID No.107 for the TRAP antigenic fragment fused to,
iv. the amino acid sequence of SEQ ID No.110 or SEQ ID No.111 for the 11-09 antigen, Specific embodiments of the nucleic acid constructs of the invention is one whose nucleotide sequence is SEQ ID No. 115 or SEQ ID No.119 or SEQ ID No. 121 (for *Plasmodium berghei*) or SEQ ID No. 117 (for *Plasmodium falciparum*).

The nucleic acids originating from the *Plasmodium* parasite may be adapted where necessary to reflect the changes carried out in the original *Plasmodium* antigen. In particular codon(s) corresponding to the deleted amino acid residues may be deleted from the original sequence or codon(s) encoding the additional amino acid residues may be introduced in the sequence. Additionally the nucleic acid sequence may contain sequences for the control of transcription and/or for the control of expression, and/or may contain sequences for ligation to a distinct nucleic acid such as for ligation to a plasmid or a vector genome. Hence the nucleic acid may contain one or more of sequences for restriction site(s), Kozak sequence, promoter or other sequences as disclosed herein and illustrated in the examples. The particular nucleic acid of the invention may accordingly contain or be devoid of the specific non coding sequences disclosed in the sequences illustrated as SEQ ID No. 84 to 87.

In a particular embodiment the invention relates to the herein defined chimeric antigenic polypeptides provided in a combination or in a composition of compounds wherein said combination or composition further comprises as active ingredients one or more antigenic polypeptide(s) of a *Plasmodium* parasite which is not contained in the chimeric antigenic polypeptide, or a polynucleotide encoding the antigenic polypeptide(s), or a vector, in particular a viral vector, especially a lentiviral vector, wherein such vector expresses such antigenic polypeptide(s) of a *Plasmodium* parasite.

In particular, each additional antigenic polypeptide is selected from the group of the circumsporozoite protein (CSP), the metallopeptidase (Bergheilysin/Falcilysin), the GPI-anchored protein P113, the pore-forming like protein SPECT2, or respectively and independently of each other a polypeptidic derivative of any of these antigenic polypeptides wherein said polypeptidic derivative keeps protective properties of the antigen from which it derives in the combination of compounds of the invention.

Accordingly, the combination or composition of compounds including the chimeric antigenic polypeptide defined herein comprises 2, 3, 4, 5, 6, 7 or 8 antigens or polynucleotides encoding such antigenic polypeptides, or a vector, in particular a viral vector, especially lentiviral vector(s), wherein such vector expresses the same or alternatively consists in a combination or a composition of 2, 3, 4, 5, 6, 7 or 8 antigens or viral, especially lentiviral vector(s) expressing the same. In a particular embodiment wherein the combination or composition of compounds comprises a chimeric antigenic polypeptide which is a fusion of 4 antigens or antigenic fragments as defined herein at least 1 antigens or viral vector(s) expressing same is present in the combination or composition and consists of or comprises the circumsporozoite protein (CSP) or a derivative thereof as disclosed herein.

In a particular embodiment of the invention, a combination of compounds is a set of distinct active ingredients present as separate formulation for administration wherein one active ingredient consists of an antigenic polypeptide of a *Plasmodium* parasite or a polynucleotide encoding this antigenic polypeptide or the active ingredient consists of a vector, in particular a viral vector, especially a lentiviral vector, expressing such antigenic polypeptide of a *Plasmodium* parasite, wherein said set of active ingredients encompasses chimeric antigenic polypeptides of PE stage antigens of a *Plasmodium* parasite as defined herein or viral vector, in particular lentiviral vectors expressing such chimeric antigenic polypeptide and other(s) active ingredient(s) consist(s) of other PE stage antigens of a *Plasmodium* parasite which may be chosen from the circumsporozoite protein (CSP) when it is not present in the chimeric antigenic polypeptide, the metallopeptidase (Bergheilysin/Falcilysin), the GPI-anchored protein P113, the pore-forming like protein SPECT2, or a variant thereof, and a polypeptidic derivative of any of these antigenic polypeptides wherein said polypeptidic derivative keeps protective properties of the antigen from which it derives in the combination of compounds of the invention.

The invention also concerns the active ingredients in admixture in a single composition. Said ingredients whether they are provided for administration as polypeptides (native, recombinant or synthetic), as polynucleotides such as RNA and DNA molecules (modified or not), or as vectors, in particular viral vectors, especially lentiviral vectors capable of expressing said antigenic polypeptides are described as distinct "active ingredients" which means according to the invention, that they individually elicit the immune response against the parasite or that they modulate and in particular broaden and/or enhance qualitatively or quantitatively the immune response which is raised in the host by other antigenic polypeptides in particular by the chimeric antigenic polypeptide provided by or expressed from the combination or the composition of compounds and hence have their own activity or effect on the qualitative and/or quantitative immune response elicited by the combination or composition, in such a way that the combination or composition of compounds elicits a protective response against a *Plasmodium* infection or against the parasite-induced condition or disease. In addition to being distinct active ingredients, the antigenic polypeptides defined herein are collectively an active ingredient suitable to elicit a protective immune response against a *Plasmodium* infection or against the parasite-induced condition or disease. The expression "vector relates to biological or chemical entities suitable for the delivery of the polynucleotides encoding the antigenic polypeptides of the combination of compounds to the cells of the host administered with such vectors. Vectors are well known in the art and may be viral vectors such as adenovirus vectors, especially a vector prepared using Chimpanzee Adenovirus, vector based on pox virus such as MVA-based vectors, canarypox-based vectors, vaccinia-based vectors obtained using modified vaccinia virus, vectors based on Herpes virus such as CMV-based vectors, vesiculovirus-based vectors, measles virus, flavivirus-based vectors or Yellow Fever virus. Vectors obtained from these viruses are disclosed in the art in a way that would enable the person skilled in the art to prepare them. Alternatively and preferably lentivirus vectors are suitable for the preparation of the active ingredients, combination or composition of compounds of the invention, in particular vectors obtained using lentiviruses which infect human, or depending on the host concerned by the protection sought, lentiviruses that infect animals. Examples of such lentivivuses are disclosed herein and the invention relates in particular to the use of HIV vectors, especially HIV-1 vectors. Details for the construction for HIV-1 vectors are provided herein and each disclosed embodiment in this regard is intended to be provided for application with each embodiment relating to the disclosure of the antigenic polypeptides, in particular the chimeric antigenic polypeptides of the invention.

The expressions "*Plasmodium* parasite" and "malaria parasite" are used interchangeably in the present application. They designate every and all forms of the parasite that are associated with the various stages of the parasite cycle in the mammalian, especially human host, including in particular sporozoites, especially sporozoites inoculated in the host skin and present in the blood flow after inoculation, or sporozoites developing in the hepatocytes (liver-stages), merozoites, including especially merozoites produced in the hepatocytes and merozoites produced in the red-blood cells, or merozoites developing in the red-blood cells (blood-stages). These various forms of the parasite are characterized by multiple specific antigens many of which are well known and identified in the art and some of which are still unknown and to which no biological function has yet been assigned. The antigens can often be designated or classified in groups by reference to their expression according to the stage of the infection. *Plasmodium* parasites according to the present disclosure encompass parasites infecting human hosts and parasites infecting non-human mammals especially rodents and in particular mice. Accordingly, *Plasmodium falciparum, Plasmodium vivax, Plasmodium yoelii* and *Plasmodium berghei* are particular examples of these parasites. *Plasmodium cynomolgi* and *Plasmodium knowlesi* are primarily infectious for macaques, but can also cause human infection. By the expression "antigenic polypeptide", it is intended according to the present invention a polypeptide which is a chimeric antigenic polypeptide and may be a fusion of native antigens or antigenic fragments thereof of a *Plasmodium* parasite, or expression product of a gene, codon-optimized or not, of a *Plasmodium* parasite, in particular of *P. berghei, P. cynomolgi* or of a *Plasmodium* parasite infecting humans such as *P. falciparum* or *P. vivax*. The application also relates to modified version of such antigenic polypeptides designated as "polypeptidic derivative thereof" used in the chimeric antigenic polypeptide which derivatives can be a fragment of the native antigen of the parasite and especially a truncated version of such native antigen or a fragment obtained by deletion of 1 to 15, in particular 1 to 10 or 1 to 3 amino acid residues of the native antigen (or otherwise designated “original antigen”) or a modified version thereof as a result of post-translational modifications. A derivative polypeptide has an amino acid sequence which is sufficient to provide one or several epitope(s) in particular T cell epitopes and more particularly CD8+ T cell epitopes and which keeps the protective properties leading to the protective activity of the antigenic polypeptide from which it derives and/or exhibits such protective properties when encompassed in the combination or in the composition of compounds of the invention. The protective properties of the reference antigen may even be improved with the derivative. Various examples of derivatives of the antigenic disclosed herein are illustrated in the examples. It may accordingly have a length of at least about 4 amino acid for B epitopes or at least about 8 amino acid residues and in particular from about 8 to about 19 amino acid residues for sequential T epitopes. In a particular embodiment, the recombinant polynucleotide of the lentiviral vector encodes a fragment of an antigen of the malaria parasite, especially a fragment which results from the deletion of contiguous amino acid residues of the full-length (i.e., native) antigen, such as deletion at the junction of the fusion partners for the chimeric antigenic polypeptide provided it keeps the capacity of the native antigen to elicit an immune response in a host. The polypeptidic derivative as defined hereabove should be considered an alternative for the preparation of the chimeric antigenic polypeptide in any definitions or embodiments of the invention unless it appears irrelevant in the context of the disclosure.

The expressions “T-epitope” and “B-epitope” refer to antigenic determinants that are involved respectively in the adaptive immune response driven by T cells and in the immune response driven by B cells. In particular said T-epitopes and respectively B-epitopes elicit T cell, respectively B cell immune response when delivered to the host in suitable conditions. According to a particular embodiment the antigenic polypeptides targeted according to the invention and the polypeptide derivatives of these antigenic polypeptides comprise epitope(s) mediating $CD8^+$ T cell response. In a particular embodiment, alternatively or cumulatively, the antigenic polypeptides of the invention and the polypeptide derivatives of these antigenic polypeptides comprise epitope(s) mediating an antibody response. In a preferred embodiment, the chimeric antigenic polypeptide, the combination or the composition of compounds all together comprise or enable expression of T and B epitopes and therefore elicit both cellular and humoral immune response in a host.

In a particular embodiment of the invention, the combination or the composition of compounds comprises, at least one, preferably at least two antigenic polypeptide(s) including at least one chimeric antigenic polypeptide or when provided as a polynucleotide or as a recombinant vector, especially lentiviral vector the combination or the composition of compounds comprises at least one, preferably at least two recombinant polynucleotide(s) which encodes an antigenic polypeptide(s) wherein said antigenic polypeptide(s) is chimeric antigenic polypeptide or encompasses the latter together with the circumsporozoite protein (CSP) (if not present in the chimeric antigenic polypeptide) of a *Plasmodium* parasite selected from the group of *Plasmodium falciparum, Plasmodium malariae, Plasmodium vivax, Plasmodium ovale* or *Plasmodium knowlesi* and *Plasmodium berghei*, in particular the group of *Plasmodium falciparum* and *Plasmodium vivax*. It is especially a truncated version of the CSP and in particular a polypeptide devoid of the GPI anchoring motif of the CSP. In such combination or composition of compounds, additional polypeptide(s) or polynucleotide(s) may be contained in the viral, especially lentiviral vector(s) and they are also selected in the above disclosed groups of *Plasmodium* parasites.

In a particular embodiment of the active ingredient, the combination or the composition of compounds of the invention are provided as polynucleotides or as vectors, In particular lentiviral vectors expressing antigenic polypeptides are provided wherein the vectors have or comprise in their genome (vector genome) a recombinant polynucleotide which encodes at least a chimeric antigenic polypeptide of *Plasmodium berghei* as illustrated in the examples or advantageously an orthologous sequence of *Plasmodium falciparum*, or *Plasmodium vivax* as disclosed or illustrated herein e.g., a polypeptide corresponding to a fragment of said antigen In a particular embodiment of the invention, the active ingredient, the combination or the composition of compounds comprises or consists in separate active ingredients or separate compositions of single or of multiple active ingredients. These active ingredients provided as separate compositions or packages in the combination may be used for separate administration to the host or to the contrary for combined administration.

In another particular embodiment of the invention, the combination of compounds comprises or consists in an admixture of all the active ingredients, otherwise stated consists in a single composition of said active ingredient(s).

Accordingly chimeric antigenic polypeptides of the invention may especially be provided as the expression product of a vector, in particular of lentiviral vectors, in particular HIV-1 based vectors, wherein each vector expresses the chimeric antigenic polypeptide. This type of vector may be used alone or may be provided with additional identical or different vectors that express further antigenic polypeptide(s) of *Plasmodium* parasite, in particular of the same *Plasmodium* parasite. Thus a collection of vectors may be provided that expresses all the antigenic polypeptides suitable to elicit an immune response when administered in a host in need thereof. This collection of vectors may be provided as a single composition for administration or as separate compositions for administration to the host simultaneously or separately in time.

In another embodiment, the active ingredients are or comprise nucleic acid, in particular DNA or RNA that encodes the chimeric antigenic polypeptides of the invention.

When used as such, the chimeric antigenic polypeptide or their coding nucleic acid, advantageously provided in a vector such as a lentiviral vector as disclosed herein, or alternatively when used together in a combination or composition these antigenic polypeptides, nucleic acids or vectors consisting of the chimeric antigenic polypeptide of the invention or their coding nucleic acid (especially when provided as vectors expressing the same)=constitute active ingredients that may be regarded as suitable for the elicitation of a protective immune response, preferably a sterile protection against stringent challenge of immunized non-human mammal with *Plasmodium* parasite from which the polypeptides originate. Accordingly the compounds of the invention provide a response to the need for efficient alternative against *Plasmodium* infection by devising active ingredients which may be used for the elaboration of a vaccine candidate in human host.

Whatever its presentation as one or more compositions, the combination or the composition of compounds of the invention provides individual and collective active ingredients (as antigenic polypeptides or as vector particles especially lentiviral vector particles) which constitute collectively the qualitative composition for a dose of a candidate medicine product.

In a particular embodiment of the combination of compounds or composition of the invention, the active ingredients consist of chimeric antigenic polypeptides of a human-infecting *Plasmodium* parasite or consist of nucleic acids or of lentiviral vector(s) expressing antigenic polypeptides of a human-infecting *Plasmodium* parasite, or consist in a mixture or an association of such chimeric antigenic polypeptides with additional antigenic polypeptides of the *Plasmodium* parasite or nucleic acids or viral vectors expressing the chimeric antigenic polypeptides and possibly additional antigenic polypeptides, especially lentiviral vectors, in particular wherein the *Plasmodium* parasite is *Plasmodium falciparum* or *Plasmodium vivax*.

Specific polypeptidic derivatives disclosed for use according to the invention are in particular obtained by substitution of amino acid residues in the original sequence of the *Plasmodium* antigen and/or by point mutations (such as substitution, insertion or deletion) or deletion(s) of short sequence(s) in said original sequence, to the extent that the derived polypeptide keeps essentially the immunogenic properties of the polypeptide from which it derives. Derivatives can thus be illustrated by the polypeptides including in their sequence residues originating from the polynucleotide construct from which they are obtained such as amino acid residues resulting from the presence of a Kozak sequence in the polynucleotide. Other derivatives may be obtained by conservative substitution of amino acid residue(s), especially amino acid substitution of less than 20% in particular less than 15% or less than 5%, in particular less than 3% or less than 2% of the original amino acid residues of the sequence of the antigen. Without considering the optional addition of functional amino acid sequence(s) to the natural or mutated ORF (Open Reading Frame) of the antigenic polypeptide, such derivatives obtained by substitution, in particular conservative substitutions of amino acid residues, have in particular the same length as the original sequence from which they derive. Alternatively, when the derivative polypeptide has an ORF which consists in a mutant by deletion or by addition with respect to the original ORF, the length of the mutated ORF determined in respect of the number of amino acid residues in the expressed polypeptide derivative is advantageously at least 95% of the length of the original sequence, preferably at least 97%; 98% or 99% identical to the original sequence.

In a particular embodiment of the active ingredients comprise or consist of human lentiviral vector(s) expressing the chimeric antigenic polypeptides including, in a particular embodiment, when obtained using polypeptidic derivatives of *Plasmodium* antigens, in particular HIV-1 lentiviral vector(s). In a particular embodiment these human vector(s) expressing the chimeric antigenic polypeptides further express additional antigenic polypeptides of *Plasmodium* parasite and such vectors are expressed:

- either individually from separate vectors and/or,
- from one or more vectors wherein at least one vector expresses more than one antigenic polypeptide, including the chimeric antigenic polypeptide.

In a particular embodiment wherein the active ingredients are lentiviral vectors, especially HIV-1 based vectors, each lentiviral vector is a replication-incompetent pseudotyped lentiviral vector, in particular a replication-incompetent pseudotyped HIV-1 lentiviral vector, wherein said vector contains a genome comprising a mammal codon-optimized synthetic nucleic acid, in particular a human-codon optimized synthetic nucleic acid, wherein said synthetic nucleic acid encodes the antigenic polypeptide(s) of a *Plasmodium* parasite infecting a mammal, in particular a human host, or a polypeptidic derivative thereof. The malaria parasite may be in particular *Plasmodium falciparum, Plasmodium vivax, P. knowlesi, P. cynomolgi, P. malariae, P. ovale.*

Use of codon-optimized sequences in the genome of the vector particles allows in particular strong expression of the antigenic polypeptide in the cells of the host administered with the vector, especially by improving mRNA stability or reducing secondary structures. In addition the expressed antigenic polypeptide undergoes post translational modifications which are suitable for processing of the antigenic polypeptide in the cells of the host, in particular by modifying translation modification sites (such as glycosylation sites) in the encoded polypeptide. Codon optimization tools are well known in the art, including algorithms and services such as those made available by GeneArt (Life technologies-USA) and DNA2.0 (Menlo Park, California—USA). In a particular embodiment codon-optimization is carried out on the ORF sequence encoding the antigenic polypeptide or its derivative and the optimization is carried out prior to the introduction of the sequence encoding the ORF into the plasmid intended for the preparation of the vector genome. In another embodiment additional sequences of the vector genome are also codon-optimized.

The active ingredients consisting of the viral vectors may be integrative pseudotyped lentiviral vectors, especially replication-incompetent integrative pseudotyped lentiviral vectors, in particular a HIV-1 vector. Such lentiviral vectors may in addition contain a genome comprising a mammal-codon optimized synthetic nucleic acid, in particular a human-codon optimized synthetic nucleic acid, wherein said synthetic nucleic acid encodes the antigenic polypeptide(s) of a *Plasmodium* parasite infecting a mammal such as disclosed herein, in particular a parasite infecting a human host, or a polypeptidic derivative thereof as disclosed herein.

Alternatively the lentiviral vector and in particular the HIV-1 based vector may be a non-integrative replication-incompetent pseudotyped lentiviral vector.

A particular embodiment of a lentiviral vector suitable to achieve the invention relates to a lentiviral vector whose genome is obtained from the pTRIP vector plasmid wherein the *Plasmodium* synthetic nucleic acid encoding the antigenic polypeptide or polypeptidic derivative thereof has been cloned under control of a promoter functional in mammalian cells, in particular the human beta-2 microglobulin promoter, and wherein the vector optionally comprises post-transcriptional regulatory element of the woodchuck hepatitis virus (WPRE).

In a further embodiment of the invention, the lentiviral vector expressing the chimeric antigenic polypeptide(s) according to the features herein described is pseudotyped with the glycoprotein G from a Vesicular Stomatitis Virus (V-SVG) of Indiana or of New-Jersey serotype.

The particular features of such lentiviral vectors will be further discussed in detail below.

The chimeric antigenic polypeptides of the invention may advantageously be expressed from nucleic acid molecules characterized by the following sequences, and in particular are expressed from mammalian codon-optimized synthetic nucleic acids: SEQ ID No. 115, SEQ ID No.117, SEQ ID No. 119, SEQ ID No. 121.

Codon optimization of the polynucleotide may influence post translational modifications of the encoded polypeptide, in particular when it is expressed in mammalian cells and therefore enables the expression of polypeptides which harbor structural features which distinguish over those of the polypeptide encoded by the corresponding non-optimized sequence (Mauro V. P. and Chappell S. A. Trends Mol Med-2014 November; 20(11): 604-613).

Similarly the lentiviral vectors expressing the antigenic polypeptides in the combination of compounds may advantageously contain in their genome nucleic acid molecules which are mammalian codon-optimized synthetic nucleic acids characterized by the following sequences: SEQ ID No. 115, SEQ ID No.117, SEQ ID No. 119, SEQ ID No. 121. Additionally the nucleic acid of the invention may be a polynucleotide comprising one of the following DNA sequences: SEQ ID No. 115, SEQ ID No.117, SEQ ID No. 119, SEQ ID No. 121 or with a RNA sequence deducted from such DNA sequence. The invention also relates to a formulation suitable for administration to a mammalian host comprising an active ingredient as defined herein or a combination or a composition of compounds according to any one of the definitions provided herein, as active ingredient for protection against a *Plasmodium* infection or against the parasite-induced condition or disease, together with excipient(s) suitable for administration to a host in need thereof, in particular a human host.

In another aspect of the invention the active ingredient or the combination or the composition of compounds of the invention or the formulation comprising the same is for use in the protective immunisation against malaria parasite infection or against parasite-induced condition or disease, in a mammalian host, especially a human host, optionally in association with an appropriate delivery vehicle and optionally with an adjuvant component and/or with an immunostimulant component.

Accordingly, the active ingredient, the combination or the composition of compounds, in particular the lentiviral vector particles of the invention, when administered to a host in needs thereof, especially to a mammalian in particular to a human host, elicits an immune response, encompassing activation of naïve lymphocytes and generation of effector T-cell response and generation of immune memory antigen-specific T-cell response against antigen(s) of the malaria parasite. The immune response may additionally involve a humoral response against antigenic polypeptides delivered to or expressed in the host following administration of the combination of compounds. The immune response may either prevent the infection by the malaria parasite when such parasite is inoculated as sporozoite to the host or may prevent the onset or the development of a pathological state resulting from inoculation of malaria parasite in the form of sporozoite or prevent the onset or the development of the consequences of the generation of further forms of said parasite such a merozoite forms.

Accordingly, the active ingredients, the combination or the composition of compounds of the invention are suitable for the elicitation of a protective immune response against the parasite infection or against the parasite-induced disease or condition. Such response enables in particular, control or inhibition of the onset of the pathology caused by inoculation of the parasite or by the induction of the exo-erythrocytic i.e., hepatic, stage of the cycle of the malaria parasite and in an advantageous embodiment this response is suitable to prevent, alleviate or inhibit the onset or development of the erythrocytic stage of said parasite. Advantageously, it has been observed that the active ingredient, the combination or the composition of compounds of the invention especially when the active ingredients are provided as lentiviral vector particles used in a single administration regimen or in a prime-boost regimen of administration enable the development of a protective immunity and especially enable a sterilizing protection against the malaria parasite-induced pathology. Such a sterilizing protection may result from controlling the consequences of the infection at the stage of liver infection, if not before, in the cycle of the parasite.

In a particular embodiment of the invention, the active ingredient, the combination or the composition of compounds, especially when the active ingredients are provided as lentiviral vector(s) is a suspension formulated with a suitable administration vehicle for administration to the host. Physiologically acceptable vehicles may be chosen with respect to the administration route of the immunization composition. In a preferred embodiment administration may be carried out by injection, in particular intramuscularly or, for children by intranasal administration or topical skin application. An active ingredient, a combination or a composition of compounds of the invention is used for protective immunisation against malaria parasite infection or against parasite-induced disease or condition in a mammalian host, especially in a human host, said use involving an immunisation pattern comprising administering an effective amount of the active ingredients to elicit the cellular and/or humoral immune response of the host, possibly as a prime and where appropriate later in time administering an effective amount of said active ingredients to boost the cellular immune response of the host, and optionally repeating (once or several times) said administration step for boosting, wherein if the active ingredients are provided as the lentiviral particles administered in each of the priming or boosting steps they are pseudotyped with distinct pseudotyping envelope protein(s) which do not cross-neutralise with each other, and wherein said priming and boosting steps are separated in time by at least 6 weeks, in particular by at least 8 weeks.

Details on the administration regimen will be discussed further below.

The active ingredient, the combination of the composition of compounds of the invention especially as lentiviral vector is especially used in a particular embodiment for the protective immunization against malaria parasite infection or against parasite-induced pathology in mammalian, host, especially in a human host to obtain at least a cellular immune response (T-cell immune response), particularly a CD8-mediated cellular immune response or a CD4-mediated cellular immune response i.e., an immune response which is mediated by activated cells harbouring CD8 or CD4 receptors, preferably Cytotoxic T lymphocytes (CTL) and memory T cell response are advantageously targeted when defining the immunization regimen of the lentiviral particles of the invention.

The immune response can also involve a humoral response i.e., antibodies, elicited by said compounds, produced against said at least one antigenic polypeptide. In a particular embodiment, said humoral response is a protective humoral response. The protective humoral response results mainly in maturated antibodies, having a high affinity for their antigen, such as IgG or IgM. In a particular aspect, the protective humoral response is T-cell dependent. In a particular embodiment, the protective humoral response induces the production of neutralizing antibodies.

In a particular embodiment of the invention, the active ingredient, the combination or the composition of compounds of the invention especially when the active ingredients are lentiviral vectors, even when used in a form which has defective integrase, is able to elicit an early immune response. The expression "early immune response" refers to a protective immune response (protection against the parasite or against the parasite-induced pathology) that is conferred within about one week after the administration of the product.

In another particularly advantageous embodiment, the immune response conferred by the active ingredient, the combination or the composition of compounds of the invention especially as lentiviral particles is a long-lasting immune response i.e., said immune response encompasses memory cells response and in particular central memory cells response; in a particular embodiment it can be still detected at least several months.

When the immune response includes a humoral response, the long-lasting response can be shown by the detection of specific antibodies, by any suitable methods such as ELISA, immunofluorescence (IFA), focus reduction neutralization tests (FRNT), immunoprecipitation, or Western blotting.

According to a particular aspect of the use of the active ingredient, the combination or the composition of compounds of the invention, the active ingredients are designed to enable performing a prime-boost administration in a host in need thereof, where the first administration step elicits an immune, especially cellular, immune response and the later administration step(s) boost(s) the immune reaction including the cellular immune response. For each step of administration, it is preferred that the pseudotyping envelope protein(s) of the vector particles is(are) different from the one used in the other step(s), especially originate from different viruses, in particular different VSVs. In the prime-boost regimen, the administered combination of compounds of each step comprises lentiviral vectors as defined herein which collectively express all the antigenic polypeptides. Accordingly, active ingredients, combinations or compositions of compounds may be provided to perform the prime-boost regimen which comprise compounds that are distinct lentiviral particles at least due to the difference in their pseudotyping envelope proteins.

Accordingly, when a prime-boost regimen is selected, active ingredients, combinations or compositions of compounds containing said lentiviral vectors can be provided in separate packages or can be presented in a common package for a separate use thereof.

Therefore, the notice included in the packages and comprising the directions for use, may indicate the sequence order for the administration of the active ingredients, combinations or compositions of compounds and the time slot for their administration, for priming and subsequently boosting an immune reaction in a host.

In accordance with the invention when the active ingredients, combination or compositions of compounds are used in a prime-boost regimen, a first active ingredient/combination or composition of compounds is provided which contains lentiviral vector particles pseudotyped with a first determined pseudotyping envelope G protein obtained from the VSV, strain New-Jersey, and a second active ingredient/combination or composition of compounds is provided which contains lentiviral viral vector particles pseudotyped with a second determined pseudotyping envelope G protein obtained from a VSV, strain Indiana. The order of use in the prime-boost regimen of the first and second compounds thus described may alternatively be inversed. Thus, the lentiviral vector particles contained in the separate active ingredients/compounds of the combinations or compositions of the invention when intended for use in a prime-boost regiment are distinct from each other, at least due to the particular pseudotyping envelope protein(s) used for pseudotyping the vector particles.

In the examples which follow where mice models have been treated according to the prime-boost regimen with lentiviral vector particles of the invention, It has been shown by the inventors that mice immunized according to such a regimen and challenged after the last immunization step exhibit a sterile protection for a significant proportion of the vaccinated mice (more than 80%) which illustrates that the compounds of the invention elicit an effective protection in a host, and would therefore constitute a suitable candidate vaccine for immunization especially in a human host.

The invention relates, in a particular embodiment, to the active ingredients/combination or composition of compounds of the invention especially as lentiviral vector particles as defined herein, for the protective immunization against malaria parasite infection or against parasite-induced pathology in a mammalian host, especially in a human host, in a dosage regimen comprising separately provided active ingredients wherein the dose of the active ingredients intended for priming and boosting the cellular immune response is a moderate dose and the dose intended for boosting the cellular immune response is higher than the dose for priming.

Accordingly, the dose of lentiviral vectors intended for priming and boosting the cellular immune response which is used in the administration pattern, comprises from $10^5$ TU to $10^{10}$ TU of each type of viral particles especially from $10^5$ to $10^7$, when integrative vectors are used. The dose intended for priming and boosting comprises from $10^7$ to $10^{10}$ of each type of lentiviral particles when integrative-incompetent vectors are used. The invention also concerns the use of the combination of compounds of the invention especially as lentiviral vector according to the definitions given herein, for the manufacture of an immunogenic active ingredients or composition for prophylactic immunisation against malaria parasite infection or against parasite-induced pathology in a mammalian host, especially in a human host.

The invention also concerns a method of providing immunization in a mammalian host, especially in a human host, comprising the step of administering the active ingredients or the combination or composition of compounds of the invention especially as lentiviral vectors of the invention to elicit the immune response, and optionally repeating the administration steps one or several times, to boost said response, in accordance with the present disclosure.

In a particular embodiment of the invention, the active ingredient, the combination or the composition of compounds especially provided as lentiviral vector(s) may be used in association with an adjuvant compound suitable for administration to a mammalian, especially a human host, and/or with an immunostimulant compound, together with an appropriate delivery vehicle.

The active ingredients, combination or composition of compounds quoted above can be injected in a host via different routes: subcutaneous (s.c.), intradermal (i.d.), intramuscular (i.m.) or intravenous (i.v.) injection, oral administration and mucosal or skin administration, especially intranasal administration or inhalation. The quantity to be administered (dosage) depends on the subject to be treated, including considering the condition of the patient, the state of the individual's immune system, the route of administration and the size of the host. Suitable dosages range expressed with respect to the content in equivalent transducing units of vector particles (for HIV-1 lentiviral vectors) can be determined.

Other examples and features of the invention will be apparent when reading the examples and the figures which illustrate the preparation and application of the lentiviral vector particles with features that may be individually combined with the definitions given in the present description.

Detailed Description of the Lentiviral Vectors for Use According to the Invention The invention accordingly involves lentiviral vector which are lentiviral particles (i.e. vector particles), and which may be replication-incompetent lentiviral vectors, especially replication-incompetent HIV-1 based vectors characterized in that (i) they are pseudotyped with a determined heterologous viral envelope protein or viral envelope proteins originating from a RNA virus which is not HIV and (ii) they comprise in their genome at least one recombinant polynucleotide encoding at least one antigenic polypeptide (or polypeptide derivative thereof) carrying epitope(s) of a pre-erythrocytic stage antigen of a *Plasmodium* parasite or a polypeptidic derivative thereof wherein the parasite is capable of infecting a mammalian host, and wherein said epitope(s) encompass(es) T-epitope(s).

In a particular embodiment of the invention, the encoded chimeric antigenic polypeptide of pre-erythrocytic stage antigens of a *Plasmodium* parasite further comprises B-epitope(s).

The chimeric antigenic polypeptides or derivatives thereof expressed by the vectors are those disclosed herein in any aspects of the invention, in particular in the description of the combination of compounds of the invention.

According to a particular embodiment of the invention, the lentiviral vectors are either designed to express proficient (i.e., integrative-competent) or deficient (i.e., integrative-incompetent) particles.

The preparation of the lentiviral vectors is well known from the skilled person and has been extensively disclosed in the literature (confer for review Sakuma T. et al (Biochem. J. (2012) 443, 603-618). The preparation of such vectors is also illustrated herein in the Examples.

In a particular embodiment of the invention, the polynucleotide(s) encoding the antigenic polypeptides (ORF) of the lentiviral vector has(have) been mammal-codon optimized (CO) in particular human-codon optimized. Optionally the lentiviral sequences of the genome of said particles have also a mammal-codon optimized nucleotide sequence. In a particular aspect of the invention the codon optimization has been carried out for expression in mouse cells. In another embodiment the sequence the polynucleotide(s) encoding the antigenic polypeptides of the lentiviral vector has(have) been human-codon optimized (CO).

It has been observed that codon optimized nucleotide sequences, especially when optimized for expression in mammalian and in particular in human cells, enable the production of higher yield of particles in such mammalian or human cells. Production cells are illustrated in the examples. Accordingly, when lentiviral vector particles of the invention are administered to a mammalian, especially to a human host, higher amounts of particles are produced in said host which favour the elicitation of a strong immune response.

The lentiviral vector (i.e., lentiviral vectors particles or lentiviral-based vector particles) defined in the present invention are pseudotyped lentiviral vectors consisting of vector particles bearing envelope protein or envelope proteins which originate from a virus different from the particular lentivirus (especially a virus different from HIV, in particular HIV-1), which provides the vector genome of the lentiviral vector particles. Accordingly, said envelope protein or envelope proteins, are "heterologous" viral envelope protein or viral envelope proteins with respect to the vector genome of the particles. In the following pages, reference will also be made to "envelope protein(s)" to encompass any type of envelope protein or envelope proteins suitable to perform the invention. When reference is made to "lentiviral" vectors (lentiviral-based vectors) in the application, it relates in particular, to HIV-based vectors and especially HIV-1-based vectors.

The lentiviral vectors suitable to perform the invention are so-called replacement vectors, meaning that the sequences of the original lentivirus encoding the lentiviral proteins are essentially deleted in the genome of the vector or, when present, are modified, and especially mutated, especially truncated, to prevent expression of biologically active lentiviral proteins, in particular, in the case of HIV, to prevent the expression by said transfer vector, of functional ENV, GAG, and POL proteins and optionally of further structural and/or accessory and/or regulatory proteins of the lentivirus, especially of HIV. In a particular embodiment, the lentiviral vector is a first-generation vector, in particular a first-generation of a HIV-based vector which is characterized in that it is obtained using separate plasmids to provide (i) the packaging construct, (ii) the envelope and (iii) the transfer vector genome. Alternatively it may be a second-generation vector, in particular a second-generation of a HIV-based vector which in addition, is devoid of viral accessory proteins (such as in the case of HIV-1, Vif, Vpu, Vpr or Nef) and therefore includes only four out of nine HIV full genes: gag, pol, tat and rev. In another embodiment, the vector is a third-generation vector, in particular a third-generation of a HIV-based vector which is furthermore devoid of said viral accessory proteins and also is Tat-independent; these third-generation vectors may be obtained using 4 plasmids to provide the functional elements of the vector, including one plasmid encoding the Rev protein of HIV when the vector is based on HIV-1. Such vector system comprises only three of the nine genes of HIV-1. The structure and design of such generations of HIV-based vectors is well known in the art.

The "vector genome" of the vector particles is a recombinant nucleic acid which also comprises comprises as a recombined sequence the polynucleotide or transgene of interest encoding one or more antigenic polypeptide(s) or polypeptide derivative thereof of malaria parasite as disclosed herein. The lentiviral-based sequence and polynucleotide/transgene of the vector genome are borne by a plasmid vector thus giving rise to the "transfer vector" also referred to as "sequence vector". Accordingly, these expressions are used interchangeably in the present description. According to a particular embodiment, a vector genome prepared for the invention comprises a nucleic acid having a sequence selected in the group of SEQ ID No. 10, 13, 16, 19, 22, 25, 28, 31, 34, 37, 40, 43, 46, 48, 51, 54, 57, 60, 63, 66, 69, 72, 75, 78, 81 95, 97, 99, 101, 103, 105, 107, 109, 111, 113, 115, 117, 119, 121 or 123 or comprises a plurality of these sequences encoding antigenic polypeptides or derivatives thereof. The vector genome as defined herein accordingly contains, apart from the so-called recombinant polynucleotide(s) encoding the antigenic polypeptide(s) or polypeptide derivative thereof of malaria parasite placed under control of proper regulatory sequences for its expression, the sequences of the original lentiviral genome which are non-coding regions of said genome, and are necessary to provide recognition signals for DNA or RNA synthesis and processing (mini-viral genome). These sequences are cis-acting sequences necessary for packaging (ψ), reverse transcription (LTRs possibly mutated with respect to the original ones) and transcription and optionally integration (RRE) and furthermore for the particular purpose of the invention, they contain a functional sequence favouring nuclear import in cells and accordingly transgene transfer efficiency in said cells, which element is described as a DNA Flap element that contains or consists of the so-called central cPPT-CTS nucleotidic domain present in lentiviral genome sequences especially in HIV-1 or in some retroelements such as those of yeasts.

The structure and composition of the vector genome used to prepare the lentiviral vectors of the invention are based on the principles described in the art and on examples of such lentiviral vectors primarily disclosed in (Zennou et al, 2000; Firat H. et al, 2002; VandenDriessche T. et al). Constructs of this type have been deposited at the CNCM (Institut Pasteur, France) as will be referred to herein. In this respect reference is also made to the disclosure, including to the deposited biological material, in patent applications WO 99/55892, WO 01/27300 and WO 01/27304.

According to a particular embodiment of the invention, a vector genome may be a replacement vector in which all the viral protein coding sequences between the 2 long terminal repeats (LTRs) have been replaced by the recombinant polynucleotide encoding the polypeptide of the malaria parasite, and wherein the DNA-Flap element has been re-inserted in association with the required cis-acting sequences described herein. Further features relating to the composition of the vector genome are disclosed in relation to the preparation of the particles.

In a particular embodiment of the invention one lentiviral vector encodes one antigenic polypeptide of the *Plasmodium* parasite.

In a particular embodiment, a lentiviral vector of the invention may comprise in its genome one or more than one recombinant polynucleotide encoding at least one antigenic polypeptide carrying epitope(s) of a pre-erythrocytic stage antigen as disclosed herein. In particular, said vector genome comprises two polynucleotides which are consecutive or separated on the genome and which encode different polypeptides of either the same or distinct antigens of the pre-erythrocytic stage of a *Plasmodium* parasite or different antigenic polypeptidic derivatives of distinct antigens of the parasite.

In a particular embodiment, the vector genome contains two or more recombinant polynucleotides, each of them encoding a distinct antigenic polypeptide and each polypeptide originating from a different antigen of the pre-erythrocytic stage as disclosed herein, including the CSP antigen and at least one of the Ag40 or Ag45 antigens, and optionally one or more, including all the antigenic polypeptides selected from the group of the thrombospondin related anonymous protein (TRAP), the inhibitor of cysteine protease (ICP), the metallopeptidase (Falcilysin), the GPI-anchored protein P113, the pore-forming like protein SPECT2 of the *Plasmodium* parasites disclosed herein or derivatives thereof.

The description made herein in respect to antigenic polypeptides similarly applies to polypeptidic derivatives thereof.

Particular features of the lentiviral vectors used in accordance with the various embodiments of the invention are also disclosed in the Examples, such features being either taken alone or in combination to produce the vectors.

According to the invention, the lentiviral vector particles are pseudotyped with a heterologous viral envelope protein or viral polyprotein of envelope originating from a RNA virus which is not the lentivirus providing the lentiviral sequences of the genome of the lentiviral particles.

As examples of typing envelope proteins for the preparation of the lentiviral vector, the invention relates to viral transmembrane glycosylated (so-called G proteins) envelope protein(s) of a Vesicular Stomatitis Virus (VSV), which is(are) for example chosen in the group of VSV-G protein(s) of the Indiana strain and VSV-G protein(s) of the New Jersey strain.

Other examples of VSV-G proteins that may be used to pseudotype the lentiviral vectors of the invention encompass VSV-G glycoprotein may especially be chosen among species classified in the vesiculovirus genus: Carajas virus (CJSV), Chandipura virus (CHPV), Cocal virus (COCV), Isfahan virus (ISFV), Maraba virus (MARAV), Piry virus (PIRYV), Vesicular stomatitis Alagoas virus (VSAV), Vesicular stomatitis Indiana virus (VSIV) and Vesicular stomatitis New Jersey virus (VSNJV) and/or stains provisionally classified in the vesiculovirus genus as Grass carp rhabdovirus, BeAn 157575 virus (BeAn 157575), Boteke virus (BTKV), Calchaqui virus (CQIV), Eel virus American (EVA), Gray Lodge virus (GLOV), Jurona virus (JURV), Klamath virus (KLAV), Kwatta virus (KWAV), La Joya virus (LJV), Malpais Spring virus (MSPV), Mount Elgon bat virus (MEBV), Perinet virus (PERV), Pike fry rhabdovirus (PFRV), Porton virus (PORV), Radi virus (RADIV), Spring viremia of carp virus (SVCV), Tupaia virus (TUPV), Ulcerative disease rhabdovirus (UDRV) and Yug Bogdanovac virus (YBV).

The envelope glycoprotein of the vesicular stomatitis virus (VSV-G) is a transmembrane protein that functions as the surface coat of the wild type viral particles. It is also a suitable coat protein for engineered lentiviral vectors. Presently, nine virus species are definitively classified in the VSV gender, and nineteen rhabdoviruses are provisionally classified in this gender, all showing various degrees of cross-neutralisation. When sequenced, the protein G genes indicate sequence similarities. The VSV-G protein presents a N-terminal ectodomain, a transmembrane region and a C-terminal cytoplasmic tail. It is exported to the cell surface via the transGolgi network (endoplasmic reticulum and Golgi apparatus).

Vesicular stomatitis Indiana virus (VSIV) and Vesicular stomatitis New Jersey virus (VSNJV) are preferred strains to pseudotype the lentiviral vectors of the invention, or to design recombinant envelope protein(s) to pseudotype the lentiviral vectors. Their VSV-G proteins are disclosed in GenBank, where several strains are presented. For VSV-G New Jersey strain reference is especially made to the sequence having accession number V01214. For VSV-G of the Indiana strain, reference is made to the sequence having accession number AAA48370.1 in Genbank corresponding to strain J02428.

Said viral envelope protein(s) are capable of uptake by antigen presenting cells and especially by dendritic cells including by liver dendritic cells by mean of fusion and/or of endocytosis. In a particular embodiment, the efficiency of the uptake may be used as a feature to choose the envelope of a VSV for pseudotyping. In this respect the relative titer of transduction (Titer DC/Titer of other transduced cells e.g. 293T cells) may be considered as a test and envelope having a relative good ability to fuse with DC would be preferred.

Antigen Presenting Cells (APC) and especially Dentritic cells (DC) are proper target cells for pseudotyped lentiviral vectors which are used as immune compositions accordingly.

The VSV-G envelope protein(s) are expressed from a polynucleotide containing the coding sequence for said protein(s), which polynucleotide is inserted in a plasmid (designated envelope expression plasmid or pseudotyping env plasmid) used for the preparation of the lentiviral vector particles of the invention. The polynucleotide encoding the envelope protein(s) is under the control of regulatory sequences for the transcription and/or expression of the coding sequence (including optionally post-transcriptional regulatory elements (PRE) especially a polynucleotide such as the element of the Woodchuck hepatitis virus, i.e. the WPRE sequence, obtainable from Invitrogen).

Accordingly, a nucleic acid construct is provided which comprises an internal promoter suitable for the use in mammalian cells, especially in human cells in vivo and the nucleic acid encoding the envelope protein under the control of said promoter. A plasmid containing this construct is used for transfection or for transduction of cells suitable for the preparation of vector particles. Promoters may in particular be selected for their properties as constitutive promoters, tissue-specific promoters, or inducible promoters. Examples of suitable promoters encompass the promoters of the following genes: MHC Class1 promoters, human beta-2 microglobulin gene (P2M promoter), EF1a, human PGK, PPI (preproinsulin), thiodextrin, HLA DR invariant chain (P33), HLA DR alpha chain, Ferritin L chain or Ferritin H chain, Chymosin beta 4, Chymosin beta 10, Cystatin Ribosomal Protein L41, CMVie or chimeric promoters such as GAG (CMV early enhancer/chicken β actin) disclosed in Jones S. et al (Jones S. et al Human Gene Therapy, 20:630-640 (June 2009)).

These promoters may also be used in regulatory expression sequences involved in the expression of gag-pol derived proteins from the encapsidation plasmids, and/or to express the antigenic polypeptides from the transfer vector.

Alternatively, when the envelope expression plasmid is intended for expression in stable packaging cell lines, especially for stable expression as continuously expressed viral particles, the internal promoter to express the envelope protein(s) is advantageously an inducible promoter such as one disclosed in Cockrell A. S. et al. (Mol. Biotechnol. (2007) 36:184-204). As examples of such promoters, reference is made to tetracycline and ecdysone inducible promoters. The packaging cell line may be the STAR packaging cell line (ref Cockrell A. S. et al (2007), Ikedia Y. et al (2003) Nature Biotechnol. 21: 569-572) or a SODk packaging cell line, such as SODk0 derived cell lines, including SODk1 and SODk3 (ref Cockrell A. S. et al (2007), Cockrell A; S.et al (2006) Molecular Therapy, 14: 276-284, Xu K. et al. (2001),Kafri T. et al (1999) Journal of Virol. 73:576-584).

According to the invention, the lentiviral vector are the product recovered from co-transfection of mammalian cells, with:

- a vector plasmid comprising (i) lentiviral, especially HIV-1, cis-active sequences necessary for packaging, reverse transcription, and transcription and further comprising a functional lentiviral, especially derived from HIV-1, DNA flap element and (ii) a polynucleotide encoding one or more chimeric antigenic polypeptide(s) (or polypeptide derivative thereof) of a malaria parasite as disclosed herein under the control of regulatory expression sequences, and optionally comprising sequences for integration into the genome of the host cell;
- an expression plasmid encoding a pseudotyping envelope derived from a RNA virus, said expression plasmid comprising a polynucleotide encoding an envelope protein or proteins for pseudotyping, wherein said envelope pseudotyping protein is advantageously from a VSV and is in particular a VSV-G of the Indianan strain or of the New Jersey strain and,
- an encapsidation plasmid, which either comprises lentiviral, especially HIV-1, gag-pol packaging sequences suitable for the production of integration-competent vector particles or modified gag-pol packaging sequences suitable for the production of integration-deficient vector particles.

The invention thus also concerns lentiviral vector particles as described above, which are the product recovered from a stable cell line transfected with:

- a vector plasmid comprising (i) lentiviral, especially HIV-1, cis-active sequences necessary for packaging, reverse transcription, and transcription and further comprising a functional lentiviral, especially HIV-1, DNA flap element and optionally comprising cis-active sequences necessary for integration, said vector plasmid further comprising (ii) a polynucleotide of a codon-optimized sequence for murine or for human of the gene encoding the chimeric antigenic polypeptide (or a derivative thereof) of a *Plasmodium* parasite as disclosed herein, under the control of regulatory expression sequences, especially a promoter;
- a VSV-G envelope expression plasmid comprising a polynucleotide encoding a VSV-G envelope protein in particular VSV-G of the Indiana strain or of the New Jersey strain, wherein said polynucleotide is under the control of regulating expression sequences, in particular regulatory expression sequences comprising an inducible promoter, and;
- an encapsidation plasmid, wherein the encapsidation plasmid either comprises lentiviral, especially HIV-1, gag-pol coding sequences suitable for the production of integration-competent vector particles or modified gag-pol coding sequences suitable for the production of integration-deficient vector particles, wherein said gag-pol sequences are from the same lentivirus sub-family as the DNA flap element, wherein said lentiviral gag-pol or modified gag-pol sequence is under the control of regulating expression sequences.

The stable cell lines expressing the vector particles of the invention are in particular obtained by transduction of the plasmids.

The polynucleotide encodes at least one antigenic polypeptide of a malaria parasite according to any embodiment disclosed in the present specification. In particular, it encodes a polypeptide which is a truncated mammalian, especially human, codon-optimized sequence coding for such antigenic polypeptide of *Plasmodium falciparum, Plasmodium vivax* or *Plasmodium berghei.*

In a particular embodiment, the polynucleotide encodes antigenic polypeptides of the malaria parasite in particular chimeric antigenic polypeptides as defined herein. Accordingly, the vector plasmid may comprise one or several expression cassettes for the expression of the various antigenic polypeptides or may comprise bicistronic or multicistronic expression cassettes where the polynucleotides encoding the chimeric polypeptide and optionally additional various polypeptides are separated by an IRES sequence of viral origin (Internal Ribosome Entry Site), or it may encode fusion protein(s).

The internal promoter contained the vector genome and controlling the expression of the polynucleotide encoding a chimeric antigenic polypeptide of the malaria parasite (as a transgene or in an expression cassette) and optionally additional antigens or derivatives thereof may be selected from the promoters of the following genes: MHC Class 1 promoters, such as human beta-2 microglobuline gene (P2M promoter), or EF1α, human PGK, PPI (preproinsulin), thiodextrin, HLA DR invariant chain (P33), HLA DR alpha chain, Ferritin L chain or Ferritin H chain, Chymosin beta 4, Chimosin beta 10, or Cystatin Ribosomal Protein L41 CMVie or chimeric promoters such as GAG(CMV early enhancer/chicken β actin) disclosed in Jones S. et al (2009).

A promoter among the above cited internal promoters may also be selected for the expression of the envelope protein(s) and packaging (gag-pol derived) proteins.

Alternatively, vector particles can be produced from co-transfection of the plasmids disclosed herein, in stable packaging cell lines which thus become capable of continuously secreting vector particles. Promoters used in the regulatory expression sequences involved for the expression of the envelope protein(s) are advantageously inducible promoters.

The following particular embodiments may be carried out when preparing the lentiviral vector based on human lentivirus, and especially based on HIV-1 virus.

According to the invention, the genome of the lentiviral vector is derived from a human lentivirus, especially from the HIV lentivirus. In particular, the pseudotyped lentiviral vector is an HIV-based vector, such as an HIV-1, or HIV-2 based vector, in particular is derived from HIV-1M, for example from the BRU or LAI isolates. Alternatively, the lentiviral vector providing the necessary sequences for the vector genome may be originating from lentiviruses such as EIAV, CAEV, VISNA, FIV, BIV, SIV, HIV-2, HIV-O which are capable of transducing mammalian cells.

As stated above, when considering it apart from the recombinant polynucleotide that it finally contains, the vector genome is a replacement vector in which the nucleic acid between the 2 long terminal repeats (LTRs) in the original lentivirus genome have been restricted to cis-acting sequences for DNA or RNA synthesis and processing, including for the efficient delivery of the transgene to the nuclear of cells in the host, or at least are deleted or mutated for essential nucleic acid segments that would enable the expression of lentiviral structure proteins including biological functional GAG polyprotein and possibly POL and ENV proteins.

In a particular embodiment, the 5' LTR and 3' LTR sequences of the lentivirus are used in the vector genome, but the 3'-LTR at least is modified with respect to the 3'LTR of the original lentivirus at least in the U3 region which for example can be deleted or partially deleted for the enhancer. The 5'LTR may also be modified, especially in its promoter region where for example a Tat-independent promoter may be substituted for the U3 endogenous promoter.

In a particular embodiment the vector genome comprises one or several of the coding sequences for Vif-, Vpr, Vpu- and Nef-accessory genes (for HIV-1 lentiviral vectors). Alternatively, these sequences can be deleted independently or each other or can be non-functional (second-generation lentiviral vector).

The vector genome of the lentiviral vector particles comprises, as an inserted cis-acting fragment, at least one polynucleotide consisting in the DNA flap element or containing such DNA flap element. In a particular embodiment, the DNA flap is inserted upstream of the polynucleotide encoding the chimeric antigenic polypeptide of *Plasmodium* parasite, and similarly upstream of the polynucleotide encoding additional antigenic polypeptide of *Plasmodium* parasite if any and is advantageously—although not necessarily—located in an approximate central position in the vector genome. A DNA flap suitable for the invention may be obtained from a retrovirus, especially from a lentivirus, in particular a human lentivirus especially a HIV-1 retrovirus, or from a retrovirus-like organism such as retrotransposon. It may be alternatively obtained from the CAEV (Caprine Arthritis Encephalitis Virus) virus, the EIAV (Equine Infectious Anaemia Virus) virus, the VISNA virus, the SIV (Simian Immunodeficiency Virus) virus or the FIV (Feline Immunodeficiency Virus) virus. The DNA flap may be either prepared synthetically (chemical synthesis) or by amplification of the DNA providing the DNA Flap from the appropriate source as defined above such as by Polymerase chain reaction (PCR). In a more preferred embodiment, the DNA flap is obtained from an HIV retrovirus, for example HIV-1 or HIV-2 virus including any isolate of these two types.

The DNA flap (also designated cPPT/CTS) (defined in Zennou V. et al. ref 27, 2000, Cell vol 101, 173-185 or in WO 99/55892 and WO 01/27304), is a structure which is central in the genome of some lentiviruses especially in HIV, where it gives rise to a 3-stranded DNA structure normally synthesized during especially HIV reverse transcription and which acts as a cis-determinant of HIV genome nuclear import. The DNA flap enables a central strand displacement event controlled in cis by the central polypurine tract (cPPT) and the central termination sequence (CTS) during reverse transcription. When inserted in lentiviral-derived vectors, the polynucleotide enabling the DNA flap to be produced during reverse-transcription, stimulates gene transfer efficiency and complements the level of nuclear import to wild-type levels (Zennou et al., Cell, 2000 Cell vol 101, 173-185 or in WO 99/55892 and WO 01/27304).

Sequences of DNA flaps have been disclosed in the prior art, especially in the above cited patent applications. These sequences are also disclosed in the sequence of SEQ ID No1 from position 2056 to position 2179. They are preferably inserted as a fragment, optionally with additional flanking sequences, in the vector genome, in a position which is preferably near the centre of said vector genome. Alternatively they may be inserted immediately upstream from the promoter controlling the expression of the polynucleotide(s) encoding the antigenic polypeptide. Said fragments comprising the DNA flap, inserted in the vector genome may have a sequence of about 80 to about 200 bp, depending on its origin and preparation.

According to a particular embodiment, a DNA flap has a nucleotide sequence of about 90 to about 140 nucleotides.

In HIV-1, the DNA flap is a stable 99-nucleotide-long plus strand overlap. When used in the genome vector of the lentiviral vector of the invention, it may be inserted as a longer sequence, especially when it is prepared as a PCR fragment. A particular appropriate polynucleotide comprising the structure providing the DNA flap is a 124-base pair polymerase chain reaction (PCR) fragment encompassing the cPPT and CTS regions of the HIV-1 DNA (as disclosed in SEQ ID N No. 1).

It is specified that the DNA flap used in the genome vector and the polynucleotides of the encapsidation plasmid encoding the GAG and POL polyproteins should originate from the same lentivirus sub-family or from the same retrovirus-like organism.

Preferably, the other cis-activating sequences of the genome vector also originate from the same lentivirus or retrovirus-like organism, as the one providing the DNA flap.

The vector genome may further comprise one or several unique restriction site(s) for cloning the recombinant polynucleotide.

In a preferred embodiment, in said vector genome, the 3' LTR sequence of the lentiviral vector genome is devoid of at least the activator (enhancer) and possibly the promoter of the U3 region. In another particular embodiment, the 3' LTR region is devoid of the U3 region (delta U3). In this respect, reference is made to the description in WO 01/27300 and WO 01/27304.

In a particular embodiment, in the vector genome, the U3 region of the LTR 5' is replaced by a non lentiviral U3 or by a promoter suitable to drive tat-independent primary transcription. In such a case, the vector is independent of tat transactivator (third generation vector).

The vector genome also comprises the psi (y) packaging signal. The packaging signal is derived from the N-terminal fragment of the gag ORF. In a particular embodiment, its sequence could be modified by frameshift mutation(s) in order to prevent any interference of a possible transcription/translation of gag peptide, with that of the transgene.

The vector genome may optionally also comprise elements selected among a splice donor site (SD), a splice acceptor site (SA) and/or a Rev-responsive element (RRE). According to a particular embodiment, the vector plasmid (or added genome vector) comprises the following cis-acting sequences for a transgenic expression cassette:

1. The LTR sequence (Long-Terminal Repeat), required for reverse transcription, the sequences required for transcription and including optionally sequences for viral DNA integration. The 3' LTR is deleted in the U3 region at least for the promoter to provide SIN vectors (Self-inactivating), without perturbing the functions necessary for gene transfer, for two major reasons: first, to avoid trans-activation of a host gene, once the DNA is integrated in the genome and secondly to allow self-inactivation of the viral cis-sequences after retrotranscription. Optionally, the tat-dependent U3 sequence from the 5'-LTR which drives transcription of the genome is replaced by a non endogenous promoter sequence. Thus, in target cells only sequences from the internal promoter will be transcribed (transgene).
2. The ψ region, necessary for viral RNA encapsidation.
3. The RRE sequence (REV Responsive Element) allowing export of viral messenger RNA from the nucleus to the cytosol after binding of the Rev protein.
4. The DNA flap element (cPPT/CTS) to facilitate nuclear import.
5. Optionally post-transcriptional regulatory elements, especially elements that improve the expression of the antigenic polypeptides in dendritic cells, such as the WPRE cis-active sequence (Woodchuck hepatitis B virus Post-Responsive Element) also added to optimize stability of mRNA (Zufferey et al., 1999), the matrix or scaffold attachment regions (SAR and MAR sequences) such as those of the immunoglobulin-kappa gene (Park F. et al Mol Ther 2001; 4: 164-173).

The lentiviral vector of the invention is non replicative (replication-incompetent) i.e., the vector and lentiviral vector genome are regarded as suitable to alleviate concerns regarding replication competent lentiviruses and especially are not able to form new particles budding from the infected host cell after administration. This may be achieved in well known ways as the result of the absence in the lentiviral genome of the gag, pol or env genes, or their absence as "functional genes". The gag and pol genes are thus, only provided in trans. This can also be achieved by deleting other viral coding sequence(s) and/or cis-acting genetic elements needed for particles formation.

By "functional" it is meant a gene that is correctly transcribed, and/or correctly expressed. Thus, if present in the lentiviral vector genome of the invention in this embodiment contains sequences of the gag, pol, or env are individually either not transcribed or incompletely transcribed; the expression "incompletely transcribed" refers to the alteration in the transcripts gag, gag-pro or gag-pro-pol, one of these or several of these being not transcribed. Other sequences involved in lentiviral replication may also be mutated in the vector genome, in order to achieve this status. The absence of replication of the lentiviral vector should be distinguished from the replication of the lentiviral genome. Indeed, as described before, the lentiviral genome may contain an origin of replication ensuring the replication of the lentiviral vector genome without ensuring necessarily the replication of the vector particles.

In order to obtain lentiviral vectors according to the invention, the vector genome (as a vector plasmid) must be encapsidated in particles or pseudo-particles. Accordingly, lentiviral proteins, except the envelope proteins, have to be provided in trans to the vector genome in the producing system, especially in producing cells, together with the vector genome, having recourse to at least one encapsidation plasmid carrying the gag gene and either the pol lentiviral gene or an integrative-incompetent pol gene, and preferably lacking some or all of the coding sequences for Vif-, Vpr, Vpu- and Nef-accessory genes and optionally lacking Tat (for HIV-1 lentiviral vectors).

A further plasmid is used, which carries a polynucleotide encoding the envelope pseudotyping protein(s) selected for pseudotyping lentiviral vector particles.

In a preferred embodiment, the packaging plasmid encodes only the lentiviral proteins essential for viral particle synthesis. Accessory genes whose presence in the plasmid could raise safety concerns are accordingly removed. Accordingly, viral proteins brought in trans for packaging are respectively as illustrated for those originating from HIV-1:

1. GAG proteins for building of the matrix (MA, with apparent Molecular Weight p17), the capsid (CA, p24) and nucleocapsid (NC, p6).
2. POL encoded enzymes: integrase, protease and reverse transcriptase.
3. TAT and REV regulatory proteins, when TAT is necessary for the initiation of LTR-mediated transcription; TAT expression may be omitted if the U3 region of 5'LTR is substituted for a promoter driving tat-independent transcription. REV may be modified and accordingly used for example in a recombinant protein which would enable recognition of a domain replacing the RRE sequence in the vector genome, or used as a fragment enabling binding to the RRE sequence through its RBD (RNA Binding Domain).

In order to avoid any packaging of the mRNA generated from the genes contained in the packaging plasmid in the viral particles, the ψ region is removed from the packaging plasmid. A heterologous promoter is inserted in the plasmid to avoid recombination issues and a poly-A tail is added 3' from the sequences encoding the proteins. Appropriate promoters have been disclosed above.

The envelope plasmid encodes the envelope protein(s) for pseudotyping which are disclosed herein, under the control of an internal promoter, as disclosed herein.

Any or all the described plasmids for the preparation of the lentiviral vector particles of the invention may be codon optimized (CO) in the segment encoding proteins. Codon optimization according to the invention is preferably performed to improve translation of the coding sequences contained in the plasmids, in mammalian cells, murine or especially human cells. According to the invention, codon optimization is especially suited to directly or indirectly improve the preparation of the vector particles or to improve their uptake by the cells of the host to whom they are administered, or to improve the efficiency of the transfer of the polynucleotide encoding the antigenic polypeptide of the malaria parasite (transgene) in the genome of the transduced cells of the host. Methods for optimizing codons are well known in the art and codon optimization is especially performed using available programs to that effect. Codon optimization is illustrated for the coding sequences used in the examples.

In a particular embodiment of the invention, the pseudotyped lentiviral vector is also, or alternatively, integrative-competent, thus enabling the integration of the vector genome and of the recombinant polynucleotide which it contains into the genome of the transduced cells or in the cells of the host to whom it has been administered.

In another particular embodiment of the invention, the pseudotyped lentiviral vector is also, or alternatively, integrative-incompetent. In such a case, the vector genome and thus the recombinant polynucleotide which it contains do not integrate into the genome of the transduced cells or in the cells of the host to whom it has been administered.

The present invention relates to the use of a lentiviral vector wherein the expressed integrase protein is defective and which further comprises a polynucleotide especially encoding at least one antigenic polypeptide carrying epitope(s) of a pre-erythrocytic stage antigen of a *Plasmodium* parasite, in an immunogenic composition.

By "integration-incompetent", it is meant that the integrase, preferably of lentiviral origin, is devoid of the capacity of integration of the lentiviral genome into the genome of the host cells i.e., an integrase protein mutated to specifically alter its integrase activity.

Integration-incompetent lentiviral vectors are obtained by modifying the pol gene encoding the Integrase, resulting in a mutated pol gene encoding an integrative deficient integrase, said modified pol gene being contained in the encapsidation plasmid. Such integration-incompetent lentiviral vectors have been described in patent application WO 2006/010834. Accordingly the integrase capacity of the protein is altered whereas the correct expression from the encapsidation plasmid of the GAG, PRO and POL proteins and/or the formation of the capsid and hence of the vector particles, as well as other steps of the viral cycle, preceding or subsequent to the integration step, such as the reverse transcription, the nuclear import, stay intact. An integrase is said defective when the integration that it should enable is altered in a way that an integration step takes place less than 1 over 1000, preferably less than 1 over 10000, when compared to a lentiviral vector containing a corresponding wild-type integrase.

In a particular embodiment of the invention, the defective integrase results from a mutation of class 1, preferably amino acid substitutions (one-amino acid substitution) or short deletions fulfilling the requirements of the expression of a defective integrase.

The mutation is carried out within the pol gene. These vectors may carry a defective integrase with the mutation D64V in the catalytic domain of the enzyme, which specifically blocks the DNA cleaving and joining reactions of the integration step. The D64V mutation decreases integration of pseudotyped HIV-1 up to 1/10,000 of wild type, but keep their ability to transduce non dividing cells, allowing efficient transgene expression.

Other mutations in the pol gene which are suitable to affect the integrase capacity of the integrase of HIV-1 are the following: H12N, H12C, H16C, H16V, S81 R, D41A, K42A, H51A, Q53C, D55V, D64E, D64V, E69A, K71A, E85A, E87A, D116N, D1161, D116A, N120G, N1201, N120E, E152G, E152A, D-35-E, K156E, K156A, E157A, K159E, K159A, K160A, R166A, D167A, E170A, H171A, K173A, K186Q, K186T, K188T, E198A, R199C, R199T, R199A, D202A, K211A, Q214L, Q216L, Q221 L, W235F, W235E, K236S, K236A, K246A, G247W, D253A, R262A, R263A and K264H. In a particular embodiment, mutation in the pol gene is performed at either of the following positions D64, D116 or E152, or at several of these positions which are in the catalytic site of the protein. Any substitution at these positions is suitable, including those described above.

Another proposed substitution is the replacement of the amino acids residues RRK (positions 262 to 264) by the amino acids residues AAH.

In a particular embodiment of the invention, when the lentiviral vector is integration-incompetent, the lentiviral genome further comprises an origin of replication (ori), whose sequence is dependent on the nature of cells where the lentiviral genome has to be expressed. Said origin of replication may be from eukaryotic origin, preferably of mammalian origin, most preferably of human origin. It may alternatively be of viral origin, especially coming from DNA circular episomic viruses, such as SV40 or RPS.

It is an advantageous embodiment of the invention to have an origin or replication inserted in the lentiviral genome of the lentiviral vector of the invention. Indeed, when the lentiviral genome does not integrate into the cell host genome (because of the defective integrase), the lentiviral genome is lost in cells that undergo frequent cell divisions; this is particularly the case in immune cells, such as B or T cells. The presence of an origin of replication ensures that at least one lentiviral genome is present in each cell, even after cell division, accordingly maximizing the efficiency of the immune response.

The lentiviral vector genome of said lentiviral vectors of the invention may especially be derived from HIV-1 plasmid pTRIPΔU3.CMV-GFP deposited at the CNCM (Paris, France) on Oct. 11, 1999 under number 1-2330 (also described in WO01/27300) or variants thereof. The sequence of such variants are provided as SEQ ID No.1 or 2. When the vector genome is derived from these particular plasmids, a sequence of a recombinant polynucleotide encoding an antigenic polypeptide of a *Plasmodium* parasite as disclosed in the present application is inserted therein, in addition or in replacement of the GFP coding fragment. The GFP coding sequence may also be substituted by a different marker. The CMV promoter may also be substituted by another promoter, especially one of the promoters disclosed above, especially in relation to the expression of the transgene.

The WPRE sequence also contained in the particular deposited pTRIP vectors may optionally be deleted.

Vector particles may be produced after transfection of appropriate cells (such as mammalian cells or human cells, such as Human Embryonic Kidney cells illustrated by 293 T cells) by said plasmids, or by other processes. In the cells used for the expression of the lentiviral particles, all or some of the plasmids may be used to stably express their coding polynucleotides, or to transiently or semi-stably express their coding polynucleotides.

The concentration of particles produced can be determined by measuring the P24 (capsid protein for HIV-1) content of cell supernatants.

The lentiviral vector of the invention, once administered into the host, infects cells of the host, possibly specific cells, depending on the envelope proteins it was pseudotyped with. The infection leads to the release of the lentiviral vector genome into the cytoplasm of the host cell where the retrotranscription takes place. Once under a triplex form (via the DNA flap), the lentiviral vector genome is imported into the nucleus, where the polynucleotide(s) encoding polypeptide(s) of antigen(s) of the malaria parasite is (are) expressed via the cellular machinery. When non-dividing cells are transduced (such as DC), the expression may be stable. When dividing cells are transduced, such as B cells, the expression is temporary in absence of origin of replication in the lentiviral genome, because of nucleic acid dilution and cell division. The expression may be longer by providing an origin of replication ensuring a proper diffusion of the lentiviral vector genome into daughter cells after cell division. The stability and/or expression may also be increased by insertion of MAR (Matrix Associated Region) or SAR (Scaffold Associated Region) elements in the vector genome.

Indeed, these SAR or MAR regions are AT-rich sequences and enable to anchor the lentiviral genome to the matrix of the cell chromosome, thus regulating the transcription of the polynucleotide encoding at least one antigenic polypeptide, and particularly stimulating gene expression of the transgene and improving chromatin accessibility.

If the lentiviral genome is non integrative, it does not integrate into the host cell genome. Nevertheless, the at least one polypeptide encoded by the transgene is sufficiently expressed and longer enough to be processed, associated with MHC molecules and finally directed towards the cell surface. Depending on the nature of the polynucleotide(s) encoding antigenic polypeptide(s) of a malaria parasite, the at least one polypeptide epitope associated with the MHC molecule triggers a humoral or a cellular immune response.

Unless otherwise stated, or unless technically not relevant, the characteristics disclosed in the present application with respect to any of the various features, embodiments or examples of the structure or use of the lentiviral particles, especially regarding their envelope protein(s), or the recombinant polynucleotide, may be combined according to any possible combinations.

The invention further relates to a combination of compounds for separate administration to a mammalian host, which comprises at least:

(i) lentiviral vector particles of the invention which are pseudotyped with a first determined heterologous viral envelope pseudotyping protein or viral envelope pseudotyping proteins; such first pseudotyping protein may be from the New-Jersey strain of VSV;

(ii) provided separately from lentiviral vector particles in (i), lentiviral vector particles of the invention which are pseudotyped with a second determined heterologous viral envelope pseudotyping protein or viral envelope pseudotyping proteins distinct from said first heterologous viral envelope pseudotyping protein(s); such second pseudotyping protein may be from the Indiana strain of VSV.

The invention also relates to a polynucleotide which is a codon-optimized nucleic acid encoding a pre-erythrocytic stage chimeric antigen of a *Plasmodium* parasite, wherein said polynucleotide is selected from the group of: SEQ ID No. 115, SEQ ID No.117, SEQ ID No. 119, SEQ ID No. 121.

Codon optimisation reflected in the above sequences has been carried out for expression in mice when polynucleotides encoding antigens of *P. berghei* are concerned. It has been carried out for expression in human cells when polynucleotides encoding antigens of *P. falciparum* or of *P. vivax* are concerned.

The invention also concerns the use of the above polynucleotides for the design of alternative forms of nucleic acids also suitable for the preparation of the vectors of the invention, wherein the thus obtained nucleic acids are RNAs of modified DNAs such as threose nucleic acids (TNAs), glycol nucleic acids (GNAs),peptide nucleic acids (PNAs), locked nucleic acids (LNAs) with either known configuration or ethylene nucleic acids (ENA) or cyclohexenyl nucleic acids (CeNA) or hybrids or combinations thereof. In particular when carrying out the preparation of the vector genome of the invention, hybrid molecules can be used wherein the polynucleotide encoding the antigenic polypeptide of the malaria parasite as disclosed herein is expressed from one of the above disclosed forms of sequences. According to an embodiment of the invention, the nucleotide sequence of the vector genome is a chimeric sequence encompassing a modified nucleic acid for the transcription of the antigenic polypeptide.

In another embodiment of the invention, possibly in combination with the above disclosed alternative forms of the nucleic acid, the polynucleotide encoding the antigenic polypeptide is structurally modified and/or chemically modified. Illustrative thereof a polynucleotide comprises a Kozak consensus sequence in its 5' region. Such polynucleotides encompassing Kozak consensus sequences are especially illustrated herein. Other nucleic acid sequences that are not of lentiviral origin may be present in the vector genome are IRES sequence(s) (Internal Ribosome entry site) suitable to initiate polypeptide synthesis WPRE sequence as post-transcriptional regulatory element to stabilize the produced RNA.

According to another embodiment of the invention, if multiple heterologous polypeptides are encoded by one vector genome, the coding sequences may optionally be separated by a linker moiety which is either a nucleic acid based molecule or a non-nucleic acid based molecule. Such a molecule may be a functionalized linker molecule aimed at recognizing a 3' functionalized nucleic acid to which it shall be linked. A sequence suitable to function as a linker may alternatively be a nucleic acid which encodes a self-cleaving peptide, such as a 2A peptide.

The invention relates to a collection of polynucleotides thus described wherein a polynucleotide encodes a chimeric antigenic polypeptide as defined herein and another polynucleotide encodes one or more additional antigenic polypeptides of the malaria parasite as described herein for the purpose of the invention, provided the collection of these polynucleotides is suitable for the preparation of the active ingredients of the combination or composition of compounds of the invention.

The invention also relates to the use of the polynucleotides thus disclosed, for the preparation of a collection of lentiviral vectors, in particular HIV-1 based vectors, wherein a vector comprises in its genome, at least one of these polynucleotides, provided the collection of lentiviral vectors enables the expression of all antigenic polypeptides encoded by the polynucleotides.

Further features and properties of the present invention, including features to be used in the embodiments described above will be described in the examples and figures which follow and may accordingly be used to characterise the invention.

LEGENDS OF THE FIGURES

FIG. 1. Schema of plasmids used in the production of Lentiviral Particles.

Figure 2:
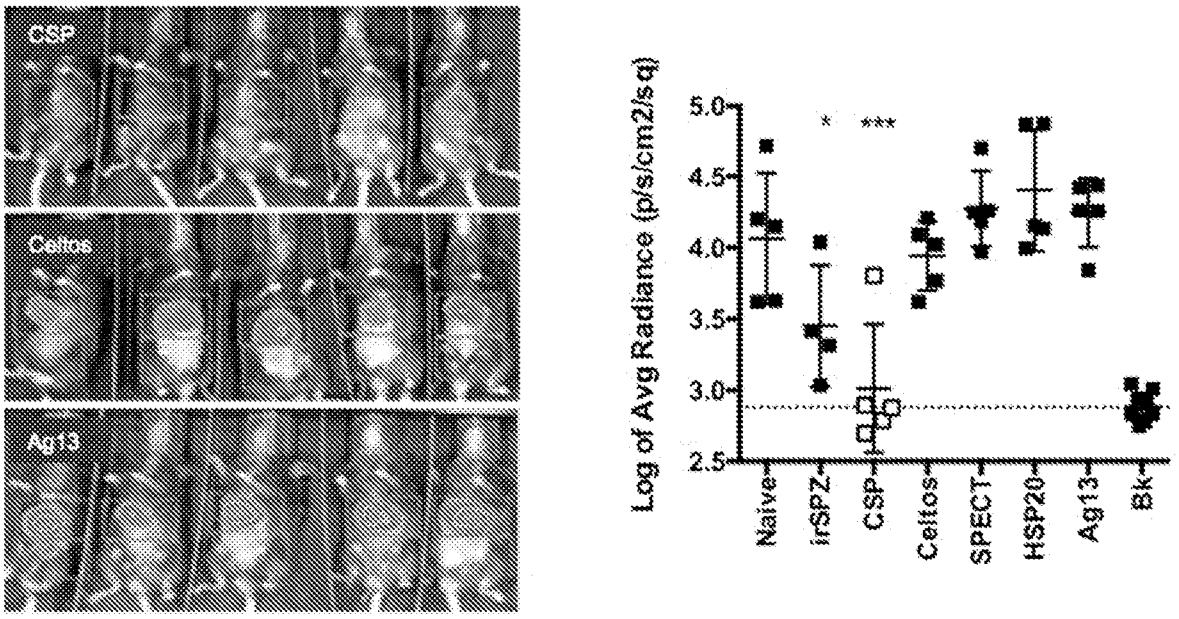

FIG. 2. C57BL/6 mice (n=5) were immunized intramuscularly with $5\times10^7$ TU of $VSV^{IND}$ pseudotyped lentiviral particles coding for the antigens, CSP, Celtos SPECT, HSP20 and Ag13. As a positive control of protection, mice were immunized with 50 k irradiated sporozoites via intravenous injection. Thirty days after immunization, the animals were challenged with 10,000 bioluminescent sporozoites micro-injected subcutaneously in the mice footpad. The parasite load in the liver was quantified two days later by bioluminescence as shown in the picture for CSP, Celtos and Ag13. The graph shows the quantification of the liver infection represented as the log of average radiance (squares). Dotted line represents the average of background signal (Bk) of a non-infected region. $^{*}P<0.05$ and $^{***}P<0.001$ (ANOVA).

Figure 3:
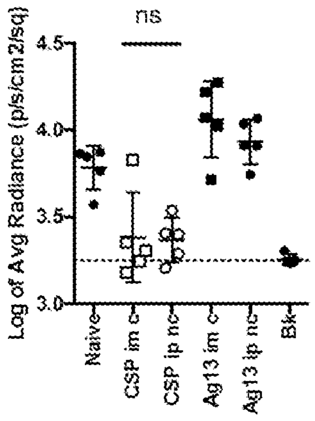

FIG. 3. C57BL/6 mice (n=5 per group) were immunized or not (naïve) with $5\times10^7$ TU of $VSV^{IND}$ LPs carrying Ag13 (negative control) and CSP (positive control). The groups receiving concentrated LPs were inoculated intramuscularly in the thigh muscle with 50 uL of vector (Ag13 im c and CSP im c). The groups receiving non-concentrated LPs were inoculated intraperitoneally with 700 uL of vector (Ag13 ip nc and CSP ip nc). Thirty days after immunization, the animals were challenged with 5,000 luciferase-expressing sporozoites, micro-injected subcutaneously in the mice footpad. The parasite load in the liver was quantified two days later by bioluminescence as shown in the FIG. 2. The graph shows the average and sd of the log of average radiance in the liver two days after SPZ inoculation. Dotted line represents the average of background signal (Bk). ns, not significant (ANOVA).

Figure 4:
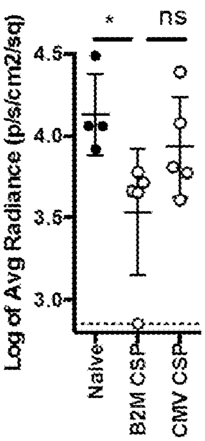

FIG. 4. C57BL/6 mice (n=4-5 per group) were intraperitoneally immunized or not (naïve) with $1\times10^7$ TU of non concentrated $VSV^{IND}$ CSP LPs under the control of CMV or B2M promoters (CMV CSP and B2M CSP, respectively). Thirty days after immunization, the animals were challenged with 5,000 luciferase-expressing sporozoites micro-injected subcutaneously in the mice footpad. The parasite load in the liver was quantified two days later by bioluminescence as shown in the FIG. 2. The graph shows the average and sd of the log of average radiance in the liver two days after SPZ inoculation. Dotted line represents the average of background signal (Bk). $^{*}P<0.05$; ns, not significant (ANOVA).

Figure 5:
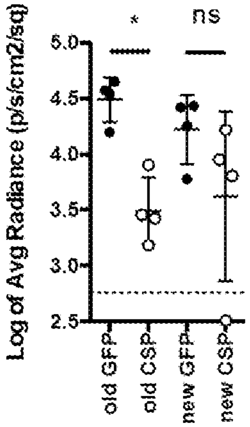

FIG. 5. 4 and 7 weeks-old C57BL/6 mice (n=4-per group) were acclimated for 3 weeks (old groups) and 3 days (new groups). These age-matched groups were then intraperitoneally immunized with $1\times10^7$ TU of non concentrated $VSV^{IND}$ B2M CSP or GFP LPs. Thirty days after immunization, the animals were challenged with 5,000 luciferase-expressing sporozoites micro-injected subcutaneously in the mice footpad. The parasite load in the liver was quantified two days later by bioluminescence as shown in the FIG. 2. The graph shows the average and sd of the log of average radiance in the liver two days after SPZ inoculation. Dotted line represents the average of background signal (Bk). $^{*}P<0.05$; ns, not significant (ANOVA).

Figure 6:
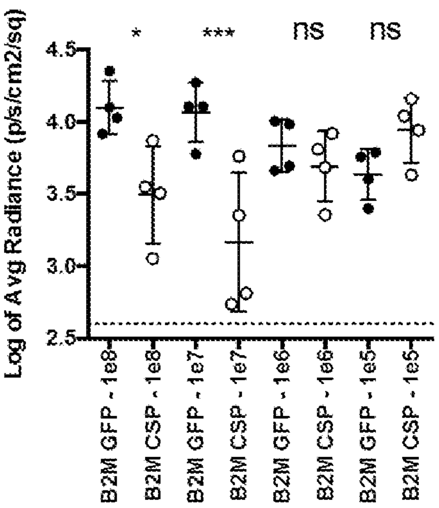

FIG. 6. 4 weeks-old C57BL/6 mice (n=4-per group) were acclimated for 3 weeks (old groups) and intraperitoneally immunized with different doses of non-concentrated $VSV^{IND}$ B2M CSP (black) or GFP (white) LPs. Thirty days after immunization, the animals were challenged with 5,000 luciferase-expressing sporozoites micro-injected subcutaneously in the mice footpad. The parasite load in the liver was quantified two days later by bioluminescence as shown in the FIG. 2. The graph shows the average and sd of the log of average radiance in the liver two days after SPZ inoculation. Dotted line represents the average of background signal (Bk). $^{*}P<0.05$; $^{***}P<0.001$; ns, not significant (ANOVA).

Figure 7:
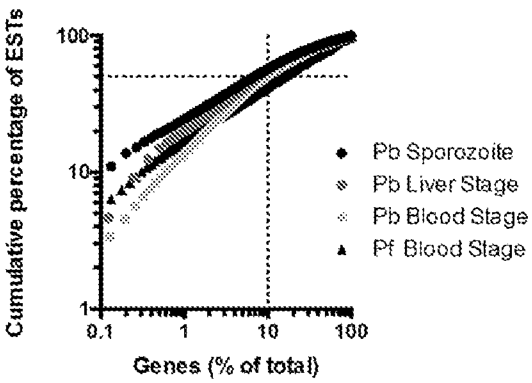

FIG. 7. Analysis of Sporozoite, Liver Stage and Blood Stage cDNA libraries of *Plasmodium berghei* (Pb) and *falciparum* (Pf) deposited in Plasmodb. The percentage of each expression sequence tag (EST) was normalized to the total number of ESTs and represented cumulatively. Each symbol represents one gene, ranked by EST abundance (higher to lower) and represented as % of total ESTs. Of note ~10% of genes (most abundant) are responsible for ~50% of total ESTs (dotted lines).

Figure 8:
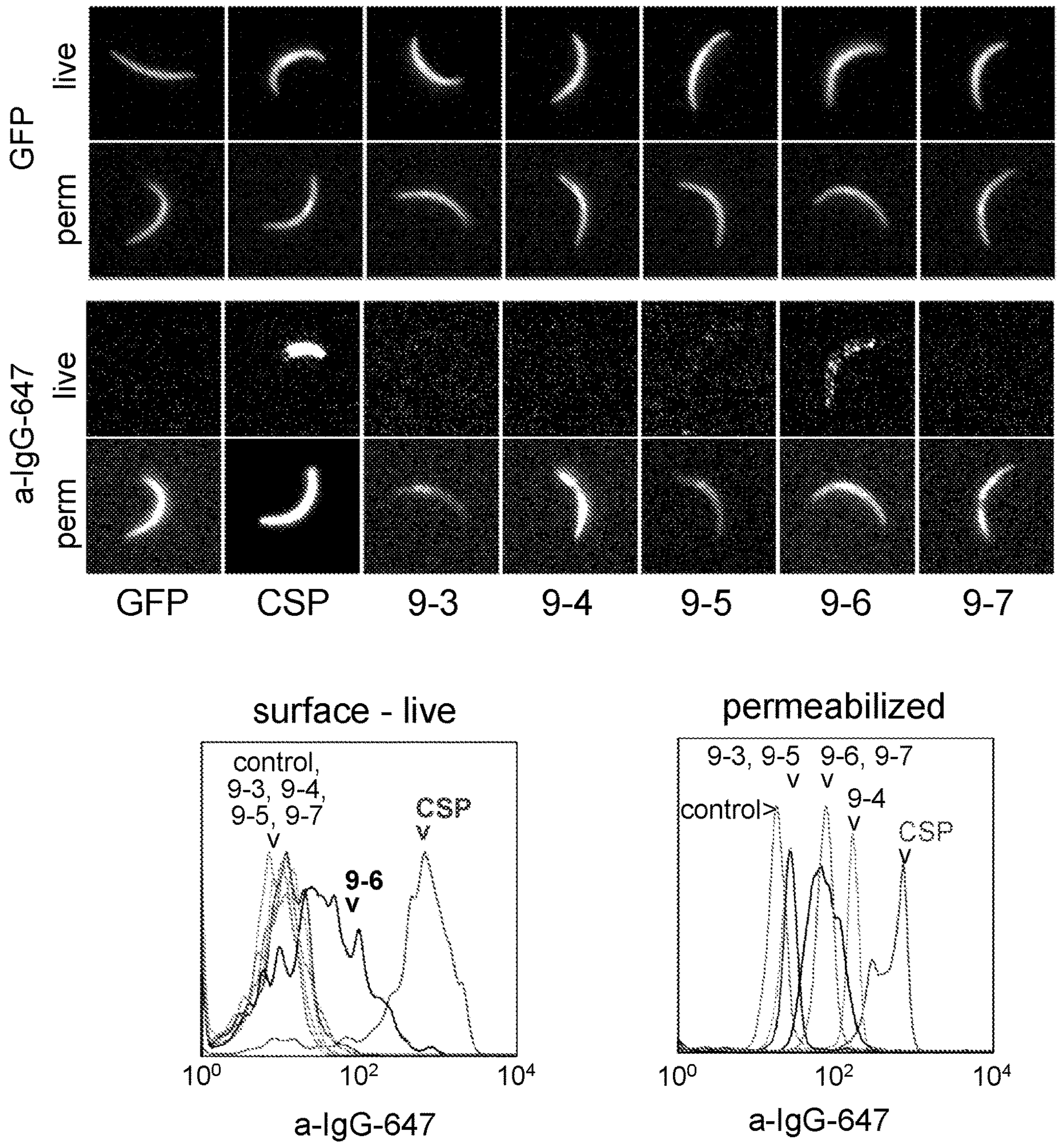

FIG. 8. Expression and surface localization of antigens. GFP-expressing Pb sporozoites were fixed with 2% of PFA and permeabilized with 0.1% of Triton X100 (perm) or not (live). Parasites were incubated with the indicated immunesera (1/50) for one hour on ice, washed and revealed with goat anti-mouse secondary antibody labelled with AlexaFluor 647. Sporozoites were then analysed by cytometry as shown in the right histograms (surface, staining using live non-permeabilized SPZ; permeabilized, staining using fixed and permeabilized SPZ) or by fluorescence microscopy, as depicted in the pictures. Notice that CSP and antigen 9-6 present a surface pattern staining both by cytometry and microscopy.

Figure 9:
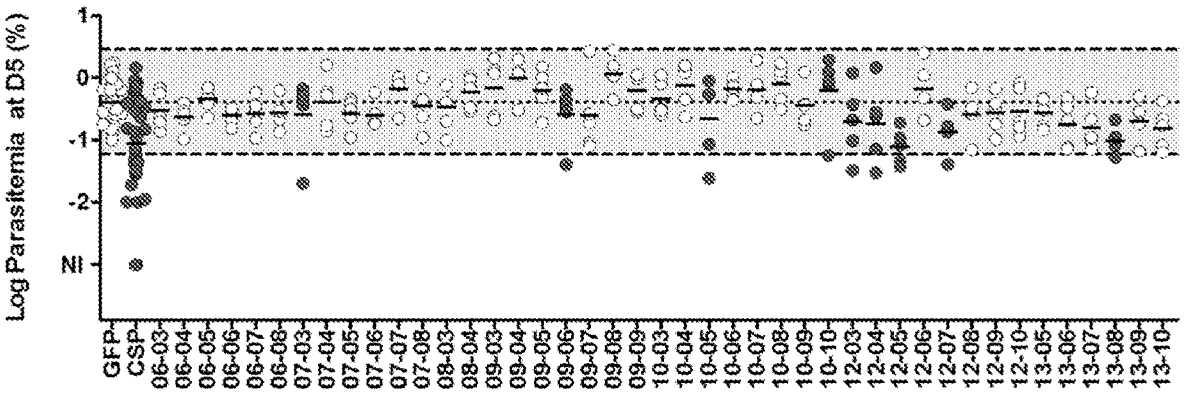

FIG. 9. Targeted screening of protective antigens. 4 weeks-old C57BL/6 mice (n=5 per group) were acclimated for 3 weeks and intraperitoneally immunized with a single dose of $1\times10^7$ TU of non-concentrated $VSV^{IND}$ B2M LPs. Thirty days after immunization, the animals were challenged with 5,000 GFP-expressing sporozoites micro-injected subcutaneously in the mice footpad. The parasite infection was measured by flow cytometry. The graph shows the average of the log of parasitemia (trace, individual mice represented by circles) immunized with the indicated plasmodial antigens. Bold dotted lines represent the 95% tolerance interval of GFP log normal distribution. Mice with parasitemia below the lower limit of the tolerance interval are considered protected. Top dotted line is the average of control and bottom dotted line represents non-infected (NI) mice.

Figure 10:
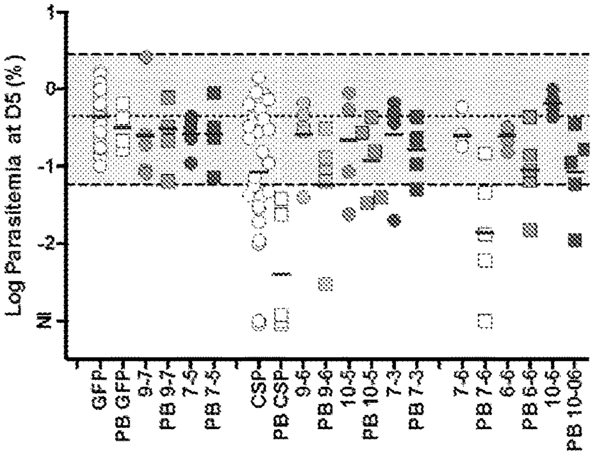

FIG. 10. Comparison of protection induced by one or two immunization doses. 4 weeks-old C57BL/6 mice (n=5 per group) were acclimated for 3 weeks and intraperitoneally immunized with a first dose of $5\times10^5$ TU of non-concentrated $VSV^{NJ}$ B2M LPs. Thirty days after the first immunization, the animals received a second dose of $1\times10^7$ TU of non-concentrated $VSV^{IND}$ B2M LPs. Thirty days later, mice were challenged with 5,000 GFP-expressing sporozoites micro-injected subcutaneously in the footpad. The parasite infection was measured by flow cytometry. The graph shows the log of parasitemia at day 5 post-inoculation of individual challenged mice that received two immunization doses (Squares, PB). Circles represent mice that received only one immunization dose of LPs (data from experiment shown in FIG. 9). Traces represents the average of the Log Parasitemia. Bold dotted lines represent the 95% tolerance interval of GFP log normal distribution. Mice below the lower limit of tolerance interval are considered protected. NI, non-infected mice.

Figure 11:
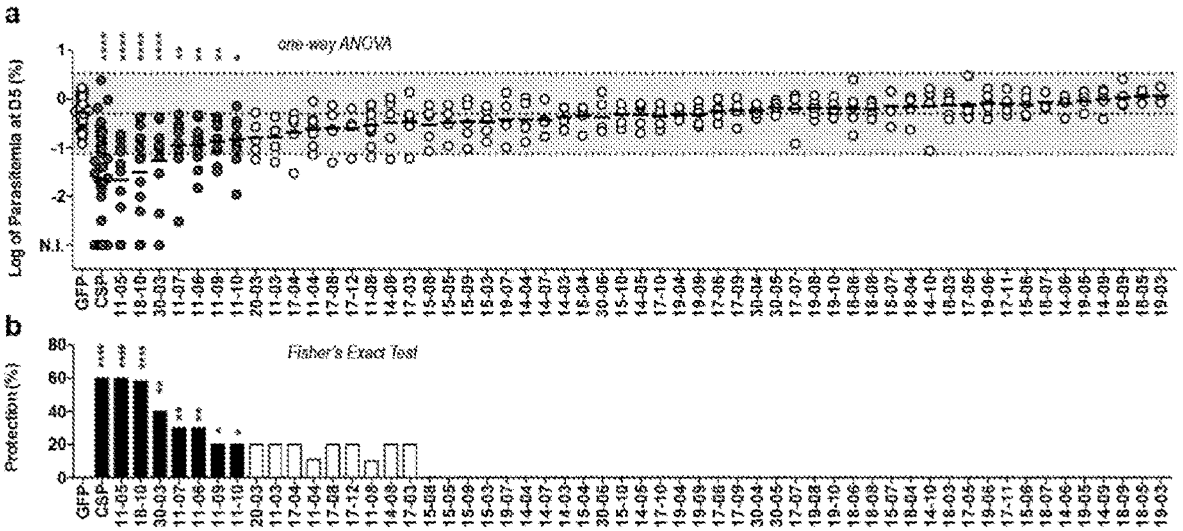

FIG. 11. Targeted Screening of Protective Antigens. 4 weeks-old C57BL/6 mice (n=5-10 per group) were acclimated for 3 weeks and intraperitoneally immunized with a first dose of 5×10$^5$ TU of non-concentrated VSV$^{NJ}$ B2M LPs. Thirty days after the first immunization, the animals received a second dose of 1×10$^7$ TU of non-concentrated VSV$^{IND}$ B2M LPs. Third days later, mice were challenged with 5,000 GFP-expressing sporozoites micro-injected subcutaneously in the footpad. The parasite blood infection was measured by flow cytometry. (a.) The upper graph shows the log of parasitemia of individual mouse at day 5 post-infection. Traces represent the mean of the log parasitemia. The average of the GFP group (control of protection) is represented by the dotted middle line. The superior and inferior dotted lines delineate the 95% tolerance interval (grey box) of the GFP control group. The CSP group is the positive control of protection. NI (not infected=no parasitemia at day 10 post-infection, located at the limit of detection of our method of parasitemia quantification). Black circles represent antigens where there was a significant decrease in the averaged log parasitemia and therefore are considered protective (ANOVA). (b) The bottom graph represents the percentage of protected mice (% of animals below the 95% tolerance interval). Black bars represent protective antigens (Fisher's Exact test). *P<0.05, P<0.01, **P<0.0001.

Figure 12:
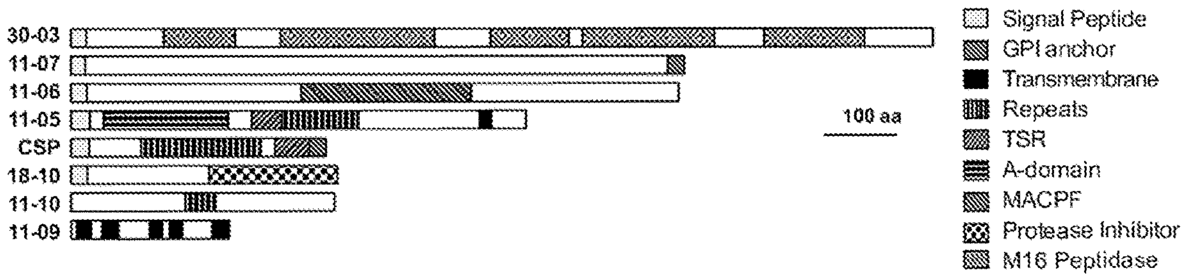

FIG. 12. Structure of *P. berghei* protective antigens. Conserved structural and functional domains are represented by boxes according to the code on the right. GPI (glycosylphosphatidylinositol), TSR (thrombospondin type I repeat), MACPF (membrane attack complex/perforin).

Figure 13:
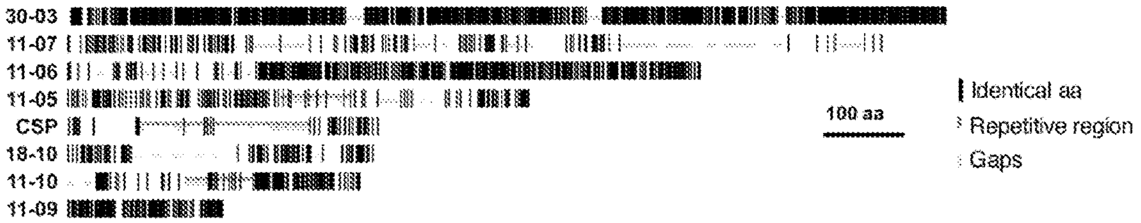

FIG. 13. Protective antigens are conserved among plasmodial species. Amino acid sequences of protective orthologous antigens from rodent-infecting *P. berghei*, macaque-infecting *P. cynomolgi*, and human-infecting *P. falciparum* and *P. vivax* parasites were aligned by MUltiple Sequence Comparison by Log- Expectation (MUSCLE). Vertical black bars represent identical amino acids conserved in the four plasmodial species, short dark gray bars represent repetitive regions and short light gray bars, insertional gaps used for the alignment.

Figure 14:
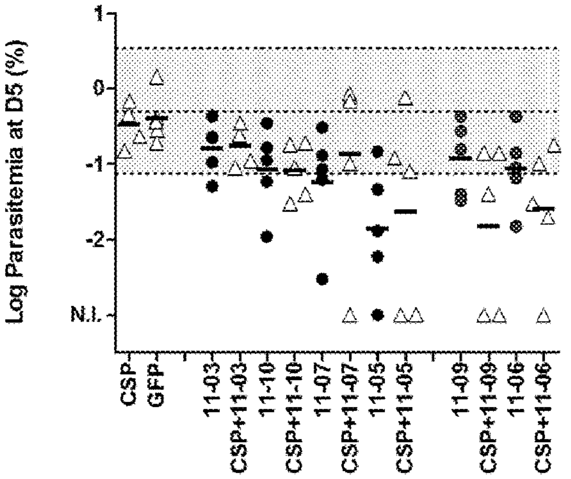

FIG. 14. Protection induced by combination of down-selected protective antigens with a sub-optimal dose of CSP. Mice were immunized twice, four weeks apart, with a sub-optimal dose of CSP (5×10$^5$ TU of non-concentrated VSV$^{NJ}$ B2M LP in the first immunization and 5×10$^6$ TU of non-concentrated VSV$^{IND}$ B2M LP in the second immunization, white triangle, CSP) and the usual dose of protective plasmodial antigens (CSP+11-03, +11-05, +11-06, +11-07, +11-09 and +11-10; triangles). As negative control mice were immunized with the usual, two doses of GFP. 4 weeks after the second immunization dose, animals were challenged with 5,000 sporozoites.

Figure 15:
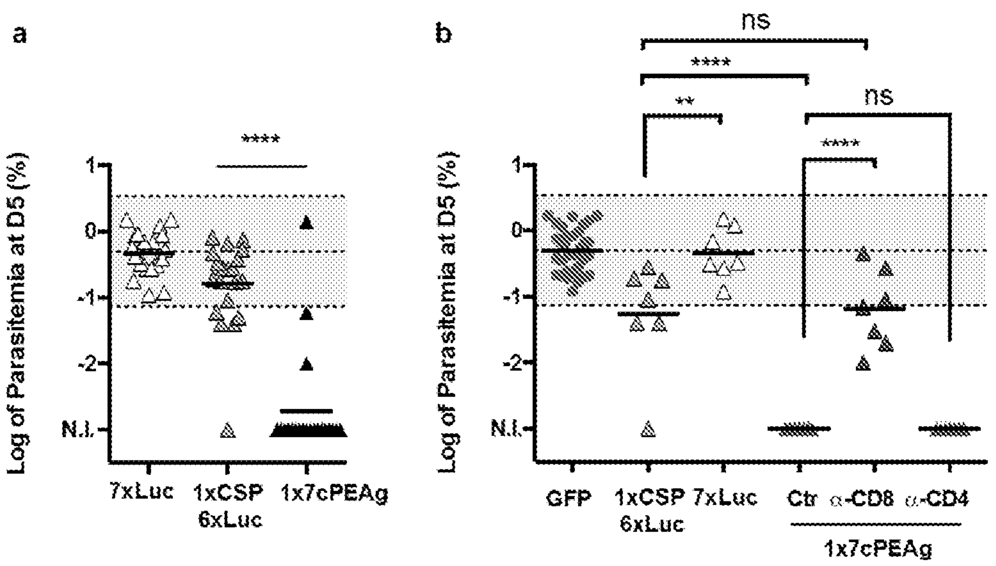

FIG. 15. Sterile protection induced by a multigenic combination. Mice were immunized twice, four weeks apart, with 7x the individual dose (1dose=5×10$^5$ TU of non-concentrated VSV$^{NJ}$ B2M LPs in the first immunization/1×10$^7$ TU of non-concentrated VSV$^{IND}$ B2M LPs in the second immunization) of the control antigen AL11-luciferase (Luc, white triangles), with the individual dose of CSP plus 6×Luc (gray triangles), or with the individual doses of CSP and of 6 conserved PE antigens (11-05, 11-06, 11-07, 11-09, 11-10 and 18-10; black triangles, 7cPEAg). 4 weeks after the second immunization dose, mice were challenged with 5,000 GFP SPZs. Both graphs show the individual log of parasitemia at day 5 post-challenge. (a) The graph shows the pooled results of three independent experiments. Number of sterile protected/challenged mice: 7×Luc (0/21), 1×CSP 6×Luc (1/20) and 1×7cPEAg (18/21). (b) Three and one day before sporozoite challenge, 1×7cPEAg immunized mice were injected with 400 μg of control (Ctr), CD4-depleting (a-CD4+, clone GK1.5) and CD8-depleting (a-CD8+, clone 2.43) monoclonal antibodies. GFP data comes from experiment showed in FIG. 11 (gray circles). Number of sterile protected/challenged mice: 7×Luc (0/7), 1×CSP 6×Luc (1/7) and 1×7cPEAg (ctr, 7/7; a-CD8, 0/7 and a-CD4, 7/7). Notice that depletion of CD8+ cells abolished sterile protection. *P<0.05, P<0.01, **P<0.0001 (ANOVA).

Figure 16:
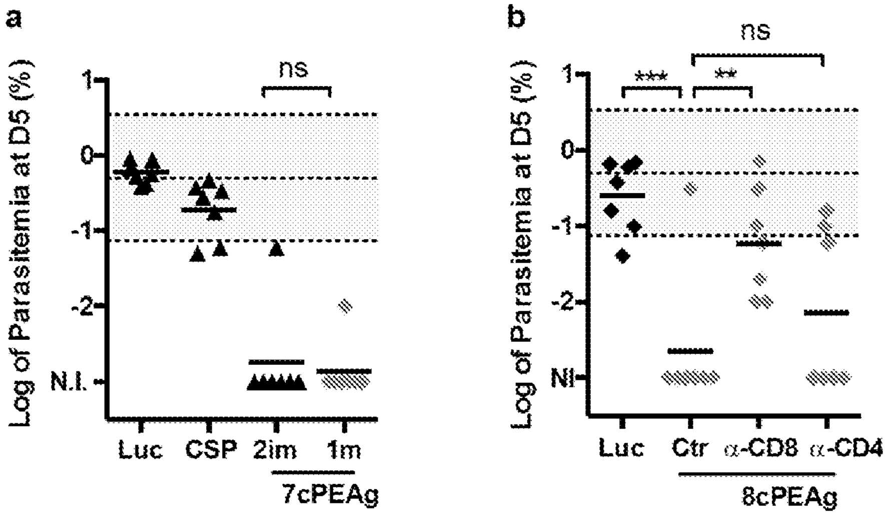

FIG. 16. Sterile protection induced by a multigenic combination in a single immunization dose. (a) Mice were immunized twice, four weeks apart, with 7× the individual dose (1dose=5×10$^5$ TU of non-concentrated VSV$^{NJ}$ B2M LPs in the first immunization/1×10$^7$ TU of non-concentrated VSV$^{IND}$ B2M LPs in the second immunization) of the control antigen AL11-luciferase (Luc, black triangles), with the individual dose of CSP plus 6×Luc (CSP, black triangles), or with the individual dose of CSP and of 6 conserved PE antigens (11-05, 11-06, 11-07, 11-09, 11-10 and 18-10; black triangles; 2 im 7cPEAg). Alternatively, mice were administered only with the second individual immunization dose (1×10$^7$ TU) of CSP and of 6 conserved PE antigens (11-05, 11-06, 11-07, 11-09, 11-10 and 18-10; grey diamonds; 1 im 7cPEAg). 4 weeks after the second immunization dose, mice were challenged with 5,000 GFP SPZs. The graph shows the individual log of parasitemia at day 5 post-challenge. Black bars are the average of log of parasitemia. Number of sterile protected/challenged mice: Luc (0/7), CSP (0/7), 2im 7cPEAg (6/7) and 1m 7cPEAg (6/7). (b) Mice were immunized once with 9× the individual dose (1 dose=1×10$^7$ TU of non-concentrated VSV$^{IND}$ B2M LPs) of the control antigen AL11-luciferase (Luc, black diamonds), or with the individual doses of CSP+ of 7 conserved PE antigens (11-05, 11-06, 11-07, 11-09, 11-10, 18-10, 30-03A and 30-03B; grey diamonds; 8cPEAg). Three and one day before sporozoite challenge, 8cPEAg immunized mice were injected with 400 μg of control (Ctr), CD4-depleting (a-CD4+, clone GK1.5) and CD8-depleting (a-CD8+, clone 2.43) monoclonal antibodies. 4 weeks after the single immunization dose, mice were challenged with 5,000 GFP SPZs. The graph shows the individual log of parasitemia at day 5 post-challenge. Black bars are the average of log of parasitemia. Number of sterile protected/challenged mice: 7×Luc (0/7) and 8cPEAg (ctr, 6/7; a-CD8, 0/7 and a-CD4, 4/7). Notice that depletion of CD8+ cells abolished protection. *P<0.05; P<0.01; **P<0.0001; ns, P>0.05 (ANOVA).

Figure 17:
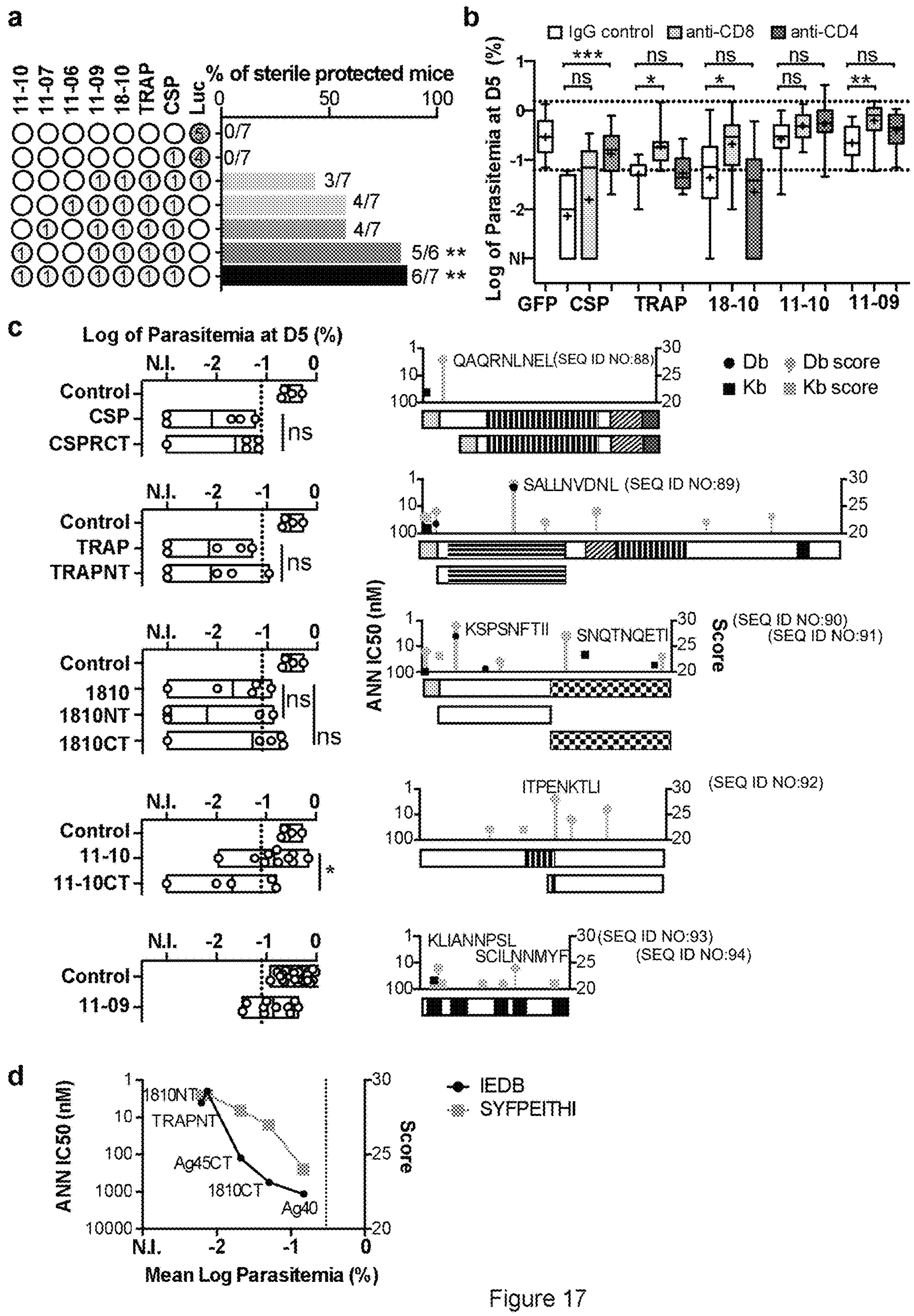

FIG. 17. Sterile protection induced by a minimal combination of 5 PE antigens. (a) Mice were immunized twice, four weeks apart, with the individual dose multiplied by the number indicated in the circles (1dose=5×10$^5$ TU of non-concentrated VSV$^{NJ}$ B2M LPs in the first immunization/1×10$^7$ TU of non-concentrated VSV$^{IND}$ B2M LPs in the second immunization). For example, for the control antigen AL11-luciferase (LUC), animals were immunized with 5× the individual dose. All groups received 5 doses, with exception of the positive control of protection that received 7 doses of LPs (7PEAg). 4 weeks after the second immunization dose, mice were challenged with 5,000 GFP SPZs. Bars represents the percentage of sterile protected mice. The numbers of sterile protected/challenged mice are shown at the right of bars. **P<0.01 (Fisher's Exact test). (b) Mice were immunized twice, four weeks apart, with the individual dose (1dose=$5\times10^5$ TU of non-concentrated $VSV^{NJ}$ B2M LPs in the first immunization/$1\times10^7$ TU of non-concentrated $VSV^{IND}$ B2M LPs in the second immunization) of the control antigen GFP (GFP, black circles) or with the individual dose of CSP, TRAP, 18-10, 11-09 or 11-10 (grey triangles). Three and one day before sporozoite challenge, immunized mice were injected with 400 μg of control (Ctr), CD4-depleting (a-CD4+, clone GK1.5) and CD8-depleting (a-CD8+, clone 2.43) monoclonal antibodies. 4 weeks after the second immunization dose, mice were challenged with 5,000 GFP SPZs. Graphs show the average ±sd of log of parasitemia at day 5 post-challenge. *P<0.05; ns, P>0.05 (ANOVA). (c) The 5 down-selected protective antigens were split according the presence of predicted CD8 T cell epitopes and respecting conserved structural domains as depicted by the schematic representation of the antigens. The graphs above the schematic proteins represent the distribution of epitopes predicted to bind to H2Kb (8 aa) and H2Kd (9 aa) MHC class I molecules using SYFPEITHI (score) and IEDB ANN IC 50 (nM). The graphs on the left of schematic proteins represent the protection induced by these constructs, where bars are the average ±sd of log of parasitemia at day 5 post-challenge. Data shown for antigen 11-09 come from FIG. 11. Dotted line represents the inferior limit of the tolerance interval of the control calculated in the FIG. 11. *P<0.05; ns, P>0.05 (ANOVA). (d) Correlation of the best epitope predicted to bind to MHC class I molecules in the segments of CD8+ T cell dependent PE antigens and mean protective activity obtained from 17c. Circles show the IC50 using IEDB ANN software and squares the score values using SYFPEITHI. Dotted line shows the average of Luc control.

Figure 18:
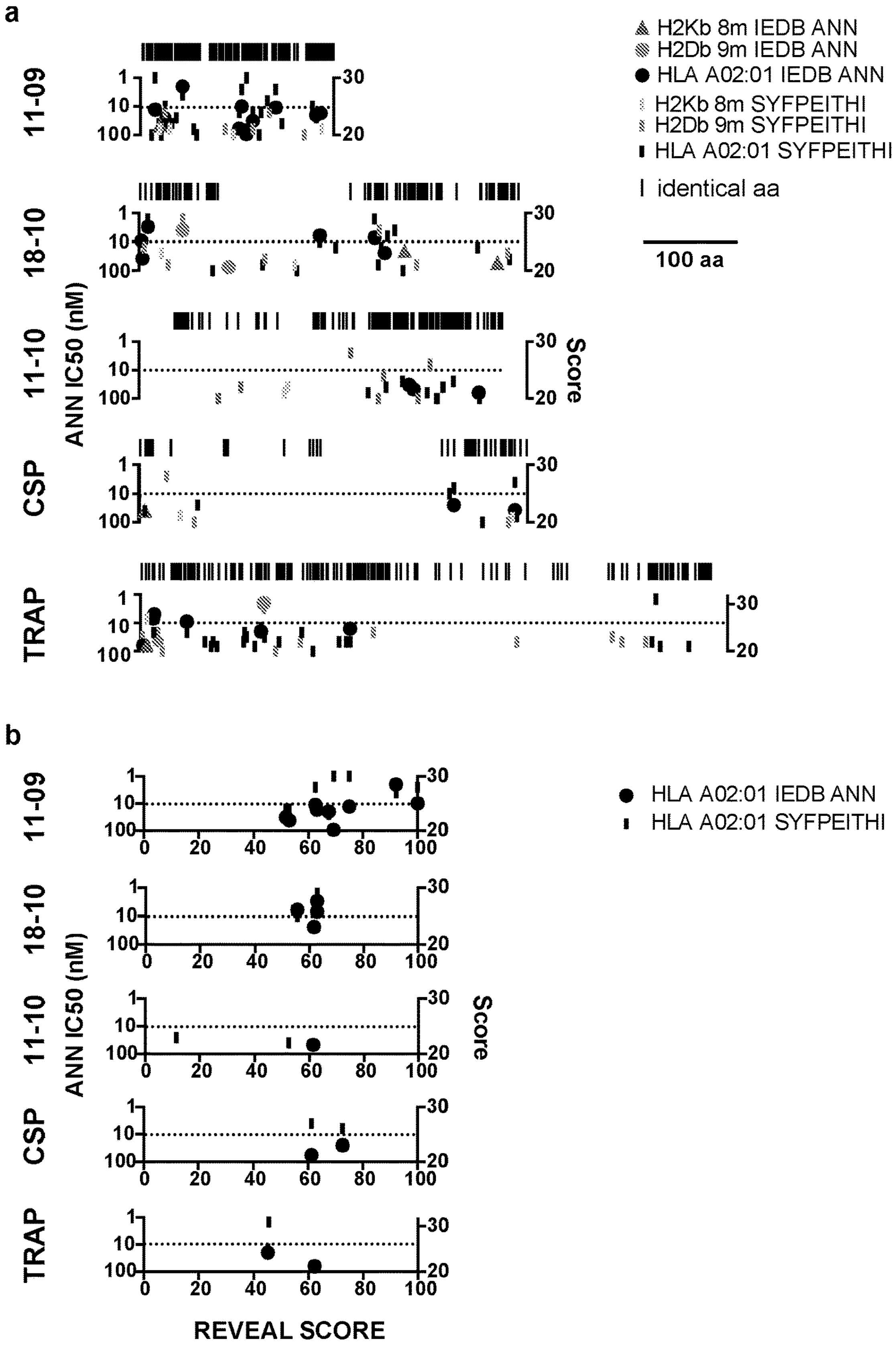

FIG. 18. Clustering of CD8 T cell epitopes in conserved amino acid regions and binding of predicted Pf epitopes to HLA A02:01. Amino acid sequences of protective orthologous antigens from rodent-infecting *P. berghei*, macaque-infecting *P. cynomolgi*, and human-infecting *P. falciparum* and *P. vivax* parasites were aligned by MUltiple Sequence Comparison by Log- Expectation (MUSCLE). Vertical black bars represent identical amino acids conserved in the four plasmodial species. The graph shows the distribution of Pb epitopes predicted to bind to H2Kb (8 aa) and H2Kd (9 aa) MHC class I molecules or of Pf epitopes predicted to bind to the HLA A02:01 (9 mers) using SYFPEITHI (score) and IEDB ANN IC50 (nM). The best predicted HLA binders were tested in the assay of stabilization of MHC class I molecule in the presence of peptide and β2-microglobulin (REVEAL® Score). The score of 100 corresponds to the binding of a positive control peptide. Notice the clustering of epitopes in regions of conserved amino acids.

Figure 19:
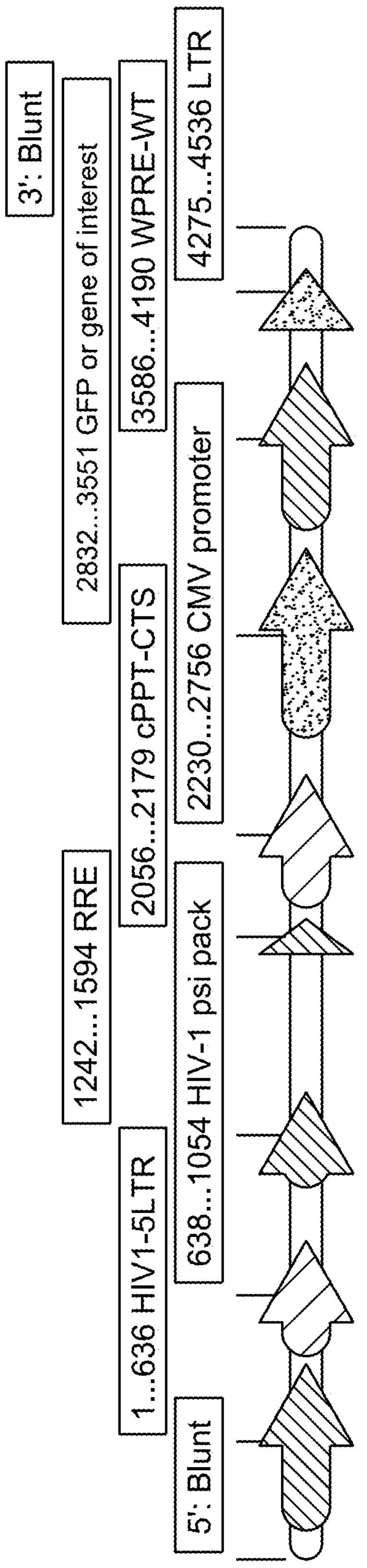

FIG. 19. plasmid used to produce VSV-pseutdotyped lentiviral particles: pTRIP CMV GFP The sequence of the plasmid is constituted by the following functional regions wherein the cis-active lentiviral regions are derived from the HIV genome, and the promoter driving the expression of the protein (GFP) is CMV:

The insert in the plasmid that provides the vector genome is composed as follows:

LTR-ψ-RRE-cPPT/CTS-CMV-GFP-WPRE-AU3LTR, wherein

LTR is Long Terminal Repeat

Psi (ψ) is Packaging signal

RRE is Rev Responsive Element

CMV is Immediate early CytoMegaloVirus promoter cPPT is central PolyPurine Tract, and wherein the nucleotide segment from cPPT to CTS forms the flap sequence CTS is Central Termination Sequence WPRE is Woodchuck hepatitis virus Post Regulatory Element The nucleotide sequence is provided as SEQ ID No.1

Figure 20:
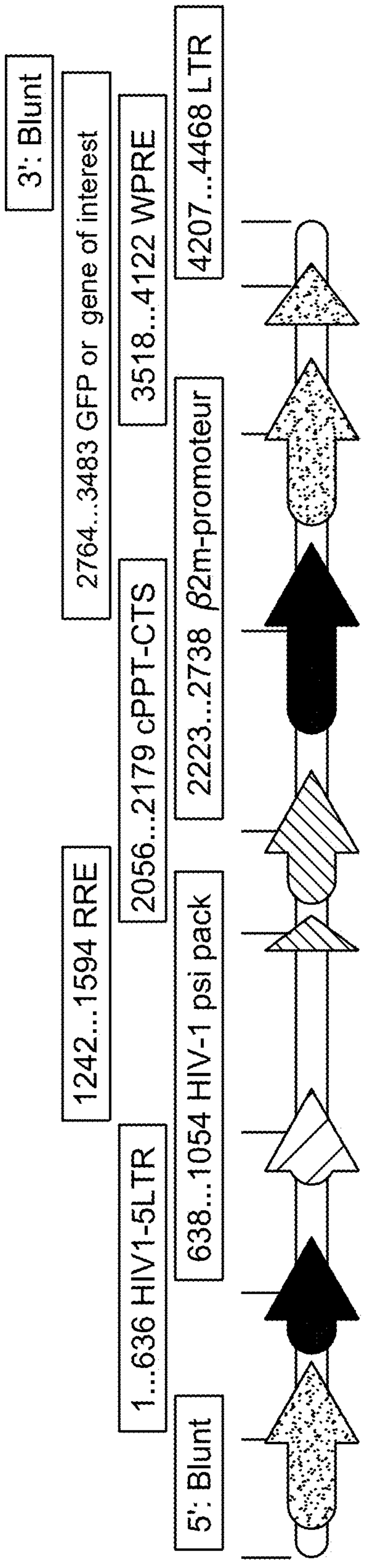

FIG. 20: alternative plasmid (to the plasmid of FIG. 19) used to produce VSV-pseutdotyped lentiviral particles: pTRIP B2M GFP The insert in the plasmid that provides the vector genome is composed as follows: LTR-ψ-RRE-cPPT/CTS-B2M—GFP-WPRE-ΔU3LTR.

The nucleotide sequence is provided as SEQ ID No.2..

Figure 21:
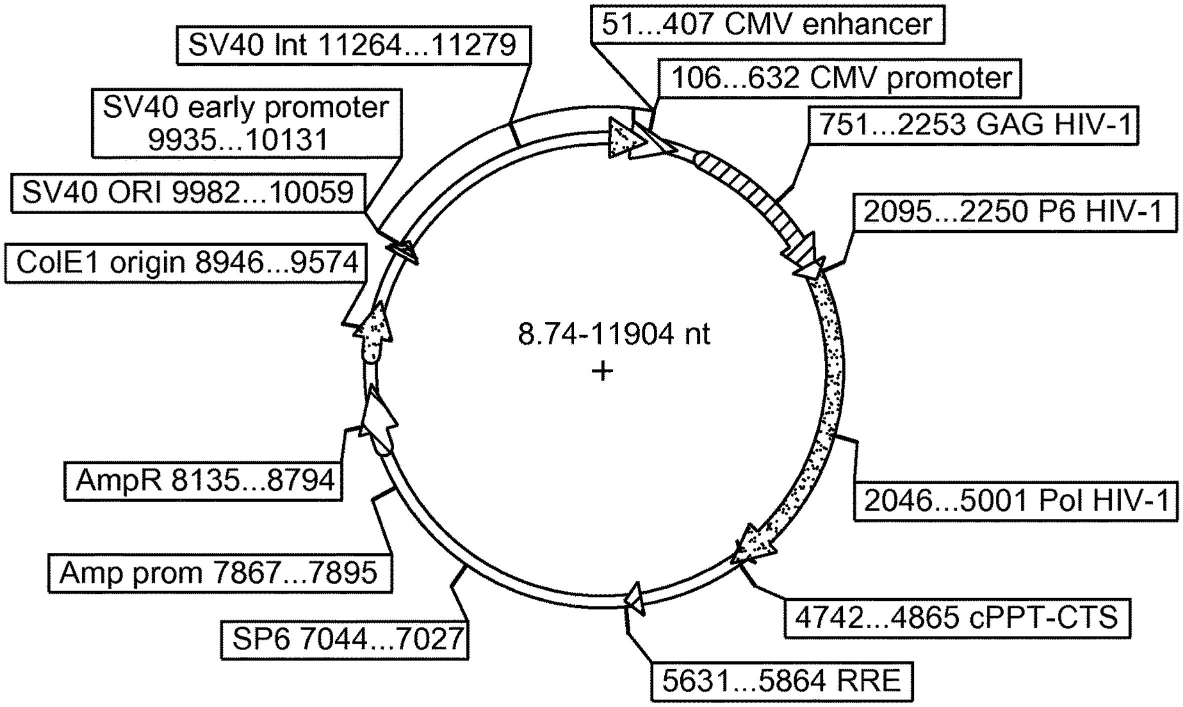

FIG. 21. plasmid used to produce VSV-pseutdotyped lentiviral particles: packaging 8.74 plasmid The plasmid provides the required GAG and POL coding sequences of the HIV-1 lentivirus under the control of the CMV promoter.

The nucleotide sequence is provided as SEQ ID No.3.

Figure 22:
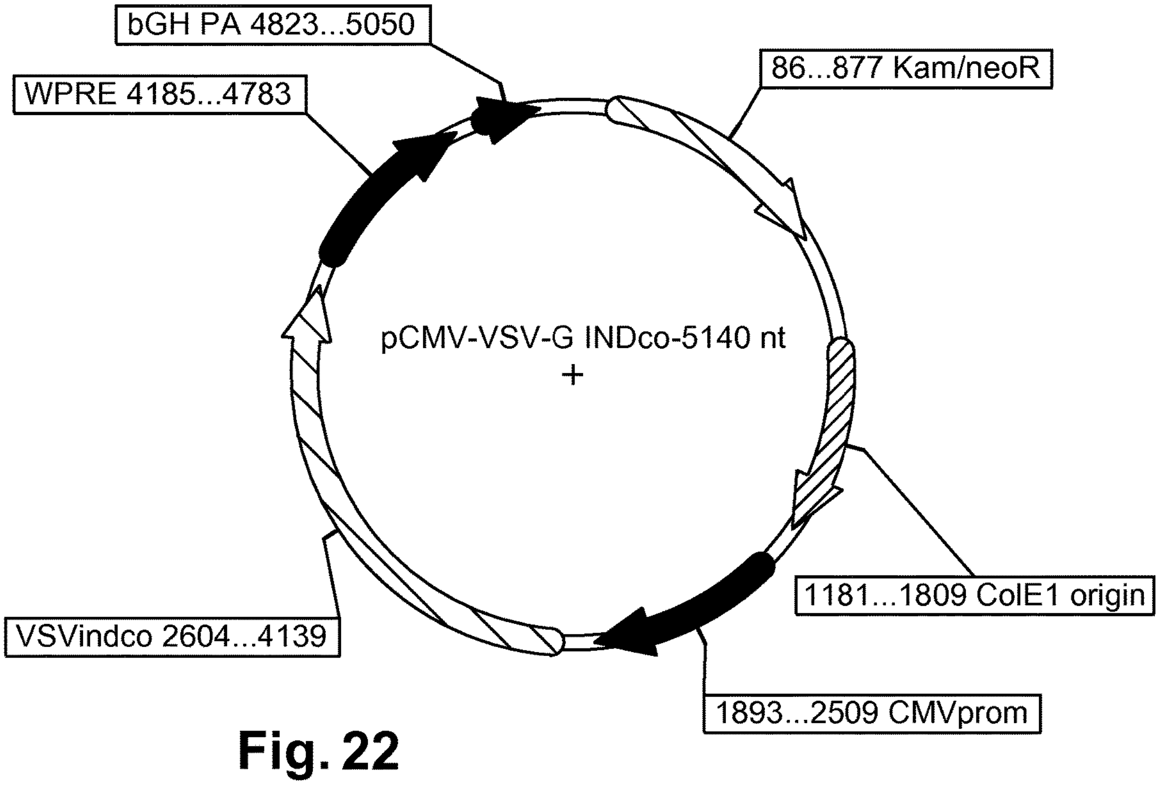

FIG. 22. plasmid used to produce VSV-pseutdotyped lentiviral particles: encapsidation plasmid pCMV-VSV-IN-Dco The envelope protein is the VSV-G of the Indiana strain and the coding sequence has been mouse-codon optimized.

The nucleotide sequence is provided as SEQ ID No.4.

Figure 23:
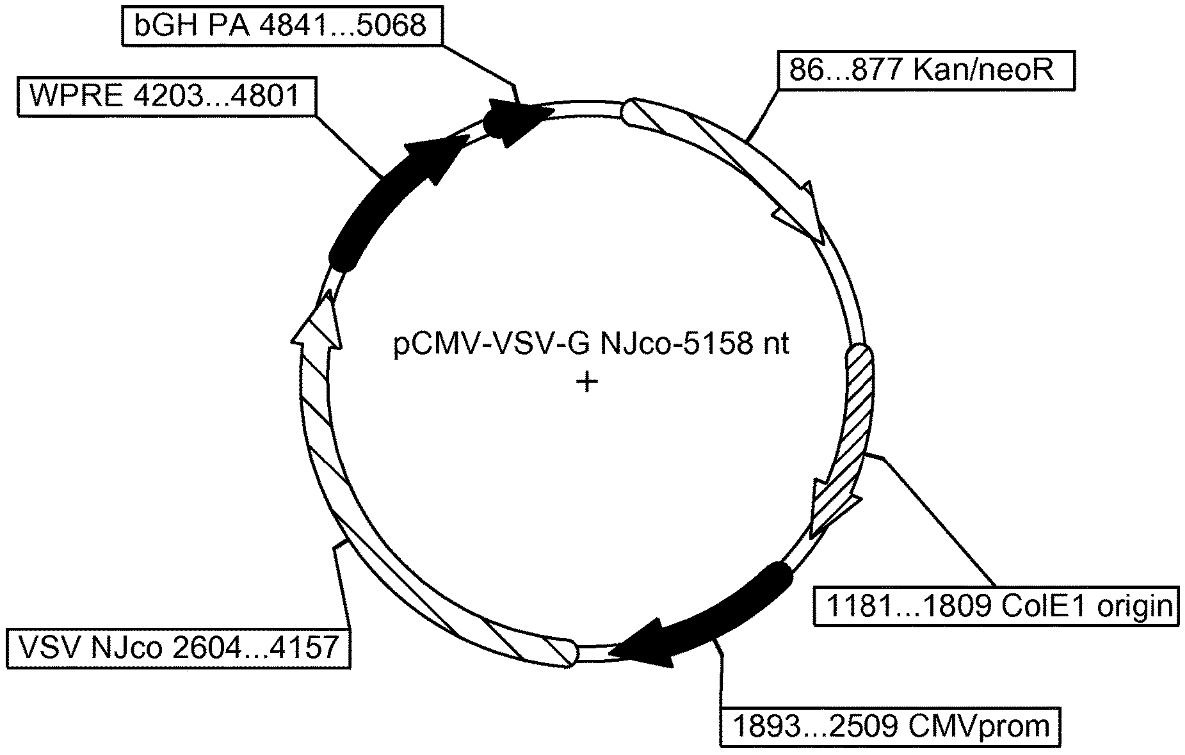

FIG. 23. alternative plasmid (to plasmid of FIG. 22) used to produce VSV-pseutdotyped lentiviral particles: encapsidation plasmid pCMV-VSV-NJco The envelope protein is the VSV-G of the New-Jersey strain and the coding sequence has been mouse-codon optimized.

The nucleotide sequence is provided as SEQ ID No.5.

Figure 24:
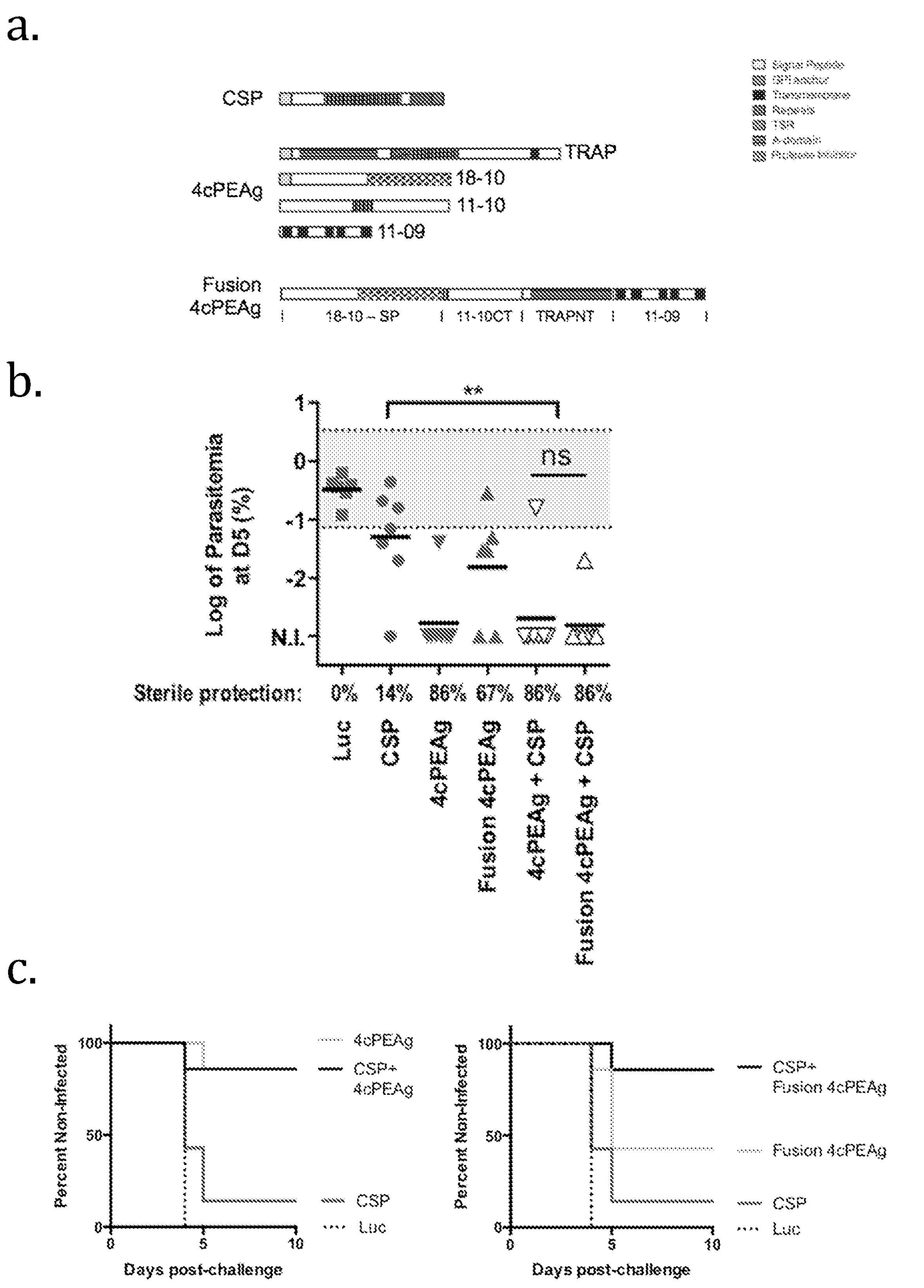

FIG. 24. Sterile protection induced by two immunization doses of the Fusion 4cPEAg+CSP.

(a) Scheme of antigens used in the experimental groups. CSP refers to the PbCSP. 4cPEAg refers to the combination of PbTRAP, antigen Pb18-10, antigen Pb11-10 and antigen Pb11-09. Fusion 4cPEAg refers to the chimeric antigen formed by the fusof the antigen Pb18-10 without its signal peptide (SP), followed by the protective domains 11-10CT and TRAPNT, and the antigen Pb11-09. GPI (glycosylphosphatidylinositol), TSR (thrombospondin type I repeat).

(b) Four weeks-old C57BL/6 mice (n=6-7 per group) were acclimated for 3 weeks and immunized intraperitoneally with $5\times10^5$ TU/antigen using non-concentrated $VSV^{NJ}$ B2M LPs. Four weeks after the first immunization, all groups received intraperitoneally $3\times10^7$ TU per respective antigen of concentrated VSVIND B2M LPs. Four weeks after the second immunization, mice were challenged with the microinjection of 5,000 GFP PbSPZs in the footpad. The graph shows the log of parasitemia of individual mouse at day 5 post-challenge. Traces represent the mean of the log parasitemia. The superior and inferior dotted lines delineate the 95% tolerance interval (grey box) of the control group established in the experiment of FIG. 11. NI (not infected). Sterile protection indicates the percentage of mice with no detectable parasitemia at day 10 post-challenge. (c) Profile of protection of challenged mice.

Figure 25:
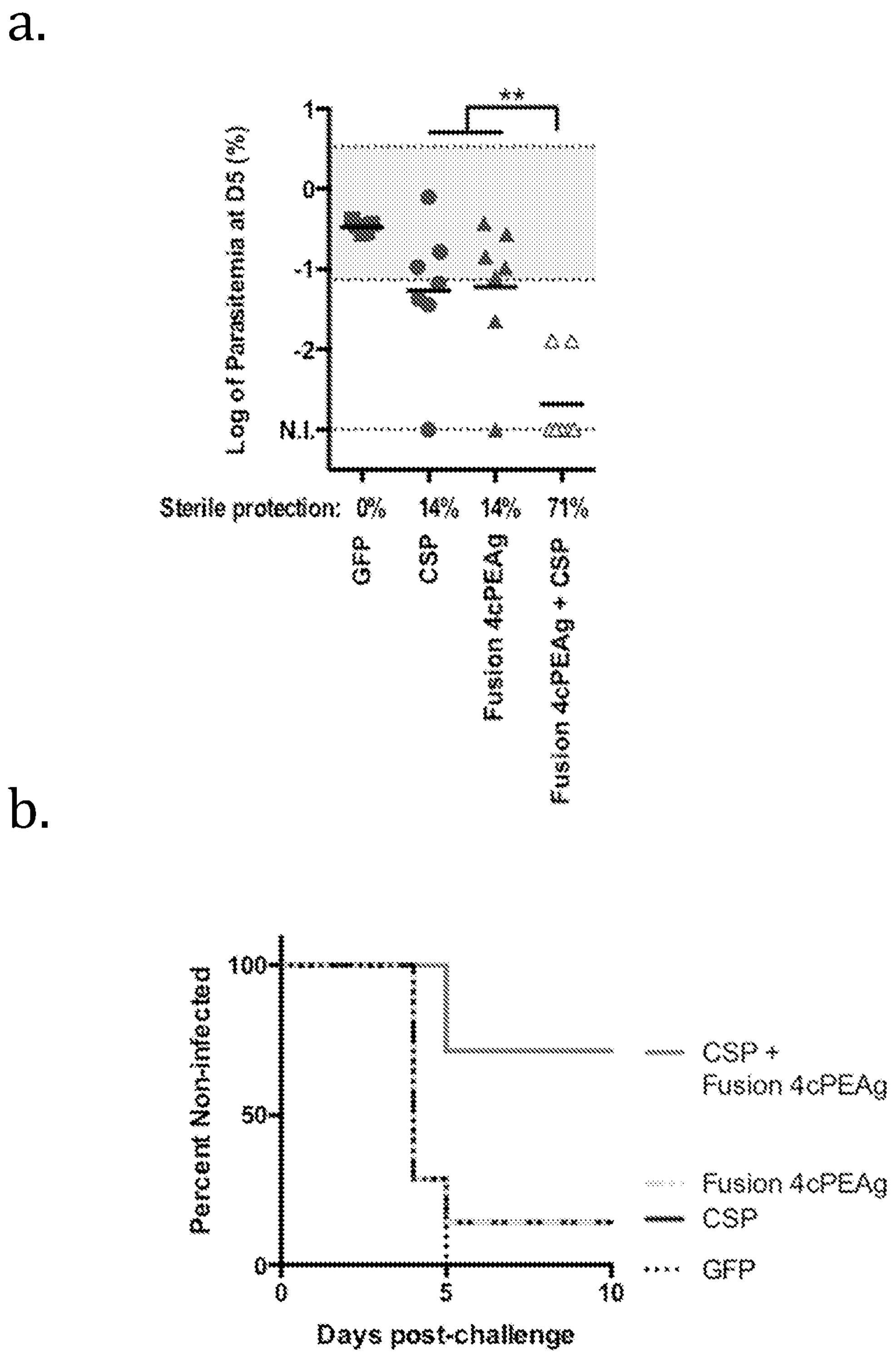

FIG. 25. Sterile protection induced by a single immunization doses of the Fusion 4cPEAg+CSP.

(a) Four weeks-old C57BL/6 mice (n=5-7 per group) were acclimated for 3 weeks and immunized intraperitoneally with $1\times10^7$ TU of GFP $VSV^{NJ}$ B2M LPs or $1\times10^7$ TU of CSP $VSV^{IND}$ B2M LPs, in the presence or not of $4\times10^7$ TU of Fusion 4cPEAg $VSV^{IND}$ B2M LPs. Four weeks after the first immunization, mice were challenged with the microinjection of 5,000 GFP PbSPZs in the footpad. The graph shows the log of parasitemia of individual mouse at day 5 post-challenge. Traces represent the mean of the log parasitemia. The superior and inferior dotted lines delineate the 95% tolerance interval (grey box) of the control group established in the experiment of FIG. 11. NI (not infected). Sterile protection indicates the percentage of mice with no detectable parasitemia at day 10 post-challenge. (b) Profile of protection of challenged mice.

Figure 26:
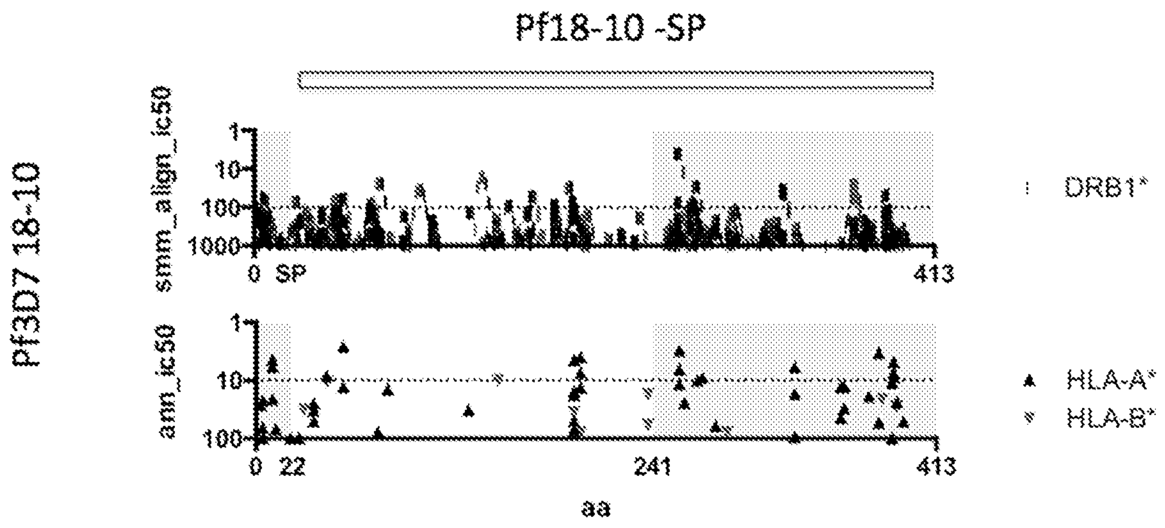
Figure 26:
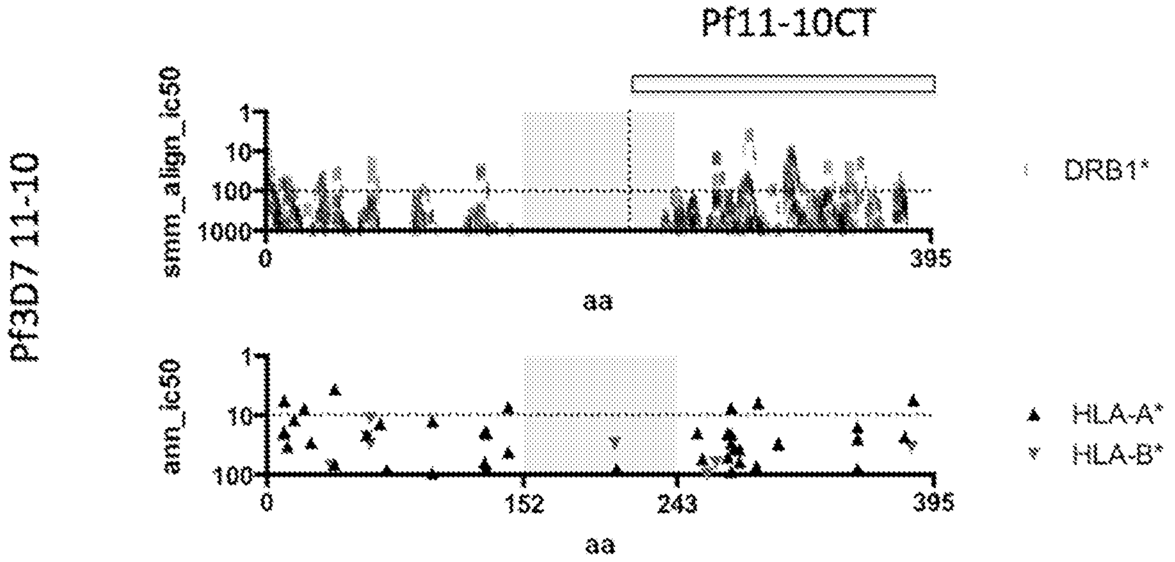
Figure 26:
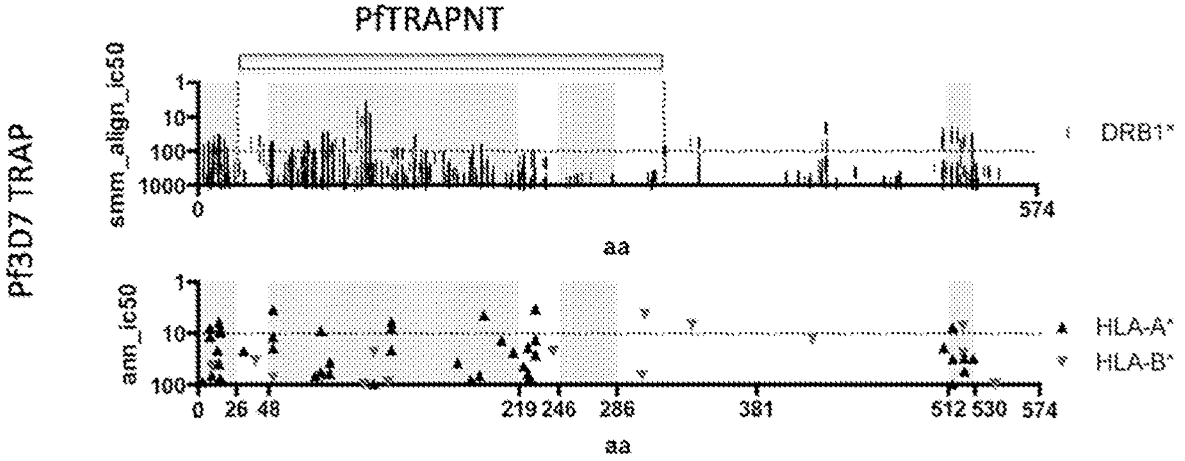
Figure 26:
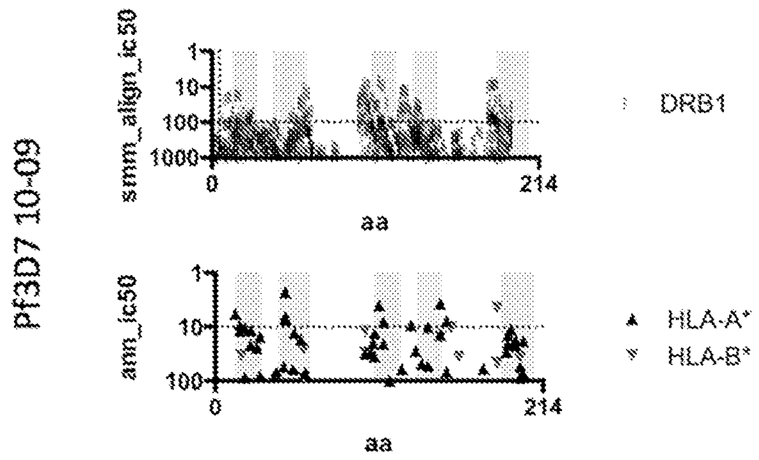
Figure 26:
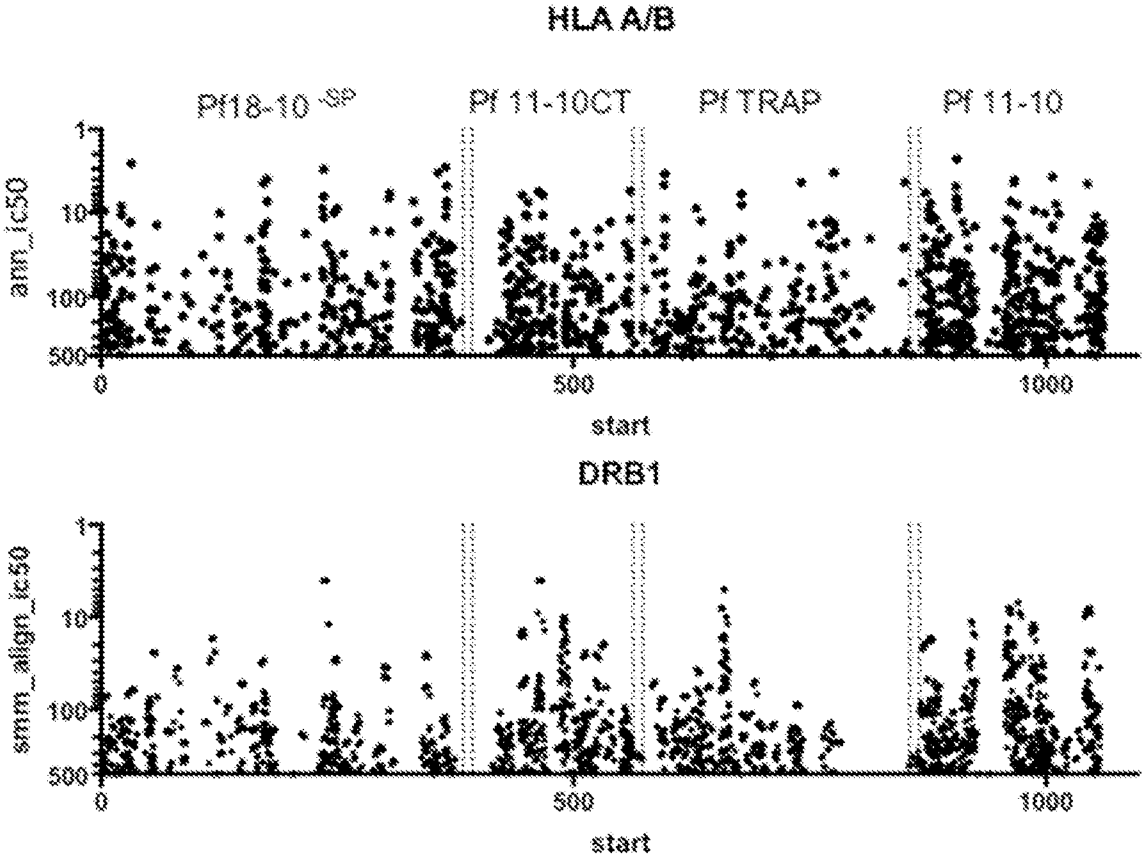

FIG. 26. *P. falciparum* 4cPEAg fusion.

Epitopes from the Pf 4cPEAgs predicted to bind to the Human Leukocyte Antigen (HLA) were identified using the immune epitope database (iedb; www.iedb. org). (a-c) Bars represent epitopes predicted to bind on the HLA-DRB1*01:01, *03:01, *04:01, *04:05, *07:01, *08:02, *09:01, *11:01, *12:01, *13:02 and *15:01. Triangles represent epitopes predicted to bind to the HLA A*01:01, *02:01, *02:03, *02:06, *03:01, *11:01, *23:01,*24:02, *26:01, *30:01, *30:02, *31:01, *32:01, *33:01, *68:01 and *68:02. Inverted triangles represent epitopes predicted to bind to the HLA-B*07:02, *08:01, *15:01, *35:01, *40:01, *44:02, *44:03, *51:01, *53:01, *57:01 and *58:01. White horizontal bars represent the regions used to design the Pf 4cPEAg fusion based on the content of class I and II predicted epitopes and structural/sequence similarity with the protective domains tested using *P. berghei*. Gray shadows represent conserved structural domains depicted in the FIGS. 12 and 24*a*. SP, signal peptide. Antigens are (a) Pf18-10, (b) Pf11-10, (c) PfTRAP, (d) Pf11-09. (e) Selected regions of the Pf 4cPEAgs (white bars) were chimerized generating the Pf 4cPEAg Fusion. The dotted lines represent the junction between two adjacent antigens/protective domains and show the absence of formation of neo-epitopes.

FIGS. 27 to 41: FIGS. 27 to 41 describe the DNA and respective amino acid sequences of the nucleic acids and polypeptides disclosed in the Table that follows under SEQ ID No. 95 to 124. The figures show the Kozak sequence (nucleotides 1-of SEQ ID NO:84), BamHI site (SEQ ID NO:86), and XhoI site (SEQ ID NO:87).

The following table provides the list and identification of the sequences contained in the sequence listing.

| SEQ ID No. | Sequence designation | Origin | Type |
|---|---|---|---|
| 1 | pTRIP CMV GFP | | DNA |
| 2 | pTRIP B2M GFP | | DNA |
| 3 | PACKAGING 8.74 PLASMID | | DNA |
| 4 | pCMV-VSV-INDco | | DNA |
| 5 | pCMV-VSV-Njco | | DNA |
| 6 | eGFP | | DNA |
| 7 | eGFP protein | | protein |
| 8 | AL11-Luciferase | | protein |
| 9 | AL11-Luciferase | | protein |
| 10 | circumsporozoite (CS) protein (CSP) mouseCO + Kozak | *P. berghei* ANKA strain | DNA |
| 11 | PbCSP (mouseCO + Kozak) | *P. berghei* ANKA strain | protein |
| 12 | PbCSP | *P. berghei* ANKA strain | protein |
| 13 | PfCSP humanCO + Kozak | *P falciparum* 3D7 strain | DNA |
| 14 | PfCSP (humanC0 + Kozak) | *P falciparum* 3D7 strain | protein |
| 15 | PfCSP | *P falciparum* | protein |
| 16 | PvCSP humanCO + Kozak | *P vivax* Sal-1 strain | DNA |
| 17 | PvCSP (humanCO + Kozak) | *P vivax* Sal-1 strain | protein |
| 18 | PvCSP | *P vivax* Sal-1 strain | protein |
| 19 | thrombospondin-related anonymous protein (PbTRAP) mouseCO + Kozak | *P. berghei* ANKA strain | DNA |

-continued

| SEQ ID No. | Sequence designation | Origin | Type |
|---|---|---|---|
| 20 | PbTRAP (mouseCO + Kozak) | *P. berghei* ANKA strain | protein |
| 21 | PbTRAP | *P. berghei* ANKA strain | protein |
| 22 | PfTRAP humanCO + Kozak | *P falciparum* 3D7 strain | DNA |
| 23 | PfTRAP (humanCO + Kozak) | *P falciparum* 3D7 strain | protein |
| 24 | PfTRAP | *P falciparum* | protein |
| 25 | PvTRAPhumanCO | *P vivax* Sal-1 strain | DNA |
| 26 | PvTRAP | *P vivax* Sal-1 strain | protein |
| 27 | PvTRAP | *P vivax* | protein |
| 28 | inhibitor of cysteine proteases (ICP) mouseCO + Kozak | *P. berghei* ANKA strain | DNA |
| 29 | PbICP (mouseCO + Kozak) | *P. berghei* ANKA strain | protein |
| 30 | PbICP | *P. berghei* ANKA strain | protein |
| 31 | PfICP humanCO | *P falciparum* 3D7 strain | DNA |
| 32 | PfICP | *P falciparum* 3D7 strain | protein |
| 33 | PfICP | *P falciparum* | protein |
| 34 | PvICP humanCO + Kozac | *P vivax* Sal-1 strain | DNA |
| 35 | PvICP (humanCO + Kozac) | *P vivax* Sal-1 strain | protein |
| 36 | PvICP | *P vivax* | protein |
| 37 | Bergheilysin-A-mouseCO + Kozak | *P. berghei* ANKA strain | DNA |
| 38 | Bergheilysin-A (1-777, mouse CO + Kozak) | *P. berghei* ANKA strain | protein |
| 39 | Bergheilysin entire ORF (1-1149) | P. berghei ANKA strain | protein |
| 40 | Falcilysin human CO + Kozak | *P falciparum* 3D7 strain | DNA |
| 41 | Falcilysin (human CO + Kozak) | *P falciparum* 3D7 strain | protein |
| 42 | Falcilysin | *P falciparum* 3D7 strain | protein |
| 43 | PvFalcilysin human CO + Kozak | *P vivax* Sal-1 strain | DNA |
| 44 | PvFalcilysin (humanCO + Kozak) | *P vivax* Sal-1 strain | protein |
| 45 | PvFalcilysin | *P vivax* Sal-1 strain | protein |
| 46 | Bergheilysin-B- mouseCO + Kozak + signal peptide (SP) | *P. berghei* ANKA strain | DNA |
| 47 | Bergheilysin-B (SP + 778-1149, mouse CO + Kozak) | *P. berghei* ANKA strain | protein |
| 48 | perforin like protein 1 (SPECT2) mouseCO + Kozak | *P. berghei* ANKA strain | DNA |
| 49 | PbSPECT2 (mouseCO + Kozak) | *P. berghei* ANKA strain | protein |
| 50 | PbSPECT2 | *P. berghei* ANKA strain | protein |
| 51 | PfSPECT2 human CO + Kozak | *P falciparum* 3D7 strain | DNA |
| 52 | PfSPECT2 (humanCO + Kozak) | *P falciparum* 3D7 strain | protein |
| 53 | PfSPECT2 | *P falciparum* | protein |
| 54 | PvSPECT2 human CO + Kozak | *P vivax* Sal-1 strain | DNA |
| 55 | PvSPECT2 (human CO + Kozak) | *P vivax* Sal-1 strain | protein |
| 56 | PvSPECT2 | *P vivax* | protein |
| 57 | GPI_P113 mouseCO + Kozak | *P. berghei* ANKA strain | DNA |
| 58 | Pb GPI_P113 (mouseCO + Kozak) | *P. berghei* ANKA strain | protein |
| 59 | Pb GPI_P113 | *P. berghei* ANKA strain | protein |
| 60 | PfP113 human CO + Kozak | *P falciparum* 3D7 strain | DNA |

-continued

| SEQ ID No. | Sequence designation | Origin | Type |
|---|---|---|---|
| 61 | PfP113 (human CO + Kozak) | *P falciparum* 3D7 strain | protein |
| 62 | P113 | *P falciparum* | protein |
| 63 | PvP113 human CO + Kozak | *P vivax* Sal-1 strain | DNA |
| 64 | PvP113 (human CO + Kozak) | *P vivax* Sal-1 strain | protein |
| 65 | P113 | *P vivax* | protein |
| 66 | PbAg40 mouse CO + Kozak | *P. berghei* ANKA strain | DNA |
| 67 | PbAg40 (mouse CO + Kozak) | *P. berghei* ANKA strain | protein |
| 68 | PbAg40 | *P. berghei* ANKA strain | protein |
| 69 | PfAg40 human CO + Kozak | *P falciparum* 3D7 strain | DNA |
| 70 | PfAg40 (human CO + Kozak) | *P falciparum* 3D7 strain | protein |
| 71 | Ag40 | *P falciparum* | protein |
| 72 | PvAg40 human CO + Kozak | *P vivax* Sal-1 strain | DNA |
| 73 | PvAg40 (human CO + Kozak) | *P vivax* Sal-1 strain | protein |
| 74 | PvAg40 | *P vivax* Sal-1 strain | protein |
| 75 | PbAg45 mouse CO + Kozak | *P. berghei* ANKA strain | DNA |
| 76 | PbAg45 (mouse CO + Kozak) | *P. berghei* ANKA strain | protein |
| 77 | PbAg45 | *P. berghei* ANKA strain | protein |
| 78 | PfAg45 human CO + Kozak | *P falciparum* 3D7 strain | DNA |
| 79 | PfAg45 (human CO + Kozak) | *P falciparum* 3D7 strain | protein |
| 80 | PfAg45 | *P falciparum* | protein |
| 81 | PvAg45 human CO + Kozak | *P vivax* Sal-1 strain | DNA |
| 82 | PvAg45 (human CO + Kozak) | *P vivax* Sal-1 strain | protein |
| 83 | PvAg45 | *P vivax* | protein |
| 84 | Kozak consensus sequence | | DNA |
| 85 | Kozak consensus sequence | | DNA |
| 86 | BamHI site | | DNA |
| 87 | XhoI site | | DNA |
| 88-94 | CD8 T cell epitopes | | protein |

DNA and amino acid sequences used in the chimeric fusion antigenic polypeptides for *P. berghei* and *P. falciparum*

| SEQ ID N. | Description of sequence |
|---|---|
| 95 | DNA sequence of PD *Plasmodium berghei* ANKA 18-10NT—mouse codon optimized, with adaptors and Kozak sequence (372 bp) |
| 96 | Amino acid sequence of PD *Plasmodium berghei* ANKA 18-10NT (117 aa) |
| 97 | DNA sequence of PD *Plasmodium berghei* ANKA 18-10CT—mouse codon optimized, with adaptors and Kozak sequence (528 bp). |
| 98 | Amino acid sequence of PD *Plasmodium berghei* ANKA 18-10CT (169 aa) |
| 99 | DNA sequence of PD *Plasmodium falciparum* 3D7 18-10 minus Signal Peptide (SP⁻), human codon optimized, with adaptors and Kozak sequence (1197 bp). |
| 100 | Amino acid sequence of PD *Plasmodium falciparum* 3D7 18-10-SP (392 aa) |
| 101 | DNA sequence of PD *Plasmodium berghei* ANKA 11-10CT—mouse codon optimized, with adaptors and Kozak sequence (528 bp). |

-continued

| SEQ ID N. | Description of sequence |
|---|---|
| 102 | Amino acid sequence of PD *Plasmodium berghei* ANKA 11-10CT (169 aa) |
| 103 | DNA sequence of PD *Plasmodium falciparum* 3D7 11-10CT—human codon optimized, with adaptors and Kozak sequence (561 bp). |
| 104 | Amino acid sequence of PD *Plasmodium falciparum* 3D7 11-10CT (180 aa) |
| 105 | DNA sequence of PD *Plasmodium berghei* ANKA TRAP NT—mouse codon optimized, with adaptors and Kozak sequence (747 bp). |
| 106 | Amino acid sequence of PD *Plasmodium berghei* ANKA TRAP NT (242 aa) |
| 107 | DNA sequence of PD *Plasmodium falciparum* 3D7 TRAP NT—human codon optimized, with adaptors and Kozak sequence (903 bp). |
| 108 | Amino acid sequence of PD *Plasmodium falciparum* 3D7 TRAP NT (294 aa) |
| 109 | DNA sequence of PD *Plasmodium berghei* ANKA 11-09—mouse codon optimized, with adaptors and Kozak sequence (654 bp). |
| 110 | Amino acid sequence of PD *Plasmodium berghei* ANKA 11-09 (211 aa) |
| 111 | DNA sequence of PD *Plasmodium falciparum* 3D7 11-09—human codon optimized, with adaptors and Kozak sequence (642 bp). |
| 112 | Amino acid sequence of PD *Plasmodium falciparum* 3D7 11-09 (207 aa) |
| 113 | DNA sequence of *Plasmodium berghei* ANKA Fusion of PDPb18-10NT and PD Pb18-10CT—mouse codon optimized + ATG (852pb) |
| 114 | Amino acid sequence of *Plasmodium berghei* ANKA Fusion of PD Pb18-10NT and PD Pb18-10CT (284aa) |
| 115 | DNA sequence of *Plasmodium berghei* ANKA Fusion 4cPEAg—mouse codon optimized, with adaptors and Kozak sequence (2715 bp). |
| 116 | Amino acid sequence of *Plasmodium berghei* ANKA Fusion 4cPEAg (898 aa). |
| 117 | DNA sequence of *Plasmodium falciparum* 3D7 Fusion 4cPEAg—human codon optimized, with adaptors and Kozak sequence (3234 bp). |
| 118 | Amino acid sequence of *Plasmodium falciparum* 3D7 Fusion 4cPEAg (1070 aa) |
| 119 | DNA sequence of *Plasmodium berghei* Fusion 5cPEAg—mouse codon optimized, with adaptors and Kozak sequence (3597 bp). |
| 120 | Amino acid sequence of *Plasmodium berghei* Fusion 5cPEAg SP⁻ (1192 aa) |
| 121 | DNA sequence of *Plasmodium berghei* Fusion 5cPEAg SP⁺—mouse codon optimized, with adaptors and Kozak sequence (3663 bp). |
| 122 | Amino acid sequence of *Plasmodium berghei* Fusion 5cPEAg SP⁺ (1214 aa) |
| 123 | DNA sequence of *Plasmodium berghei* ANKA CSP—mouse codon optimized, with adaptors and Kozak sequence (1044 bp). |
| 124 | Amino acid sequence of *Plasmodium berghei* ANKA CSP (341 aa) |

Additional information relating to some of the sequences disclosed in the above table are provided in the table below.

| SEQ ID | GenBank | strain | pubmed |
|---|---|---|---|
| 15 | BAM84930.1 | *Plasmodium falciparum* isolate Pal97-042 origin: Philippines | 23295064 |
| | ACO49323 | *Plasmodium falciparum*" isolate A5 origin: Thailand | 19460323 |
| 18 | AAA29535.1 | *P. vivax* (strain Thai; isolate NYU Thai) origin: Thailand | 2290443 |
| 24[(1)] | EWC74605.1 | *Plasmodium falciparum* UGT5.1 strain origin: Uganda | |
| 27 | AIU97014.1 | *Plasmodium vivax* isolate = "TMS38" origin: Thailand | |

-continued

| SEQ ID | GenBank | strain | pubmed |
|---|---|---|---|
| 36[(3)] | KMZ87332.1 | *Plasmodium vivax* Brazil I strain | |
| 56 | KMZ82648.1 | *Plasmodium vivax* India VII | |
| 65 | KMZ78214.1 | *Plasmodium vivax* India VII | |
| 83 | KMZ90984.1 | *Plasmodium vivax* Mauritania I | |

[(1)]https://www.ncbi.nlm.nih.govhiosample/SAMN01737342
[(2)]https://www.ncbi.nlm.nih.gov/biosample/SAMEA2394724
[(3)]https://www.ncbi.nlm.nih.gov/biosample/SAMN00710434

EXAMPLES

To approach the complex problem of identifying protective antigens, the inventors devised a functional screening to identify and combine novel PE protective antigens using a rodent malaria model where mice (C57BL/6) are extremely susceptible to *Plasmodium berghei* (Pb) sporozoite infection. In this model, sterilizing protection induced by live irradiated sporozoites is mediated by antibodies and mainly by CD8 T cell responses against sporozoites and liver stages, respectively. The inventors' screening strategy was designed based on four main features: i) parameterized selection of 55 PE antigens based on abundance, orthology, predicted topology and function, ii) synthesis of codon-optimized antigens to avoid AT-rich plasmodial sequences and maximize the expression in mammalian cells, iii) immunization using HIV-based lentiviral vector that elicits strong humoral and cellular responses[11,12] and iv) measurement of protection after a stringent challenge of sporozoites inoculated subcutaneously in the immunized mice.

1. Setting Up the Parameters of the Screening.

In a proof-of-concept experiment aimed at validating the viability of the strategy to screen antigens at a medium-throughput, the inventors ordered mouse-codon optimized synthetic genes of Pb CSP (SEQ ID No. 11), a known protective antigen, and of more 4 other sporozoite antigens (Celtos, SPECT, HSP20 and Ag13), which were previously correlated with protection[13]. The synthetic plasmodial genes were cloned in to the pTRIP vector plasmid, which drives their expression in mammalian cells via the immediate-early cytomegalovirus promoter (CMV) and the post-transcriptional regulatory element of woodchuck hepatitis virus (WPRE) (FIG. 1, SEQ ID No. 1). These two elements assure a strong expression of the antigen in a wide variety of mouse cells in vivo. HIV-1 derived lentiviral particles were produced by transient co-transfection of HEK 293T cells with three helper plasmids encoding separate packaging functions, the pTRIP vector plasmid containing the synthetic plasmodial gene, the envelope expression plasmid encoding the glycoprotein G from the Vesicular Stomatitis Virus, Indiana ($VSV^{IND}$) or New Jersey ($VSV^{NJ}$) serotypes, and the p8.74 encapsidation plasmid (FIG. 1). This co-transfection generates integrative but replication-incompetent pseudotyped lentiviral particles capable of transducing dividing and non-dividing cells—including dendritic cells—and inducing potent cellular[6] and humoral[7] memory responses. The particles were collected 48 hours after co-transfection and each batch of vector were titrated in HeLa cells by quantitative PCR. This functional titration assay gives the concentration of particles capable to transfer one copy of the gene per cell and will be expressed in Transducing Units (TU)/mL. Plasmid sequences are shown in the figures and their sequences are provided in the sequence listing.

Groups of five mice were immunized with a single intra-muscular dose of 5e7 TU of ultracentrifugation-concentrated $VSV^{IND}$ pseudotyped lentiviral particles (LPs). Thirty days after immunization, mice were challenged with 10,000 bioluminescent sporozoites inoculated sub-cutaneously in the footpad. Two days later, the parasite load in the liver was measured by bioluminescence. Surprisingly, CSP-immunization decreased 15×-fold the parasite load in the liver after a challenge using 10,000 bioluminescent sporozoites, versus a 5×-fold decrease in animals immunized intravenously with 50,000 irradiated sporozoites, our golden standard of protection (FIG. 2). This preliminary and promising result validated the high performance of the present method to functionally identify new protective antigens and showed the feasibility to scale-up our test samples.

The inventors next aimed at the transposition of these optimal experimental conditions to those of a larger screening. This transposition included the validation of the use of non-concentrated LPs, the choice of the best promoter driving the expression of the plasmodial antigens, and the dose of immunization.

The first parameter tested was the use of non-concentrated, instead of concentrated LPs, to avoid a costly and time consuming ultracentrifugation concentration step in the protocol of LP production, which requires large volumes of non-concentrated LP suspensions. FIG. 3 shows that there is no significant difference between protection induced by the same dose ($5\times10^7$ TU) of concentrated LPs injected intramuscularly (CS im c, 50 μL) and non-concentrated LPs injected intraperitoneally (CS ip nc, 700 μL). Protection was measured by reduction in the liver infection, as assessed by bioluminescence after a challenge of 5,000 sporozoites injected subcutaneously 30 days following immunization. As negative control of protection the inventors used mice immunized with Pb Ag13, determined previously as a non-protective antigen (FIG. 1). Next two promoters were tested to identify which one induced the best protection using the codon optimized Pb CSP. The inventors compared the use of the strong and constitutive cytomegalovirus (CMV) promoter versus a human beta-2 microglobulin (B2M) promoter, which direct gene expression in many cell types, particularly in dendritic cells. FIG. 4 shows that CSP-induced protection was slightly better, although not statistically significant, using the B2M promoter at an immunization dose of $1\times10^7$ TU of non-concentrated LP. Therefore the inventors further adopted this promoter in our constructs.

During this period of optimization the inventors observed some variations in the CSP-induced protection using the same stock of LPs, as can be seen in the FIG. 4. The inventors asked if this variability could be due to the process of mouse acclimation, including the modification of mouse microbiota. To test this hypothesis a group of mice purchased from Elevage Janvier (4 weeks-old) was reared in the animal facility for 3 weeks before immunization (group old). A second group of mice (7 weeks-old) was purchased and put in cages 3 days before the immunization (group new). Both groups were intraperitoneally immunized with $1\times10^7$ TU of non-concentrated LPs. As shown in the FIG. 5, mouse acclimation of 3 weeks resulted in a significant and more homogeneous protection when compared to 3 days of acclimation. Consequently, the inventors adopted this period of acclimation in all our subsequent experiments.

Next, the best protective immunization dose was tested, ranging from $1\times10^8$ to $1\times10^5$ TU of B2M CSP non-concentrated LPs. As shown in FIG. 6, significant protection was observed using $10^7$ and $10^8$ TU, and the best protective activity was observed using an immunization dose of $1 \times 10^7$ TU. In this experiment the inventors also observed a gradual loss of SPZ infectivity over time, as evidenced in the GFP groups, due to the use of a single SPZ stock to challenge all animals. To reduce the multiple shocks of temperature due to the manipulation of the stock tube, kept on ice between injections, the inventors prepared a SPZ stock for each group in the subsequent challenges and this variation disappeared.

In summary, an immunization protocol was set up based on CSP that relied on a single intraperitoneal injection of 107 TU of non-concentrated $VSV^{IND}$ B2M LP in C57BL/6 mice of 7 weeks-old, acclimated for 3 weeks in the animal facility. In the pooled data, this protocol leaded in average to a ~5-fold decrease in the parasite liver load, as assessed by bioluminescence imaging, using a subcutaneous challenge of 5,000 luciferase-expressing SPZ.

However, this bioluminescent method of detection of parasites presents some disadvantages such as the use and associated costs of anesthesia and luminescent substrate, limited capacity of analysis of a few animals per acquisition, being time-consuming and not sensible enough to predict sterile protection. Therefore, the inventors decided to use fluorescent parasites to check protection by measuring parasitemia at day 4, 5, 6 and 10 post-inoculation by flow cytometry. The inventors analyze at least 100,000 red blood cells, which gives the sensibility to detect a parasitemia of 0.001%. At day 4 to 6, parasites grow exponentially in the blood therefore the log transform of parasitemia can be fitted using a linear regression where the slope represents the time of parasite replication per day. Consequently, the inventors use this parameter to determine if the immunization impacts the parasite growth in the blood. For quantifying protection, the inventors used the log of parasitemia at day 5 post inoculation. This represents an indirect measure of liver infection and it is more robust than the measure at day 4 because more events of infected blood cells are registered. Finally the inventors defined that immunized mice are sterile protected if infected red blood cells are not detected after 10 days post inoculation. After defining the protocol of immunization and the method for the quantification of parasite infection the inventors started to screen the protective activity of down-selected antigens.

2. Parameterized Selection of Antigens

By merging proteomic and transcriptomic data using PlasmoDB (www.plasmodb. org), the inventors identified ~9000 genes expressed in plasmodial pre-erythrocytic stages—salivary gland sporozoites and liver-stages—of three different plasmodial species, with 3654 syntenic orthologs in *Plasmodium falciparum* (Pf), the most lethal human-infecting plasmodial species. By analyzing the repertoire of pathogen transcripts, as inferred by the amount of expressed sequence tags (ESTs) obtained in cDNA libraries of different stages and species of malaria parasites, the inventors have observed that ~50% of the total amount of ESTs are coming from only ~10% of genes represented in these libraries, corresponding to approximately 100 genes in these libraries (FIG. 7). Therefore, by focusing on the ~100 most abundant transcribed genes the inventors could target about 50% of the putative (to be translated) antigenic mass of a given parasite stage. Accordingly, the inventors selected ~50 abundantly transcribed genes coding for conserved proteins with high probability of being expressed/presented on the surface of the parasite/infected cell, giving priority to candidates containing T cell epitopes predicted by IEDB MHC binding algorithm (http: // tools.iedb.org/mhci/). A Kozak consensus sequence, a translational start site, was added to these down-selected genes, which were then mammalian codon-optimized and synthesized by MWG Eurofins (listed in the figures). These synthetic codon-optimized down-selected plasmodial genes were then cloned into the B2M pTRIP plasmid and produced as non-concentrated $VSV^{IND}$ LPs.

3. First Screening of Protective Antigens Using a Single Dose of LPs

Usually, 6-10 plasmodial antigens were tested by experiment, with a negative (GFP) and positive (CSP) control of protection. After three weeks post-immunization, the immune-sera were tested on permeabilized and non-permeabilized sporozoites, allowing the determination of (i) the efficiency of the host humoral response and therefore the immunogenicity of the lentivirus-delivered antigen, and (ii) the localization of the parasite antigen (surface vs intracellular). As shown in the FIG. 8, where the inventors immunized mice with putative GPI-anchored antigens, surface antigens were identified by flow cytometry and immunofluorescence (CSP and 9-6). The sera of GFP and CSP group served, respectively, as positive control for intracellular and surface antigen localization.

Four weeks post-immunization the animals were challenged with 5,000 GFP-expressing sporozoites, microinjected in the footpad of immunized mice. Parasitemia was determined by flow cytometry. To define protection, parasitemia of all GFP groups (day 5 post-infection, n=35) was log transformed, pooled and the 95% tolerance interval was calculated (FIG. 9). All animals below the inferior limit of the tolerance interval, which represents a ~8-fold decrease in parasitemia compared to the mean log of parasitemia of the GFP group, were considered protected. As positive control, 43% of animals (15/35) were protected by CSP immunization with a mean decrease of ~5 fold in comparison to the GFP group. 9% of them (3/35) became sterile protected after sporozoite challenge.

In the first set of 43 antigens tested (FIG. 9), we identified 9 PE antigens that protected at least one out of five immunized mice (black circles; 07-03, 09-06, 10-05, 10-10, 12-03, 12-04, 12-05, 12-07 and 13-08). Three of them were also identified as sporozoite surface antigens (09-06, 10-05 and 10-10).

To verify the robustness of our screening, the inventors selected 4 protective antigens (CSP, 09-06, 10-05 and 07-03), 6 non-protective antigens (GFP, 09-07, 07-05, 07-06, 06-06 and 10-06), and instead of only one immunization dose, the inventors administered one dose of $5 \times 10^5$ TU of non-concentrated $VSV^{NJ}$ B2M LPs and one month later, a second dose of $1 \times 10^7$ TU of $VSV^{IND}$ B2M LPs. As shown in the FIG. 10, the inventors observed three patterns of infection profile when the inventors compared one (circles, data from FIG. 9) and two immunization doses (squares, PB). For the non-protective antigens GFP, 09-07 and 07-05, the second dose of LP did not change the profile of infection, as expected. For the protective antigens CSP (***$P<0.001$), 09-06, 10-05 and 07-03, the second dose of LP increased the number of protected mice and/or decreased the average parasitemia, also, as expected. Notably, the non-protective antigens 07-06, 06-06 and 10-06 as assessed by one dose of LP immunization, showed a strong protective activity, including a sterile protected mice (PB 7-6), when administered twice in mice.

These results validated some of our protective antigens detected with a single immunization dose, but also showed that some good protective antigens were not detected in our first screen, leading to the decision of repeating the screening using two immunization doses.

4. Second Screening of Protective Antigens Using Two Doses of LP

By functionally screening the protective activity of 55 down-selected plasmodial PE antigens using the protocol of two immunization doses, the inventors identified 16 antigens that protected at least one immunized mice per group. Among these 16 antigens, 7 of them (black circles/bars in the FIG. 11) conferred significant protection when compared to animals immunized with the GFP, both when analysing the number of protected mice (Fisher's Exact test) or the mean of the log parasitemia (ANOVA).

All of them presented a similar or an inferior protective activity when compared individually to our standard of protection, the CSP (FIG. 11). Five of them are molecules with assigned function (11-05, 11-06, 11-07, 30-03 and 18-10) and two are proteins with no predicted function (11-09 and 11-10). The structure of these Pb protective antigens is shown in the FIG. 12 and the alignment of these proteins with their respective orthologs from human-infecting parasites, *P. falciparum* (Pf) and *P. vivax* (Pv), and macaque-infecting parasite *P. cynomolgi*, is represented in the FIG. 13. As shown in table I, the percentage of identical amino acids between orthologs varied from 75 to 38% (Pb vs Pf), 78 to 33% (Pb vs Pv) and 79 to 26% (Pf vs Pv). The most conserved genes (>50% identity) are 30-03, 11-09, 11-10 and 11-06 orthologs.

Antigens with divergent repetitive sequences are penalized in the alignment by insertional gaps, presenting less percentage of identity.

TABLE I

Percent Identity Matrix created by CLUSTAL 2.1. Amino acid sequence of Pb antigen swere pBlasted against Pf and Pv taxids (organism) and the best matched sequence was used to align the orthologous proteins using MUSCLE(http://www.ebi.ac.uk/Tool/msa/muscle). The table shows the percentage of identical amino acids between species. Raw data is presented in the figures

| | Amino acid identity (%) | | |
|---|---|---|---|
| Antigen | Pb/Pf | Pb/Pv | Pf/Pv |
| 30-03 | 74.65 | 77.90 | 73 |
| 11-09 | 66.19 | 66.19 | 79.05 |
| 11-06 | 64.92 | 63.40 | 64.44 |
| 11-10 | 56.94 | 50.15 | 62.28 |
| CSP | 42.06 | 33.53 | 26.36 |
| 18-10 | 39.60 | 41.23 | 49.30 |
| 11-05 | 38.75 | 44.67 | 42.86 |
| 11-07 | 37.53 | 33.42 | 46.30 |

In a decreasing order of protection the first antigen identified is TRAP[14] (thrombospondin related anonymous protein; 11-05) (SEQ ID No 20 and 21), which validated our method of screening since immunization with TRAP is known to induce protection both in rodents[15] and humans[16]. TRAP is a type I transmembrane protein harbouring two extracellular adhesive domains, a von Willebrand factor type A domain and a thrombospondin type 1 domain, followed by a proline-rich repetitive region. TRAP is stored in micronemal secretory vesicles and following parasite activation, the protein is translocated to the surface of sporozoites where it serves as a linker between a solid substrate and the cytoplasmic motor of sporozoites. Intriguingly, anti-TRAP antibodies do not impair parasite motility and infectivity[17] CD8+ T cells seem to mediate the protection mediated by TRAP immunization[10,15,16,11].

The second protective antigen identified is an inhibitor of cysteine protease (ICP, 18-10)[19] (SEQ ID No 29, 30). ICP seems to be involved in the motility and infectivity capacity of sporozoites via the processing of CSP[20,21], as well as, in the parasite intra-hepatic development[22]. Although the protein does not present structural signatures of membrane localization, there is evidence that the protein is located on the surface of sporozoites[19,20]. Opposing results are published regarding the secretion of the protein following parasite activation[21,22]. Similarly, there are contradictory results regarding the inhibition of host cell invasion by sporozoites in vitro in the presence of anti-ICP immune sera[20,23].

The third protective antigen identified is a metallopeptidase (Falcilysin/Bergheilysin, 30-03)[24] (SEQ ID No 38 for Bergheilysin A, No 47 for Bergheilysin B, and No 39 for the entire Bergheilysin ORF). This protease seems to be involved in the catabolism of hemoblobin in the parasite blood stages[25]. A H-$2K^b$-restricted CD8 T cell epitope was recently described during the parasite blood infection[25] suggesting that CD8 T cells could mediate the protection elicited by the antigen 30-03 during the hepatic infection.

The fourth protective antigen is a GPI-anchored protein (P113, 11-07) (SEQ ID No.58 and 59) initially described in blood stages[16] and also expressed in PE stages. P113 seems to be important for liver infection, dispensable for blood infection, but its precise function is unclear[17].

The fifth antigen is the pore-forming like protein SPECT2 (11-06)[28] (SEQ ID No 49 and 50). This protein has a membrane attack complex/perforin (MACPF) domain and is involved in the sporozoite cell traversal activity, being important for the progression of sporozoites in the dermis[29] and survival to phagocytosis in the liver[30].

The sixth antigen identified is a hypothetical protein that the inventors called 11-09 or Ag40 (SEQ ID No 67 and 68). This protein has 4-5 annotated transmembrane domains. Deletion of the gene coding for the antigen 11-09 caused impairment of Pb parasite development in the liver.

The seventh antigen is also a hypothetical protein that the inventors called 11-10 or Ag45 (SEQ ID No 76 and 77). This protein doesn't have annotated domains, but possesses a central region with negatively charged amino acids. Recently the 11-10 ortholog of *Plasmodium yoelii*, another rodent-infecting plasmodial species, was also identified as a protective antigen[21]. The deletion of the gene coding for the antigen 11-blocked the Pb sporozoite invasion of salivary glands and completely abolished the capacity of sporozoites to infect the liver.

To determine if CSP based protection could be additively or synergistically improved by the combination of antigens, the inventors assessed the protection elicited by a sub-optimal dose of CSP ($5\times10^5$ TU of $VSV^{NJ}$/ $5\times10^6$ TU of $VSV^{IND}$ B2M LPs) in the absence or presence of a usual dose of protective antigens ($5\times10^5$ TU of $VSV^{NJ}$/$1\times10^7$ TU of $VSV^{IND}$ B2M LPs). This protection induced by CSP+ protective antigens was compared to the protection elicited by these antigens alone (data from FIG. 11). As negative control the inventors used animals immunized with the usual dose of GFP LPs. FIG. 14 shows that 4 antigens when combined with a sub-optimal dose of CSP (CSP+11-03, +11-10, +11-07 and +11-05, triangles) did not change the average of protection when compared to the protective activity elicited by these antigens administered alone. For two antigens, the antigen combination (CSP+11-09 and CSP+11-06) showed a tendency of better protection (~10 fold), but not statistically significant.

5. Identification of Multi-Antigenic Formulations Capable of Sterilizing Sporozoite Infection Via a CD8+ T Cell Response Since testing all possible combinations of antigens was technically unfeasible, the inventors decided to evaluate the protection elicited by the combination of these multiple protective antigens. Remarkably, two immunizations of mice with the combination of CSP and 6 of these antigens (11-05, 11-06, 11-07, 11-09, 11-10, 18-10) elicited sterile protection in the vast majority of challenged animals (7PEAg, 86-100%, FIG. 15). This percentage of sterile protection was far superior to the protection conferred by CSP in the same experimental conditions (0-14%). Depletion of CD8+ cells (α-CD8) just before the challenge, but not of CD4+ cells, decreased this protection to the level of that induced by CSP, suggesting that CD8+ T cells mediate the extra-protection elicited by the addition of these 6 PE antigens.

The same protective efficacy was observed using only a single immunization for the 7PEAg or for the 7PEAg+30-03 (FIGS. 16*a* and 16*b,* 8PEAg), as well as, the dependence on CD8+ T cells for the sterilizing immunity of 8PEAg (FIGS. 16*b*). Since the antigen 30-03 is a large molecule and did not improve sterile protection when administered with the 7PEAg, the inventors excluded it from further analysis.

6. Design of a Chimeric Antigen Containing the Protective Domains of Down-Selected PE Antigens To determine a minimal antigenic composition capable of eliciting this additional protective CD8+ T cell response, the inventors first identified the antigens whose protective activity was dependent on these T cells. Protection induced by two immunizations using TRAP, 18-10 and 11-09 was significantly reduced after depletion of CD8+ cells, as shown in the FIG. 17*b*. Protection induced by two immunizations using 11-10 was reduced after depletion of CD8+ cells but it was not statistically significant (FIG. 17*b*). Therefore the inventors grouped CSP with the CD8+ dependent protective antigens, TRAP, 18-10 and 11-09 and added separately 11-10, 11-07 and 11-06 to identify a minimal antigenic combination capable of sterile protect immunized animals like the complete combination of antigens. As shown in FIG. 17*a*, the combination of 5 antigens, CSP+TRAP, 18-10, Ag40 and Ag45 induced comparable level of sterile protection elicited by the combination of the 7PEAg.

In order to combine the protective domains of each of these 5 antigens in a single chimeric molecule and thus avoid the costs associated with the production and delivery of five different antigens, the inventors mapped the protective regions of each antigen according to the localization of predicted epitopes binding to MHC class I molecules (FIG. 17*c* and 18) and structural-functional conserved motifs (FIG. 12, 13, 17*c* and 18).

As shown in the FIG. 17*c*, all tested domains presented either a better (11-10CT) or similar protective activity when compared to the entire antigen. The level of mean protection elicited by the domains of antigens inducing protective CD8+ T cells correlated with the score ($P<0.01$) or affinity ($P=0.01$) of CD8+ T cell epitopes respectively predicted by SYFPEITHI and IEDB (SEQ ID NO:89 to SEQ ID NO:94) (FIGS. 17*c* and 17*d*). Importantly, the mapping of protective domains allowed the reduction of ~2000 basepairs in the final chimeric PE antigen construct. Due to its small size, Ag40 was not split in domains and the data presented in the FIG. 17*c* comes from the experiment showed in the FIG. 11.

Analysis of the distribution of epitopes of Pb antigens predicted to bind to MHC class I molecules of C57BL/6 mice (H2-$K^b$, H2-$D^b$) or of the Pf orthologues predicted to bind to HLA A02:01, a high prevalent human HLA allele, revealed that most of predicted good binders are clustering in the regions that are conserved among different plasmodial species (Pb, Pc, Pv and Pf, FIG. 18). This renders possible the utilization of the Pb protective regions mapped in the FIG. 17 to select the correspondent regions in the Pf orthologues. In addition, the inventors validated the binding of the best predicted Pf epitopes to the HLA A02:01 class I molecule using the REVEAL® binding assay developed by Proimmune, which allows the quantification of the binding and stabilization of the complex formed by the tested peptide, HLA A02:01 and β2-microglobulin (FIG. 18).

In summary, using a parameterized selection of antigens, a screening based on lentiviral vaccination and a direct measurement of protection in vivo against a stringent sporozoite challenge, the inventors identified 8 protective antigens, including the vaccine candidates CSP and TRAP, out of 55 tested antigens. All these 8 antigens are conserved across several plasmodial species. Remarkably, immunization using a combination of seven or eight of these antigens elicited sterile protection in the vast majority of challenged mice, either using one or two immunizations. More importantly, this protection was far superior than the one elicited by CSP, so far the best protective PE antigen. Depletion of CD8+ T cells abolished sterilizing immunity, indicating that these cells are essential for this protective phenotype, similarly to the protection conferred by irradiated sporozoites. A minimal combination of 5 of these antigens was also capable of eliciting sterile protection in most of challenged animals. Mapping of the protective domains of these 5 antigens allowed the design of a chimeric antigen containing the fused protective domains of these 5 down-selected antigens. The human-infecting parasite orthologs of these protective antigens, or of their protective domains are potential candidates for being used in the development of a malaria vaccine formulation containing multiple protective antigens or multiple protective domains fused in a single molecule.

Chimeric antigenic polypeptide as a fusion of Protective Domains of *Plasmodium* antigens and immunogenic response Immunization using a combination of CSP and 6 or 7 of screened conserved protective antigens delivered by lentiviral particles, were shown to confer sterile protection in ≈85% of mice challenged with 5,000 sporozoites (FIG. 16). Extra-protection induced by the addition of these antigens to CSP was abolished after depletion of CD8+ T cells.

The inventors have also shown that combination of four pre-erythrocytic conserved protective antigens (4cPEAg i.e., 4 separated antigens used in combination for administration) administered together with CSP elicited sterile protection at a similar level of that of the combination using 7 or 8 antigens (FIG. 17). To further reduce the total size of antigens, the protective domains of these four antigens were selected based on amino acid conservation among plasmodial species and the presence of CD8+ T cell epitopes predicted to be good binders to class I MHC molecules (FIGS. 17 and 18). Their protective activity was then tested and compared to the protection elicited by the entire antigen. After identification of the protective domains (PD) of these 4cPEAg the inventors elaborated the construction of a chimeric antigen and selected a first construct formed by the fusion of 4 antigenic domains, i.e., the PD of the antigen 18-10NT (N-terminal)+18-10CT (C-terminal), with the PD 11-10CT, followed by the PD TRAPNT and the antigen 11-09. This chimeric antigen was called Fusion 4cPEAg and it is structure is shown in the FIG. 24*a*. A particular amino acid sequence of this construct together with its DNA is provided as SEQ ID No.116 and 115 for *Plasmodium Berghei*. When tested in a protocol of two immunization doses administered four weeks apart and in combination with CSP ($5\times10^5$ TU and $3\times10^7$ TU of LPs per antigen in the first and second immunization, respectively) Fusion 4cPEAg of *P. berghei* was as efficient as the combination of the 4cPEAg, sterilizing the infection of six out of seven challenged mice (FIG. 24*b*, Fusion 4cPEAg+CSP versus 4cPEAg+CSP). Notably, using this immunization dose, the 4cPEAg in the absence of CSP elicited the same level of sterile protection obtained with the combination of the 7cPEAg (FIG. 15). Single immunization with CSP ($1\times10^7$ TU) or the Fusion 4cPEAg ($4\times10^7$ TU), despite decreasing in almost ten fold the average parasitemia, only minimally sterilely protected the challenged mice (1 out of 7, FIG. 25, CSP and Fusion 4cPEAg groups). On the other hand, when combined, Fusion 4cPEAg+CSP sterilely protected 5 out of the 7 challenged mice (FIG. 25, Fusion 4PEAg+CSP group), achieving similar level of sterile protection of combinations using 5, 7 and 8cPEAgs (FIGS. 15-17).

This data confirmed the protective efficacy of the chimeric antigen prepared as a fusion of the protective domains, which satisfactorily substituted the 4cPEAg.

Since predicted CD8+ T cell epitopes clustered in conserved regions of the antigens, independently of the plasmodial species and MHC class I restriction (FIG. 18), this particularity was used to select the regions of *P. falciparum* 4cPEAg, corresponding to the protective domains of *P. berghei* 4cPEAg. To strengthen the analysis showed in the FIG. 18, more HLA class I and II allelles were analyzed, including the mapping of 9-mers peptides predicted to bind to HLA-DRB1*01:01, *03:01, *04:01, *04:05, *07:01, *08:02, *09:01, *11:01, *12:01, *13:02 and *15:01, to the HLA A*01:01, *02:01, *02:03, *02:06, *03:01, *11:01, *23:01, *24:02, *26:01, *30:01, *30:02, *31:01, *32:01, *33:01, *68:01 and *68:02., and to the HLA-B*07:02, *08:01, *15:01, *35:01, *40:01, *44:02, *44:03, *51:01, *53:01, *57:01 and *58:01 (FIG. 26). This extended analysis corroborated the initial observation, using the HLA A*02:01 and the H2Db/Kb (FIG. 18), that good binders tend to cluster in regions associated with structural/functional conserved domains, transmembrane domains, as well as in signal peptide and GPI-anchoring sequences. Based on this clustering of epitopes, the sequences/structures of *P. berghei* antigens were used to retrieve the cognate regions in *P. falciparum* antigens as shown in the FIG. 26. These putative protective domains were fused as in *P. berghei* avoiding the creation of neo-epitopes in the junction of antigens/protective domains as shown in the FIG. 26*e*. When inevitable, an amino acid residue was introduced in the fusion sequence to avoid the creation of neo-epitopes with high binding affinity to HLA. The only amino acid added in the Pf fusion 4cPE Ag was a glutamic acid (E) at the end of the Pf11-10CT. the amino acid sequence of the obtained construct and its DNA is provided as SEQ ID No.118 and 117

A further chimeric construct was designed in order to benefit from the immune response elicited by the CSP protein, taking into consideration that the lentiviral particles were shown to sustain the presence of large antigens. accordingly a fusion of antigens or their protective domains was prepared, adding the CSP antigen to the fusion 4cPE Ag in a structure containing the CSP devoid, or not, of its signal peptide and devoid of its GPI followed by the PD 18-10NT and CT, the PD 11-10CT, followed by the PD TRAPNT and the antigen 11-09. The construct obtained for *P. berghei* has the amino acid sequence of SEQ ID No. 120 and the DNA of SEQ ID No. 121 or has the amino acid sequence of SEQ ID No. 122 and the DNA of SEQ ID No. 123. Specific amino acid residues were deleted from the original antigens where appropriate in order to preclude the formation of neo-epitopes.

Material and Methods

Parasite Strains:

*Plasmodium berghei* ANKA strain constitutively expressing the GFP under the control of the hsp70 promoter (Ishino et al, 2006) was used in the challenges using parasitemia, quantified by flow cytometry, as protective readout. *Plasmodium berghei* ANKA strain constitutively expressing a GFP-luciferase fusion under the control of the eef-1alfa promoter (Franke-Fayard et al, 2008) was used in the challenges using liver infection, assessed by bioluminescence, as protective readout. Of note, parasitemia quantified using hsp70-gfp parasites was at least 10 times more sensible than using eef-1a gfp:luc parasites due to more intense expression level of GFP.

Ishino T, Orito Y, Chinzei Y, Yuda M (2006) A calcium-dependent protein kinase regulates *Plasmodium* ookinete access to the midgut epithelial cell. Mol Microbiol 59:1175-1184.

Franke-Fayard B, Djokovic D, Dooren M W, Ramesar J, Waters A P, et al. (2008) Simple and sensitive antimalarial drug screening in vitro and in vivo using transgenic luciferase expressing *Plasmodium berghei* parasites. *Int J Parasitol* 38:1651-1662.

Mouse Strains:

C57BL/6 Rj and Swiss mice were purchased from Elevage Janvier (France). All experiments were approved by the Animal Care and Use Committee of Institut Pasteur (CETEA 2013-0093) and were performed in accordance with European guidelines and regulations (MESR-01324).

Production of Lentiviral Particles Stock:

Down-selected plasmodial antigens were synthesized by Eurofins MWG as mouse codon-optimized genes with the addition of a Kozak consensus sequence (GCCACCATGGCT(C) (SEQ ID No. 85 and 86), representing the first 12 nucleotides in the coding sequences of the antigenic polypeptides), encompassing the first translated ATG. This modification adds an extra alanine after the first methionine. A BamHI (GGATCC-SEQ ID No.87) and Xho I (CTCGAG-SEQ ID No.88) restriction sites were also inserted in the 5' and 3' extremities of the construct, respectively. These synthetic codon-optimized genes were then cloned into the BamHI and Xho I restriction sites of the pTRIP plasmid harboring either the CMV or B2M promoter (FIGS. 16 and 17). Lentiviral particles were produced by transient calcium co-transfection of HEK 293T cells with three helper plasmids encoding separate packaging functions, the pTRIP vector plasmid containing the synthetic plasmodial gene, the envelope expression plasmid encoding the glycoprotein G from VSV (Vesicular Stomatitis Virus, Indiana (FIG. 19) or New Jersey (FIG. 20) serotypes) and the p8.74 encapsidation plasmid (FIG. 18), containing the structural, accessory and regulatory genes of HIV. This co-transfection will generate integrative but replication-incompetent pseudotyped lentiviral particles. At 24 hours post-transfection, the cell culture medium was replaced by serum-free DMEM. Supernatants were collected at 48 hours post-transfection, clarified by low-speed centrifugation, and stored at −80° C. The lentiviral vector stocks were titrated by real-time PCR on cell lysates from transduced HEK 293T cells and titer were expressed as transcription unit (TU) per ml.

Immunization Protocol:

For the screening using one single dose of LPs, 4 weeks-old C57BL/6 mice (n=5 per group per experiment) were acclimated for 3 weeks and intraperitoneally immunized with a single dose of $1\times10^7$ TU of non-concentrated $VSV^{IND}$ B2M LPs. For the protocol using two immunization doses. 4 weeks-old C57BL/6 mice (n=5 per group per experiment) were acclimated for 3 weeks and intraperitoneally immunized with a first dose of $5\times10^5$ TU of non-concentrated $VSV^{NJ}$ B2M LPs. Thirty days after the first immunization, the animals received a second dose of $1\times10^7$ TU of non-concentrated $VSV^{IND}$ B2M LPs. For testing combinations of a sub-optimal dose of CSP+an optimal dose of down-selected antigens, mice were immunized twice, four weeks apart, with a sub-optimal dose of CSP ($5\times10^5$ TU of non-concentrated $VSV^{NJ}$ B2M LP in the first immunization and $5\times10^6$ TU of non-concentrated $VSV^{IND}$ B2M LP in the second immunization) and the usual dose of protective plasmodial antigens ($5\times10^5$ TU of non-concentrated $VSV^{NJ}$ B2M LP in the first immunization and $1\times10^7$ TU of non-concentrated $VSV^{IND}$ B2M LP in the second immunization). For testing the combination of multiple antigens, mice were immunized twice, four weeks apart, with 7× the individual dose (1dose=$5\times10^5$ TU of non-concentrated $VSV^{NJ}$ B2M LPs in the first immunization/$1\times10^7$ TU of non-concentrated $VSV^{IND}$ B2M LPs in the second immunization) of the control antigen All 1-luciferase (Luc), with the individual dose of CSP plus 6 doses of Luc or with the individual doses of CSP and of the 6 conserved PE antigens (11-05, 11-06, 11-07, 11-09, 11-10 and 18-10). For this experiment the inventors used ultrafiltration and lenti-X (Clontech) concentrated stocks. The average volume of injection was 500 uL of LPs diluted in DMEM.

In all cases, thirty days after last immunization, mice were challenged with 5,000 GFP-expressing sporozoites micro-injected subcutaneously in the mice footpad.

Sporozoite Challenge:

*Anopheles stephensi* (Sda500 strain) mosquitoes were reared using standard procedures. 3-5 days after emergence, mosquitoes were fed on infected Swiss mice with a parasitemia superior to 2%, and kept as described in Amino et al, 2007. Between 20 and 23 days post-feeding, the salivary glands of infected mosquitoes were dissected in PBS, collected in 20 uL of sterile PBS on ice and disrupted using an eppendorf pestle. The suspension of parasites was filtered through a nylon mesh of 40 um, counted using Kova glasstic slide (Hycor) and adjusted to a concentration of 5,000 or 10,000 sporozoites/uL with sterile PBS. This suspension was divided in individual tubes, one for each group of immunized mice (n=4-7 per group), and kept on ice until the challenge. One microliter of parasite suspension was injected in the right footpad of mice using a Nanofil syringe (World Precision Instruments) with a 35 GA bevelled needle (NF35BV).

Amino R, Thiberge S, Blazquez S, Baldacci P, Renaud O, et al. (2007) Imaging malaria sporozoites in the dermis of the mammalian host. Nat Protoc 2:1705-1712.

Measurement of Parasite Infection:

Hepatic parasite loads were quantified at ~44h by bioluminescence in fur shaved mice infected with GFP LUC parasites. Infected mice were first anesthetized with isoflurane and injected subcutaneously with D-luciferin (150 mg/kg, Caliper LifeSciences). After a 5 minutes incubation allowing the distribution of the substrate in the body of the anesthetized animals, mice were transferred to the stage of an intensified charge-coupled device photon-counting video camera box where anesthesia was maintained with 2.5% isoflurane delivered via nose cones. After 5 minutes of signal acquisition controlled by the Living Image software (Xenogen Corporation), animals were returned to their cage. Automated detection of bioluminescence signals by the system resulted in the generation of bioluminescence signal maps superimposed to the gray-scale photograph of the experimental mice. These images were then quantified using the Living Image software. Briefly, regions of interest (ROI) encompassing the liver were manually defined, applied to all animals and the average radiance within these ROIs was automatically calculated. Background signal was measured in the lower region of the abdomen, and the average values of background signal obtained.

Alternatively, blood infection was assessed by flow cytometry using hsp70-GFP parasites. At day 4, 5, 6 and >10 post-challenge, a millimetric excision was performed in the tail of mice allowing the collection of a drop of blood that was readily diluted in 500 uL of PBS. This diluted blood was analyzed using a flow cytometer. 500,000 events were analyzed at day 4 post-challenge and 100,000 events in the subsequent days. Non-infected mice after day 10 were considered as sterile protected.

Statistical Analysis:

Parasitemia data from GFP immunized control were log transformed and pooled for the calculation of 95% tolerance of interval with 95% of certitude. For the immunization protocol of one dose this limit comprised the interval of the mean value ±2.49 SD (mean=−0.3906, SD=0.3392, n=35). Similarly, for the immunization protocol of two doses this limit comprised the interval of the mean value ±2.51 (mean=−0.3002, SD=0.3305, n=33). All mice with a log parasitemia inferior to the lower limit (mean−2.5 SD) were considered as significantly different from the control mice ($P<0.05$), and therefore considered as protected. In the protocol using two immunization doses, the difference in the numbers of protected mice, following the definition above, between the test group and the GFP control group was assessed using the Fisher's exact test. The average of the log parasitemia of the groups with significant differences in the Fisher's Test were compared to the GFP group using one-way ANOVA (Holm-Sidak's multiple comparison test).

REFERENCES 1. http: // www. who. int/mediacentre/factsheets/fs094/en/
2. RTS, S Clinical Trials Partnership. Lancet. 2015; 4; 386(9988):31-45.
3. Moorthy V S, Ballou W R. Malar J. 2009; 8: 312.
4. http: // www.who. int/immunization/topics/malaria/vaccine_roadmap/en/
5. Seder R A, et al. *Science.* 2013; 341:1359-65.
6. Amino R, Menard R. *Nature.* 2012; 484(7395):S22-3
7. Kester K E, et al. 2014. pii: S0264-410X(14)00822-6.
8. Mishra S, et al. *Vaccine.* 2011; 29(43):7335-42.
9. Murphy S C, Kas A, Stone B C, Bevan M J. *Proc Natl Acad Sci USA.* 2013; 110(15):6055-60.
10. Hafalla J C, et al. PLoS Pathog. 2013; 9(5):e1003303.
11. Iglesias, M. C., et al. J Gene Med. 2006; 8, 265-274.
12. Firat, H., et al. J Gene Med. 2002; 4, 38-45.
13. Doolan D L, et al. Proc Natl Acad Sci USA. 2003; 100:9952-7.
14. Robson K J, et al. Nature. 1988; 335(6185):79-82.
15. Khusmith S, et al. Science. 1991; 252(5006):715-8.
16. Ewer K J, et al. Nat Commun. 2013; 4:2836.
17. Gantt S, et al. Infect Immun. 2000; 68(6):3667-73.
18. Khusmith S, Sedegah M, Hoffman S L. *Infect Immun.* 1994; 62(7):2979-83.

19. LaCrue A N, et al. Mol Biochem Parasitol. 2006; 148(2):199-209.
20. Rennenberg A et al. PLoS Pathog. 2010; 6(3):e1000825.
21. Boysen K E, Matuschewski K. MBio. 2013; 4(6): e00874-13.
22. Lehmann C, et al. PLoS Pathog. 2014; 10(8):e1004336.
23. Pei Y, et al. Cell Microbiol. 2013 September; 15(9): 1508-26.
24. Eggleson K K, Duffin K L, Goldberg D E. J Biol Chem.;274(45):32411-7.
25. Poh C M, Howland S W, Grotenbreg G M, Renia L. Infect Immun. 2014; 82(11):4854-64.
26. Gilson P R, et al. Mol Cell Proteomics. 2006; 5(7):1286-99.
27. Offeddu V, Rauch M, Silvie O, Matuschewski K. Mol Biochem Parasitol. 2014; 193(2):101-9.
28. Ishino T, Chinzei Y, Yuda M. Cell Microbiol. 2005; 7(2):199-208.
29. Amino R, et al. Cell Host Microbe. 2008 Feb. 14; 3(2):88-96.
30. Tavares J, et al. J Exp Med. 2013; 210(5):905-15.
31. Speake C, et al. PLoS One. 2016; 11(7):e0159449.

The invention claimed is:

1. A nucleic acid molecule encoding a chimeric antigenic polypeptide comprising a fusion of antigens of a *Plasmodium* parasite capable of infecting human or antigenic fragments thereof;

wherein said antigens are selected from:

a) a thrombospondin related anonymous protein (TRAP) antigen of SEQ ID NO: 23, SEQ ID NO: 24, SEQ ID NO: 26, or SEQ ID NO: 27, b) an 18-10 (inhibitor of cysteine protease (ICP) antigen of SEQ ID NO: 32, SEQ ID NO: 33, SEQ ID NO: 35, or SEQ ID NO: 36, c) an 11-10 (Ag45) antigen of SEQ ID NO: 79, SEQ ID NO: 80, SEQ ID NO: 82, or SEQ ID NO: 83, and d) an 11-09 (Ag40) antigen of SEQ ID NO: 70, SEQ ID NO: 71, SEQ ID NO: 73, SEQ ID NO: 74;

and wherein said antigenic fragments have an amino acid sequence with at least 95% amino acid identity with said antigens.

2. The nucleic acid molecule of claim 1, wherein the primary structure of the chimeric antigenic polypeptide results from a fusion in any order of the following antigenic fragments:

the TRAP antigenic fragment of SEQ ID NO: 108, the 18-10 (ICP) antigenic fragment of SEQ ID NO: 100, the 11-10 (Ag45) antigenic fragment of SEQ ID NO: 104, and the 11-09 (Ag40) antigenic fragment of SEQ ID NO: 112.

3. The nucleic acid molecule of claim 1, which encodes a chimeric antigenic polypeptide whose amino acid sequence comprises:

a) the amino acid sequence of SEQ ID NO: 100 or a fragment thereof having a deletion of 1 to 10 amino acid residues, b) the amino acid sequence of SEQ ID NO:104 or a fragment thereof having a deletion of 1 to 10 amino acid residues, c) the amino acid sequence of SEQ ID NO:108 or a fragment thereof having a deletion of 1 to 10 amino acid residues, and d) the amino acid sequence of SEQ ID NO:112 or a fragment thereof having a deletion of 1 to 10 amino acid residues.

4. The nucleic acid molecule of claim 3, which encodes a chimeric antigenic polypeptide whose amino acid sequence comprises:

a) a fragment of the amino acid sequence of SEQ ID NO: 100 having a deletion of 1 to 10 amino acid residues from the N-terminal end, b) a fragment of the amino acid sequence of SEQ ID NO:104 having a deletion of 1 to 10 amino acid residues from the N-terminal end, c) a fragment of the amino acid sequence of SEQ ID NO:108 having a deletion of 1 to 10 amino acid residues from the N-terminal end, and d) a fragment of the amino acid sequence of SEQ ID NO:112 having a deletion of 1 to 10 amino acid residues from the N-terminal end.

5. The nucleic acid molecule of claim 2, wherein the amino acid sequence of the chimeric antigenic polypeptide:

a) comprises 1 to 3 additional junctional amino acid residues at the junction of SEQ ID NO:104 for the 11-10 (Ag45) antigenic fragment and SEQ ID NO:108 for the TRAP antigenic fragment; and/or b) comprises a deletion of MA contiguous amino acid residues at the N-terminal end of SEQ ID NO:112 for the 11-9 antigen, and/or c) comprises a deletion of M residue at the N-terminal end of SEQ ID NO:104 for the 11-10 antigenic fragment and at the N-terminal end of SEQ ID NO:108 for the TRAP antigenic fragment.

6. The nucleic acid molecule of claim 1, wherein all the antigens or antigenic fragments thereof are from *Plasmodium falciparum* or from *Plasmodium vivax*.

7. The nucleic acid molecule of claim 1, wherein the amino acid sequence of the chimeric antigenic polypeptide is SEQ ID NO:118.

8. The nucleic acid molecule of claim 1, which comprises the following polynucleotides:

a) a polynucleotide having the sequence of SEQ ID NO: 99 for the 18-10 (ICP) antigenic fragment, b) a polynucleotide having the sequence of SEQ ID NO:103 for the 11-10 (Ag45) antigenic fragment, c) a polynucleotide having the sequence of SEQ ID NO:107 for the TRAP antigenic fragment, and d) a polynucleotide having the sequence of SEQ ID NO: 111 for the 11-09 (Ag40) antigenic fragment.

9. The nucleic acid molecule of claim 1, which is the polynucleotide of SEQ ID NO:117.

10. A vector comprising the nucleic acid molecule of claim 1.

* * * * *

SEQUENCE LISTING

```
<160> NUMBER OF SEQ ID NOS: 124

<210> SEQ ID NO 1
<211> LENGTH: 4536
<212> TYPE: DNA
<213> ORGANISM: Artificial Sequence
<220> FEATURE:
<223> OTHER INFORMATION: pTRIP CMV GFP

<400> SEQUENCE: 1

tggaagggct aattcactcc caacgaagac aagatatcct tgatctgtgg atctaccaca     60

cacaaggcta cttccctgat tagcagaact acacaccagg gccagggatc agatatccac    120

tgacctttgg atggtgctac aagctagtac cagttgagcc agagaagtta gaagaagcca    180

acaaaggaga gaacaccagc ttgttacaac ctgtgagcct gcatgggatg gatgacccgg    240

agagagaagt gttagagtgg aggtttgaca gccgcctagc atttcatcac ggtggcccga    300

gagctgcatc cggagtactt caagaactgc tgatatcgag cttgctacaa gggactttcc    360

gctggggac tttccaggga ggcgtggcct gggcgggact ggggagtggc gagccctcag    420

atcctgcata taagcagctg ctttttgcct gtactgggtc tctctggtta gaccagatct    480

gagcctggga gctctctggc taactaggga acccactgct taagcctcaa taaagcttgc    540

cttgagtgct tcaagtagtg tgtgcccgtc tgttgtgtga ctctggtaac tagagatccc    600

tcagaccctt ttagtcagtg tggaaaatct ctagcagtgg cgcccgaaca gggacttgaa    660

agcgaaaggg aaaccagagg agctctctcg acgcaggact cggcttgctg aagcgcgcac    720

ggcaagaggc gaggggcggc gactggtgag tacgccaaaa attttgacta gcggaggcta    780

gaaggagaga gatgggtgcg agagcgtcag tattaagcgg gggagaatta gatcgcgatg    840

ggaaaaaatt cggttaaggc cagggggaaa gaaaaaatat aaattaaaac atatagtatg    900

ggcaagcagg gagctagaac gattcgcagt taatcctggc ctgttagaaa catcagaagg    960

ctgtagacaa atactgggac agctacaacc atcccttcag acaggatcag aagaacttag   1020

atcattatat aatacagtag caaccctcta ttgtgtgcat caaaggatag agataaaaga   1080

caccaaggaa gctttagaca agatagagga agagcaaaac aaaagtaaga ccaccgcaca   1140

gcaagcggcc gctgatcttc agacctggag gaggagatat gagggacaat tggagaagtg   1200

aattatataa atataaagta gtaaaaattg aaccattagg agtagcaccc accaaggcaa   1260

agagaagagt ggtgcagaga gaaaaaagag cagtgggaat aggagctttg ttccttgggt   1320

tcttgggagc agcaggaagc actatgggcg cagcgtcaat gacgctgacg gtacaggcca   1380

gacaattatt gtctggtata gtgcagcagc agaacaattt gctgagggct attgaggcgc   1440

aacagcatct gttgcaactc acagtctggg gcatcaagca gctccaggca agaatcctgg   1500

ctgtggaaag atacctaaag gatcaacagc tcctggggat ttggggttgc tctggaaaac   1560
```

-continued

```
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaatttta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgt   2220
ggagttccgc gttacataac ttacggtaaa tggcccgcct ggctgaccgc ccaacgaccc   2280
ccgcccattg acgtcaataa tgacgtatgt tcccatagta acgccaatag ggactttcca   2340
ttgacgtcaa tgggtggagt atttacggta aactgcccac ttggcagtac atcaagtgta   2400
tcatatgcca agtacgcccc ctattgacgt caatgacggt aaatggcccg cctggcatta   2460
tgcccagtac atgaccttat gggactttcc tacttggcag tacatctacg tattagtcat   2520
cgctattacc atggtgatgc ggttttggca gtacatcaat gggcgtggat agcggtttga   2580
ctcacgggga tttccaagtc tccaccccat tgacgtcaat gggagtttgt tttggcacca   2640
aaatcaacgg gactttccaa aatgtcgtaa caactccgcc ccattgacgc aaatgggcgg   2700
taggcgtgta cggtgggagg tctatataag cagagctcgt ttagtgaacc gtcagatcgc   2760
ctggagacgc catccacgct gttttgacct ccatagaaga caccgcgatc ggatccccac   2820
cggtcgccac catggtgagc aagggcgagg agctgttcac cggggtggtg cccatcctgg   2880
tcgagctgga cggcgacgta aacggccaca agttcagcgt gtccggcgag ggcgagggcg   2940
atgccaccta cggcaagctg accctgaagt tcatctgcac caccggcaag ctgcccgtgc   3000
cctggcccac cctcgtgacc accctgacct acggcgtgca gtgcttcagc cgctaccccg   3060
accacatgaa gcagcacgac ttcttcaagt ccgccatgcc cgaaggctac gtccaggagc   3120
gcaccatctt cttcaaggac gacggcaact acaagacccg cgccgaggtg aagttcgagg   3180
gcgacaccct ggtgaaccgc atcgagctga agggcatcga cttcaaggag gacggcaaca   3240
tcctggggca caagctggag tacaactaca acagccacaa cgtctatatc atggccgaca   3300
agcagaagaa cggcatcaag gtgaacttca agatccgcca caacatcgag gacggcagcg   3360
tgcagctcgc cgaccactac cagcagaaca cccccatcgg cgacggcccc gtgctgctgc   3420
ccgacaacca ctacctgagc acccagtccg ccctgagcaa agaccccaac gagaagcgcg   3480
atcacatggt cctgctggag ttcgtgaccg ccgccgggat cactctcggc atggacgagc   3540
tgtacaagta aagcggccgc gactctagct cgagctcaag cttcgaattc ccgataatca   3600
acctctggat tacaaaattt gtgaaagatt gactggtatt cttaactatg ttgctccttt   3660
tacgctatgt ggatacgctg ctttaatgcc tttgtatcat gctattgctt cccgtatggc   3720
tttcattttc tcctccttgt ataaatcctg gttgctgtct ctttatgagg agttgtggcc   3780
cgttgtcagg caacgtggcg tggtgtgcac tgtgtttgct gacgcaaccc ccactggttg   3840
gggcattgcc accacctgtc agctcctttc cgggactttc gctttccccc tccctattgc   3900
cacggcggaa ctcatcgccg cctgccttgc ccgctgctgg acaggggctc ggctgttggg   3960
```

```
cactgacaat tccgtggtgt tgtcggggaa gctgacgtcc tttccatggc tgctcgcctg   4020

tgttgccacc tggattctgc gcgggacgtc cttctgctac gtcccttcgg ccctcaatcc   4080

agcggacctt ccttcccgcg gcctgctgcc ggctctgcgg cctcttccgc gtcttcgcct   4140

tcgccctcag acgagtcgga tctccctttg ggccgcctcc ccgcatcggg aattctgcag   4200

tcgacggtac ctttaagacc aatgacttac aaggcagctg tagatcttag ccacttttta   4260

aaagaaaagg ggggactgga agggctaatt cactcccaac gaagacaaga tcgtcgagag   4320

atgctgcata taagcagctg ctttttgctt gtactgggtc tctctggtta gaccagatct   4380

gagcctggga gctctctggc taactaggga acccactgct taagcctcaa taaagcttgc   4440

cttgagtgct tcaagtagtg tgtgcccgtc tgttgtgtga ctctggtaac tagagatccc   4500

tcagaccctt ttagtcagtg tggaaaatct ctagca                             4536
```

<210> SEQ ID NO 2
<211> LENGTH: 4468
<212> TYPE: DNA
<213> ORGANISM: Artificial Sequence
<220> FEATURE:
<223> OTHER INFORMATION: pTRIP B2M GFP

<400> SEQUENCE: 2

```
tggaagggct aattcactcc caacgaagac aagatatcct tgatctgtgg atctaccaca     60

cacaaggcta cttccctgat tagcagaact acacaccagg gccagggatc agatatccac    120

tgacctttgg atggtgctac aagctagtac cagttgagcc agagaagtta gaagaagcca    180

acaaaggaga gaacaccagc ttgttacaac ctgtgagcct gcatgggatg gatgacccgg    240

agagagaagt gttagagtgg aggtttgaca gccgcctagc atttcatcac ggtggcccga    300

gagctgcatc cggagtactt caagaactgc tgatatcgag cttgctacaa gggactttcc    360

gctgggggac tttccaggga ggcgtggcct gggcgggact ggggagtggc gagccctcag    420

atcctgcata taagcagctg ctttttgcct gtactgggtc tctctggtta gaccagatct    480

gagcctggga gctctctggc taactaggga acccactgct taagcctcaa taaagcttgc    540

cttgagtgct tcaagtagtg tgtgcccgtc tgttgtgtga ctctggtaac tagagatccc    600

tcagaccctt ttagtcagtg tggaaaatct ctagcagtgg cgcccgaaca gggacttgaa    660

agcgaaaggg aaaccagagg agctctctcg acgcaggact cggcttgctg aagcgcgcac    720

ggcaagaggc gaggggcggc gactggtgag tacgccaaaa attttgacta gcggaggcta    780

gaaggagaga gatgggtgcg agagcgtcag tattaagcgg gggagaatta gatcgcgatg    840

ggaaaaaatt cggttaaggc cagggggaaa gaaaaaatat aaattaaaac atatagtatg    900

ggcaagcagg gagctagaac gattcgcagt taatcctggc ctgttagaaa catcagaagg    960

ctgtagacaa atactgggac agctacaacc atcccttcag acaggatcag aagaacttag   1020

atcattatat aatacagtag caaccctcta ttgtgtgcat caaaggatag agataaaaga   1080

caccaaggaa gctttagaca agatagagga agagcaaaac aaaagtaaga ccaccgcaca   1140

gcaagcggcc gctgatcttc agacctggag gaggagatat gagggacaat tggagaagtg   1200

aattatataa atataaagta gtaaaaattg aaccattagg agtagcaccc accaaggcaa   1260

agagaagagt ggtgcagaga gaaaaaagag cagtgggaat aggagctttg ttccttgggt   1320

tcttgggagc agcaggaagc actatgggcg cagcgtcaat gacgctgacg gtacaggcca   1380

gacaattatt gtctggtata gtgcagcagc agaacaattt gctgagggct attgaggcgc   1440
```

-continued

```
aacagcatct gttgcaactc acagtctggg gcatcaagca gctccaggca agaatcctgg   1500
ctgtggaaag atacctaaag gatcaacagc tcctggggat ttggggttgc tctggaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaatttta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgc   2220
cggaaaccct gcagggaatt ccccagctgt agttataaac agaagttctc cttctgctag   2280
gtagcattca aagatcttaa tcttctgggt ttccgttttc tcgaatgaaa aatgcaggtc   2340
cgagcagtta actggcgggg gcaccattag caagtcactt agcatctctg gggccagtct   2400
gcaaagcgag gggcagcct taatgtgcct ccagcctgaa gtcctagaat gagcgcccgg   2460
tgtcccaagc tggggcgcgc accccagatc ggagggcgcc gatgtacaga cagcaaactc   2520
acccagtcta gtgcatgcct tcttaaacat cacgagactc taagaaaagg aaactgaaaa   2580
cgggaaagtc cctctctcta acctggcact gcgtcgctgg cttggagaca ggtgacggtc   2640
cctgcgggcc ttgtcctgat tggctgggca cgcgtttaat ataagtggag gcgtcgcgct   2700
ggcgggcatt cctgaagctg acagcattcg ggccgagcga tcggatcccc accggtcgcc   2760
accatggtga gcaagggcga ggagctgttc accggggtgg tgcccatcct ggtcgagctg   2820
gacggcgacg taaacggcca caagttcagc gtgtccggcg agggcgaggg cgatgccacc   2880
tacggcaagc tgaccctgaa gttcatctgc accaccggca agctgcccgt gccctggccc   2940
accctcgtga ccaccctgac ctacggcgtg cagtgcttca gccgctaccc cgaccacatg   3000
aagcagcacg acttcttcaa gtccgccatg cccgaaggct acgtccagga gcgcaccatc   3060
ttcttcaagg acgacggcaa ctacaagacc cgcgccgagg tgaagttcga gggcgacacc   3120
ctggtgaacc gcatcgagct gaagggcatc gacttcaagg aggacggcaa catcctgggg   3180
cacaagctgg agtacaacta caacagccac aacgtctata tcatggccga caagcagaag   3240
aacggcatca aggtgaactt caagatccgc cacaacatcg aggacggcag cgtgcagctc   3300
gccgaccact accagcagaa cacccccatc ggcgacggcc ccgtgctgct gcccgacaac   3360
cactacctga gcacccagtc cgccctgagc aaagacccca acgagaagcg cgatcacatg   3420
gtcctgctgg agttcgtgac cgccgccggg atcactctcg gcatggacga gctgtacaag   3480
taaagcggcc gcgactctag ctcgagctca agcttcgaat tcccgataat caacctctgg   3540
attacaaaat ttgtgaaaga ttgactggta ttcttaacta tgttgctcct tttacgctat   3600
gtggatacgc tgctttaatg cctttgtatc atgctattgc ttcccgtatg gctttcattt   3660
tctcctcctt gtataaatcc tggttgctgt ctctttatga ggagttgtgg cccgttgtca   3720
ggcaacgtgg cgtggtgtgc actgtgtttg ctgacgcaac ccccactggt tggggcattg   3780
ccaccacctg tcagctcctt tccgggactt tcgctttccc cctccctatt gccacggcgg   3840
```

aactcatcgc cgcctgcctt gcccgctgct ggacaggggc tcggctgttg ggcactgaca 3900
attccgtggt gttgtcgggg aagctgacgt cctttccatg gctgctcgcc tgtgttgcca 3960
cctggattct gcgcgggacg tccttctgct acgtcccttc ggccctcaat ccagcggacc 4020
ttccttcccg cggcctgctg ccggctctgc ggcctcttcc gcgtcttcgc cttcgccctc 4080
agacgagtcg gatctccctt tgggccgcct ccccgcatcg ggaattctgc agtcgacggt 4140
acctttaaga ccaatgactt acaaggcagc tgtagatctt agccactttt taaaagaaaa 4200
ggggggactg gaagggctaa ttcactccca acgaagacaa gatcgtcgag agatgctgca 4260
tataagcagc tgctttttgc ttgtactggg tctctctggt tagaccagat ctgagcctgg 4320
gagctctctg gctaactagg gaacccactg cttaagcctc aataaagctt gccttgagtg 4380
cttcaagtag tgtgtgcccg tctgttgtgt gactctggta actagagatc cctcagaccc 4440
ttttagtcag tgtggaaaat ctctagca 4468

<210> SEQ ID NO 3
<211> LENGTH: 11904
<212> TYPE: DNA
<213> ORGANISM: Artificial Sequence
<220> FEATURE:
<223> OTHER INFORMATION: PACKAGING 8.74 PLASMID

<400> SEQUENCE: 3
gggctgcagg aattaattcg agctcgcccg acattgatta ttgactagtt attaatagta 60
atcaattacg gggtcattag ttcatagccc atatatggag ttccgcgtta cataacttac 120
ggtaaatggc ccgcctggct gaccgcccaa cgacccccgc ccattgacgt caataatgac 180
gtatgttccc atagtaacgc caatagggac tttccattga cgtcaatggg tggagtattt 240
acggtaaact gcccacttgg cagtacatca agtgtatcat atgccaagta cgccccctat 300
tgacgtcaat gacggtaaat ggcccgcctg gcattatgcc cagtacatga ccttatggga 360
ctttcctact tggcagtaca tctacgtatt agtcatcgct attaccatgg tgatgcggtt 420
ttggcagtac atcaatgggc gtggatagcg gtttgactca cggggatttc caagtctcca 480
ccccattgac gtcaatggga gtttgttttg gcaccaaaat caacgggact ttccaaaatg 540
tcgtaacaac tccgccccat tgacgcaaat gggcggtagg cgtgtacggt gggaggtcta 600
tataagcaga gctcgtttag tgaaccgtca gatcgcctgg agacgccatc cacgctgttt 660
tgacctccat agaagacacc gggaccgatc cagcctccgc ggccgcgttg acgcgcacgg 720
caagaggcga ggggcggcga ctggtgagag atgggtgcga gagcgtcagt attaagcggg 780
ggagaattag atcgatggga aaaaattcgg ttaaggccag ggggaaagaa aaaatataaa 840
ttaaaacata tagtatgggc aagcagggag ctagaacgat tcgcagttaa tcctggcctg 900
ttagaaacat cagaaggctg tagacaaata ctgggacagc tacaaccatc ccttcagaca 960
ggatcagaag aacttagatc attatataat acagtagcaa ccctctattg tgtgcatcaa 1020
aggatagaga taaaagacac caaggaagct ttagacaaga tagaggaaga gcaaaacaaa 1080
agtaagaaaa aagcacagca agcagcagct gacacaggac acagcaatca ggtcagccaa 1140
aattacccta tagtgcagaa catccagggg caaatggtac atcaggccat atcacctaga 1200
actttaaatg catgggtaaa agtagtagaa gagaaggctt tcagcccaga agtgataccc 1260
atgttttcag cattatcaga aggagccacc ccacaagatt taaacaccat gctaaacaca 1320
gtggggggac atcaagcagc catgcaaatg ttaaaagaga ccatcaatga ggaagctgca 1380

```
gaatgggata gagtgcatcc agtgcatgca gggcctattg caccaggcca gatgagagaa   1440
ccaaggggaa gtgacatagc aggaactact agtacccttc aggaacaaat aggatggatg   1500
acacataatc cacctatccc agtaggagaa atctataaaa gatggataat cctgggatta   1560
aataaaatag taagaatgta tagccctacc agcattctgg acataagaca aggaccaaag   1620
gaacccttta gagactatgt agaccgattc tataaaactc taagagccga gcaagcttca   1680
caagaggtaa aaaattggat gacagaaacc ttgttggtcc aaaatgcgaa cccagattgt   1740
aagactattt taaaagcatt gggaccagga gcgacactag aagaaatgat gacagcatgt   1800
cagggagtgg ggggacccgg ccataaagca agagttttgg ctgaagcaat gagccaagta   1860
acaaatccag ctaccataat gatacagaaa ggcaatttta ggaaccaaag aaagactgtt   1920
aagtgtttca attgtggcaa agaagggcac atagccaaaa attgcagggc ccctaggaaa   1980
aagggctgtt ggaaatgtgg aaaggaagga caccaaatga aagattgtac tgagagacag   2040
gctaattttt tagggaagat ctggccttcc cacaagggaa ggccagggaa ttttcttcag   2100
agcagaccag agccaacagc cccaccagaa gagagcttca ggtttgggga agagacaaca   2160
actccctctc agaagcagga gccgatagac aaggaactgt atcctttagc ttccctcaga   2220
tcactctttg gcagcgaccc ctcgtcacaa taaagatagg ggggcaatta aaggaagctc   2280
tattagatac aggagcagat gatacagtat tagaagaaat gaatttgcca ggaagatgga   2340
aaccaaaaat gataggggga attggaggtt ttatcaaagt aagacagtat gatcagatac   2400
tcatagaaat ctgcggacat aaagctatag gtacagtatt agtaggacct acacctgtca   2460
acataattgg aagaaatctg ttgactcaga ttggctgcac tttaaatttt cccattagtc   2520
ctattgagac tgtaccagta aaattaaagc caggaatgga tggcccaaaa gttaaacaat   2580
ggccattgac agaagaaaaa ataaaagcat tagtagaaat ttgtacagaa atggaaaagg   2640
aaggaaaaat ttcaaaaatt gggcctgaaa atccatacaa tactccagta tttgccataa   2700
agaaaaaaga cagtactaaa tggagaaaat tagtagattt cagagaactt aataagagaa   2760
ctcaagattt ctgggaagtt caattaggaa taccacatcc tgcagggtta aaacagaaaa   2820
aatcagtaac agtactggat gtgggcgatg catatttttc agttccctta gataaagact   2880
tcaggaagta tactgcattt accataccta gtataaacaa tgagacacca gggattagat   2940
atcagtacaa tgtgcttcca cagggatgga aaggatcacc agcaatattc cagtgtagca   3000
tgacaaaaat cttagagcct tttagaaaac aaaatccaga catagtcatc tatcaataca   3060
tggatgattt gtatgtagga tctgacttag aaatagggca gcatagaaca aaaatagagg   3120
aactgagaca acatctgttg aggtggggat ttaccacacc agacaaaaaa catcagaaag   3180
aacctccatt cctttggatg ggttatgaac tccatcctga taaatggaca gtacagccta   3240
tagtgctgcc agaaaaggac agctggactg tcaatgacat acagaaatta gtgggaaaat   3300
tgaattgggc aagtcagatt tatgcaggga ttaaagtaag gcaattatgt aaacttctta   3360
ggggaaccaa agcactaaca gaagtagtac cactaacaga agaagcagag ctagaactgg   3420
cagaaaacag ggagattcta aaagaaccgg tacatggagt gtattatgac ccatcaaaag   3480
acttaatagc agaaatacag aagcaggggc aaggccaatg gacatatcaa atttatcaag   3540
agccatttaa aaatctgaaa acaggaaagt atgcaagaat gaagggtgcc cacactaatg   3600
atgtgaaaca attaacagag gcagtacaaa aaatagccac agaaagcata gtaatatggg   3660
gaaagactcc taaatttaaa ttacccatac aaaaggaaac atgggaagca tggtggacag   3720
agtattggca agccacctgg attcctgagt gggagtttgt caatacccct cccttagtga   3780
```

```
agttatggta ccagttagag aaagaaccca taataggagc agaaactttc tatgtagatg   3840
gggcagccaa tagggaaact aaattaggaa aagcaggata tgtaactgac agaggaagac   3900
aaaaagttgt ccccctaacg gacacaacaa atcagaagac tgagttacaa gcaattcatc   3960
tagctttgca ggattcggga ttagaagtaa acatagtgac agactcacaa tatgcattgg   4020
gaatcattca agcacaacca gataagagtg aatcagagtt agtcagtcaa ataatagagc   4080
agttaataaa aaaggaaaaa gtctacctgg catgggtacc agcacacaaa ggaattggag   4140
gaaatgaaca agtagataaa ttggtcagtg ctggaatcag gaaagtacta tttttagatg   4200
gaatagataa ggcccaagaa gaacatgaga aatatcacag taattggaga gcaatggcta   4260
gtgattttaa cctaccacct gtagtagcaa aagaaatagt agccagctgt gataaatgtc   4320
agctaaaagg ggaagccatg catggacaag tagactgtag cccaggaata tggcagctag   4380
attgtacaca tttagaagga aaagttatct tggtagcagt tcatgtagcc agtggatata   4440
tagaagcaga agtaattcca gcagagacag ggcaagaaac agcatacttc ctcttaaaat   4500
tagcaggaag atggccagta aaaacagtac atacagacaa tggcagcaat ttcaccagta   4560
ctacagttaa ggccgcctgt tggtgggcgg ggatcaagca ggaatttggc attccctaca   4620
atccccaaag tcaaggagta atagaatcta tgaataaaga attaaagaaa attataggac   4680
aggtaagaga tcaggctgaa catcttaaga cagcagtaca aatggcagta ttcatccaca   4740
attttaaaag aaaagggggg attggggggt acagtgcagg ggaaagaata gtagacataa   4800
tagcaacaga catacaaact aaagaattac aaaaacaaat tacaaaaatt caaaattttc   4860
gggtttatta cagggacagc agagatccag tttggaaagg accagcaaag ctcctctgga   4920
aaggtgaagg ggcagtagta atacaagata atagtgacat aaaagtagtg ccaagaagaa   4980
aagcaaagat catcagggat tatggaaaac agatggcagg tgatgattgt gtggcaagta   5040
gacaggatga ggattaacac atggaattct gcaacaactg ctgtttatcc atttcagaat   5100
tgggtgtcga catagcagaa taggcgttac tcgacagagg agagcaagaa atggagccag   5160
tagatcctag actagagccc tggaagcatc caggaagtca gcctaaaact gcttgtacca   5220
attgctattg taaaaagtgt tgctttcatt gccaagtttg tttcatgaca aaagccttag   5280
gcatctccta tggcaggaag aagcggagac agcgacgaag agctcatcag aacagtcaga   5340
ctcatcaagc ttctctatca aagcagtaag tagtacatgt aatgcaacct ataatagtag   5400
caatagtagc attagtagta gcaataataa tagcaatagt tgtgtggtcc atagtaatca   5460
tagaatatag gaaaatggcc gctgatcttc agacctggag gaggagatat gagggacaat   5520
tggagaagtg aattatataa atataaagta gtaaaaattg aaccattagg agtagcaccc   5580
accaaggcaa agagaagagt ggtgcagaga gaaaaaagag cagtgggaat aggagctttg   5640
ttccttgggt tcttgggagc agcaggaagc actatgggcg cagcgtcaat gacgctgacg   5700
gtacaggcca gacaattatt gtctggtata gtgcagcagc agaacaattt gctgagggct   5760
attgaggcgc aacagcatct gttgcaactc acagtctggg gcatcaagca gctccaggca   5820
agaatcctgg ctgtggaaag atacctaaag gatcaacagc tcctggggat ttggggttgc   5880
tctggaaaac tcatttgcac cactgctgtg ccttggaatg ctagttggag taataaatct   5940
ctggaacaga tttggaatca cacgacctgg atggagtggg acagagaaat taacaattac   6000
acaagcttaa tacactcctt aattgaagaa tcgcaaaacc agcaagaaaa gaatgaacaa   6060
gaattattgg aattagataa atgggcaagt ttgtggaatt ggtttaacat aacaaattgg   6120
```

```
ctgtggtata taaaattatt cataatgata gtaggaggct tggtaggttt aagaatagtt   6180
tttgctgtac tttctatagt gaatagagtt aggcagggat attcaccatt atcgtttcag   6240
acccacctcc caaccccgag gggacccgac aggcccgaag gaatagaaga agaaggtgga   6300
gagagagaca gagacagatc cattcgatta gtgaacggat ccttggcact tatctgggac   6360
gatctgcgga gcctgtgcct cttcagctac caccgcttga gagacttact cttgattgta   6420
acgaggattg tggaacttct gggacgcagg gggtgggaag ccctcaaata ttggtggaat   6480
ctcctacaat attggagtca ggagctaaag aatagtgctg ttagcttgct caatgccaca   6540
gccatagcag tagctgaggg gacagatagg gttatagaag tagtacaagg agcttgtaga   6600
gctattcgcc acatacctag aagaataaga cagggcttgg aaaggatttt gctataagct   6660
cgagtgacct tcagaccttg gcactggagg tggcccggca gaagcgcggc atcgtggatc   6720
agtgctgcac cagcatctgc tctctctacc aactggagaa ctactgcaac taggcccacc   6780
actaccctgt ccacccctct gcaatgaata aaacctttga aagagcacta caagttgtgt   6840
gtacatgcgt gcatgtgcat atgtggtgcg gggggaacat gagtggggct ggctggagtg   6900
gcgatgataa gctgtcaaac atgagaatta attcttgaag acgaaagggc ctcgtgatac   6960
gcctattttt ataggttaat gtcatgataa taatggtttc ttagtctaga attaattccg   7020
tgtattctat agtgtcacct aaatcgtatg tgtatgatac ataaggttat gtattaattg   7080
tagccgcgtt ctaacgacaa tatgtacaag cctaattgtg tagcatctgg cttactgaag   7140
cagaccctat catctctctc gtaaactgcc gtcagagtcg gtttggttgg acgaaccttc   7200
tgagtttctg gtaacgccgt cccgcacccg gaaatggtca gcgaaccaat cagcagggtc   7260
atcgctagcc agatcctcta cgccggacgc atcgtggccg gcatcaccgg cgccacaggt   7320
gcggttgctg gcgcctatat cgccgacatc accgatgggg aagatcgggc tcgccacttc   7380
gggctcatga gcgcttgttt cggcgtgggt atggtggcag gccccgtggc cgggggactg   7440
ttgggcgcca tctccttgca tgcaccattc cttgcggcgg cggtgctcaa cggcctcaac   7500
ctactactgg gctgcttcct aatgcaggag tcgcataagg gagagcgtcg aatggtgcac   7560
tctcagtaca atctgctctg atgccgcata gttaagccag ccccgacacc cgccaacacc   7620
cgctgacgcg ccctgacggg cttgtctgct cccggcatcc gcttacagac aagctgtgac   7680
cgtctccggg agctgcatgt gtcagaggtt ttcaccgtca tcaccgaaac gcgcgagacg   7740
aaagggcctc gtgatacgcc tatttttata ggttaatgtc atgataataa tggtttctta   7800
gacgtcaggt ggcacttttc ggggaaatgt gcgcggaacc cctatttgtt tatttttcta   7860
aatacattca aatatgtatc cgctcatgag acaataaccc tgataaatgc ttcaataata   7920
ttgaaaaagg aagagtatga gtattcaaca tttccgtgtc gcccttattc ccttttttgc   7980
ggcattttgc cttcctgttt ttgctcaccc agaaacgctg gtgaaagtaa aagatgctga   8040
agatcagttg ggtgcacgag tgggttacat cgaactggat ctcaacagcg gtaagatcct   8100
tgagagtttt cgccccgaag aacgttttcc aatgatgagc acttttaaag ttctgctatg   8160
tggcgcggta ttatcccgta ttgacgccgg gcaagagcaa ctcggtcgcc gcatacacta   8220
ttctcagaat gacttggttg agtactcacc agtcacagaa aagcatctta cggatggcat   8280
gacagtaaga gaattatgca gtgctgccat aaccatgagt gataacactg cggccaactt   8340
acttctgaca acgatcggag gaccgaagga gctaaccgct tttttgcaca acatggggga   8400
tcatgtaact cgccttgatc gttgggaacc ggagctgaat gaagccatac caaacgacga   8460
gcgtgacacc acgatgcctg tagcaatggc aacaacgttg cgcaaactat taactggcga   8520
```

```
actacttact ctagcttccc ggcaacaatt aatagactgg atggaggcgg ataaagttgc   8580
aggaccactt ctgcgctcgg cccttccggc tggctggttt attgctgata aatctggagc   8640
cggtgagcgt gggtctcgcg gtatcattgc agcactgggg ccagatggta agccctcccg   8700
tatcgtagtt atctacacga cggggagtca ggcaactatg gatgaacgaa atagacagat   8760
cgctgagata ggtgcctcac tgattaagca ttggtaactg tcagaccaag tttactcata   8820
tatactttag attgatttaa aacttcattt ttaatttaaa aggatctagg tgaagatcct   8880
ttttgataat ctcatgacca aaatccctta acgtgagttt tcgttccact gagcgtcaga   8940
ccccgtagaa aagatcaaag gatcttcttg agatcctttt tttctgcgcg taatctgctg   9000
cttgcaaaca aaaaaaccac cgctaccagc ggtggtttgt ttgccggatc aagagctacc   9060
aactcttttt ccgaaggtaa ctggcttcag cagagcgcag ataccaaata ctgttcttct   9120
agtgtagccg tagttaggcc accacttcaa gaactctgta gcaccgccta catacctcgc   9180
tctgctaatc ctgttaccag tggctgctgc cagtggcgat aagtcgtgtc ttaccgggtt   9240
ggactcaaga cgatagttac cggataaggc gcagcggtcg ggctgaacgg ggggttcgtg   9300
cacacagccc agcttggagc gaacgaccta caccgaactg agatacctac agcgtgagct   9360
atgagaaagc gccacgcttc ccgaagggag aaaggcggac aggtatccgg taagcggcag   9420
ggtcggaaca ggagagcgca cgagggagct tccaggggga aacgcctggt atctttatag   9480
tcctgtcggg tttcgccacc tctgacttga gcgtcgattt ttgtgatgct cgtcaggggg   9540
gcggagccta tggaaaaacg ccagcaacgc ggccttttta cggttcctgg ccttttgctg   9600
gccttttgct cacatgttct ttcctgcgtt atcccctgat tctgtggata accgtattac   9660
cgcctttgag tgagctgata ccgctcgccg cagccgaacg accgagcgca gcgagtcagt   9720
gagcgaggaa gcggaagagc gcccaatacg caaaccgcct ctccccgcgc gttggccgat   9780
tcattaatgc agctgtggaa tgtgtgtcag ttagggtgtg gaaagtcccc aggctcccca   9840
gcaggcagaa gtatgcaaag catgcatctc aattagtcag caaccaggtg tggaaagtcc   9900
ccaggctccc cagcaggcag aagtatgcaa agcatgcatc tcaattagtc agcaaccata   9960
gtcccgcccc taactccgcc catcccgccc ctaactccgc ccagttccgc ccattctccg  10020
ccccatggct gactaatttt ttttatttat gcagaggccg aggccgcctc ggcctctgag  10080
ctattccaga agtagtgagg aggctttttt ggaggcctag gcttttgcaa aaagcttgga  10140
cacaagacag gcttgcgaga tatgtttgag aataccactt tatcccgcgt cagggagagg  10200
cagtgcgtaa aaagacgcgg actcatgtga aatactggtt tttagtgcgc cagatctcta  10260
taatctcgcg caacctattt tcccctcgaa cactttttaa gccgtagata aacaggctgg  10320
gacacttcac atgagcgaaa aatacatcgt cacctgggac atgttgcaga tccatgcacg  10380
taaactcgca agccgactga tgccttctga acaatggaaa ggcattattg ccgtaagccg  10440
tggcggtctg taccgggtgc gttactggcg cgtgaactgg gtattcgtca tgtcgatacc  10500
gtttgtattt ccagctacga tcacgacaac cagcgcgagc ttaaagtgct gaaacgcgca  10560
gaaggcgatg gcgaaggctt catcgttatt gatgacctgg tggataccgg tggtactgcg  10620
gttgcgattc gtgaaatgta tccaaaagcg cactttgtca ccatcttcgc aaaaccggct  10680
ggtcgtccgc tggttgatga ctatgttgtt gatatcccgc aagatacctg gattgaacag  10740
ccgtgggata tgggcgtcgt attcgtcccg ccaatctccg gtcgctaatc ttttcaacgc  10800
ctggcactgc cgggcgttgt tctttttaac ttcaggcggg ttacaatagt ttccagtaag  10860
```

tattctggag gctgcatcca tgacacaggc aaacctgagc gaaaccctgt tcaaaccccg 10920
ctttaaacat cctgaaacct cgacgctagt ccgccgcttt aatcacggcg cacaaccgcc 10980
tgtgcagtcg gcccttgatg gtaaaaccat ccctcactgg tatcgcatga ttaaccgtct 11040
gatgtggatc tggcgcggca ttgacccacg cgaaatcctc gacgtccagg cacgtattgt 11100
gatgagcgat gccgaacgta ccgacgatga tttatacgat acggtgattg gctaccgtgg 11160
cggcaactgg atttatgagt gggccccgga tctttgtgaa ggaaccttac ttctgtggtg 11220
tgacataatt ggacaaacta cctacagaga tttaaagctc taaggtaaat ataaaatttt 11280
taagtgtata atgtgttaaa ctactgattc taattgtttg tgtattttag attccaacct 11340
atggaactga tgaatgggag cagtggtgga atgcctttaa tgaggaaaac ctgttttgct 11400
cagaagaaat gccatctagt gatgatgagg ctactgctga ctctcaacat tctactcctc 11460
caaaaaagaa gagaaaggta gaagacccca aggactttcc ttcagaattg ctaagttttt 11520
tgagtcatgc tgtgtttagt aatagaactc ttgcttgctt tgctatttac accacaaagg 11580
aaaaagctgc actgctatac aagaaaatta tggaaaaata ttctgtaacc tttataagta 11640
ggcataacag ttataatcat aacatactgt tttttcttac tccacacagg catagagtgt 11700
ctgctattaa taactatgct caaaaattgt gtacctttag ctttttaatt tgtaaagggg 11760
ttaataagga atatttgatg tatagtgcct tgactagaga tcataatcag ccataccaca 11820
tttgtagagg ttttacttgc tttaaaaaac ctcccacacc tccccctgaa cctgaaacat 11880
aaaatgaatg caattgttgt tgtt 11904

<210> SEQ ID NO 4
<211> LENGTH: 5140
<212> TYPE: DNA
<213> ORGANISM: Artificial Sequence
<220> FEATURE:
<223> OTHER INFORMATION: pCMV-VSV-INDco

<400> SEQUENCE: 4
ctggatggct ttctcgccgc caaggatctg atggcgcagg ggatcaagct ctgatcaaga 60
gacaggatga ggatcgtttc gcatgattga acaagatgga ttgcacgcag gttctccggc 120
cgcttgggtg gagaggctat tcggctatga ctgggcacaa cagacaatcg gctgctctga 180
tgccgccgtg ttccggctgt cagcgcaggg gcgcccggtt ctttttgtca agaccgacct 240
gtccggtgcc ctgaatgaac tgcaagacga ggcagcgcgg ctatcgtggc tggccacgac 300
gggcgttcct tgcgcagctg tgctcgacgt tgtcactgaa gcgggaaggg actggctgct 360
attgggcgaa gtgccggggc aggatctcct gtcatctcac cttgctcctg ccgagaaagt 420
atccatcatg gctgatgcaa tgcggcggct gcatacgctt gatccggcta cctgcccatt 480
cgaccaccaa gcgaaacatc gcatcgagcg agcacgtact cggatggaag ccggtcttgt 540
cgatcaggat gatctggacg aagagcatca ggggctcgcg ccagccgaac tgttcgccag 600
gctcaaggcg agcatgcccg acggcgagga tctcgtcgtg acccatggcg atgcctgctt 660
gccgaatatc atggtggaaa atggccgctt ttctggattc atcgactgtg gccggctggg 720
tgtggcggac cgctatcagg acatagcgtt ggctacccgt gatattgctg aagagcttgg 780
cggcgaatgg gctgaccgct tcctcgtgct ttacggtatc gccgctcccg attcgcagcg 840
catcgccttc tatcgccttc ttgacgagtt cttctgaatt attaacgctt acaatttcct 900
gatgcggtat tttctcctta cgcatctgtg cggtatttca caccgcatac aggtggcact 960
tttcggggaa atgtgcgcgg aacccctatt tgtttatttt tctaaataca ttcaaatatg 1020

```
tatccgctca tgagacaata accctgataa atgcttcaat aatagcacgt gctaaaactt   1080
cattttttaat ttaaaaggat ctaggtgaag atcctttttg ataatctcat gaccaaaatc   1140
ccttaacgtg agttttcgtt ccactgagcg tcagaccccg tagaaaagat caaaggatct   1200
tcttgagatc cttttttttct gcgcgtaatc tgctgcttgc aaacaaaaaa accaccgcta   1260
ccagcggtgg tttgtttgcc ggatcaagag ctaccaactc tttttccgaa ggtaactggc   1320
ttcagcagag cgcagatacc aaatactgtc cttctagtgt agccgtagtt aggccaccac   1380
ttcaagaact ctgtagcacc gcctacatac ctcgctctgc taatcctgtt accagtggct   1440
gctgccagtg gcgataagtc gtgtcttacc gggttggact caagacgata gttaccggat   1500
aaggcgcagc ggtcgggctg aacggggggt tcgtgcacac agcccagctt ggagcgaacg   1560
acctacaccg aactgagata cctacagcgt gagctatgag aaagcgccac gcttcccgaa   1620
gggagaaagg cggacaggta tccggtaagc ggcagggtcg gaacaggaga gcgcacgagg   1680
gagcttccag ggggaaacgc ctggtatctt tatagtcctg tcgggtttcg ccacctctga   1740
cttgagcgtc gatttttgtg atgctcgtca ggggggcgga gcctatggaa aaacgccagc   1800
aacgcggcct ttttacggtt cctgggcttt tgctggcctt ttgctcacat gttcttgact   1860
cttcgcgatg tacgggccag atatacgcgt tgacattgat tattgactag ttattaatag   1920
taatcaatta cggggtcatt agttcatagc ccatatatgg agttccgcgt tacataactt   1980
acggtaaatg gcccgcctgg ctgaccgccc aacgaccccc gcccattgac gtcaataatg   2040
acgtatgttc ccatagtaac gccaataggg actttccatt gacgtcaatg ggtggactat   2100
ttacggtaaa ctgcccactt ggcagtacat caagtgtatc atatgccaag tacgccccct   2160
attgacgtca atgacggtaa atggcccgcc tggcattatg cccagtacat gaccttatgg   2220
gactttccta cttggcagta catctacgta ttagtcatcg ctattaccat ggtgatgcgg   2280
ttttggcagt acatcaatgg gcgtggatag cggtttgact cacggggatt tccaagtctc   2340
caccccattg acgtcaatgg gagtttgttt tggcaccaaa atcaacggga ctttccaaaa   2400
tgtcgtaaca actccgcccc attgacgcaa atgggcggta ggcgtgtacg gtgggaggtc   2460
tatataagca gagctctctg gctaactaga gaacccactg cttactggct tatcgaaatt   2520
aatacgactc actataggga gacccaagct ggctagcgtt taaacttaag cttggtaccg   2580
agctcggatc ctgatcagcc accatgaaat gcctgctcta tctggccttc ctgttcatcg   2640
gcgtgaactg caagttcacc atcgtgttcc cccacaacca gaagggcaac tggaagaacg   2700
tgcccagcaa ctaccactac tgccccagca gcagcgacct gaactggcac aacgacctga   2760
tcggcaccgc cctgcaggtg aagatgccca agagccacaa ggccattcag gctgatggct   2820
ggatgtgtca tgccagcaag tgggtgacca cctgcgactt ccggtggtac ggccccaagt   2880
acatcaccca cagcatccgc agcttcaccc ccagcgtgga gcagtgcaaa gagagcatcg   2940
agcagaccaa gcagggcacc tggctgaacc ccggcttccc cccccagtcc tgcggctacg   3000
ccaccgtgac cgacgccgag gccgtgatcg tgcaggtgac cccccaccac gtgctggtcg   3060
acgagtacac cggcgagtgg gtggacagcc agttcatcaa cggcaagtgc agcaactaca   3120
tctgccctac cgtgcacaac agcaccacct ggcacagcga ctacaaggtg aaaggcctgt   3180
gcgacagcaa cctgatcagc atggacatca cctttttcag cgaggacggc gagctgtcca   3240
gcctgggcaa agagggcacc ggcttcagaa gcaactactt cgcctacgag acaggcggca   3300
aggcctgcaa gatgcagtac tgcaagcact ggggcgtgcg gctgcctagc ggcgtgtggt   3360
```

```
tcgagatggc cgacaaggac ctgttcgccg ctgcccggtt ccctgagtgc cccgagggca   3420

gcagcatcag cgcccccagc cagaccagcg tggacgtgag cctgatccag gacgtggaga   3480

gaatcctgga ctacagcctg tgccaggaaa cctggtccaa gatcagagcc ggcctgccca   3540

tcagccccgt ggacctgagc tacctggccc ccaagaaccc cggcaccggc ccagccttca   3600

ccatcatcaa tggcaccctg aagtacttcg agacacggta catcagagtg gacattgccg   3660

cccctatcct gagccggatg gtgggcatga tcagcggcac caccaccgag cgggagctgt   3720

gggacgactg gccccctac gaggatgtgg agatcggccc caacggcgtg ctgcggacca   3780

gcagcggcta caagttcccc ctgtacatga tcggccacgg catgctggac agcgacctgc   3840

acctgagcag caaggcccag gtgttcgagc acccccacat ccaggacgcc gccagccagc   3900

tgcccgacga cgagagcctg ttcttcggcg acaccggcct gagcaagaac cccatcgaac   3960

tggtggaggg ctggttcagc agctggaaga gcagcattgc cagctttttc ttcatcatcg   4020

gcctgatcat cgggctgttt ctggtgctga gagtgggcat ccacctgtgc atcaagctga   4080

agcacaccaa gaagcggcag atctacaccg acatcgagat gaatcgcctg ggaagtaag    4140

aattctgcag atatccagca cagtggcggc cgctcgagtg tacaaattcc cgataatcaa   4200

cctctggatt acaaaatttg tgaaagattg actggtattc ttaactatgt tgctcctttt   4260

acgctatgtg gatacgctgc tttaatgcct ttgtatcatg ctattgcttc ccgtatggct   4320

ttcattttct cctccttgta taaatcctgg ttgctgtctc tttatgagga gttgtggccc   4380

gttgtcaggc aacgtggcgt ggtgtgcact gtgtttgctg acgcaacccc cactggttgg   4440

ggcattgcca ccacctgtca gctcctttcc gggactttcg ctttccccct ccctattgcc   4500

acggcggaac tcatcgccgc ctgccttgcc cgctgctgga caggggctcg gctgttgggc   4560

actgacaatt ccgtggtgtt gtcggggaag ctgacgtcct ttccatcgct gctcgcctgt   4620

gttgccacct ggattctgcg cgggacgtcc ttctgctacg tcccttcggc cctcaatcca   4680

gcggaccttc cttcccgcgg cctgctgccg gctctgcggc ctcttccgcg tcttcgcctt   4740

cgccctcaga cgagtcggat ctccctttgg gccgcctccc cgctcgagtc tagagggccc   4800

gtttaaaccc gctgatcagc ctcgactgtg ccttctagtt gccagccatc tgttgtttgc   4860

ccctcccccg tgccttcctt gaccctggaa ggtgccactc ccactgtcct ttcctaataa   4920

aatgaggaaa ttgcatcgca ttgtctgagt aggtgtcatt ctattctggg gggtggggtg   4980

gggcaggaca gcaaggggga ggattgggaa gacaatagca ggcatgctgg ggatgcggtg   5040

ggctctatgg cttctactgg gcggttttat ggacagcaag cgaaccggaa ttgccagctg   5100

gggcgccctc tggtaaggtt gggaagccct gcaaagtaaa                         5140
```

<210> SEQ ID NO 5
<211> LENGTH: 5158
<212> TYPE: DNA
<213> ORGANISM: Artificial Sequence
<220> FEATURE:
<223> OTHER INFORMATION: pCMV-VSV-Njco

<400> SEQUENCE: 5

```
ctggatggct ttctcgccgc caaggatctg atggcgcagg ggatcaagct ctgatcaaga     60

gacaggatga ggatcgtttc gcatgattga acaagatgga ttgcacgcag gttctccggc    120

cgcttgggtg gagaggctat tcggctatga ctgggcacaa cagacaatcg gctgctctga    180

tgccgccgtg ttccggctgt cagcgcaggg gcgcccggtt ctttttgtca agaccgacct    240

gtccggtgcc ctgaatgaac tgcaagacga ggcagcgcgg ctatcgtggc tggccacgac    300
```

-continued

```
gggcgttcct tgcgcagctg tgctcgacgt tgtcactgaa gcgggaaggg actggctgct    360
attgggcgaa gtgccggggc aggatctcct gtcatctcac cttgctcctg ccgagaaagt    420
atccatcatg gctgatgcaa tgcggcggct gcatacgctt gatccggcta cctgcccatt    480
cgaccaccaa gcgaaacatc gcatcgagcg agcacgtact cggatggaag ccggtcttgt    540
cgatcaggat gatctggacg aagagcatca ggggctcgcg ccagccgaac tgttcgccag    600
gctcaaggcg agcatgcccg acggcgagga tctcgtcgtg acccatggcg atgcctgctt    660
gccgaatatc atggtggaaa atggccgctt ttctggattc atcgactgtg gccggctggg    720
tgtggcggac cgctatcagg acatagcgtt ggctacccgt gatattgctg aagagcttgg    780
cggcgaatgg gctgaccgct tcctcgtgct ttacggtatc gccgctcccg attcgcagcg    840
catcgccttc tatcgccttc ttgacgagtt cttctgaatt attaacgctt acaatttcct    900
gatgcggtat tttctcctta cgcatctgtg cggtatttca caccgcatac aggtggcact    960
tttcggggaa atgtgcgcgg aacccctatt tgtttatttt tctaaataca ttcaaatatg   1020
tatccgctca tgagacaata accctgataa atgcttcaat aatagcacgt gctaaaactt   1080
catttttaat ttaaaaggat ctaggtgaag atcctttttg ataatctcat gaccaaaatc   1140
ccttaacgtg agttttcgtt ccactgagcg tcagaccccg tagaaaagat caaaggatct   1200
tcttgagatc ctttttttct gcgcgtaatc tgctgcttgc aaacaaaaaa accaccgcta   1260
ccagcggtgg tttgtttgcc ggatcaagag ctaccaactc tttttccgaa ggtaactggc   1320
ttcagcagag cgcagatacc aaatactgtc cttctagtgt agccgtagtt aggccaccac   1380
ttcaagaact ctgtagcacc gcctacatac ctcgctctgc taatcctgtt accagtggct   1440
gctgccagtg gcgataagtc gtgtcttacc gggttggact caagacgata gttaccggat   1500
aaggcgcagc ggtcgggctg aacggggggt tcgtgcacac agcccagctt ggagcgaacg   1560
acctacaccg aactgagata cctacagcgt gagctatgag aaagcgccac gcttcccgaa   1620
gggagaaagg cggacaggta tccggtaagc ggcagggtcg gaacaggaga gcgcacgagg   1680
gagcttccag ggggaaacgc ctggtatctt tatagtcctg tcgggtttcg ccacctctga   1740
cttgagcgtc gatttttgtg atgctcgtca ggggggcgga gcctatggaa aaacgccagc   1800
aacgcggcct ttttacggtt cctgggcttt tgctggcctt ttgctcacat gttcttgact   1860
cttcgcgatg tacgggccag atatacgcgt tgacattgat tattgactag ttattaatag   1920
taatcaatta cggggtcatt agttcatagc ccatatatgg agttccgcgt tacataactt   1980
acggtaaatg gcccgcctgg ctgaccgccc aacgaccccc gcccattgac gtcaataatg   2040
acgtatgttc ccatagtaac gccaataggg actttccatt gacgtcaatg ggtggactat   2100
ttacggtaaa ctgcccactt ggcagtacat caagtgtatc atatgccaag tacgccccct   2160
attgacgtca atgacggtaa atggcccgcc tggcattatg cccagtacat gaccttatgg   2220
gactttccta cttggcagta catctacgta ttagtcatcg ctattaccat ggtgatgcgg   2280
ttttggcagt acatcaatgg gcgtggatag cggtttgact cacggggatt tccaagtctc   2340
caccccattg acgtcaatgg gagtttgttt tggcaccaaa atcaacggga ctttccaaaa   2400
tgtcgtaaca actccgcccc attgacgcaa atgggcggta ggcgtgtacg gtgggaggtc   2460
tatataagca gagctctctg gctaactaga gaacccactg cttactggct tatcgaaatt   2520
aatacgactc actataggga gacccaagct ggctagcgtt taaacttaag cttggtaccg   2580
agctcggatc ctgatcagcc accatgctgt catatctgat ctttgccctg gctgtgagcc   2640
```

-continued caatcctcgg aaagatcgaa atcgtgttcc cacaacacac cacaggggac tggaagcgcg 2700
tgccccacga gtacaactac tgcccgacct cagccgacaa gaatagccac ggcacgcaga 2760
ccggcatccc tgtggagctg accatgccca aggggctcac aacgcaccaa gtcgaaggct 2820
tcatgtgcca cagcgctctc tggatgacaa cctgcgattt tcgctggtat ggccccaagt 2880
acatcacgca cagcatccac aatgaggaac caaccgacta ccagtgcctc gaagccatca 2940
agtcatacaa ggatggggtg agcttcaacc ccggcttccc gccccaatca tgtggctacg 3000
gcaccgtgac cgacgccgag gcccacatcg tgaccgtgac accccactca gtcaaggtgg 3060
acgagtacac aggcgaatgg atcgaccccc acttcatcgg gggccgctgt aagggccaaa 3120
tctgcgagac cgtgcacaac agcaccaagt ggtttacgtc atcagacggc gaaagcgtgt 3180
gcagccaact gtttacgctc gtgggcggca tcttctttag cgacagcgag gagatcacca 3240
gcatgggcct cccggagaca ggaatccgca gcaactactt tccgtacatc agcaccgagg 3300
gaatctgtaa gatgcctttt tgccgcaagc agggatataa gctgaagaat gacctgtggt 3360
tccagatcat ggacccggac ctggacaaga ccgtccgcga tctgccccac atcaaggact 3420
gtgatctgtc atcaagcatc atcacccccg gagaacacgc cacggacatc agcctcatca 3480
gcgatgtgga gcgcatcctc gactacgctc tctgccagaa cacatggagc aagatcgaaa 3540
gcggcgaacc catcacccca gtggacctga gctatctcgg cccaaagaac cccggcgtgg 3600
ggcccgtgtt caccatcatc aacgggagcc tgcactactt tacaagcaag tatctgcgcg 3660
tggagctcga aagcccagtc atcccccgca tggaggggaa ggtggccggg acccgcatcg 3720
tgcgccagct gtgggaccag tggttccctt ttggcgaggt ggaaatcggc cccaacggcg 3780
tgctgaagac caagcaagga tataagttcc cgctgcacat catcgggacg ggcgaagtgg 3840
acagcgatat caagatggag cgcgtggtca agcactggga gcacccacac atcgaggctg 3900
ctcagacctt tctcaagaag gacgataccg gcgaagtcct gtattacggg gatacgggag 3960
tgagcaagaa ccctgtggag ctggtggaag gctggttcag cggatggcgc tcaagcctga 4020
tgggcgtgct ggccgtcatc atcggatttg tgatcctgat gttcctcatc aagctgatcg 4080
gcgtgctgtc aagcctgttc cgccctaagc gccgcccaat ctacaagagc gacgtcgaga 4140
tggcccactt tcgctaagaa ttctgcagat atccagcaca gtggcggccg ctcgagtgta 4200
caaattcccg ataatcaacc tctggattac aaaatttgtg aaagattgac tggtattctt 4260
aactatgttg ctccttttac gctatgtgga tacgctgctt taatgccttt gtatcatgct 4320
attgcttccc gtatggcttt cattttctcc tccttgtata aatcctggtt gctgtctctt 4380
tatgaggagt tgtggcccgt tgtcaggcaa cgtggcgtgg tgtgcactgt gtttgctgac 4440
gcaaccccca ctggttgggg cattgccacc acctgtcagc tcctttccgg gactttcgct 4500
ttccccctcc ctattgccac ggcggaactc atcgccgcct gccttgcccg ctgctggaca 4560
ggggctcggc tgttgggcac tgacaattcc gtggtgttgt cggggaagct gacgtccttt 4620
ccatcgctgc tcgcctgtgt tgccacctgg attctgcgcg ggacgtcctt ctgctacgtc 4680
ccttcggccc tcaatccagc ggaccttcct tcccgcggcc tgctgccggc tctgcggcct 4740
cttccgcgtc ttcgccttcg ccctcagacg agtcggatct ccctttgggc cgcctccccg 4800
ctcgagtcta gagggcccgt ttaaacccgc tgatcagcct cgactgtgcc ttctagttgc 4860
cagccatctg ttgtttgccc ctcccccgtg ccttccttga ccctggaagg tgccactccc 4920
actgtccttt cctaataaaa tgaggaaatt gcatcgcatt gtctgagtag gtgtcattct 4980
attctggggg gtggggtggg gcaggacagc aagggggagg attgggaaga caatagcagg 5040

```
catgctgggg atgcggtggg ctctatggct tctactgggc ggttttatgg acagcaagcg   5100

aaccggaatt gccagctggg gcgccctctg gtaaggttgg gaagccctgc aaagtaaa     5158


<210> SEQ ID NO 6
<211> LENGTH: 720
<212> TYPE: DNA
<213> ORGANISM: Artificial Sequence
<220> FEATURE:
<223> OTHER INFORMATION: eGFP

<400> SEQUENCE: 6

atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagtaa    720


<210> SEQ ID NO 7
<211> LENGTH: 239
<212> TYPE: PRT
<213> ORGANISM: Artificial Sequence
<220> FEATURE:
<223> OTHER INFORMATION: eGFP protein

<400> SEQUENCE: 7

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160
```

```
Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 8
<211> LENGTH: 1725
<212> TYPE: DNA
<213> ORGANISM: Artificial Sequence
<220> FEATURE:
<223> OTHER INFORMATION: A111-Luciferase

<400> SEQUENCE: 8

ggatccgcca ccatggccgc agccgcagcc gtgaagaact ggatgactca aacgctcgcc     60

gctgcaatgg aagatgccaa aaacattaag aagggcccag cgccattcta cccactcgaa    120

gacgggaccg ccggcgagca gctgcacaaa gccatgaagc gctacgccct ggtgcccggc    180

accatcgcct ttaccgacgc acatatcgag gtggacatta cctacgccga gtacttcgag    240

atgagcgttc ggctggcaga agctatgaag cgctatgggc tgaatacaaa ccatcggatc    300

gtggtgtgca gcgagaatag cttgcagttc ttcatgcccg tgttgggtgc cctgttcatc    360

ggtgtggctg tggccccagc taacgacatc tacaacgagc gcgagctgct gaacagcatg    420

ggcatcagcc agcccaccgt cgtattcgtg agcaagaaag ggctgcaaaa gatcctcaac    480

gtgcaaaaga agctaccgat catacaaaag atcatcatca tggatagcaa gaccgactac    540

cagggcttcc aaagcatgta caccttcgtg acttcccatt tgccacccgg cttcaacgag    600

tacgacttcg tgcccgagag cttcgaccgg gacaaaacca tcgccctgat catgaacagt    660

agtggcagta ccggattgcc caagggcgta gccctaccgc accgcaccgc ttgtgtccga    720

ttcagtcatg cccgcgaccc catcttcggc aaccagatca tccccgacac cgctatcctc    780

agcgtggtgc catttcacca cggcttcggc atgttcacca cgctgggcta cttgatctgc    840

ggctttcggg tcgtgctcat gtaccgcttc gaggaggagc tattcttgcg cagcttgcaa    900

gactataaga ttcaatctgc cctgctggtg cccacactat ttagcttctt cgctaagagc    960

actctcatcg acaagtacga cctaagcaac ttgcacgaga tcgccagcgg cggggcgccg   1020

ctcagcaagg aggtaggtga ggccgtggcc aaacgcttcc acctaccagg catccgccag   1080

ggctacggcc tgacagaaac aaccagcgcc attctgatca cccccgaagg ggacgacaag   1140

cctggcgcag taggcaaggt ggtgcccttc ttcgaggcta aggtggtgga cttggacacc   1200

ggtaagacac tgggtgtgaa ccagcgcggc gagctgtgcg tccgtggccc catgatcatg   1260

agcggctacg ttaacaaccc cgaggctaca aacgctctca tcgacaagga cggctggctg   1320

cacagcggcg acatcgccta ctgggacgag gacgagcact tcttcatcgt ggaccggctg   1380

aagagcctga tcaaatacaa gggctaccag gtagccccag ccgaactgga gagcatcctg   1440

ctgcaacacc ccaacatctt cgacgccggg gtcgccggcc tgcccgacga cgatgccggc   1500

gagctgcccg ccgcagtcgt cgtgctggaa cacggtaaaa ccatgaccga gaaggagatc   1560

gtggactatg tggccagcca ggttacaacc gccaagaagc tgcgcggtgg tgttgtgttc   1620
```

```
gtggacgagg tgcctaaagg actgaccggc aagttggacg cccgcaagat ccgcgagatt   1680

ctcattaagg ccaagaaggg cggcaagatc gccgtgtaac tcgag                  1725


<210> SEQ ID NO 9
<211> LENGTH: 568
<212> TYPE: PRT
<213> ORGANISM: Artificial Sequence
<220> FEATURE:
<223> OTHER INFORMATION: A111-Luciferase

<400> SEQUENCE: 9

Met Ala Ala Ala Ala Ala Val Lys Asn Trp Met Thr Gln Thr Leu Ala
1               5                   10                  15

Ala Ala Met Glu Asp Ala Lys Asn Ile Lys Lys Gly Pro Ala Pro Phe
            20                  25                  30

Tyr Pro Leu Glu Asp Gly Thr Ala Gly Glu Gln Leu His Lys Ala Met
        35                  40                  45

Lys Arg Tyr Ala Leu Val Pro Gly Thr Ile Ala Phe Thr Asp Ala His
    50                  55                  60

Ile Glu Val Asp Ile Thr Tyr Ala Glu Tyr Phe Glu Met Ser Val Arg
65                  70                  75                  80

Leu Ala Glu Ala Met Lys Arg Tyr Gly Leu Asn Thr Asn His Arg Ile
                85                  90                  95

Val Val Cys Ser Glu Asn Ser Leu Gln Phe Phe Met Pro Val Leu Gly
            100                 105                 110

Ala Leu Phe Ile Gly Val Ala Val Ala Pro Ala Asn Asp Ile Tyr Asn
        115                 120                 125

Glu Arg Glu Leu Leu Asn Ser Met Gly Ile Ser Gln Pro Thr Val Val
    130                 135                 140

Phe Val Ser Lys Lys Gly Leu Gln Lys Ile Leu Asn Val Gln Lys Lys
145                 150                 155                 160

Leu Pro Ile Ile Gln Lys Ile Ile Ile Met Asp Ser Lys Thr Asp Tyr
                165                 170                 175

Gln Gly Phe Gln Ser Met Tyr Thr Phe Val Thr Ser His Leu Pro Pro
            180                 185                 190

Gly Phe Asn Glu Tyr Asp Phe Val Pro Glu Ser Phe Asp Arg Asp Lys
        195                 200                 205

Thr Ile Ala Leu Ile Met Asn Ser Ser Gly Ser Thr Gly Leu Pro Lys
    210                 215                 220

Gly Val Ala Leu Pro His Arg Thr Ala Cys Val Arg Phe Ser His Ala
225                 230                 235                 240

Arg Asp Pro Ile Phe Gly Asn Gln Ile Ile Pro Asp Thr Ala Ile Leu
                245                 250                 255

Ser Val Val Pro Phe His His Gly Phe Gly Met Phe Thr Thr Leu Gly
            260                 265                 270

Tyr Leu Ile Cys Gly Phe Arg Val Val Leu Met Tyr Arg Phe Glu Glu
        275                 280                 285

Glu Leu Phe Leu Arg Ser Leu Gln Asp Tyr Lys Ile Gln Ser Ala Leu
    290                 295                 300

Leu Val Pro Thr Leu Phe Ser Phe Phe Ala Lys Ser Thr Leu Ile Asp
305                 310                 315                 320

Lys Tyr Asp Leu Ser Asn Leu His Glu Ile Ala Ser Gly Gly Ala Pro
                325                 330                 335

Leu Ser Lys Glu Val Gly Glu Ala Val Ala Lys Arg Phe His Leu Pro
            340                 345                 350
```

```
Gly Ile Arg Gln Gly Tyr Gly Leu Thr Glu Thr Thr Ser Ala Ile Leu
        355                 360                 365

Ile Thr Pro Glu Gly Asp Asp Lys Pro Gly Ala Val Gly Lys Val Val
    370                 375                 380

Pro Phe Phe Glu Ala Lys Val Val Asp Leu Asp Thr Gly Lys Thr Leu
385                 390                 395                 400

Gly Val Asn Gln Arg Gly Glu Leu Cys Val Arg Gly Pro Met Ile Met
                405                 410                 415

Ser Gly Tyr Val Asn Asn Pro Glu Ala Thr Asn Ala Leu Ile Asp Lys
            420                 425                 430

Asp Gly Trp Leu His Ser Gly Asp Ile Ala Tyr Trp Asp Glu Asp Glu
        435                 440                 445

His Phe Phe Ile Val Asp Arg Leu Lys Ser Leu Ile Lys Tyr Lys Gly
    450                 455                 460

Tyr Gln Val Ala Pro Ala Glu Leu Glu Ser Ile Leu Leu Gln His Pro
465                 470                 475                 480

Asn Ile Phe Asp Ala Gly Val Ala Gly Leu Pro Asp Asp Asp Ala Gly
                485                 490                 495

Glu Leu Pro Ala Ala Val Val Val Leu Glu His Gly Lys Thr Met Thr
            500                 505                 510

Glu Lys Glu Ile Val Asp Tyr Val Ala Ser Gln Val Thr Thr Ala Lys
        515                 520                 525

Lys Leu Arg Gly Gly Val Val Phe Val Asp Glu Val Pro Lys Gly Leu
    530                 535                 540

Thr Gly Lys Leu Asp Ala Arg Lys Ile Arg Glu Ile Leu Ile Lys Ala
545                 550                 555                 560

Lys Lys Gly Gly Lys Ile Ala Val
                565
```

<210> SEQ ID NO 10
<211> LENGTH: 1026
<212> TYPE: DNA
<213> ORGANISM: Plasmodium berghei
<220> FEATURE:
<221> NAME/KEY: misc_feature
<223> OTHER INFORMATION: circumsporozoite (CS) protein (CSP)

<400> SEQUENCE: 10

```
atggccaaga agtgtaccat actggtcgtt gcgtcacttc tgttggtcaa ttctctgctc     60

ccaggctatg gacagaacaa atccattcag gcacagagga acctcaacga actctgctac    120

aatgaaggga atgacaataa gctgtatcac gtgctgaatt ccaagaacgg caaaatctac    180

aatcgcaaca cagtaaatcg gttgcttgcc gatgcacccg agggtaagaa gaatgaaaag    240

aagaatgaga aaatcgagcg caacaacaag cttaaacagc caccgcctcc tcctaaccca    300

aatgacccac cgccacccaa tccaaacgac ccaccgcctc ccaaccctaa cgatcctcca    360

ccgcccaacc ctaatgaccc accacctccc aatgcaaacg atccaccccc tcctaacgct    420

aacgaccctg ctccacccaa cgctaacgat cccgcgcccc ccaatgccaa cgaccccgca    480

ccacctaatg ccaacgatcc cgccccgccc aatgctaatg atcctccacc acccaaccca    540

aacgaccctg cccctcctaa tgctaacgat ccaccacctc ccaatccgaa tgatcccgct    600

ccacctcagg ggaacaacaa ccctcagccc caacctagac cacagccgca gccccaaccc    660

caaccccagc cccagcctca accccagccc cagccacgtc cgcagcctca gcctcaacct    720

ggaggcaaca ataacaacaa gaataacaac aacgacgaca gctacattcc aagtgccgag    780
```

aaaattctgg agtttgttaa gcagatccga gacagcataa ccgaagaatg gtcacagtgt 840
aacgtgacgt gtggatctgg catcagagtg aggaaacgga agggttccaa taagaaagca 900
gaggatctga ctctggagga cattgataca gagatctgca aaatggacaa atgcagctct 960
atcttcaaca tcgtgagtaa tagcctcggg tttgtgattc tgctggtcct ggtgttcttc 1020
aattga 1026

<210> SEQ ID NO 11
<211> LENGTH: 341
<212> TYPE: PRT
<213> ORGANISM: Plasmodium berghei
<220> FEATURE:
<221> NAME/KEY: misc_feature
<223> OTHER INFORMATION: CSP

<400> SEQUENCE: 11

Met Ala Lys Lys Cys Thr Ile Leu Val Val Ala Ser Leu Leu Leu Val
1 5 10 15

Asn Ser Leu Leu Pro Gly Tyr Gly Gln Asn Lys Ser Ile Gln Ala Gln
20 25 30

Arg Asn Leu Asn Glu Leu Cys Tyr Asn Glu Gly Asn Asp Asn Lys Leu
35 40 45

Tyr His Val Leu Asn Ser Lys Asn Gly Lys Ile Tyr Asn Arg Asn Thr
50 55 60

Val Asn Arg Leu Leu Ala Asp Ala Pro Glu Gly Lys Lys Asn Glu Lys
65 70 75 80

Lys Asn Glu Lys Ile Glu Arg Asn Asn Lys Leu Lys Gln Pro Pro Pro
85 90 95

Pro Pro Asn Pro Asn Asp Pro Pro Pro Pro Asn Pro Asn Asp Pro Pro
100 105 110

Pro Pro Asn Pro Asn Asp Pro Pro Pro Pro Asn Pro Asn Asp Pro Pro
115 120 125

Pro Pro Asn Ala Asn Asp Pro Pro Pro Pro Asn Ala Asn Asp Pro Ala
130 135 140

Pro Pro Asn Ala Asn Asp Pro Ala Pro Pro Asn Ala Asn Asp Pro Ala
145 150 155 160

Pro Pro Asn Ala Asn Asp Pro Ala Pro Pro Asn Ala Asn Asp Pro Pro
165 170 175

Pro Pro Asn Pro Asn Asp Pro Ala Pro Pro Asn Ala Asn Asp Pro Pro
180 185 190

Pro Pro Asn Pro Asn Asp Pro Ala Pro Pro Gln Gly Asn Asn Asn Pro
195 200 205

Gln Pro Gln Pro Arg Pro Gln Pro Gln Pro Gln Pro Gln Pro Gln Pro
210 215 220

Gln Pro Gln Pro Gln Pro Gln Pro Arg Pro Gln Pro Gln Pro Gln Pro
225 230 235 240

Gly Gly Asn Asn Asn Asn Lys Asn Asn Asn Asn Asp Asp Ser Tyr Ile
245 250 255

Pro Ser Ala Glu Lys Ile Leu Glu Phe Val Lys Gln Ile Arg Asp Ser
260 265 270

Ile Thr Glu Glu Trp Ser Gln Cys Asn Val Thr Cys Gly Ser Gly Ile
275 280 285

Arg Val Arg Lys Arg Lys Gly Ser Asn Lys Lys Ala Glu Asp Leu Thr
290 295 300

```
Leu Glu Asp Ile Asp Thr Glu Ile Cys Lys Met Asp Lys Cys Ser Ser
305                 310                 315                 320

Ile Phe Asn Ile Val Ser Asn Ser Leu Gly Phe Val Ile Leu Leu Val
                325                 330                 335

Leu Val Phe Phe Asn
            340


<210> SEQ ID NO 12
<211> LENGTH: 340
<212> TYPE: PRT
<213> ORGANISM: Plasmodium berghei
<220> FEATURE:
<221> NAME/KEY: misc_feature
<223> OTHER INFORMATION: CSP

<400> SEQUENCE: 12

Met Lys Lys Cys Thr Ile Leu Val Val Ala Ser Leu Leu Leu Val Asn
1               5                   10                  15

Ser Leu Leu Pro Gly Tyr Gly Gln Asn Lys Ser Ile Gln Ala Gln Arg
            20                  25                  30

Asn Leu Asn Glu Leu Cys Tyr Asn Glu Gly Asn Asp Asn Lys Leu Tyr
        35                  40                  45

His Val Leu Asn Ser Lys Asn Gly Lys Ile Tyr Asn Arg Asn Thr Val
    50                  55                  60

Asn Arg Leu Leu Ala Asp Ala Pro Glu Gly Lys Lys Asn Glu Lys Lys
65                  70                  75                  80

Asn Glu Lys Ile Glu Arg Asn Asn Lys Leu Lys Gln Pro Pro Pro Pro
                85                  90                  95

Pro Asn Pro Asn Asp Pro Pro Pro Pro Asn Pro Asn Asp Pro Pro Pro
            100                 105                 110

Pro Asn Pro Asn Asp Pro Pro Pro Pro Asn Pro Asn Asp Pro Pro Pro
        115                 120                 125

Pro Asn Ala Asn Asp Pro Pro Pro Pro Asn Ala Asn Asp Pro Ala Pro
    130                 135                 140

Pro Asn Ala Asn Asp Pro Ala Pro Pro Asn Ala Asn Asp Pro Ala Pro
145                 150                 155                 160

Pro Asn Ala Asn Asp Pro Ala Pro Pro Asn Ala Asn Asp Pro Pro Pro
                165                 170                 175

Pro Asn Pro Asn Asp Pro Ala Pro Pro Asn Ala Asn Asp Pro Pro Pro
            180                 185                 190

Pro Asn Pro Asn Asp Pro Ala Pro Pro Gln Gly Asn Asn Asn Pro Gln
        195                 200                 205

Pro Gln Pro Arg Pro Gln Pro Gln Pro Gln Pro Gln Pro Gln Pro Gln
    210                 215                 220

Pro Gln Pro Gln Pro Gln Pro Arg Pro Gln Pro Gln Pro Gln Pro Gly
225                 230                 235                 240

Gly Asn Asn Asn Asn Lys Asn Asn Asn Asn Asp Asp Ser Tyr Ile Pro
                245                 250                 255

Ser Ala Glu Lys Ile Leu Glu Phe Val Lys Gln Ile Arg Asp Ser Ile
            260                 265                 270

Thr Glu Glu Trp Ser Gln Cys Asn Val Thr Cys Gly Ser Gly Ile Arg
        275                 280                 285

Val Arg Lys Arg Lys Gly Ser Asn Lys Lys Ala Glu Asp Leu Thr Leu
    290                 295                 300

Glu Asp Ile Asp Thr Glu Ile Cys Lys Met Asp Lys Cys Ser Ser Ile
305                 310                 315                 320
```

```
Phe Asn Ile Val Ser Asn Ser Leu Gly Phe Val Ile Leu Leu Val Leu
                325                 330                 335

Val Phe Phe Asn
            340


<210> SEQ ID NO 13
<211> LENGTH: 1203
<212> TYPE: DNA
<213> ORGANISM: Artificial Sequence
<220> FEATURE:
<223> OTHER INFORMATION: PfCSPhumanCO

<400> SEQUENCE: 13

gccaccatgg ctatgagaaa gctcgcgatc ctttccgtga gctcattcct gtttgtcgaa     60

gccttgttcc aggagtatca gtgctatgga tcatcctcca acacaagagt gctcaacgaa    120

ctgaactatg acaatgccgg tactaacctc tacaatgaac tggagatgaa ctactacggc    180

aaacaggaga actggtattc cctgaagaag aattccagat cactgggcga aaacgacgat    240

gggaataatg aggataacga gaagttgcgg aaaccaaagc acaagaagtt gaaacaaccc    300

gccgacggaa accctgatcc taacgccaac ccaaatgtag atcccaacgc caacccaaac    360

gtcgatccca atgccaatcc caatgttgac cccaatgcaa accctaatgc aaatcccaat    420

gccaatccca atgcaaatcc taatgctaat ccaaacgcca accctaacgc gaaccccaac    480

gccaatccta acgcaaatcc taacgcaaat cctaatgcca accctaatgc gaacccgaac    540

gctaatccta acgctaatcc gaatgcaaat ccaaatgcaa atccgaacgc caatcccaac    600

gtagacccaa atgcaaaccc gaacgctaac ccgaacgcaa acccaaacgc caatccgaac    660

gctaatccca atgctaatcc caacgctaac cccaatgcca acccgaatgc caaccccaat    720

gcgaatccaa atgcgaaccc aaacgccaat ccgaatgcga atcctaacgc taacccaaat    780

gctaatccaa acgctaatcc aaatgcgaac cccaatgcga atccaaataa gaacaatcag    840

gggaatggtc agggccataa catgcctaac gaccccaacc gaaatgtgga cgagaacgct    900

aacgcaaaca gcgctgtaaa gaacaacaac aatgaggagc cttctgacaa gcacatcaaa    960

gagtacctga ataaaatcca gaacagtctt tctacggaat ggtccccatg tagtgttact   1020

tgtggcaatg ggattcaagt caggatcaaa ccaggctctg cgaataagcc taaggatgaa   1080

ctggattatg ccaatgacat cgagaagaaa atatgcaaga tggagaagtg cagtagcgtg   1140

ttcaatgtcg taaactcaag cataggtctg ataatggtac tgagctttct gttcctcaac   1200

taa                                                                 1203


<210> SEQ ID NO 14
<211> LENGTH: 398
<212> TYPE: PRT
<213> ORGANISM: Artificial Sequence
<220> FEATURE:
<223> OTHER INFORMATION: PfCSP

<400> SEQUENCE: 14

Met Ala Met Arg Lys Leu Ala Ile Leu Ser Val Ser Ser Phe Leu Phe
1               5                   10                  15

Val Glu Ala Leu Phe Gln Glu Tyr Gln Cys Tyr Gly Ser Ser Ser Asn
            20                  25                  30

Thr Arg Val Leu Asn Glu Leu Asn Tyr Asp Asn Ala Gly Thr Asn Leu
        35                  40                  45
```

```
Tyr Asn Glu Leu Glu Met Asn Tyr Tyr Gly Lys Gln Glu Asn Trp Tyr
    50                  55                  60

Ser Leu Lys Lys Asn Ser Arg Ser Leu Gly Glu Asn Asp Asp Gly Asn
65                  70                  75                  80

Asn Glu Asp Asn Glu Lys Leu Arg Lys Pro Lys His Lys Lys Leu Lys
                85                  90                  95

Gln Pro Ala Asp Gly Asn Pro Asp Pro Asn Ala Asn Pro Asn Val Asp
            100                 105                 110

Pro Asn Ala Asn Pro Asn Val Asp Pro Asn Ala Asn Pro Asn Val Asp
        115                 120                 125

Pro Asn Ala Asn Pro Asn Ala Asn Pro Asn Ala Asn Pro Asn Ala Asn
    130                 135                 140

Pro Asn Ala Asn Pro Asn Ala Asn Pro Asn Ala Asn Pro Asn Ala Asn
145                 150                 155                 160

Pro Asn Ala Asn Pro Asn Ala Asn Pro Asn Ala Asn Pro Asn Ala Asn
                165                 170                 175

Pro Asn Ala Asn Pro Asn Ala Asn Pro Asn Ala Asn Pro Asn Ala Asn
            180                 185                 190

Pro Asn Ala Asn Pro Asn Val Asp Pro Asn Ala Asn Pro Asn Ala Asn
        195                 200                 205

Pro Asn Ala Asn Pro Asn Ala Asn Pro Asn Ala Asn Pro Asn Ala Asn
    210                 215                 220

Pro Asn Ala Asn Pro Asn Ala Asn Pro Asn Ala Asn Pro Asn Ala Asn
225                 230                 235                 240

Pro Asn Ala Asn Pro Asn Ala Asn Pro Asn Ala Asn Pro Asn Ala Asn
                245                 250                 255

Pro Asn Ala Asn Pro Asn Ala Asn Pro Asn Ala Asn Pro Asn Ala Asn
            260                 265                 270

Pro Asn Lys Asn Asn Gln Gly Asn Gly Gln Gly His Asn Met Pro Asn
        275                 280                 285

Asp Pro Asn Arg Asn Val Asp Glu Asn Ala Asn Ala Asn Ser Ala Val
    290                 295                 300

Lys Asn Asn Asn Asn Glu Glu Pro Ser Asp Lys His Ile Lys Glu Tyr
305                 310                 315                 320

Leu Asn Lys Ile Gln Asn Ser Leu Ser Thr Glu Trp Ser Pro Cys Ser
                325                 330                 335

Val Thr Cys Gly Asn Gly Ile Gln Val Arg Ile Lys Pro Gly Ser Ala
            340                 345                 350

Asn Lys Pro Lys Asp Glu Leu Asp Tyr Ala Asn Asp Ile Glu Lys Lys
        355                 360                 365

Ile Cys Lys Met Glu Lys Cys Ser Ser Val Phe Asn Val Val Asn Ser
    370                 375                 380

Ser Ile Gly Leu Ile Met Val Leu Ser Phe Leu Phe Leu Asn
385                 390                 395
```

<210> SEQ ID NO 15
<211> LENGTH: 423
<212> TYPE: PRT
<213> ORGANISM: Artificial Sequence
<220> FEATURE:
<223> OTHER INFORMATION: CSP

<400> SEQUENCE: 15

```
Met Arg Lys Leu Ala Ile Leu Ser Val Ser Ser Phe Leu Phe Val Glu
1               5                   10                  15
```

```
Ala Leu Phe Gln Glu Tyr Gln Cys Tyr Gly Ser Ser Ser Asn Thr Arg
            20                  25                  30

Val Leu Asn Glu Leu Asn Tyr Asp Asn Ala Gly Thr Asn Leu Tyr Asn
        35                  40                  45

Glu Leu Glu Met Asn Tyr Tyr Gly Lys Gln Glu Asn Trp Tyr Ser Leu
    50                  55                  60

Lys Lys Asn Ser Arg Ser Leu Gly Glu Asn Asp Asp Gly Asn Asn Asn
65                  70                  75                  80

Asn Gly Asp Asn Gly Arg Glu Gly Lys Asp Glu Asp Lys Arg Asp Gly
                85                  90                  95

Asn Asn Glu Asp Asn Glu Lys Leu Arg Lys Pro Lys His Lys Lys Leu
            100                 105                 110

Lys Gln Pro Gly Asp Gly Asn Pro Asp Pro Asn Ala Asn Pro Asn Val
        115                 120                 125

Asp Pro Asn Ala Asn Pro Asn Val Asp Pro Asn Ala Asn Pro Asn Val
    130                 135                 140

Asp Pro Asn Ala Asn Pro Asn Ala Asn Pro Asn Ala Asn Pro Asn Ala
145                 150                 155                 160

Asn Pro Asn Ala Asn Pro Asn Ala Asn Pro Asn Ala Asn Pro Asn Ala
                165                 170                 175

Asn Pro Asn Ala Asn Pro Asn Ala Asn Pro Asn Ala Asn Pro Asn Val
            180                 185                 190

Asp Pro Asn Ala Asn Pro Asn Ala Asn Pro Asn Ala Asn Pro Asn Ala
        195                 200                 205

Asn Pro Asn Ala Asn Pro Asn Ala Asn Pro Asn Ala Asn Pro Asn Ala
    210                 215                 220

Asn Pro Asn Ala Asn Pro Asn Ala Asn Pro Asn Ala Asn Pro Asn Ala
225                 230                 235                 240

Asn Pro Asn Ala Asn Pro Asn Ala Asn Pro Asn Ala Asn Pro Asn Ala
                245                 250                 255

Asn Pro Asn Ala Asn Pro Asn Ala Asn Pro Asn Ala Asn Pro Asn Ala
            260                 265                 270

Asn Pro Asn Ala Asn Pro Asn Ala Asn Pro Asn Ala Asn Pro Asn Ala
        275                 280                 285

Asn Pro Asn Ala Asn Pro Asn Ala Asn Pro Asn Lys Asn Asn Gln Gly
    290                 295                 300

Asn Gly Gln Gly His Asn Met Pro Asn Asp Pro Asn Arg Asn Val Asp
305                 310                 315                 320

Glu Asn Ala Asn Ala Asn Asn Ala Val Lys Asn Asn Asn Asn Glu Glu
                325                 330                 335

Pro Ser Asp Lys His Ile Thr Glu Tyr Leu Lys Lys Ile Gln Asn Ser
            340                 345                 350

Leu Ser Thr Glu Trp Ser Pro Cys Ser Val Thr Cys Gly Asn Gly Ile
        355                 360                 365

Gln Val Arg Ile Lys Pro Gly Ser Ala Gly Lys Ser Lys Asp Glu Leu
    370                 375                 380

Asp Tyr Glu Asn Asp Ile Glu Lys Lys Ile Cys Lys Met Glu Lys Cys
385                 390                 395                 400

Ser Ser Val Phe Asn Val Val Asn Ser Ser Ile Gly Leu Ile Met Val
                405                 410                 415

Leu Ser Phe Leu Phe Leu Asn
            420
```

<210> SEQ ID NO 16
<211> LENGTH: 1143
<212> TYPE: DNA
<213> ORGANISM: Artificial Sequence
<220> FEATURE:
<223> OTHER INFORMATION: PvCSPhumanCO

<400> SEQUENCE: 16
gccaccatgg ctaagaactt cattctgctt gccgtaagct ctattctctt ggtagacttg 60
tttccaacac actgtggaca taatgtagat ctcagtaaag caattaacct caatggtgtt 120
aattttaata atgtagacgc atcctctctc ggcgcggcac acgtgggtca aagtgccagt 180
agggggcgcg gactcggcga gaacccggac gacgaagaag gggatgcgaa aaagaagaag 240
gatgggaaga aggcagaacc caagaatcca agggagaata agctgaagca gccaggagat 300
agagctgacg gccagcctgc cggcgatagg gccgacggac aacccgcggg agaccgcgcg 360
gatggccaac ctgcgggtga ccgcgctgac gggcagcccg caggagacag agccgccgga 420
caacccgccg gcgaccgagc ggatggtcag cccgcgggcg atcgagcgga cggtcagcca 480
gctggagatc gcgcggacgg acaacctgcg ggggacaggg ctgacggtca accagccggt 540
gatagagcag cgggccaacc ggcaggggac cgagccgcag ggcagcccgc cggggacagg 600
gctgacgggc agccagcggg ggatagggcc gccggtcaac ctgcaggcga tcgagctgac 660
ggccaacccg cgggtgaccg ggcagccggc caacctgctg gggatcgagc agacggacag 720
ccggccggag atcgggccgc tggccaaccg gctggagaca gagccgctgg tcaacctgcc 780
ggagatcggg ccgctgggca ggccgcgggt gacagggcag ccggacaagc agcagggggg 840
aacgccggtg gacaaggaca gaacaatgag ggtgcgaatg ccccgaatga aaagagcgtt 900
aaagagtacc tggataaggt tagagcaacc gtaggcaccg aatggacccc ctgctccgtg 960
acttgcgggg taggtgttcg ggtcaggcgg agggtcaatg cggcgaacaa gaaaccggaa 1020
gatctgactt tgaacgatct tgaaacagat gtatgcacga tggacaagtg tgctggcata 1080
tttaacgtag tcagtaactc tctcggcctt gtgatcctct tggtcttggc gctgtttaac 1140
tag 1143

<210> SEQ ID NO 17
<211> LENGTH: 378
<212> TYPE: PRT
<213> ORGANISM: Plasmodium vivax
<220> FEATURE:
<221> NAME/KEY: misc_feature
<223> OTHER INFORMATION: PvCSP

<400> SEQUENCE: 17

Met Ala Lys Asn Phe Ile Leu Leu Ala Val Ser Ser Ile Leu Leu Val
1 5 10 15

Asp Leu Phe Pro Thr His Cys Gly His Asn Val Asp Leu Ser Lys Ala
20 25 30

Ile Asn Leu Asn Gly Val Asn Phe Asn Asn Val Asp Ala Ser Ser Leu
35 40 45

Gly Ala Ala His Val Gly Gln Ser Ala Ser Arg Gly Arg Gly Leu Gly
50 55 60

Glu Asn Pro Asp Asp Glu Glu Gly Asp Ala Lys Lys Lys Lys Asp Gly
65 70 75 80

Lys Lys Ala Glu Pro Lys Asn Pro Arg Glu Asn Lys Leu Lys Gln Pro
85 90 95

```
Gly Asp Arg Ala Asp Gly Gln Pro Ala Gly Asp Arg Ala Asp Gly Gln
            100                 105                 110

Pro Ala Gly Asp Arg Ala Asp Gly Gln Pro Ala Gly Asp Arg Ala Asp
        115                 120                 125

Gly Gln Pro Ala Gly Asp Arg Ala Ala Gly Gln Pro Ala Gly Asp Arg
    130                 135                 140

Ala Asp Gly Gln Pro Ala Gly Asp Arg Ala Asp Gly Gln Pro Ala Gly
145                 150                 155                 160

Asp Arg Ala Asp Gly Gln Pro Ala Gly Asp Arg Ala Asp Gly Gln Pro
                165                 170                 175

Ala Gly Asp Arg Ala Ala Gly Gln Pro Ala Gly Asp Arg Ala Ala Gly
            180                 185                 190

Gln Pro Ala Gly Asp Arg Ala Asp Gly Gln Pro Ala Gly Asp Arg Ala
        195                 200                 205

Ala Gly Gln Pro Ala Gly Asp Arg Ala Asp Gly Gln Pro Ala Gly Asp
    210                 215                 220

Arg Ala Ala Gly Gln Pro Ala Gly Asp Arg Ala Asp Gly Gln Pro Ala
225                 230                 235                 240

Gly Asp Arg Ala Ala Gly Gln Pro Ala Gly Asp Arg Ala Ala Gly Gln
                245                 250                 255

Pro Ala Gly Asp Arg Ala Ala Gly Gln Ala Ala Gly Asp Arg Ala Ala
            260                 265                 270

Gly Gln Ala Ala Gly Gly Asn Ala Gly Gly Gln Gly Gln Asn Asn Glu
        275                 280                 285

Gly Ala Asn Ala Pro Asn Glu Lys Ser Val Lys Glu Tyr Leu Asp Lys
    290                 295                 300

Val Arg Ala Thr Val Gly Thr Glu Trp Thr Pro Cys Ser Val Thr Cys
305                 310                 315                 320

Gly Val Gly Val Arg Val Arg Arg Arg Val Asn Ala Ala Asn Lys Lys
                325                 330                 335

Pro Glu Asp Leu Thr Leu Asn Asp Leu Glu Thr Asp Val Cys Thr Met
            340                 345                 350

Asp Lys Cys Ala Gly Ile Phe Asn Val Val Ser Asn Ser Leu Gly Leu
        355                 360                 365

Val Ile Leu Leu Val Leu Ala Leu Phe Asn
    370                 375


<210> SEQ ID NO 18
<211> LENGTH: 368
<212> TYPE: PRT
<213> ORGANISM: Plasmodium vivax
<220> FEATURE:
<221> NAME/KEY: misc_feature
<223> OTHER INFORMATION: CSP

<400> SEQUENCE: 18

Met Lys Asn Phe Ile Leu Leu Ala Val Ser Ser Ile Leu Leu Val Asp
1               5                   10                  15

Leu Phe Pro Thr His Cys Gly His Asn Val Asp Leu Ser Lys Ala Ile
            20                  25                  30

Asn Leu Asn Gly Val Asn Phe Asn Asn Val Asp Ala Ser Ser Leu Gly
        35                  40                  45

Ala Ala His Val Gly Gln Ser Ala Ser Arg Gly Arg Gly Leu Gly Glu
    50                  55                  60

Asn Pro Asp Asp Glu Glu Gly Asp Ala Lys Lys Lys Lys Asp Gly Lys
65                  70                  75                  80
```

```
Lys Ala Glu Pro Lys Asn Pro Arg Glu Asn Lys Leu Lys Gln Pro Gly
                85                  90                  95

Asp Arg Ala Asp Gly Gln Pro Ala Gly Asp Arg Ala Asp Gly Gln Pro
            100                 105                 110

Ala Gly Asp Arg Ala Asp Gly Gln Pro Ala Gly Asp Arg Ala Gly Gln
        115                 120                 125

Pro Ala Gly Asp Arg Ala Asp Gly Gln Pro Ala Gly Asp Arg Ala Asp
    130                 135                 140

Gly Gln Pro Ala Gly Asp Arg Ala Asp Gly Gln Pro Ala Gly Asp Arg
145                 150                 155                 160

Ala Asp Gly Gln Pro Ala Gly Asp Arg Ala Gly Gln Pro Ala Gly Asp
                165                 170                 175

Arg Ala Gly Gln Pro Ala Gly Asp Arg Ala Asp Gly Gln Pro Ala Gly
            180                 185                 190

Asp Arg Ala Gly Gln Pro Ala Gly Asp Arg Ala Asp Gly Gln Pro Ala
        195                 200                 205

Gly Asp Arg Ala Gly Gln Pro Ala Gly Asp Arg Ala Asp Gly Gln Pro
    210                 215                 220

Ala Gly Asp Arg Ala Gly Gln Pro Ala Gly Asp Arg Ala Gly Gln Pro
225                 230                 235                 240

Ala Gly Asp Arg Ala Gly Gln Pro Ala Gly Asp Arg Ala Gly Gln Pro
                245                 250                 255

Ala Gly Asn Gly Ala Gly Gly Gln Ala Ala Gly Gly Asn Ala Gly Gly
            260                 265                 270

Gln Gly Gln Asn Asn Glu Gly Ala Asn Ala Pro Asn Glu Lys Ser Val
        275                 280                 285

Lys Glu Tyr Leu Asp Lys Val Arg Ala Thr Val Gly Thr Glu Trp Thr
    290                 295                 300

Pro Cys Ser Val Thr Cys Gly Val Gly Val Arg Val Arg Arg Arg Val
305                 310                 315                 320

Asn Ala Ala Asn Lys Lys Pro Glu Asp Leu Thr Leu Asn Asp Leu Glu
                325                 330                 335

Thr Asp Val Cys Thr Met Asp Lys Cys Ala Gly Ile Phe Asn Val Val
            340                 345                 350

Ser Asn Ser Leu Gly Leu Val Ile Leu Leu Val Leu Ala Leu Phe Asn
        355                 360                 365
```

<210> SEQ ID NO 19
<211> LENGTH: 1842
<212> TYPE: DNA
<213> ORGANISM: Plasmodium berghei
<220> FEATURE:
<221> NAME/KEY: misc_feature
<223> OTHER INFORMATION: thrombospondin-related anonymous protein (TRAP)

<400> SEQUENCE: 19

```
ggatccgcca ccatggctaa gcttctgggg aacagtaaat acttctttgt ggtcctgctg     60

ctgtgcatta gcgttttcct caacggtcag gagattctgg acgaaatcaa gtactctgag    120

gaggtctgca acgaacaaat cgatctccac attctgctgg atgggagtgg cagcataggt    180

cactctaact ggatcagtca cgtgataccc atgctgacaa cccttgtgga caatttgaac    240

atcagccgcg atgagatcaa tatctccatg accttgttct ccacttatgc cagggaactt    300

gtgagactta agagatatgg gtctacaagc aaagccagtc tgaggttcat catcgcgcaa    360

ctccagaata actattctcc tcatggaacg acaaatctga ctagcgccct gttgaatgtg    420
```

```
gacaatctca ttcagaagaa aatgaatcgc cctaatgcca ttcagctcgt gattatcctt    480

actgacggca tccctaacaa tctgaagaag tccactactg ttgtcaacca gctgaagaag    540

aaggacgtca atgtcgctat tattggtgtt ggcgccggag taaacaatat gtttaaccgt    600

atattggtag gatgtggaaa acttgggcct tgtccctact actcttatgg ctcttgggat    660

caagcacaaa ccatgatcaa accatttctc tcaaaggtct gtcaggaagt ggagaaagtg    720

gcactgtgcg gtaagtggga ggagtggagt gagtgttcaa ccacttgcga caacggaacg    780

aaaataagga agcgaaaggt tctccatccc aactgtgccg gggaaatgac agccccatgt    840

aaagtgcggg actgtcctcc caaacctgta gcccctccgg tcattcccat caaagtccct    900

gacgtgcctg tgaaaccagt cgaacctatt gagcccgccg agccagcaga gccagcagaa    960

ccagcagagc ctgcagaacc cgccgaaccc gctgagcccg cggagcccgc cgaacccgct   1020

gaaccggcag aacccgcgga accagcggag cctgcagagc cagctgagcc tgctgaaccg   1080

gcggagcccg ctgaaccagc cgagcctgct aaaccggccg aaccggcaga gcccgctgag   1140

cctgccgagc cagcggaacc agttaacccc gataatccta tcctgccgat caagcccgag   1200

gagccatctg gtggagccga gccattgaat ccagaggtcg agaatccctt tatcatcccc   1260

gacgaaccca tcgaacccat tattgcgcca ggagctgtac cggataagcc catcattcct   1320

gaggaatcaa atgagctgcc aaacaatctt ccagagtctc cctccgatag tcaggtggag   1380

tatcctcggc caaacgacaa tggggataac agcaacaaca caatcaattc caacaagaac   1440

ataccaaata agcatgtgcc tcctacagac gacaacccct acaagggcca ggaagaacga   1500

atccctaagc cgcatcggag caacgacgaa tacatttact acaataatgc taacaataac   1560

gacaagctgg agcccgagat accctctaag gattacgagg aaaacaagag caagaaacag   1620

agcaaaagca acaatggcta taagatcgcc ggcggcataa ttggcgggct ggctattatc   1680

ggctgcattg gagtgggcta taacttcata gccgggtcct ccgccgccgc tatggctgga   1740

gaggcggcac cttttgagga cgtgatggct gatgatgaga aggggatcgt ggaaaacgaa   1800

cagttcaaac tgccagagga caatgattgg aattgactcg ag                      1842
```

<210> SEQ ID NO 20
<211> LENGTH: 607
<212> TYPE: PRT
<213> ORGANISM: Plasmodium berghei
<220> FEATURE:
<221> NAME/KEY: misc_feature
<223> OTHER INFORMATION: TRAP

<400> SEQUENCE: 20

```
Met Ala Lys Leu Leu Gly Asn Ser Lys Tyr Phe Phe Val Val Leu Leu
1               5                   10                  15

Leu Cys Ile Ser Val Phe Leu Asn Gly Gln Glu Ile Leu Asp Glu Ile
            20                  25                  30

Lys Tyr Ser Glu Glu Val Cys Asn Glu Gln Ile Asp Leu His Ile Leu
        35                  40                  45

Leu Asp Gly Ser Gly Ser Ile Gly His Ser Asn Trp Ile Ser His Val
    50                  55                  60

Ile Pro Met Leu Thr Thr Leu Val Asp Asn Leu Asn Ile Ser Arg Asp
65                  70                  75                  80

Glu Ile Asn Ile Ser Met Thr Leu Phe Ser Thr Tyr Ala Arg Glu Leu
                85                  90                  95
```

```
Val Arg Leu Lys Arg Tyr Gly Ser Thr Ser Lys Ala Ser Leu Arg Phe
            100                 105                 110

Ile Ile Ala Gln Leu Gln Asn Asn Tyr Ser Pro His Gly Thr Thr Asn
        115                 120                 125

Leu Thr Ser Ala Leu Leu Asn Val Asp Asn Leu Ile Gln Lys Lys Met
    130                 135                 140

Asn Arg Pro Asn Ala Ile Gln Leu Val Ile Ile Leu Thr Asp Gly Ile
145                 150                 155                 160

Pro Asn Asn Leu Lys Lys Ser Thr Thr Val Val Asn Gln Leu Lys Lys
                165                 170                 175

Lys Asp Val Asn Val Ala Ile Ile Gly Val Gly Ala Gly Val Asn Asn
            180                 185                 190

Met Phe Asn Arg Ile Leu Val Gly Cys Gly Lys Leu Gly Pro Cys Pro
        195                 200                 205

Tyr Tyr Ser Tyr Gly Ser Trp Asp Gln Ala Gln Thr Met Ile Lys Pro
    210                 215                 220

Phe Leu Ser Lys Val Cys Gln Glu Val Glu Lys Val Ala Leu Cys Gly
225                 230                 235                 240

Lys Trp Glu Glu Trp Ser Glu Cys Ser Thr Thr Cys Asp Asn Gly Thr
                245                 250                 255

Lys Ile Arg Lys Arg Lys Val Leu His Pro Asn Cys Ala Gly Glu Met
            260                 265                 270

Thr Ala Pro Cys Lys Val Arg Asp Cys Pro Pro Lys Pro Val Ala Pro
        275                 280                 285

Pro Val Ile Pro Ile Lys Val Pro Asp Val Pro Val Lys Pro Val Glu
    290                 295                 300

Pro Ile Glu Pro Ala Glu Pro Ala Glu Pro Ala Glu Pro Ala Glu Pro
305                 310                 315                 320

Ala Glu Pro Ala Glu Pro Ala Glu Pro Ala Glu Pro Ala Glu Pro Ala
                325                 330                 335

Glu Pro Ala Glu Pro Ala Glu Pro Ala Glu Pro Ala Glu Pro Ala Glu
            340                 345                 350

Pro Ala Glu Pro Ala Glu Pro Ala Glu Pro Ala Glu Pro Ala Lys Pro
        355                 360                 365

Ala Glu Pro Ala Glu Pro Ala Glu Pro Ala Glu Pro Ala Glu Pro Val
    370                 375                 380

Asn Pro Asp Asn Pro Ile Leu Pro Ile Lys Pro Glu Glu Pro Ser Gly
385                 390                 395                 400

Gly Ala Glu Pro Leu Asn Pro Glu Val Glu Asn Pro Phe Ile Ile Pro
                405                 410                 415

Asp Glu Pro Ile Glu Pro Ile Ile Ala Pro Gly Ala Val Pro Asp Lys
            420                 425                 430

Pro Ile Ile Pro Glu Glu Ser Asn Glu Leu Pro Asn Asn Leu Pro Glu
        435                 440                 445

Ser Pro Ser Asp Ser Gln Val Glu Tyr Pro Arg Pro Asn Asp Asn Gly
    450                 455                 460

Asp Asn Ser Asn Asn Thr Ile Asn Ser Asn Lys Asn Ile Pro Asn Lys
465                 470                 475                 480

His Val Pro Pro Thr Asp Asp Asn Pro Tyr Lys Gly Gln Glu Glu Arg
                485                 490                 495

Ile Pro Lys Pro His Arg Ser Asn Asp Glu Tyr Ile Tyr Tyr Asn Asn
            500                 505                 510
```

Ala Asn Asn Asn Asp Lys Leu Glu Pro Glu Ile Pro Ser Lys Asp Tyr
        515                 520                 525

Glu Glu Asn Lys Ser Lys Lys Gln Ser Lys Ser Asn Asn Gly Tyr Lys
    530                 535                 540

Ile Ala Gly Gly Ile Ile Gly Gly Leu Ala Ile Ile Gly Cys Ile Gly
545                 550                 555                 560

Val Gly Tyr Asn Phe Ile Ala Gly Ser Ser Ala Ala Ala Met Ala Gly
                565                 570                 575

Glu Ala Ala Pro Phe Glu Asp Val Met Ala Asp Asp Glu Lys Gly Ile
            580                 585                 590

Val Glu Asn Glu Gln Phe Lys Leu Pro Glu Asp Asn Asp Trp Asn
        595                 600                 605

<210> SEQ ID NO 21
<211> LENGTH: 606
<212> TYPE: PRT
<213> ORGANISM: Plasmodium berghei
<220> FEATURE:
<221> NAME/KEY: misc_feature
<223> OTHER INFORMATION: TRAP

<400> SEQUENCE: 21

Met Lys Leu Leu Gly Asn Ser Lys Tyr Phe Phe Val Val Leu Leu Leu
1               5                   10                  15

Cys Ile Ser Val Phe Leu Asn Gly Gln Glu Ile Leu Asp Glu Ile Lys
            20                  25                  30

Tyr Ser Glu Glu Val Cys Asn Glu Gln Ile Asp Leu His Ile Leu Leu
        35                  40                  45

Asp Gly Ser Gly Ser Ile Gly His Ser Asn Trp Ile Ser His Val Ile
    50                  55                  60

Pro Met Leu Thr Thr Leu Val Asp Asn Leu Asn Ile Ser Arg Asp Glu
65                  70                  75                  80

Ile Asn Ile Ser Met Thr Leu Phe Ser Thr Tyr Ala Arg Glu Leu Val
                85                  90                  95

Arg Leu Lys Arg Tyr Gly Ser Thr Ser Lys Ala Ser Leu Arg Phe Ile
            100                 105                 110

Ile Ala Gln Leu Gln Asn Asn Tyr Ser Pro His Gly Thr Thr Asn Leu
        115                 120                 125

Thr Ser Ala Leu Leu Asn Val Asp Asn Leu Ile Gln Lys Lys Met Asn
    130                 135                 140

Arg Pro Asn Ala Ile Gln Leu Val Ile Ile Leu Thr Asp Gly Ile Pro
145                 150                 155                 160

Asn Asn Leu Lys Lys Ser Thr Thr Val Val Asn Gln Leu Lys Lys Lys
                165                 170                 175

Asp Val Asn Val Ala Ile Ile Gly Val Gly Ala Gly Val Asn Asn Met
            180                 185                 190

Phe Asn Arg Ile Leu Val Gly Cys Gly Lys Leu Gly Pro Cys Pro Tyr
        195                 200                 205

Tyr Ser Tyr Gly Ser Trp Asp Gln Ala Gln Thr Met Ile Lys Pro Phe
    210                 215                 220

Leu Ser Lys Val Cys Gln Glu Val Glu Lys Val Ala Leu Cys Gly Lys
225                 230                 235                 240

Trp Glu Glu Trp Ser Glu Cys Ser Thr Thr Cys Asp Asn Gly Thr Lys
                245                 250                 255

Ile Arg Lys Arg Lys Val Leu His Pro Asn Cys Ala Gly Glu Met Thr
            260                 265                 270

```
Ala Pro Cys Lys Val Arg Asp Cys Pro Pro Lys Pro Val Ala Pro Pro
        275                 280                 285

Val Ile Pro Ile Lys Val Pro Asp Val Pro Val Lys Pro Val Glu Pro
    290                 295                 300

Ile Glu Pro Ala Glu Pro Ala Glu Pro Ala Glu Pro Ala Glu Pro Ala
305                 310                 315                 320

Glu Pro Ala Glu Pro Ala Glu Pro Ala Glu Pro Ala Glu Pro Ala Glu
                325                 330                 335

Pro Ala Glu Pro Ala Glu Pro Ala Glu Pro Ala Glu Pro Ala Glu Pro
            340                 345                 350

Ala Glu Pro Ala Glu Pro Ala Glu Pro Ala Glu Pro Ala Lys Pro Ala
        355                 360                 365

Glu Pro Ala Glu Pro Ala Glu Pro Ala Glu Pro Ala Glu Pro Val Asn
    370                 375                 380

Pro Asp Asn Pro Ile Leu Pro Ile Lys Pro Glu Glu Pro Ser Gly Gly
385                 390                 395                 400

Ala Glu Pro Leu Asn Pro Glu Val Glu Asn Pro Phe Ile Ile Pro Asp
                405                 410                 415

Glu Pro Ile Glu Pro Ile Ile Ala Pro Gly Ala Val Pro Asp Lys Pro
            420                 425                 430

Ile Ile Pro Glu Glu Ser Asn Glu Leu Pro Asn Asn Leu Pro Glu Ser
        435                 440                 445

Pro Ser Asp Ser Gln Val Glu Tyr Pro Arg Pro Asn Asp Asn Gly Asp
    450                 455                 460

Asn Ser Asn Asn Thr Ile Asn Ser Asn Lys Asn Ile Pro Asn Lys His
465                 470                 475                 480

Val Pro Pro Thr Asp Asp Asn Pro Tyr Lys Gly Gln Glu Glu Arg Ile
                485                 490                 495

Pro Lys Pro His Arg Ser Asn Asp Glu Tyr Ile Tyr Tyr Asn Asn Ala
            500                 505                 510

Asn Asn Asn Asp Lys Leu Glu Pro Glu Ile Pro Ser Lys Asp Tyr Glu
        515                 520                 525

Glu Asn Lys Ser Lys Lys Gln Ser Lys Ser Asn Asn Gly Tyr Lys Ile
    530                 535                 540

Ala Gly Gly Ile Ile Gly Gly Leu Ala Ile Ile Gly Cys Ile Gly Val
545                 550                 555                 560

Gly Tyr Asn Phe Ile Ala Gly Ser Ser Ala Ala Ala Met Ala Gly Glu
                565                 570                 575

Ala Ala Pro Phe Glu Asp Val Met Ala Asp Asp Glu Lys Gly Ile Val
            580                 585                 590

Glu Asn Glu Gln Phe Lys Leu Pro Glu Asp Asn Asp Trp Asn
        595                 600                 605
```

<210> SEQ ID NO 22
<211> LENGTH: 1734
<212> TYPE: DNA
<213> ORGANISM: Artificial Sequence
<220> FEATURE:
<223> OTHER INFORMATION: thrombospondin-related anonymous protein (TRAP)

<400> SEQUENCE: 22

```
gccaccatgg ctaatcactt gggcaacgtg aagtacctgg tgatagtgtt cctgatcttc     60

ttcgacctgt ttctggtcaa cggcagagat gtgcagaaca acatagtcga cgagattaag    120

tacagagagg aggtgtgcaa tgacgaggtg gatctctacc tgctgatgga ctgtagcggg    180
```

```
tcaatacgac ggcacaattg ggttaatcat gctgtcccct tggctatgaa gctgatccag    240
cagctcaatc tgaacgataa tgccattcac ctgtatgctt ccgtgttcag caataatgca    300
agggagatca ttcgcctcca cagtgacgct agtaagaata aggagaaagc cctgatcatc    360
atcaaatccc tgcttagcac caaccttccc tatggcaaga ccaatctcac agacgcgctt    420
ctgcaggtaa ggaagcatct gaacgatcgc atcaacagag agaatgcgaa tcagctggta    480
gtaatcctga ctgatgggat tcccgattcc atccaggaca gcctgaagga atcaaggaag    540
ctcagcgata gaggggtgaa aatcgcagtt ttcggaatcg gtcaggggat taacgtggcc    600
tttaatcgct ttctggtggg atgtcatcca tctgatggga aatgcaatct gtatgccgat    660
tctgcgtggg agaatgtgaa gaacgtgatt ggccccttta tgaaagccgt gtgcgtagag    720
gtggagaaaa ccgcctcctg tggagtttgg gacgaatgga gcccctgttc cgttacttgc    780
gggaaaggga cccgaagtcg caagagagaa atccttcacg agggttgcac ttctgaactc    840
caagagcaat gcgaggagga aaggtgtctc cctaaacgag aaccccttga tgtgcctgac    900
gaacctgagg acgatcaacc aagaccaagg ggagacaact tcgccgtcga gaaacccaat    960
gagaatatca ttgacaacaa tccacaggag ccatcaccta atccagagga aggcaaaggc   1020
gaaaacccta acggttttga cttggacgag aatccggaaa atccacccaa cccgcctaac   1080
cctccaaatc caccaaaccc tccgaatcct cctaaccctg atatccccga gcaagagcct   1140
aatattccag aggatagcga aaaggaggtc ccctctgacg tccctaagaa ccctgaagat   1200
gatcgcgaag agaactttga catacccaag aaacccgaga ataaacacga taatcagaac   1260
aatctcccga acgataaatc tgaccgctac attccataca gtccattgag cccaaaggtc   1320
ttggataatg aacggaaaca gtccgaccct caatcacagg acaataacgg taatcgtcat   1380
gttccgaact ccgaagatcg ggaaacaagg ccccatgggc gtaacaacga aaaccggagc   1440
tataaccgga agcacaacaa cacacccaag cacccggaac gggaagaaca tgagaagccc   1500
gataacaaca agaagaaggc aggctctgac aacaaataca aaatagccgg aggtattgcc   1560
ggaggattgg cactgctggc ctgcgctggc cttgcttaca agttcgtcgt tccaggcgcc   1620
gcaacgccct atgcaggcga accagctccc tttgacgaga cactgggaga agaggacaaa   1680
gacctggacg agcctgaaca gttcagactg cccgaggaaa acgagtggaa ttaa         1734
```

```
<210> SEQ ID NO 23
<211> LENGTH: 575
<212> TYPE: PRT
<213> ORGANISM: Artificial Sequence
<220> FEATURE:
<223> OTHER INFORMATION: PfTRAP

<400> SEQUENCE: 23

Met Ala Asn His Leu Gly Asn Val Lys Tyr Leu Val Ile Val Phe Leu
1               5                   10                  15

Ile Phe Phe Asp Leu Phe Leu Val Asn Gly Arg Asp Val Gln Asn Asn
            20                  25                  30

Ile Val Asp Glu Ile Lys Tyr Arg Glu Glu Val Cys Asn Asp Glu Val
        35                  40                  45

Asp Leu Tyr Leu Leu Met Asp Cys Ser Gly Ser Ile Arg Arg His Asn
    50                  55                  60

Trp Val Asn His Ala Val Pro Leu Ala Met Lys Leu Ile Gln Gln Leu
65                  70                  75                  80
```

```
Asn Leu Asn Asp Asn Ala Ile His Leu Tyr Ala Ser Val Phe Ser Asn
                85                  90                  95

Asn Ala Arg Glu Ile Ile Arg Leu His Ser Asp Ala Ser Lys Asn Lys
            100                 105                 110

Glu Lys Ala Leu Ile Ile Ile Lys Ser Leu Leu Ser Thr Asn Leu Pro
        115                 120                 125

Tyr Gly Lys Thr Asn Leu Thr Asp Ala Leu Leu Gln Val Arg Lys His
    130                 135                 140

Leu Asn Asp Arg Ile Asn Arg Glu Asn Ala Asn Gln Leu Val Val Ile
145                 150                 155                 160

Leu Thr Asp Gly Ile Pro Asp Ser Ile Gln Asp Ser Leu Lys Glu Ser
                165                 170                 175

Arg Lys Leu Ser Asp Arg Gly Val Lys Ile Ala Val Phe Gly Ile Gly
            180                 185                 190

Gln Gly Ile Asn Val Ala Phe Asn Arg Phe Leu Val Gly Cys His Pro
        195                 200                 205

Ser Asp Gly Lys Cys Asn Leu Tyr Ala Asp Ser Ala Trp Glu Asn Val
    210                 215                 220

Lys Asn Val Ile Gly Pro Phe Met Lys Ala Val Cys Val Glu Val Glu
225                 230                 235                 240

Lys Thr Ala Ser Cys Gly Val Trp Asp Glu Trp Ser Pro Cys Ser Val
                245                 250                 255

Thr Cys Gly Lys Gly Thr Arg Ser Arg Lys Arg Glu Ile Leu His Glu
            260                 265                 270

Gly Cys Thr Ser Glu Leu Gln Glu Gln Cys Glu Glu Glu Arg Cys Leu
        275                 280                 285

Pro Lys Arg Glu Pro Leu Asp Val Pro Asp Glu Pro Glu Asp Asp Gln
    290                 295                 300

Pro Arg Pro Arg Gly Asp Asn Phe Ala Val Glu Lys Pro Asn Glu Asn
305                 310                 315                 320

Ile Ile Asp Asn Asn Pro Gln Glu Pro Ser Pro Asn Pro Glu Glu Gly
                325                 330                 335

Lys Gly Glu Asn Pro Asn Gly Phe Asp Leu Asp Glu Asn Pro Glu Asn
            340                 345                 350

Pro Pro Asn Pro Pro Asn Pro Pro Asn Pro Pro Asn Pro Pro Asn Pro
        355                 360                 365

Pro Asn Pro Asp Ile Pro Glu Gln Glu Pro Asn Ile Pro Glu Asp Ser
    370                 375                 380

Glu Lys Glu Val Pro Ser Asp Val Pro Lys Asn Pro Glu Asp Asp Arg
385                 390                 395                 400

Glu Glu Asn Phe Asp Ile Pro Lys Lys Pro Glu Asn Lys His Asp Asn
                405                 410                 415

Gln Asn Asn Leu Pro Asn Asp Lys Ser Asp Arg Tyr Ile Pro Tyr Ser
            420                 425                 430

Pro Leu Ser Pro Lys Val Leu Asp Asn Glu Arg Lys Gln Ser Asp Pro
        435                 440                 445

Gln Ser Gln Asp Asn Asn Gly Asn Arg His Val Pro Asn Ser Glu Asp
    450                 455                 460

Arg Glu Thr Arg Pro His Gly Arg Asn Asn Glu Asn Arg Ser Tyr Asn
465                 470                 475                 480

Arg Lys His Asn Asn Thr Pro Lys His Pro Glu Arg Glu Glu His Glu
                485                 490                 495
```

Lys Pro Asp Asn Asn Lys Lys Lys Ala Gly Ser Asp Asn Lys Tyr Lys
500 505 510

Ile Ala Gly Gly Ile Ala Gly Gly Leu Ala Leu Leu Ala Cys Ala Gly
515 520 525

Leu Ala Tyr Lys Phe Val Val Pro Gly Ala Ala Thr Pro Tyr Ala Gly
530 535 540

Glu Pro Ala Pro Phe Asp Glu Thr Leu Gly Glu Glu Asp Lys Asp Leu
545 550 555 560

Asp Glu Pro Glu Gln Phe Arg Leu Pro Glu Glu Asn Glu Trp Asn
565 570 575

<210> SEQ ID NO 24
<211> LENGTH: 560
<212> TYPE: PRT
<213> ORGANISM: Artificial Sequence
<220> FEATURE:
<223> OTHER INFORMATION: TRAP

<400> SEQUENCE: 24

Met Asn His Leu Gly Asn Val Lys Tyr Leu Val Ile Val Phe Leu Ile
1 5 10 15

Phe Phe Asp Leu Phe Leu Val Asn Gly Arg Asp Val Gln Asn Asn Ile
20 25 30

Val Asp Glu Ile Lys Tyr Arg Glu Glu Val Cys Asn Asp Glu Val Asp
35 40 45

Leu Tyr Leu Leu Met Asp Cys Ser Gly Ser Ile Arg Arg His Asn Trp
50 55 60

Val Asn His Ala Val Pro Leu Ala Met Lys Leu Ile Gln Gln Leu Asn
65 70 75 80

Leu Asn Glu Asn Ala Ile His Leu Tyr Ala Asn Val Phe Ser Asn Asn
85 90 95

Ala Arg Glu Ile Ile Arg Leu His Ser Asp Ala Ser Lys Asn Lys Glu
100 105 110

Lys Ala Leu Ser Ile Ile Lys Ser Leu Leu Ser Thr Asn Leu Pro Phe
115 120 125

Gly Arg Thr Asn Leu Thr Asp Ala Leu Leu Gln Val Arg Lys His Leu
130 135 140

Asn Asp Arg Ile Asn Arg Glu Asn Ala Asn Gln Leu Val Val Ile Leu
145 150 155 160

Thr Asp Gly Ile Pro Asn Ser Ile Gln Asp Ser Leu Lys Glu Ser Arg
165 170 175

Lys Leu Ser Asp Arg Gly Val Lys Ile Ala Val Phe Gly Ile Gly Gln
180 185 190

Gly Ile Asn Val Ala Phe Asn Arg Phe Leu Val Gly Cys His Pro Ser
195 200 205

Asp Gly Lys Cys Asn Leu Tyr Ala Asp Ser Ala Trp Glu Asn Val Lys
210 215 220

Asn Val Ile Gly Pro Phe Met Lys Ala Val Cys Val Glu Val Glu Lys
225 230 235 240

Thr Ala Ser Cys Gly Val Trp Asp Glu Trp Ser Pro Cys Ser Val Thr
245 250 255

Cys Gly Lys Gly Thr Arg Ser Arg Lys Arg Glu Ile Leu His Glu Gly
260 265 270

Cys Thr Ser Glu Leu Gln Glu Gln Cys Glu Glu Glu Arg Cys Pro Pro
275 280 285

Lys Trp Glu Pro Leu Asp Val Pro Asp Asp Pro Glu Asp Asp Gln Pro
    290                 295                 300

Arg Pro Arg Gly Asp Asn Ser Ser Val Gln Lys Pro Glu Glu Asn Ile
305                 310                 315                 320

Ile Asp Asn Asn Pro Gln Glu Pro Ser Pro Asn Pro Glu Glu Gly Lys
                325                 330                 335

Gly Glu Asn Pro Asn Gly Phe Asp Leu Asp Glu Asn Pro Glu Asn Pro
            340                 345                 350

Pro Asn Pro Asp Ile Pro Gln Gln Glu Pro Asn Ile Pro Glu Asp Ser
        355                 360                 365

Glu Lys Glu Val Pro Ser Asp Val Pro Lys Asn Pro Glu Asp Asp Arg
    370                 375                 380

Glu Glu Asn Phe Asp Ile Pro Lys Lys Pro Glu Asn Lys His Asp Asn
385                 390                 395                 400

Gln Asn Asn Leu Pro Asn Asp Lys Ser Asp Arg Tyr Ile Pro Tyr Ser
                405                 410                 415

Pro Leu Pro Pro Asn Val Leu Asp Asn Glu Arg Lys Gln Ser Asp Pro
            420                 425                 430

Gln Ser Gln Asp Asn Asn Gly Asn Arg His Val Pro Asn Ser Glu Asp
        435                 440                 445

Arg Glu Thr Arg Pro His Gly Arg Asn Asn Glu Asn Arg Ser Tyr Asn
    450                 455                 460

Arg Lys His Asn Asp Thr Pro Lys His Pro Glu Arg Glu Glu His Glu
465                 470                 475                 480

Lys Pro Asp Asn Asn Lys Lys Lys Gly Gly Ser Ser Asp Asn Lys Tyr
                485                 490                 495

Lys Ile Ala Gly Gly Ile Ala Gly Gly Leu Ala Leu Leu Ala Cys Ala
            500                 505                 510

Gly Leu Ala Tyr Lys Phe Val Val Pro Gly Ala Ala Thr Pro Tyr Ala
        515                 520                 525

Gly Glu Pro Ala Pro Phe Asp Glu Thr Leu Gly Glu Glu Asp Lys Asp
    530                 535                 540

Leu Asp Glu Pro Glu Gln Phe Arg Leu Pro Glu Glu Asn Glu Trp Asn
545                 550                 555                 560

<210> SEQ ID NO 25
<211> LENGTH: 1680
<212> TYPE: DNA
<213> ORGANISM: Artificial Sequence
<220> FEATURE:
<223> OTHER INFORMATION: PvTRAPhumanCO

<400> SEQUENCE: 25
gccaccatgg ctaagctgct gcagaacaag tcttatctcc tggtcgtgtt cctgctttac 60
gtatccatat ttgcacgggg agatgaaaaa gttgtagatg aggtaaagta cagcgaggag 120
gtatgcaacg aatctgtcga tctctatctt ctcgtagatg gctctggtag tattgggtat 180
ccgaactgga taactaaggt aattcctatg ctgaacggtc ttattaatag tttgagcctc 240
agtcgagaca cgatcaatct ctatatgaat ctcttcggaa attacactac agaactcata 300
cggctgggct ctgggcagag tatagataaa cgacaggctc tgtcaaaggt gactgaactt 360
agaaagacct acacgccata tggcactact aacatgacag ccgcgcttga tgaagtccaa 420
aagcacctta atgatagagt gaaccgagag aaagcgatac aacttgtcat attgatgacc 480
gacggggtgc ccaactcaaa atacagggcg ctggaggtcg caaataaact gaagcaacgc 540

-continued aatgtttcct tggccgttat tggtgtcgga caaggaatca accatcagtt caatcggctg 600
atcgcgggct gccgacctcg ggagccgaac tgcaaatttt actcttatgc tgattggaat 660
gaggccgtag cacttataaa gccctttatt gctaaggtat gcacagaagt tgagcgcgtt 720
gccaactgtg gaccctggga cccctggacc gcgtgtagcg ttacgtgcgg caggggaacg 780
cactccaggt ctcgcccttc attgcatgaa aagtgcacta cccatatggt gtctgaatgt 840
gaagaggggg aatgcccagt ggagcctgag ccactgccag tacctgcgcc actcccaacg 900
gttccagaag atgtaaatcc gcgagacacg gacgacgaaa atgagaaccc gaacttcaac 960
aagggactgg acgtgccgga tgaagatgat gacgaagtac cgcccgcgaa tgaaggtgcg 1020
gatggcaacc cagtcgagga aaatgttttc ccgcctgctg acgatagcgt tcctgatgag 1080
agtaacgtgc tgcctctccc tccggcagtc ccaggcgggt cctctgagga gttcccggcg 1140
gacgttcaga acaatcccga ctctcctgaa gagctgccga tggagcaaga agtgcctcaa 1200
gataataacg tgaatgaacc agagagatcc gatagcaacg gttatggcgt aaatgagaag 1260
gtgataccta atcccctcga caatgagcga gacatggcca ataagaataa gaccgttcac 1320
ccaggccgga aggacagcgc gagagatcga tatgcccgcc cccatggttc cactcatgtc 1380
aataataata gagccaatga gaactcagac ataccaaaca acccagtacc ttctgattac 1440
gaacagccgg aggacaaggc taaaaagtcc tccaataacg gctataaaat cgctggtgga 1500
gtgatcgctg ggctcgcgtt ggttgggtgc gtcggtttcg cgtataactt cgtagcgggt 1560
ggaggcgctg ctggtatggc aggcgaaccg gctccctttg acgaagctat ggccgaagac 1620
gaaaaagacg tagccgaagc ggaccagttc aaattgcctg aggacaacga ttggaattaa 1680

<210> SEQ ID NO 26
<211> LENGTH: 557
<212> TYPE: PRT
<213> ORGANISM: Plasmodium vivax
<220> FEATURE:
<221> NAME/KEY: misc_feature
<223> OTHER INFORMATION: PvTRAP

<400> SEQUENCE: 26

Met Ala Lys Leu Leu Gln Asn Lys Ser Tyr Leu Leu Val Val Phe Leu
1 5 10 15

Leu Tyr Val Ser Ile Phe Ala Arg Gly Asp Glu Lys Val Val Asp Glu
20 25 30

Val Lys Tyr Ser Glu Glu Val Cys Asn Glu Ser Val Asp Leu Tyr Leu
35 40 45

Leu Val Asp Gly Ser Gly Ser Ile Gly Tyr Pro Asn Trp Ile Thr Lys
50 55 60

Val Ile Pro Met Leu Asn Gly Leu Ile Asn Ser Leu Ser Leu Ser Arg
65 70 75 80

Asp Thr Ile Asn Leu Tyr Met Asn Leu Phe Gly Asn Tyr Thr Thr Glu
85 90 95

Leu Ile Arg Leu Gly Ser Gly Gln Ser Ile Asp Lys Arg Gln Ala Leu
100 105 110

Ser Lys Val Thr Glu Leu Arg Lys Thr Tyr Thr Pro Tyr Gly Thr Thr
115 120 125

Asn Met Thr Ala Ala Leu Asp Glu Val Gln Lys His Leu Asn Asp Arg
130 135 140

Val Asn Arg Glu Lys Ala Ile Gln Leu Val Ile Leu Met Thr Asp Gly
145 150 155 160

```
Val Pro Asn Ser Lys Tyr Arg Ala Leu Glu Val Ala Asn Lys Leu Lys
                165                 170                 175

Gln Arg Asn Val Ser Leu Ala Val Ile Gly Val Gly Gln Gly Ile Asn
            180                 185                 190

His Gln Phe Asn Arg Leu Ile Ala Gly Cys Arg Pro Arg Glu Pro Asn
        195                 200                 205

Cys Lys Phe Tyr Ser Tyr Ala Asp Trp Asn Glu Ala Val Ala Leu Ile
    210                 215                 220

Lys Pro Phe Ile Ala Lys Val Cys Thr Glu Val Glu Arg Val Ala Asn
225                 230                 235                 240

Cys Gly Pro Trp Asp Pro Trp Thr Ala Cys Ser Val Thr Cys Gly Arg
                245                 250                 255

Gly Thr His Ser Arg Ser Arg Pro Ser Leu His Glu Lys Cys Thr Thr
            260                 265                 270

His Met Val Ser Glu Cys Glu Glu Gly Glu Cys Pro Val Glu Pro Glu
        275                 280                 285

Pro Leu Pro Val Pro Ala Pro Leu Pro Thr Val Pro Glu Asp Val Asn
    290                 295                 300

Pro Arg Asp Thr Asp Asp Glu Asn Glu Asn Pro Asn Phe Asn Lys Gly
305                 310                 315                 320

Leu Asp Val Pro Asp Glu Asp Asp Asp Glu Val Pro Pro Ala Asn Glu
                325                 330                 335

Gly Ala Asp Gly Asn Pro Val Glu Glu Asn Val Phe Pro Pro Ala Asp
            340                 345                 350

Asp Ser Val Pro Asp Glu Ser Asn Val Leu Pro Leu Pro Pro Ala Val
        355                 360                 365

Pro Gly Gly Ser Ser Glu Glu Phe Pro Ala Asp Val Gln Asn Asn Pro
    370                 375                 380

Asp Ser Pro Glu Glu Leu Pro Met Glu Gln Glu Val Pro Gln Asp Asn
385                 390                 395                 400

Asn Val Asn Glu Pro Glu Arg Ser Asp Ser Asn Gly Tyr Gly Val Asn
                405                 410                 415

Glu Lys Val Ile Pro Asn Pro Leu Asp Asn Glu Arg Asp Met Ala Asn
            420                 425                 430

Lys Asn Lys Thr Val His Pro Gly Arg Lys Asp Ser Ala Arg Asp Arg
        435                 440                 445

Tyr Ala Arg Pro His Gly Ser Thr His Val Asn Asn Asn Arg Ala Asn
    450                 455                 460

Glu Asn Ser Asp Ile Pro Asn Asn Pro Val Pro Ser Asp Tyr Glu Gln
465                 470                 475                 480

Pro Glu Asp Lys Ala Lys Lys Ser Ser Asn Asn Gly Tyr Lys Ile Ala
                485                 490                 495

Gly Gly Val Ile Ala Gly Leu Ala Leu Val Gly Cys Val Gly Phe Ala
            500                 505                 510

Tyr Asn Phe Val Ala Gly Gly Gly Ala Ala Gly Met Ala Gly Glu Pro
        515                 520                 525

Ala Pro Phe Asp Glu Ala Met Ala Glu Asp Glu Lys Asp Val Ala Glu
    530                 535                 540

Ala Asp Gln Phe Lys Leu Pro Glu Asp Asn Asp Trp Asn
545                 550                 555
```

<210> SEQ ID NO 27
<211> LENGTH: 556
<212> TYPE: PRT

<213> ORGANISM: Plasmodium vivax
<220> FEATURE:
<221> NAME/KEY: misc_feature
<223> OTHER INFORMATION: TRAP

<400> SEQUENCE: 27

```
Met Lys Leu Leu Gln Asn Lys Ser Tyr Leu Leu Val Val Phe Leu Leu
1               5                   10                  15

Tyr Val Ser Ile Phe Ala Arg Gly Asp Glu Lys Val Val Asp Glu Val
            20                  25                  30

Lys Tyr Ser Glu Glu Val Cys Asn Glu Ser Val Asp Leu Tyr Leu Leu
        35                  40                  45

Val Asp Gly Ser Gly Ser Ile Gly Tyr Pro Asn Trp Ile Thr Lys Val
    50                  55                  60

Ile Pro Met Leu Asn Gly Leu Ile Asn Ser Leu Ser Leu Ser Arg Asp
65                  70                  75                  80

Thr Ile Asn Leu Tyr Met Asn Leu Phe Gly Asn Tyr Thr Thr Glu Leu
                85                  90                  95

Ile Arg Leu Gly Ser Gly Gln Ser Ile Asp Lys Arg Gln Ala Leu Ser
            100                 105                 110

Lys Val Thr Glu Leu Arg Lys Ser Tyr Ser Pro Tyr Gly Thr Thr Asn
        115                 120                 125

Met Thr Ala Ala Leu Asp Glu Val Gln Lys His Leu Asn Asp Arg Val
    130                 135                 140

Asn Arg Glu Lys Ala Ile Gln Leu Val Ile Leu Met Thr Asp Gly Ile
145                 150                 155                 160

Pro Asn Ser Lys Tyr Thr Ala Leu Glu Val Ala Lys Lys Leu Lys Gln
                165                 170                 175

Arg Asn Val Ser Leu Ala Val Ile Gly Ile Gly Gln Gly Ile Asn His
            180                 185                 190

Gln Phe Asn Arg Leu Ile Ala Gly Cys Arg Pro Arg Glu Ser Asn Cys
        195                 200                 205

Lys Phe Tyr Ser Tyr Ala Asp Trp Asn Glu Ala Val Ala Leu Ile Lys
    210                 215                 220

Pro Phe Ile Ala Lys Val Cys Thr Glu Val Glu Arg Val Ala Asn Cys
225                 230                 235                 240

Gly Pro Trp Asp Pro Trp Thr Ala Cys Ser Val Thr Cys Gly Arg Gly
                245                 250                 255

Thr His Ser Arg Ser Arg Pro Ser Leu His Glu Gly Cys Thr Thr His
            260                 265                 270

Met Val Ser Glu Cys Glu Glu Gly Glu Cys Pro Val Glu Pro Glu Pro
        275                 280                 285

Leu Pro Val Pro Ala Pro Leu Pro Thr Val Pro Glu Asp Val Asn Pro
    290                 295                 300

Arg Asp Thr Asp Asp Glu Asn Glu Asn Pro Asn Phe Asn Lys Gly Leu
305                 310                 315                 320

Asp Val Pro Glu Glu Asp Asp Asp Glu Val Pro Pro Ala Asn Glu Arg
                325                 330                 335

Ala Asp Gly Asn Pro Val Glu Glu Asn Val Phe Pro Pro Ala Asp Asp
            340                 345                 350

Ser Val Pro Asp Glu Ser Asn Val Leu Pro Leu Pro Pro Ala Val Pro
        355                 360                 365

Gly Gly Ser Ser Glu Glu Phe Pro Ala Asp Val Gln Asn Asn Pro Asp
    370                 375                 380
```

```
Ser Pro Glu Glu Leu Pro Met Glu Gln Glu Val Pro Gln Asp Asn Asn
385                 390                 395                 400

Val Asn Glu Pro Glu Arg Ser Asp Ser Asn Gly Tyr Gly Val Asn Glu
                405                 410                 415

Lys Val Ile Pro Asn Pro Leu Asp Asn Glu Arg Asp Met Ala Asn Lys
            420                 425                 430

Asn Lys Thr Val His Pro Asp Arg Lys Asp Ser Ala Arg Asp Arg Tyr
        435                 440                 445

Ala Arg Pro His Gly Ser Thr His Val Asn Asn Asn Arg Ala Asn Glu
    450                 455                 460

Asn Ser Asp Ile Pro Asn Asn Pro Val Pro Ser Asp Tyr Glu Gln Pro
465                 470                 475                 480

Glu Asp Lys Ala Lys Lys Ser Ser Asn Asn Gly Tyr Lys Ile Ala Gly
                485                 490                 495

Gly Val Ile Ala Gly Leu Ala Leu Val Gly Cys Val Gly Phe Ala Tyr
            500                 505                 510

Asn Phe Val Ala Gly Gly Gly Ala Ala Gly Met Ala Gly Glu Pro Ala
        515                 520                 525

Pro Phe Asp Glu Ala Met Ala Glu Asp Glu Lys Asp Val Ala Glu Ala
    530                 535                 540

Asp Gln Phe Lys Leu Pro Glu Asp Asn Asp Trp Asn
545                 550                 555
```

```
<210> SEQ ID NO 28
<211> LENGTH: 1086
<212> TYPE: DNA
<213> ORGANISM: Artificial Sequence
<220> FEATURE:
<223> OTHER INFORMATION: inhibitor of cysteine proteases (ICP)

<400> SEQUENCE: 28

ggatccgcca ccatggctaa atccattacc ttctttgtgt tcaacatttg cagcattttg     60

gctctgctga gtcactgtga ggacaatgac atctacagct tcgacattgt caatgagaca    120

aattggctga agatcgccaa gaacatcttc aaaggcaagt ctcctagcaa tttcacgatc    180

ataccgttta acaataccgg tagttctaac gataacgagt caaacaagga ggaatcagta    240

ctgctgatca gaaagaagat caaaagcaac aagaatcacg atagttccat cattagtggt    300

gacactgtta acggggacat tagtgacctg aattatacgg ctagcaactt ttccgataac    360

tctgaggaca tagaagataa ccagaaatat cccacaacca gctacaatag tttcaaccat    420

ctcaattcca atatcgcctt taacgaagag tccgaataca ttgagattaa tagcgagtct    480

gacttggaga acaagatcaa ggacatcaac atcaaatcca atcttgagga aaacaatacc    540

atgaacgaat ccggcaaagt ggatagcaag tatgagctca ctggggacga gaaatgtggt    600

aaaagcctga agctcggcaa catcagcaat cagacaaacc aggaaaccat aacccaaagc    660

ctgtcagttg gagagattct gtgcattgac ctcgaaggga atgcaggaac aggctatctg    720

tgggtgttgc tgggcataca caaggatgag ccaatcataa accccgagaa cttcccaacc    780

aaactgacaa agaagtcttt cttttccgag gaaataagtg tgactcagcc aaagaagtac    840

aagatcgatg agcatgattc ttcaaagaat gtgaatcgcg aaatcgaaag ccctgaacag    900

aaggagtccg actcaaagcc caagaaacct cagatgcaac ttcttggagg accagatcgg    960
```

atgaggtcag tcatcaaagg acacaaacct ggcaaatatt acattgtgta ctcttactat 1020
cgaccgtttt ctcccacttc tggggcgaac actaaaatca tttacgtcac agtacagtga 1080
ctcgag 1086

<210> SEQ ID NO 29
<211> LENGTH: 355
<212> TYPE: PRT
<213> ORGANISM: Plasmodium berghei
<220> FEATURE:
<221> NAME/KEY: misc_feature
<223> OTHER INFORMATION: ICP

<400> SEQUENCE: 29

```
Met Ala Lys Ser Ile Thr Phe Phe Val Phe Asn Ile Cys Ser Ile Leu
1               5                   10                  15

Ala Leu Leu Ser His Cys Glu Asp Asn Asp Ile Tyr Ser Phe Asp Ile
            20                  25                  30

Val Asn Glu Thr Asn Trp Leu Lys Ile Ala Lys Asn Ile Phe Lys Gly
        35                  40                  45

Lys Ser Pro Ser Asn Phe Thr Ile Ile Pro Phe Asn Asn Thr Gly Ser
    50                  55                  60

Ser Asn Asp Asn Glu Ser Asn Lys Glu Glu Ser Val Leu Leu Ile Arg
65                  70                  75                  80

Lys Lys Ile Lys Ser Asn Lys Asn His Asp Ser Ser Ile Ile Ser Gly
                85                  90                  95

Asp Thr Val Asn Gly Asp Ile Ser Asp Leu Asn Tyr Thr Ala Ser Asn
            100                 105                 110

Phe Ser Asp Asn Ser Glu Asp Ile Glu Asp Asn Gln Lys Tyr Pro Thr
        115                 120                 125

Thr Ser Tyr Asn Ser Phe Asn His Leu Asn Ser Asn Ile Ala Phe Asn
    130                 135                 140

Glu Glu Ser Glu Tyr Ile Glu Ile Asn Ser Glu Ser Asp Leu Glu Asn
145                 150                 155                 160

Lys Ile Lys Asp Ile Asn Ile Lys Ser Asn Leu Glu Glu Asn Asn Thr
                165                 170                 175

Met Asn Glu Ser Gly Lys Val Asp Ser Lys Tyr Glu Leu Thr Gly Asp
            180                 185                 190

Glu Lys Cys Gly Lys Ser Leu Lys Leu Gly Asn Ile Ser Asn Gln Thr
        195                 200                 205

Asn Gln Glu Thr Ile Thr Gln Ser Leu Ser Val Gly Glu Ile Leu Cys
    210                 215                 220

Ile Asp Leu Glu Gly Asn Ala Gly Thr Gly Tyr Leu Trp Val Leu Leu
225                 230                 235                 240

Gly Ile His Lys Asp Glu Pro Ile Ile Asn Pro Glu Asn Phe Pro Thr
                245                 250                 255

Lys Leu Thr Lys Lys Ser Phe Phe Ser Glu Glu Ile Ser Val Thr Gln
            260                 265                 270

Pro Lys Lys Tyr Lys Ile Asp Glu His Asp Ser Ser Lys Asn Val Asn
        275                 280                 285

Arg Glu Ile Glu Ser Pro Glu Gln Lys Glu Ser Asp Ser Lys Pro Lys
    290                 295                 300

Lys Pro Gln Met Gln Leu Leu Gly Gly Pro Asp Arg Met Arg Ser Val
305                 310                 315                 320
```

```
Ile Lys Gly His Lys Pro Gly Lys Tyr Tyr Ile Val Tyr Ser Tyr Tyr
                325                 330                 335

Arg Pro Phe Ser Pro Thr Ser Gly Ala Asn Thr Lys Ile Ile Tyr Val
            340                 345                 350

Thr Val Gln
        355


<210> SEQ ID NO 30
<211> LENGTH: 354
<212> TYPE: PRT
<213> ORGANISM: Plasmodium berghei
<220> FEATURE:
<221> NAME/KEY: misc_feature
<223> OTHER INFORMATION: ICP

<400> SEQUENCE: 30

Met Lys Ser Ile Thr Phe Phe Val Phe Asn Ile Cys Ser Ile Leu Ala
1               5                   10                  15

Leu Leu Ser His Cys Glu Asp Asn Asp Ile Tyr Ser Phe Asp Ile Val
            20                  25                  30

Asn Glu Thr Asn Trp Leu Lys Ile Ala Lys Asn Ile Phe Lys Gly Lys
        35                  40                  45

Ser Pro Ser Asn Phe Thr Ile Ile Pro Phe Asn Asn Thr Gly Ser Ser
    50                  55                  60

Asn Asp Asn Glu Ser Asn Lys Glu Glu Ser Val Leu Leu Ile Arg Lys
65                  70                  75                  80

Lys Ile Lys Ser Asn Lys Asn His Asp Ser Ser Ile Ile Ser Gly Asp
                85                  90                  95

Thr Val Asn Gly Asp Ile Ser Asp Leu Asn Tyr Thr Ala Ser Asn Phe
            100                 105                 110

Ser Asp Asn Ser Glu Asp Ile Glu Asp Asn Gln Lys Tyr Pro Thr Thr
        115                 120                 125

Ser Tyr Asn Ser Phe Asn His Leu Asn Ser Asn Ile Ala Phe Asn Glu
    130                 135                 140

Glu Ser Glu Tyr Ile Glu Ile Asn Ser Glu Ser Asp Leu Glu Asn Lys
145                 150                 155                 160

Ile Lys Asp Ile Asn Ile Lys Ser Asn Leu Glu Glu Asn Asn Thr Met
                165                 170                 175

Asn Glu Ser Gly Lys Val Asp Ser Lys Tyr Glu Leu Thr Gly Asp Glu
            180                 185                 190

Lys Cys Gly Lys Ser Leu Lys Leu Gly Asn Ile Ser Asn Gln Thr Asn
        195                 200                 205

Gln Glu Thr Ile Thr Gln Ser Leu Ser Val Gly Glu Ile Leu Cys Ile
    210                 215                 220

Asp Leu Glu Gly Asn Ala Gly Thr Gly Tyr Leu Trp Val Leu Leu Gly
225                 230                 235                 240

Ile His Lys Asp Glu Pro Ile Ile Asn Pro Glu Asn Phe Pro Thr Lys
                245                 250                 255

Leu Thr Lys Lys Ser Phe Phe Ser Glu Glu Ile Ser Val Thr Gln Pro
            260                 265                 270

Lys Lys Tyr Lys Ile Asp Glu His Asp Ser Ser Lys Asn Val Asn Arg
        275                 280                 285

Glu Ile Glu Ser Pro Glu Gln Lys Glu Ser Asp Ser Lys Pro Lys Lys
    290                 295                 300
```

```
Pro Gln Met Gln Leu Leu Gly Gly Pro Asp Arg Met Arg Ser Val Ile
305                 310                 315                 320

Lys Gly His Lys Pro Gly Lys Tyr Tyr Ile Val Tyr Ser Tyr Tyr Arg
                325                 330                 335

Pro Phe Ser Pro Thr Ser Gly Ala Asn Thr Lys Ile Ile Tyr Val Thr
            340                 345                 350

Val Gln


<210> SEQ ID NO 31
<211> LENGTH: 1251
<212> TYPE: DNA
<213> ORGANISM: Artificial Sequence
<220> FEATURE:
<223> OTHER INFORMATION: PfICPhumanCO

<400> SEQUENCE: 31

gccaccatgg ctaatctgtt ggtgttcttt tgcttctttc tgttgtcttg catcgtacac      60

ctctctcgtt gttctgacaa caattcatat agctttgaga tcgtgaatcg gagcacatgg     120

ctcaacattg ctgaacggat attcaaaggc aatgcaccat tcaactttac tattataccg     180

tacaactatg tgaacaatag tactgaagag aataataaca aagactctgt ccttctgata     240

agcaagaatc tgaagaattc ctcaaaccca gtggacgaaa ataaccacat cattgactca     300

accaagaaga acacgtccaa taacaacaat aataacagca atatcgtcgg aatatacgaa     360

agtcaggtac atgaggagaa gattaaagag gacaatacaa gacaggataa tatcaacaag     420

aaggaaaacg agataatcaa caataaccat cagatccctg tgtccaacat cttttcagag     480

aacattgaca acaacaagaa ctacattgag agcaactaca agagcaccta taacaataat     540

cccgagttga ttcatagcac agatttcatt ggcagtaata acaaccacac tttcaatttc     600

ctgtctcgct ataacaactc agtgctgaac aacatgcaag ggaataccaa agttccaggg     660

aatgttcccg aactgaaagc ccgcattttc tccgaggaag aaaacaccga agtcgaaagc     720

gccgaaaaca atcacactaa cagtctgaat cctaacgagt cttgtgatca aatcatcaaa     780

ctgggcgata tcattaacag cgtcaatgag aagatcatca gcatcaatag tacggtgaat     840

aacgtgctct gcataaatct ggattccgtc aatggcaatg gcttcgtttg gacccttctt     900

ggggtacaca agaagaaacc cctgattgac ccctccaatt ttcccactaa aagggtgact     960

cagtcctacg tttcacctga catttccgtt acaaaccctg tgccaattcc aaagaacagc    1020

aacaccaaca aagatgacag catcaataat aaacaggatg gttcccagaa taacacaaca    1080

acgaatcact ttccgaagcc tagagagcaa ctcgtgggtg gatcttctat gctgatcagt    1140

aagatcaaac cccataaacc cggaaagtat ttcatcgtgt atagctacta cagaccattt    1200

gaccctacaa gggataccaa cacccgaatt gtggagctga atgtccagta a             1251


<210> SEQ ID NO 32
<211> LENGTH: 414
<212> TYPE: PRT
<213> ORGANISM: Plasmodium falciparum
<220> FEATURE:
<221> NAME/KEY: misc_feature
<223> OTHER INFORMATION: PfICP

<400> SEQUENCE: 32

Met Ala Asn Leu Leu Val Phe Phe Cys Phe Phe Leu Leu Ser Cys Ile
1               5                   10                  15
```

```
Val His Leu Ser Arg Cys Ser Asp Asn Asn Ser Tyr Ser Phe Glu Ile
            20                  25                  30

Val Asn Arg Ser Thr Trp Leu Asn Ile Ala Glu Arg Ile Phe Lys Gly
        35                  40                  45

Asn Ala Pro Phe Asn Phe Thr Ile Ile Pro Tyr Asn Tyr Val Asn Asn
    50                  55                  60

Ser Thr Glu Glu Asn Asn Asn Lys Asp Ser Val Leu Leu Ile Ser Lys
65                  70                  75                  80

Asn Leu Lys Asn Ser Ser Asn Pro Val Asp Glu Asn Asn His Ile Ile
                85                  90                  95

Asp Ser Thr Lys Lys Asn Thr Ser Asn Asn Asn Asn Asn Asn Ser Asn
            100                 105                 110

Ile Val Gly Ile Tyr Glu Ser Gln Val His Glu Glu Lys Ile Lys Glu
        115                 120                 125

Asp Asn Thr Arg Gln Asp Asn Ile Asn Lys Lys Glu Asn Glu Ile Ile
    130                 135                 140

Asn Asn Asn His Gln Ile Pro Val Ser Asn Ile Phe Ser Glu Asn Ile
145                 150                 155                 160

Asp Asn Asn Lys Asn Tyr Ile Glu Ser Asn Tyr Lys Ser Thr Tyr Asn
                165                 170                 175

Asn Asn Pro Glu Leu Ile His Ser Thr Asp Phe Ile Gly Ser Asn Asn
            180                 185                 190

Asn His Thr Phe Asn Phe Leu Ser Arg Tyr Asn Asn Ser Val Leu Asn
        195                 200                 205

Asn Met Gln Gly Asn Thr Lys Val Pro Gly Asn Val Pro Glu Leu Lys
    210                 215                 220

Ala Arg Ile Phe Ser Glu Glu Glu Asn Thr Glu Val Glu Ser Ala Glu
225                 230                 235                 240

Asn Asn His Thr Asn Ser Leu Asn Pro Asn Glu Ser Cys Asp Gln Ile
                245                 250                 255

Ile Lys Leu Gly Asp Ile Ile Asn Ser Val Asn Glu Lys Ile Ile Ser
            260                 265                 270

Ile Asn Ser Thr Val Asn Asn Val Leu Cys Ile Asn Leu Asp Ser Val
        275                 280                 285

Asn Gly Asn Gly Phe Val Trp Thr Leu Leu Gly Val His Lys Lys Lys
    290                 295                 300

Pro Leu Ile Asp Pro Ser Asn Phe Pro Thr Lys Arg Val Thr Gln Ser
305                 310                 315                 320

Tyr Val Ser Pro Asp Ile Ser Val Thr Asn Pro Val Pro Ile Pro Lys
                325                 330                 335

Asn Ser Asn Thr Asn Lys Asp Asp Ser Ile Asn Asn Lys Gln Asp Gly
            340                 345                 350

Ser Gln Asn Asn Thr Thr Thr Asn His Phe Pro Lys Pro Arg Glu Gln
        355                 360                 365

Leu Val Gly Gly Ser Ser Met Leu Ile Ser Lys Ile Lys Pro His Lys
    370                 375                 380

Pro Gly Lys Tyr Phe Ile Val Tyr Ser Tyr Tyr Arg Pro Phe Asp Pro
385                 390                 395                 400

Thr Arg Asp Thr Asn Thr Arg Ile Val Glu Leu Asn Val Gln
                405                 410
```

<210> SEQ ID NO 33
<211> LENGTH: 413

<212> TYPE: PRT
<213> ORGANISM: Plasmodium falciparum
<220> FEATURE:
<221> NAME/KEY: misc_feature
<223> OTHER INFORMATION: ICP

<400> SEQUENCE: 33

```
Met Asn Leu Leu Val Phe Phe Cys Phe Phe Leu Leu Ser Cys Ile Val
1               5                   10                  15

His Leu Ser Arg Cys Ser Asp Asn Asn Ser Tyr Ser Phe Glu Ile Val
            20                  25                  30

Asn Arg Ser Thr Trp Leu Asn Ile Ala Glu Arg Ile Phe Lys Gly Asn
        35                  40                  45

Ala Pro Phe Asn Phe Thr Ile Ile Pro Tyr Asn Tyr Val Asn Asn Ser
    50                  55                  60

Thr Glu Glu Asn Asn Asn Lys Asp Ser Val Leu Leu Ile Ser Lys Asn
65                  70                  75                  80

Leu Lys Asn Ser Ser Asn Pro Val Asp Glu Asn Asn His Ile Ile Asp
                85                  90                  95

Ser Thr Lys Lys Asn Thr Ser Asn Asn Asn Asn Asn Asn Ser Asn Ile
            100                 105                 110

Val Gly Ile Tyr Glu Ser Gln Val His Glu Glu Lys Ile Lys Glu Asp
        115                 120                 125

Asn Thr Arg Gln Asp Asn Ile Asn Lys Lys Glu Asn Glu Ile Ile Asn
    130                 135                 140

Asn Asn His Gln Ile Pro Val Ser Asn Ile Phe Ser Glu Asn Ile Asp
145                 150                 155                 160

Asn Asn Lys Asn Tyr Ile Glu Ser Asn Tyr Lys Ser Thr Tyr Asn Asn
                165                 170                 175

Asn Pro Glu Leu Ile His Ser Thr Asp Phe Ile Gly Ser Asn Asn Asn
            180                 185                 190

His Thr Phe Asn Phe Leu Ser Arg Tyr Asn Asn Ser Val Leu Asn Asn
        195                 200                 205

Met Gln Gly Asn Thr Lys Val Pro Gly Asn Val Pro Glu Leu Lys Ala
    210                 215                 220

Arg Ile Phe Ser Glu Glu Glu Asn Thr Glu Val Glu Ser Ala Glu Asn
225                 230                 235                 240

Asn His Thr Asn Ser Leu Asn Pro Asn Glu Ser Cys Asp Gln Ile Ile
                245                 250                 255

Lys Leu Gly Asp Ile Ile Asn Ser Val Asn Glu Lys Ile Ile Ser Ile
            260                 265                 270

Asn Ser Thr Val Asn Asn Val Leu Cys Ile Asn Leu Asp Ser Val Asn
        275                 280                 285

Gly Asn Gly Phe Val Trp Thr Leu Leu Gly Val His Lys Lys Lys Pro
    290                 295                 300

Leu Ile Asp Pro Ser Asn Phe Pro Thr Lys Arg Val Thr Gln Ser Tyr
305                 310                 315                 320

Val Ser Pro Asp Ile Ser Val Thr Asn Pro Val Pro Ile Pro Lys Asn
                325                 330                 335

Ser Asn Thr Asn Lys Asp Asp Ser Ile Asn Asn Lys Gln Asp Gly Ser
            340                 345                 350

Gln Asn Asn Thr Thr Thr Asn His Phe Pro Lys Pro Arg Glu Gln Leu
        355                 360                 365

Val Gly Gly Ser Ser Met Leu Ile Ser Lys Ile Lys Pro His Lys Pro
    370                 375                 380
```

```
Gly Lys Tyr Phe Ile Val Tyr Ser Tyr Tyr Arg Pro Phe Asp Pro Thr
385                 390                 395                 400

Arg Asp Thr Asn Thr Arg Ile Val Glu Leu Asn Val Gln
                405                 410


<210> SEQ ID NO 34
<211> LENGTH: 1104
<212> TYPE: DNA
<213> ORGANISM: Artificial Sequence
<220> FEATURE:
<223> OTHER INFORMATION: PvICPhumanCO

<400> SEQUENCE: 34

gccaccatgg ctaagttgtc tagcctgttc tgcctggttg tgtgttctag tgttgcccac      60

ctctcttcct gtagtgatca aaacacttat agttttgata ttgttaatcg aaacacttgg     120

tacagcatag ccaagaaaat ctttcaaggc acgacccccct gtaatttcac tgtaatccct    180

agttcctatg tcaacaactc tgacggagtg tctacgagtg atgattccgt actgctcatc     240

cgcaaaaagc tcaaggatcc gagtgaagct ggccttgacg gatcttcagt ttctggttca     300

tccagttctg gaaacagtca ctccggttct gcaccttgtt gtgataaggg tacccccgct     360

aaagaggcag agctgaaatt ttctacaaag tttgagggcg atgactatgc taagctgaga     420

gattctctga gccttataga caagtcactc cgagaagagt caagctcaga ggaggacagt     480

aagatggaag atagtcaggt cggtgaagta actcatgaag agactatcac ctacaacatg     540

cccgaagaat atatgcccca gaacatttcc gaggtattga tcggtgccgc tgaagaggat     600

aggacatacg cgttgaaggg ggacgagccg tgtgatgtgt acttgaaact tggcgagata     660

atcaatggaa ctaatgaaaa gactatcgag tattctctcc aaaaaaataa gatactgtgc     720

gttcaactcg aagcaattgg gggaaatgga tacctctggg ctctcctcgg cgtacacaaa     780

gaaaaacccc aaatcaaccc agaggagttt ccacgaaaaa agatcacaaa atctttttc      840

accaatgaga tatccgtcac gcagcctaaa gcagtgcaaa agaacaaatc taataatgga     900

ggtgagagca gttcaaactc acctggctat gggaaacccc ccgcaagcga acagctcggg     960

ggatttgtgg gtggcacatc catgcttcag agtatagtaa aggctcataa agagggcacc    1020

tttttcgtag tttatagcta ctaccgcccc ttcgacccta ccgccaacgc caacacgaag    1080

atactcaaac ttacggtttc atag                                          1104


<210> SEQ ID NO 35
<211> LENGTH: 365
<212> TYPE: PRT
<213> ORGANISM: Artificial Sequence
<220> FEATURE:
<223> OTHER INFORMATION: PVICP humanco + kozac
<220> FEATURE:
<221> NAME/KEY: misc_feature
<223> OTHER INFORMATION: PvICP

<400> SEQUENCE: 35

Met Ala Lys Leu Ser Ser Leu Phe Cys Leu Val Val Cys Ser Ser Val
1               5                   10                  15

Ala His Leu Ser Ser Cys Ser Asp Gln Asn Thr Tyr Ser Phe Asp Ile
            20                  25                  30

Val Asn Arg Asn Thr Trp Tyr Ser Ile Ala Lys Lys Ile Phe Gln Gly
        35                  40                  45

Thr Thr Pro Cys Asn Phe Thr Val Ile Pro Ser Ser Tyr Val Asn Asn
    50                  55                  60
```

```
Ser Asp Gly Val Ser Thr Ser Asp Asp Ser Val Leu Leu Ile Arg Lys
65                  70                  75                  80

Lys Leu Lys Asp Pro Ser Glu Ala Gly Leu Asp Gly Ser Ser Val Ser
                85                  90                  95

Gly Ser Ser Ser Ser Gly Asn Ser His Ser Gly Ser Ala Pro Cys Cys
            100                 105                 110

Asp Lys Gly Thr Pro Ala Lys Glu Ala Glu Leu Lys Phe Ser Thr Lys
        115                 120                 125

Phe Glu Gly Asp Asp Tyr Ala Lys Leu Arg Asp Ser Leu Ser Leu Ile
    130                 135                 140

Asp Lys Ser Leu Arg Glu Glu Ser Ser Ser Glu Glu Asp Ser Lys Met
145                 150                 155                 160

Glu Asp Ser Gln Val Gly Glu Val Thr His Glu Glu Thr Ile Thr Tyr
                165                 170                 175

Asn Met Pro Glu Glu Tyr Met Pro Gln Asn Ile Ser Glu Val Leu Ile
            180                 185                 190

Gly Ala Ala Glu Glu Asp Arg Thr Tyr Ala Leu Lys Gly Asp Glu Pro
        195                 200                 205

Cys Asp Val Tyr Leu Lys Leu Gly Glu Ile Ile Asn Gly Thr Asn Glu
    210                 215                 220

Lys Thr Ile Glu Tyr Ser Leu Gln Lys Asn Lys Ile Leu Cys Val Gln
225                 230                 235                 240

Leu Glu Ala Ile Gly Gly Asn Gly Tyr Leu Trp Ala Leu Leu Gly Val
                245                 250                 255

His Lys Glu Lys Pro Gln Ile Asn Pro Glu Glu Phe Pro Arg Lys Lys
            260                 265                 270

Ile Thr Lys Ser Phe Phe Thr Asn Glu Ile Ser Val Thr Gln Pro Lys
        275                 280                 285

Ala Val Gln Lys Asn Lys Ser Asn Asn Gly Gly Glu Ser Ser Ser Asn
    290                 295                 300

Ser Pro Gly Tyr Gly Lys Pro Pro Ala Ser Glu Gln Leu Gly Gly Phe
305                 310                 315                 320

Val Gly Gly Thr Ser Met Leu Gln Ser Ile Val Lys Ala His Lys Glu
                325                 330                 335

Gly Thr Phe Phe Val Val Tyr Ser Tyr Tyr Arg Pro Phe Asp Pro Thr
            340                 345                 350

Ala Asn Ala Asn Thr Lys Ile Leu Lys Leu Thr Val Ser
        355                 360                 365
```

<210> SEQ ID NO 36
<211> LENGTH: 359
<212> TYPE: PRT
<213> ORGANISM: Plasmodium vivax
<220> FEATURE:
<221> NAME/KEY: misc_feature
<223> OTHER INFORMATION: ICP

<400> SEQUENCE: 36

```
Met Lys Leu Ser Ser Leu Phe Cys Leu Val Val Cys Ser Ser Val Ala
1               5                   10                  15

His Leu Ser Ser Cys Ser Asp Gln Asn Thr Tyr Ser Phe Asp Ile Val
            20                  25                  30

Asn Arg Asn Thr Trp Tyr Ser Ile Ala Lys Lys Ile Phe Gln Gly Thr
        35                  40                  45
```

```
Thr Pro Cys Asn Phe Thr Val Ile Pro Ser Ser Tyr Val Asn Asn Ser
    50                  55                  60

Asp Gly Val Ser Thr Ser Asp Asp Ser Val Leu Leu Ile Arg Lys Lys
65                  70                  75                  80

Leu Lys Asp Pro Ser Glu Ala Gly Leu Asp Gly Ser Ser Val Ser Gly
                85                  90                  95

Asn Ser His Ser Gly Ser Ala Pro Cys Cys Asp Lys Gly Thr Pro Ala
            100                 105                 110

Lys Glu Ala Glu Leu Asn Phe Ser Thr Lys Phe Glu Gly Asp Asp Tyr
        115                 120                 125

Ala Lys Leu Arg Asp Ser Leu Ser Leu Ile Asp Lys Ser Leu Arg Glu
    130                 135                 140

Glu Ser Ser Ser Glu Glu Asp Ser Lys Met Glu Asp Ser Gln Val Gly
145                 150                 155                 160

Glu Val Thr His Glu Glu Thr Ile Thr Tyr Asn Met Pro Glu Glu Tyr
                165                 170                 175

Met Pro Gln Asn Ile Ser Glu Val Leu Ile Gly Ala Ala Glu Glu Asp
            180                 185                 190

Arg Thr Tyr Ala Leu Lys Gly Asp Glu Pro Cys Asp Val Tyr Leu Lys
        195                 200                 205

Leu Gly Glu Ile Ile Asn Gly Thr Asn Glu Lys Thr Ile Glu Tyr Ser
    210                 215                 220

Leu Gln Lys Asn Lys Ile Leu Cys Val Gln Leu Glu Ala Ile Gly Gly
225                 230                 235                 240

Asn Gly Tyr Leu Trp Ala Leu Leu Gly Val His Lys Glu Lys Pro Gln
                245                 250                 255

Ile Asn Pro Glu Glu Phe Pro Arg Lys Lys Ile Thr Lys Ser Phe Phe
            260                 265                 270

Thr Asn Glu Ile Ser Val Thr Gln Pro Lys Ala Val Gln Lys Asn Lys
        275                 280                 285

Ser Asn Asn Gly Gly Glu Ser Ser Ser Asn Ser Pro Gly Tyr Gly Lys
    290                 295                 300

Pro Pro Ala Ser Glu Gln Leu Gly Gly Phe Val Gly Gly Thr Ser Met
305                 310                 315                 320

Leu Gln Ser Ile Val Lys Ala His Lys Glu Gly Thr Phe Phe Val Val
                325                 330                 335

Tyr Ser Tyr Tyr Arg Pro Phe Asp Pro Thr Ala Asn Ala Asn Thr Lys
            340                 345                 350

Ile Leu Lys Leu Thr Val Ser
        355
```

<210> SEQ ID NO 37
<211> LENGTH: 2355
<212> TYPE: DNA
<213> ORGANISM: Artificial Sequence
<220> FEATURE:
<223> OTHER INFORMATION: Falcilysin, Bergheilysin-A-CO

<400> SEQUENCE: 37

```
ggatccgcca ccatggctaa attgatgaag gttttgggtt acatcaacat tattaccaac     60

tgcgtgaatg gaatcctctg caaaggtgac aagaaaaggt actccatctt caccaataat    120

tacatctaca gcatatcaac cctcaataat tatagctttg ctgcaacaat gaacaaaatg    180

cccgcttggg ttaacgagaa atgtccagaa cacaaaagct acgacatcgt tgagaagcgc    240
```

```
tacaatgaga acctcaatct cacgtacaca gtctatgagc acaagaaggc caagactcag    300

gtcatagcac tggggtctaa cgatcctctc gacgctgagc aagcatttgg cttctacgtg    360

aaaaccctga cgcattcaga taaaggcatt ccgcacatac tggaacacac tgtcctgagt    420

ggctctaaga atttcaacta caaggactca atggggcttt tggagaaagg caccctgaac    480

acacacctga atgcctacac cttcaatgac aggaccatct acatggccgg gagtatgaac    540

aatagggatt tctttaacat tatggccgtc tacatggata gcgtgttcca gcctaacgta    600

ctggaaaaca aattcatctt ccagacagag ggatggacct atgaggtaga gaagctgaag    660

gaggaggaga agaacctcga cattcccaag attaaggact acaaggtgtc ttttaacgga    720

atcgtgtata atgagatgaa gggtgcgttt agcaatcctc tgcaggacct gtattatgaa    780

gtgatgagaa acatgttccc cgacaacgta cacagtaaca tctccggagg agatcctaaa    840

gaaataccaa atctgtcata tgaagagttt aaggagtttt actacaagaa ttacaatccg    900

aagaaaatca aagtgttctt tttctccaaa aataatccga cagagctgct caactttgtg    960

gacaactatc tctgtcagct ggacttcacg aaatatcggg atgatgctgt ggaacatgtc   1020

aattaccaag aataccgcaa aggcccattc tatattaaga agaaattcgc tgatcactca   1080

gaagagaaag aaaatcttgc ctccgtgagt tggcttctga atcccaagaa acacaagaat   1140

tccgatactg atctctctct ggagtctcct acagactatt tcgccttgct catcatcaat   1200

aatctgctta ctcataccag tgagagcgtc ctgtacaaag ccctgataga atccggattg   1260

gggaatagta ttgtagatcg agggctgaat gattccctgg ttcagtatgt gttcagcatc   1320

ggcctgaaag gcataaaaga gaagaacgag aagaacatct ccctggacaa ggtccactac   1380

gaggtggaaa agatcgttct tgaggcactg aaaaaagtgg tcaaagaagg tttcaataag   1440

tcagcagttg aggcagccat taacaatatt gagttcgtcc tgaaagaagc caatctcaag   1500

atctccaaat ctatagactt tgtgtttgaa atggccagca gactgaacta tggcaaagat   1560

ccactgctga tctttgagtt tgaaaagcat ctcaacgtag tgaaggacaa gatcaagaac   1620

gagcctaaat acctggagaa gtatgtggag aaacatcttc tgaacaatga tcatcgagtc   1680

gttattctgc tggaagggga tgaaaactat ggcaccgaac aggagaaact ggaaaaggac   1740

atgctgaaga agcggattga aagcttcact gagaaagaaa aggagaatat tatcacagac   1800

ttcgaaaatc ttacgaagta caagaacact gaggaatctc ccgaacatct ggacaagttt   1860

cccatcatta gcattagcga cctcaatgga aagactttgg agatccccgt gaaccctttc   1920

tttaccaacc tgaacaacga gaacaacatg cagcactata atgagacaaa gaacaaccaa   1980

accctggtca aagaaaacat ggaccgtttc attaacaaat acattctcaa caaggatgga   2040

aacgataaga acgacagcaa gaacgcggat gtgccaatgc tgatttatga aatcccaaca   2100

tctggcatat tgtatctgca gtttatcttc tctctggata accttacact ggaagaattg   2160

tcctacctga atctgtttaa aagcttgata ctggagaaca agactaacaa gagatcaagt   2220

gaagagtttg tgatcttgcg ggagaagaat attgggaata tgatgaccaa tgttgctctt   2280

cttagcacat ccgatcgcct caatgtgact gacaaatata atgcgaaagg tttctttaac   2340

tttgagtaac tcgag                                                   2355
```

<210> SEQ ID NO 38
<211> LENGTH: 778
<212> TYPE: PRT
<213> ORGANISM: Plasmodium berghei
<220> FEATURE:
<221> NAME/KEY: misc_feature
<223> OTHER INFORMATION: Falcilysin, Bergheilysin-A

<400> SEQUENCE: 38

Met Ala Lys Leu Met Lys Val Leu Gly Tyr Ile Asn Ile Ile Thr Asn
1               5                   10                  15

Cys Val Asn Gly Ile Leu Cys Lys Gly Asp Lys Lys Arg Tyr Ser Ile
            20                  25                  30

Phe Thr Asn Asn Tyr Ile Tyr Ser Ile Ser Thr Leu Asn Asn Tyr Ser
        35                  40                  45

Phe Ala Ala Thr Met Asn Lys Met Pro Ala Trp Val Asn Glu Lys Cys
    50                  55                  60

Pro Glu His Lys Ser Tyr Asp Ile Val Glu Lys Arg Tyr Asn Glu Asn
65                  70                  75                  80

Leu Asn Leu Thr Tyr Thr Val Tyr Glu His Lys Lys Ala Lys Thr Gln
                85                  90                  95

Val Ile Ala Leu Gly Ser Asn Asp Pro Leu Asp Ala Glu Gln Ala Phe
            100                 105                 110

Gly Phe Tyr Val Lys Thr Leu Thr His Ser Asp Lys Gly Ile Pro His
        115                 120                 125

Ile Leu Glu His Thr Val Leu Ser Gly Ser Lys Asn Phe Asn Tyr Lys
    130                 135                 140

Asp Ser Met Gly Leu Leu Glu Lys Gly Thr Leu Asn Thr His Leu Asn
145                 150                 155                 160

Ala Tyr Thr Phe Asn Asp Arg Thr Ile Tyr Met Ala Gly Ser Met Asn
                165                 170                 175

Asn Arg Asp Phe Phe Asn Ile Met Ala Val Tyr Met Asp Ser Val Phe
            180                 185                 190

Gln Pro Asn Val Leu Glu Asn Lys Phe Ile Phe Gln Thr Glu Gly Trp
        195                 200                 205

Thr Tyr Glu Val Glu Lys Leu Lys Glu Glu Glu Lys Asn Leu Asp Ile
    210                 215                 220

Pro Lys Ile Lys Asp Tyr Lys Val Ser Phe Asn Gly Ile Val Tyr Asn
225                 230                 235                 240

Glu Met Lys Gly Ala Phe Ser Asn Pro Leu Gln Asp Leu Tyr Tyr Glu
                245                 250                 255

Val Met Arg Asn Met Phe Pro Asp Asn Val His Ser Asn Ile Ser Gly
            260                 265                 270

Gly Asp Pro Lys Glu Ile Pro Asn Leu Ser Tyr Glu Glu Phe Lys Glu
        275                 280                 285

Phe Tyr Tyr Lys Asn Tyr Asn Pro Lys Lys Ile Lys Val Phe Phe Phe
    290                 295                 300

Ser Lys Asn Asn Pro Thr Glu Leu Leu Asn Phe Val Asp Asn Tyr Leu
305                 310                 315                 320

Cys Gln Leu Asp Phe Thr Lys Tyr Arg Asp Asp Ala Val Glu His Val
                325                 330                 335

Asn Tyr Gln Glu Tyr Arg Lys Gly Pro Phe Tyr Ile Lys Lys Lys Phe
            340                 345                 350

Ala Asp His Ser Glu Glu Lys Glu Asn Leu Ala Ser Val Ser Trp Leu
        355                 360                 365

Leu Asn Pro Lys Lys His Lys Asn Ser Asp Thr Asp Leu Ser Leu Glu
    370                 375                 380

Ser Pro Thr Asp Tyr Phe Ala Leu Leu Ile Ile Asn Asn Leu Leu Thr
385                 390                 395                 400

His Thr Ser Glu Ser Val Leu Tyr Lys Ala Leu Ile Glu Ser Gly Leu
405 410 415

Gly Asn Ser Ile Val Asp Arg Gly Leu Asn Asp Ser Leu Val Gln Tyr
420 425 430

Val Phe Ser Ile Gly Leu Lys Gly Ile Lys Glu Lys Asn Glu Lys Asn
435 440 445

Ile Ser Leu Asp Lys Val His Tyr Glu Val Glu Lys Ile Val Leu Glu
450 455 460

Ala Leu Lys Lys Val Val Lys Glu Gly Phe Asn Lys Ser Ala Val Glu
465 470 475 480

Ala Ala Ile Asn Asn Ile Glu Phe Val Leu Lys Glu Ala Asn Leu Lys
485 490 495

Ile Ser Lys Ser Ile Asp Phe Val Phe Glu Met Ala Ser Arg Leu Asn
500 505 510

Tyr Gly Lys Asp Pro Leu Leu Ile Phe Glu Phe Glu Lys His Leu Asn
515 520 525

Val Val Lys Asp Lys Ile Lys Asn Glu Pro Lys Tyr Leu Glu Lys Tyr
530 535 540

Val Glu Lys His Leu Leu Asn Asn Asp His Arg Val Val Ile Leu Leu
545 550 555 560

Glu Gly Asp Glu Asn Tyr Gly Thr Glu Gln Glu Lys Leu Glu Lys Asp
565 570 575

Met Leu Lys Lys Arg Ile Glu Ser Phe Thr Glu Lys Glu Lys Glu Asn
580 585 590

Ile Ile Thr Asp Phe Glu Asn Leu Thr Lys Tyr Lys Asn Thr Glu Glu
595 600 605

Ser Pro Glu His Leu Asp Lys Phe Pro Ile Ile Ser Ile Ser Asp Leu
610 615 620

Asn Gly Lys Thr Leu Glu Ile Pro Val Asn Pro Phe Phe Thr Asn Leu
625 630 635 640

Asn Asn Glu Asn Asn Met Gln His Tyr Asn Glu Thr Lys Asn Asn Gln
645 650 655

Thr Leu Val Lys Glu Asn Met Asp Arg Phe Ile Asn Lys Tyr Ile Leu
660 665 670

Asn Lys Asp Gly Asn Asp Lys Asn Asp Ser Lys Asn Ala Asp Val Pro
675 680 685

Met Leu Ile Tyr Glu Ile Pro Thr Ser Gly Ile Leu Tyr Leu Gln Phe
690 695 700

Ile Phe Ser Leu Asp Asn Leu Thr Leu Glu Glu Leu Ser Tyr Leu Asn
705 710 715 720

Leu Phe Lys Ser Leu Ile Leu Glu Asn Lys Thr Asn Lys Arg Ser Ser
725 730 735

Glu Glu Phe Val Ile Leu Arg Glu Lys Asn Ile Gly Asn Met Met Thr
740 745 750

Asn Val Ala Leu Leu Ser Thr Ser Asp Arg Leu Asn Val Thr Asp Lys
755 760 765

Tyr Asn Ala Lys Gly Phe Phe Asn Phe Glu
770 775

<210> SEQ ID NO 39
<211> LENGTH: 1149
<212> TYPE: PRT
<213> ORGANISM: Plasmodium berghei
<220> FEATURE:
<221> NAME/KEY: misc_feature
<223> OTHER INFORMATION: Falcilysin, Bergheilysin-A

<400> SEQUENCE: 39

Met Lys Leu Met Lys Val Leu Gly Tyr Ile Asn Ile Ile Thr Asn Cys
1               5                   10                  15

Val Asn Gly Ile Leu Cys Lys Gly Asp Lys Lys Arg Tyr Ser Ile Phe
            20                  25                  30

Thr Asn Asn Tyr Ile Tyr Ser Ile Ser Thr Leu Asn Asn Tyr Ser Phe
        35                  40                  45

Ala Ala Thr Met Asn Lys Met Pro Ala Trp Val Asn Glu Lys Cys Pro
    50                  55                  60

Glu His Lys Ser Tyr Asp Ile Val Glu Lys Arg Tyr Asn Glu Asn Leu
65                  70                  75                  80

Asn Leu Thr Tyr Thr Val Tyr Glu His Lys Lys Ala Lys Thr Gln Val
                85                  90                  95

Ile Ala Leu Gly Ser Asn Asp Pro Leu Asp Ala Glu Gln Ala Phe Gly
            100                 105                 110

Phe Tyr Val Lys Thr Leu Thr His Ser Asp Lys Gly Ile Pro His Ile
        115                 120                 125

Leu Glu His Thr Val Leu Ser Gly Ser Lys Asn Phe Asn Tyr Lys Asp
    130                 135                 140

Ser Met Gly Leu Leu Glu Lys Gly Thr Leu Asn Thr His Leu Asn Ala
145                 150                 155                 160

Tyr Thr Phe Asn Asp Arg Thr Ile Tyr Met Ala Gly Ser Met Asn Asn
                165                 170                 175

Arg Asp Phe Phe Asn Ile Met Ala Val Tyr Met Asp Ser Val Phe Gln
            180                 185                 190

Pro Asn Val Leu Glu Asn Lys Phe Ile Phe Gln Thr Glu Gly Trp Thr
        195                 200                 205

Tyr Glu Val Glu Lys Leu Lys Glu Glu Glu Lys Asn Leu Asp Ile Pro
    210                 215                 220

Lys Ile Lys Asp Tyr Lys Val Ser Phe Asn Gly Ile Val Tyr Asn Glu
225                 230                 235                 240

Met Lys Gly Ala Phe Ser Asn Pro Leu Gln Asp Leu Tyr Tyr Glu Val
                245                 250                 255

Met Arg Asn Met Phe Pro Asp Asn Val His Ser Asn Ile Ser Gly Gly
            260                 265                 270

Asp Pro Lys Glu Ile Pro Asn Leu Ser Tyr Glu Glu Phe Lys Glu Phe
        275                 280                 285

Tyr Tyr Lys Asn Tyr Asn Pro Lys Lys Ile Lys Val Phe Phe Phe Ser
    290                 295                 300

Lys Asn Asn Pro Thr Glu Leu Leu Asn Phe Val Asp Asn Tyr Leu Cys
305                 310                 315                 320

Gln Leu Asp Phe Thr Lys Tyr Arg Asp Asp Ala Val Glu His Val Asn
                325                 330                 335

Tyr Gln Glu Tyr Arg Lys Gly Pro Phe Tyr Ile Lys Lys Lys Phe Ala
            340                 345                 350

Asp His Ser Glu Glu Lys Glu Asn Leu Ala Ser Val Ser Trp Leu Leu
        355                 360                 365

Asn Pro Lys Lys His Lys Asn Ser Asp Thr Asp Leu Ser Leu Glu Ser
    370                 375                 380

Pro Thr Asp Tyr Phe Ala Leu Leu Ile Ile Asn Asn Leu Leu Thr His
385                 390                 395                 400

-continued

```
Thr Ser Glu Ser Val Leu Tyr Lys Ala Leu Ile Glu Ser Gly Leu Gly
                405                 410                 415

Asn Ser Ile Val Asp Arg Gly Leu Asn Asp Ser Leu Val Gln Tyr Val
            420                 425                 430

Phe Ser Ile Gly Leu Lys Gly Ile Lys Glu Lys Asn Glu Lys Asn Ile
        435                 440                 445

Ser Leu Asp Lys Val His Tyr Glu Val Glu Lys Ile Val Leu Glu Ala
    450                 455                 460

Leu Lys Lys Val Val Lys Glu Gly Phe Asn Lys Ser Ala Val Glu Ala
465                 470                 475                 480

Ala Ile Asn Asn Ile Glu Phe Val Leu Lys Glu Ala Asn Leu Lys Ile
                485                 490                 495

Ser Lys Ser Ile Asp Phe Val Phe Glu Met Ala Ser Arg Leu Asn Tyr
            500                 505                 510

Gly Lys Asp Pro Leu Leu Ile Phe Glu Phe Glu Lys His Leu Asn Val
        515                 520                 525

Val Lys Asp Lys Ile Lys Asn Glu Pro Lys Tyr Leu Glu Lys Tyr Val
    530                 535                 540

Glu Lys His Leu Leu Asn Asn Asp His Arg Val Val Ile Leu Leu Glu
545                 550                 555                 560

Gly Asp Glu Asn Tyr Gly Thr Glu Gln Glu Lys Leu Glu Lys Asp Met
                565                 570                 575

Leu Lys Lys Arg Ile Glu Ser Phe Thr Glu Lys Glu Lys Glu Asn Ile
            580                 585                 590

Ile Thr Asp Phe Glu Asn Leu Thr Lys Tyr Lys Asn Thr Glu Glu Ser
        595                 600                 605

Pro Glu His Leu Asp Lys Phe Pro Ile Ile Ser Ile Ser Asp Leu Asn
    610                 615                 620

Gly Lys Thr Leu Glu Ile Pro Val Asn Pro Phe Phe Thr Asn Leu Asn
625                 630                 635                 640

Asn Glu Asn Asn Met Gln His Tyr Asn Glu Thr Lys Asn Asn Gln Thr
                645                 650                 655

Leu Val Lys Glu Asn Met Asp Arg Phe Ile Asn Lys Tyr Ile Leu Asn
            660                 665                 670

Lys Asp Gly Asn Asp Lys Asn Asp Ser Lys Asn Ala Asp Val Pro Met
        675                 680                 685

Leu Ile Tyr Glu Ile Pro Thr Ser Gly Ile Leu Tyr Leu Gln Phe Ile
    690                 695                 700

Phe Ser Leu Asp Asn Leu Thr Leu Glu Glu Leu Ser Tyr Leu Asn Leu
705                 710                 715                 720

Phe Lys Ser Leu Ile Leu Glu Asn Lys Thr Asn Lys Arg Ser Ser Glu
                725                 730                 735

Glu Phe Val Ile Leu Arg Glu Lys Asn Ile Gly Asn Met Met Thr Asn
            740                 745                 750

Val Ala Leu Leu Ser Thr Ser Asp Arg Leu Asn Val Thr Asp Lys Tyr
        755                 760                 765

Asn Ala Lys Gly Phe Phe Asn Phe Glu Met His Met Leu Ser His Lys
    770                 775                 780

Cys Asn Asp Ala Leu Glu Ile Ala Leu Glu Ala Leu Lys Glu Ser Asp
785                 790                 795                 800

Phe Ser Asn Lys Lys Lys Val Ile Glu Ile Leu Lys Arg Lys Ile Asn
                805                 810                 815
```

```
Gly Met Lys Thr Thr Phe Ala Ser Lys Gly His Ser Ile Leu Ile Lys
            820                 825                 830

Tyr Val Lys Ser Arg Ile Asn Ser Lys Tyr Tyr Ala Tyr Asp Leu Ile
        835                 840                 845

His Gly Tyr Asp Asn Tyr Leu Lys Leu Gln Glu Gln Leu Lys Leu Ala
    850                 855                 860

Glu Thr Asn Tyr Glu Ser Leu Glu Ala Ile Leu Asn Arg Ile Arg Lys
865                 870                 875                 880

Lys Ile Phe Lys Arg Asn Asn Leu Ile Met Asn Val Thr Val Asp Pro
                885                 890                 895

Gly Thr Ile Asp Gln Leu Phe Ala Lys Ser Lys Asn Ser Phe Asn Asn
            900                 905                 910

Leu Leu Ser Tyr Phe Asp Glu Asn Glu Ser Tyr Cys Ser Lys Asn Asp
        915                 920                 925

Ser Phe Asn Lys Val Val Gly Trp Asn Lys Glu Ile Gln Glu Lys Lys
    930                 935                 940

Leu Leu Glu Gly Glu Glu Val Lys Lys Glu Leu Leu Val Val Pro Thr
945                 950                 955                 960

Phe Val Asn Ser Val Ser Met Ser Gly Val Leu Phe Asn Lys Gly Glu
                965                 970                 975

Tyr Leu Asp Pro Ser Phe Thr Val Ile Val Ala Ala Leu Lys Asn Ser
            980                 985                 990

Tyr Leu Trp Glu Thr Val Arg Gly  Leu Asn Gly Ala Tyr  Gly Val Phe
        995                 1000                1005

Ala Asp  Ile Glu Tyr Asp Gly  Thr Val Val Phe Leu  Ser Ala Arg
    1010                 1015                 1020

Asp Pro  Asn Leu Glu Lys Thr  Leu Gln Thr Phe Arg  Glu Ala Ala
    1025                 1030                 1035

Gln Gly  Leu Arg Lys Met Ala  Asp Val Met Thr Lys  Asn Asp Leu
    1040                 1045                 1050

Leu Arg  Tyr Ile Ile Asn Ala  Ile Gly Thr Ile Asp  Arg Pro Arg
    1055                 1060                 1065

Arg Gly  Val Glu Leu Ser Lys  Leu Ser Phe Ser Arg  Ile Ile Ser
    1070                 1075                 1080

Asn Glu  Thr Glu Gln Asp Arg  Ile Glu Phe Arg Asn  Arg Val Met
    1085                 1090                 1095

Asn Thr  Lys Lys Glu Asp Phe  Tyr Lys Phe Ala Asp  Leu Leu Glu
    1100                 1105                 1110

Lys Lys  Val Lys Glu Phe Glu  Lys Asn Val Val Ile  Ile Thr Ser
    1115                 1120                 1125

Lys Glu  Lys Ala Asn Glu Tyr  Ile Asn Asn Val Asp  Asn Asp Phe
    1130                 1135                 1140

Lys Lys  Ile Leu Ile Glu
    1145
```

<210> SEQ ID NO 40
<211> LENGTH: 3591
<212> TYPE: DNA
<213> ORGANISM: Artificial Sequence
<220> FEATURE:
<223> OTHER INFORMATION: PfFalcilysin Human CO

<400> SEQUENCE: 40

```
gccaccatgg ctaatcttac caaacttatg aaagtaatag gatatataaa cattataact     60
aattgtgtac aatcttttac taacagagcg gacaagaaga ggtacaatgt ttttgcaaag    120
tctttcatca atacgataaa cacgaacctg tacaccttca aagcggtgat gtcaaaaacg    180
cctgaatgga tccatgagaa atctcccaaa cacaacagtt atgacataat tgagaaacgc    240
tataatgaag agttcaaaat gacatacacg gtttatcaac ataaaaaagc aaagacgcag    300
gtaatttcac tcggtacgaa cgacccactt gatgtcgaac aggcctttgc cttctatgta    360
aagactctga cccactctgg gaaggggatt ccccacatcc tcgaacacag tgtcctctca    420
gggagtaaaa attacaacta caaaaattcc attggactcc ttgagaaggg aactctgcac    480
acccacctta acgcatacac cttcaatgac cgaactgtgt acatggccgg ttctatgaat    540
aacaaagact tcttcaatat aatgggcgtc tatatggaca gtgtcttcca acctaatgta    600
ctggaaaaca aatacatatt cgagacggag ggatggactt acgaggtgga aaagctgaaa    660
gaggatgaga agggaaaagc tgagattcca cagatgaaag attataaagt atctttcaac    720
ggaattgttt ataatgaaat gaagggtgcc ttgtcttccc cgttggaaga tctttaccat    780
gaagagatga agtatatgtt cccagacaac gtccactcta ataacagtgg cggagaccca    840
aaagagatca caaacttgac ctatgaggag ttcaaggagt tctattacaa aaactataat    900
ccaaaaaaag ttaaagtgtt cttcttttca aagaacaacc caacggagct tctcaatttc    960
gtagaccagt acctcggaca gctggactac agcaaatacc gcgacgatgc tgttgaaagt   1020
gttgaatacc aaacgtataa aaaaggacct ttctacatta aaaaaaagta tggggaccat   1080
agcgaagaga aggagaatct tgtttccgta gcgtggcttc tgaaccccaa ggttgacaag   1140
actaacaatc ataataataa ccatagtaat aaccaatcta gcgaaaataa tggttactcc   1200
aacggctccc actctagcga tttgtccttg gagaatccca cggactattt cgtgctcttg   1260
attatcaata acctccttat acatacccca gaaagcgtcc tgtacaaggc cctcacagat   1320
tgcgggctgg gaaataatgt aattgatagg ggtttgaatg attcacttgt ccaatacatt   1380
ttcagtattg ggctgaaggg aatcaaacgc aacaatgaaa aaattaaaaa cttcgataaa   1440
gtgcactatg aagtagaaga cgtaattatg aatgctctca aaaaagtggt caaggaggga   1500
ttcaataaat ccgccgtaga agccagcata aataatatcg agtttatcct gaaagaagcc   1560
aatttgaaaa cttcaaaatc tatagatttc gtttttgaga tgacttccaa gctcaattat   1620
aatagggatc cactgctgat cttcgagttt gagaaatatc ttaatattgt gaagaataag   1680
attaagaacg aacctatgta tttggagaag tttgttgaaa aacacttcat caacaacgca   1740
catcggtcag tgatccttct tgagggggac gagaactatg cacaggaaca ggaaaacctt   1800
gagaaacaag aactgaagaa acgcatagag aacttcaatg agcaggagaa agagcaagtc   1860
attaagaact tcgaggagct gtccaagtac aagaacgcgg aagagagccc ggaacacttg   1920
aacaagtttc caataatctc catttccgac ctcaataaga aaacactgga agtcccagtt   1980
aacgtctact tcacgaacat caacgaaaac aacaatataa tggagacata taacaagctg   2040
aagacaaatg agcacatgct taaggacaac atggacgtgt ttctcaaaaa atacgttctc   2100
aaaaacgata agcacaacac caacaataat aacaacaata ataataatat ggactactct   2160
ttcaccgaaa ctaaatatga aggaaatgtg ccaatccttg tgtacgaaat gccgacgact   2220
ggaatagtct atttgcagtt cgttttctcc ctcgatcacc tgaccgtaga cgagctcgcc   2280
```

```
tatttgaatt tgttcaagac acttatcttg gagaacaaga caaacaaacg ctccagtgag   2340

gatttcgtca ttttgagaga aaaaaatatt gggtcaatgt cagcgaatgt ggcgctctac   2400

agcaaggacg accacctgaa cgtaaccgac aagtataacg cgcaagcact cttcaatctg   2460

gaaatgcacg tactttctca taaatgcaac gatgcgctga acattgccct tgaagctgtt   2520

aaagaatctg acttcagtaa taaaaaaaag gtcatagata tccttaagag gaagattaat   2580

ggaatgaaaa ctacgttctc agaaaaagga tatgctatac tgatgaaata cgttaaagcc   2640

catcttaata gcaagcatta cgcccataac ataatttatg ggtacgaaaa ctatttgaag   2700

ctgcaagagc aattggagct tgcagaaaac gattttaaaa cattggagaa tattttggtg   2760

agaataagaa acaaaatctt taacaaaaaa aacttgatgg tcagcgtgac gtccgactat   2820

ggtgctctca aacacctgtt tgtgaatagc aacgaatcct tgaaaaacct tgtaagttac   2880

ttcgaggaaa acgataagta tatcaacgat atgcagaata aagtgaatga ccctaccgtc   2940

atggggtgga atgaagaaat caagtctaaa aagctgttcg acgaggagaa ggtgaaaaag   3000

gagttctttg tcttgccgac ctttgtcaac agcgtctcaa tgagtggtat cctgttcaag   3060

ccgggcgaat atctcgaccc gagtttcact gtcatcgttg cggccctgaa aaatagctat   3120

ttgtgggaca cagttcgagg acttaacggg gcttacggtg tattcgctga tatcgaatac   3180

gatggctctg tagtatttct ttcagctcga gaccccaatc tcgaaaagac cctcgccact   3240

ttccgagaat ctgctaaagg attgcgcaaa atggctgaca ccatgacaga gaacgatttg   3300

cttcggtata ttattaacac aattggcacg atcgacaagc ctcgacgagg gatagaactt   3360

tctaagctgt cattccttag acttatttcc aacgagtcag agcaagatcg ggtggagttc   3420

cggaaacgga taatgaacac aaaaaaggaa gatttctata aattcgcaga tcttcttgag   3480

agcaaagtaa atgaattcga aaaaaatatc gttatcataa caacaaaaga aaaggccaac   3540

gaatatatag caaacgtaga tggcgagttt aagaaagtct tgatcgagtg a           3591
```

```
<210> SEQ ID NO 41
<211> LENGTH: 1194
<212> TYPE: PRT
<213> ORGANISM: Plasmodium falciparum
<220> FEATURE:
<221> NAME/KEY: misc_feature
<223> OTHER INFORMATION: PfFalcilysin

<400> SEQUENCE: 41

Met Ala Asn Leu Thr Lys Leu Met Lys Val Ile Gly Tyr Ile Asn Ile
1               5                   10                  15

Ile Thr Asn Cys Val Gln Ser Phe Thr Asn Arg Ala Asp Lys Lys Arg
            20                  25                  30

Tyr Asn Val Phe Ala Lys Ser Phe Ile Asn Thr Ile Asn Thr Asn Leu
        35                  40                  45

Tyr Thr Phe Lys Ala Val Met Ser Lys Thr Pro Glu Trp Ile His Glu
    50                  55                  60

Lys Ser Pro Lys His Asn Ser Tyr Asp Ile Ile Glu Lys Arg Tyr Asn
65                  70                  75                  80

Glu Glu Phe Lys Met Thr Tyr Thr Val Tyr Gln His Lys Lys Ala Lys
                85                  90                  95

Thr Gln Val Ile Ser Leu Gly Thr Asn Asp Pro Leu Asp Val Glu Gln
            100                 105                 110

Ala Phe Ala Phe Tyr Val Lys Thr Leu Thr His Ser Gly Lys Gly Ile
        115                 120                 125
```

```
Pro His Ile Leu Glu His Ser Val Leu Ser Gly Ser Lys Asn Tyr Asn
    130                 135                 140

Tyr Lys Asn Ser Ile Gly Leu Leu Glu Lys Gly Thr Leu His Thr His
145                 150                 155                 160

Leu Asn Ala Tyr Thr Phe Asn Asp Arg Thr Val Tyr Met Ala Gly Ser
                165                 170                 175

Met Asn Asn Lys Asp Phe Phe Asn Ile Met Gly Val Tyr Met Asp Ser
            180                 185                 190

Val Phe Gln Pro Asn Val Leu Glu Asn Lys Tyr Ile Phe Glu Thr Glu
        195                 200                 205

Gly Trp Thr Tyr Glu Val Glu Lys Leu Lys Glu Asp Glu Lys Gly Lys
    210                 215                 220

Ala Glu Ile Pro Gln Met Lys Asp Tyr Lys Val Ser Phe Asn Gly Ile
225                 230                 235                 240

Val Tyr Asn Glu Met Lys Gly Ala Leu Ser Ser Pro Leu Glu Asp Leu
                245                 250                 255

Tyr His Glu Glu Met Lys Tyr Met Phe Pro Asp Asn Val His Ser Asn
            260                 265                 270

Asn Ser Gly Gly Asp Pro Lys Glu Ile Thr Asn Leu Thr Tyr Glu Glu
        275                 280                 285

Phe Lys Glu Phe Tyr Tyr Lys Asn Tyr Asn Pro Lys Lys Val Lys Val
    290                 295                 300

Phe Phe Phe Ser Lys Asn Asn Pro Thr Glu Leu Leu Asn Phe Val Asp
305                 310                 315                 320

Gln Tyr Leu Gly Gln Leu Asp Tyr Ser Lys Tyr Arg Asp Asp Ala Val
                325                 330                 335

Glu Ser Val Glu Tyr Gln Thr Tyr Lys Lys Gly Pro Phe Tyr Ile Lys
            340                 345                 350

Lys Lys Tyr Gly Asp His Ser Glu Glu Lys Glu Asn Leu Val Ser Val
        355                 360                 365

Ala Trp Leu Leu Asn Pro Lys Val Asp Lys Thr Asn Asn His Asn Asn
    370                 375                 380

Asn His Ser Asn Asn Gln Ser Ser Glu Asn Asn Gly Tyr Ser Asn Gly
385                 390                 395                 400

Ser His Ser Ser Asp Leu Ser Leu Glu Asn Pro Thr Asp Tyr Phe Val
                405                 410                 415

Leu Leu Ile Ile Asn Asn Leu Leu Ile His Thr Pro Glu Ser Val Leu
            420                 425                 430

Tyr Lys Ala Leu Thr Asp Cys Gly Leu Gly Asn Asn Val Ile Asp Arg
        435                 440                 445

Gly Leu Asn Asp Ser Leu Val Gln Tyr Ile Phe Ser Ile Gly Leu Lys
    450                 455                 460

Gly Ile Lys Arg Asn Asn Glu Lys Ile Lys Asn Phe Asp Lys Val His
465                 470                 475                 480

Tyr Glu Val Glu Asp Val Ile Met Asn Ala Leu Lys Lys Val Val Lys
                485                 490                 495

Glu Gly Phe Asn Lys Ser Ala Val Glu Ala Ser Ile Asn Asn Ile Glu
            500                 505                 510

Phe Ile Leu Lys Glu Ala Asn Leu Lys Thr Ser Lys Ser Ile Asp Phe
        515                 520                 525

Val Phe Glu Met Thr Ser Lys Leu Asn Tyr Asn Arg Asp Pro Leu Leu
    530                 535                 540
```

```
Ile Phe Glu Phe Glu Lys Tyr Leu Asn Ile Val Lys Asn Lys Ile Lys
545                 550                 555                 560

Asn Glu Pro Met Tyr Leu Glu Lys Phe Val Glu Lys His Phe Ile Asn
                565                 570                 575

Asn Ala His Arg Ser Val Ile Leu Leu Glu Gly Asp Glu Asn Tyr Ala
            580                 585                 590

Gln Glu Gln Glu Asn Leu Glu Lys Gln Glu Leu Lys Lys Arg Ile Glu
        595                 600                 605

Asn Phe Asn Glu Gln Glu Lys Glu Gln Val Ile Lys Asn Phe Glu Glu
    610                 615                 620

Leu Ser Lys Tyr Lys Asn Ala Glu Glu Ser Pro Glu His Leu Asn Lys
625                 630                 635                 640

Phe Pro Ile Ile Ser Ile Ser Asp Leu Asn Lys Lys Thr Leu Glu Val
                645                 650                 655

Pro Val Asn Val Tyr Phe Thr Asn Ile Asn Glu Asn Asn Asn Ile Met
            660                 665                 670

Glu Thr Tyr Asn Lys Leu Lys Thr Asn Glu His Met Leu Lys Asp Asn
        675                 680                 685

Met Asp Val Phe Leu Lys Lys Tyr Val Leu Lys Asn Asp Lys His Asn
    690                 695                 700

Thr Asn Asn Asn Asn Asn Asn Asn Asn Asn Met Asp Tyr Ser Phe Thr
705                 710                 715                 720

Glu Thr Lys Tyr Glu Gly Asn Val Pro Ile Leu Val Tyr Glu Met Pro
                725                 730                 735

Thr Thr Gly Ile Val Tyr Leu Gln Phe Val Phe Ser Leu Asp His Leu
            740                 745                 750

Thr Val Asp Glu Leu Ala Tyr Leu Asn Leu Phe Lys Thr Leu Ile Leu
        755                 760                 765

Glu Asn Lys Thr Asn Lys Arg Ser Ser Glu Asp Phe Val Ile Leu Arg
    770                 775                 780

Glu Lys Asn Ile Gly Ser Met Ser Ala Asn Val Ala Leu Tyr Ser Lys
785                 790                 795                 800

Asp Asp His Leu Asn Val Thr Asp Lys Tyr Asn Ala Gln Ala Leu Phe
                805                 810                 815

Asn Leu Glu Met His Val Leu Ser His Lys Cys Asn Asp Ala Leu Asn
            820                 825                 830

Ile Ala Leu Glu Ala Val Lys Glu Ser Asp Phe Ser Asn Lys Lys Lys
        835                 840                 845

Val Ile Asp Ile Leu Lys Arg Lys Ile Asn Gly Met Lys Thr Thr Phe
    850                 855                 860

Ser Glu Lys Gly Tyr Ala Ile Leu Met Lys Tyr Val Lys Ala His Leu
865                 870                 875                 880

Asn Ser Lys His Tyr Ala His Asn Ile Ile Tyr Gly Tyr Glu Asn Tyr
                885                 890                 895

Leu Lys Leu Gln Glu Gln Leu Glu Leu Ala Glu Asn Asp Phe Lys Thr
            900                 905                 910

Leu Glu Asn Ile Leu Val Arg Ile Arg Asn Lys Ile Phe Asn Lys Lys
        915                 920                 925

Asn Leu Met Val Ser Val Thr Ser Asp Tyr Gly Ala Leu Lys His Leu
    930                 935                 940

Phe Val Asn Ser Asn Glu Ser Leu Lys Asn Leu Val Ser Tyr Phe Glu
945                 950                 955                 960
```

```
Glu Asn Asp Lys Tyr Ile Asn Asp Met Gln Asn Lys Val Asn Asp Pro
                965                 970                 975

Thr Val Met Gly Trp Asn Glu Glu Ile Lys Ser Lys Lys Leu Phe Asp
            980                 985                 990

Glu Glu Lys Val Lys Lys Glu Phe  Phe Val Leu Pro Thr  Phe Val Asn
        995                 1000                 1005

Ser Val  Ser Met Ser Gly Ile  Leu Phe Lys Pro Gly  Glu Tyr Leu
    1010                 1015                 1020

Asp Pro  Ser Phe Thr Val Ile  Val Ala Ala Leu Lys  Asn Ser Tyr
    1025                 1030                 1035

Leu Trp  Asp Thr Val Arg Gly  Leu Asn Gly Ala Tyr  Gly Val Phe
    1040                 1045                 1050

Ala Asp  Ile Glu Tyr Asp Gly  Ser Val Val Phe Leu  Ser Ala Arg
    1055                 1060                 1065

Asp Pro  Asn Leu Glu Lys Thr  Leu Ala Thr Phe Arg  Glu Ser Ala
    1070                 1075                 1080

Lys Gly  Leu Arg Lys Met Ala  Asp Thr Met Thr Glu  Asn Asp Leu
    1085                 1090                 1095

Leu Arg  Tyr Ile Ile Asn Thr  Ile Gly Thr Ile Asp  Lys Pro Arg
    1100                 1105                 1110

Arg Gly  Ile Glu Leu Ser Lys  Leu Ser Phe Leu Arg  Leu Ile Ser
    1115                 1120                 1125

Asn Glu  Ser Glu Gln Asp Arg  Val Glu Phe Arg Lys  Arg Ile Met
    1130                 1135                 1140

Asn Thr  Lys Lys Glu Asp Phe  Tyr Lys Phe Ala Asp  Leu Leu Glu
    1145                 1150                 1155

Ser Lys  Val Asn Glu Phe Glu  Lys Asn Ile Val Ile  Ile Thr Thr
    1160                 1165                 1170

Lys Glu  Lys Ala Asn Glu Tyr  Ile Ala Asn Val Asp  Gly Glu Phe
    1175                 1180                 1185

Lys Lys  Val Leu Ile Glu
    1190
```

<210> SEQ ID NO 42
<211> LENGTH: 1193
<212> TYPE: PRT
<213> ORGANISM: Plasmodium falciparum
<220> FEATURE:
<221> NAME/KEY: misc_feature
<223> OTHER INFORMATION: Falcilysin

<400> SEQUENCE: 42

```
Met Asn Leu Thr Lys Leu Met Lys Val Ile Gly Tyr Ile Asn Ile Ile
1               5                   10                  15

Thr Asn Cys Val Gln Ser Phe Thr Asn Arg Ala Asp Lys Lys Arg Tyr
            20                  25                  30

Asn Val Phe Ala Lys Ser Phe Ile Asn Thr Ile Asn Thr Asn Leu Tyr
        35                  40                  45

Thr Phe Lys Ala Val Met Ser Lys Thr Pro Glu Trp Ile His Glu Lys
    50                  55                  60

Ser Pro Lys His Asn Ser Tyr Asp Ile Ile Glu Lys Arg Tyr Asn Glu
65                  70                  75                  80

Glu Phe Lys Met Thr Tyr Thr Val Tyr Gln His Lys Lys Ala Lys Thr
                85                  90                  95

Gln Val Ile Ser Leu Gly Thr Asn Asp Pro Leu Asp Val Glu Gln Ala
            100                 105                 110
```

```
Phe Ala Phe Tyr Val Lys Thr Leu Thr His Ser Gly Lys Gly Ile Pro
        115                 120                 125

His Ile Leu Glu His Ser Val Leu Ser Gly Ser Lys Asn Tyr Asn Tyr
    130                 135                 140

Lys Asn Ser Ile Gly Leu Leu Glu Lys Gly Thr Leu His Thr His Leu
145                 150                 155                 160

Asn Ala Tyr Thr Phe Asn Asp Arg Thr Val Tyr Met Ala Gly Ser Met
                165                 170                 175

Asn Asn Lys Asp Phe Phe Asn Ile Met Gly Val Tyr Met Asp Ser Val
            180                 185                 190

Phe Gln Pro Asn Val Leu Glu Asn Lys Tyr Ile Phe Glu Thr Glu Gly
        195                 200                 205

Trp Thr Tyr Glu Val Glu Lys Leu Lys Glu Asp Glu Lys Gly Lys Ala
    210                 215                 220

Glu Ile Pro Gln Met Lys Asp Tyr Lys Val Ser Phe Asn Gly Ile Val
225                 230                 235                 240

Tyr Asn Glu Met Lys Gly Ala Leu Ser Ser Pro Leu Glu Asp Leu Tyr
                245                 250                 255

His Glu Glu Met Lys Tyr Met Phe Pro Asp Asn Val His Ser Asn Asn
            260                 265                 270

Ser Gly Gly Asp Pro Lys Glu Ile Thr Asn Leu Thr Tyr Glu Glu Phe
        275                 280                 285

Lys Glu Phe Tyr Tyr Lys Asn Tyr Asn Pro Lys Lys Val Lys Val Phe
    290                 295                 300

Phe Phe Ser Lys Asn Asn Pro Thr Glu Leu Leu Asn Phe Val Asp Gln
305                 310                 315                 320

Tyr Leu Gly Gln Leu Asp Tyr Ser Lys Tyr Arg Asp Asp Ala Val Glu
                325                 330                 335

Ser Val Glu Tyr Gln Thr Tyr Lys Lys Gly Pro Phe Tyr Ile Lys Lys
            340                 345                 350

Lys Tyr Gly Asp His Ser Glu Glu Lys Glu Asn Leu Val Ser Val Ala
        355                 360                 365

Trp Leu Leu Asn Pro Lys Val Asp Lys Thr Asn Asn His Asn Asn Asn
    370                 375                 380

His Ser Asn Asn Gln Ser Ser Glu Asn Asn Gly Tyr Ser Asn Gly Ser
385                 390                 395                 400

His Ser Ser Asp Leu Ser Leu Glu Asn Pro Thr Asp Tyr Phe Val Leu
                405                 410                 415

Leu Ile Ile Asn Asn Leu Leu Ile His Thr Pro Glu Ser Val Leu Tyr
            420                 425                 430

Lys Ala Leu Thr Asp Cys Gly Leu Gly Asn Asn Val Ile Asp Arg Gly
        435                 440                 445

Leu Asn Asp Ser Leu Val Gln Tyr Ile Phe Ser Ile Gly Leu Lys Gly
    450                 455                 460

Ile Lys Arg Asn Asn Glu Lys Ile Lys Asn Phe Asp Lys Val His Tyr
465                 470                 475                 480

Glu Val Glu Asp Val Ile Met Asn Ala Leu Lys Lys Val Val Lys Glu
                485                 490                 495

Gly Phe Asn Lys Ser Ala Val Glu Ala Ser Ile Asn Asn Ile Glu Phe
            500                 505                 510

Ile Leu Lys Glu Ala Asn Leu Lys Thr Ser Lys Ser Ile Asp Phe Val
        515                 520                 525
```

-continued

```
Phe Glu Met Thr Ser Lys Leu Asn Tyr Asn Arg Asp Pro Leu Leu Ile
    530                 535                 540

Phe Glu Phe Glu Lys Tyr Leu Asn Ile Val Lys Asn Lys Ile Lys Asn
545                 550                 555                 560

Glu Pro Met Tyr Leu Glu Lys Phe Val Glu Lys His Phe Ile Asn Asn
                565                 570                 575

Ala His Arg Ser Val Ile Leu Leu Glu Gly Asp Glu Asn Tyr Ala Gln
            580                 585                 590

Glu Gln Glu Asn Leu Glu Lys Gln Glu Leu Lys Lys Arg Ile Glu Asn
        595                 600                 605

Phe Asn Glu Gln Glu Lys Glu Gln Val Ile Lys Asn Phe Glu Glu Leu
    610                 615                 620

Ser Lys Tyr Lys Asn Ala Glu Glu Ser Pro Glu His Leu Asn Lys Phe
625                 630                 635                 640

Pro Ile Ile Ser Ile Ser Asp Leu Asn Lys Lys Thr Leu Glu Val Pro
                645                 650                 655

Val Asn Val Tyr Phe Thr Asn Ile Asn Glu Asn Asn Asn Ile Met Glu
            660                 665                 670

Thr Tyr Asn Lys Leu Lys Thr Asn Glu His Met Leu Lys Asp Asn Met
        675                 680                 685

Asp Val Phe Leu Lys Lys Tyr Val Leu Lys Asn Asp Lys His Asn Thr
    690                 695                 700

Asn Asn Asn Asn Asn Asn Asn Asn Asn Met Asp Tyr Ser Phe Thr Glu
705                 710                 715                 720

Thr Lys Tyr Glu Gly Asn Val Pro Ile Leu Val Tyr Glu Met Pro Thr
                725                 730                 735

Thr Gly Ile Val Tyr Leu Gln Phe Val Phe Ser Leu Asp His Leu Thr
            740                 745                 750

Val Asp Glu Leu Ala Tyr Leu Asn Leu Phe Lys Thr Leu Ile Leu Glu
        755                 760                 765

Asn Lys Thr Asn Lys Arg Ser Ser Glu Asp Phe Val Ile Leu Arg Glu
    770                 775                 780

Lys Asn Ile Gly Ser Met Ser Ala Asn Val Ala Leu Tyr Ser Lys Asp
785                 790                 795                 800

Asp His Leu Asn Val Thr Asp Lys Tyr Asn Ala Gln Ala Leu Phe Asn
                805                 810                 815

Leu Glu Met His Val Leu Ser His Lys Cys Asn Asp Ala Leu Asn Ile
            820                 825                 830

Ala Leu Glu Ala Val Lys Glu Ser Asp Phe Ser Asn Lys Lys Lys Val
        835                 840                 845

Ile Asp Ile Leu Lys Arg Lys Ile Asn Gly Met Lys Thr Thr Phe Ser
    850                 855                 860

Glu Lys Gly Tyr Ala Ile Leu Met Lys Tyr Val Lys Ala His Leu Asn
865                 870                 875                 880

Ser Lys His Tyr Ala His Asn Ile Ile Tyr Gly Tyr Glu Asn Tyr Leu
                885                 890                 895

Lys Leu Gln Glu Gln Leu Glu Leu Ala Glu Asn Asp Phe Lys Thr Leu
            900                 905                 910

Glu Asn Ile Leu Val Arg Ile Arg Asn Lys Ile Phe Asn Lys Lys Asn
        915                 920                 925

Leu Met Val Ser Val Thr Ser Asp Tyr Gly Ala Leu Lys His Leu Phe
    930                 935                 940
```

```
Val Asn Ser Asn Glu Ser Leu Lys Asn Leu Val Ser Tyr Phe Glu Glu
945                 950                 955                 960

Asn Asp Lys Tyr Ile Asn Asp Met Gln Asn Lys Val Asn Asp Pro Thr
                965                 970                 975

Val Met Gly Trp Asn Glu Glu Ile Lys Ser Lys Lys Leu Phe Asp Glu
            980                 985                 990

Glu Lys Val Lys Lys Glu Phe Phe  Val Leu Pro Thr Phe  Val Asn Ser
        995                 1000                 1005

Val Ser  Met Ser Gly Ile Leu  Phe Lys Pro Gly Glu  Tyr Leu Asp
    1010                 1015                 1020

Pro Ser  Phe Thr Val Ile Val  Ala Ala Leu Lys Asn  Ser Tyr Leu
    1025                 1030                 1035

Trp Asp  Thr Val Arg Gly Leu  Asn Gly Ala Tyr Gly  Val Phe Ala
    1040                 1045                 1050

Asp Ile  Glu Tyr Asp Gly Ser  Val Val Phe Leu Ser  Ala Arg Asp
    1055                 1060                 1065

Pro Asn  Leu Glu Lys Thr Leu  Ala Thr Phe Arg Glu  Ser Ala Lys
    1070                 1075                 1080

Gly Leu  Arg Lys Met Ala Asp  Thr Met Thr Glu Asn  Asp Leu Leu
    1085                 1090                 1095

Arg Tyr  Ile Ile Asn Thr Ile  Gly Thr Ile Asp Lys  Pro Arg Arg
    1100                 1105                 1110

Gly Ile  Glu Leu Ser Lys Leu  Ser Phe Leu Arg Leu  Ile Ser Asn
    1115                 1120                 1125

Glu Ser  Glu Gln Asp Arg Val  Glu Phe Arg Lys Arg  Ile Met Asn
    1130                 1135                 1140

Thr Lys  Lys Glu Asp Phe Tyr  Lys Phe Ala Asp Leu  Leu Glu Ser
    1145                 1150                 1155

Lys Val  Asn Glu Phe Glu Lys  Asn Ile Val Ile Ile  Thr Thr Lys
    1160                 1165                 1170

Glu Lys  Ala Asn Glu Tyr Ile  Ala Asn Val Asp Gly  Glu Phe Lys
    1175                 1180                 1185

Lys Val  Leu Ile Glu
    1190


<210> SEQ ID NO 43
<211> LENGTH: 3471
<212> TYPE: DNA
<213> ORGANISM: Artificial Sequence
<220> FEATURE:
<223> OTHER INFORMATION: PvFalcilysin Human CO

<400> SEQUENCE: 43

gccaccatgg ctaaactgat gagggtcttt ggttatctta acataattac taactgcgtt     60

aacggacttc tctgtaaagc ggagaaacgc aaatataacg tctttacgaa cagctttatc    120

tattctatct ctacaacaaa tctgtactcc ttcacggcca tgatgaacaa atcacccgag    180

tgggtgcagg aaaagtgtcc cgagcacaag tcttataaca tccttgaaaa gcggttttct    240

gataaattcc aaatgacgta tacagtgtac gagcacaaaa aagcgaaaac ccaagtcatt    300

gccctcggca gcaatgaccc tctggacgtt gagcagactt ttgcctttta cgtaaagacc    360

ctgacgaact caggtaaggg tattcctcac atactcgagc acacagtttt gagcgggagc    420

aaaaatttca attacaaaga tagcatggga ctcctggaaa agggaacact taacacccat    480

ttgaatgcgt atactttcaa cgacaggact gtgtatatgg cggggtctat gaataataga    540
```

```
gactttttca acataatggc ggtgtatatg gatagcgtgt ttcaaccgaa tgttcttgaa     600
aataagttta tcttccaaac ggaaggatgg acctacgaag tggaaaagtt gaaagatgag     660
gagaagaacg ctgatgtacc gaaaattaaa gattataagg tttcctacaa tggtatagtc     720
tattccgaaa tgaaagggag cttctcctct cccctgcaat atctttatta tttgatcatg     780
aaaaacatct tccctgacaa cgtccattct aacataagtg gaggggaccc taaggagatt     840
ccaacgctca cgtatgagga attcaaagag ttctactata agaattacaa tcctaaaaaa     900
attaaagtca ttttcttcag caaaaacaat cctacagagt tgttgaattt cgtcgacgat     960
tatttgaacc agctcgactt tactaaatac agagacgatg cagtagaaaa cgttaattat    1020
caggagtaca agaaggggcc attctatgtt aagaagaaat ttgcggatca cagtgaggaa    1080
aaggaaaatc ttgtttccat ttcatggctt ctcaacccga aaaaaaatga cctcctggat    1140
gttgatctta gccttgaaag cccccaagac tacttcgctt tgttgattat taacaacctt    1200
ctgacgcaca ccaccgaatc tgtgctttac aaggcgctta ttgactgcgg tttgggtaac    1260
accgttatcg atacaggcct tgacgacagc ctggtacagt tcatattttc tataggtctg    1320
aagggtatca aggaaaagaa tgaaaagaac gtatcattgg acgttgtcca ttatgaagtg    1380
gaaaaggtgg ttctcaaagc gctccaaaaa gtagtggatg aaggcttcaa caaatcagcg    1440
gtcgaggcca gcattaacaa catagaattc gttttgaaag aagccaatct taaaacgtcc    1500
aaaagcgtgg actacatatt tgaaatggct tccaggctga attataatag agaccctctg    1560
ctgatctttg aattcgagaa gcacttgaac gtcgttaaag ataagatcaa gaatgaacca    1620
aagtatttgg agaaattcat tgagaaacac tttataaaca ataaccatcg ggctgtcatc    1680
ttgatggagg gtgatgaaaa ctatgggaaa gaacaggagg atttggaaaa ggagactttg    1740
aaaaagaaga tcgaatcact cacggaaaaa gaacgggacg acataatagt tgatttcgag    1800
aacctgacaa agtataagaa catggtcgag agccccgaac atttggataa ttttcccatc    1860
atctctatca gcgatctgaa caaagaaacg ctggaaatcc ctgctaatgc atatttcacg    1920
tccacggcag aggaaaataa tatggaaaag tacaataaag tgaaggcaag cgaggatgtt    1980
atgaagaaaa acatggacca cctcatcgac aaatatgttc tgaaaggagc gcaaggaggc    2040
gctgctaccg acggtgcagc caaacagggt gattccagcg atggtgaaat ccccatgctc    2100
gtttacgaga tgcctaccag tggaatcttg tatctgcaat ttatctttaa cctcgatcat    2160
ctgagcctgg aggaaatgtc atatctcaat ctctttaaga tgctcatcct tgagaacaaa    2220
actatgaaac gctcctctga ggagtttgtc attttgaggg aaaagaatat cggcaacata    2280
atggctaacg tcgccttgta tagtatcagc gatcacctca aggtcacttc taaatacaac    2340
gctcacggtc tgttcaattt tgaaatgcat gtattgagtc acaagtgcaa tgagtctttg    2400
gaaattgcct tggaagctct caaggactct gattttagca acaagaagaa aatagtggag    2460
atcctgaaac ggaagatcaa cggcatgaag acggtcttct cttctaaagg ctactcactt    2520
ctcctcaagt atgtaaagtc acaaatgaat gcaaaatact acgctcatga tttggttttt    2580
ggatacggca actatttgaa gttgcaagaa cagctcaagc tcgccgaaag tgactttcca    2640
cagttcgagc agattctcaa cagaatccga aataagattt tcactaagaa gaatctgctg    2700
atcagcgtga ccagtgacgc tgcagcgttg gatcaactgt ttgtgcatag caaggaatcc    2760
ctgaagaacc ttcttgggta tttcgaagag aatgatgcca agtctggaga ggctgagacc    2820
atagggtgga atgaggagat taaacaatca aaagtgatcg aaaaggaaca aaagaagaag    2880
```

gaattctttg taataccaac atttgtcaat gcagtatcaa tggctggaat gttgtttaat 2940
gagaaggagt tcctggatcc gtctttcata gttatcgtgg ccgcattgaa aaactcatac 3000
ctttgggaga ccgtgagggg actcaacggg gcatatggag tttttgctga tatagaatac 3060
gatggtgccg tcgtgttctt gtcagcccgc gatccgaatc tggaaaagac gctgcaaacg 3120
ttcaaggagt ctgctcaagg gttgagaaag atggcggata caatgaccaa aaatgacctt 3180
cggcgctaca taatcaatgc gatcggcaat attgataagc cgagacgggg tgttgagctc 3240
tcaaagctct cacttttgag aattatatct aatgaaacca aacaggaccg aatcgacttt 3300
cgcaagagga ttatggagac gacgaaggaa gacttctata aattcgctga cttgcttgaa 3360
aagaagattg cagaatttga aaagaatatt gttattatca catctaagga aaaagcctca 3420
gaatacagca ctaacgtaga ccaggatttt aagcagattc atatcgagta g 3471

<210> SEQ ID NO 44
<211> LENGTH: 1154
<212> TYPE: PRT
<213> ORGANISM: Plasmodium vivax
<220> FEATURE:
<221> NAME/KEY: misc_feature
<223> OTHER INFORMATION: PvFalcilysin

<400> SEQUENCE: 44

Met Ala Lys Leu Met Arg Val Phe Gly Tyr Leu Asn Ile Ile Thr Asn
1 5 10 15

Cys Val Asn Gly Leu Leu Cys Lys Ala Glu Lys Arg Lys Tyr Asn Val
20 25 30

Phe Thr Asn Ser Phe Ile Tyr Ser Ile Ser Thr Thr Asn Leu Tyr Ser
35 40 45

Phe Thr Ala Met Met Asn Lys Ser Pro Glu Trp Val Gln Glu Lys Cys
50 55 60

Pro Glu His Lys Ser Tyr Asn Ile Leu Glu Lys Arg Phe Ser Asp Lys
65 70 75 80

Phe Gln Met Thr Tyr Thr Val Tyr Glu His Lys Lys Ala Lys Thr Gln
85 90 95

Val Ile Ala Leu Gly Ser Asn Asp Pro Leu Asp Val Glu Gln Thr Phe
100 105 110

Ala Phe Tyr Val Lys Thr Leu Thr Asn Ser Gly Lys Gly Ile Pro His
115 120 125

Ile Leu Glu His Thr Val Leu Ser Gly Ser Lys Asn Phe Asn Tyr Lys
130 135 140

Asp Ser Met Gly Leu Leu Glu Lys Gly Thr Leu Asn Thr His Leu Asn
145 150 155 160

Ala Tyr Thr Phe Asn Asp Arg Thr Val Tyr Met Ala Gly Ser Met Asn
165 170 175

Asn Arg Asp Phe Phe Asn Ile Met Ala Val Tyr Met Asp Ser Val Phe
180 185 190

Gln Pro Asn Val Leu Glu Asn Lys Phe Ile Phe Gln Thr Glu Gly Trp
195 200 205

Thr Tyr Glu Val Glu Lys Leu Lys Asp Glu Glu Lys Asn Ala Asp Val
210 215 220

Pro Lys Ile Lys Asp Tyr Lys Val Ser Tyr Asn Gly Ile Val Tyr Ser
225 230 235 240

Glu Met Lys Gly Ser Phe Ser Ser Pro Leu Gln Tyr Leu Tyr Tyr Leu
245 250 255

-continued

```
Ile Met Lys Asn Ile Phe Pro Asp Asn Val His Ser Asn Ile Ser Gly
            260                 265                 270

Gly Asp Pro Lys Glu Ile Pro Thr Leu Thr Tyr Glu Glu Phe Lys Glu
        275                 280                 285

Phe Tyr Tyr Lys Asn Tyr Asn Pro Lys Lys Ile Lys Val Ile Phe Phe
    290                 295                 300

Ser Lys Asn Asn Pro Thr Glu Leu Leu Asn Phe Val Asp Asp Tyr Leu
305                 310                 315                 320

Asn Gln Leu Asp Phe Thr Lys Tyr Arg Asp Asp Ala Val Glu Asn Val
                325                 330                 335

Asn Tyr Gln Glu Tyr Lys Lys Gly Pro Phe Tyr Val Lys Lys Lys Phe
            340                 345                 350

Ala Asp His Ser Glu Glu Lys Glu Asn Leu Val Ser Ile Ser Trp Leu
        355                 360                 365

Leu Asn Pro Lys Lys Asn Asp Leu Leu Asp Val Asp Leu Ser Leu Glu
    370                 375                 380

Ser Pro Gln Asp Tyr Phe Ala Leu Leu Ile Ile Asn Asn Leu Leu Thr
385                 390                 395                 400

His Thr Thr Glu Ser Val Leu Tyr Lys Ala Leu Ile Asp Cys Gly Leu
                405                 410                 415

Gly Asn Thr Val Ile Asp Thr Gly Leu Asp Asp Ser Leu Val Gln Phe
            420                 425                 430

Ile Phe Ser Ile Gly Leu Lys Gly Ile Lys Glu Lys Asn Glu Lys Asn
        435                 440                 445

Val Ser Leu Asp Val Val His Tyr Glu Val Glu Lys Val Val Leu Lys
    450                 455                 460

Ala Leu Gln Lys Val Val Asp Glu Gly Phe Asn Lys Ser Ala Val Glu
465                 470                 475                 480

Ala Ser Ile Asn Asn Ile Glu Phe Val Leu Lys Glu Ala Asn Leu Lys
                485                 490                 495

Thr Ser Lys Ser Val Asp Tyr Ile Phe Glu Met Ala Ser Arg Leu Asn
            500                 505                 510

Tyr Asn Arg Asp Pro Leu Leu Ile Phe Glu Phe Glu Lys His Leu Asn
        515                 520                 525

Val Val Lys Asp Lys Ile Lys Asn Glu Pro Lys Tyr Leu Glu Lys Phe
    530                 535                 540

Ile Glu Lys His Phe Ile Asn Asn Asn His Arg Ala Val Ile Leu Met
545                 550                 555                 560

Glu Gly Asp Glu Asn Tyr Gly Lys Glu Gln Glu Asp Leu Glu Lys Glu
                565                 570                 575

Thr Leu Lys Lys Lys Ile Glu Ser Leu Thr Glu Lys Glu Arg Asp Asp
            580                 585                 590

Ile Ile Val Asp Phe Glu Asn Leu Thr Lys Tyr Lys Asn Met Val Glu
        595                 600                 605

Ser Pro Glu His Leu Asp Asn Phe Pro Ile Ile Ser Ile Ser Asp Leu
    610                 615                 620

Asn Lys Glu Thr Leu Glu Ile Pro Ala Asn Ala Tyr Phe Thr Ser Thr
625                 630                 635                 640

Ala Glu Glu Asn Asn Met Glu Lys Tyr Asn Lys Val Lys Ala Ser Glu
                645                 650                 655

Asp Val Met Lys Lys Asn Met Asp His Leu Ile Asp Lys Tyr Val Leu
            660                 665                 670
```

```
Lys Gly Ala Gln Gly Gly Ala Ala Thr Asp Gly Ala Ala Lys Gln Gly
        675                 680                 685

Asp Ser Ser Asp Gly Glu Ile Pro Met Leu Val Tyr Glu Met Pro Thr
    690                 695                 700

Ser Gly Ile Leu Tyr Leu Gln Phe Ile Phe Asn Leu Asp His Leu Ser
705                 710                 715                 720

Leu Glu Glu Met Ser Tyr Leu Asn Leu Phe Lys Met Leu Ile Leu Glu
                725                 730                 735

Asn Lys Thr Met Lys Arg Ser Ser Glu Glu Phe Val Ile Leu Arg Glu
            740                 745                 750

Lys Asn Ile Gly Asn Ile Met Ala Asn Val Ala Leu Tyr Ser Ile Ser
        755                 760                 765

Asp His Leu Lys Val Thr Ser Lys Tyr Asn Ala His Gly Leu Phe Asn
    770                 775                 780

Phe Glu Met His Val Leu Ser His Lys Cys Asn Glu Ser Leu Glu Ile
785                 790                 795                 800

Ala Leu Glu Ala Leu Lys Asp Ser Asp Phe Ser Asn Lys Lys Lys Ile
                805                 810                 815

Val Glu Ile Leu Lys Arg Lys Ile Asn Gly Met Lys Thr Val Phe Ser
            820                 825                 830

Ser Lys Gly Tyr Ser Leu Leu Leu Lys Tyr Val Lys Ser Gln Met Asn
        835                 840                 845

Ala Lys Tyr Tyr Ala His Asp Leu Val Phe Gly Tyr Gly Asn Tyr Leu
    850                 855                 860

Lys Leu Gln Glu Gln Leu Lys Leu Ala Glu Ser Asp Phe Pro Gln Phe
865                 870                 875                 880

Glu Gln Ile Leu Asn Arg Ile Arg Asn Lys Ile Phe Thr Lys Lys Asn
                885                 890                 895

Leu Leu Ile Ser Val Thr Ser Asp Ala Ala Ala Leu Asp Gln Leu Phe
            900                 905                 910

Val His Ser Lys Glu Ser Leu Lys Asn Leu Leu Gly Tyr Phe Glu Glu
        915                 920                 925

Asn Asp Ala Lys Ser Gly Glu Ala Glu Thr Ile Gly Trp Asn Glu Glu
    930                 935                 940

Ile Lys Gln Ser Lys Val Ile Glu Lys Glu Gln Lys Lys Lys Glu Phe
945                 950                 955                 960

Phe Val Ile Pro Thr Phe Val Asn Ala Val Ser Met Ala Gly Met Leu
                965                 970                 975

Phe Asn Glu Lys Glu Phe Leu Asp Pro Ser Phe Ile Val Ile Val Ala
            980                 985                 990

Ala Leu Lys Asn Ser Tyr Leu Trp  Glu Thr Val Arg Gly  Leu Asn Gly
        995                 1000                 1005

Ala Tyr  Gly Val Phe Ala Asp  Ile Glu Tyr Asp Gly  Ala Val Val
    1010                 1015                 1020

Phe Leu  Ser Ala Arg Asp Pro  Asn Leu Glu Lys Thr  Leu Gln Thr
    1025                 1030                 1035

Phe Lys  Glu Ser Ala Gln Gly  Leu Arg Lys Met Ala  Asp Thr Met
    1040                 1045                 1050

Thr Lys  Asn Asp Leu Arg Arg  Tyr Ile Ile Asn Ala  Ile Gly Asn
    1055                 1060                 1065

Ile Asp  Lys Pro Arg Arg Gly  Val Glu Leu Ser Lys  Leu Ser Leu
    1070                 1075                 1080
```

```
Leu Arg  Ile Ile Ser Asn Glu  Thr Lys Gln Asp Arg  Ile Asp Phe
    1085                1090                1095

Arg Lys  Arg Ile Met Glu Thr  Thr Lys Glu Asp Phe  Tyr Lys Phe
    1100                1105                1110

Ala Asp  Leu Leu Glu Lys Lys  Ile Ala Glu Phe Glu  Lys Asn Ile
    1115                1120                1125

Val Ile  Ile Thr Ser Lys Glu  Lys Ala Ser Glu Tyr  Ser Thr Asn
    1130                1135                1140

Val Asp  Gln Asp Phe Lys Gln  Ile His Ile Glu
    1145                1150


<210> SEQ ID NO 45
<211> LENGTH: 1153
<212> TYPE: PRT
<213> ORGANISM: Plasmodium vivax
<220> FEATURE:
<221> NAME/KEY: misc_feature
<223> OTHER INFORMATION: Falcilysin

<400> SEQUENCE: 45

Met Lys Leu Met Arg Val Phe Gly Tyr Leu Asn Ile Ile Thr Asn Cys
1               5                   10                  15

Val Asn Gly Leu Leu Cys Lys Ala Glu Lys Arg Lys Tyr Asn Val Phe
            20                  25                  30

Thr Asn Ser Phe Ile Tyr Ser Ile Ser Thr Thr Asn Leu Tyr Ser Phe
        35                  40                  45

Thr Ala Met Met Asn Lys Ser Pro Glu Trp Val Gln Glu Lys Cys Pro
    50                  55                  60

Glu His Lys Ser Tyr Asn Ile Leu Glu Lys Arg Phe Ser Asp Lys Phe
65                  70                  75                  80

Gln Met Thr Tyr Thr Val Tyr Glu His Lys Lys Ala Lys Thr Gln Val
                85                  90                  95

Ile Ala Leu Gly Ser Asn Asp Pro Leu Asp Val Glu Gln Thr Phe Ala
            100                 105                 110

Phe Tyr Val Lys Thr Leu Thr Asn Ser Gly Lys Gly Ile Pro His Ile
        115                 120                 125

Leu Glu His Thr Val Leu Ser Gly Ser Lys Asn Phe Asn Tyr Lys Asp
    130                 135                 140

Ser Met Gly Leu Leu Glu Lys Gly Thr Leu Asn Thr His Leu Asn Ala
145                 150                 155                 160

Tyr Thr Phe Asn Asp Arg Thr Val Tyr Met Ala Gly Ser Met Asn Asn
                165                 170                 175

Arg Asp Phe Phe Asn Ile Met Ala Val Tyr Met Asp Ser Val Phe Gln
            180                 185                 190

Pro Asn Val Leu Glu Asn Lys Phe Ile Phe Gln Thr Glu Gly Trp Thr
        195                 200                 205

Tyr Glu Val Glu Lys Leu Lys Asp Glu Glu Lys Asn Ala Asp Val Pro
    210                 215                 220

Lys Ile Lys Asp Tyr Lys Val Ser Tyr Asn Gly Ile Val Tyr Ser Glu
225                 230                 235                 240

Met Lys Gly Ser Phe Ser Ser Pro Leu Gln Tyr Leu Tyr Tyr Leu Ile
                245                 250                 255

Met Lys Asn Ile Phe Pro Asp Asn Val His Ser Asn Ile Ser Gly Gly
            260                 265                 270

Asp Pro Lys Glu Ile Pro Thr Leu Thr Tyr Glu Glu Phe Lys Glu Phe
        275                 280                 285
```

```
Tyr Tyr Lys Asn Tyr Asn Pro Lys Lys Ile Lys Val Ile Phe Phe Ser
    290                 295                 300

Lys Asn Asn Pro Thr Glu Leu Leu Asn Phe Val Asp Asp Tyr Leu Asn
305                 310                 315                 320

Gln Leu Asp Phe Thr Lys Tyr Arg Asp Asp Ala Val Glu Asn Val Asn
                325                 330                 335

Tyr Gln Glu Tyr Lys Lys Gly Pro Phe Tyr Val Lys Lys Lys Phe Ala
            340                 345                 350

Asp His Ser Glu Glu Lys Glu Asn Leu Val Ser Ile Ser Trp Leu Leu
        355                 360                 365

Asn Pro Lys Lys Asn Asp Leu Leu Asp Val Asp Leu Ser Leu Glu Ser
    370                 375                 380

Pro Gln Asp Tyr Phe Ala Leu Leu Ile Ile Asn Asn Leu Leu Thr His
385                 390                 395                 400

Thr Thr Glu Ser Val Leu Tyr Lys Ala Leu Ile Asp Cys Gly Leu Gly
                405                 410                 415

Asn Thr Val Ile Asp Thr Gly Leu Asp Asp Ser Leu Val Gln Phe Ile
            420                 425                 430

Phe Ser Ile Gly Leu Lys Gly Ile Lys Glu Lys Asn Glu Lys Asn Val
        435                 440                 445

Ser Leu Asp Val Val His Tyr Glu Val Glu Lys Val Val Leu Lys Ala
    450                 455                 460

Leu Gln Lys Val Val Asp Glu Gly Phe Asn Lys Ser Ala Val Glu Ala
465                 470                 475                 480

Ser Ile Asn Asn Ile Glu Phe Val Leu Lys Glu Ala Asn Leu Lys Thr
                485                 490                 495

Ser Lys Ser Val Asp Tyr Ile Phe Glu Met Ala Ser Arg Leu Asn Tyr
            500                 505                 510

Asn Arg Asp Pro Leu Leu Ile Phe Glu Phe Glu Lys His Leu Asn Val
        515                 520                 525

Val Lys Asp Lys Ile Lys Asn Glu Pro Lys Tyr Leu Glu Lys Phe Ile
    530                 535                 540

Glu Lys His Phe Ile Asn Asn Asn His Arg Ala Val Ile Leu Met Glu
545                 550                 555                 560

Gly Asp Glu Asn Tyr Gly Lys Glu Gln Glu Asp Leu Glu Lys Glu Thr
                565                 570                 575

Leu Lys Lys Lys Ile Glu Ser Leu Thr Glu Lys Glu Arg Asp Asp Ile
            580                 585                 590

Ile Val Asp Phe Glu Asn Leu Thr Lys Tyr Lys Asn Met Val Glu Ser
        595                 600                 605

Pro Glu His Leu Asp Asn Phe Pro Ile Ile Ser Ile Ser Asp Leu Asn
    610                 615                 620

Lys Glu Thr Leu Glu Ile Pro Ala Asn Ala Tyr Phe Thr Ser Thr Ala
625                 630                 635                 640

Glu Glu Asn Asn Met Glu Lys Tyr Asn Lys Val Lys Ala Ser Glu Asp
                645                 650                 655

Val Met Lys Lys Asn Met Asp His Leu Ile Asp Lys Tyr Val Leu Lys
            660                 665                 670

Gly Ala Gln Gly Gly Ala Ala Thr Asp Gly Ala Ala Lys Gln Gly Asp
        675                 680                 685

Ser Ser Asp Gly Glu Ile Pro Met Leu Val Tyr Glu Met Pro Thr Ser
    690                 695                 700
```

```
Gly Ile Leu Tyr Leu Gln Phe Ile Phe Asn Leu Asp His Leu Ser Leu
705                 710                 715                 720

Glu Glu Met Ser Tyr Leu Asn Leu Phe Lys Met Leu Ile Leu Glu Asn
                725                 730                 735

Lys Thr Met Lys Arg Ser Ser Glu Glu Phe Val Ile Leu Arg Glu Lys
            740                 745                 750

Asn Ile Gly Asn Ile Met Ala Asn Val Ala Leu Tyr Ser Ile Ser Asp
        755                 760                 765

His Leu Lys Val Thr Ser Lys Tyr Asn Ala His Gly Leu Phe Asn Phe
    770                 775                 780

Glu Met His Val Leu Ser His Lys Cys Asn Glu Ser Leu Glu Ile Ala
785                 790                 795                 800

Leu Glu Ala Leu Lys Asp Ser Asp Phe Ser Asn Lys Lys Lys Ile Val
                805                 810                 815

Glu Ile Leu Lys Arg Lys Ile Asn Gly Met Lys Thr Val Phe Ser Ser
            820                 825                 830

Lys Gly Tyr Ser Leu Leu Leu Lys Tyr Val Lys Ser Gln Met Asn Ala
        835                 840                 845

Lys Tyr Tyr Ala His Asp Leu Val Phe Gly Tyr Gly Asn Tyr Leu Lys
    850                 855                 860

Leu Gln Glu Gln Leu Lys Leu Ala Glu Ser Asp Phe Pro Gln Phe Glu
865                 870                 875                 880

Gln Ile Leu Asn Arg Ile Arg Asn Lys Ile Phe Thr Lys Lys Asn Leu
                885                 890                 895

Leu Ile Ser Val Thr Ser Asp Ala Ala Ala Leu Asp Gln Leu Phe Val
            900                 905                 910

His Ser Lys Glu Ser Leu Lys Asn Leu Leu Gly Tyr Phe Glu Glu Asn
        915                 920                 925

Asp Ala Lys Ser Gly Glu Ala Glu Thr Ile Gly Trp Asn Glu Glu Ile
    930                 935                 940

Lys Gln Ser Lys Val Ile Glu Lys Glu Gln Lys Lys Lys Glu Phe Phe
945                 950                 955                 960

Val Ile Pro Thr Phe Val Asn Ala Val Ser Met Ala Gly Met Leu Phe
                965                 970                 975

Asn Glu Lys Glu Phe Leu Asp Pro Ser Phe Ile Val Ile Val Ala Ala
            980                 985                 990

Leu Lys Asn Ser Tyr Leu Trp Glu  Thr Val Arg Gly Leu  Asn Gly Ala
        995                 1000                 1005

Tyr Gly  Val Phe Ala Asp Ile  Glu Tyr Asp Gly Ala  Val Val Phe
    1010                 1015                 1020

Leu Ser  Ala Arg Asp Pro Asn  Leu Glu Lys Thr Leu  Gln Thr Phe
    1025                 1030                 1035

Lys Glu  Ser Ala Gln Gly Leu  Arg Lys Met Ala Asp  Thr Met Thr
    1040                 1045                 1050

Lys Asn  Asp Leu Arg Arg Tyr  Ile Ile Asn Ala Ile  Gly Asn Ile
    1055                 1060                 1065

Asp Lys  Pro Arg Arg Gly Val  Glu Leu Ser Lys Leu  Ser Leu Leu
    1070                 1075                 1080

Arg Ile  Ile Ser Asn Glu Thr  Lys Gln Asp Arg Ile  Asp Phe Arg
    1085                 1090                 1095

Lys Arg  Ile Met Glu Thr Thr  Lys Glu Asp Phe Tyr  Lys Phe Ala
    1100                 1105                 1110
```

```
Asp Leu  Leu Glu Lys Lys Ile  Ala Glu Phe Glu Lys  Asn Ile Val
    1115                 1120                 1125

Ile Ile  Thr Ser Lys Glu Lys  Ala Ser Glu Tyr Ser  Thr Asn Val
    1130                 1135                 1140

Asp Gln  Asp Phe Lys Gln Ile  His Ile Glu
    1145                 1150
```

<210> SEQ ID NO 46
<211> LENGTH: 1227
<212> TYPE: DNA
<213> ORGANISM: Artificial Sequence
<220> FEATURE:
<223> OTHER INFORMATION: Falcilysin, Bergheilysin-B-CO

<400> SEQUENCE: 46

```
ggatccgcca ccatggctaa actcatgaag gtcttggggt atatcaacat catcacgaat     60

tgcgtgaatg gcatactgtg taaaggcgat aagaagcgat acatgcacat gctctcccat    120

aagtgtaacg acgctctgga gattgcgctg gaagccctga aagaaagcga tttcagcaat    180

aagaagaaag tgattgaaat cctgaagagg aaaatcaatg gcatgaaaac cacgtttgcc    240

agcaaaggtc actcaatact gattaagtac gtgaagtctc ggattaatag caaatattac    300

gcttatgacc tgattcatgg gtatgacaac tatctgaagc tccaggaaca gcttaaactg    360

gcggagacaa actacgagag tctggaagcc atacttaatc gcatcaggaa gaagatcttt    420

aagcggaaca atctgatcat gaacgtgact gtcgatccag gaactattga tcagctgttt    480

gccaaatcca agaatagctt caacaacctt ctgtcatact ttgacgagaa cgagagctac    540

tgctctaaga atgactcctt caacaaagtg gtaggctgga acaaggagat tcaggagaag    600

aagctgcttg aaggagagga ggtcaagaaa gagctcttgg tcgtacccac atttgtgaac    660

agtgtctcta tgagtggagt gctgttcaac aaaggcgaat atcttgaccc ctcattcacc    720

gtaatcgttg cagccttgaa aaactcatac ctttgggaga cagttcgagg actgaatgga    780

gcttatgggg tgtttgccga catagagtat gacggtactg tcgttttcct gagtgcaaga    840

gatccgaatc tggaaaagac tctccaaacc tttcgtgaag cagcacaagg tctgcgtaaa    900

atggctgatg tgatgacaaa gaatgatctt ctgcggtata tcattaacgc tattgggacc    960

atcgatagac ctcgcagagg cgttgagttg tccaagctgt ccttctctcg cataataagc   1020

aacgaaaccg aacaggacag gattgaattc aggaaccggg tgatgaatac caagaaagag   1080

gatttctaca aatttgcgga tttgctcgaa aagaaagtca aggaatttga gaagaatgtg   1140

gtgatcatca catctaagga gaaagccaac gagtacatca acaatgttga caatgacttc   1200

aagaagatcc tcattgagta actcgag                                       1227
```

<210> SEQ ID NO 47
<211> LENGTH: 402
<212> TYPE: PRT
<213> ORGANISM: Plasmodium Berghei
<220> FEATURE:
<221> NAME/KEY: misc_feature
<223> OTHER INFORMATION: Falcilysin, Bergheilysin-B

<400> SEQUENCE: 47

```
Met Ala Lys Leu Met Lys Val Leu Gly Tyr Ile Asn Ile Ile Thr Asn
1               5                   10                  15

Cys Val Asn Gly Ile Leu Cys Lys Gly Asp Lys Lys Arg Tyr Met His
            20                  25                  30
```

Met Leu Ser His Lys Cys Asn Asp Ala Leu Glu Ile Ala Leu Glu Ala
35 40 45

Leu Lys Glu Ser Asp Phe Ser Asn Lys Lys Lys Val Ile Glu Ile Leu
50 55 60

Lys Arg Lys Ile Asn Gly Met Lys Thr Thr Phe Ala Ser Lys Gly His
65 70 75 80

Ser Ile Leu Ile Lys Tyr Val Lys Ser Arg Ile Asn Ser Lys Tyr Tyr
85 90 95

Ala Tyr Asp Leu Ile His Gly Tyr Asp Asn Tyr Leu Lys Leu Gln Glu
100 105 110

Gln Leu Lys Leu Ala Glu Thr Asn Tyr Glu Ser Leu Glu Ala Ile Leu
115 120 125

Asn Arg Ile Arg Lys Lys Ile Phe Lys Arg Asn Asn Leu Ile Met Asn
130 135 140

Val Thr Val Asp Pro Gly Thr Ile Asp Gln Leu Phe Ala Lys Ser Lys
145 150 155 160

Asn Ser Phe Asn Asn Leu Leu Ser Tyr Phe Asp Glu Asn Glu Ser Tyr
165 170 175

Cys Ser Lys Asn Asp Ser Phe Asn Lys Val Val Gly Trp Asn Lys Glu
180 185 190

Ile Gln Glu Lys Lys Leu Leu Glu Gly Glu Glu Val Lys Lys Glu Leu
195 200 205

Leu Val Val Pro Thr Phe Val Asn Ser Val Ser Met Ser Gly Val Leu
210 215 220

Phe Asn Lys Gly Glu Tyr Leu Asp Pro Ser Phe Thr Val Ile Val Ala
225 230 235 240

Ala Leu Lys Asn Ser Tyr Leu Trp Glu Thr Val Arg Gly Leu Asn Gly
245 250 255

Ala Tyr Gly Val Phe Ala Asp Ile Glu Tyr Asp Gly Thr Val Val Phe
260 265 270

Leu Ser Ala Arg Asp Pro Asn Leu Glu Lys Thr Leu Gln Thr Phe Arg
275 280 285

Glu Ala Ala Gln Gly Leu Arg Lys Met Ala Asp Val Met Thr Lys Asn
290 295 300

Asp Leu Leu Arg Tyr Ile Ile Asn Ala Ile Gly Thr Ile Asp Arg Pro
305 310 315 320

Arg Arg Gly Val Glu Leu Ser Lys Leu Ser Phe Ser Arg Ile Ile Ser
325 330 335

Asn Glu Thr Glu Gln Asp Arg Ile Glu Phe Arg Asn Arg Val Met Asn
340 345 350

Thr Lys Lys Glu Asp Phe Tyr Lys Phe Ala Asp Leu Leu Glu Lys Lys
355 360 365

Val Lys Glu Phe Glu Lys Asn Val Val Ile Ile Thr Ser Lys Glu Lys
370 375 380

Ala Asn Glu Tyr Ile Asn Asn Val Asp Asn Asp Phe Lys Lys Ile Leu
385 390 395 400

Ile Glu

<210> SEQ ID NO 48
<211> LENGTH: 2454
<212> TYPE: DNA
<213> ORGANISM: Plasmodium Berghei
<220> FEATURE:
<221> NAME/KEY: misc_feature
<223> OTHER INFORMATION: perforin like protein 1 (SPECT2)

<400> SEQUENCE: 48

```
ggatccgcca ccatggctaa gatgcggaac attaagaaat cacttccggt gctcttcatt     60
ctcttgtgca tttatcagca gtactttata aactctctcc gtatttccgt ccgcaacaat    120
aagaaccaca gggatgaaaa caaattcaac aagaatatgg agcttggtac gatggagaaa    180
cccatcaaca ttctttgcaa tgacgtcagc tgtaacacag agaataacat ttctttcgta    240
aaccagaaga aaaaggaaat agatagtgac agcgacctct ataacatgtt cgatgacgac    300
gcctctacct ccgctggtga tgacgaagat gactatgacg actacacaga tgataagaac    360
gctgagatca aagatgaaga gcaaaatgag cacatcgaca agatcgacca gaagaaggat    420
aagaaacgca cattctctat caataagcag gaggaagaaa tcaacgaaaa taaaaacaaa    480
acggagaaat tcttcaagaa atacaagttt aacgacgcca actcagaagg ggacgacgat    540
gagtcagaca ccgatgacga gaatttggac aactccacgg agaacagcta cgaggaaaac    600
aagaatcccg agaacgttat cgacaagcat atggccgtat ttcctgggct ctattttgtg    660
gggatcggct acgatattct gttcgggaat cctctcggag aaaccgattc tctgagcgac    720
cctggttata gagcacagat ttacctgttg aattgggaat tctcaaacca tggcatcgcc    780
aacgatctgc acacgctcca accaattaat gcctggattc ggaaagagaa tgcatgctca    840
cgagttgaat ccatcaacga atgttcctct gttagtgagt atacaaagaa tctgtcagtg    900
gacgtaagtg tatcaggcag ctatatgggc ttcggcagtt tctccgctag cactgggtac    960
aagaaattca ttaacgagat aagcaagaga acatccaaga cctactttat aaagagcaac   1020
tgcatcaagt ataccatcgg acttccacct tatgtgccat gggagcatac cactgcttac   1080
atgaatgcgg tgaatattct gccaaaggaa tttaccggcc tggatggaga cagcgaatgc   1140
acaccggatg tttacgagca gaagaagatg actaaacagt gtaagaacgt gcaactgtgg   1200
attcagttct ttaagaccta tggtacacac ataatcgtgg aggctcaatt gggagggaaa   1260
ataaccaaaa tcatcaatgt ctctaacaca agcgtgaacc agatgaagaa ggatggcgtc   1320
agtgtgaaag cccagatcca ggctcagttt ggttttgcaa gtgtgggcgg tagtacaagc   1380
gtgtcaagtg acaatagcac taagaacgac aatagcagct acgacatgtc tgagaaactc   1440
gtggttatcg gagggaatcc tataaaagac gtcaccaaag aggagaatct gtacgaatgg   1500
agcaaaacag tgtcctctaa ccccatgcct atccacatca agctgctgcc aatctataag   1560
tccttcgata gtgaggaact gaaagagtct tacgagaaag cggttctcta ctacaccagg   1620
ctttatggca gctctcccca cggaactatt cagaaagatg agaacgacat catcaaaatc   1680
ttgacggcca gtaccaccat cactaaaatt ggtgctccac ccataacagc ggaatgtcca   1740
cataatcaag tggtgctgtt tgggtatgtc ctgaagcaga acttctggga caacacctcc   1800
aacctgaagg gatacgacat tgagatctgt gaggctggac tgaatagttg cacgtccaaa   1860
cagggaagta caaacaagta cgatgtgagc tatctgtaca ttgaatgtgg cacacaggca   1920
atgtcattct ccgatcaagt cataaccgca tccaacacta cttacaatac catcaagtgt   1980
cccaatgact acactattat ctttggattc gggttttcct ctagctccgg taagggagtt   2040
tctgccatgc acacccacat tacatcctgt agacccggca tgaaaagctg ctccctgaat   2100
atgggcaaca gcaatgacaa gaactacatg tacctggtgt gcgtcgatgc cacaatctgg   2160
tctggcatta atgagctgac tattgtggcc aaagatgatt ttcacggcgc agtgaatagg   2220
tctaagcagt tcaatgatgg cgaattggta ctgtcctgtc aggaaaatgg cactatcctg   2280
```

```
acagggttca ctggggagac tcatacctct agcccgtatg tcaagagccc ttttagcaag   2340

tgtcttaaat cactgaagag ctgctcagtc catgggagtg gacaatctat cggatatacc   2400

aactataagt cactgttttc catcatactg tgcaagaacg gtgagtgact cgag         2454


<210> SEQ ID NO 49
<211> LENGTH: 811
<212> TYPE: PRT
<213> ORGANISM: Plasmodium Berghei
<220> FEATURE:
<221> NAME/KEY: misc_feature
<223> OTHER INFORMATION: perforin like protein 1 (SPECT2)

<400> SEQUENCE: 49

Met Ala Lys Met Arg Asn Ile Lys Lys Ser Leu Pro Val Leu Phe Ile
1               5                   10                  15

Leu Leu Cys Ile Tyr Gln Gln Tyr Phe Ile Asn Ser Leu Arg Ile Ser
            20                  25                  30

Val Arg Asn Asn Lys Asn His Arg Asp Glu Asn Lys Phe Asn Lys Asn
        35                  40                  45

Met Glu Leu Gly Thr Met Glu Lys Pro Ile Asn Ile Leu Cys Asn Asp
    50                  55                  60

Val Ser Cys Asn Thr Glu Asn Asn Ile Ser Phe Val Asn Gln Lys Lys
65                  70                  75                  80

Lys Glu Ile Asp Ser Asp Ser Asp Leu Tyr Asn Met Phe Asp Asp Asp
                85                  90                  95

Ala Ser Thr Ser Ala Gly Asp Asp Glu Asp Asp Tyr Asp Asp Tyr Thr
            100                 105                 110

Asp Asp Lys Asn Ala Glu Ile Lys Asp Glu Glu Gln Asn Glu His Ile
        115                 120                 125

Asp Lys Ile Asp Gln Lys Lys Asp Lys Lys Arg Thr Phe Ser Ile Asn
    130                 135                 140

Lys Gln Glu Glu Glu Ile Asn Glu Asn Lys Asn Lys Thr Glu Lys Phe
145                 150                 155                 160

Phe Lys Lys Tyr Lys Phe Asn Asp Ala Asn Ser Glu Gly Asp Asp Asp
                165                 170                 175

Glu Ser Asp Thr Asp Asp Glu Asn Leu Asp Asn Ser Thr Glu Asn Ser
            180                 185                 190

Tyr Glu Glu Asn Lys Asn Pro Glu Asn Val Ile Asp Lys His Met Ala
        195                 200                 205

Val Phe Pro Gly Leu Tyr Phe Val Gly Ile Gly Tyr Asp Ile Leu Phe
    210                 215                 220

Gly Asn Pro Leu Gly Glu Thr Asp Ser Leu Ser Asp Pro Gly Tyr Arg
225                 230                 235                 240

Ala Gln Ile Tyr Leu Leu Asn Trp Glu Phe Ser Asn His Gly Ile Ala
                245                 250                 255

Asn Asp Leu His Thr Leu Gln Pro Ile Asn Ala Trp Ile Arg Lys Glu
            260                 265                 270

Asn Ala Cys Ser Arg Val Glu Ser Ile Asn Glu Cys Ser Ser Val Ser
        275                 280                 285

Glu Tyr Thr Lys Asn Leu Ser Val Asp Val Ser Val Ser Gly Ser Tyr
    290                 295                 300

Met Gly Phe Gly Ser Phe Ser Ala Ser Thr Gly Tyr Lys Lys Phe Ile
305                 310                 315                 320

Asn Glu Ile Ser Lys Arg Thr Ser Lys Thr Tyr Phe Ile Lys Ser Asn
                325                 330                 335
```

```
Cys Ile Lys Tyr Thr Ile Gly Leu Pro Pro Tyr Val Pro Trp Glu His
            340                 345                 350

Thr Thr Ala Tyr Met Asn Ala Val Asn Ile Leu Pro Lys Glu Phe Thr
        355                 360                 365

Gly Leu Asp Gly Asp Ser Glu Cys Thr Pro Asp Val Tyr Glu Gln Lys
    370                 375                 380

Lys Met Thr Lys Gln Cys Lys Asn Val Gln Leu Trp Ile Gln Phe Phe
385                 390                 395                 400

Lys Thr Tyr Gly Thr His Ile Ile Val Glu Ala Gln Leu Gly Gly Lys
                405                 410                 415

Ile Thr Lys Ile Ile Asn Val Ser Asn Thr Ser Val Asn Gln Met Lys
            420                 425                 430

Lys Asp Gly Val Ser Val Lys Ala Gln Ile Gln Ala Gln Phe Gly Phe
        435                 440                 445

Ala Ser Val Gly Gly Ser Thr Ser Val Ser Ser Asp Asn Ser Thr Lys
    450                 455                 460

Asn Asp Asn Ser Ser Tyr Asp Met Ser Glu Lys Leu Val Val Ile Gly
465                 470                 475                 480

Gly Asn Pro Ile Lys Asp Val Thr Lys Glu Glu Asn Leu Tyr Glu Trp
                485                 490                 495

Ser Lys Thr Val Ser Ser Asn Pro Met Pro Ile His Ile Lys Leu Leu
            500                 505                 510

Pro Ile Tyr Lys Ser Phe Asp Ser Glu Glu Leu Lys Glu Ser Tyr Glu
        515                 520                 525

Lys Ala Val Leu Tyr Tyr Thr Arg Leu Tyr Gly Ser Ser Pro His Gly
    530                 535                 540

Thr Ile Gln Lys Asp Glu Asn Asp Ile Ile Lys Ile Leu Thr Ala Ser
545                 550                 555                 560

Thr Thr Ile Thr Lys Ile Gly Ala Pro Pro Ile Thr Ala Glu Cys Pro
                565                 570                 575

His Asn Gln Val Val Leu Phe Gly Tyr Val Leu Lys Gln Asn Phe Trp
            580                 585                 590

Asp Asn Thr Ser Asn Leu Lys Gly Tyr Asp Ile Glu Ile Cys Glu Ala
        595                 600                 605

Gly Leu Asn Ser Cys Thr Ser Lys Gln Gly Ser Thr Asn Lys Tyr Asp
    610                 615                 620

Val Ser Tyr Leu Tyr Ile Glu Cys Gly Thr Gln Ala Met Ser Phe Ser
625                 630                 635                 640

Asp Gln Val Ile Thr Ala Ser Asn Thr Thr Tyr Asn Thr Ile Lys Cys
                645                 650                 655

Pro Asn Asp Tyr Thr Ile Ile Phe Gly Phe Gly Phe Ser Ser Ser Ser
            660                 665                 670

Gly Lys Gly Val Ser Ala Met His Thr His Ile Thr Ser Cys Arg Pro
        675                 680                 685

Gly Met Lys Ser Cys Ser Leu Asn Met Gly Asn Ser Asn Asp Lys Asn
    690                 695                 700

Tyr Met Tyr Leu Val Cys Val Asp Ala Thr Ile Trp Ser Gly Ile Asn
705                 710                 715                 720

Glu Leu Thr Ile Val Ala Lys Asp Asp Phe His Gly Ala Val Asn Arg
                725                 730                 735

Ser Lys Gln Phe Asn Asp Gly Glu Leu Val Leu Ser Cys Gln Glu Asn
            740                 745                 750
```

```
Gly Thr Ile Leu Thr Gly Phe Thr Gly Glu Thr His Thr Ser Ser Pro
        755                 760                 765

Tyr Val Lys Ser Pro Phe Ser Lys Cys Leu Lys Ser Leu Lys Ser Cys
    770                 775                 780

Ser Val His Gly Ser Gly Gln Ser Ile Gly Tyr Thr Asn Tyr Lys Ser
785                 790                 795                 800

Leu Phe Ser Ile Ile Leu Cys Lys Asn Gly Glu
                805                 810


<210> SEQ ID NO 50
<211> LENGTH: 810
<212> TYPE: PRT
<213> ORGANISM: Plasmodium berghei
<220> FEATURE:
<221> NAME/KEY: misc_feature
<223> OTHER INFORMATION: SPECT2

<400> SEQUENCE: 50

Met Lys Met Arg Asn Ile Lys Lys Ser Leu Pro Val Leu Phe Ile Leu
1               5                   10                  15

Leu Cys Ile Tyr Gln Gln Tyr Phe Ile Asn Ser Leu Arg Ile Ser Val
            20                  25                  30

Arg Asn Asn Lys Asn His Arg Asp Glu Asn Lys Phe Asn Lys Asn Met
        35                  40                  45

Glu Leu Gly Thr Met Glu Lys Pro Ile Asn Ile Leu Cys Asn Asp Val
    50                  55                  60

Ser Cys Asn Thr Glu Asn Asn Ile Ser Phe Val Asn Gln Lys Lys Lys
65                  70                  75                  80

Glu Ile Asp Ser Asp Ser Asp Leu Tyr Asn Met Phe Asp Asp Asp Ala
                85                  90                  95

Ser Thr Ser Ala Gly Asp Asp Glu Asp Asp Tyr Asp Asp Tyr Thr Asp
            100                 105                 110

Asp Lys Asn Ala Glu Ile Lys Asp Glu Glu Gln Asn Glu His Ile Asp
        115                 120                 125

Lys Ile Asp Gln Lys Lys Asp Lys Lys Arg Thr Phe Ser Ile Asn Lys
    130                 135                 140

Gln Glu Glu Glu Ile Asn Glu Asn Lys Asn Lys Thr Glu Lys Phe Phe
145                 150                 155                 160

Lys Lys Tyr Lys Phe Asn Asp Ala Asn Ser Glu Gly Asp Asp Asp Glu
                165                 170                 175

Ser Asp Thr Asp Asp Glu Asn Leu Asp Asn Ser Thr Glu Asn Ser Tyr
            180                 185                 190

Glu Glu Asn Lys Asn Pro Glu Asn Val Ile Asp Lys His Met Ala Val
        195                 200                 205

Phe Pro Gly Leu Tyr Phe Val Gly Ile Gly Tyr Asp Ile Leu Phe Gly
    210                 215                 220

Asn Pro Leu Gly Glu Thr Asp Ser Leu Ser Asp Pro Gly Tyr Arg Ala
225                 230                 235                 240

Gln Ile Tyr Leu Leu Asn Trp Glu Phe Ser Asn His Gly Ile Ala Asn
                245                 250                 255

Asp Leu His Thr Leu Gln Pro Ile Asn Ala Trp Ile Arg Lys Glu Asn
            260                 265                 270

Ala Cys Ser Arg Val Glu Ser Ile Asn Glu Cys Ser Ser Val Ser Glu
        275                 280                 285

Tyr Thr Lys Asn Leu Ser Val Asp Val Ser Val Ser Gly Ser Tyr Met
    290                 295                 300
```

```
Gly Phe Gly Ser Phe Ser Ala Ser Thr Gly Tyr Lys Lys Phe Ile Asn
305                 310                 315                 320

Glu Ile Ser Lys Arg Thr Ser Lys Thr Tyr Phe Ile Lys Ser Asn Cys
                325                 330                 335

Ile Lys Tyr Thr Ile Gly Leu Pro Pro Tyr Val Pro Trp Glu His Thr
            340                 345                 350

Thr Ala Tyr Met Asn Ala Val Asn Ile Leu Pro Lys Glu Phe Thr Gly
        355                 360                 365

Leu Asp Gly Asp Ser Glu Cys Thr Pro Asp Val Tyr Glu Gln Lys Lys
    370                 375                 380

Met Thr Lys Gln Cys Lys Asn Val Gln Leu Trp Ile Gln Phe Phe Lys
385                 390                 395                 400

Thr Tyr Gly Thr His Ile Ile Val Glu Ala Gln Leu Gly Gly Lys Ile
                405                 410                 415

Thr Lys Ile Ile Asn Val Ser Asn Thr Ser Val Asn Gln Met Lys Lys
            420                 425                 430

Asp Gly Val Ser Val Lys Ala Gln Ile Gln Ala Gln Phe Gly Phe Ala
        435                 440                 445

Ser Val Gly Gly Ser Thr Ser Val Ser Ser Asp Asn Ser Thr Lys Asn
    450                 455                 460

Asp Asn Ser Ser Tyr Asp Met Ser Glu Lys Leu Val Val Ile Gly Gly
465                 470                 475                 480

Asn Pro Ile Lys Asp Val Thr Lys Glu Glu Asn Leu Tyr Glu Trp Ser
                485                 490                 495

Lys Thr Val Ser Ser Asn Pro Met Pro Ile His Ile Lys Leu Leu Pro
            500                 505                 510

Ile Tyr Lys Ser Phe Asp Ser Glu Glu Leu Lys Glu Ser Tyr Glu Lys
        515                 520                 525

Ala Val Leu Tyr Tyr Thr Arg Leu Tyr Gly Ser Ser Pro His Gly Thr
    530                 535                 540

Ile Gln Lys Asp Glu Asn Asp Ile Ile Lys Ile Leu Thr Ala Ser Thr
545                 550                 555                 560

Thr Ile Thr Lys Ile Gly Ala Pro Pro Ile Thr Ala Glu Cys Pro His
                565                 570                 575

Asn Gln Val Val Leu Phe Gly Tyr Val Leu Lys Gln Asn Phe Trp Asp
            580                 585                 590

Asn Thr Ser Asn Leu Lys Gly Tyr Asp Ile Glu Ile Cys Glu Ala Gly
        595                 600                 605

Leu Asn Ser Cys Thr Ser Lys Gln Gly Ser Thr Asn Lys Tyr Asp Val
    610                 615                 620

Ser Tyr Leu Tyr Ile Glu Cys Gly Thr Gln Ala Met Ser Phe Ser Asp
625                 630                 635                 640

Gln Val Ile Thr Ala Ser Asn Thr Thr Tyr Asn Thr Ile Lys Cys Pro
                645                 650                 655

Asn Asp Tyr Thr Ile Ile Phe Gly Phe Gly Phe Ser Ser Ser Ser Gly
            660                 665                 670

Lys Gly Val Ser Ala Met His Thr His Ile Thr Ser Cys Arg Pro Gly
        675                 680                 685

Met Lys Ser Cys Ser Leu Asn Met Gly Asn Ser Asn Asp Lys Asn Tyr
    690                 695                 700

Met Tyr Leu Val Cys Val Asp Ala Thr Ile Trp Ser Gly Ile Asn Glu
705                 710                 715                 720
```

```
Leu Thr Ile Val Ala Lys Asp Asp Phe His Gly Ala Val Asn Arg Ser
                725                 730                 735

Lys Gln Phe Asn Asp Gly Glu Leu Val Leu Ser Cys Gln Glu Asn Gly
            740                 745                 750

Thr Ile Leu Thr Gly Phe Thr Gly Glu Thr His Thr Ser Ser Pro Tyr
        755                 760                 765

Val Lys Ser Pro Phe Ser Lys Cys Leu Lys Ser Leu Lys Ser Cys Ser
    770                 775                 780

Val His Gly Ser Gly Gln Ser Ile Gly Tyr Thr Asn Tyr Lys Ser Leu
785                 790                 795                 800

Phe Ser Ile Ile Leu Cys Lys Asn Gly Glu
                805                 810


<210> SEQ ID NO 51
<211> LENGTH: 2538
<212> TYPE: DNA
<213> ORGANISM: Artificial Sequence
<220> FEATURE:
<223> OTHER INFORMATION: PfSPECT2 human CO

<400> SEQUENCE: 51

gccaccatgg ctaagctgag aatcctcaag aagcactatt atgtcgtgtt tatccttctg     60

tatctgtatg acatcagctg cttcaagtgc attcggctga acaaccgttc catctacaag    120

aacaagtaca agaataacgt gcacatagga accaatgaga atatcaggag tattgagaag    180

tatagcaacg tgctgtgtaa cagcatcttg tgtaagaacg ataaaatctc tagcttcatt    240

aaccagagga agaatgtgga tgacgacgat gagtctgaga acgatgacat gtacgagagc    300

accacagctg gctcttctag tgaaacggac aacgagagcg atgaagaaga gaatgacagc    360

agtgacaaca ataatagcga tgaggaacag atagagaact ccaacaacaa taattctgac    420

gaggaacaga atgactcctc ttccaacgac aataatgatg aggagaatga ggaacaggac    480

gacgtcatgg acaatgacca aaacgataag aagatcaagc atagcttcaa tctcgccaac    540

gagagtaaac acactaaaga ggaacgagtg aaagaagaga aaaagctgaa gatctatgac    600

ttcataaacg acaaggagaa aagacttaac tttaatggcg atcagaaaga tgaagataac    660

gaggagaacg atgataaaga tgagaacacg cttgagaatc ggaatatcat ctccaaacac    720

acttcagtgt ttcctggcct gtacttcatc gggattgggt ataacctcct cttcgggaac    780

cccttgggtg aagctgattc ccttatcgat ccaggttatc gggcgcaaat ttacctgatg    840

gaatgggctc tcagcaagga aggcattgcc aacgacctga gcactctgca acccgtgaat    900

ggatggatac gaaaggagaa tgcctgctcc agagttgaat ctattacaga atgcagctct    960

atatctgact acaccaaatc cctgtcagcg gaggcaaagg ttagtggctc ttattgggga   1020

atcgcctcct tctcagcatc caccgggtat agctcttttc tccacgaggt gacaaaacgc   1080

agcaagaaaa ccttcctcgt gaaatccaac tgtgtgaaat acactatcgg gcttcctccc   1140

tatattccct gggacaagac cacggcctac aagaatgccg taaatgaact gccagctgta   1200

tttaccggtt tggataaaga atccgaatgt ccctctgatg tgtacgaaga gaacaagaca   1260

aaatcaaact gcgagaacgt gagtctgtgg atgaagttct tcgacattta tggcactcac   1320

atcatttatg aaagtcaatt gggaggaaag ataacaaaga ttatcaatgt ttccacctca   1380

agtattgagc agatgaagaa aaatggagtc tcagtcaaag cgaaaattca agcacagttt   1440

gggtttggtt cagccggtgg ctcaaccgac gtgaatagca gtaactcctc cgcaaatgat   1500

gagcagtctt acgacatgaa tgaacagctg atcgtcatag gagggaatcc gatcaaagac   1560
```

```
gtcaccaagg aggagaatct gtttgagtgg tctaaaactg tgacaaacca tcctatgccg   1620

atcaacatta aactgactcc cattagcgac agttttgact cagacgacct gaaagaatcc   1680

tatgataaag ccatcatcta ctattctcgc ctgtacggac tgtcccctca tgacacaatg   1740

cagaaggatg acaaggatat tatcaagatc ctgaccaacg ctgatacggt taccaagaac   1800

tcagctcctc caatcaacgc tcagtgtcct catgggaaag tcgttatgtt cggattcagc   1860

ctgaagcaga atttctggga caacaccaac gcactcaaag gatacaacat cgaagtctgc   1920

gaagcaggga gcaattcttg cactagcaaa caagggagca gcaataaata cgatacatct   1980

tacctttaca tggaatgtgg cgatcagcca ttgcccttta gcgagcaggt gattagcgag   2040

agtacaagta cctataatac cgtgaaatgt ccgaatgatt actccattct cctgggcttc   2100

ggaatatcaa gtagctcagg gaggataaat agcgctgaat atgtctacag cacaccatgt   2160

attcccggca tgaagtcctg cagcctcaat atgaataatg acaaccagaa gtcatacatc   2220

tacgtgctgt gtgtagatac tacgatctgg agtggcgtga acaacctgag cctggttgcc   2280

cttgatggcg cacatggtaa ggtaaaccgc agtaagaagt actccgacgg tgaactggtt   2340

ggcacctgtc cactggacgg cacagtcctg actggattta aggttgagtt tcacacttca   2400

tctccatatg tgcagacacc tttcgagaaa tgcgccaaaa gcttgaaagc ctgctccgta   2460

catggctccg gtcacgccat tggcattcag aactttaagt cactgttcat atacatgttg   2520

tgcaagaaca ataagtaa                                                 2538
```

```
<210> SEQ ID NO 52
<211> LENGTH: 843
<212> TYPE: PRT
<213> ORGANISM: Plasmodium falciparum
<220> FEATURE:
<221> NAME/KEY: misc_feature
<223> OTHER INFORMATION: PfSPECT2

<400> SEQUENCE: 52

Met Ala Lys Leu Arg Ile Leu Lys Lys His Tyr Tyr Val Val Phe Ile
1               5                   10                  15

Leu Leu Tyr Leu Tyr Asp Ile Ser Cys Phe Lys Cys Ile Arg Leu Asn
            20                  25                  30

Asn Arg Ser Ile Tyr Lys Asn Lys Tyr Lys Asn Asn Val His Ile Gly
        35                  40                  45

Thr Asn Glu Asn Ile Arg Ser Ile Glu Lys Tyr Ser Asn Val Leu Cys
    50                  55                  60

Asn Ser Ile Leu Cys Lys Asn Asp Lys Ile Ser Ser Phe Ile Asn Gln
65                  70                  75                  80

Arg Lys Asn Val Asp Asp Asp Asp Glu Ser Glu Asn Asp Asp Met Tyr
                85                  90                  95

Glu Ser Thr Thr Ala Gly Ser Ser Ser Glu Thr Asp Asn Glu Ser Asp
            100                 105                 110

Glu Glu Glu Asn Asp Ser Ser Asp Asn Asn Asn Ser Asp Glu Glu Gln
        115                 120                 125

Ile Glu Asn Ser Asn Asn Asn Asn Ser Asp Glu Glu Gln Asn Asp Ser
    130                 135                 140

Ser Ser Asn Asp Asn Asn Asp Glu Glu Asn Glu Glu Gln Asp Asp Val
145                 150                 155                 160

Met Asp Asn Asp Gln Asn Asp Lys Lys Ile Lys His Ser Phe Asn Leu
                165                 170                 175
```

```
Ala Asn Glu Ser Lys His Thr Lys Glu Glu Arg Val Lys Glu Glu Lys
            180                 185                 190

Lys Leu Lys Ile Tyr Asp Phe Ile Asn Asp Lys Glu Lys Arg Leu Asn
        195                 200                 205

Phe Asn Gly Asp Gln Lys Asp Glu Asp Asn Glu Glu Asn Asp Asp Lys
    210                 215                 220

Asp Glu Asn Thr Leu Glu Asn Arg Asn Ile Ile Ser Lys His Thr Ser
225                 230                 235                 240

Val Phe Pro Gly Leu Tyr Phe Ile Gly Ile Gly Tyr Asn Leu Leu Phe
                245                 250                 255

Gly Asn Pro Leu Gly Glu Ala Asp Ser Leu Ile Asp Pro Gly Tyr Arg
            260                 265                 270

Ala Gln Ile Tyr Leu Met Glu Trp Ala Leu Ser Lys Glu Gly Ile Ala
        275                 280                 285

Asn Asp Leu Ser Thr Leu Gln Pro Val Asn Gly Trp Ile Arg Lys Glu
    290                 295                 300

Asn Ala Cys Ser Arg Val Glu Ser Ile Thr Glu Cys Ser Ser Ile Ser
305                 310                 315                 320

Asp Tyr Thr Lys Ser Leu Ser Ala Glu Ala Lys Val Ser Gly Ser Tyr
                325                 330                 335

Trp Gly Ile Ala Ser Phe Ser Ala Ser Thr Gly Tyr Ser Ser Phe Leu
            340                 345                 350

His Glu Val Thr Lys Arg Ser Lys Lys Thr Phe Leu Val Lys Ser Asn
        355                 360                 365

Cys Val Lys Tyr Thr Ile Gly Leu Pro Pro Tyr Ile Pro Trp Asp Lys
    370                 375                 380

Thr Thr Ala Tyr Lys Asn Ala Val Asn Glu Leu Pro Ala Val Phe Thr
385                 390                 395                 400

Gly Leu Asp Lys Glu Ser Glu Cys Pro Ser Asp Val Tyr Glu Glu Asn
                405                 410                 415

Lys Thr Lys Ser Asn Cys Glu Asn Val Ser Leu Trp Met Lys Phe Phe
            420                 425                 430

Asp Ile Tyr Gly Thr His Ile Ile Tyr Glu Ser Gln Leu Gly Gly Lys
        435                 440                 445

Ile Thr Lys Ile Ile Asn Val Ser Thr Ser Ser Ile Glu Gln Met Lys
    450                 455                 460

Lys Asn Gly Val Ser Val Lys Ala Lys Ile Gln Ala Gln Phe Gly Phe
465                 470                 475                 480

Gly Ser Ala Gly Gly Ser Thr Asp Val Asn Ser Ser Asn Ser Ser Ala
                485                 490                 495

Asn Asp Glu Gln Ser Tyr Asp Met Asn Glu Gln Leu Ile Val Ile Gly
            500                 505                 510

Gly Asn Pro Ile Lys Asp Val Thr Lys Glu Glu Asn Leu Phe Glu Trp
        515                 520                 525

Ser Lys Thr Val Thr Asn His Pro Met Pro Ile Asn Ile Lys Leu Thr
    530                 535                 540

Pro Ile Ser Asp Ser Phe Asp Ser Asp Asp Leu Lys Glu Ser Tyr Asp
545                 550                 555                 560

Lys Ala Ile Ile Tyr Tyr Ser Arg Leu Tyr Gly Leu Ser Pro His Asp
                565                 570                 575

Thr Met Gln Lys Asp Asp Lys Asp Ile Ile Lys Ile Leu Thr Asn Ala
            580                 585                 590
```

Asp Thr Val Thr Lys Asn Ser Ala Pro Pro Ile Asn Ala Gln Cys Pro
595 600 605

His Gly Lys Val Val Met Phe Gly Phe Ser Leu Lys Gln Asn Phe Trp
610 615 620

Asp Asn Thr Asn Ala Leu Lys Gly Tyr Asn Ile Glu Val Cys Glu Ala
625 630 635 640

Gly Ser Asn Ser Cys Thr Ser Lys Gln Gly Ser Ser Asn Lys Tyr Asp
645 650 655

Thr Ser Tyr Leu Tyr Met Glu Cys Gly Asp Gln Pro Leu Pro Phe Ser
660 665 670

Glu Gln Val Ile Ser Glu Ser Thr Ser Thr Tyr Asn Thr Val Lys Cys
675 680 685

Pro Asn Asp Tyr Ser Ile Leu Leu Gly Phe Gly Ile Ser Ser Ser Ser
690 695 700

Gly Arg Ile Asn Ser Ala Glu Tyr Val Tyr Ser Thr Pro Cys Ile Pro
705 710 715 720

Gly Met Lys Ser Cys Ser Leu Asn Met Asn Asn Asp Asn Gln Lys Ser
725 730 735

Tyr Ile Tyr Val Leu Cys Val Asp Thr Thr Ile Trp Ser Gly Val Asn
740 745 750

Asn Leu Ser Leu Val Ala Leu Asp Gly Ala His Gly Lys Val Asn Arg
755 760 765

Ser Lys Lys Tyr Ser Asp Gly Glu Leu Val Gly Thr Cys Pro Leu Asp
770 775 780

Gly Thr Val Leu Thr Gly Phe Lys Val Glu Phe His Thr Ser Ser Pro
785 790 795 800

Tyr Val Gln Thr Pro Phe Glu Lys Cys Ala Lys Ser Leu Lys Ala Cys
805 810 815

Ser Val His Gly Ser Gly His Ala Ile Gly Ile Gln Asn Phe Lys Ser
820 825 830

Leu Phe Ile Tyr Met Leu Cys Lys Asn Asn Lys
835 840

<210> SEQ ID NO 53
<211> LENGTH: 842
<212> TYPE: PRT
<213> ORGANISM: Plasmodium falciparum
<220> FEATURE:
<221> NAME/KEY: misc_feature
<223> OTHER INFORMATION: SPECT2

<400> SEQUENCE: 53

Met Lys Leu Arg Ile Leu Lys Lys His Tyr Tyr Val Val Phe Ile Leu
1 5 10 15

Leu Tyr Leu Tyr Asp Ile Ser Cys Phe Lys Cys Ile Arg Leu Asn Asn
20 25 30

Arg Ser Ile Tyr Lys Asn Lys Tyr Lys Asn Asn Val His Ile Gly Thr
35 40 45

Asn Glu Asn Ile Arg Ser Ile Glu Lys Tyr Ser Asn Val Leu Cys Asn
50 55 60

Ser Ile Leu Cys Lys Asn Asp Lys Ile Ser Ser Phe Ile Asn Gln Arg
65 70 75 80

Lys Asn Val Asp Asp Asp Asp Glu Ser Glu Asn Asp Asp Met Tyr Glu
85 90 95

```
Ser Thr Thr Ala Gly Ser Ser Ser Glu Thr Asp Asn Glu Ser Asp Glu
            100                 105                 110

Glu Glu Asn Asp Ser Ser Asp Asn Asn Asn Ser Asp Glu Glu Gln Ile
        115                 120                 125

Glu Asn Ser Asn Asn Asn Asn Ser Asp Glu Glu Gln Asn Asp Ser Ser
    130                 135                 140

Ser Asn Asp Asn Asn Asp Glu Glu Asn Glu Glu Gln Asp Asp Val Met
145                 150                 155                 160

Asp Asn Asp Gln Asn Asp Lys Lys Ile Lys His Ser Phe Asn Leu Ala
                165                 170                 175

Asn Glu Ser Lys His Thr Lys Glu Glu Arg Val Lys Glu Glu Lys Lys
            180                 185                 190

Leu Lys Ile Tyr Asp Phe Ile Asn Asp Lys Glu Lys Arg Leu Asn Phe
        195                 200                 205

Asn Gly Asp Gln Lys Asp Glu Asp Asn Glu Glu Asn Asp Asp Lys Asp
    210                 215                 220

Glu Asn Thr Leu Glu Asn Arg Asn Ile Ile Ser Lys His Thr Ser Val
225                 230                 235                 240

Phe Pro Gly Leu Tyr Phe Ile Gly Ile Gly Tyr Asn Leu Leu Phe Gly
                245                 250                 255

Asn Pro Leu Gly Glu Ala Asp Ser Leu Ile Asp Pro Gly Tyr Arg Ala
            260                 265                 270

Gln Ile Tyr Leu Met Glu Trp Ala Leu Ser Lys Glu Gly Ile Ala Asn
        275                 280                 285

Asp Leu Ser Thr Leu Gln Pro Val Asn Gly Trp Ile Arg Lys Glu Asn
    290                 295                 300

Ala Cys Ser Arg Val Glu Ser Ile Thr Glu Cys Ser Ser Ile Ser Asp
305                 310                 315                 320

Tyr Thr Lys Ser Leu Ser Ala Glu Ala Lys Val Ser Gly Ser Tyr Trp
                325                 330                 335

Gly Ile Ala Ser Phe Ser Ala Ser Thr Gly Tyr Ser Ser Phe Leu His
            340                 345                 350

Glu Val Thr Lys Arg Ser Lys Lys Thr Phe Leu Val Lys Ser Asn Cys
        355                 360                 365

Val Lys Tyr Thr Ile Gly Leu Pro Pro Tyr Ile Pro Trp Asp Lys Thr
    370                 375                 380

Thr Ala Tyr Lys Asn Ala Val Asn Glu Leu Pro Ala Val Phe Thr Gly
385                 390                 395                 400

Leu Asp Lys Glu Ser Glu Cys Pro Ser Asp Val Tyr Glu Glu Asn Lys
                405                 410                 415

Thr Lys Ser Asn Cys Glu Asn Val Ser Leu Trp Met Lys Phe Phe Asp
            420                 425                 430

Ile Tyr Gly Thr His Ile Ile Tyr Glu Ser Gln Leu Gly Gly Lys Ile
        435                 440                 445

Thr Lys Ile Ile Asn Val Ser Thr Ser Ser Ile Glu Gln Met Lys Lys
    450                 455                 460

Asn Gly Val Ser Val Lys Ala Lys Ile Gln Ala Gln Phe Gly Phe Gly
465                 470                 475                 480

Ser Ala Gly Gly Ser Thr Asp Val Asn Ser Ser Asn Ser Ser Ala Asn
                485                 490                 495

Asp Glu Gln Ser Tyr Asp Met Asn Glu Gln Leu Ile Val Ile Gly Gly
            500                 505                 510
```

```
Asn Pro Ile Lys Asp Val Thr Lys Glu Glu Asn Leu Phe Glu Trp Ser
        515                 520                 525

Lys Thr Val Thr Asn His Pro Met Pro Ile Asn Ile Lys Leu Thr Pro
    530                 535                 540

Ile Ser Asp Ser Phe Asp Ser Asp Asp Leu Lys Glu Ser Tyr Asp Lys
545                 550                 555                 560

Ala Ile Ile Tyr Tyr Ser Arg Leu Tyr Gly Leu Ser Pro His Asp Thr
                565                 570                 575

Met Gln Lys Asp Asp Lys Asp Ile Ile Lys Ile Leu Thr Asn Ala Asp
            580                 585                 590

Thr Val Thr Lys Asn Ser Ala Pro Pro Ile Asn Ala Gln Cys Pro His
        595                 600                 605

Gly Lys Val Val Met Phe Gly Phe Ser Leu Lys Gln Asn Phe Trp Asp
    610                 615                 620

Asn Thr Asn Ala Leu Lys Gly Tyr Asn Ile Glu Val Cys Glu Ala Gly
625                 630                 635                 640

Ser Asn Ser Cys Thr Ser Lys Gln Gly Ser Ser Asn Lys Tyr Asp Thr
                645                 650                 655

Ser Tyr Leu Tyr Met Glu Cys Gly Asp Gln Pro Leu Pro Phe Ser Glu
            660                 665                 670

Gln Val Ile Ser Glu Ser Thr Ser Thr Tyr Asn Thr Val Lys Cys Pro
        675                 680                 685

Asn Asp Tyr Ser Ile Leu Leu Gly Phe Gly Ile Ser Ser Ser Ser Gly
    690                 695                 700

Arg Ile Asn Ser Ala Glu Tyr Val Tyr Ser Thr Pro Cys Ile Pro Gly
705                 710                 715                 720

Met Lys Ser Cys Ser Leu Asn Met Asn Asn Asp Asn Gln Lys Ser Tyr
                725                 730                 735

Ile Tyr Val Leu Cys Val Asp Thr Thr Ile Trp Ser Gly Val Asn Asn
            740                 745                 750

Leu Ser Leu Val Ala Leu Asp Gly Ala His Gly Lys Val Asn Arg Ser
        755                 760                 765

Lys Lys Tyr Ser Asp Gly Glu Leu Val Gly Thr Cys Pro Leu Asp Gly
    770                 775                 780

Thr Val Leu Thr Gly Phe Lys Val Glu Phe His Thr Ser Ser Pro Tyr
785                 790                 795                 800

Val Gln Thr Pro Phe Glu Lys Cys Ala Lys Ser Leu Lys Ala Cys Ser
                805                 810                 815

Val His Gly Ser Gly His Ala Ile Gly Ile Gln Asn Phe Lys Ser Leu
            820                 825                 830

Phe Ile Tyr Met Leu Cys Lys Asn Asn Lys
        835                 840
```

<210> SEQ ID NO 54
<211> LENGTH: 2541
<212> TYPE: DNA
<213> ORGANISM: Artificial sequence
<220> FEATURE:
<223> OTHER INFORMATION: Synthetic sequence
<220> FEATURE:
<221> NAME/KEY: misc_feature
<223> OTHER INFORMATION: PvSPECT2 human CO

<400> SEQUENCE: 54

```
gccaccatgg ctaagccaag aaatataaac tctctgttgg ccatatggtg tattctcttc      60

tcaatctgtg agtacggcta tgtgggatct ttgagaatag gtcttcggag aaactatagt     120
```

```
caaggggact cctctgatcg gctcgggggt agtgacgtgg acgtgagacg gtccggcgag    180
cttatggacc tcggtaagaa cgcaaacatc ctctgcaata acatcagctg taacagtaaa    240
aaagaggctt cttttctgag tcagaaaaaa caacttgagg atgacgatga cgacgagctg    300
gccgcgctgt acaatgatga tgatgacgat gctagcacaa ccactggggg gggttcagaa    360
actagcgatg acgacgagct tgaactccct gatcaggacg aaggtgcgga cgagggtgaa    420
gcagaggacc aactcgcgac acaggaggat tccgacaact cagggaccga ccaaggtctg    480
aaaaaaaaag taaaccttag ccgccacgaa aagttgatag aagacaaaaa acaacagaca    540
gagaatactt ttaagaagta caggtttggg gatgaggagg aagagtcaga ggagaaatcc    600
ccggggaaat ctaagtcact cgatccaagc agcctcgatg atgacgacgg cgaaggtgat    660
gatgatgatg atggcgacga gagagaaaag aagcaaagta atacaaggaa agccatgaag    720
aaggacttgg atgttttccc agggctttac tttgcaggca tcggatacga tagcctcttc    780
ggaaaccccc tgggcgaggc tgacagcttg accgatcccg ggtaccgggg ccaaatcata    840
ctcatgaact gggaactctc aaataaggga gttgcgaatg atcttgcgac attgcaacct    900
ctgaatggat ggatccgcaa ggaaaatgcg tgcagtcgag cagaatctat aaaagagtgt    960
tcttcagtat cagactacac gaaaaatttg accgcagagg catctgtatc tggctcctac   1020
atgggctttg gagcttttag tgctagtact ggttataaga aatttttgca agaagccagt   1080
aaacgcacgt ccaaaactta tctggtaaaa agcaattgcg tgaaatacac ggtcgggctc   1140
cctccttatg tgcgctggga gcagacgacc gcctttaaga acgctgtgaa cgggttgcca   1200
ccgcatttca ccggactgga ggccgactct gaatgcgcct ctgatgtcta cgaacaaaag   1260
aagacatctg aagaatgcga aaccgtacat gcctggatac gctttttaa gacttatgga   1320
acacacgtga tcatggaagc acagcttggc ggcaaaataa caaagattat ccgggtcgag   1380
aatagctccg tcaatcaaat gaagaaagac ggagtcagcg tgaaagccca gatcaaagcc   1440
caattcggct ttgcatctgt gggggaagc acaaacgtct ctagtgacca tagttcaaaa   1500
aagaacgagg ataattatga gatgtctgag cagctggtag tgattggagg caacccaatc   1560
aaggatgtga cgaaagaaga aaatctctat gagtggtcta aaacggtctc aacaaatccg   1620
atgcctatca atatcaagct cctgccgatt agcactatct ttgactccga cgatctgaaa   1680
aatagttacg aaaaggcatt gatctactac actcgcttgt atggcttttc accccatgat   1740
acaatgcaaa aagatgaaaa ggatattgtt aagatcctga cggccagcac cacagtcaca   1800
aagacaggcc cgccgcctat atctgcagag tgtccgcata atatggtggt cttgttcggt   1860
ttcgtagtca aacagaattt ttgggatcat acgaacaaac tccagagtta tgaaatggag   1920
atttgtgaaa gcggtgccag ctcatgcacg tctaagcagg gaaatacaaa taagtatgac   1980
gtatcctata cgtatattga gtgcggacca caggcattgc cgttcactga gcaggttgta   2040
tctgtatccg gtacaacata taactctgtt aaatgcccga atgactacag cgtgttgttt   2100
ggctttggaa tggctacgag ttctggcagg caccaaagtg cgctttatag ctatttcaca   2160
ccatgtcgac cagggctcaa aagctgtagc ttgaatatga acgaacatga tgataagtct   2220
tacatttacc tggtctgcgt cgacgcgact atctggacgg gacttaacgc gttgagcatg   2280
atcgcgaaag acgatttgca cagtgccgtg aaccggtacc aacaattcaa tgatggagag   2340
ctggttgtga cgtgtcctag cgagggcact atactgactg gattctatgg ggagacccat   2400
acctccagtc catatgttac tgtacctttt gggaaatgcg caaagtcatt gaaagcctgt   2460
```

```
tctgttcatg ggtccggcca agccataggc attcacaatt atagaacttt gttcacagtc   2520

gcactgtgta agaataatta g                                             2541


<210> SEQ ID NO 55
<211> LENGTH: 844
<212> TYPE: PRT
<213> ORGANISM: Plasmodium vivax
<220> FEATURE:
<221> NAME/KEY: misc_feature
<223> OTHER INFORMATION: PvSPECT2

<400> SEQUENCE: 55

Met Ala Lys Pro Arg Asn Ile Asn Ser Leu Leu Ala Ile Trp Cys Ile
1               5                   10                  15

Leu Phe Ser Ile Cys Glu Tyr Gly Tyr Val Gly Ser Leu Arg Ile Gly
            20                  25                  30

Leu Arg Arg Asn Tyr Ser Gln Gly Asp Ser Ser Asp Arg Leu Gly Gly
        35                  40                  45

Ser Asp Val Asp Val Arg Arg Ser Gly Glu Leu Met Asp Leu Gly Lys
    50                  55                  60

Asn Ala Asn Ile Leu Cys Asn Asn Ile Ser Cys Asn Ser Lys Lys Glu
65                  70                  75                  80

Ala Ser Phe Leu Ser Gln Lys Lys Gln Leu Glu Asp Asp Asp Asp Asp
                85                  90                  95

Glu Leu Ala Ala Leu Tyr Asn Asp Asp Asp Asp Asp Ala Ser Thr Thr
            100                 105                 110

Thr Gly Gly Gly Ser Glu Thr Ser Asp Asp Asp Glu Leu Glu Leu Pro
        115                 120                 125

Asp Gln Asp Glu Gly Ala Asp Glu Gly Glu Ala Glu Asp Gln Leu Ala
    130                 135                 140

Thr Gln Glu Asp Ser Asp Asn Ser Gly Thr Asp Gln Gly Leu Lys Lys
145                 150                 155                 160

Lys Val Asn Leu Ser Arg His Glu Lys Leu Ile Glu Asp Lys Lys Gln
                165                 170                 175

Gln Thr Glu Asn Thr Phe Lys Lys Tyr Arg Phe Gly Asp Glu Glu Glu
            180                 185                 190

Glu Ser Glu Glu Lys Ser Pro Gly Lys Ser Lys Ser Leu Asp Pro Ser
        195                 200                 205

Ser Leu Asp Asp Asp Asp Gly Glu Gly Asp Asp Asp Asp Asp Gly Asp
    210                 215                 220

Glu Arg Glu Lys Lys Gln Ser Asn Thr Arg Lys Ala Met Lys Lys Asp
225                 230                 235                 240

Leu Asp Val Phe Pro Gly Leu Tyr Phe Ala Gly Ile Gly Tyr Asp Ser
                245                 250                 255

Leu Phe Gly Asn Pro Leu Gly Glu Ala Asp Ser Leu Thr Asp Pro Gly
            260                 265                 270

Tyr Arg Gly Gln Ile Ile Leu Met Asn Trp Glu Leu Ser Asn Lys Gly
        275                 280                 285

Val Ala Asn Asp Leu Ala Thr Leu Gln Pro Leu Asn Gly Trp Ile Arg
    290                 295                 300

Lys Glu Asn Ala Cys Ser Arg Ala Glu Ser Ile Lys Glu Cys Ser Ser
305                 310                 315                 320

Val Ser Asp Tyr Thr Lys Asn Leu Thr Ala Glu Ala Ser Val Ser Gly
                325                 330                 335
```

```
Ser Tyr Met Gly Phe Gly Ala Phe Ser Ala Ser Thr Gly Tyr Lys Lys
            340                 345                 350

Phe Leu Gln Glu Ala Ser Lys Arg Thr Ser Lys Thr Tyr Leu Val Lys
        355                 360                 365

Ser Asn Cys Val Lys Tyr Thr Val Gly Leu Pro Pro Tyr Val Arg Trp
    370                 375                 380

Glu Gln Thr Thr Ala Phe Lys Asn Ala Val Asn Gly Leu Pro Pro His
385                 390                 395                 400

Phe Thr Gly Leu Glu Ala Asp Ser Glu Cys Ala Ser Asp Val Tyr Glu
                405                 410                 415

Gln Lys Lys Thr Ser Glu Glu Cys Glu Thr Val His Ala Trp Ile Arg
            420                 425                 430

Phe Phe Lys Thr Tyr Gly Thr His Val Ile Met Glu Ala Gln Leu Gly
        435                 440                 445

Gly Lys Ile Thr Lys Ile Ile Arg Val Glu Asn Ser Ser Val Asn Gln
    450                 455                 460

Met Lys Lys Asp Gly Val Ser Val Lys Ala Gln Ile Lys Ala Gln Phe
465                 470                 475                 480

Gly Phe Ala Ser Val Gly Gly Ser Thr Asn Val Ser Ser Asp His Ser
                485                 490                 495

Ser Lys Lys Asn Glu Asp Asn Tyr Glu Met Ser Glu Gln Leu Val Val
            500                 505                 510

Ile Gly Gly Asn Pro Ile Lys Asp Val Thr Lys Glu Glu Asn Leu Tyr
        515                 520                 525

Glu Trp Ser Lys Thr Val Ser Thr Asn Pro Met Pro Ile Asn Ile Lys
    530                 535                 540

Leu Leu Pro Ile Ser Thr Ile Phe Asp Ser Asp Asp Leu Lys Asn Ser
545                 550                 555                 560

Tyr Glu Lys Ala Leu Ile Tyr Tyr Thr Arg Leu Tyr Gly Phe Ser Pro
                565                 570                 575

His Asp Thr Met Gln Lys Asp Glu Lys Asp Ile Val Lys Ile Leu Thr
            580                 585                 590

Ala Ser Thr Thr Val Thr Lys Thr Gly Pro Pro Pro Ile Ser Ala Glu
        595                 600                 605

Cys Pro His Asn Met Val Val Leu Phe Gly Phe Val Val Lys Gln Asn
    610                 615                 620

Phe Trp Asp His Thr Asn Lys Leu Gln Ser Tyr Glu Met Glu Ile Cys
625                 630                 635                 640

Glu Ser Gly Ala Ser Ser Cys Thr Ser Lys Gln Gly Asn Thr Asn Lys
                645                 650                 655

Tyr Asp Val Ser Tyr Thr Tyr Ile Glu Cys Gly Pro Gln Ala Leu Pro
            660                 665                 670

Phe Thr Glu Gln Val Val Ser Val Ser Gly Thr Thr Tyr Asn Ser Val
        675                 680                 685

Lys Cys Pro Asn Asp Tyr Ser Val Leu Phe Gly Phe Gly Met Ala Thr
    690                 695                 700

Ser Ser Gly Arg His Gln Ser Ala Leu Tyr Ser Tyr Phe Thr Pro Cys
705                 710                 715                 720

Arg Pro Gly Leu Lys Ser Cys Ser Leu Asn Met Asn Glu His Asp Asp
                725                 730                 735

Lys Ser Tyr Ile Tyr Leu Val Cys Val Asp Ala Thr Ile Trp Thr Gly
            740                 745                 750
```

```
Leu Asn Ala Leu Ser Met Ile Ala Lys Asp Asp Leu His Ser Ala Val
        755                 760                 765

Asn Arg Tyr Gln Gln Phe Asn Asp Gly Glu Leu Val Val Thr Cys Pro
    770                 775                 780

Ser Glu Gly Thr Ile Leu Thr Gly Phe Tyr Gly Glu Thr His Thr Ser
785                 790                 795                 800

Ser Pro Tyr Val Thr Val Pro Phe Gly Lys Cys Ala Lys Ser Leu Lys
                805                 810                 815

Ala Cys Ser Val His Gly Ser Gly Gln Ala Ile Gly Ile His Asn Tyr
            820                 825                 830

Arg Thr Leu Phe Thr Val Ala Leu Cys Lys Asn Asn
        835                 840


<210> SEQ ID NO 56
<211> LENGTH: 843
<212> TYPE: PRT
<213> ORGANISM: Plasmodium vivax
<220> FEATURE:
<221> NAME/KEY: misc_feature
<223> OTHER INFORMATION: SPECT2

<400> SEQUENCE: 56

Met Lys Pro Arg Asn Ile Asn Ser Leu Leu Ala Ile Trp Cys Ile Leu
1               5                   10                  15

Phe Ser Ile Cys Glu Tyr Gly Tyr Val Gly Ser Leu Arg Ile Gly Leu
            20                  25                  30

Arg Arg Asn Tyr Ser Gln Gly Asp Ser Ser Asp Arg Leu Gly Gly Ser
        35                  40                  45

Asp Val Asp Val Arg Arg Ser Gly Glu Leu Met Asp Phe Gly Lys Asn
    50                  55                  60

Ala Asn Ile Leu Cys Asn Asn Ile Ser Cys Asn Ser Lys Lys Glu Ala
65                  70                  75                  80

Ser Phe Leu Ser Gln Lys Lys Gln Leu Glu Asp Asp Asp Asp Asp Glu
                85                  90                  95

Leu Ala Ala Leu Tyr Asn Asp Asp Asp Asp Asp Ala Ser Thr Thr Thr
            100                 105                 110

Gly Gly Gly Ser Glu Thr Ser Asp Asp Asp Glu Leu Glu Leu Pro Asp
        115                 120                 125

Gln Asp Glu Gly Ala Asp Glu Gly Glu Ala Glu Asp Gln Leu Ala Thr
    130                 135                 140

Gln Glu Asp Ser Asp Asn Ser Gly Thr Asp Gln Gly Leu Lys Lys Lys
145                 150                 155                 160

Val Ser Leu Ser Arg His Glu Lys Leu Ile Glu Asp Lys Lys Gln Gln
                165                 170                 175

Thr Glu Asn Thr Phe Lys Lys Tyr Arg Phe Gly Asp Glu Glu Glu Glu
            180                 185                 190

Ser Glu Glu Lys Ser Pro Gly Lys Ser Lys Ser Leu Asp Pro Ser Ser
        195                 200                 205

Leu Asp Asp Asp Asp Gly Glu Gly Asp Asp Asp Asp Asp Gly Asp Glu
    210                 215                 220

Arg Glu Lys Lys Gln Ser Asn Thr Arg Lys Ala Met Lys Lys Asp Leu
225                 230                 235                 240

Asp Val Phe Pro Gly Leu Tyr Phe Ala Gly Ile Gly Tyr Asp Ser Leu
                245                 250                 255

Phe Gly Asn Pro Leu Gly Glu Ala Asp Ser Leu Thr Asp Pro Gly Tyr
            260                 265                 270
```

```
Arg Gly Gln Ile Ile Leu Met Asn Trp Glu Leu Ser Asn Lys Gly Val
        275                 280                 285

Ala Asn Asp Leu Ala Thr Leu Gln Pro Leu Asn Gly Trp Ile Arg Lys
    290                 295                 300

Glu Asn Ala Cys Ser Arg Ala Glu Ser Ile Lys Glu Cys Ser Ser Val
305                 310                 315                 320

Ser Asp Tyr Thr Lys Asn Leu Thr Ala Glu Ala Ser Val Ser Gly Ser
                325                 330                 335

Tyr Met Gly Phe Gly Ala Phe Ser Ala Ser Thr Gly Tyr Lys Lys Phe
            340                 345                 350

Leu Gln Glu Ala Ser Lys Arg Thr Ser Lys Thr Tyr Leu Val Lys Ser
        355                 360                 365

Asn Cys Val Lys Tyr Thr Val Gly Leu Pro Pro Tyr Val Arg Trp Glu
    370                 375                 380

Gln Thr Thr Ala Phe Lys Asn Ala Val Asn Gly Leu Pro Pro His Phe
385                 390                 395                 400

Thr Gly Leu Glu Ala Asp Ser Glu Cys Ala Ser Asp Val Tyr Glu Gln
                405                 410                 415

Lys Lys Thr Ser Glu Glu Cys Glu Thr Val His Ala Trp Ile Arg Phe
            420                 425                 430

Phe Lys Thr Tyr Gly Thr His Val Ile Met Glu Ala Gln Leu Gly Gly
        435                 440                 445

Lys Ile Thr Lys Ile Ile Arg Val Glu Asn Ser Ser Val Asn Gln Met
    450                 455                 460

Lys Lys Asp Gly Val Ser Val Lys Ala Gln Ile Lys Ala Gln Phe Gly
465                 470                 475                 480

Phe Ala Ser Val Gly Gly Ser Thr Asn Val Ser Ser Asp His Ser Ser
                485                 490                 495

Lys Lys Asn Glu Asp Asn Tyr Glu Met Ser Glu Gln Leu Val Val Ile
            500                 505                 510

Gly Gly Asn Pro Ile Lys Asp Val Thr Lys Glu Glu Asn Leu Tyr Glu
        515                 520                 525

Trp Ser Lys Thr Val Ser Thr Asn Pro Met Pro Ile Asn Ile Lys Leu
    530                 535                 540

Leu Pro Ile Ser Thr Ile Phe Asp Ser Asp Asp Leu Lys Asn Ser Tyr
545                 550                 555                 560

Glu Lys Ala Leu Ile Tyr Tyr Thr Arg Leu Tyr Gly Phe Ser Pro His
                565                 570                 575

Asp Thr Met Gln Lys Asp Glu Lys Asp Ile Val Lys Ile Leu Thr Ala
            580                 585                 590

Ser Thr Thr Val Thr Lys Thr Gly Pro Pro Pro Ile Ser Ala Glu Cys
        595                 600                 605

Pro His Asn Met Val Val Leu Phe Gly Phe Val Val Lys Gln Asn Phe
    610                 615                 620

Trp Asp His Thr Asn Lys Leu Gln Ser Tyr Glu Met Glu Ile Cys Glu
625                 630                 635                 640

Ser Gly Ala Ser Ser Cys Thr Ser Lys Gln Gly Asn Thr Asn Lys Tyr
                645                 650                 655

Asp Val Ser Tyr Thr Tyr Ile Glu Cys Gly Pro Gln Ala Leu Pro Phe
            660                 665                 670

Thr Glu Gln Val Val Ser Val Ser Gly Thr Thr Tyr Asn Ser Val Lys
        675                 680                 685
```

```
Cys Pro Asn Asp Tyr Ser Val Leu Phe Gly Phe Gly Met Ala Thr Ser
    690                 695                 700

Ser Gly Arg His Gln Ser Ala Leu Tyr Ser Tyr Phe Thr Pro Cys Arg
705                 710                 715                 720

Pro Gly Leu Lys Ser Cys Ser Leu Asn Met Asn Glu His Asp Asp Lys
                725                 730                 735

Ser Tyr Ile Tyr Leu Val Cys Val Asp Ala Thr Ile Trp Thr Gly Leu
            740                 745                 750

Asn Ala Leu Ser Met Ile Ala Lys Asp Asp Leu His Ser Ala Val Asn
        755                 760                 765

Arg Tyr Gln Gln Phe Asn Asp Gly Glu Leu Val Val Thr Cys Pro Ser
    770                 775                 780

Glu Gly Thr Ile Leu Thr Gly Phe Tyr Gly Glu Thr His Thr Ser Ser
785                 790                 795                 800

Pro Tyr Val Thr Val Pro Phe Gly Lys Cys Ala Lys Ser Leu Lys Ala
                805                 810                 815

Cys Ser Val His Gly Ser Gly Gln Ala Ile Gly Ile His Asn Tyr Arg
            820                 825                 830

Thr Leu Phe Thr Val Ala Leu Cys Lys Asn Asn
        835                 840
```

<210> SEQ ID NO 57
<211> LENGTH: 2478
<212> TYPE: DNA
<213> ORGANISM: Plasmodium berghei
<220> FEATURE:
<221> NAME/KEY: misc_feature
<223> OTHER INFORMATION: GPI_P113

<400> SEQUENCE: 57

```
ggatccgcca ccatggctaa gatcttcctg tttagtttct tcttcgtatg gttccagtat     60

tgctattcta agaacccctc agactacgct catagcattg tctctaattt tgagtccgag    120

aatacgttga agtgtttgaa aggcaacgtg tatatacttc aatgtcagat caagtgcatg    180

aactcaaaca acgagatcat atacaaggag tgtctcaacg atatcgaaaa gatttgcaaa    240

gataagaaaa catgcagtta ttacttcgac tacatcttca aaaccaagaa tcacaagctt    300

agaaacaaca acaataacaa catctacatc gacaattgca tcgattccga caagaatgag    360

atcaaatcta ccttcacctg tgtcctcaat ccattgctgg aatttgacaa taacaaccac    420

gtcatttata acttcctgct gaacaacaag aacaatgaca agatcgtctg taaaaatagc    480

aacatatata ttaacaacgc tactattcac tataccttct ccgacattaa gtttaaagac    540

gtgactagct acataaaaga gaaatgtaac gagaaaacta attgcgtgat aaacccctat    600

tctatccaaa ccgatatcct gaatgagaag aacgacgcat atctgctgaa ctcatacatc    660

agcatatcct tcgcatgtgt gaaaattaac ctggaaagct atctgtacgg aggtgatatc    720

gatgaatttg atcagataaa cgatgaagaa aatgaggaca ataagtacct ggatcacaat    780

gatctcgatg aaaaaaatga ggaaattatt tccctgaaga acgaaatcaa cgacatcctg    840

aatgacgaga agatcgataa catcgccgag aagctgaaga ttgcgaaatt tacaataagc    900

aagaaaatca acgaggagat caagaagaag aacgacatct ttaacaacct ggccaacgac    960

atctaccagt tcatcggtaa cgagtactac tttacttccg acatcaaaga catgattgaa   1020

gataggtaca atgaactgaa caaaacatct cagtctgact tgtattacat ttaccttctg   1080

aatgtgtttg acattgaaaa gatttacggg atctacctgt ctagttatca ggagcgactg   1140
```

```
cagcagatcc tgcaaaccaa catgacaaat ctggactatg ttgagaagaa gattggaagc   1200

ttgcggaaca tttacatgtt cctgtataaa aagagtaaga agtataacgc gctggatatc   1260

ttcgacgaat actacgatta tgtgctcaat tacaatgact tcgctaaaga caatgagata   1320

atcagcgccg acattttcat taagtcaaaa cctgatatcc ctcaactcaa tttcgagatc   1380

aacaatgaga acaagaacgt gaagtataaa gacgttaccg atcttgacga gctggataac   1440

ctcaacagga taaatagaat tatcaatatc cggaatgtgc tggtcaagca gctcaagatc   1500

ctttacaacc agagaaataa catatttatc aaacaggcca tgctggtgaa atcatactgc   1560

tacaaaaatc cactggatat tacggatttc agcagcatct tcaagaataa ctacaataag   1620

ttgaaatacg acgcctataa ggagggcaat ggacacatta acgtggccga caaaatcaat   1680

ccaaactttg tcgtgaaata cctgaacaat ctttataaac agcatgttaa caagaattat   1740

atcctgaaca gctgggaccc taaatacaat cgcatgaata agaagattaa gatcattctc   1800

attttggggt atggccaggt aatccagatc gagaaacaga ttaaccgtca tataggcaag   1860

tacaacgccc tgcttgaaaa ggcaaccctc tataacgtgg gaaatctctt tacacagact   1920

acgaatattt tgaacgacat ctcaggctca ctgaacgatg ggcttgaccc gaacatccat   1980

gatcaggagg atgtcactgt cgttgaatcc tctgaaagta acaagctcgc agaacctgag   2040

gaacccattg agaaggtaga ggttgatagg gtagagaaat ccgatgatgc caataatgcc   2100

actcaacaag tgacaggaac agacgaggcc aattacgata cagctagcgg gaatagtacc   2160

aacatcaaca ttgacaacat agactatggt gtggacgaat ctatccgaat tattaagtac   2220

tccaaggctg aggaggatga atataatgag agcggcaata acgaaaatga aaacaacgag   2280

aataacgaga acgagaacaa tgaaaatgag aacaacgaga atgagaataa tgagaatgaa   2340

aataacgaga acgaaaatat agaactgaag aatatagaac acgaaaacaa atccaacgca   2400

tctagcgctt ccctcagtaa cattttcttt acctttatca ttgcagctct gtttatccgc   2460

ccctttctgt gactcgag                                                 2478
```

<210> SEQ ID NO 58
<211> LENGTH: 819
<212> TYPE: PRT
<213> ORGANISM: Plasmodium berghei
<220> FEATURE:
<221> NAME/KEY: misc_feature
<223> OTHER INFORMATION: GPI_P113

<400> SEQUENCE: 58

```
Met Ala Lys Ile Phe Leu Phe Ser Phe Phe Phe Val Trp Phe Gln Tyr
1               5                   10                  15

Cys Tyr Ser Lys Asn Pro Ser Asp Tyr Ala His Ser Ile Val Ser Asn
            20                  25                  30

Phe Glu Ser Glu Asn Thr Leu Lys Cys Leu Lys Gly Asn Val Tyr Ile
        35                  40                  45

Leu Gln Cys Gln Ile Lys Cys Met Asn Ser Asn Asn Glu Ile Ile Tyr
    50                  55                  60

Lys Glu Cys Leu Asn Asp Ile Glu Lys Ile Cys Lys Asp Lys Lys Thr
65                  70                  75                  80

Cys Ser Tyr Tyr Phe Asp Tyr Ile Phe Lys Thr Lys Asn His Lys Leu
                85                  90                  95

Arg Asn Asn Asn Asn Asn Asn Ile Tyr Ile Asp Asn Cys Ile Asp Ser
            100                 105                 110
```

```
Asp Lys Asn Glu Ile Lys Ser Thr Phe Thr Cys Val Leu Asn Pro Leu
        115                 120                 125

Leu Glu Phe Asp Asn Asn Asn His Val Ile Tyr Asn Phe Leu Leu Asn
    130                 135                 140

Asn Lys Asn Asn Asp Lys Ile Val Cys Lys Asn Ser Asn Ile Tyr Ile
145                 150                 155                 160

Asn Asn Ala Thr Ile His Tyr Thr Phe Ser Asp Ile Lys Phe Lys Asp
                165                 170                 175

Val Thr Ser Tyr Ile Lys Glu Lys Cys Asn Glu Lys Thr Asn Cys Val
            180                 185                 190

Ile Asn Pro Tyr Ser Ile Gln Thr Asp Ile Leu Asn Glu Lys Asn Asp
        195                 200                 205

Ala Tyr Leu Leu Asn Ser Tyr Ile Ser Ile Ser Phe Ala Cys Val Lys
    210                 215                 220

Ile Asn Leu Glu Ser Tyr Leu Tyr Gly Gly Asp Ile Asp Glu Phe Asp
225                 230                 235                 240

Gln Ile Asn Asp Glu Glu Asn Glu Asp Asn Lys Tyr Leu Asp His Asn
                245                 250                 255

Asp Leu Asp Glu Lys Asn Glu Glu Ile Ile Ser Leu Lys Asn Glu Ile
            260                 265                 270

Asn Asp Ile Leu Asn Asp Glu Lys Ile Asp Asn Ile Ala Glu Lys Leu
        275                 280                 285

Lys Ile Ala Lys Phe Thr Ile Ser Lys Lys Ile Asn Glu Glu Ile Lys
    290                 295                 300

Lys Lys Asn Asp Ile Phe Asn Asn Leu Ala Asn Asp Ile Tyr Gln Phe
305                 310                 315                 320

Ile Gly Asn Glu Tyr Tyr Phe Thr Ser Asp Ile Lys Asp Met Ile Glu
                325                 330                 335

Asp Arg Tyr Asn Glu Leu Asn Lys Thr Ser Gln Ser Asp Leu Tyr Tyr
            340                 345                 350

Ile Tyr Leu Leu Asn Val Phe Asp Ile Glu Lys Ile Tyr Gly Ile Tyr
        355                 360                 365

Leu Ser Ser Tyr Gln Glu Arg Leu Gln Gln Ile Leu Gln Thr Asn Met
    370                 375                 380

Thr Asn Leu Asp Tyr Val Glu Lys Lys Ile Gly Ser Leu Arg Asn Ile
385                 390                 395                 400

Tyr Met Phe Leu Tyr Lys Lys Ser Lys Lys Tyr Asn Ala Leu Asp Ile
                405                 410                 415

Phe Asp Glu Tyr Tyr Asp Tyr Val Leu Asn Tyr Asn Asp Phe Ala Lys
            420                 425                 430

Asp Asn Glu Ile Ile Ser Ala Asp Ile Phe Ile Lys Ser Lys Pro Asp
        435                 440                 445

Ile Pro Gln Leu Asn Phe Glu Ile Asn Asn Glu Asn Lys Asn Val Lys
    450                 455                 460

Tyr Lys Asp Val Thr Asp Leu Asp Glu Leu Asp Asn Leu Asn Arg Ile
465                 470                 475                 480

Asn Arg Ile Ile Asn Ile Arg Asn Val Leu Val Lys Gln Leu Lys Ile
                485                 490                 495

Leu Tyr Asn Gln Arg Asn Asn Ile Phe Ile Lys Gln Ala Met Leu Val
            500                 505                 510

Lys Ser Tyr Cys Tyr Lys Asn Pro Leu Asp Ile Thr Asp Phe Ser Ser
        515                 520                 525
```

```
Ile Phe Lys Asn Asn Tyr Asn Lys Leu Lys Tyr Asp Ala Tyr Lys Glu
    530                 535                 540

Gly Asn Gly His Ile Asn Val Ala Asp Lys Ile Asn Pro Asn Phe Val
545                 550                 555                 560

Val Lys Tyr Leu Asn Asn Leu Tyr Lys Gln His Val Asn Lys Asn Tyr
                565                 570                 575

Ile Leu Asn Ser Trp Asp Pro Lys Tyr Asn Arg Met Asn Lys Lys Ile
            580                 585                 590

Lys Ile Ile Leu Ile Leu Gly Tyr Gly Gln Val Ile Gln Ile Glu Lys
        595                 600                 605

Gln Ile Asn Arg His Ile Gly Lys Tyr Asn Ala Leu Leu Glu Lys Ala
    610                 615                 620

Thr Leu Tyr Asn Val Gly Asn Leu Phe Thr Gln Thr Thr Asn Ile Leu
625                 630                 635                 640

Asn Asp Ile Ser Gly Ser Leu Asn Asp Gly Leu Asp Pro Asn Ile His
                645                 650                 655

Asp Gln Glu Asp Val Thr Val Val Glu Ser Ser Glu Ser Asn Lys Leu
            660                 665                 670

Ala Glu Pro Glu Glu Pro Ile Glu Lys Val Glu Val Asp Arg Val Glu
        675                 680                 685

Lys Ser Asp Asp Ala Asn Asn Ala Thr Gln Gln Val Thr Gly Thr Asp
    690                 695                 700

Glu Ala Asn Tyr Asp Thr Ala Ser Gly Asn Ser Thr Asn Ile Asn Ile
705                 710                 715                 720

Asp Asn Ile Asp Tyr Gly Val Asp Glu Ser Ile Arg Ile Ile Lys Tyr
                725                 730                 735

Ser Lys Ala Glu Glu Asp Glu Tyr Asn Glu Ser Gly Asn Asn Glu Asn
            740                 745                 750

Glu Asn Asn Glu Asn Asn Glu Asn Glu Asn Asn Glu Asn Glu Asn Asn
        755                 760                 765

Glu Asn Glu Asn Asn Glu Asn Glu Asn Asn Glu Asn Glu Asn Ile Glu
    770                 775                 780

Leu Lys Asn Ile Glu His Glu Asn Lys Ser Asn Ala Ser Ser Ala Ser
785                 790                 795                 800

Leu Ser Asn Ile Phe Phe Thr Phe Ile Ile Ala Ala Leu Phe Ile Arg
                805                 810                 815

Pro Phe Leu
```

```
<210> SEQ ID NO 59
<211> LENGTH: 818
<212> TYPE: PRT
<213> ORGANISM: Plasmodium berghei
<220> FEATURE:
<221> NAME/KEY: misc_feature
<223> OTHER INFORMATION: P113

<400> SEQUENCE: 59

Met Lys Ile Phe Leu Phe Ser Phe Phe Phe Val Trp Phe Gln Tyr Cys
1               5                   10                  15

Tyr Ser Lys Asn Pro Ser Asp Tyr Ala His Ser Ile Val Ser Asn Phe
            20                  25                  30

Glu Ser Glu Asn Thr Leu Lys Cys Leu Lys Gly Asn Val Tyr Ile Leu
        35                  40                  45

Gln Cys Gln Ile Lys Cys Met Asn Ser Asn Asn Glu Ile Ile Tyr Lys
    50                  55                  60
```

```
Glu Cys Leu Asn Asp Ile Glu Lys Ile Cys Lys Asp Lys Lys Thr Cys
65                  70                  75                  80

Ser Tyr Tyr Phe Asp Tyr Ile Phe Lys Thr Lys Asn His Lys Leu Arg
                85                  90                  95

Asn Asn Asn Asn Asn Asn Ile Tyr Ile Asp Asn Cys Ile Asp Ser Asp
            100                 105                 110

Lys Asn Glu Ile Lys Ser Thr Phe Thr Cys Val Leu Asn Pro Leu Leu
        115                 120                 125

Glu Phe Asp Asn Asn Asn His Val Ile Tyr Asn Phe Leu Leu Asn Asn
    130                 135                 140

Lys Asn Asn Asp Lys Ile Val Cys Lys Asn Ser Asn Ile Tyr Ile Asn
145                 150                 155                 160

Asn Ala Thr Ile His Tyr Thr Phe Ser Asp Ile Lys Phe Lys Asp Val
                165                 170                 175

Thr Ser Tyr Ile Lys Glu Lys Cys Asn Glu Lys Thr Asn Cys Val Ile
            180                 185                 190

Asn Pro Tyr Ser Ile Gln Thr Asp Ile Leu Asn Glu Lys Asn Asp Ala
        195                 200                 205

Tyr Leu Leu Asn Ser Tyr Ile Ser Ile Ser Phe Ala Cys Val Lys Ile
    210                 215                 220

Asn Leu Glu Ser Tyr Leu Tyr Gly Gly Asp Ile Asp Glu Phe Asp Gln
225                 230                 235                 240

Ile Asn Asp Glu Glu Asn Glu Asp Asn Lys Tyr Leu Asp His Asn Asp
                245                 250                 255

Leu Asp Glu Lys Asn Glu Glu Ile Ile Ser Leu Lys Asn Glu Ile Asn
            260                 265                 270

Asp Ile Leu Asn Asp Glu Lys Ile Asp Asn Ile Ala Glu Lys Leu Lys
        275                 280                 285

Ile Ala Lys Phe Thr Ile Ser Lys Lys Ile Asn Glu Glu Ile Lys Lys
    290                 295                 300

Lys Asn Asp Ile Phe Asn Asn Leu Ala Asn Asp Ile Tyr Gln Phe Ile
305                 310                 315                 320

Gly Asn Glu Tyr Tyr Phe Thr Ser Asp Ile Lys Asp Met Ile Glu Asp
                325                 330                 335

Arg Tyr Asn Glu Leu Asn Lys Thr Ser Gln Ser Asp Leu Tyr Tyr Ile
            340                 345                 350

Tyr Leu Leu Asn Val Phe Asp Ile Glu Lys Ile Tyr Gly Ile Tyr Leu
        355                 360                 365

Ser Ser Tyr Gln Glu Arg Leu Gln Gln Ile Leu Gln Thr Asn Met Thr
    370                 375                 380

Asn Leu Asp Tyr Val Glu Lys Lys Ile Gly Ser Leu Arg Asn Ile Tyr
385                 390                 395                 400

Met Phe Leu Tyr Lys Lys Ser Lys Lys Tyr Asn Ala Leu Asp Ile Phe
                405                 410                 415

Asp Glu Tyr Tyr Asp Tyr Val Leu Asn Tyr Asn Asp Phe Ala Lys Asp
            420                 425                 430

Asn Glu Ile Ile Ser Ala Asp Ile Phe Ile Lys Ser Lys Pro Asp Ile
        435                 440                 445

Pro Gln Leu Asn Phe Glu Ile Asn Asn Glu Asn Lys Asn Val Lys Tyr
    450                 455                 460

Lys Asp Val Thr Asp Leu Asp Glu Leu Asp Asn Leu Asn Arg Ile Asn
465                 470                 475                 480
```

```
Arg Ile Ile Asn Ile Arg Asn Val Leu Val Lys Gln Leu Lys Ile Leu
                485                 490                 495

Tyr Asn Gln Arg Asn Asn Ile Phe Ile Lys Gln Ala Met Leu Val Lys
            500                 505                 510

Ser Tyr Cys Tyr Lys Asn Pro Leu Asp Ile Thr Asp Phe Ser Ser Ile
        515                 520                 525

Phe Lys Asn Asn Tyr Asn Lys Leu Lys Tyr Asp Ala Tyr Lys Glu Gly
    530                 535                 540

Asn Gly His Ile Asn Val Ala Asp Lys Ile Asn Pro Asn Phe Val Val
545                 550                 555                 560

Lys Tyr Leu Asn Asn Leu Tyr Lys Gln His Val Asn Lys Asn Tyr Ile
                565                 570                 575

Leu Asn Ser Trp Asp Pro Lys Tyr Asn Arg Met Asn Lys Lys Ile Lys
            580                 585                 590

Ile Ile Leu Ile Leu Gly Tyr Gly Gln Val Ile Gln Ile Glu Lys Gln
        595                 600                 605

Ile Asn Arg His Ile Gly Lys Tyr Asn Ala Leu Leu Glu Lys Ala Thr
    610                 615                 620

Leu Tyr Asn Val Gly Asn Leu Phe Thr Gln Thr Thr Asn Ile Leu Asn
625                 630                 635                 640

Asp Ile Ser Gly Ser Leu Asn Asp Gly Leu Asp Pro Asn Ile His Asp
                645                 650                 655

Gln Glu Asp Val Thr Val Val Glu Ser Ser Glu Ser Asn Lys Leu Ala
            660                 665                 670

Glu Pro Glu Glu Pro Ile Glu Lys Val Glu Val Asp Arg Val Glu Lys
        675                 680                 685

Ser Asp Asp Ala Asn Asn Ala Thr Gln Gln Val Thr Gly Thr Asp Glu
    690                 695                 700

Ala Asn Tyr Asp Thr Ala Ser Gly Asn Ser Thr Asn Ile Asn Ile Asp
705                 710                 715                 720

Asn Ile Asp Tyr Gly Val Asp Glu Ser Ile Arg Ile Ile Lys Tyr Ser
                725                 730                 735

Lys Ala Glu Glu Asp Glu Tyr Asn Glu Ser Gly Asn Asn Glu Asn Glu
            740                 745                 750

Asn Asn Glu Asn Asn Glu Asn Glu Asn Asn Glu Asn Glu Asn Asn Glu
        755                 760                 765

Asn Glu Asn Asn Glu Asn Glu Asn Asn Glu Asn Glu Asn Ile Glu Leu
    770                 775                 780

Lys Asn Ile Glu His Glu Asn Lys Ser Asn Ala Ser Ser Ala Ser Leu
785                 790                 795                 800

Ser Asn Ile Phe Phe Thr Phe Ile Ile Ala Ala Leu Phe Ile Arg Pro
                805                 810                 815

Phe Leu


<210> SEQ ID NO 60
<211> LENGTH: 2919
<212> TYPE: DNA
<213> ORGANISM: Artificial Sequence
<220> FEATURE:
<223> OTHER INFORMATION: PfP113 human CO

<400> SEQUENCE: 60

gccaccatgg ctaagatccc gttctttatt ctgcacatcc tcctcctgca gtttctgctt      60

tgtctgatac gctgttatgt gcacaatgat gtgattaagt tcggtgagga gaatagcctg     120
```

```
aagtgctctc agggaaactt gtatgtgttg cactgtgagg tgcagtgcct taatggcaat    180
aatgagatta tccacaagag gtgtaatgac gacattgaga aaaagtgcaa cggcaataat    240
aaatgcatat acttctttga gtacgaactg cggaagaaaa cacaaagctt tcgaaataag    300
aattctatcg agatttccga gtgtgtcgaa agcgagcaga acgaagtgaa aacctcaact    360
acctgtctcc tgagcaattc ctttattctt gacgaggcct ttatacagta tttcttcttc    420
ataaagaaca agaacgaaga gcctgtgatt tgtaaggatg ggaatatcaa cattaagagt    480
gcactcctgc actctccgtt ctgtgaaatc aaactcaagg acatttccga atatatacgc    540
aaaaagtgtg acaacaacaa ggaatgcctt atagatcctc tcgatgttca gaagaatttg    600
ctgaacgaag aagatccctg ctacatcaat aacagttacg tatctgtgaa tgtggtctgc    660
aacaaagagg aggagatagg ggatgagagc actgacagct catcaatgga gatccaggac    720
tcaacatcaa atgagcaaga cgagaatgtt aaaggaatgt caagcagcca agagatgaac    780
tcaaacaacg atgaaaacaa aaaccaagac aacgaaagcg acgatgacgt caataataat    840
aacaacaata acaatgatga ccaggacgag caaggaaacg atggcgatgt caccagctct    900
atgaacaaga atgaggacaa caaggatttg gagcatggtt cctccaatga tgtcaataac    960
aacactgaca ccttggttaa caacaaagag aataaggagt tcgtccttaa agagaagtct   1020
agccttactt ctaaaattaa caaagagctg gctcatagaa ctgccctgtt taacaaactt   1080
gcagacaaca tatcacttct gcttaacaag aaatacgatt ccttcgaaat taaggatgtg   1140
ctggaagata ggtacaacga gatgaagagg gacgcaaacc ccgatgtcta ctacatatac   1200
ctgatggata ctctggatat tgaaaagatc gaagatatca acctggaaga ggttaagatg   1260
tctctgctgg catcactgaa agaaacgatg aacaaaattg atacgatcga aaagaaaatc   1320
gaagaattta agaacaagta catctccttg tataacaagg tgaaaaccac aatgcccgaa   1380
ctctttgacc tgaatgagga tcttgtactg ctctacaacg attttccctt tgacaacggc   1440
atgatcagct ccgacatctt ctttaagtac aatccttccg agaacatcat ggatcatcag   1500
gaaatggtga agaaagggag tatcaccgaa gatgaactca ggattgttaa cgatcttgag   1560
ccactggata actatagacg tcgtaaacga attacagagc tgagaaagat tctggtggag   1620
aagctgcgga ttctgtacct ggagaagaac aatctcttca atacacaggc gagttgcatc   1680
aagagctatt gctataagaa tcctctgaac ctcaaaacct tggaagtgct cttgaagaag   1740
aactactata gactgaagga gaataaagat tacgatgttg tatccagcat tatccagcat   1800
ctcgacaatg tagacgccaa caagaagaag aaatggctga cccatgaacg gatactgaag   1860
aagctccaag ttctgattgc cgaaggctat aagcggatca acgagaaaga aaaggacatc   1920
gaccgaagaa tggctgtcta caatgccctc tatgagaaag cacagtctta caacctgcag   1980
aagcttttca acgactccaa cgattttctg aagaaatatg ccataatggg aaacagtttc   2040
gacgacggcg atgaggtttt cggttcccaa agctcaaact ttaacatctt cgatagcaat   2100
aacaccgacc agaacaatga gcaagagcag ccaaagcaag atgaccagct tttgaacaat   2160
aataacgatg acgtgctctc agagtcaaac aatgagaata aagagaaaac aagtgatgac   2220
gctactcata aggagactca ggagaaaagc gaccaggaac cttcccagaa cattcaggag   2280
gacaactccg atgagaaaca tgccgaaaac gaggagaacg tagaacagat cgaaactgat   2340
agtaatgtca gcgaagaagc caatgacgag aataaggata acatgcagac aaccactgac   2400
gaaggaaccg aagaacttca gcagaatgac gaagatgcgg agagtctgac caaggagaat   2460
```

-continued

```
tccaaatctg aggagcagga gaatgaagat tctactgacg ccgaggcgat tgataaagag   2520

gaagttgaaa cggaagagaa gggaaaggac gaacagaaga aagatgagca gaaggagcag   2580

gatgaggaag aggatggaga gaaagaaaat aagcacaaga gctccgaaac taccaatgag   2640

actgtgaccg acatcgagga aaataagaac gaggtcaaag gtgaggagca tcttcagggg   2700

tctgagcaga gcattgaggc ttccgaatca tcccagaaag atgagactaa agaaacagag   2760

gacaaggagg aatacgtgaa cgctaatgat gacgaatctt ctgaggagga cacgacgcct   2820

aacgagacaa ataaaaccga caacgggtca agtttcttct tcgcgatgag caatgcactt   2880

ctcgtgatct tgctgttgct tttcatcgaa ttcctgtaa                          2919
```

```
<210> SEQ ID NO 61
<211> LENGTH: 970
<212> TYPE: PRT
<213> ORGANISM: Plasmodium falciparum
<220> FEATURE:
<221> NAME/KEY: misc_feature
<223> OTHER INFORMATION: PfP113

<400> SEQUENCE: 61

Met Ala Lys Ile Pro Phe Phe Ile Leu His Ile Leu Leu Leu Gln Phe
1               5                   10                  15

Leu Leu Cys Leu Ile Arg Cys Tyr Val His Asn Asp Val Ile Lys Phe
            20                  25                  30

Gly Glu Glu Asn Ser Leu Lys Cys Ser Gln Gly Asn Leu Tyr Val Leu
        35                  40                  45

His Cys Glu Val Gln Cys Leu Asn Gly Asn Asn Glu Ile Ile His Lys
    50                  55                  60

Arg Cys Asn Asp Asp Ile Glu Lys Lys Cys Asn Gly Asn Asn Lys Cys
65                  70                  75                  80

Ile Tyr Phe Phe Glu Tyr Glu Leu Arg Lys Lys Thr Gln Ser Phe Arg
                85                  90                  95

Asn Lys Asn Ser Ile Glu Ile Ser Glu Cys Val Glu Ser Glu Gln Asn
            100                 105                 110

Glu Val Lys Thr Ser Thr Thr Cys Leu Leu Ser Asn Ser Phe Ile Leu
        115                 120                 125

Asp Glu Ala Phe Ile Gln Tyr Phe Phe Phe Ile Lys Asn Lys Asn Glu
    130                 135                 140

Glu Pro Val Ile Cys Lys Asp Gly Asn Ile Asn Ile Lys Ser Ala Leu
145                 150                 155                 160

Leu His Ser Pro Phe Cys Glu Ile Lys Leu Lys Asp Ile Ser Glu Tyr
                165                 170                 175

Ile Arg Lys Lys Cys Asp Asn Asn Lys Glu Cys Leu Ile Asp Pro Leu
            180                 185                 190

Asp Val Gln Lys Asn Leu Leu Asn Glu Glu Asp Pro Cys Tyr Ile Asn
        195                 200                 205

Asn Ser Tyr Val Ser Val Asn Val Val Cys Asn Lys Glu Glu Glu Ile
    210                 215                 220

Gly Asp Glu Ser Thr Asp Ser Ser Ser Met Glu Ile Gln Asp Ser Thr
225                 230                 235                 240

Ser Asn Glu Gln Asp Glu Asn Val Lys Gly Met Ser Ser Ser Gln Glu
                245                 250                 255

Met Asn Ser Asn Asn Asp Glu Asn Lys Asn Gln Asp Asn Glu Ser Asp
            260                 265                 270
```

```
Asp Asp Val Asn Asn Asn Asn Asn Asn Asn Asn Asp Asp Gln Asp Glu
        275                 280                 285

Gln Gly Asn Asp Gly Asp Val Thr Ser Ser Met Asn Lys Asn Glu Asp
    290                 295                 300

Asn Lys Asp Leu Glu His Gly Ser Ser Asn Asp Val Asn Asn Asn Thr
305                 310                 315                 320

Asp Thr Leu Val Asn Asn Lys Glu Asn Lys Glu Phe Val Leu Lys Glu
                325                 330                 335

Lys Ser Ser Leu Thr Ser Lys Ile Asn Lys Glu Leu Ala His Arg Thr
            340                 345                 350

Ala Leu Phe Asn Lys Leu Ala Asp Asn Ile Ser Leu Leu Leu Asn Lys
        355                 360                 365

Lys Tyr Asp Ser Phe Glu Ile Lys Asp Val Leu Glu Asp Arg Tyr Asn
    370                 375                 380

Glu Met Lys Arg Asp Ala Asn Pro Asp Val Tyr Tyr Ile Tyr Leu Met
385                 390                 395                 400

Asp Thr Leu Asp Ile Glu Lys Ile Glu Asp Ile Asn Leu Glu Glu Val
                405                 410                 415

Lys Met Ser Leu Leu Ala Ser Leu Lys Glu Thr Met Asn Lys Ile Asp
            420                 425                 430

Thr Ile Glu Lys Lys Ile Glu Glu Phe Lys Asn Lys Tyr Ile Ser Leu
        435                 440                 445

Tyr Asn Lys Val Lys Thr Thr Met Pro Glu Leu Phe Asp Leu Asn Glu
    450                 455                 460

Asp Leu Val Leu Leu Tyr Asn Asp Phe Pro Phe Asp Asn Gly Met Ile
465                 470                 475                 480

Ser Ser Asp Ile Phe Phe Lys Tyr Asn Pro Ser Glu Asn Ile Met Asp
                485                 490                 495

His Gln Glu Met Val Lys Lys Gly Ser Ile Thr Glu Asp Glu Leu Arg
            500                 505                 510

Ile Val Asn Asp Leu Glu Pro Leu Asp Asn Tyr Arg Arg Arg Lys Arg
        515                 520                 525

Ile Thr Glu Leu Arg Lys Ile Leu Val Glu Lys Leu Arg Ile Leu Tyr
    530                 535                 540

Leu Glu Lys Asn Asn Leu Phe Asn Thr Gln Ala Ser Cys Ile Lys Ser
545                 550                 555                 560

Tyr Cys Tyr Lys Asn Pro Leu Asn Leu Lys Thr Leu Glu Val Leu Leu
                565                 570                 575

Lys Lys Asn Tyr Tyr Arg Leu Lys Glu Asn Lys Asp Tyr Asp Val Val
            580                 585                 590

Ser Ser Ile Ile Gln His Leu Asp Asn Val Asp Ala Asn Lys Lys Lys
        595                 600                 605

Lys Trp Leu Thr His Glu Arg Ile Leu Lys Lys Leu Gln Val Leu Ile
    610                 615                 620

Ala Glu Gly Tyr Lys Arg Ile Asn Glu Lys Glu Lys Asp Ile Asp Arg
625                 630                 635                 640

Arg Met Ala Val Tyr Asn Ala Leu Tyr Glu Lys Ala Gln Ser Tyr Asn
                645                 650                 655

Leu Gln Lys Leu Phe Asn Asp Ser Asn Asp Phe Leu Lys Lys Tyr Ala
            660                 665                 670

Ile Met Gly Asn Ser Phe Asp Asp Gly Asp Glu Val Phe Gly Ser Gln
        675                 680                 685
```

```
Ser Ser Asn Phe Asn Ile Phe Asp Ser Asn Asn Thr Asp Gln Asn Asn
    690                 695                 700

Glu Gln Glu Gln Pro Lys Gln Asp Asp Gln Leu Leu Asn Asn Asn Asn
705                 710                 715                 720

Asp Asp Val Leu Ser Glu Ser Asn Asn Glu Asn Lys Glu Lys Thr Ser
                725                 730                 735

Asp Asp Ala Thr His Lys Glu Thr Gln Glu Lys Ser Asp Gln Glu Pro
            740                 745                 750

Ser Gln Asn Ile Gln Glu Asp Asn Ser Asp Glu Lys His Ala Glu Asn
        755                 760                 765

Glu Glu Asn Val Glu Gln Ile Glu Thr Asp Ser Asn Val Ser Glu Glu
    770                 775                 780

Ala Asn Asp Glu Asn Lys Asp Asn Met Gln Thr Thr Thr Asp Glu Gly
785                 790                 795                 800

Thr Glu Glu Leu Gln Gln Asn Asp Glu Asp Ala Glu Ser Leu Thr Lys
                805                 810                 815

Glu Asn Ser Lys Ser Glu Glu Gln Glu Asn Glu Asp Ser Thr Asp Ala
            820                 825                 830

Glu Ala Ile Asp Lys Glu Glu Val Glu Thr Glu Glu Lys Gly Lys Asp
        835                 840                 845

Glu Gln Lys Lys Asp Glu Gln Lys Glu Gln Asp Glu Glu Glu Asp Gly
    850                 855                 860

Glu Lys Glu Asn Lys His Lys Ser Ser Glu Thr Thr Asn Glu Thr Val
865                 870                 875                 880

Thr Asp Ile Glu Glu Asn Lys Asn Glu Val Lys Gly Glu Glu His Leu
                885                 890                 895

Gln Gly Ser Glu Gln Ser Ile Glu Ala Ser Glu Ser Ser Gln Lys Asp
            900                 905                 910

Glu Thr Lys Glu Thr Glu Asp Lys Glu Glu Tyr Val Asn Ala Asn Asp
        915                 920                 925

Asp Glu Ser Ser Glu Glu Asp Thr Thr Pro Asn Glu Thr Asn Lys Thr
    930                 935                 940

Asp Asn Gly Ser Ser Phe Phe Phe Ala Met Ser Asn Ala Leu Leu Val
945                 950                 955                 960

Ile Leu Leu Leu Leu Phe Ile Glu Phe Leu
                965                 970


<210> SEQ ID NO 62
<211> LENGTH: 969
<212> TYPE: PRT
<213> ORGANISM: Plasmodium falciparum
<220> FEATURE:
<221> NAME/KEY: misc_feature
<223> OTHER INFORMATION: PfP113

<400> SEQUENCE: 62

Met Lys Ile Pro Phe Phe Ile Leu His Ile Leu Leu Leu Gln Phe Leu
1               5                   10                  15

Leu Cys Leu Ile Arg Cys Tyr Val His Asn Asp Val Ile Lys Phe Gly
            20                  25                  30

Glu Glu Asn Ser Leu Lys Cys Ser Gln Gly Asn Leu Tyr Val Leu His
        35                  40                  45

Cys Glu Val Gln Cys Leu Asn Gly Asn Asn Glu Ile Ile His Lys Arg
    50                  55                  60

Cys Asn Asp Asp Ile Glu Lys Lys Cys Asn Gly Asn Asn Lys Cys Ile
65                  70                  75                  80
```

```
Tyr Phe Phe Glu Tyr Glu Leu Arg Lys Lys Thr Gln Ser Phe Arg Asn
                85                  90                  95

Lys Asn Ser Ile Glu Ile Ser Glu Cys Val Glu Ser Glu Gln Asn Glu
            100                 105                 110

Val Lys Thr Ser Thr Thr Cys Leu Leu Ser Asn Ser Phe Ile Leu Asp
        115                 120                 125

Glu Ala Phe Ile Gln Tyr Phe Phe Phe Ile Lys Asn Lys Asn Glu Glu
    130                 135                 140

Pro Val Ile Cys Lys Asp Gly Asn Ile Asn Ile Lys Ser Ala Leu Leu
145                 150                 155                 160

His Ser Pro Phe Cys Glu Ile Lys Leu Lys Asp Ile Ser Glu Tyr Ile
                165                 170                 175

Arg Lys Lys Cys Asp Asn Asn Lys Glu Cys Leu Ile Asp Pro Leu Asp
            180                 185                 190

Val Gln Lys Asn Leu Leu Asn Glu Glu Asp Pro Cys Tyr Ile Asn Asn
        195                 200                 205

Ser Tyr Val Ser Val Asn Val Val Cys Asn Lys Glu Glu Glu Ile Gly
    210                 215                 220

Asp Glu Ser Thr Asp Ser Ser Ser Met Glu Ile Gln Asp Ser Thr Ser
225                 230                 235                 240

Asn Glu Gln Asp Glu Asn Val Lys Gly Met Ser Ser Ser Gln Glu Met
                245                 250                 255

Asn Ser Asn Asn Asp Glu Asn Lys Asn Gln Asp Asn Glu Ser Asp Asp
            260                 265                 270

Asp Val Asn Asn Asn Asn Asn Asn Asn Asn Asp Asp Gln Asp Glu Gln
        275                 280                 285

Gly Asn Asp Gly Asp Val Thr Ser Ser Met Asn Lys Asn Glu Asp Asn
    290                 295                 300

Lys Asp Leu Glu His Gly Ser Ser Asn Asp Val Asn Asn Asn Thr Asp
305                 310                 315                 320

Thr Leu Val Asn Asn Lys Glu Asn Lys Glu Phe Val Leu Lys Glu Lys
                325                 330                 335

Ser Ser Leu Thr Ser Lys Ile Asn Lys Glu Leu Ala His Arg Thr Ala
            340                 345                 350

Leu Phe Asn Lys Leu Ala Asp Asn Ile Ser Leu Leu Leu Asn Lys Lys
        355                 360                 365

Tyr Asp Ser Phe Glu Ile Lys Asp Val Leu Glu Asp Arg Tyr Asn Glu
    370                 375                 380

Met Lys Arg Asp Ala Asn Pro Asp Val Tyr Tyr Ile Tyr Leu Met Asp
385                 390                 395                 400

Thr Leu Asp Ile Glu Lys Ile Glu Asp Ile Asn Leu Glu Glu Val Lys
                405                 410                 415

Met Ser Leu Leu Ala Ser Leu Lys Glu Thr Met Asn Lys Ile Asp Thr
            420                 425                 430

Ile Glu Lys Lys Ile Glu Glu Phe Lys Asn Lys Tyr Ile Ser Leu Tyr
        435                 440                 445

Asn Lys Val Lys Thr Thr Met Pro Glu Leu Phe Asp Leu Asn Glu Asp
    450                 455                 460

Leu Val Leu Leu Tyr Asn Asp Phe Pro Phe Asp Asn Gly Met Ile Ser
465                 470                 475                 480

Ser Asp Ile Phe Phe Lys Tyr Asn Pro Ser Glu Asn Ile Met Asp His
                485                 490                 495
```

```
Gln Glu Met Val Lys Lys Gly Ser Ile Thr Glu Asp Glu Leu Arg Ile
            500                 505                 510

Val Asn Asp Leu Glu Pro Leu Asp Asn Tyr Arg Arg Arg Lys Arg Ile
        515                 520                 525

Thr Glu Leu Arg Lys Ile Leu Val Glu Lys Leu Arg Ile Leu Tyr Leu
    530                 535                 540

Glu Lys Asn Asn Leu Phe Asn Thr Gln Ala Ser Cys Ile Lys Ser Tyr
545                 550                 555                 560

Cys Tyr Lys Asn Pro Leu Asn Leu Lys Thr Leu Glu Val Leu Leu Lys
                565                 570                 575

Lys Asn Tyr Tyr Arg Leu Lys Glu Asn Lys Asp Tyr Asp Val Val Ser
            580                 585                 590

Ser Ile Ile Gln His Leu Asp Asn Val Asp Ala Asn Lys Lys Lys Lys
        595                 600                 605

Trp Leu Thr His Glu Arg Ile Leu Lys Lys Leu Gln Val Leu Ile Ala
    610                 615                 620

Glu Gly Tyr Lys Arg Ile Asn Glu Lys Glu Lys Asp Ile Asp Arg Arg
625                 630                 635                 640

Met Ala Val Tyr Asn Ala Leu Tyr Glu Lys Ala Gln Ser Tyr Asn Leu
                645                 650                 655

Gln Lys Leu Phe Asn Asp Ser Asn Asp Phe Leu Lys Lys Tyr Ala Ile
            660                 665                 670

Met Gly Asn Ser Phe Asp Asp Gly Asp Glu Val Phe Gly Ser Gln Ser
        675                 680                 685

Ser Asn Phe Asn Ile Phe Asp Ser Asn Asn Thr Asp Gln Asn Asn Glu
    690                 695                 700

Gln Glu Gln Pro Lys Gln Asp Asp Gln Leu Leu Asn Asn Asn Asn Asp
705                 710                 715                 720

Asp Val Leu Ser Glu Ser Asn Asn Glu Asn Lys Glu Lys Thr Ser Asp
                725                 730                 735

Asp Ala Thr His Lys Glu Thr Gln Glu Lys Ser Asp Gln Glu Pro Ser
            740                 745                 750

Gln Asn Ile Gln Glu Asp Asn Ser Asp Glu Lys His Ala Glu Asn Glu
        755                 760                 765

Glu Asn Val Glu Gln Ile Glu Thr Asp Ser Asn Val Ser Glu Glu Ala
    770                 775                 780

Asn Asp Glu Asn Lys Asp Asn Met Gln Thr Thr Thr Asp Glu Gly Thr
785                 790                 795                 800

Glu Glu Leu Gln Gln Asn Asp Glu Asp Ala Glu Ser Leu Thr Lys Glu
                805                 810                 815

Asn Ser Lys Ser Glu Glu Gln Glu Asn Glu Asp Ser Thr Asp Ala Glu
            820                 825                 830

Ala Ile Asp Lys Glu Glu Val Glu Thr Glu Glu Lys Gly Lys Asp Glu
        835                 840                 845

Gln Lys Lys Asp Glu Gln Lys Glu Gln Asp Glu Glu Glu Asp Gly Glu
    850                 855                 860

Lys Glu Asn Lys His Lys Ser Ser Glu Thr Thr Asn Glu Thr Val Thr
865                 870                 875                 880

Asp Ile Glu Glu Asn Lys Asn Glu Val Lys Gly Glu Glu His Leu Gln
                885                 890                 895

Gly Ser Glu Gln Ser Ile Glu Ala Ser Glu Ser Ser Gln Lys Asp Glu
            900                 905                 910
```

```
Thr Lys Glu Thr Glu Asp Lys Glu Glu Tyr Val Asn Ala Asn Asp Asp
        915                 920                 925

Glu Ser Ser Glu Glu Asp Thr Thr Pro Asn Glu Thr Asn Lys Thr Asp
    930                 935                 940

Asn Gly Ser Ser Phe Phe Phe Ala Met Ser Asn Ala Leu Leu Val Ile
945                 950                 955                 960

Leu Leu Leu Leu Phe Ile Glu Phe Leu
                965
```

<210> SEQ ID NO 63
<211> LENGTH: 3141
<212> TYPE: DNA
<213> ORGANISM: Artificial Sequence
<220> FEATURE:
<223> OTHER INFORMATION: PvP113 human CO

<400> SEQUENCE: 63

```
gccaccatgg ctaagctccc gcccctctgc aggttgccac ttgcgctggt gcttctttgt     60

ctgacatcca gagcgcgctg ttatgtacac aacgacgtga tgaaatttgg tgaagaaaac    120

tctctcaagt gttcacaagg gtctctctac atccttcact gcgaggtcaa gtgtgtgaat    180

gcaaagaaca gaatcatcca ccgaagttgc atcgaccagg ttgaggcgaa gtgcatgggc    240

aacgccaaat gtaagtacta ttttgactat gtcgtgaaat cccgcggaca gagtttgcgg    300

aacaaaaatg aaatcgaaat agaagaatgc gtggaatccg aacggaatga gattaagacg    360

tccacaactt gccttctgtc aaattcattt ttgctggatg agacctacat tcaatatttc    420

tttttcatca aaaacaaaaa tgaagaaccc ataacgtgtc gagacggtag actgagcgta    480

aagagtgcga tacttcatag tcccttttgc aaaataaatc ttaaggacat cactgagatt    540

ctcaagagac aatgcgatca cagtaaggag tgcgtcatta atccgtatgt cctccaaaaa    600

gatgcattga atgagagaga ccagtgttac attaacaact catatgtctc actcaatgtc    660

gtttgcacca aagaagggga ggagcaacca gaagagagtg gacataaaca gaagagggat    720

gacgacgtgg acgaaaccga ggaaggctca tatgacgtct ctgcggatca gaacaaatca    780

gcaatagtcg gcgagggaaa cgatgatccg gaatccctgg gtgaagaaga tgagctttca    840

gagactaacg aggcagttga tctcattatg aactccaagg aaagctttga aaacaaaatt    900

cggaaggcga agtcaatact tctctcacag atgaacgagc aggaggtgaa aaagaatgca    960

atattcaaga aactcgggga agagctttcc aaaatggtcc tccagaaata tgaaccaagt   1020

gatctgaaag acttgatcga ggacaggtat aatgaaatga gacggtcccc tgaccaagac   1080

ctttattatc tctaccttat agatacactc gaaataaata aaatggaaga tcttgacgtg   1140

actgcactgc aagaccagct cgctatattg ttggaagagc agatgggcaa gatgaatcgc   1200

attgagaaaa cgattaaccg attgaggaaa aaataccttt ctatttacaa caaagcgaag   1260

aacaagaaag ttaaagacat ttacgatgaa ggagttgatc ctgtactcac gtacgacgac   1320

ttcgcgcacg gcaacggcat tattacggca gatattttct ttaagtataa gcctgccatt   1380

aagccgttga cttttagcaa atctaatgcc tctgaggagc gggggtcatc caaaaaaaaa   1440

gagtacaagg accttcttga gatggacgcg ctggatgagt acaaccggaa gaaacggata   1500

actgacatgc gaaacggtct gatggagact ttgaagaaaa tgtattacgc aaaaaaatggg   1560

atattcaata atctggcgag ttgcattaag tcatattgct ataaaaggcc tctcaacctt   1620

aatgcacttt cctccgttct taaaagaaat tttgaaaatc ttcgagagaa aaaatcaacc   1680
```

```
gatccagtgg cccccatagt cagatatttg caaaaggtca gtggcgaggt tggcggggaa   1740

gtgggaggcg cggctggcgg tgctgcgggg ggtgctgcaa gtggtgccgc atcaggagct   1800

gtcagtgaag cagtaggagg cgccataggt ggggctgtgg gcgaggcatc tatcgcagta   1860

aatccgcccc gatgggaaaa atcacgacga attcttcaaa agctcaaggc tttgctgcac   1920

ctgggttatc aacaggcact ggacaaagag ttggagatcg acgagaggac tgacaaatac   1980

aacgctctga atgagaaagc aaaagaatat aaccttcagc ggcttttttc cgagtcagac   2040

aagttgctta agaaggtcgc aatgcttacg tcagccagtg aaagtgcaga tgaagtattc   2100

ggtaaccaag cgagcttttt cgatgtttac agaggagagg cagcgtcaca aaaaggagta   2160

gccgccagtg aaaagggcgt agctgcaaga gagaaaggag tcgccgcgag tgagaagggg   2220

gtcgcggcat cagaaaaggg tgtggcggcc agcgagaagg gtgtcgcggc atcagaaaaa   2280

ggtgttgccg caagccaaaa aggcggagaa acgtctgagg aaggggaggc tgccagtcaa   2340

aaggatgttg ctacgtccga ggagggtgga gctagcagcg agaaacgcga tgacgacgag   2400

atgaatccgc ccgacgaagg gtatgagtcc gctaaggaag acggggagaa tgcacaagat   2460

gacgacagcg gcggaaatgc tgaacccgta gagggaaaag caggcgaaag tgaagacgct   2520

gatggggtaa atgccggctc caataaagaa ggtgaggatg ggagagagcgt tgaagaagaa   2580

gctgcggaag gggaagcggc acccaaggag gaggctgcag acggagaaga tgctccggag   2640

gaggaagccg agggtgagga tgccccagaa gaagaggccg atggcgaaga cgccccgaag   2700

gaggaggcta ctgacggaga ggacgcccct aaagaggaag aggccgaagg tgaggatgca   2760

agcaaggacg aggaggccga cgaaggctca actgacgagg aagaagccgc cgacggcggg   2820

agtactgatg ctacagcagc cgatgaagct gcaggcggag tcgcggacca aaacgacgtg   2880

cccgttaagg gagaagactc agatggcgcg gaatctgatg gagcagaaga tgccgccact   2940

gaaattaggg gtgaggctga agccggtgaa gaggccgcgg agcaacctac tggagaggcc   3000

gtagtcaaag ggattccga gggcggggct tctgggctgg aaaccgagaa gaagggagac   3060

gacgggggct ccttcttcca aggtctttcc cgagtgttgc ttactgttct tgcaatactt   3120

tccttggaat ttctcctttg a                                              3141
```

<210> SEQ ID NO 64
<211> LENGTH: 1044
<212> TYPE: PRT
<213> ORGANISM: Plasmodium vivax
<220> FEATURE:
<221> NAME/KEY: misc_feature
<223> OTHER INFORMATION: PvP113

<400> SEQUENCE: 64

```
Met Ala Lys Leu Pro Pro Leu Cys Arg Leu Pro Leu Ala Leu Val Leu
1               5                   10                  15

Leu Cys Leu Thr Ser Arg Ala Arg Cys Tyr Val His Asn Asp Val Met
            20                  25                  30

Lys Phe Gly Glu Glu Asn Ser Leu Lys Cys Ser Gln Gly Ser Leu Tyr
        35                  40                  45

Ile Leu His Cys Glu Val Lys Cys Val Asn Ala Lys Asn Arg Ile Ile
    50                  55                  60

His Arg Ser Cys Ile Asp Gln Val Glu Ala Lys Cys Met Gly Asn Ala
65                  70                  75                  80

Lys Cys Lys Tyr Tyr Phe Asp Tyr Val Val Lys Ser Arg Gly Gln Ser
                85                  90                  95
```

-continued

```
Leu Arg Asn Lys Asn Glu Ile Glu Ile Glu Glu Cys Val Glu Ser Glu
            100                 105                 110

Arg Asn Glu Ile Lys Thr Ser Thr Thr Cys Leu Leu Ser Asn Ser Phe
        115                 120                 125

Leu Leu Asp Glu Thr Tyr Ile Gln Tyr Phe Phe Phe Ile Lys Asn Lys
    130                 135                 140

Asn Glu Glu Pro Ile Thr Cys Arg Asp Gly Arg Leu Ser Val Lys Ser
145                 150                 155                 160

Ala Ile Leu His Ser Pro Phe Cys Lys Ile Asn Leu Lys Asp Ile Thr
                165                 170                 175

Glu Ile Leu Lys Arg Gln Cys Asp His Ser Lys Glu Cys Val Ile Asn
            180                 185                 190

Pro Tyr Val Leu Gln Lys Asp Ala Leu Asn Glu Arg Asp Gln Cys Tyr
        195                 200                 205

Ile Asn Asn Ser Tyr Val Ser Leu Asn Val Val Cys Thr Lys Glu Gly
    210                 215                 220

Glu Glu Gln Pro Glu Glu Ser Gly His Lys Gln Lys Arg Asp Asp Asp
225                 230                 235                 240

Val Asp Glu Thr Glu Glu Gly Ser Tyr Asp Val Ser Ala Asp Gln Asn
                245                 250                 255

Lys Ser Ala Ile Val Gly Glu Gly Asn Asp Asp Pro Glu Ser Leu Gly
            260                 265                 270

Glu Glu Asp Glu Leu Ser Glu Thr Asn Glu Ala Val Asp Leu Ile Met
        275                 280                 285

Asn Ser Lys Glu Ser Phe Glu Asn Lys Ile Arg Lys Ala Lys Ser Ile
    290                 295                 300

Leu Leu Ser Gln Met Asn Glu Gln Glu Val Lys Lys Asn Ala Ile Phe
305                 310                 315                 320

Lys Lys Leu Gly Glu Glu Leu Ser Lys Met Val Leu Gln Lys Tyr Glu
                325                 330                 335

Pro Ser Asp Leu Lys Asp Leu Ile Glu Asp Arg Tyr Asn Glu Met Arg
            340                 345                 350

Arg Ser Pro Asp Gln Asp Leu Tyr Tyr Leu Tyr Leu Ile Asp Thr Leu
        355                 360                 365

Glu Ile Asn Lys Met Glu Asp Leu Asp Val Thr Ala Leu Gln Asp Gln
    370                 375                 380

Leu Ala Ile Leu Leu Glu Glu Gln Met Gly Lys Met Asn Arg Ile Glu
385                 390                 395                 400

Lys Thr Ile Asn Arg Leu Arg Lys Lys Tyr Leu Ser Ile Tyr Asn Lys
                405                 410                 415

Ala Lys Asn Lys Lys Val Lys Asp Ile Tyr Asp Glu Gly Val Asp Pro
            420                 425                 430

Val Leu Thr Tyr Asp Asp Phe Ala His Gly Asn Gly Ile Ile Thr Ala
        435                 440                 445

Asp Ile Phe Phe Lys Tyr Lys Pro Ala Ile Lys Pro Leu Thr Phe Ser
    450                 455                 460

Lys Ser Asn Ala Ser Glu Glu Arg Gly Ser Ser Lys Lys Lys Glu Tyr
465                 470                 475                 480

Lys Asp Leu Leu Glu Met Asp Ala Leu Asp Glu Tyr Asn Arg Lys Lys
                485                 490                 495

Arg Ile Thr Asp Met Arg Asn Gly Leu Met Glu Thr Leu Lys Lys Met
            500                 505                 510
```

```
Tyr Tyr Ala Lys Asn Gly Ile Phe Asn Asn Leu Ala Ser Cys Ile Lys
        515                 520                 525

Ser Tyr Cys Tyr Lys Arg Pro Leu Asn Leu Asn Ala Leu Ser Ser Val
    530                 535                 540

Leu Lys Arg Asn Phe Glu Asn Leu Arg Glu Lys Lys Ser Thr Asp Pro
545                 550                 555                 560

Val Ala Pro Ile Val Arg Tyr Leu Gln Lys Val Ser Gly Glu Val Gly
                565                 570                 575

Gly Glu Val Gly Gly Ala Ala Gly Gly Ala Ala Gly Gly Ala Ala Ser
            580                 585                 590

Gly Ala Ala Ser Gly Ala Val Ser Glu Ala Val Gly Gly Ala Ile Gly
        595                 600                 605

Gly Ala Val Gly Glu Ala Ser Ile Ala Val Asn Pro Pro Arg Trp Glu
    610                 615                 620

Lys Ser Arg Arg Ile Leu Gln Lys Leu Lys Ala Leu Leu His Leu Gly
625                 630                 635                 640

Tyr Gln Gln Ala Leu Asp Lys Glu Leu Glu Ile Asp Glu Arg Thr Asp
                645                 650                 655

Lys Tyr Asn Ala Leu Asn Glu Lys Ala Lys Glu Tyr Asn Leu Gln Arg
            660                 665                 670

Leu Phe Ser Glu Ser Asp Lys Leu Leu Lys Lys Val Ala Met Leu Thr
        675                 680                 685

Ser Ala Ser Glu Ser Ala Asp Glu Val Phe Gly Asn Gln Ala Ser Phe
    690                 695                 700

Phe Asp Val Tyr Arg Gly Glu Ala Ala Ser Gln Lys Gly Val Ala Ala
705                 710                 715                 720

Ser Glu Lys Gly Val Ala Ala Arg Glu Lys Gly Val Ala Ala Ser Glu
                725                 730                 735

Lys Gly Val Ala Ala Ser Glu Lys Gly Val Ala Ala Ser Glu Lys Gly
            740                 745                 750

Val Ala Ala Ser Glu Lys Gly Val Ala Ala Ser Gln Lys Gly Gly Glu
        755                 760                 765

Thr Ser Glu Glu Gly Glu Ala Ala Ser Gln Lys Asp Val Ala Thr Ser
    770                 775                 780

Glu Glu Gly Gly Ala Ser Ser Glu Lys Arg Asp Asp Asp Glu Met Asn
785                 790                 795                 800

Pro Pro Asp Glu Gly Tyr Glu Ser Ala Lys Glu Asp Gly Glu Asn Ala
                805                 810                 815

Gln Asp Asp Asp Ser Gly Gly Asn Ala Glu Pro Val Glu Gly Lys Ala
            820                 825                 830

Gly Glu Ser Glu Asp Ala Asp Gly Val Asn Ala Gly Ser Asn Lys Glu
        835                 840                 845

Gly Glu Asp Gly Glu Ser Val Glu Glu Glu Ala Ala Glu Gly Glu Ala
    850                 855                 860

Ala Pro Lys Glu Glu Ala Ala Asp Gly Glu Asp Ala Pro Glu Glu Glu
865                 870                 875                 880

Ala Glu Gly Glu Asp Ala Pro Glu Glu Glu Ala Asp Gly Glu Asp Ala
                885                 890                 895

Pro Lys Glu Glu Ala Thr Asp Gly Glu Asp Ala Pro Lys Glu Glu Glu
            900                 905                 910

Ala Glu Gly Glu Asp Ala Ser Lys Asp Glu Glu Ala Asp Glu Gly Ser
        915                 920                 925
```

```
Thr Asp Glu Glu Glu Ala Ala Asp Gly Gly Ser Thr Asp Ala Thr Ala
    930                 935                 940

Ala Asp Glu Ala Ala Gly Gly Val Ala Asp Gln Asn Asp Val Pro Val
945                 950                 955                 960

Lys Gly Glu Asp Ser Asp Gly Ala Glu Ser Asp Gly Ala Glu Asp Ala
                965                 970                 975

Ala Thr Glu Ile Arg Gly Glu Ala Glu Ala Gly Glu Glu Ala Ala Glu
            980                 985                 990

Gln Pro Thr Gly Glu Ala Val Val  Lys Gly Asp Ser Glu  Gly Gly Ala
        995                 1000                1005

Ser Gly  Leu Glu Thr Glu Lys  Lys Gly Asp Asp Gly  Gly Ser Phe
    1010                1015                1020

Phe Gln  Gly Leu Ser Arg Val  Leu Leu Thr Val Leu  Ala Ile Leu
    1025                1030                1035

Ser Leu  Glu Phe Leu Leu
    1040


<210> SEQ ID NO 65
<211> LENGTH: 969
<212> TYPE: PRT
<213> ORGANISM: Plasmodium vivax
<220> FEATURE:
<221> NAME/KEY: misc_feature
<223> OTHER INFORMATION: P113

<400> SEQUENCE: 65

Met Lys Leu Pro Pro Leu Cys Arg Leu Pro Leu Ala Leu Val Leu Leu
1               5                   10                  15

Cys Leu Thr Ser Arg Ala Arg Cys Tyr Val His Asn Asp Val Met Lys
            20                  25                  30

Phe Gly Glu Glu Asn Ser Leu Lys Cys Ser Gln Gly Ser Leu Tyr Ile
        35                  40                  45

Leu His Cys Glu Val Lys Cys Val Asn Ala Lys Asn Arg Ile Ile His
    50                  55                  60

Arg Ser Cys Ile Asp Gln Val Glu Ala Lys Cys Met Gly Asn Ala Lys
65                  70                  75                  80

Cys Lys Tyr Tyr Phe Asp Tyr Val Val Lys Ser Arg Gly Gln Ser Leu
                85                  90                  95

Arg Asn Lys Asn Glu Ile Glu Ile Glu Glu Cys Val Glu Ser Glu Arg
            100                 105                 110

Asn Glu Ile Lys Thr Ser Thr Thr Cys Leu Leu Ser Asn Ser Phe Leu
        115                 120                 125

Leu Asp Glu Thr Tyr Ile Gln Tyr Phe Phe Phe Ile Lys Asn Lys Asn
    130                 135                 140

Glu Glu Pro Ile Thr Cys Arg Asp Gly Arg Leu Ser Val Lys Ser Ala
145                 150                 155                 160

Ile Leu His Ser Pro Phe Cys Lys Ile Asn Leu Lys Asp Ile Thr Glu
                165                 170                 175

Ile Leu Lys Arg Gln Cys Asp His Ser Lys Glu Cys Val Ile Asn Pro
            180                 185                 190

Tyr Val Leu Gln Lys Asp Ala Leu Asn Glu Arg Asp Gln Cys Tyr Ile
        195                 200                 205

Asn Asn Ser Tyr Val Ser Leu Asn Val Val Cys Thr Lys Glu Gly Glu
    210                 215                 220

Glu Gln Pro Glu Glu Ser Gly His Lys Gln Lys Arg Asp Asp Asp Val
225                 230                 235                 240
```

```
Asp Glu Thr Glu Glu Gly Ser Tyr Asp Val Ser Ala Asp Gln Asn Lys
                245                 250                 255

Ser Ala Ile Val Gly Glu Gly Asn Asp Asp Pro Glu Ser Leu Gly Glu
            260                 265                 270

Glu Asp Glu Leu Ser Glu Thr Asn Glu Ala Val Asp Leu Ile Met Asn
        275                 280                 285

Ser Lys Glu Ser Phe Glu Asn Lys Ile Arg Lys Ala Lys Ser Ile Leu
    290                 295                 300

Leu Ser Gln Met Asn Glu Gln Glu Val Lys Lys Asn Ala Ile Phe Lys
305                 310                 315                 320

Lys Leu Gly Glu Glu Leu Ser Lys Met Val Leu Gln Lys Tyr Glu Pro
                325                 330                 335

Ser Asp Leu Lys Asp Leu Ile Glu Asp Arg Tyr Asn Glu Met Arg Arg
            340                 345                 350

Ser Pro Asp Gln Asp Leu Tyr Tyr Leu Tyr Leu Ile Asp Thr Leu Glu
        355                 360                 365

Ile Asn Lys Met Glu Asn Leu Asp Val Thr Ala Leu Gln Asp Gln Leu
    370                 375                 380

Ala Ile Leu Leu Glu Glu Gln Met Gly Lys Met Asn Arg Ile Glu Lys
385                 390                 395                 400

Thr Ile Asn Arg Leu Arg Lys Lys Tyr Leu Ser Ile Tyr Asn Lys Ala
                405                 410                 415

Lys Asn Lys Lys Val Lys Asp Ile Tyr Asp Glu Gly Val Asp Pro Val
            420                 425                 430

Leu Thr Tyr Asp Asp Phe Ala His Gly Asn Gly Ile Ile Thr Ala Asp
        435                 440                 445

Ile Phe Phe Lys Tyr Lys Pro Ala Ile Lys Pro Leu Thr Phe Ser Lys
    450                 455                 460

Ser Asn Ala Ser Glu Glu Arg Gly Ser Ser Lys Lys Lys Glu Tyr Lys
465                 470                 475                 480

Asp Leu Leu Glu Met Asp Ala Leu Asp Glu Tyr Asn Arg Lys Lys Arg
                485                 490                 495

Ile Thr Asp Met Arg Asn Gly Leu Met Glu Thr Leu Lys Lys Met Tyr
            500                 505                 510

Tyr Ala Lys Asn Gly Ile Phe Asn Asn Leu Ala Ser Cys Ile Lys Ser
        515                 520                 525

Tyr Cys Tyr Lys Arg Pro Leu Asn Leu Asn Ala Leu Ser Ser Val Leu
    530                 535                 540

Lys Arg Asn Phe Glu Asn Leu Arg Glu Lys Lys Ser Thr Asp Pro Val
545                 550                 555                 560

Ala Pro Ile Val Arg Tyr Leu Gln Lys Lys Ser Arg Arg Ile Leu Gln
                565                 570                 575

Lys Leu Lys Ala Leu Leu His Leu Gly Tyr Gln Gln Ala Leu Asp Lys
            580                 585                 590

Glu Leu Glu Ile Asp Glu Arg Thr Asp Lys Tyr Asn Ala Leu Asn Glu
        595                 600                 605

Lys Ala Lys Glu Tyr Asn Leu Gln Arg Leu Phe Ser Glu Ser Asp Lys
    610                 615                 620

Leu Leu Lys Lys Val Ala Met Leu Thr Ser Ala Ser Glu Ser Ala Asp
625                 630                 635                 640

Glu Val Phe Gly Asn Gln Ala Ser Phe Phe Asp Val Tyr Arg Gly Glu
                645                 650                 655
```

-continued

```
Ala Ala Ser Glu Lys Gly Val Ala Ala Ser Gln Lys Gly Gly Glu Thr
            660                 665                 670

Ser Glu Glu Gly Glu Ala Ala Ser Gln Lys Asp Val Ala Thr Ser Glu
        675                 680                 685

Glu Gly Gly Ala Ser Ser Glu Lys Arg Asp Asp Asp Glu Met Asn Pro
    690                 695                 700

Pro Asp Glu Gly Tyr Glu Ser Ala Lys Glu Asp Gly Glu Asn Ala Gln
705                 710                 715                 720

Asp Asp Asp Ser Gly Gly Asn Ala Glu Pro Val Glu Gly Lys Ala Gly
                725                 730                 735

Glu Ser Glu Asp Ala Asp Gly Val Asn Ala Gly Ser Asn Lys Glu Gly
            740                 745                 750

Glu Asp Gly Glu Ser Val Glu Glu Glu Ala Ala Glu Gly Glu Ala Ala
        755                 760                 765

Pro Lys Glu Glu Ala Ala Asp Gly Glu Asp Ala Pro Glu Glu Glu Ala
    770                 775                 780

Glu Gly Glu Asp Ala Pro Lys Glu Glu Ala Ala Asp Gly Glu Ala Ser
785                 790                 795                 800

Ser Lys Glu Glu Glu Thr Asp Gly Glu Val Ala Pro Glu Glu Ala Ala
                805                 810                 815

Asp Gly Glu Asp Ala Pro Lys Glu Glu Ala Thr Asp Gly Glu Asp Ala
            820                 825                 830

Pro Lys Glu Glu Glu Ala Glu Gly Glu Asp Ala Ser Lys Asp Glu Glu
        835                 840                 845

Ala Asp Glu Gly Ser Thr Asp Glu Glu Glu Ala Ala Asp Gly Gly Ser
    850                 855                 860

Thr Asp Ala Thr Ala Ala Asp Glu Ala Ala Gly Gly Val Ala Asp Gln
865                 870                 875                 880

Asn Asp Val Pro Val Lys Gly Glu Asp Ser Asp Gly Ala Glu Ser Asp
                885                 890                 895

Gly Ala Glu Asp Ala Ala Thr Glu Ile Arg Gly Glu Ala Glu Ala Gly
            900                 905                 910

Glu Glu Ala Ala Glu Gln Pro Thr Gly Glu Ala Val Val Lys Gly Asp
        915                 920                 925

Ser Glu Gly Gly Ala Ser Gly Leu Glu Thr Glu Lys Lys Gly Asp Asp
    930                 935                 940

Gly Gly Ser Phe Phe Gln Gly Leu Ser Arg Val Leu Leu Thr Val Leu
945                 950                 955                 960

Ala Ile Leu Ser Leu Glu Phe Leu Leu
                965
```

<210> SEQ ID NO 66
<211> LENGTH: 654
<212> TYPE: DNA
<213> ORGANISM: Plasmodium berghei
<220> FEATURE:
<221> NAME/KEY: misc_feature
<223> OTHER INFORMATION: Ag40

<400> SEQUENCE: 66

```
ggatccgcca ccatggctgg ggcgagtatg agccacttgc agtgtctgac atctgttgct     60

ggtctgtcct ctatcgtcat gtcaatgttc cccaaactca ttgccaataa tccttccctg    120

tttagaccac tgctcaacat ttcctgggga tatctgttcg gaagcactgt atggctgtgc    180

ttcttcagtg agattgggtt ggtcaggaga atcaatgctc ctaaacggaa gaatctgcca    240
```

```
gagaatgcag aacaagccaa agaacagctg aaggagatca agaacaacga aggcgatttt    300

aaccgacgca atatcgactt caagtacttc tttagccttt ccacaatctt ctctagcata    360

ctgctgctta gcacagtgaa actcgccaac aacaatctgc agttgaggat ctgttccacc    420

attgtgtcac tgagttgcat actgaacaat atgtactttc agaacaagat acactcactt    480

gcactgaaga aagagagtct ctttaaggac atgatcgatc gtccgaaaga taccactatt    540

ctggtgaacc tgaagaagaa caagaccgac tttcacatcc atcatggcct ttctctgctc    600

ttgctctata gcagcttctt tggcctcact ccctacattt tcacgtgact cgag          654
```

<210> SEQ ID NO 67
<211> LENGTH: 211
<212> TYPE: PRT
<213> ORGANISM: Plasmodium berghei
<220> FEATURE:
<221> NAME/KEY: misc_feature
<223> OTHER INFORMATION: Ag40

<400> SEQUENCE: 67

```
Met Ala Gly Ala Ser Met Ser His Leu Gln Cys Leu Thr Ser Val Ala
1               5                   10                  15

Gly Leu Ser Ser Ile Val Met Ser Met Phe Pro Lys Leu Ile Ala Asn
            20                  25                  30

Asn Pro Ser Leu Phe Arg Pro Leu Leu Asn Ile Ser Trp Gly Tyr Leu
        35                  40                  45

Phe Gly Ser Thr Val Trp Leu Cys Phe Phe Ser Glu Ile Gly Leu Val
    50                  55                  60

Arg Arg Ile Asn Ala Pro Lys Arg Lys Asn Leu Pro Glu Asn Ala Glu
65                  70                  75                  80

Gln Ala Lys Glu Gln Leu Lys Glu Ile Lys Asn Asn Glu Gly Asp Phe
                85                  90                  95

Asn Arg Arg Asn Ile Asp Phe Lys Tyr Phe Phe Ser Leu Ser Thr Ile
            100                 105                 110

Phe Ser Ser Ile Leu Leu Leu Ser Thr Val Lys Leu Ala Asn Asn Asn
        115                 120                 125

Leu Gln Leu Arg Ile Cys Ser Thr Ile Val Ser Leu Ser Cys Ile Leu
    130                 135                 140

Asn Asn Met Tyr Phe Gln Asn Lys Ile His Ser Leu Ala Leu Lys Lys
145                 150                 155                 160

Glu Ser Leu Phe Lys Asp Met Ile Asp Arg Pro Lys Asp Thr Thr Ile
                165                 170                 175

Leu Val Asn Leu Lys Lys Asn Lys Thr Asp Phe His Ile His His Gly
            180                 185                 190

Leu Ser Leu Leu Leu Leu Tyr Ser Ser Phe Phe Gly Leu Thr Pro Tyr
        195                 200                 205

Ile Phe Thr
    210
```

<210> SEQ ID NO 68
<211> LENGTH: 210
<212> TYPE: PRT
<213> ORGANISM: Plasmodium berghei
<220> FEATURE:
<221> NAME/KEY: misc_feature
<223> OTHER INFORMATION: Ag40

<400> SEQUENCE: 68

Met Gly Ala Ser Met Ser His Leu Gln Cys Leu Thr Ser Val Ala Gly
1 5 10 15

Leu Ser Ser Ile Val Met Ser Met Phe Pro Lys Leu Ile Ala Asn Asn
20 25 30

Pro Ser Leu Phe Arg Pro Leu Leu Asn Ile Ser Trp Gly Tyr Leu Phe
35 40 45

Gly Ser Thr Val Trp Leu Cys Phe Phe Ser Glu Ile Gly Leu Val Arg
50 55 60

Arg Ile Asn Ala Pro Lys Arg Lys Asn Leu Pro Glu Asn Ala Glu Gln
65 70 75 80

Ala Lys Glu Gln Leu Lys Glu Ile Lys Asn Asn Glu Gly Asp Phe Asn
85 90 95

Arg Arg Asn Ile Asp Phe Lys Tyr Phe Phe Ser Leu Ser Thr Ile Phe
100 105 110

Ser Ser Ile Leu Leu Leu Ser Thr Val Lys Leu Ala Asn Asn Asn Leu
115 120 125

Gln Leu Arg Ile Cys Ser Thr Ile Val Ser Leu Ser Cys Ile Leu Asn
130 135 140

Asn Met Tyr Phe Gln Asn Lys Ile His Ser Leu Ala Leu Lys Lys Glu
145 150 155 160

Ser Leu Phe Lys Asp Met Ile Asp Arg Pro Lys Asp Thr Thr Ile Leu
165 170 175

Val Asn Leu Lys Lys Asn Lys Thr Asp Phe His Ile His His Gly Leu
180 185 190

Ser Leu Leu Leu Leu Tyr Ser Ser Phe Phe Gly Leu Thr Pro Tyr Ile
195 200 205

Phe Thr
210

<210> SEQ ID NO 69
<211> LENGTH: 642
<212> TYPE: DNA
<213> ORGANISM: Artificial Sequence
<220> FEATURE:
<223> OTHER INFORMATION: PfAg40 human CO

<400> SEQUENCE: 69
gccaccatgg ctgggtgtac agtctctaat ctcaaatgcg tgaccaatgt ggcaggactg 60
gcaagtctgg ttatcagtct gtttccgaaa ctcatcataa agaacccaca agtgcttcga 120
ccactgctga atgtgtcctg gggttatctg tttggtagca ccttttggct gtgcttcttc 180
tccgaagtag gactgcttcg cagcctgaag aacatgaaag ggtacctttt gcctgaatca 240
gccagtgagg cgaagaagct tctcgaagag atgaagaact ctgagggcga tttcaatcgg 300
agatcactgg acttccagta cttcttttcc ctcgctacgt tgttctcagg cattctgttg 360
ctgagcacag tgaagttggc caaccataac ctgcagctta ggcttagtag ctctgtggtc 420
gtcatcacat cactgctgaa tagcctgtat ctgcacaata aagtgcataa tctgaaaagc 480
aagaaagaaa gcctctataa cgactttatt gccaatccca agaacgagaa aactgtcgct 540
gatctgaaga agaacaagaa agagtttcac atctttcacg gattgtccgt tctctctctc 600
tacgtttcct tcttcggcct gactccctac attttcacct aa 642

<210> SEQ ID NO 70

<211> LENGTH: 211
<212> TYPE: PRT
<213> ORGANISM: Plasmodium falciparum
<220> FEATURE:
<221> NAME/KEY: misc_feature
<223> OTHER INFORMATION: PfAg40

<400> SEQUENCE: 70

Met Ala Gly Cys Thr Val Ser Asn Leu Lys Cys Val Thr Asn Val Ala
1               5                   10                  15

Gly Leu Ala Ser Leu Val Ile Ser Leu Phe Pro Lys Leu Ile Ile Lys
            20                  25                  30

Asn Pro Gln Val Leu Arg Pro Leu Leu Asn Val Ser Trp Gly Tyr Leu
        35                  40                  45

Phe Gly Ser Thr Phe Trp Leu Cys Phe Phe Ser Glu Val Gly Leu Leu
    50                  55                  60

Arg Ser Leu Lys Asn Met Lys Gly Val Pro Leu Pro Glu Ser Ala Ser
65                  70                  75                  80

Glu Ala Lys Lys Leu Leu Glu Glu Met Lys Asn Ser Glu Gly Asp Phe
                85                  90                  95

Asn Arg Arg Ser Leu Asp Phe Gln Tyr Phe Phe Ser Leu Ala Thr Leu
            100                 105                 110

Phe Ser Gly Ile Leu Leu Leu Ser Thr Val Lys Leu Ala Asn His Asn
        115                 120                 125

Leu Gln Leu Arg Leu Ser Ser Ser Val Val Val Ile Thr Ser Leu Leu
    130                 135                 140

Asn Ser Leu Tyr Leu His Asn Lys Val His Asn Leu Lys Ser Lys Lys
145                 150                 155                 160

Glu Ser Leu Tyr Asn Asp Phe Ile Ala Asn Pro Lys Asn Glu Lys Thr
                165                 170                 175

Val Ala Asp Leu Lys Lys Asn Lys Lys Glu Phe His Ile Phe His Gly
            180                 185                 190

Leu Ser Val Leu Ser Leu Tyr Val Ser Phe Phe Gly Leu Thr Pro Tyr
        195                 200                 205

Ile Phe Thr
    210

<210> SEQ ID NO 71
<211> LENGTH: 210
<212> TYPE: PRT
<213> ORGANISM: Plasmodium falciparum
<220> FEATURE:
<221> NAME/KEY: misc_feature
<223> OTHER INFORMATION: Ag40

<400> SEQUENCE: 71

Met Gly Cys Thr Val Ser Asn Leu Lys Cys Val Thr Asn Val Ala Gly
1               5                   10                  15

Leu Ala Ser Leu Val Ile Ser Leu Phe Pro Lys Leu Ile Ile Lys Asn
            20                  25                  30

Pro Gln Val Leu Arg Pro Leu Leu Asn Val Ser Trp Gly Tyr Leu Phe
        35                  40                  45

Gly Ser Thr Phe Trp Leu Cys Phe Phe Ser Glu Val Gly Leu Leu Arg
    50                  55                  60

Ser Leu Lys Asn Met Lys Gly Val Pro Leu Pro Glu Ser Ala Ser Glu
65                  70                  75                  80

Ala Lys Lys Leu Leu Glu Glu Met Lys Asn Ser Glu Gly Asp Phe Asn
                85                  90                  95

```
Arg Arg Ser Leu Asp Phe Gln Tyr Phe Phe Ser Leu Ala Thr Leu Phe
            100                 105                 110

Ser Gly Ile Leu Leu Leu Ser Thr Val Lys Leu Ala Asn His Asn Leu
        115                 120                 125

Gln Leu Arg Leu Ser Ser Ser Val Val Val Ile Thr Ser Leu Leu Asn
    130                 135                 140

Ser Leu Tyr Leu His Asn Lys Val His Asn Leu Lys Ser Lys Lys Glu
145                 150                 155                 160

Ser Leu Tyr Asn Asp Phe Ile Ala Asn Pro Lys Asn Glu Lys Thr Val
                165                 170                 175

Ala Asp Leu Lys Lys Asn Lys Lys Glu Phe His Ile Phe His Gly Leu
            180                 185                 190

Ser Val Leu Ser Leu Tyr Val Ser Phe Phe Gly Leu Thr Pro Tyr Ile
        195                 200                 205

Phe Thr
    210


<210> SEQ ID NO 72
<211> LENGTH: 639
<212> TYPE: DNA
<213> ORGANISM: Artificial Sequence
<220> FEATURE:
<223> OTHER INFORMATION: PvAg40 human CO + kozac

<400> SEQUENCE: 72

gccaccatgg gggcgacggt atcatatctt agatgcgtga ccagtatagc agggctgagc      60

agcctcgtgc tgtctttgtt tcccaagctg attatgaaaa accctcaggt actccgacca     120

ctccttaaca ttagctgggg ttatttgttt ggctcaacct tttggttgtg tttgttctcc     180

gaagtaggac ttttccggtc cctgaaaaat atgaagcgca taccaatccc tgaaaacgca     240

gaagaggcta agaagcaatt ggaggagatg aaaagcatgg aaggggattt taccaggcgc     300

agggaagatt tccaatattt ttttggtttt tccaccttgt tttctggtat tcttcttctc     360

agtacggtaa gacttgcgaa tcacaacatg caactgagga tttccagtac catcgttgcc     420

cttagctgcc tgctcaataa cttgtacctt cagaataagg tacattctct taaaatccaa     480

aaagaaaacc tgtacaacga actcatccgc aatcctaagt cagagacgac tatagcggag     540

attaagaaaa acaaaaaaga tttccatata taccacggct tgtccctgtt gtccctttac     600

ataagcttcc tcggccttac tccatatata tttacctag                            639


<210> SEQ ID NO 73
<211> LENGTH: 210
<212> TYPE: PRT
<213> ORGANISM: Plasmodium vivax
<220> FEATURE:
<221> NAME/KEY: misc_feature
<223> OTHER INFORMATION: PvAg40

<400> SEQUENCE: 73

Met Gly Ala Thr Val Ser Tyr Leu Arg Cys Val Thr Ser Ile Ala Gly
1               5                   10                  15

Leu Ser Ser Leu Val Leu Ser Leu Phe Pro Lys Leu Ile Met Lys Asn
            20                  25                  30

Pro Gln Val Leu Arg Pro Leu Leu Asn Ile Ser Trp Gly Tyr Leu Phe
        35                  40                  45

Gly Ser Thr Phe Trp Leu Cys Leu Phe Ser Glu Val Gly Leu Phe Arg
    50                  55                  60
```

Ser Leu Lys Asn Met Lys Arg Ile Pro Ile Pro Glu Asn Ala Glu Glu
65 70 75 80

Ala Lys Lys Gln Leu Glu Glu Met Lys Ser Met Glu Gly Asp Phe Thr
85 90 95

Arg Arg Arg Glu Asp Phe Gln Tyr Phe Phe Gly Phe Ser Thr Leu Phe
100 105 110

Ser Gly Ile Leu Leu Leu Ser Thr Val Arg Leu Ala Asn His Asn Met
115 120 125

Gln Leu Arg Ile Ser Ser Thr Ile Val Ala Leu Ser Cys Leu Leu Asn
130 135 140

Asn Leu Tyr Leu Gln Asn Lys Val His Ser Leu Lys Ile Gln Lys Glu
145 150 155 160

Asn Leu Tyr Asn Glu Leu Ile Arg Asn Pro Lys Ser Glu Thr Thr Ile
165 170 175

Ala Glu Ile Lys Lys Asn Lys Lys Asp Phe His Ile Tyr His Gly Leu
180 185 190

Ser Leu Leu Ser Leu Tyr Ile Ser Phe Leu Gly Leu Thr Pro Tyr Ile
195 200 205

Phe Thr
210

<210> SEQ ID NO 74
<211> LENGTH: 210
<212> TYPE: PRT
<213> ORGANISM: Plasmodium vivax
<220> FEATURE:
<221> NAME/KEY: misc_feature
<223> OTHER INFORMATION: Ag40

<400> SEQUENCE: 74

Met Gly Ala Thr Val Ser Tyr Leu Arg Cys Val Thr Ser Ile Ala Gly
1 5 10 15

Leu Ser Ser Leu Val Leu Ser Leu Phe Pro Lys Leu Ile Met Lys Asn
20 25 30

Pro Gln Val Leu Arg Pro Leu Leu Asn Ile Ser Trp Gly Tyr Leu Phe
35 40 45

Gly Ser Thr Phe Trp Leu Cys Leu Phe Ser Glu Val Gly Leu Phe Arg
50 55 60

Ser Leu Lys Asn Met Lys Arg Ile Pro Ile Pro Glu Asn Ala Glu Glu
65 70 75 80

Ala Lys Lys Gln Leu Glu Glu Met Lys Ser Met Glu Gly Asp Phe Thr
85 90 95

Arg Arg Arg Glu Asp Phe Gln Tyr Phe Phe Gly Phe Ser Thr Leu Phe
100 105 110

Ser Gly Ile Leu Leu Leu Ser Thr Val Arg Leu Ala Asn His Asn Met
115 120 125

Gln Leu Arg Ile Ser Ser Thr Ile Val Ala Leu Ser Cys Leu Leu Asn
130 135 140

Asn Leu Tyr Leu Gln Asn Lys Val His Ser Leu Lys Ile Gln Lys Glu
145 150 155 160

Asn Leu Tyr Asn Glu Leu Ile Arg Asn Pro Lys Ser Glu Thr Thr Ile
165 170 175

Ala Glu Ile Lys Lys Asn Lys Lys Asp Phe His Ile Tyr His Gly Leu
180 185 190

```
Ser Leu Leu Ser Leu Tyr Ile Ser Phe Leu Gly Leu Thr Pro Tyr Ile
        195                 200                 205

Phe Thr
    210


<210> SEQ ID NO 75
<211> LENGTH: 1077
<212> TYPE: DNA
<213> ORGANISM: Plasmodium berghei
<220> FEATURE:
<221> NAME/KEY: misc_feature
<223> OTHER INFORMATION: Ag45

<400> SEQUENCE: 75

ggatccgcca ccatggcttc ttactcaaac tcttccatta agcagaaatc cgatagtgtg      60

agtgtctaca atactcggac tggaaatgtc agtaaaactc gcttgatccg tctgcaaaat     120

gggcattacc gtagagtggt cgacattagc aataaggacg agaaggagat tctcttcagg     180

acatgtgctt gcgcttgtcc aacacctcga aatgaggaga cacgcaaaac ctatatgcca     240

cctctgaaca atgtgtctac cgtagcgtat agaaagcgga tctattcttc ctttgggaat     300

aaggacggta acgatacagg caacaacgag agcataacag aacatgagga cccgattagg     360

accttttccg aaacgacaag taggcaggaa agtaccatcg acgacaaaac ggagactagc     420

atcaatagca aggaaacaga tgatggcaac cagtttggaa ggttgtttga agaactggag     480

gagaaagagg atgaactgat tgaggaaaag gaggaggagc tgatagaaga gaaggaggag     540

gaacttatag aggagaaaga agaagagctg atcgaagaga aagaggaaat cacccctgag     600

aacaaaaccc tcataatgcc ctctaaaact ctgatgaagg gcattaagac caacatttac     660

ttcctgtcaa acaaggaaaa gatccaagtg cttatgtgct ataactacaa gtgtgatgcc     720

gttgtgttcg agaaagacac ctttctgcgc tatctctaca tcaagagcat caataatatc     780

atcctgaacg aaagaatgat tgaacagttg tgcaagaacg aaaacctgaa gtacatcctt     840

gcctgcaaca gcatagtggt tgaatcaagc gacttcatca aacccctgat cattgagttt     900

gagtcatcca cttccaagaa catcttcgta aagcacatta agcacaatag ccagaaagaa     960

atggacatca acaagttcaa cgagtatatg cgggatctca aaagcaatga gaagctcaga    1020

ctgaagaaag tcgagcgatt ccactctatt aatctggcag ccaagaaatg actcgag       1077


<210> SEQ ID NO 76
<211> LENGTH: 352
<212> TYPE: PRT
<213> ORGANISM: Plasmodium berghei
<220> FEATURE:
<221> NAME/KEY: misc_feature
<223> OTHER INFORMATION: Ag45

<400> SEQUENCE: 76

Met Ala Ser Tyr Ser Asn Ser Ser Ile Lys Gln Lys Ser Asp Ser Val
1               5                   10                  15

Ser Val Tyr Asn Thr Arg Thr Gly Asn Val Ser Lys Thr Arg Leu Ile
            20                  25                  30

Arg Leu Gln Asn Gly His Tyr Arg Arg Val Val Asp Ile Ser Asn Lys
        35                  40                  45

Asp Glu Lys Glu Ile Leu Phe Arg Thr Cys Ala Cys Ala Cys Pro Thr
    50                  55                  60

Pro Arg Asn Glu Glu Thr Arg Lys Thr Tyr Met Pro Pro Leu Asn Asn
65                  70                  75                  80
```

Val Ser Thr Val Ala Tyr Arg Lys Arg Ile Tyr Ser Ser Phe Gly Asn
85 90 95

Lys Asp Gly Asn Asp Thr Gly Asn Asn Glu Ser Ile Thr Glu His Glu
100 105 110

Asp Pro Ile Arg Thr Phe Ser Glu Thr Thr Ser Arg Gln Glu Ser Thr
115 120 125

Ile Asp Asp Lys Thr Glu Thr Ser Ile Asn Ser Lys Glu Thr Asp Asp
130 135 140

Gly Asn Gln Phe Gly Arg Leu Phe Glu Glu Leu Glu Glu Lys Glu Asp
145 150 155 160

Glu Leu Ile Glu Glu Lys Glu Glu Glu Leu Ile Glu Glu Lys Glu Glu
165 170 175

Glu Leu Ile Glu Glu Lys Glu Glu Glu Leu Ile Glu Glu Lys Glu Glu
180 185 190

Ile Thr Pro Glu Asn Lys Thr Leu Ile Met Pro Ser Lys Thr Leu Met
195 200 205

Lys Gly Ile Lys Thr Asn Ile Tyr Phe Leu Ser Asn Lys Glu Lys Ile
210 215 220

Gln Val Leu Met Cys Tyr Asn Tyr Lys Cys Asp Ala Val Val Phe Glu
225 230 235 240

Lys Asp Thr Phe Leu Arg Tyr Leu Tyr Ile Lys Ser Ile Asn Asn Ile
245 250 255

Ile Leu Asn Glu Arg Met Ile Glu Gln Leu Cys Lys Asn Glu Asn Leu
260 265 270

Lys Tyr Ile Leu Ala Cys Asn Ser Ile Val Val Glu Ser Ser Asp Phe
275 280 285

Ile Lys Pro Leu Ile Ile Glu Phe Glu Ser Ser Thr Ser Lys Asn Ile
290 295 300

Phe Val Lys His Ile Lys His Asn Ser Gln Lys Glu Met Asp Ile Asn
305 310 315 320

Lys Phe Asn Glu Tyr Met Arg Asp Leu Lys Ser Asn Glu Lys Leu Arg
325 330 335

Leu Lys Lys Val Glu Arg Phe His Ser Ile Asn Leu Ala Ala Lys Lys
340 345 350

<210> SEQ ID NO 77
<211> LENGTH: 351
<212> TYPE: PRT
<213> ORGANISM: Plasmodium berghei
<220> FEATURE:
<221> NAME/KEY: misc_feature
<223> OTHER INFORMATION: Ag45

<400> SEQUENCE: 77

Met Ser Tyr Ser Asn Ser Ser Ile Lys Gln Lys Ser Asp Ser Val Ser
1 5 10 15

Val Tyr Asn Thr Arg Thr Gly Asn Val Ser Lys Thr Arg Leu Ile Arg
20 25 30

Leu Gln Asn Gly His Tyr Arg Arg Val Val Asp Ile Ser Asn Lys Asp
35 40 45

Glu Lys Glu Ile Leu Phe Arg Thr Cys Ala Cys Ala Cys Pro Thr Pro
50 55 60

Arg Asn Glu Glu Thr Arg Lys Thr Tyr Met Pro Pro Leu Asn Asn Val
65 70 75 80

```
Ser Thr Val Ala Tyr Arg Lys Arg Ile Tyr Ser Ser Phe Gly Asn Lys
                85                  90                  95

Asp Gly Asn Asp Thr Gly Asn Asn Glu Ser Ile Thr Glu His Glu Asp
            100                 105                 110

Pro Ile Arg Thr Phe Ser Glu Thr Thr Ser Arg Gln Glu Ser Thr Ile
        115                 120                 125

Asp Asp Lys Thr Glu Thr Ser Ile Asn Ser Lys Glu Thr Asp Asp Gly
    130                 135                 140

Asn Gln Phe Gly Arg Leu Phe Glu Glu Leu Glu Glu Lys Glu Asp Glu
145                 150                 155                 160

Leu Ile Glu Glu Lys Glu Glu Glu Leu Ile Glu Glu Lys Glu Glu Glu
                165                 170                 175

Leu Ile Glu Glu Lys Glu Glu Glu Leu Ile Glu Glu Lys Glu Glu Ile
            180                 185                 190

Thr Pro Glu Asn Lys Thr Leu Ile Met Pro Ser Lys Thr Leu Met Lys
        195                 200                 205

Gly Ile Lys Thr Asn Ile Tyr Phe Leu Ser Asn Lys Glu Lys Ile Gln
    210                 215                 220

Val Leu Met Cys Tyr Asn Tyr Lys Cys Asp Ala Val Val Phe Glu Lys
225                 230                 235                 240

Asp Thr Phe Leu Arg Tyr Leu Tyr Ile Lys Ser Ile Asn Asn Ile Ile
                245                 250                 255

Leu Asn Glu Arg Met Ile Glu Gln Leu Cys Lys Asn Glu Asn Leu Lys
            260                 265                 270

Tyr Ile Leu Ala Cys Asn Ser Ile Val Val Glu Ser Ser Asp Phe Ile
        275                 280                 285

Lys Pro Leu Ile Ile Glu Phe Glu Ser Ser Thr Ser Lys Asn Ile Phe
    290                 295                 300

Val Lys His Ile Lys His Asn Ser Gln Lys Glu Met Asp Ile Asn Lys
305                 310                 315                 320

Phe Asn Glu Tyr Met Arg Asp Leu Lys Ser Asn Glu Lys Leu Arg Leu
                325                 330                 335

Lys Lys Val Glu Arg Phe His Ser Ile Asn Leu Ala Ala Lys Lys
            340                 345                 350
```

<210> SEQ ID NO 78
<211> LENGTH: 1197
<212> TYPE: DNA
<213> ORGANISM: Artificial Sequence
<220> FEATURE:
<223> OTHER INFORMATION: PfAg45 human CO

<400> SEQUENCE: 78

```
gccaccatgg cttcagatta ctttacaatt ctgtccaata ttttcacaag cactagcctg     60

aagaagaaat acagttcccg gttgagcaca aaatccaaga agaaccaaaa gcgagtcaaa    120

ctgataagac tgcggaatgg acattttcgc cgaattgtgg atatttccaa cattgacgag    180

aagagcatct tccccagaag ctgtactttt gcgtcaatta gcagtgctag caaagaaaac    240

gagaggaaga attcaagcga ggacacaaaa gaacctcagg agaatctgta tggcaaatca    300

aacacttcaa gctctatcac gataaagatc aatttcgacg aaagcgatga gaacaagagt    360

gatcaggata accactctat cgataccatt agcgacatct cttttaccca gacttcacgc    420

aaatctcttg aaattgaaag taatacctat gagagttatc gcgaagtgga gaaggaggac    480

attgaggagg aggaggaaga ggagaaagaa gaagaatatg aggaggaaga agaagaagag    540
```

gaatacgaag aggaagagga agaagaggag gaagagtatg aggaggaggg tctgaaaacc 600
gaagaggaga aggaagaaga taataaggag gtagagccag aagaggagct taaagaagaa 660
gatgacaagg aggttgagcc tgaggaggag aaggagaatg agcagaagaa agaagaacaa 720
gaggagaata acctcgaagc tcccagcaaa acactgatga aaggggttaa gaccaacata 780
tacttcctgt ctaccaaaga gcggatagaa gcactcatgt gctacaacta catatccaac 840
gccattattt tcgaaaaggg caagtttctc cgttatatct tcatgaacaa tgtcaacaat 900
atcatcgtga acgagcacat gatcaatatg ttgtgcaaga aggaaaagat caaatacatc 960
ctgtcatcta actccatcat cattgaaagc aacgacttca tcaaaccgct catcattgag 1020
tttgacagta acatctctaa gaagatcttt gtcaaacact tgaaaatggt ggactccttc 1080
aaactggatg acaagctgta cagggagtac ctgaatgacc tttctgaaca tgagagggat 1140
agactgaaac atgtggagtc cttctattcc aatgccataa aggtgcacaa tacgtaa 1197

<210> SEQ ID NO 79
<211> LENGTH: 396
<212> TYPE: PRT
<213> ORGANISM: Plasmodium falciparum
<220> FEATURE:
<221> NAME/KEY: misc_feature
<223> OTHER INFORMATION: PfAg45

<400> SEQUENCE: 79

Met Ala Ser Asp Tyr Phe Thr Ile Leu Ser Asn Ile Phe Thr Ser Thr
1 5 10 15

Ser Leu Lys Lys Lys Tyr Ser Ser Arg Leu Ser Thr Lys Ser Lys Lys
20 25 30

Asn Gln Lys Arg Val Lys Leu Ile Arg Leu Arg Asn Gly His Phe Arg
35 40 45

Arg Ile Val Asp Ile Ser Asn Ile Asp Glu Lys Ser Ile Phe Pro Arg
50 55 60

Ser Cys Thr Phe Ala Ser Ile Ser Ser Ala Ser Lys Glu Asn Glu Arg
65 70 75 80

Lys Asn Ser Ser Glu Asp Thr Lys Glu Pro Gln Glu Asn Leu Tyr Gly
85 90 95

Lys Ser Asn Thr Ser Ser Ser Ile Thr Ile Lys Ile Asn Phe Asp Glu
100 105 110

Ser Asp Glu Asn Lys Ser Asp Gln Asp Asn His Ser Ile Asp Thr Ile
115 120 125

Ser Asp Ile Ser Phe Thr Gln Thr Ser Arg Lys Ser Leu Glu Ile Glu
130 135 140

Ser Asn Thr Tyr Glu Ser Tyr Arg Glu Val Glu Lys Glu Asp Ile Glu
145 150 155 160

Glu Glu Glu Glu Glu Glu Lys Glu Glu Glu Tyr Glu Glu Glu Glu Glu
165 170 175

Glu Glu Glu Tyr Glu Glu Glu Glu Glu Glu Glu Glu Glu Glu Tyr Glu
180 185 190

Glu Glu Gly Leu Lys Thr Glu Glu Glu Lys Glu Glu Asp Asn Lys Glu
195 200 205

Val Glu Pro Glu Glu Glu Leu Lys Glu Glu Asp Asp Lys Glu Val Glu
210 215 220

Pro Glu Glu Glu Lys Glu Asn Glu Gln Lys Lys Glu Glu Gln Glu Glu
225 230 235 240

```
Asn Asn Leu Glu Ala Pro Ser Lys Thr Leu Met Lys Gly Val Lys Thr
                245                 250                 255

Asn Ile Tyr Phe Leu Ser Thr Lys Glu Arg Ile Glu Ala Leu Met Cys
            260                 265                 270

Tyr Asn Tyr Ile Ser Asn Ala Ile Ile Phe Glu Lys Gly Lys Phe Leu
        275                 280                 285

Arg Tyr Ile Phe Met Asn Asn Val Asn Asn Ile Ile Val Asn Glu His
    290                 295                 300

Met Ile Asn Met Leu Cys Lys Lys Glu Lys Ile Lys Tyr Ile Leu Ser
305                 310                 315                 320

Ser Asn Ser Ile Ile Ile Glu Ser Asn Asp Phe Ile Lys Pro Leu Ile
                325                 330                 335

Ile Glu Phe Asp Ser Asn Ile Ser Lys Lys Ile Phe Val Lys His Leu
            340                 345                 350

Lys Met Val Asp Ser Phe Lys Leu Asp Asp Lys Leu Tyr Arg Glu Tyr
        355                 360                 365

Leu Asn Asp Leu Ser Glu His Glu Arg Asp Arg Leu Lys His Val Glu
    370                 375                 380

Ser Phe Tyr Ser Asn Ala Ile Lys Val His Asn Thr
385                 390                 395


<210> SEQ ID NO 80
<211> LENGTH: 395
<212> TYPE: PRT
<213> ORGANISM: Plasmodium falciparum
<220> FEATURE:
<221> NAME/KEY: misc_feature
<223> OTHER INFORMATION: Ag45

<400> SEQUENCE: 80

Met Ser Asp Tyr Phe Thr Ile Leu Ser Asn Ile Phe Thr Ser Thr Ser
1               5                   10                  15

Leu Lys Lys Lys Tyr Ser Ser Arg Leu Ser Thr Lys Ser Lys Lys Asn
            20                  25                  30

Gln Lys Arg Val Lys Leu Ile Arg Leu Arg Asn Gly His Phe Arg Arg
        35                  40                  45

Ile Val Asp Ile Ser Asn Ile Asp Glu Lys Ser Ile Phe Pro Arg Ser
    50                  55                  60

Cys Thr Phe Ala Ser Ile Ser Ser Ala Ser Lys Glu Asn Glu Arg Lys
65                  70                  75                  80

Asn Ser Ser Glu Asp Thr Lys Glu Pro Gln Glu Asn Leu Tyr Gly Lys
                85                  90                  95

Ser Asn Thr Ser Ser Ser Ile Thr Ile Lys Ile Asn Phe Asp Glu Ser
            100                 105                 110

Asp Glu Asn Lys Ser Asp Gln Asp Asn His Ser Ile Asp Thr Ile Ser
        115                 120                 125

Asp Ile Ser Phe Thr Gln Thr Ser Arg Lys Ser Leu Glu Ile Glu Ser
    130                 135                 140

Asn Thr Tyr Glu Ser Tyr Arg Glu Val Glu Lys Glu Asp Ile Glu Glu
145                 150                 155                 160

Glu Glu Glu Glu Glu Lys Glu Glu Glu Tyr Glu Glu Glu Glu Glu Glu
                165                 170                 175

Glu Glu Tyr Glu Glu Glu Glu Glu Glu Glu Glu Glu Glu Tyr Glu Glu
            180                 185                 190

Glu Gly Leu Lys Thr Glu Glu Glu Lys Glu Glu Asp Asn Lys Glu Val
        195                 200                 205
```

```
Glu Pro Glu Glu Glu Leu Lys Glu Glu Asp Asp Lys Glu Val Glu Pro
    210                 215                 220

Glu Glu Glu Lys Glu Asn Glu Gln Lys Lys Glu Glu Gln Glu Glu Asn
225                 230                 235                 240

Asn Leu Glu Ala Pro Ser Lys Thr Leu Met Lys Gly Val Lys Thr Asn
                245                 250                 255

Ile Tyr Phe Leu Ser Thr Lys Glu Arg Ile Glu Ala Leu Met Cys Tyr
            260                 265                 270

Asn Tyr Ile Ser Asn Ala Ile Ile Phe Glu Lys Gly Lys Phe Leu Arg
        275                 280                 285

Tyr Ile Phe Met Asn Asn Val Asn Asn Ile Ile Val Asn Glu His Met
    290                 295                 300

Ile Asn Met Leu Cys Lys Lys Glu Lys Ile Lys Tyr Ile Leu Ser Ser
305                 310                 315                 320

Asn Ser Ile Ile Ile Glu Ser Asn Asp Phe Ile Lys Pro Leu Ile Ile
                325                 330                 335

Glu Phe Asp Ser Asn Ile Ser Lys Lys Ile Phe Val Lys His Leu Lys
            340                 345                 350

Met Val Asp Ser Phe Lys Leu Asp Asp Lys Leu Tyr Arg Glu Tyr Leu
        355                 360                 365

Asn Asp Leu Ser Glu His Glu Arg Asp Arg Leu Lys His Val Glu Ser
    370                 375                 380

Phe Tyr Ser Asn Ala Ile Lys Val His Asn Thr
385                 390                 395
```

```
<210> SEQ ID NO 81
<211> LENGTH: 1122
<212> TYPE: DNA
<213> ORGANISM: Artificial Sequence
<220> FEATURE:
<223> OTHER INFORMATION: PvAg45 human CO + kozac

<400> SEQUENCE: 81

gccaccatgg ctaatttgag ttctcccctc ctggccttgc ccgaggaggg taagaagcga     60

agaacaaaac tcatccgact gaggaacggt cactataggc ggatagtgga catttcaaat    120

accgacgaac ggaagctcat tccttctatg tgccgctgcg cgtgtgtcac tcccagaaaa    180

gacgaagtgg agaatgaggg taagtgggaa gacgctaaga aagcaaaatc aagccaggaa    240

tatgatgaaa cttctgatta tgttgaatct gaaaagaaag agagctatat gctcgcagtc    300

aatgaggagg atcagacgga ggatatgtac tcaaagacga tcagctttac ttctataacc    360

cctacatcta taagatccga agagccagag ccaaggcgga aactctccct tctggatgtt    420

aaagaagaag aggaagagga ggaggaggaa gaagaagagg aagaagagga agaggaggaa    480

gaggaagagg aagaagagga agagaaagaa aaagaaaaag agaaggagga agaggaagaa    540

gaggaggagg aagaggaaga ggaagaggag gaggaagaag aagaggaaga tgaaatagaa    600

tctaccgcag aggaaaagga agaagagaag aagcaagtcc caccggaagg taagaaattg    660

atcgaaccct caaagaccct tatgagaggg actaagacca acatttattt tttgagtaat    720

aaggagatgg ttcaaactct gatgtgttat aattataatt gcaacgcagt ggtattcgaa    780

aaagacactt ttttgaggta tctgtacatg aagagcatca gcaacatcat cctcaacgaa    840

cgaatgatag atgaactgtg caaacaggaa gatcttaaat acgtgcttac aagcaatgct    900

atcgtgttgg aatctactga ctttcttaag cctcttataa ttgagtttga atccagtatt    960
```

```
agtaaaagag ttttcgtgcg ccacctgaag cataacgctc gcaaggaaat cgacatgaaa   1020

aaatatcatg attacatggg cgaacttaac gctaacgaga agattaggct gatgaaaatt   1080

gagcgatttc atagtttcaa caagatgatc caatgcaact ag                      1122


<210> SEQ ID NO 82
<211> LENGTH: 371
<212> TYPE: PRT
<213> ORGANISM: Plasmodium vivax
<220> FEATURE:
<221> NAME/KEY: misc_feature
<223> OTHER INFORMATION: PvAg45

<400> SEQUENCE: 82

Met Ala Asn Leu Ser Ser Pro Leu Leu Ala Leu Pro Glu Glu Gly Lys
1               5                   10                  15

Lys Arg Arg Thr Lys Leu Ile Arg Leu Arg Asn Gly His Tyr Arg Arg
            20                  25                  30

Ile Val Asp Ile Ser Asn Thr Asp Glu Arg Lys Leu Ile Pro Ser Met
        35                  40                  45

Cys Arg Cys Ala Cys Val Thr Pro Arg Lys Asp Glu Val Glu Asn Glu
    50                  55                  60

Gly Lys Trp Glu Asp Ala Lys Lys Ala Lys Ser Ser Gln Glu Tyr Asp
65                  70                  75                  80

Glu Thr Ser Asp Tyr Val Glu Ser Glu Lys Lys Glu Ser Tyr Met Leu
                85                  90                  95

Ala Val Asn Glu Glu Asp Gln Thr Glu Asp Met Tyr Ser Lys Thr Ile
            100                 105                 110

Ser Phe Thr Ser Ile Thr Pro Thr Ser Ile Arg Ser Glu Glu Pro Glu
        115                 120                 125

Pro Arg Arg Lys Leu Ser Leu Leu Asp Val Lys Glu Glu Glu Glu Glu
    130                 135                 140

Glu Glu Glu Glu Glu Glu Glu Glu Glu Glu Glu Glu Glu Glu Glu Glu
145                 150                 155                 160

Glu Glu Glu Glu Glu Glu Lys Glu Lys Glu Lys Glu Lys Glu Glu Glu
                165                 170                 175

Glu Glu Glu Glu Glu Glu Glu Glu Glu Glu Glu Glu Glu Glu Glu Glu
            180                 185                 190

Glu Glu Asp Glu Ile Glu Ser Thr Ala Glu Glu Lys Glu Glu Glu Lys
        195                 200                 205

Lys Gln Val Pro Pro Glu Gly Lys Lys Leu Ile Glu Pro Ser Lys Thr
    210                 215                 220

Leu Met Arg Gly Thr Lys Thr Asn Ile Tyr Phe Leu Ser Asn Lys Glu
225                 230                 235                 240

Met Val Gln Thr Leu Met Cys Tyr Asn Tyr Asn Cys Asn Ala Val Val
                245                 250                 255

Phe Glu Lys Asp Thr Phe Leu Arg Tyr Leu Tyr Met Lys Ser Ile Ser
            260                 265                 270

Asn Ile Ile Leu Asn Glu Arg Met Ile Asp Glu Leu Cys Lys Gln Glu
        275                 280                 285

Asp Leu Lys Tyr Val Leu Thr Ser Asn Ala Ile Val Leu Glu Ser Thr
    290                 295                 300

Asp Phe Leu Lys Pro Leu Ile Ile Glu Phe Glu Ser Ser Ile Ser Lys
305                 310                 315                 320

Arg Val Phe Val Arg His Leu Lys His Asn Ala Arg Lys Glu Ile Asp
                325                 330                 335
```

```
Met Lys Lys Tyr His Asp Tyr Met Gly Glu Leu Asn Ala Asn Glu Lys
            340                 345                 350

Ile Arg Leu Met Lys Ile Glu Arg Phe His Ser Phe Asn Lys Met Ile
        355                 360                 365

Gln Cys Asn
    370


<210> SEQ ID NO 83
<211> LENGTH: 345
<212> TYPE: PRT
<213> ORGANISM: Plasmodium vivax
<220> FEATURE:
<221> NAME/KEY: misc_feature
<223> OTHER INFORMATION: Ag45

<400> SEQUENCE: 83

Met Asn Leu Ser Ser Pro Leu Leu Ala Leu Pro Glu Glu Gly Lys Lys
1               5                   10                  15

Arg Arg Thr Lys Leu Ile Arg Leu Arg Asn Gly His Tyr Arg Arg Ile
            20                  25                  30

Val Asp Ile Ser Asn Thr Asp Glu Arg Lys Leu Ile Pro Ser Met Cys
        35                  40                  45

Arg Cys Ala Cys Val Thr Pro Arg Lys Asp Glu Val Glu Asn Glu Gly
    50                  55                  60

Lys Trp Glu Asp Ala Lys Lys Ala Lys Ser Ser Gln Glu Tyr Asp Glu
65                  70                  75                  80

Thr Ser Asp Tyr Val Glu Ser Glu Lys Lys Glu Ser Tyr Met Leu Ala
                85                  90                  95

Val Asn Glu Glu Asp Gln Thr Glu Asp Met Tyr Ser Lys Thr Ile Ser
            100                 105                 110

Phe Thr Ser Ile Thr Pro Thr Ser Ile Arg Ser Glu Glu Pro Glu Pro
        115                 120                 125

Arg Arg Lys Leu Ser Leu Leu Asp Val Lys Glu Glu Glu Glu Glu Glu
    130                 135                 140

Glu Glu Glu Glu Glu Glu Glu Glu Glu Glu Glu Glu Glu Glu Glu Glu
145                 150                 155                 160

Glu Lys Glu Glu Glu Glu Glu Glu Asp Glu Ile Glu Ser Thr Ala Glu
                165                 170                 175

Glu Lys Glu Glu Glu Lys Lys Gln Val Pro Pro Glu Gly Lys Lys Leu
            180                 185                 190

Ile Glu Pro Ser Lys Thr Leu Met Arg Gly Thr Lys Thr Asn Ile Tyr
        195                 200                 205

Phe Leu Ser Asn Lys Glu Met Val Gln Thr Leu Met Cys Tyr Asn Tyr
    210                 215                 220

Asn Cys Asn Ala Val Val Phe Glu Lys Asp Thr Phe Leu Arg Tyr Leu
225                 230                 235                 240

Tyr Met Lys Ser Ile Ser Asn Ile Ile Leu Asn Glu Arg Met Ile Asp
                245                 250                 255

Glu Leu Cys Lys Gln Glu Asp Leu Lys Tyr Val Leu Thr Ser Asn Ala
            260                 265                 270

Ile Val Leu Glu Ser Thr Asp Phe Leu Lys Pro Leu Ile Ile Glu Phe
        275                 280                 285

Glu Ser Ser Ile Ser Lys Arg Val Phe Val Arg His Leu Lys His Asn
    290                 295                 300
```

Ala Arg Lys Glu Ile Asp Met Lys Lys Tyr His Asp Tyr Met Gly Glu
305 310 315 320

Leu Asn Ala Asn Glu Lys Ile Arg Leu Met Lys Ile Glu Arg Phe His
325 330 335

Ser Phe Asn Lys Met Ile Gln Cys Asn
340 345

<210> SEQ ID NO 84
<211> LENGTH: 12
<212> TYPE: DNA
<213> ORGANISM: Artificial Sequence
<220> FEATURE:
<223> OTHER INFORMATION: Kozac consensus sequence

<400> SEQUENCE: 84
gccaccatgg ct 12

<210> SEQ ID NO 85
<211> LENGTH: 12
<212> TYPE: DNA
<213> ORGANISM: Artificial Sequence
<220> FEATURE:
<223> OTHER INFORMATION: Kozac consensus sequence

<400> SEQUENCE: 85
gccaccatgg cc 12

<210> SEQ ID NO 86
<211> LENGTH: 6
<212> TYPE: DNA
<213> ORGANISM: Artificial Sequence
<220> FEATURE:
<223> OTHER INFORMATION: BamHI site

<400> SEQUENCE: 86 ggatcc 6

<210> SEQ ID NO 87
<211> LENGTH: 6
<212> TYPE: DNA
<213> ORGANISM: Artificial Sequence
<220> FEATURE:
<223> OTHER INFORMATION: XhoI site

<400> SEQUENCE: 87 ctcgag 6

<210> SEQ ID NO 88
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 88

Gln Ala Gln Arg Asn Leu Asn Glu Leu
1 5

<210> SEQ ID NO 89
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 89

Ser Ala Leu Leu Asn Val Asp Asn Leu
1               5

<210> SEQ ID NO 90
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 90

Lys Ser Pro Ser Asn Phe Thr Ile Ile
1               5

<210> SEQ ID NO 91
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 91

Ser Asn Gln Thr Asn Gln Glu Thr Ile
1               5

<210> SEQ ID NO 92
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 92

Ile Thr Pro Glu Asn Lys Thr Leu Ile
1               5

<210> SEQ ID NO 93
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 93

Lys Leu Ile Ala Asn Asn Pro Ser Leu
1               5

<210> SEQ ID NO 94
<211> LENGTH: 9
<212> TYPE: PRT
<213> ORGANISM: Artificial Sequence
<220> FEATURE:
<223> OTHER INFORMATION: CD8 T cell epitope

<400> SEQUENCE: 94

Ser Cys Ile Leu Asn Asn Met Tyr Phe
1               5

<210> SEQ ID NO 95
<211> LENGTH: 372
<212> TYPE: DNA
<213> ORGANISM: Artificial Sequence
<220> FEATURE:
<223> OTHER INFORMATION: DNA sequence of PD Plasmodium berghei ANKA
      18-10NT

<400> SEQUENCE: 95
ggatccgcca ccatggacaa tgacatctac agcttcgaca ttgtcaatga gacaaattgg 60
ctgaagatcg ccaagaacat cttcaaaggc aagtctccta gcaatttcac gatcataccg 120
tttaacaata ccggtagttc taacgataac gagtcaaaca aggaggaatc agtactgctg 180
atcagaaaga agatcaaaag caacaagaat cacgatagtt ccatcattag tggtgacact 240
gttaacgggg acattagtga cctgaattat acggctagca acttttccga taactctgag 300
gacatagaag ataaccagaa atatcccaca accagctaca atagtttcaa ccatctcaat 360
tcctgactcg ag 372

<210> SEQ ID NO 96
<211> LENGTH: 117
<212> TYPE: PRT
<213> ORGANISM: Artificial Sequence
<220> FEATURE:
<223> OTHER INFORMATION: Amino acid sequence of PD Plasmodium berghei ANKA 18-10NT

<400> SEQUENCE: 96

Met Asp Asn Asp Ile Tyr Ser Phe Asp Ile Val Asn Glu Thr Asn Trp
1 5 10 15

Leu Lys Ile Ala Lys Asn Ile Phe Lys Gly Lys Ser Pro Ser Asn Phe
20 25 30

Thr Ile Ile Pro Phe Asn Asn Thr Gly Ser Ser Asn Asp Asn Glu Ser
35 40 45

Asn Lys Glu Glu Ser Val Leu Leu Ile Arg Lys Lys Ile Lys Ser Asn
50 55 60

Lys Asn His Asp Ser Ser Ile Ile Ser Gly Asp Thr Val Asn Gly Asp
65 70 75 80

Ile Ser Asp Leu Asn Tyr Thr Ala Ser Asn Phe Ser Asp Asn Ser Glu
85 90 95

Asp Ile Glu Asp Asn Gln Lys Tyr Pro Thr Thr Ser Tyr Asn Ser Phe
100 105 110

Asn His Leu Asn Ser
115

<210> SEQ ID NO 97
<211> LENGTH: 528
<212> TYPE: DNA
<213> ORGANISM: Artificial Sequence
<220> FEATURE:
<223> OTHER INFORMATION: DNA sequence of PD Plasmodium berghei ANKA 18-10CT

<400> SEQUENCE: 97
ggatccgcca ccatggctct cactggggac gagaaatgtg gtaaaagcct gaagctcggc 60
aacatcagca atcagacaaa ccaggaaacc ataacccaaa gcctgtcagt tggagagatt 120
ctgtgcattg acctcgaagg gaatgcagga acaggctatc tgtgggtgtt gctgggcata 180
cacaaggatg agccaatcat aaaccccgag aacttcccaa ccaaactgac aaagaagtct 240
ttcttttccg aggaaataag tgtgactcag ccaaagaagt acaagatcga tgagcatgat 300
tcttcaaaga atgtgaatcg cgaaatcgaa agccctgaac agaaggagtc cgactcaaag 360
cccaagaaac ctcagatgca acttcttgga ggaccagatc ggatgaggtc agtcatcaaa 420
ggacacaaac ctggcaaata ttacattgtg tactcttact atcgaccgtt ttctcccact 480
tctggggcga acactaaaat catttacgtc acagtacagt gactcgag 528

<210> SEQ ID NO 98
<211> LENGTH: 169
<212> TYPE: PRT
<213> ORGANISM: Artificial Sequence
<220> FEATURE:
<223> OTHER INFORMATION: Amino acid sequence of PD Plasmodium berghei
ANKA 18-10CT

<400> SEQUENCE: 98

```
Met Ala Leu Thr Gly Asp Glu Lys Cys Gly Lys Ser Leu Lys Leu Gly
1               5                   10                  15

Asn Ile Ser Asn Gln Thr Asn Gln Glu Thr Ile Thr Gln Ser Leu Ser
            20                  25                  30

Val Gly Glu Ile Leu Cys Ile Asp Leu Glu Gly Asn Ala Gly Thr Gly
        35                  40                  45

Tyr Leu Trp Val Leu Leu Gly Ile His Lys Asp Glu Pro Ile Ile Asn
    50                  55                  60

Pro Glu Asn Phe Pro Thr Lys Leu Thr Lys Lys Ser Phe Phe Ser Glu
65                  70                  75                  80

Glu Ile Ser Val Thr Gln Pro Lys Lys Tyr Lys Ile Asp Glu His Asp
                85                  90                  95

Ser Ser Lys Asn Val Asn Arg Glu Ile Glu Ser Pro Glu Gln Lys Glu
            100                 105                 110

Ser Asp Ser Lys Pro Lys Lys Pro Gln Met Gln Leu Leu Gly Gly Pro
        115                 120                 125

Asp Arg Met Arg Ser Val Ile Lys Gly His Lys Pro Gly Lys Tyr Tyr
    130                 135                 140

Ile Val Tyr Ser Tyr Tyr Arg Pro Phe Ser Pro Thr Ser Gly Ala Asn
145                 150                 155                 160

Thr Lys Ile Ile Tyr Val Thr Val Gln
                165
```

<210> SEQ ID NO 99
<211> LENGTH: 1197
<212> TYPE: DNA
<213> ORGANISM: Artificial Sequence
<220> FEATURE:
<223> OTHER INFORMATION: DNA sequence of PD Plasmodium falciparum 3D7
18-10 -SP

<400> SEQUENCE: 99

```
ggatccgcca ccatggacaa caacagctac agcttcgaga tcgtgaaccg cagcacctgg      60

ctgaacatcg ccgagcgcat cttcaagggc aacgccccct tcaacttcac catcatcccc     120

tacaactacg tgaacaacag caccgaggag aacaacaaca aggacagcgt gctgctgatc     180

agcaagaacc tgaagaacag cagcaacccc gtggacgaga acaaccacat catcgacagc     240

accaagaaga acaccagcaa caacaacaac aacaacagca acatcgtggg catctacgag     300

agccaggtgc acgaggagaa gatcaaggag gacaacaccc gccaggacaa catcaacaag     360

aaggagaacg agatcatcaa caacaaccac cagatccccg tgagcaacat cttcagcgag     420

aacatcgaca acaacaagaa ctacatcgag agcaactaca agagcaccta caacaacaac     480

cccgagctga tccacagcac cgacttcatc ggcagcaaca acaaccacac cttcaacttc     540

ctgagccgct acaacaacag cgtgctgaac aacatgcagg gcaacaccaa ggtgcccggc     600

aacgtgcccg agctgaaggc ccgcatcttc agcgaggagg agaacaccga ggtggagagc     660

gccgagaaca accacaccaa cagcctgaac cccaacgaga gctgcgacca gatcatcaag     720
```

```
ctgggcgaca tcatcaacag cgtgaacgag aagatcatca gcatcaacag caccgtgaac    780

aacgtgctgt gcatcaacct ggacagcgtg aacggcaacg gcttcgtgtg gaccctgctg    840

ggcgtgcaca agaagaagcc cctgatcgac cccagcaact tccccaccaa gcgcgtgacc    900

cagagctacg tgagccccga catcagcgtg accaaccccg tgcccatccc caagaacagc    960

aacaccaaca aggacgacag catcaacaac aagcaggacg gcagccagaa caacaccacc   1020

accaaccact tccccaagcc ccgcgagcag ctggtgggcg gcagcagcat gctgatcagc   1080

aagatcaagc cccacaagcc cggcaagtac ttcatcgtgt acagctacta ccgcccccttc  1140

gaccccaccc gcgacaccaa cacccgcatc gtggagctga acgtgcagtg actcgag      1197
```

<210> SEQ ID NO 100
<211> LENGTH: 392
<212> TYPE: PRT
<213> ORGANISM: Artificial Sequence
<220> FEATURE:
<223> OTHER INFORMATION: Amino acid sequence of PD Plasmodium falciparum
      3D7 18-10 -SP

<400> SEQUENCE: 100

```
Met Asp Asn Asn Ser Tyr Ser Phe Glu Ile Val Asn Arg Ser Thr Trp
1               5                   10                  15

Leu Asn Ile Ala Glu Arg Ile Phe Lys Gly Asn Ala Pro Phe Asn Phe
            20                  25                  30

Thr Ile Ile Pro Tyr Asn Tyr Val Asn Asn Ser Thr Glu Glu Asn Asn
        35                  40                  45

Asn Lys Asp Ser Val Leu Leu Ile Ser Lys Asn Leu Lys Asn Ser Ser
    50                  55                  60

Asn Pro Val Asp Glu Asn Asn His Ile Ile Asp Ser Thr Lys Lys Asn
65                  70                  75                  80

Thr Ser Asn Asn Asn Asn Asn Asn Ser Asn Ile Val Gly Ile Tyr Glu
                85                  90                  95

Ser Gln Val His Glu Glu Lys Ile Lys Glu Asp Asn Thr Arg Gln Asp
            100                 105                 110

Asn Ile Asn Lys Lys Glu Asn Glu Ile Ile Asn Asn Asn His Gln Ile
        115                 120                 125

Pro Val Ser Asn Ile Phe Ser Glu Asn Ile Asp Asn Asn Lys Asn Tyr
    130                 135                 140

Ile Glu Ser Asn Tyr Lys Ser Thr Tyr Asn Asn Asn Pro Glu Leu Ile
145                 150                 155                 160

His Ser Thr Asp Phe Ile Gly Ser Asn Asn Asn His Thr Phe Asn Phe
                165                 170                 175

Leu Ser Arg Tyr Asn Asn Ser Val Leu Asn Asn Met Gln Gly Asn Thr
            180                 185                 190

Lys Val Pro Gly Asn Val Pro Glu Leu Lys Ala Arg Ile Phe Ser Glu
        195                 200                 205

Glu Glu Asn Thr Glu Val Glu Ser Ala Glu Asn Asn His Thr Asn Ser
    210                 215                 220

Leu Asn Pro Asn Glu Ser Cys Asp Gln Ile Ile Lys Leu Gly Asp Ile
225                 230                 235                 240

Ile Asn Ser Val Asn Glu Lys Ile Ile Ser Ile Asn Ser Thr Val Asn
                245                 250                 255

Asn Val Leu Cys Ile Asn Leu Asp Ser Val Asn Gly Asn Gly Phe Val
            260                 265                 270
```

```
Trp Thr Leu Leu Gly Val His Lys Lys Lys Pro Leu Ile Asp Pro Ser
        275                 280                 285

Asn Phe Pro Thr Lys Arg Val Thr Gln Ser Tyr Val Ser Pro Asp Ile
    290                 295                 300

Ser Val Thr Asn Pro Val Pro Ile Pro Lys Asn Ser Asn Thr Asn Lys
305                 310                 315                 320

Asp Asp Ser Ile Asn Asn Lys Gln Asp Gly Ser Gln Asn Asn Thr Thr
                325                 330                 335

Thr Asn His Phe Pro Lys Pro Arg Glu Gln Leu Val Gly Gly Ser Ser
            340                 345                 350

Met Leu Ile Ser Lys Ile Lys Pro His Lys Pro Gly Lys Tyr Phe Ile
        355                 360                 365

Val Tyr Ser Tyr Tyr Arg Pro Phe Asp Pro Thr Arg Asp Thr Asn Thr
    370                 375                 380

Arg Ile Val Glu Leu Asn Val Gln
385                 390


<210> SEQ ID NO 101
<211> LENGTH: 528
<212> TYPE: DNA
<213> ORGANISM: Artificial Sequence
<220> FEATURE:
<223> OTHER INFORMATION: DNA sequence of PD Plasmodium berghei ANKA
      11-10CT

<400> SEQUENCE: 101

ggatccgcca ccatggctct gatcgaagag aaagaggaaa tcacccctga gaacaaaacc      60

ctcataatgc cctctaaaac tctgatgaag ggcattaaga ccaacattta cttcctgtca     120

aacaaggaaa agatccaagt gcttatgtgc tataactaca agtgtgatgc cgttgtgttc     180

gagaaagaca cctttctgcg ctatctctac atcaagagca tcaataatat catcctgaac     240

gaaagaatga ttgaacagtt gtgcaagaac gaaaacctga agtacatcct tgcctgcaac     300

agcatagtgg ttgaatcaag cgacttcatc aaacccctga tcattgagtt tgagtcatcc     360

acttccaaga acatcttcgt aaagcacatt aagcacaata gccagaaaga aatggacatc     420

aacaagttca acgagtatat gcgggatctc aaaagcaatg agaagctcag actgaagaaa     480

gtcgagcgat tccactctat taatctggca gccaagaaat gactcgag                  528


<210> SEQ ID NO 102
<211> LENGTH: 169
<212> TYPE: PRT
<213> ORGANISM: Artificial Sequence
<220> FEATURE:
<223> OTHER INFORMATION: Amino acid sequence of PD Plasmodium berghei
      ANKA 11-10CT

<400> SEQUENCE: 102

Met Ala Leu Ile Glu Glu Lys Glu Glu Ile Thr Pro Glu Asn Lys Thr
1               5                   10                  15

Leu Ile Met Pro Ser Lys Thr Leu Met Lys Gly Ile Lys Thr Asn Ile
            20                  25                  30

Tyr Phe Leu Ser Asn Lys Glu Lys Ile Gln Val Leu Met Cys Tyr Asn
        35                  40                  45

Tyr Lys Cys Asp Ala Val Val Phe Glu Lys Asp Thr Phe Leu Arg Tyr
    50                  55                  60

Leu Tyr Ile Lys Ser Ile Asn Asn Ile Ile Leu Asn Glu Arg Met Ile
65                  70                  75                  80
```

```
Glu Gln Leu Cys Lys Asn Glu Asn Leu Lys Tyr Ile Leu Ala Cys Asn
                85                  90                  95

Ser Ile Val Val Glu Ser Ser Asp Phe Ile Lys Pro Leu Ile Ile Glu
            100                 105                 110

Phe Glu Ser Ser Thr Ser Lys Asn Ile Phe Val Lys His Ile Lys His
        115                 120                 125

Asn Ser Gln Lys Glu Met Asp Ile Asn Lys Phe Asn Glu Tyr Met Arg
    130                 135                 140

Asp Leu Lys Ser Asn Glu Lys Leu Arg Leu Lys Lys Val Glu Arg Phe
145                 150                 155                 160

His Ser Ile Asn Leu Ala Ala Lys Lys
                165
```

<210> SEQ ID NO 103
<211> LENGTH: 561
<212> TYPE: DNA
<213> ORGANISM: Artificial Sequence
<220> FEATURE:
<223> OTHER INFORMATION: DNA sequence of PD Plasmodium falciparum 3D7 11-10CT

<400> SEQUENCE: 103

```
ggatccgcca ccatggagga ggacgacaag gaggtggagc ccgaggagga gaaggagaac      60

gagcagaaga aggaggagca ggaggagaac aacctggagg cccccagcaa gaccctgatg     120

aagggcgtga agaccaacat ctacttcctg agcaccaagg agcgcatcga ggccctgatg     180

tgctacaact acatcagcaa cgccatcatc ttcgagaagg gcaagttcct gcgctacatc     240

ttcatgaaca acgtgaacaa catcatcgtg aacgagcaca tgatcaacat gctgtgcaag     300

aaggagaaga tcaagtacat cctgagcagc aacagcatca tcatcgagag caacgacttc     360

atcaagcccc tgatcatcga gttcgacagc aacatcagca agaagatctt cgtgaagcac     420

ctgaagatgg tggacagctt caagctggac gacaagctgt accgcgagta cctgaacgac     480

ctgagcgagc acgagcgcga ccgcctgaag cacgtggaga gcttctacag caacgccatc     540

aaggtgcaca actgactcga g                                               561
```

<210> SEQ ID NO 104
<211> LENGTH: 180
<212> TYPE: PRT
<213> ORGANISM: Artificial Sequence
<220> FEATURE:
<223> OTHER INFORMATION: Amino acid sequence of PD Plasmodium falciparum 3D7 11-10CT

<400> SEQUENCE: 104

```
Met Glu Glu Asp Asp Lys Glu Val Glu Pro Glu Glu Glu Lys Glu Asn
1               5                   10                  15

Glu Gln Lys Lys Glu Glu Gln Glu Glu Asn Asn Leu Glu Ala Pro Ser
            20                  25                  30

Lys Thr Leu Met Lys Gly Val Lys Thr Asn Ile Tyr Phe Leu Ser Thr
        35                  40                  45

Lys Glu Arg Ile Glu Ala Leu Met Cys Tyr Asn Tyr Ile Ser Asn Ala
    50                  55                  60

Ile Ile Phe Glu Lys Gly Lys Phe Leu Arg Tyr Ile Phe Met Asn Asn
65                  70                  75                  80

Val Asn Asn Ile Ile Val Asn Glu His Met Ile Asn Met Leu Cys Lys
                85                  90                  95
```

Lys Glu Lys Ile Lys Tyr Ile Leu Ser Ser Asn Ser Ile Ile Ile Glu
100 105 110

Ser Asn Asp Phe Ile Lys Pro Leu Ile Ile Glu Phe Asp Ser Asn Ile
115 120 125

Ser Lys Lys Ile Phe Val Lys His Leu Lys Met Val Asp Ser Phe Lys
130 135 140

Leu Asp Asp Lys Leu Tyr Arg Glu Tyr Leu Asn Asp Leu Ser Glu His
145 150 155 160

Glu Arg Asp Arg Leu Lys His Val Glu Ser Phe Tyr Ser Asn Ala Ile
165 170 175

Lys Val His Asn
180

<210> SEQ ID NO 105
<211> LENGTH: 747
<212> TYPE: DNA
<213> ORGANISM: Artificial Sequence
<220> FEATURE:
<223> OTHER INFORMATION: DNA sequence of PD Plasmodium berghei ANKA TRAP NT

<400> SEQUENCE: 105
ggatccgcca ccatggctaa cggtcaggag attctggacg aaatcaagta ctctgaggag 60
gtctgcaacg aacaaatcga tctccacatt ctgctggatg ggagtggcag cataggtcac 120
tctaactgga tcagtcacgt gatacccatg ctgacaaccc ttgtggacaa tttgaacatc 180
agccgcgatg agatcaatat ctccatgacc ttgttctcca cttatgccag ggaacttgtg 240
agacttaaga gatatgggtc tacaagcaaa gccagtctga ggttcatcat cgcgcaactc 300
cagaataact attctcctca tggaacgaca aatctgacta gcgccctgtt gaatgtggac 360
aatctcattc agaagaaaat gaatcgccct aatgccattc agctcgtgat tatccttact 420
gacggcatcc ctaacaatct gaagaagtcc actactgttg tcaaccagct gaagaagaag 480
gacgtcaatg tcgctattat tggtgttggc gccggagtaa acaatatgtt taaccgtata 540
ttggtaggat gtggaaaact tgggccttgt ccctactact cttatggctc ttgggatcaa 600
gcacaaacca tgatcaaacc atttctctca aaggtctgtc aggaagtgga gaaagtggca 660
ctgtgcggta agtgggagga gtggagtgag tgttcaacca cttgcgacaa cggaacgaaa 720
ataaggaagc gaaaggtttg actcgag 747

<210> SEQ ID NO 106
<211> LENGTH: 242
<212> TYPE: PRT
<213> ORGANISM: Artificial Sequence
<220> FEATURE:
<223> OTHER INFORMATION: Amino acid sequence of PD Plasmodium berghei ANKA TRAP NT

<400> SEQUENCE: 106

Met Ala Asn Gly Gln Glu Ile Leu Asp Glu Ile Lys Tyr Ser Glu Glu
1 5 10 15

Val Cys Asn Glu Gln Ile Asp Leu His Ile Leu Leu Asp Gly Ser Gly
20 25 30

Ser Ile Gly His Ser Asn Trp Ile Ser His Val Ile Pro Met Leu Thr
35 40 45

Thr Leu Val Asp Asn Leu Asn Ile Ser Arg Asp Glu Ile Asn Ile Ser
50 55 60

```
Met Thr Leu Phe Ser Thr Tyr Ala Arg Glu Leu Val Arg Leu Lys Arg
65                  70                  75                  80

Tyr Gly Ser Thr Ser Lys Ala Ser Leu Arg Phe Ile Ile Ala Gln Leu
                85                  90                  95

Gln Asn Asn Tyr Ser Pro His Gly Thr Thr Asn Leu Thr Ser Ala Leu
            100                 105                 110

Leu Asn Val Asp Asn Leu Ile Gln Lys Lys Met Asn Arg Pro Asn Ala
        115                 120                 125

Ile Gln Leu Val Ile Ile Leu Thr Asp Gly Ile Pro Asn Asn Leu Lys
    130                 135                 140

Lys Ser Thr Thr Val Val Asn Gln Leu Lys Lys Lys Asp Val Asn Val
145                 150                 155                 160

Ala Ile Ile Gly Val Gly Ala Gly Val Asn Asn Met Phe Asn Arg Ile
                165                 170                 175

Leu Val Gly Cys Gly Lys Leu Gly Pro Cys Pro Tyr Tyr Ser Tyr Gly
            180                 185                 190

Ser Trp Asp Gln Ala Gln Thr Met Ile Lys Pro Phe Leu Ser Lys Val
        195                 200                 205

Cys Gln Glu Val Glu Lys Val Ala Leu Cys Gly Lys Trp Glu Glu Trp
    210                 215                 220

Ser Glu Cys Ser Thr Thr Cys Asp Asn Gly Thr Lys Ile Arg Lys Arg
225                 230                 235                 240

Lys Val


<210> SEQ ID NO 107
<211> LENGTH: 903
<212> TYPE: DNA
<213> ORGANISM: Artificial Sequence
<220> FEATURE:
<223> OTHER INFORMATION: DNA sequence of PD Plasmodium falciparum 3D7
      TRAP NT

<400> SEQUENCE: 107

ggatccgcca ccatggacgt gcagaacaac atcgtggacg agatcaagta ccgcgaggag      60

gtgtgcaacg acgaggtgga cctgtacctg ctgatggact gcagcggcag catccgccgc     120

cacaactggg tgaaccacgc cgtgcccctg gccatgaagc tgatccagca gctgaacctg     180

aacgacaacg ccatccacct gtacgccagc gtgttcagca acaacgcccg cgagatcatc     240

cgcctgcaca gcgacgccag caagaacaag gagaaggccc tgatcatcat caagagcctg     300

ctgagcacca acctgcccta cggcaagacc aacctgaccg acgccctgct gcaggtgcgc     360

aagcacctga acgaccgcat caaccgcgag aacgccaacc agctggtggt gatcctgacc     420

gacggcatcc ccgacagcat ccaggacagc ctgaaggaga gccgcaagct gagcgaccgc     480

ggcgtgaaga tcgccgtgtt cggcatcggc cagggcatca acgtggcctt caaccgcttc     540

ctggtgggct gccaccccag cgacggcaag tgcaacctgt acgccgacag cgcctgggag     600

aacgtgaaga acgtgatcgg cccccttcatg aaggccgtgt gcgtggaggt ggagaagacc     660

gccagctgcg gcgtgtggga cgagtggagc ccctgcagcg tgacctgcgg caagggcacc     720

cgcagccgca agcgcgagat cctgcacgag ggctgcacca gcgagctgca ggagcagtgc     780

gaggaggagc gctgcctgcc caagcgcgag cccctggacg tgcccgacga gcccgaggac     840

gaccagcccc gcccccgcgg cgacaacttc gccgtggaga agcccaacga gaactgactc     900

gag                                                                   903
```

<210> SEQ ID NO 108
<211> LENGTH: 294
<212> TYPE: PRT
<213> ORGANISM: Artificial Sequence
<220> FEATURE:
<223> OTHER INFORMATION: Amino acid sequence of PD Plasmodium falciparum 3D7 TRAP NT

<400> SEQUENCE: 108

```
Met Asp Val Gln Asn Asn Ile Val Asp Glu Ile Lys Tyr Arg Glu Glu
1               5                   10                  15

Val Cys Asn Asp Glu Val Asp Leu Tyr Leu Leu Met Asp Cys Ser Gly
            20                  25                  30

Ser Ile Arg Arg His Asn Trp Val Asn His Ala Val Pro Leu Ala Met
        35                  40                  45

Lys Leu Ile Gln Gln Leu Asn Leu Asn Asp Asn Ala Ile His Leu Tyr
    50                  55                  60

Ala Ser Val Phe Ser Asn Asn Ala Arg Glu Ile Ile Arg Leu His Ser
65                  70                  75                  80

Asp Ala Ser Lys Asn Lys Glu Lys Ala Leu Ile Ile Ile Lys Ser Leu
                85                  90                  95

Leu Ser Thr Asn Leu Pro Tyr Gly Lys Thr Asn Leu Thr Asp Ala Leu
            100                 105                 110

Leu Gln Val Arg Lys His Leu Asn Asp Arg Ile Asn Arg Glu Asn Ala
        115                 120                 125

Asn Gln Leu Val Val Ile Leu Thr Asp Gly Ile Pro Asp Ser Ile Gln
    130                 135                 140

Asp Ser Leu Lys Glu Ser Arg Lys Leu Ser Asp Arg Gly Val Lys Ile
145                 150                 155                 160

Ala Val Phe Gly Ile Gly Gln Gly Ile Asn Val Ala Phe Asn Arg Phe
                165                 170                 175

Leu Val Gly Cys His Pro Ser Asp Gly Lys Cys Asn Leu Tyr Ala Asp
            180                 185                 190

Ser Ala Trp Glu Asn Val Lys Asn Val Ile Gly Pro Phe Met Lys Ala
        195                 200                 205

Val Cys Val Glu Val Glu Lys Thr Ala Ser Cys Gly Val Trp Asp Glu
    210                 215                 220

Trp Ser Pro Cys Ser Val Thr Cys Gly Lys Gly Thr Arg Ser Arg Lys
225                 230                 235                 240

Arg Glu Ile Leu His Glu Gly Cys Thr Ser Glu Leu Gln Glu Gln Cys
                245                 250                 255

Glu Glu Glu Arg Cys Leu Pro Lys Arg Glu Pro Leu Asp Val Pro Asp
            260                 265                 270

Glu Pro Glu Asp Asp Gln Pro Arg Pro Arg Gly Asp Asn Phe Ala Val
        275                 280                 285

Glu Lys Pro Asn Glu Asn
    290
```

<210> SEQ ID NO 109
<211> LENGTH: 654
<212> TYPE: DNA
<213> ORGANISM: Artificial Sequence
<220> FEATURE:
<223> OTHER INFORMATION: DNA sequence of PD Plasmodium berghei ANKA 11-09

<400> SEQUENCE: 109
ggatccgcca ccatggctgg ggcgagtatg agccacttgc agtgtctgac atctgttgct 60
ggtctgtcct ctatcgtcat gtcaatgttc cccaaactca ttgccaataa tccttccctg 120
tttagaccac tgctcaacat ttcctgggga tatctgttcg gaagcactgt atggctgtgc 180
ttcttcagtg agattgggtt ggtcaggaga atcaatgctc ctaaacggaa gaatctgcca 240
gagaatgcag aacaagccaa agaacagctg aaggagatca agaacaacga aggcgatttt 300
aaccgacgca atatcgactt caagtacttc tttagccttt ccacaatctt ctctagcata 360
ctgctgctta gcacagtgaa actcgccaac aacaatctgc agttgaggat ctgttccacc 420
attgtgtcac tgagttgcat actgaacaat atgtactttc agaacaagat acactcactt 480
gcactgaaga aagagagtct ctttaaggac atgatcgatc gtccgaaaga taccactatt 540
ctggtgaacc tgaagaagaa caagaccgac tttcacatcc atcatggcct ttctctgctc 600
ttgctctata gcagcttctt tggcctcact ccctacattt tcacgtgact cgag 654

<210> SEQ ID NO 110
<211> LENGTH: 211
<212> TYPE: PRT
<213> ORGANISM: Artificial Sequence
<220> FEATURE:
<223> OTHER INFORMATION: Amino acid sequence of PD Plasmodium berghei ANKA 11-09

<400> SEQUENCE: 110

Met Ala Gly Ala Ser Met Ser His Leu Gln Cys Leu Thr Ser Val Ala
1 5 10 15

Gly Leu Ser Ser Ile Val Met Ser Met Phe Pro Lys Leu Ile Ala Asn
20 25 30

Asn Pro Ser Leu Phe Arg Pro Leu Leu Asn Ile Ser Trp Gly Tyr Leu
35 40 45

Phe Gly Ser Thr Val Trp Leu Cys Phe Phe Ser Glu Ile Gly Leu Val
50 55 60

Arg Arg Ile Asn Ala Pro Lys Arg Lys Asn Leu Pro Glu Asn Ala Glu
65 70 75 80

Gln Ala Lys Glu Gln Leu Lys Glu Ile Lys Asn Asn Glu Gly Asp Phe
85 90 95

Asn Arg Arg Asn Ile Asp Phe Lys Tyr Phe Phe Ser Leu Ser Thr Ile
100 105 110

Phe Ser Ser Ile Leu Leu Leu Ser Thr Val Lys Leu Ala Asn Asn Asn
115 120 125

Leu Gln Leu Arg Ile Cys Ser Thr Ile Val Ser Leu Ser Cys Ile Leu
130 135 140

Asn Asn Met Tyr Phe Gln Asn Lys Ile His Ser Leu Ala Leu Lys Lys
145 150 155 160

Glu Ser Leu Phe Lys Asp Met Ile Asp Arg Pro Lys Asp Thr Thr Ile
165 170 175

Leu Val Asn Leu Lys Lys Asn Lys Thr Asp Phe His Ile His His Gly
180 185 190

Leu Ser Leu Leu Leu Leu Tyr Ser Ser Phe Phe Gly Leu Thr Pro Tyr
195 200 205

Ile Phe Thr
210

<210> SEQ ID NO 111
<211> LENGTH: 642
<212> TYPE: DNA
<213> ORGANISM: Artificial Sequence
<220> FEATURE:
<223> OTHER INFORMATION: DNA sequence of PD Plasmodium falciparum 3D7 11-09

<400> SEQUENCE: 111

```
ggatccgcca ccatggctag caacctgaag tgcgtgacca acgtggccgg cctggccagc     60

ctggtgatca gcctgttccc caagctgatc atcaagaacc cccaggtgct gcgcccccctg    120

ctgaacgtga gctggggcta cctgttcggc agcaccttct ggctgtgctt cttcagcgag    180

gtgggcctgc tgcgcagcct gaagaacatg aagggcgtgc ccctgcccga gagcgccagc    240

gaggccaaga agctgctgga ggagatgaag aacagcgagg gcgacttcaa ccgccgcagc    300

ctggacttcc agtacttctt cagcctggcc accctgttca gcggcatcct gctgctgagc    360

accgtgaagc tggccaacca caacctgcag ctgcgcctga gcagcagcgt ggtggtgatc    420

accagcctgc tgaacagcct gtacctgcac aacaaggtgc acaacctgaa gagcaagaag    480

gagagcctgt acaacgactt catcgccaac cccaagaacg agaagaccgt ggccgacctg    540

aagaagaaca agaaggagtt ccacatcttc cacggcctga gcgtgctgag cctgtacgtg    600

agcttcttcg gcctgacccc ctacatcttc acctgactcg ag                        642
```

<210> SEQ ID NO 112
<211> LENGTH: 207
<212> TYPE: PRT
<213> ORGANISM: Artificial Sequence
<220> FEATURE:
<223> OTHER INFORMATION: Amino acid sequence of PD Plasmodium falciparum 3D7 11-09

<400> SEQUENCE: 112

```
Met Ala Ser Asn Leu Lys Cys Val Thr Asn Val Ala Gly Leu Ala Ser
1               5                   10                  15

Leu Val Ile Ser Leu Phe Pro Lys Leu Ile Ile Lys Asn Pro Gln Val
            20                  25                  30

Leu Arg Pro Leu Leu Asn Val Ser Trp Gly Tyr Leu Phe Gly Ser Thr
        35                  40                  45

Phe Trp Leu Cys Phe Phe Ser Glu Val Gly Leu Leu Arg Ser Leu Lys
    50                  55                  60

Asn Met Lys Gly Val Pro Leu Pro Glu Ser Ala Ser Glu Ala Lys Lys
65                  70                  75                  80

Leu Leu Glu Glu Met Lys Asn Ser Glu Gly Asp Phe Asn Arg Arg Ser
                85                  90                  95

Leu Asp Phe Gln Tyr Phe Phe Ser Leu Ala Thr Leu Phe Ser Gly Ile
            100                 105                 110

Leu Leu Leu Ser Thr Val Lys Leu Ala Asn His Asn Leu Gln Leu Arg
        115                 120                 125

Leu Ser Ser Ser Val Val Val Ile Thr Ser Leu Leu Asn Ser Leu Tyr
    130                 135                 140

Leu His Asn Lys Val His Asn Leu Lys Ser Lys Lys Glu Ser Leu Tyr
145                 150                 155                 160

Asn Asp Phe Ile Ala Asn Pro Lys Asn Glu Lys Thr Val Ala Asp Leu
                165                 170                 175

Lys Lys Asn Lys Lys Glu Phe His Ile Phe His Gly Leu Ser Val Leu
            180                 185                 190
```

Ser Leu Tyr Val Ser Phe Phe Gly Leu Thr Pro Tyr Ile Phe Thr
195 200 205

<210> SEQ ID NO 113
<211> LENGTH: 852
<212> TYPE: DNA
<213> ORGANISM: Artificial Sequence
<220> FEATURE:
<223> OTHER INFORMATION: DNA sequence of Plasmodium berghei ANKA Fusion of PD Pb18-10NT and PD Pb18-10CT

<400> SEQUENCE: 113
atggacaatg acatctacag cttcgacatt gtcaatgaga caaattggct gaagatcgcc 60
aagaacatct tcaaaggcaa gtctcctagc aatttcacga tcataccgtt taacaatacc 120
ggtagttcta acgataacga gtcaaacaag gaggaatcag tactgctgat cagaaagaag 180
atcaaaagca acaagaatca cgatagttcc atcattagtg gtgacactgt taacggggac 240
attagtgacc tgaattatac ggctagcaac ttttccgata actctgagga catagaagat 300
aaccagaaat atcccacaac cagctacaat agtttcaacc atctcaattc cctcactggg 360
gacgagaaat gtggtaaaag cctgaagctc ggcaacatca gcaatcagac aaaccaggaa 420
accataaccc aaagcctgtc agttggagag attctgtgca ttgacctcga agggaatgca 480
ggaacaggct atctgtgggt gttgctgggc atacacaagg atgagccaat cataaacccc 540
gagaacttcc caaccaaact gacaaagaag tctttctttt ccgaggaaat aagtgtgact 600
cagccaaaga agtacaagat cgatgagcat gattcttcaa agaatgtgaa tcgcgaaatc 660
gaaagccctg aacagaagga gtccgactca aagcccaaga aacctcagat gcaacttctt 720
ggaggaccag atcggatgag gtcagtcatc aaaggacaca aacctggcaa atattacatt 780
gtgtactctt actatcgacc gttttctccc acttctgggg cgaacactaa aatcatttac 840
gtcacagtac ag 852

<210> SEQ ID NO 114
<211> LENGTH: 284
<212> TYPE: PRT
<213> ORGANISM: Artificial Sequence
<220> FEATURE:
<223> OTHER INFORMATION: Amino acid sequence of Plasmodium berghei ANKA Fusion of PD Pb18-10NT and PD Pb18-10CT

<400> SEQUENCE: 114

Met Asp Asn Asp Ile Tyr Ser Phe Asp Ile Val Asn Glu Thr Asn Trp
1 5 10 15

Leu Lys Ile Ala Lys Asn Ile Phe Lys Gly Lys Ser Pro Ser Asn Phe
20 25 30

Thr Ile Ile Pro Phe Asn Asn Thr Gly Ser Ser Asn Asp Asn Glu Ser
35 40 45

Asn Lys Glu Glu Ser Val Leu Leu Ile Arg Lys Lys Ile Lys Ser Asn
50 55 60

Lys Asn His Asp Ser Ser Ile Ile Ser Gly Asp Thr Val Asn Gly Asp
65 70 75 80

Ile Ser Asp Leu Asn Tyr Thr Ala Ser Asn Phe Ser Asp Asn Ser Glu
85 90 95

Asp Ile Glu Asp Asn Gln Lys Tyr Pro Thr Thr Ser Tyr Asn Ser Phe
100 105 110

Asn His Leu Asn Ser Leu Thr Gly Asp Glu Lys Cys Gly Lys Ser Leu
115 120 125

```
Lys Leu Gly Asn Ile Ser Asn Gln Thr Asn Gln Glu Thr Ile Thr Gln
    130                 135                 140

Ser Leu Ser Val Gly Glu Ile Leu Cys Ile Asp Leu Glu Gly Asn Ala
145                 150                 155                 160

Gly Thr Gly Tyr Leu Trp Val Leu Leu Gly Ile His Lys Asp Glu Pro
                165                 170                 175

Ile Ile Asn Pro Glu Asn Phe Pro Thr Lys Leu Thr Lys Lys Ser Phe
            180                 185                 190

Phe Ser Glu Glu Ile Ser Val Thr Gln Pro Lys Lys Tyr Lys Ile Asp
        195                 200                 205

Glu His Asp Ser Ser Lys Asn Val Asn Arg Glu Ile Glu Ser Pro Glu
    210                 215                 220

Gln Lys Glu Ser Asp Ser Lys Pro Lys Lys Pro Gln Met Gln Leu Leu
225                 230                 235                 240

Gly Gly Pro Asp Arg Met Arg Ser Val Ile Lys Gly His Lys Pro Gly
                245                 250                 255

Lys Tyr Tyr Ile Val Tyr Ser Tyr Tyr Arg Pro Phe Ser Pro Thr Ser
            260                 265                 270

Gly Ala Asn Thr Lys Ile Ile Tyr Val Thr Val Gln
        275                 280


<210> SEQ ID NO 115
<211> LENGTH: 2715
<212> TYPE: DNA
<213> ORGANISM: Artificial Sequence
<220> FEATURE:
<223> OTHER INFORMATION: DNA sequence of Plasmodium berghei ANKA Fusion
      4cPEAg

<400> SEQUENCE: 115

ggatccgcca ccatggacaa tgacatctac agcttcgaca ttgtcaatga gacaaattgg      60

ctgaagatcg ccaagaacat cttcaaaggc aagtctccta gcaatttcac gatcataccg     120

tttaacaata ccggtagttc taacgataac gagtcaaaca aggaggaatc agtactgctg     180

atcagaaaga agatcaaaag caacaagaat cacgatagtt ccatcattag tggtgacact     240

gttaacgggg acattagtga cctgaattat acggctagca acttttccga taactctgag     300

gacatagaag ataaccagaa atatcccaca accagctaca atagtttcaa ccatctcaat     360

tccctcactg ggacgagaa atgtggtaaa agcctgaagc tcggcaacat cagcaatcag     420

acaaaccagg aaaccataac ccaaagcctg tcagttggag agattctgtg cattgacctc     480

gaagggaatg caggaacagg ctatctgtgg gtgttgctgg gcatacacaa ggatgagcca     540

atcataaacc ccgagaactt cccaaccaaa ctgacaaaga agtctttctt ttccgaggaa     600

ataagtgtga ctcagccaaa gaagtacaag atcgatgagc atgattcttc aaagaatgtg     660

aatcgcgaaa tcgaaagccc tgaacagaag gagtccgact caaagcccaa gaaacctcag     720

atgcaacttc ttggaggacc agatcggatg aggtcagtca tcaaaggaca caaacctggc     780

aaatattaca ttgtgtactc ttactatcga ccgttttctc ccacttctgg ggcgaacact     840

aaaatcattt acgtcacagt acagctgatc gaagagaaag aggaaatcac ccctgagaac     900

aaaaccctca taatgccctc taaaactctg atgaagggca ttaagaccaa catttacttc     960

ctgtcaaaca aggaaaagat ccaagtgctt atgtgctata actacaagtg tgatgccgtt    1020

gtgttcgaga aagacacctt tctgcgctat ctctacatca agagcatcaa taatatcatc    1080

ctgaacgaaa gaatgattga acagttgtgc aagaacgaaa acctgaagta catccttgcc    1140
```

```
tgcaacagca tagtggttga atcaagcgac ttcatcaaac ccctgatcat tgagtttgag   1200
tcatccactt ccaagaacat cttcgtaaag cacattaagc acaatagcca gaaagaaatg   1260
gacatcaaca agttcaacga gtatatgcgg gatctcaaaa gcaatgagaa gctcagactg   1320
aagaaagtcg agcgattcca ctctattaat ctggcagcca agaaacagga gattctggac   1380
gaaatcaagt actctgagga ggtctgcaac gaacaaatcg atctccacat tctgctggat   1440
gggagtggca gcataggtca ctctaactgg atcagtcacg tgatacccat gctgacaacc   1500
cttgtggaca atttgaacat cagccgcgat gagatcaata tctccatgac cttgttctcc   1560
acttatgcca gggaacttgt gagacttaag agatatgggt ctacaagcaa agccagtctg   1620
aggttcatca tcgcgcaact ccagaataac tattctcctc atggaacgac aaatctgact   1680
agcgccctgt tgaatgtgga caatctcatt cagaagaaaa tgaatcgccc taatgccatt   1740
cagctcgtga ttatccttac tgacggcatc cctaacaatc tgaagaagtc cactactgtt   1800
gtcaaccagc tgaagaagaa ggacgtcaat gtcgctatta ttggtgttgg cgccggagta   1860
aacaatatgt ttaaccgtat attggtagga tgtggaaaac ttgggccttg tccctactac   1920
tcttatggct cttgggatca agcacaaacc atgatcaaac catttctctc aaaggtctgt   1980
caggaagtgg agaaagtggc actgtgcggt aagtgggagg agtggagtga gtgttcaacc   2040
acttgcgaca acggaacgaa aataaggaag cgaaaggttg gggcgagtat gagccacttg   2100
cagtgtctga catctgttgc tggtctgtcc tctatcgtca tgtcaatgtt ccccaaactc   2160
attgccaata atccttccct gtttagacca ctgctcaaca tttcctgggg atatctgttc   2220
ggaagcactg tatggctgtg cttcttcagt gagattgggt tggtcaggag aatcaatgct   2280
cctaaacgga agaatctgcc agagaatgca gaacaagcca aagaacagct gaaggagatc   2340
aagaacaacg aaggcgattt taaccgacgc aatatcgact tcaagtactt ctttagcctt   2400
tccacaatct tctctagcat actgctgctt agcacagtga aactcgccaa caacaatctg   2460
cagttgagga tctgttccac cattgtgtca ctgagttgca tactgaacaa tatgtacttt   2520
cagaacaaga tacactcact tgcactgaag aaagagagtc tctttaagga catgatcgat   2580
cgtccgaaag ataccactat tctggtgaac ctgaagaaga acaagaccga ctttcacatc   2640
catcatggcc tttctctgct cttgctctat agcagcttct ttggcctcac tccctacatt   2700
ttcacgtgac tcgag                                                    2715
```

<210> SEQ ID NO 116
<211> LENGTH: 898
<212> TYPE: PRT
<213> ORGANISM: Artificial Sequence
<220> FEATURE:
<223> OTHER INFORMATION: Amino acid sequence of Plasmodium berghei ANKA Fusion 4cPEAg

<400> SEQUENCE: 116

```
Met Asp Asn Asp Ile Tyr Ser Phe Asp Ile Val Asn Glu Thr Asn Trp
1               5                   10                  15

Leu Lys Ile Ala Lys Asn Ile Phe Lys Gly Lys Ser Pro Ser Asn Phe
            20                  25                  30

Thr Ile Ile Pro Phe Asn Asn Thr Gly Ser Ser Asn Asp Asn Glu Ser
        35                  40                  45

Asn Lys Glu Glu Ser Val Leu Leu Ile Arg Lys Lys Ile Lys Ser Asn
    50                  55                  60

Lys Asn His Asp Ser Ser Ile Ile Ser Gly Asp Thr Val Asn Gly Asp
65                  70                  75                  80
```

```
Ile Ser Asp Leu Asn Tyr Thr Ala Ser Asn Phe Ser Asp Asn Ser Glu
                85                  90                  95

Asp Ile Glu Asp Asn Gln Lys Tyr Pro Thr Thr Ser Tyr Asn Ser Phe
            100                 105                 110

Asn His Leu Asn Ser Leu Thr Gly Asp Glu Lys Cys Gly Lys Ser Leu
        115                 120                 125

Lys Leu Gly Asn Ile Ser Asn Gln Thr Asn Gln Glu Thr Ile Thr Gln
    130                 135                 140

Ser Leu Ser Val Gly Glu Ile Leu Cys Ile Asp Leu Glu Gly Asn Ala
145                 150                 155                 160

Gly Thr Gly Tyr Leu Trp Val Leu Leu Gly Ile His Lys Asp Glu Pro
                165                 170                 175

Ile Ile Asn Pro Glu Asn Phe Pro Thr Lys Leu Thr Lys Lys Ser Phe
            180                 185                 190

Phe Ser Glu Glu Ile Ser Val Thr Gln Pro Lys Lys Tyr Lys Ile Asp
        195                 200                 205

Glu His Asp Ser Ser Lys Asn Val Asn Arg Glu Ile Glu Ser Pro Glu
    210                 215                 220

Gln Lys Glu Ser Asp Ser Lys Pro Lys Lys Pro Gln Met Gln Leu Leu
225                 230                 235                 240

Gly Gly Pro Asp Arg Met Arg Ser Val Ile Lys Gly His Lys Pro Gly
                245                 250                 255

Lys Tyr Tyr Ile Val Tyr Ser Tyr Tyr Arg Pro Phe Ser Pro Thr Ser
            260                 265                 270

Gly Ala Asn Thr Lys Ile Ile Tyr Val Thr Val Gln Leu Ile Glu Glu
        275                 280                 285

Lys Glu Glu Ile Thr Pro Glu Asn Lys Thr Leu Ile Met Pro Ser Lys
    290                 295                 300

Thr Leu Met Lys Gly Ile Lys Thr Asn Ile Tyr Phe Leu Ser Asn Lys
305                 310                 315                 320

Glu Lys Ile Gln Val Leu Met Cys Tyr Asn Tyr Lys Cys Asp Ala Val
                325                 330                 335

Val Phe Glu Lys Asp Thr Phe Leu Arg Tyr Leu Tyr Ile Lys Ser Ile
            340                 345                 350

Asn Asn Ile Ile Leu Asn Glu Arg Met Ile Glu Gln Leu Cys Lys Asn
        355                 360                 365

Glu Asn Leu Lys Tyr Ile Leu Ala Cys Asn Ser Ile Val Val Glu Ser
    370                 375                 380

Ser Asp Phe Ile Lys Pro Leu Ile Ile Glu Phe Glu Ser Ser Thr Ser
385                 390                 395                 400

Lys Asn Ile Phe Val Lys His Ile Lys His Asn Ser Gln Lys Glu Met
                405                 410                 415

Asp Ile Asn Lys Phe Asn Glu Tyr Met Arg Asp Leu Lys Ser Asn Glu
            420                 425                 430

Lys Leu Arg Leu Lys Lys Val Glu Arg Phe His Ser Ile Asn Leu Ala
        435                 440                 445

Ala Lys Lys Gln Glu Ile Leu Asp Glu Ile Lys Tyr Ser Glu Glu Val
    450                 455                 460

Cys Asn Glu Gln Ile Asp Leu His Ile Leu Leu Asp Gly Ser Gly Ser
465                 470                 475                 480

Ile Gly His Ser Asn Trp Ile Ser His Val Ile Pro Met Leu Thr Thr
                485                 490                 495
```

```
Leu Val Asp Asn Leu Asn Ile Ser Arg Asp Glu Ile Asn Ile Ser Met
            500                 505                 510

Thr Leu Phe Ser Thr Tyr Ala Arg Glu Leu Val Arg Leu Lys Arg Tyr
        515                 520                 525

Gly Ser Thr Ser Lys Ala Ser Leu Arg Phe Ile Ile Ala Gln Leu Gln
    530                 535                 540

Asn Asn Tyr Ser Pro His Gly Thr Thr Asn Leu Thr Ser Ala Leu Leu
545                 550                 555                 560

Asn Val Asp Asn Leu Ile Gln Lys Lys Met Asn Arg Pro Asn Ala Ile
                565                 570                 575

Gln Leu Val Ile Ile Leu Thr Asp Gly Ile Pro Asn Asn Leu Lys Lys
            580                 585                 590

Ser Thr Thr Val Val Asn Gln Leu Lys Lys Lys Asp Val Asn Val Ala
        595                 600                 605

Ile Ile Gly Val Gly Ala Gly Val Asn Asn Met Phe Asn Arg Ile Leu
    610                 615                 620

Val Gly Cys Gly Lys Leu Gly Pro Cys Pro Tyr Tyr Ser Tyr Gly Ser
625                 630                 635                 640

Trp Asp Gln Ala Gln Thr Met Ile Lys Pro Phe Leu Ser Lys Val Cys
                645                 650                 655

Gln Glu Val Glu Lys Val Ala Leu Cys Gly Lys Trp Glu Glu Trp Ser
            660                 665                 670

Glu Cys Ser Thr Thr Cys Asp Asn Gly Thr Lys Ile Arg Lys Arg Lys
        675                 680                 685

Val Gly Ala Ser Met Ser His Leu Gln Cys Leu Thr Ser Val Ala Gly
    690                 695                 700

Leu Ser Ser Ile Val Met Ser Met Phe Pro Lys Leu Ile Ala Asn Asn
705                 710                 715                 720

Pro Ser Leu Phe Arg Pro Leu Leu Asn Ile Ser Trp Gly Tyr Leu Phe
                725                 730                 735

Gly Ser Thr Val Trp Leu Cys Phe Phe Ser Glu Ile Gly Leu Val Arg
            740                 745                 750

Arg Ile Asn Ala Pro Lys Arg Lys Asn Leu Pro Glu Asn Ala Glu Gln
        755                 760                 765

Ala Lys Glu Gln Leu Lys Glu Ile Lys Asn Asn Glu Gly Asp Phe Asn
    770                 775                 780

Arg Arg Asn Ile Asp Phe Lys Tyr Phe Phe Ser Leu Ser Thr Ile Phe
785                 790                 795                 800

Ser Ser Ile Leu Leu Leu Ser Thr Val Lys Leu Ala Asn Asn Asn Leu
                805                 810                 815

Gln Leu Arg Ile Cys Ser Thr Ile Val Ser Leu Ser Cys Ile Leu Asn
            820                 825                 830

Asn Met Tyr Phe Gln Asn Lys Ile His Ser Leu Ala Leu Lys Lys Glu
        835                 840                 845

Ser Leu Phe Lys Asp Met Ile Asp Arg Pro Lys Asp Thr Thr Ile Leu
    850                 855                 860

Val Asn Leu Lys Lys Asn Lys Thr Asp Phe His Ile His His Gly Leu
865                 870                 875                 880

Ser Leu Leu Leu Leu Tyr Ser Ser Phe Phe Gly Leu Thr Pro Tyr Ile
                885                 890                 895

Phe Thr
```

<210> SEQ ID NO 117

<211> LENGTH: 3231
<212> TYPE: DNA
<213> ORGANISM: Artificial Sequence
<220> FEATURE:
<223> OTHER INFORMATION: DNA sequence of Plasmodium falciparum 3D7
Fusion 4cPEAg

<400> SEQUENCE: 117

```
ggatccgcca ccatggacaa caacagctac agcttcgaga tcgtgaaccg cagcacctgg     60
ctgaacatcg ccgagcgcat cttcaagggc aacgccccct tcaacttcac catcatcccc    120
tacaactacg tgaacaacag caccgaggag aacaacaaca aggacagcgt gctgctgatc    180
agcaagaacc tgaagaacag cagcaacccc gtggacgaga acaaccacat catcgacagc    240
accaagaaga acaccagcaa caacaacaac aacaacagca acatcgtggg catctacgag    300
agccaggtgc acgaggagaa gatcaaggag gacaacaccc gccaggacaa catcaacaag    360
aaggagaacg agatcatcaa caacaaccac cagatccccg tgagcaacat cttcagcgag    420
aacatcgaca acaacaagaa ctacatcgag agcaactaca agagcaccta caacaacaac    480
cccgagctga tccacagcac cgacttcatc ggcagcaaca acaaccacac cttcaacttc    540
ctgagccgct acaacaacag cgtgctgaac aacatgcagg gcaacaccaa ggtgcccggc    600
aacgtgcccg agctgaaggc ccgcatcttc agcgaggagg agaacaccga ggtggagagc    660
gccgagaaca accacaccaa cagcctgaac cccaacgaga gctgcgacca gatcatcaag    720
ctgggcgaca tcatcaacag cgtgaacgag aagatcatca gcatcaacag caccgtgaac    780
aacgtgctgt gcatcaacct ggacagcgtg aacggcaacg gcttcgtgtg gaccctgctg    840
ggcgtgcaca agaagaagcc cctgatcgac cccagcaact tccccaccaa gcgcgtgacc    900
cagagctacg tgagccccga catcagcgtg accaaccccg tgcccatccc caagaacagc    960
aacaccaaca aggacgacag catcaacaac aagcaggacg gcagccagaa caacaccacc   1020
accaaccact tccccaagcc ccgcgagcag ctggtgggcg gcagcagcat gctgatcagc   1080
aagatcaagc cccacaagcc cggcaagtac ttcatcgtgt acagctacta ccgccccttc   1140
gaccccaccc gcgacaccaa cacccgcatc gtggagctga acgtgcagga ggaggacgac   1200
aaggaggtgg agcccgagga ggagaaggag aacgagcaga agaaggagga gcaggaggag   1260
aacaacctgg aggcccccag caagaccctg atgaagggcg tgaagaccaa catctacttc   1320
ctgagcacca aggagcgcat cgaggccctg atgtgctaca actacatcag caacgccatc   1380
atcttcgaga agggcaagtt cctgcgctac atcttcatga acaacgtgaa caacatcatc   1440
gtgaacgagc acatgatcaa catgctgtgc aagaaggaga agatcaagta catcctgagc   1500
agcaacagca tcatcatcga gagcaacgac ttcatcaagc ccctgatcat cgagttcgac   1560
agcaacatca gcaagaagat cttcgtgaag cacctgaaga tggtggacag cttcaagctg   1620
gacgacaagc tgtaccgcga gtacctgaac gacctgagcg agcacgagcg cgaccgcctg   1680
aagcacgtgg agagcttcta cagcaacgcc atcaaggtgc acaacgagga cgtgcagaac   1740
aacatcgtgg acgagatcaa gtaccgcgag gaggtgtgca acgacgaggt ggacctgtac   1800
ctgctgatgg actgcagcgg cagcatccgc cgccacaact gggtgaacca cgccgtgccc   1860
ctggccatga agctgatcca gcagctgaac ctgaacgaca acgccatcca cctgtacgcc   1920
agcgtgttca gcaacaacgc ccgcgagatc atccgcctgc acagcgacgc cagcaagaac   1980
aaggagaagg ccctgatcat catcaagagc ctgctgagca ccaacctgcc ctacggcaag   2040
accaacctga ccgacgccct gctgcaggtg cgcaagcacc tgaacgaccg catcaaccgc   2100
```

```
gagaacgcca accagctggt ggtgatcctg accgacggca tccccgacag catccaggac   2160

agcctgaagg agagccgcaa gctgagcgac cgcggcgtga agatcgccgt gttcggcatc   2220

ggccagggca tcaacgtggc cttcaaccgc ttcctggtgg gctgccaccc cagcgacggc   2280

aagtgcaacc tgtacgccga cagcgcctgg gagaacgtga agaacgtgat cggccccttc   2340

atgaaggccg tgtgcgtgga ggtggagaag accgccagct gcggcgtgtg ggacgagtgg   2400

agcccctgca gcgtgacctg cggcaagggc acccgcagcc gcaagcgcga gatcctgcac   2460

gagggctgca ccagcgagct gcaggagcag tgcgaggagg agcgctgcct gcccaagcgc   2520

gagcccctgg acgtgcccga cgagcccgag gacgaccagc cccgcccccg cggcgacaac   2580

ttcgccgtgg agaagcccaa cgagaacagc aacctgaagt gcgtgaccaa cgtggccggc   2640

ctggccagcc tggtgatcag cctgttcccc aagctgatca tcaagaaccc ccaggtgctg   2700

cgccccctgc tgaacgtgag ctggggctac ctgttcggca gcaccttctg gctgtgcttc   2760

ttcagcgagg tgggcctgct gcgcagcctg aagaacatga agggcgtgcc cctgcccgag   2820

agcgccagcg aggccaagaa gctgctggag gagatgaaga acagcgaggg cgacttcaac   2880

cgccgcagcc tggacttcca gtacttcttc agcctggcca ccctgttcag cggcatcctg   2940

ctgctgagca ccgtgaagct ggccaaccac aacctgcagc tgcgcctgag cagcagcgtg   3000

gtggtgatca ccagcctgct gaacagcctg tacctgcaca acaaggtgca caacctgaag   3060

agcaagaagg agagcctgta caacgacttc atcgccaacc ccaagaacga gaagaccgtg   3120

gccgacctga agaagaacaa gaaggagttc cacatcttcc acggcctgag cgtgctgagc   3180

ctgtacgtga gcttcttcgg cctgaccccc tacatcttca cctgactcga g            3231
```

```
<210> SEQ ID NO 118
<211> LENGTH: 1070
<212> TYPE: PRT
<213> ORGANISM: Artificial Sequence
<220> FEATURE:
<223> OTHER INFORMATION: Amino acid sequence of Plasmodium falciparum
      3D7 Fusion 4cPEAg

<400> SEQUENCE: 118

Met Asp Asn Asn Ser Tyr Ser Phe Glu Ile Val Asn Arg Ser Thr Trp
1               5                   10                  15

Leu Asn Ile Ala Glu Arg Ile Phe Lys Gly Asn Ala Pro Phe Asn Phe
            20                  25                  30

Thr Ile Ile Pro Tyr Asn Tyr Val Asn Asn Ser Thr Glu Glu Asn Asn
        35                  40                  45

Asn Lys Asp Ser Val Leu Leu Ile Ser Lys Asn Leu Lys Asn Ser Ser
    50                  55                  60

Asn Pro Val Asp Glu Asn Asn His Ile Ile Asp Ser Thr Lys Lys Asn
65                  70                  75                  80

Thr Ser Asn Asn Asn Asn Asn Asn Ser Asn Ile Val Gly Ile Tyr Glu
                85                  90                  95

Ser Gln Val His Glu Glu Lys Ile Lys Glu Asp Asn Thr Arg Gln Asp
            100                 105                 110

Asn Ile Asn Lys Lys Glu Asn Glu Ile Ile Asn Asn Asn His Gln Ile
        115                 120                 125

Pro Val Ser Asn Ile Phe Ser Glu Asn Ile Asp Asn Asn Lys Asn Tyr
    130                 135                 140

Ile Glu Ser Asn Tyr Lys Ser Thr Tyr Asn Asn Asn Pro Glu Leu Ile
145                 150                 155                 160
```

-continued

```
His Ser Thr Asp Phe Ile Gly Ser Asn Asn Asn His Thr Phe Asn Phe
                165                 170                 175

Leu Ser Arg Tyr Asn Asn Ser Val Leu Asn Asn Met Gln Gly Asn Thr
            180                 185                 190

Lys Val Pro Gly Asn Val Pro Glu Leu Lys Ala Arg Ile Phe Ser Glu
        195                 200                 205

Glu Glu Asn Thr Glu Val Glu Ser Ala Glu Asn Asn His Thr Asn Ser
    210                 215                 220

Leu Asn Pro Asn Glu Ser Cys Asp Gln Ile Ile Lys Leu Gly Asp Ile
225                 230                 235                 240

Ile Asn Ser Val Asn Glu Lys Ile Ile Ser Ile Asn Ser Thr Val Asn
                245                 250                 255

Asn Val Leu Cys Ile Asn Leu Asp Ser Val Asn Gly Asn Gly Phe Val
            260                 265                 270

Trp Thr Leu Leu Gly Val His Lys Lys Lys Pro Leu Ile Asp Pro Ser
        275                 280                 285

Asn Phe Pro Thr Lys Arg Val Thr Gln Ser Tyr Val Ser Pro Asp Ile
    290                 295                 300

Ser Val Thr Asn Pro Val Pro Ile Pro Lys Asn Ser Asn Thr Asn Lys
305                 310                 315                 320

Asp Asp Ser Ile Asn Asn Lys Gln Asp Gly Ser Gln Asn Asn Thr Thr
                325                 330                 335

Thr Asn His Phe Pro Lys Pro Arg Glu Gln Leu Val Gly Gly Ser Ser
            340                 345                 350

Met Leu Ile Ser Lys Ile Lys Pro His Lys Pro Gly Lys Tyr Phe Ile
        355                 360                 365

Val Tyr Ser Tyr Tyr Arg Pro Phe Asp Pro Thr Arg Asp Thr Asn Thr
    370                 375                 380

Arg Ile Val Glu Leu Asn Val Gln Glu Glu Asp Asp Lys Glu Val Glu
385                 390                 395                 400

Pro Glu Glu Glu Lys Glu Asn Glu Gln Lys Lys Glu Glu Gln Glu Glu
                405                 410                 415

Asn Asn Leu Glu Ala Pro Ser Lys Thr Leu Met Lys Gly Val Lys Thr
            420                 425                 430

Asn Ile Tyr Phe Leu Ser Thr Lys Glu Arg Ile Glu Ala Leu Met Cys
        435                 440                 445

Tyr Asn Tyr Ile Ser Asn Ala Ile Ile Phe Glu Lys Gly Lys Phe Leu
    450                 455                 460

Arg Tyr Ile Phe Met Asn Asn Val Asn Asn Ile Ile Val Asn Glu His
465                 470                 475                 480

Met Ile Asn Met Leu Cys Lys Lys Glu Lys Ile Lys Tyr Ile Leu Ser
                485                 490                 495

Ser Asn Ser Ile Ile Ile Glu Ser Asn Asp Phe Ile Lys Pro Leu Ile
            500                 505                 510

Ile Glu Phe Asp Ser Asn Ile Ser Lys Lys Ile Phe Val Lys His Leu
        515                 520                 525

Lys Met Val Asp Ser Phe Lys Leu Asp Asp Lys Leu Tyr Arg Glu Tyr
    530                 535                 540

Leu Asn Asp Leu Ser Glu His Glu Arg Asp Arg Leu Lys His Val Glu
545                 550                 555                 560

Ser Phe Tyr Ser Asn Ala Ile Lys Val His Asn Glu Asp Val Gln Asn
                565                 570                 575
```

Asn Ile Val Asp Glu Ile Lys Tyr Arg Glu Glu Val Cys Asn Asp Glu
580 585 590

Val Asp Leu Tyr Leu Leu Met Asp Cys Ser Gly Ser Ile Arg Arg His
595 600 605

Asn Trp Val Asn His Ala Val Pro Leu Ala Met Lys Leu Ile Gln Gln
610 615 620

Leu Asn Leu Asn Asp Asn Ala Ile His Leu Tyr Ala Ser Val Phe Ser
625 630 635 640

Asn Asn Ala Arg Glu Ile Ile Arg Leu His Ser Asp Ala Ser Lys Asn
645 650 655

Lys Glu Lys Ala Leu Ile Ile Ile Lys Ser Leu Leu Ser Thr Asn Leu
660 665 670

Pro Tyr Gly Lys Thr Asn Leu Thr Asp Ala Leu Leu Gln Val Arg Lys
675 680 685

His Leu Asn Asp Arg Ile Asn Arg Glu Asn Ala Asn Gln Leu Val Val
690 695 700

Ile Leu Thr Asp Gly Ile Pro Asp Ser Ile Gln Asp Ser Leu Lys Glu
705 710 715 720

Ser Arg Lys Leu Ser Asp Arg Gly Val Lys Ile Ala Val Phe Gly Ile
725 730 735

Gly Gln Gly Ile Asn Val Ala Phe Asn Arg Phe Leu Val Gly Cys His
740 745 750

Pro Ser Asp Gly Lys Cys Asn Leu Tyr Ala Asp Ser Ala Trp Glu Asn
755 760 765

Val Lys Asn Val Ile Gly Pro Phe Met Lys Ala Val Cys Val Glu Val
770 775 780

Glu Lys Thr Ala Ser Cys Gly Val Trp Asp Glu Trp Ser Pro Cys Ser
785 790 795 800

Val Thr Cys Gly Lys Gly Thr Arg Ser Arg Lys Arg Glu Ile Leu His
805 810 815

Glu Gly Cys Thr Ser Glu Leu Gln Glu Gln Cys Glu Glu Glu Arg Cys
820 825 830

Leu Pro Lys Arg Glu Pro Leu Asp Val Pro Asp Glu Pro Glu Asp Asp
835 840 845

Gln Pro Arg Pro Arg Gly Asp Asn Phe Ala Val Glu Lys Pro Asn Glu
850 855 860

Asn Ser Asn Leu Lys Cys Val Thr Asn Val Ala Gly Leu Ala Ser Leu
865 870 875 880

Val Ile Ser Leu Phe Pro Lys Leu Ile Ile Lys Asn Pro Gln Val Leu
885 890 895

Arg Pro Leu Leu Asn Val Ser Trp Gly Tyr Leu Phe Gly Ser Thr Phe
900 905 910

Trp Leu Cys Phe Phe Ser Glu Val Gly Leu Leu Arg Ser Leu Lys Asn
915 920 925

Met Lys Gly Val Pro Leu Pro Glu Ser Ala Ser Glu Ala Lys Lys Leu
930 935 940

Leu Glu Glu Met Lys Asn Ser Glu Gly Asp Phe Asn Arg Arg Ser Leu
945 950 955 960

Asp Phe Gln Tyr Phe Phe Ser Leu Ala Thr Leu Phe Ser Gly Ile Leu
965 970 975

Leu Leu Ser Thr Val Lys Leu Ala Asn His Asn Leu Gln Leu Arg Leu
980 985 990

```
Ser Ser Ser Val Val Val Ile Thr  Ser Leu Leu Asn Ser  Leu Tyr Leu
        995                 1000                 1005

His Asn  Lys Val His Asn Leu  Lys Ser Lys Lys Glu  Ser Leu Tyr
    1010                 1015                 1020

Asn Asp  Phe Ile Ala Asn Pro  Lys Asn Glu Lys Thr  Val Ala Asp
    1025                 1030                 1035

Leu Lys  Lys Asn Lys Lys Glu  Phe His Ile Phe His  Gly Leu Ser
    1040                 1045                 1050

Val Leu  Ser Leu Tyr Val Ser  Phe Phe Gly Leu Thr  Pro Tyr Ile
    1055                 1060                 1065

Phe Thr
    1070


<210> SEQ ID NO 119
<211> LENGTH: 3597
<212> TYPE: DNA
<213> ORGANISM: Artificial Sequence
<220> FEATURE:
<223> OTHER INFORMATION: DNA sequence of Plasmodium berghei Fusion
      5cPEAg

<400> SEQUENCE: 119

ggatccgcca ccatggccca gaacaaatcc attcaggcac agaggaacct caacgaactc     60

tgctacaatg aagggaatga caataagctg tatcacgtgc tgaattccaa gaacggcaaa    120

atctacaatc gcaacacagt aaatcggttg cttgccgatg cacccgaggg taagaagaat    180

gaaaagaaga atgagaaaat cgagcgcaac aacaagctta aacagccacc gcctcctcct    240

aacccaaatg acccaccgcc acccaatcca aacgacccac cgcctcccaa ccctaacgat    300

cctccaccgc ccaaccctaa tgacccacca cctcccaatg caaacgatcc accccctcct    360

aacgctaacg accctgctcc acccaacgct aacgatcccg cgcccccaa tgccaacgac    420

cccgcaccac ctaatgccaa cgatcccgcc ccgcccaatg ctaatgatcc tccaccaccc    480

aacccaaacg accctgcccc tcctaatgct aacgatccac cacctcccaa tccgaatgat    540

cccgctccac ctcaggggaa caacaaccct cagccccaac ctagaccaca gccgcagccc    600

caaccccaac cccagcccca gcctcaaccc cagccccagc cacgtccgca gcctcagcct    660

caacctggag gcaacaataa caacaagaat aacaacaacg acgacagcta cattccaagt    720

gccgagaaaa ttctggagtt tgttaagcag atccgagaca gcataaccga agaatggtca    780

cagtgtaacg tgacgtgtgg atctggcatc agagtgagga aacggaaggg ttccaataag    840

aaagcagagg atctgactct ggaggacatt gatacagaga tctgcaaaat ggacaaagac    900

aatgacatct acagcttcga cattgtcaat gagacaaatt ggctgaagat cgccaagaac    960

atcttcaaag gcaagtctcc tagcaatttc acgatcatac cgtttaacaa taccggtagt   1020

tctaacgata acgagtcaaa caaggaggaa tcagtactgc tgatcagaaa gaagatcaaa   1080

agcaacaaga atcacgatag ttccatcatt agtggtgaca ctgttaacgg ggacattagt   1140

gacctgaatt atacggctag caacttttcc gataactctg aggacataga agataaccag   1200

aaatatccca caaccagcta caatagtttc aaccatctca attccctcac tggggacgag   1260

aaatgtggta aaagcctgaa gctcggcaac atcagcaatc agacaaacca ggaaaccata   1320

acccaaagcc tgtcagttgg agagattctg tgcattgacc tcgaagggaa tgcaggaaca   1380

ggctatctgt gggtgttgct gggcatacac aaggatgagc caatcataaa ccccgagaac   1440

ttcccaacca aactgacaaa gaagtctttc ttttccgagg aaataagtgt gactcagcca   1500
```

```
aagaagtaca agatcgatga gcatgattct tcaaagaatg tgaatcgcga aatcgaaagc   1560
cctgaacaga aggagtccga ctcaaagccc aagaaacctc agatgcaact tcttggagga   1620
ccagatcgga tgaggtcagt catcaaagga cacaaacctg gcaaatatta cattgtgtac   1680
tcttactatc gaccgttttc tcccacttct ggggcgaaca ctaaaatcat ttacgtcaca   1740
gtacagctga tcgaagagaa agaggaaatc acccctgaga acaaaaccct cataatgccc   1800
tctaaaactc tgatgaaggg cattaagacc aacatttact tcctgtcaaa caaggaaaag   1860
atccaagtgc ttatgtgcta taactacaag tgtgatgccg ttgtgttcga gaaagacacc   1920
tttctgcgct atctctacat caagagcatc aataatatca tcctgaacga aagaatgatt   1980
gaacagttgt gcaagaacga aaacctgaag tacatccttg cctgcaacag catagtggtt   2040
gaatcaagcg acttcatcaa acccctgatc attgagtttg agtcatccac ttccaagaac   2100
atcttcgtaa agcacattaa gcacaatagc cagaaagaaa tggacatcaa caagttcaac   2160
gagtatatgc gggatctcaa aagcaatgag aagctcagac tgaagaaagt cgagcgattc   2220
cactctatta atctggcagc caagaaacag gagattctgg acgaaatcaa gtactctgag   2280
gaggtctgca acgaacaaat cgatctccac attctgctgg atgggagtgg cagcataggt   2340
cactctaact ggatcagtca cgtgataccc atgctgacaa cccttgtgga caatttgaac   2400
atcagccgcg atgagatcaa tatctccatg accttgttct ccacttatgc cagggaactt   2460
gtgagactta agagatatgg gtctacaagc aaagccagtc tgaggttcat catcgcgcaa   2520
ctccagaata actattctcc tcatggaacg acaaatctga ctagcgccct gttgaatgtg   2580
gacaatctca ttcagaagaa aatgaatcgc cctaatgcca ttcagctcgt gattatcctt   2640
actgacggca tccctaacaa tctgaagaag tccactactg ttgtcaacca gctgaagaag   2700
aaggacgtca atgtcgctat tattggtgtt ggcgccggag taaacaatat gtttaaccgt   2760
atattggtag gatgtggaaa acttgggcct tgtccctact actcttatgg ctcttgggat   2820
caagcacaaa ccatgatcaa accatttctc tcaaaggtct gtcaggaagt ggagaaagtg   2880
gcactgtgcg gtaagtggga ggagtggagt gagtgttcaa ccacttgcga caacggaacg   2940
aaaataagga agcgaaaggt tggggcgagt atgagccact tgcagtgtct gacatctgtt   3000
gctggtctgt cctctatcgt catgtcaatg ttccccaaac tcattgccaa taatccttcc   3060
ctgtttagac cactgctcaa catttcctgg ggatatctgt tcggaagcac tgtatggctg   3120
tgcttcttca gtgagattgg gttggtcagg agaatcaatg ctcctaaacg gaagaatctg   3180
ccagagaatg cagaacaagc caaagaacag ctgaaggaga tcaagaacaa cgaaggcgat   3240
tttaaccgac gcaatatcga cttcaagtac ttctttagcc tttccacaat cttctctagc   3300
atactgctgc ttagcacagt gaaactcgcc aacaacaatc tgcagttgag gatctgttcc   3360
accattgtgt cactgagttg catactgaac aatatgtact ttcagaacaa gatacactca   3420
cttgcactga agaaagagag tctctttaag gacatgatcg atcgtccgaa agataccact   3480
attctggtga acctgaagaa gaacaagacc gactttcaca tccatcatgg cctttctctg   3540
ctcttgctct atagcagctt ctttggcctc actccctaca ttttcacgtg actcgag      3597
```

<210> SEQ ID NO 120
<211> LENGTH: 1192
<212> TYPE: PRT
<213> ORGANISM: Artificial Sequence
<220> FEATURE:
<223> OTHER INFORMATION: Amino acid sequence of Plasmodium berghei
Fusion 5cPEAg SP

<400> SEQUENCE: 120

```
Met Ala Gln Asn Lys Ser Ile Gln Ala Gln Arg Asn Leu Asn Glu Leu
1               5                   10                  15

Cys Tyr Asn Glu Gly Asn Asp Asn Lys Leu Tyr His Val Leu Asn Ser
            20                  25                  30

Lys Asn Gly Lys Ile Tyr Asn Arg Asn Thr Val Asn Arg Leu Leu Ala
        35                  40                  45

Asp Ala Pro Glu Gly Lys Lys Asn Glu Lys Lys Asn Glu Lys Ile Glu
    50                  55                  60

Arg Asn Asn Lys Leu Lys Gln Pro Pro Pro Pro Pro Asn Pro Asn Asp
65                  70                  75                  80

Pro Pro Pro Pro Asn Pro Asn Asp Pro Pro Pro Pro Asn Pro Asn Asp
                85                  90                  95

Pro Pro Pro Pro Asn Pro Asn Asp Pro Pro Pro Pro Asn Ala Asn Asp
            100                 105                 110

Pro Pro Pro Pro Asn Ala Asn Asp Pro Ala Pro Pro Asn Ala Asn Asp
        115                 120                 125

Pro Ala Pro Pro Asn Ala Asn Asp Pro Ala Pro Pro Asn Ala Asn Asp
    130                 135                 140

Pro Ala Pro Pro Asn Ala Asn Asp Pro Pro Pro Pro Asn Pro Asn Asp
145                 150                 155                 160

Pro Ala Pro Pro Asn Ala Asn Asp Pro Pro Pro Pro Asn Pro Asn Asp
                165                 170                 175

Pro Ala Pro Pro Gln Gly Asn Asn Asn Pro Gln Pro Gln Pro Arg Pro
            180                 185                 190

Gln Pro Gln Pro Gln Pro Gln Pro Gln Pro Gln Pro Gln Pro Gln Pro
        195                 200                 205

Gln Pro Arg Pro Gln Pro Gln Pro Gln Pro Gly Gly Asn Asn Asn Asn
    210                 215                 220

Lys Asn Asn Asn Asn Asp Asp Ser Tyr Ile Pro Ser Ala Glu Lys Ile
225                 230                 235                 240

Leu Glu Phe Val Lys Gln Ile Arg Asp Ser Ile Thr Glu Glu Trp Ser
                245                 250                 255

Gln Cys Asn Val Thr Cys Gly Ser Gly Ile Arg Val Arg Lys Arg Lys
            260                 265                 270

Gly Ser Asn Lys Lys Ala Glu Asp Leu Thr Leu Glu Asp Ile Asp Thr
        275                 280                 285

Glu Ile Cys Lys Met Asp Lys Asp Asn Asp Ile Tyr Ser Phe Asp Ile
    290                 295                 300

Val Asn Glu Thr Asn Trp Leu Lys Ile Ala Lys Asn Ile Phe Lys Gly
305                 310                 315                 320

Lys Ser Pro Ser Asn Phe Thr Ile Ile Pro Phe Asn Asn Thr Gly Ser
                325                 330                 335

Ser Asn Asp Asn Glu Ser Asn Lys Glu Glu Ser Val Leu Leu Ile Arg
            340                 345                 350

Lys Lys Ile Lys Ser Asn Lys Asn His Asp Ser Ser Ile Ile Ser Gly
        355                 360                 365

Asp Thr Val Asn Gly Asp Ile Ser Asp Leu Asn Tyr Thr Ala Ser Asn
    370                 375                 380

Phe Ser Asp Asn Ser Glu Asp Ile Glu Asp Asn Gln Lys Tyr Pro Thr
385                 390                 395                 400

Thr Ser Tyr Asn Ser Phe Asn His Leu Asn Ser Leu Thr Gly Asp Glu
                405                 410                 415
```

```
Lys Cys Gly Lys Ser Leu Lys Leu Gly Asn Ile Ser Asn Gln Thr Asn
            420                 425                 430

Gln Glu Thr Ile Thr Gln Ser Leu Ser Val Gly Glu Ile Leu Cys Ile
        435                 440                 445

Asp Leu Glu Gly Asn Ala Gly Thr Gly Tyr Leu Trp Val Leu Leu Gly
    450                 455                 460

Ile His Lys Asp Glu Pro Ile Ile Asn Pro Glu Asn Phe Pro Thr Lys
465                 470                 475                 480

Leu Thr Lys Lys Ser Phe Phe Ser Glu Glu Ile Ser Val Thr Gln Pro
                485                 490                 495

Lys Lys Tyr Lys Ile Asp Glu His Asp Ser Ser Lys Asn Val Asn Arg
            500                 505                 510

Glu Ile Glu Ser Pro Glu Gln Lys Glu Ser Asp Ser Lys Pro Lys Lys
        515                 520                 525

Pro Gln Met Gln Leu Leu Gly Gly Pro Asp Arg Met Arg Ser Val Ile
    530                 535                 540

Lys Gly His Lys Pro Gly Lys Tyr Tyr Ile Val Tyr Ser Tyr Tyr Arg
545                 550                 555                 560

Pro Phe Ser Pro Thr Ser Gly Ala Asn Thr Lys Ile Ile Tyr Val Thr
                565                 570                 575

Val Gln Leu Ile Glu Glu Lys Glu Glu Ile Thr Pro Glu Asn Lys Thr
            580                 585                 590

Leu Ile Met Pro Ser Lys Thr Leu Met Lys Gly Ile Lys Thr Asn Ile
        595                 600                 605

Tyr Phe Leu Ser Asn Lys Glu Lys Ile Gln Val Leu Met Cys Tyr Asn
    610                 615                 620

Tyr Lys Cys Asp Ala Val Val Phe Glu Lys Asp Thr Phe Leu Arg Tyr
625                 630                 635                 640

Leu Tyr Ile Lys Ser Ile Asn Asn Ile Ile Leu Asn Glu Arg Met Ile
                645                 650                 655

Glu Gln Leu Cys Lys Asn Glu Asn Leu Lys Tyr Ile Leu Ala Cys Asn
            660                 665                 670

Ser Ile Val Val Glu Ser Ser Asp Phe Ile Lys Pro Leu Ile Ile Glu
        675                 680                 685

Phe Glu Ser Ser Thr Ser Lys Asn Ile Phe Val Lys His Ile Lys His
    690                 695                 700

Asn Ser Gln Lys Glu Met Asp Ile Asn Lys Phe Asn Glu Tyr Met Arg
705                 710                 715                 720

Asp Leu Lys Ser Asn Glu Lys Leu Arg Leu Lys Lys Val Glu Arg Phe
                725                 730                 735

His Ser Ile Asn Leu Ala Ala Lys Lys Gln Glu Ile Leu Asp Glu Ile
            740                 745                 750

Lys Tyr Ser Glu Glu Val Cys Asn Glu Gln Ile Asp Leu His Ile Leu
        755                 760                 765

Leu Asp Gly Ser Gly Ser Ile Gly His Ser Asn Trp Ile Ser His Val
    770                 775                 780

Ile Pro Met Leu Thr Thr Leu Val Asp Asn Leu Asn Ile Ser Arg Asp
785                 790                 795                 800

Glu Ile Asn Ile Ser Met Thr Leu Phe Ser Thr Tyr Ala Arg Glu Leu
                805                 810                 815

Val Arg Leu Lys Arg Tyr Gly Ser Thr Ser Lys Ala Ser Leu Arg Phe
            820                 825                 830
```

```
Ile Ile Ala Gln Leu Gln Asn Asn Tyr Ser Pro His Gly Thr Thr Asn
        835                 840                 845

Leu Thr Ser Ala Leu Leu Asn Val Asp Asn Leu Ile Gln Lys Lys Met
    850                 855                 860

Asn Arg Pro Asn Ala Ile Gln Leu Val Ile Ile Leu Thr Asp Gly Ile
865                 870                 875                 880

Pro Asn Asn Leu Lys Lys Ser Thr Thr Val Val Asn Gln Leu Lys Lys
                885                 890                 895

Lys Asp Val Asn Val Ala Ile Ile Gly Val Gly Ala Gly Val Asn Asn
            900                 905                 910

Met Phe Asn Arg Ile Leu Val Gly Cys Gly Lys Leu Gly Pro Cys Pro
        915                 920                 925

Tyr Tyr Ser Tyr Gly Ser Trp Asp Gln Ala Gln Thr Met Ile Lys Pro
    930                 935                 940

Phe Leu Ser Lys Val Cys Gln Glu Val Glu Lys Val Ala Leu Cys Gly
945                 950                 955                 960

Lys Trp Glu Glu Trp Ser Glu Cys Ser Thr Thr Cys Asp Asn Gly Thr
                965                 970                 975

Lys Ile Arg Lys Arg Lys Val Gly Ala Ser Met Ser His Leu Gln Cys
            980                 985                 990

Leu Thr Ser Val Ala Gly Leu Ser  Ser Ile Val Met Ser  Met Phe Pro
        995                 1000                1005

Lys Leu  Ile Ala Asn Asn Pro  Ser Leu Phe Arg Pro  Leu Leu Asn
    1010                 1015                 1020

Ile Ser  Trp Gly Tyr Leu Phe  Gly Ser Thr Val Trp  Leu Cys Phe
    1025                 1030                 1035

Phe Ser  Glu Ile Gly Leu Val  Arg Arg Ile Asn Ala  Pro Lys Arg
    1040                 1045                 1050

Lys Asn  Leu Pro Glu Asn Ala  Glu Gln Ala Lys Glu  Gln Leu Lys
    1055                 1060                 1065

Glu Ile  Lys Asn Asn Glu Gly  Asp Phe Asn Arg Arg  Asn Ile Asp
    1070                 1075                 1080

Phe Lys  Tyr Phe Phe Ser Leu  Ser Thr Ile Phe Ser  Ser Ile Leu
    1085                 1090                 1095

Leu Leu  Ser Thr Val Lys Leu  Ala Asn Asn Asn Leu  Gln Leu Arg
    1100                 1105                 1110

Ile Cys  Ser Thr Ile Val Ser  Leu Ser Cys Ile Leu  Asn Asn Met
    1115                 1120                 1125

Tyr Phe  Gln Asn Lys Ile His  Ser Leu Ala Leu Lys  Lys Glu Ser
    1130                 1135                 1140

Leu Phe  Lys Asp Met Ile Asp  Arg Pro Lys Asp Thr  Thr Ile Leu
    1145                 1150                 1155

Val Asn  Leu Lys Lys Asn Lys  Thr Asp Phe His Ile  His His Gly
    1160                 1165                 1170

Leu Ser  Leu Leu Leu Leu Tyr  Ser Ser Phe Phe Gly  Leu Thr Pro
    1175                 1180                 1185

Tyr Ile  Phe Thr
    1190
```

<210> SEQ ID NO 121
<211> LENGTH: 3663
<212> TYPE: DNA

<213> ORGANISM: Artificial Sequence
<220> FEATURE:
<223> OTHER INFORMATION: DNA sequence of Plasmodium berghei Fusion
5cPEAg SP+

<400> SEQUENCE: 121
ggatccgcca ccatggccaa gaagtgtacc atactggtcg ttgcgtcact tctgttggtc 60
aattctctgc tcccaggcta tggacagaac aaatccattc aggcacagag gaacctcaac 120
gaactctgct acaatgaagg gaatgacaat aagctgtatc acgtgctgaa ttccaagaac 180
ggcaaaatct acaatcgcaa cacagtaaat cggttgcttg ccgatgcacc cgagggtaag 240
aagaatgaaa agaagaatga gaaaatcgag cgcaacaaca agcttaaaca gccaccgcct 300
cctcctaacc caaatgaccc accgccaccc aatccaaacg acccaccgcc tcccaaccct 360
aacgatcctc caccgcccaa ccctaatgac ccaccacctc ccaatgcaaa cgatccaccc 420
cctcctaacg ctaacgaccc tgctccaccc aacgctaacg atcccgcgcc ccccaatgcc 480
aacgaccccg caccacctaa tgccaacgat cccgccccgc ccaatgctaa tgatcctcca 540
ccacccaacc caaacgaccc tgcccctcct aatgctaacg atccaccacc tcccaatccg 600
aatgatcccg ctccacctca ggggaacaac aaccctcagc cccaacctag accacagccg 660
cagccccaac cccaacccca gccccagcct caaccccagc cccagccacg tccgcagcct 720
cagcctcaac ctggaggcaa caataacaac aagaataaca acaacgacga cagctacatt 780
ccaagtgccg agaaaattct ggagtttgtt aagcagatcc gagacagcat aaccgaagaa 840
tggtcacagt gtaacgtgac gtgtggatct ggcatcagag tgaggaaacg gaagggttcc 900
aataagaaag cagaggatct gactctggag gacattgata cagagatctg caaaatggac 960
aaagacaatg acatctacag cttcgacatt gtcaatgaga caaattggct gaagatcgcc 1020
aagaacatct tcaaaggcaa gtctcctagc aatttcacga tcataccgtt taacaatacc 1080
ggtagttcta acgataacga gtcaaacaag gaggaatcag tactgctgat cagaaagaag 1140
atcaaaagca acaagaatca cgatagttcc atcattagtg gtgacactgt taacggggac 1200
attagtgacc tgaattatac ggctagcaac ttttccgata actctgagga catagaagat 1260
aaccagaaat atcccacaac cagctacaat agtttcaacc atctcaattc cctcactggg 1320
gacgagaaat gtggtaaaag cctgaagctc ggcaacatca gcaatcagac aaaccaggaa 1380
accataaccc aaagcctgtc agttggagag attctgtgca ttgacctcga agggaatgca 1440
ggaacaggct atctgtgggt gttgctgggc atacacaagg atgagccaat cataaacccc 1500
gagaacttcc caaccaaact gacaaagaag tctttctttt ccgaggaaat aagtgtgact 1560
cagccaaaga agtacaagat cgatgagcat gattcttcaa agaatgtgaa tcgcgaaatc 1620
gaaagccctg aacagaagga gtccgactca aagcccaaga aacctcagat gcaacttctt 1680
ggaggaccag atcggatgag gtcagtcatc aaaggacaca aacctggcaa atattacatt 1740
gtgtactctt actatcgacc gttttctccc acttctgggg cgaacactaa aatcatttac 1800
gtcacagtac agctgatcga agagaaagag gaaatcaccc ctgagaacaa aaccctcata 1860
atgccctcta aaactctgat gaagggcatt aagaccaaca tttacttcct gtcaaacaag 1920
gaaaagatcc aagtgcttat gtgctataac tacaagtgtg atgccgttgt gttcgagaaa 1980
gacacctttc tgcgctatct ctacatcaag agcatcaata atatcatcct gaacgaaaga 2040
atgattgaac agttgtgcaa gaacgaaaac ctgaagtaca tccttgcctg caacagcata 2100
gtggttgaat caagcgactt catcaaaccc ctgatcattg agtttgagtc atccacttcc 2160

```
aagaacatct tcgtaaagca cattaagcac aatagccaga aagaaatgga catcaacaag   2220
ttcaacgagt atatgcggga tctcaaaagc aatgagaagc tcagactgaa gaaagtcgag   2280
cgattccact ctattaatct ggcagccaag aaacaggaga ttctggacga aatcaagtac   2340
tctgaggagg tctgcaacga acaaatcgat ctccacattc tgctggatgg gagtggcagc   2400
ataggtcact ctaactggat cagtcacgtg atacccatgc tgacaaccct tgtggacaat   2460
ttgaacatca gccgcgatga gatcaatatc tccatgacct tgttctccac ttatgccagg   2520
gaacttgtga gacttaagag atatgggtct acaagcaaag ccagtctgag gttcatcatc   2580
gcgcaactcc agaataacta ttctcctcat ggaacgacaa atctgactag cgccctgttg   2640
aatgtggaca atctcattca gaagaaaatg aatcgcccta atgccattca gctcgtgatt   2700
atccttactg acggcatccc taacaatctg aagaagtcca ctactgttgt caaccagctg   2760
aagaagaagg acgtcaatgt cgctattatt ggtgttggcg ccggagtaaa caatatgttt   2820
aaccgtatat tggtaggatg tggaaaactt gggccttgtc cctactactc ttatggctct   2880
tgggatcaag cacaaaccat gatcaaacca tttctctcaa aggtctgtca ggaagtggag   2940
aaagtggcac tgtgcggtaa gtgggaggag tggagtgagt gttcaaccac ttgcgacaac   3000
ggaacgaaaa taaggaagcg aaaggttggg gcgagtatga gccacttgca gtgtctgaca   3060
tctgttgctg gtctgtcctc tatcgtcatg tcaatgttcc ccaaactcat tgccaataat   3120
ccttccctgt ttagaccact gctcaacatt tcctggggat atctgttcgg aagcactgta   3180
tggctgtgct tcttcagtga gattgggttg gtcaggagaa tcaatgctcc taaacggaag   3240
aatctgccag agaatgcaga acaagccaaa gaacagctga aggagatcaa gaacaacgaa   3300
ggcgatttta accgacgcaa tatcgacttc aagtacttct ttagcctttc cacaatcttc   3360
tctagcatac tgctgcttag cacagtgaaa ctcgccaaca acaatctgca gttgaggatc   3420
tgttccacca ttgtgtcact gagttgcata ctgaacaata tgtactttca gaacaagata   3480
cactcacttg cactgaagaa agagagtctc tttaaggaca tgatcgatcg tccgaaagat   3540
accactattc tggtgaacct gaagaagaac aagaccgact ttcacatcca tcatggcctt   3600
tctctgctct tgctctatag cagcttcttt ggcctcactc cctacatttt cacgtgactc   3660
gag                                                                 3663
```

```
<210> SEQ ID NO 122
<211> LENGTH: 1214
<212> TYPE: PRT
<213> ORGANISM: Artificial Sequence
<220> FEATURE:
<223> OTHER INFORMATION: Amino acid sequence of Plasmodium berghei
      Fusion 5cPEAg SP+

<400> SEQUENCE: 122

Met Ala Lys Lys Cys Thr Ile Leu Val Val Ala Ser Leu Leu Leu Val
1               5                   10                  15

Asn Ser Leu Leu Pro Gly Tyr Gly Gln Asn Lys Ser Ile Gln Ala Gln
            20                  25                  30

Arg Asn Leu Asn Glu Leu Cys Tyr Asn Glu Gly Asn Asp Asn Lys Leu
        35                  40                  45

Tyr His Val Leu Asn Ser Lys Asn Gly Lys Ile Tyr Asn Arg Asn Thr
    50                  55                  60

Val Asn Arg Leu Leu Ala Asp Ala Pro Glu Gly Lys Lys Asn Glu Lys
65                  70                  75                  80
```

```
Lys Asn Glu Lys Ile Glu Arg Asn Asn Lys Leu Lys Gln Pro Pro Pro
                85                  90                  95

Pro Pro Asn Pro Asn Asp Pro Pro Pro Pro Asn Pro Asn Asp Pro Pro
            100                 105                 110

Pro Pro Asn Pro Asn Asp Pro Pro Pro Pro Asn Pro Asn Asp Pro Pro
        115                 120                 125

Pro Pro Asn Ala Asn Asp Pro Pro Pro Pro Asn Ala Asn Asp Pro Ala
    130                 135                 140

Pro Pro Asn Ala Asn Asp Pro Ala Pro Pro Asn Ala Asn Asp Pro Ala
145                 150                 155                 160

Pro Pro Asn Ala Asn Asp Pro Ala Pro Pro Asn Ala Asn Asp Pro Pro
                165                 170                 175

Pro Pro Asn Pro Asn Asp Pro Ala Pro Pro Asn Ala Asn Asp Pro Pro
            180                 185                 190

Pro Pro Asn Pro Asn Asp Pro Ala Pro Pro Gln Gly Asn Asn Asn Pro
        195                 200                 205

Gln Pro Gln Pro Arg Pro Gln Pro Gln Pro Gln Pro Gln Pro Gln Pro
    210                 215                 220

Gln Pro Gln Pro Gln Pro Gln Pro Arg Pro Gln Pro Gln Pro Gln Pro
225                 230                 235                 240

Gly Gly Asn Asn Asn Asn Lys Asn Asn Asn Asn Asp Asp Ser Tyr Ile
                245                 250                 255

Pro Ser Ala Glu Lys Ile Leu Glu Phe Val Lys Gln Ile Arg Asp Ser
            260                 265                 270

Ile Thr Glu Glu Trp Ser Gln Cys Asn Val Thr Cys Gly Ser Gly Ile
        275                 280                 285

Arg Val Arg Lys Arg Lys Gly Ser Asn Lys Lys Ala Glu Asp Leu Thr
    290                 295                 300

Leu Glu Asp Ile Asp Thr Glu Ile Cys Lys Met Asp Lys Asp Asn Asp
305                 310                 315                 320

Ile Tyr Ser Phe Asp Ile Val Asn Glu Thr Asn Trp Leu Lys Ile Ala
                325                 330                 335

Lys Asn Ile Phe Lys Gly Lys Ser Pro Ser Asn Phe Thr Ile Ile Pro
            340                 345                 350

Phe Asn Asn Thr Gly Ser Ser Asn Asp Asn Glu Ser Asn Lys Glu Glu
        355                 360                 365

Ser Val Leu Leu Ile Arg Lys Lys Ile Lys Ser Asn Lys Asn His Asp
    370                 375                 380

Ser Ser Ile Ile Ser Gly Asp Thr Val Asn Gly Asp Ile Ser Asp Leu
385                 390                 395                 400

Asn Tyr Thr Ala Ser Asn Phe Ser Asp Asn Ser Glu Asp Ile Glu Asp
                405                 410                 415

Asn Gln Lys Tyr Pro Thr Thr Ser Tyr Asn Ser Phe Asn His Leu Asn
            420                 425                 430

Ser Leu Thr Gly Asp Glu Lys Cys Gly Lys Ser Leu Lys Leu Gly Asn
        435                 440                 445

Ile Ser Asn Gln Thr Asn Gln Glu Thr Ile Thr Gln Ser Leu Ser Val
    450                 455                 460

Gly Glu Ile Leu Cys Ile Asp Leu Glu Gly Asn Ala Gly Thr Gly Tyr
465                 470                 475                 480

Leu Trp Val Leu Leu Gly Ile His Lys Asp Glu Pro Ile Ile Asn Pro
                485                 490                 495
```

```
Glu Asn Phe Pro Thr Lys Leu Thr Lys Lys Ser Phe Phe Ser Glu Glu
            500                 505                 510

Ile Ser Val Thr Gln Pro Lys Lys Tyr Lys Ile Asp Glu His Asp Ser
        515                 520                 525

Ser Lys Asn Val Asn Arg Glu Ile Glu Ser Pro Glu Gln Lys Glu Ser
    530                 535                 540

Asp Ser Lys Pro Lys Lys Pro Gln Met Gln Leu Leu Gly Gly Pro Asp
545                 550                 555                 560

Arg Met Arg Ser Val Ile Lys Gly His Lys Pro Gly Lys Tyr Tyr Ile
                565                 570                 575

Val Tyr Ser Tyr Tyr Arg Pro Phe Ser Pro Thr Ser Gly Ala Asn Thr
            580                 585                 590

Lys Ile Ile Tyr Val Thr Val Gln Leu Ile Glu Glu Lys Glu Glu Ile
        595                 600                 605

Thr Pro Glu Asn Lys Thr Leu Ile Met Pro Ser Lys Thr Leu Met Lys
    610                 615                 620

Gly Ile Lys Thr Asn Ile Tyr Phe Leu Ser Asn Lys Glu Lys Ile Gln
625                 630                 635                 640

Val Leu Met Cys Tyr Asn Tyr Lys Cys Asp Ala Val Val Phe Glu Lys
                645                 650                 655

Asp Thr Phe Leu Arg Tyr Leu Tyr Ile Lys Ser Ile Asn Asn Ile Ile
            660                 665                 670

Leu Asn Glu Arg Met Ile Glu Gln Leu Cys Lys Asn Glu Asn Leu Lys
        675                 680                 685

Tyr Ile Leu Ala Cys Asn Ser Ile Val Val Glu Ser Ser Asp Phe Ile
    690                 695                 700

Lys Pro Leu Ile Ile Glu Phe Glu Ser Ser Thr Ser Lys Asn Ile Phe
705                 710                 715                 720

Val Lys His Ile Lys His Asn Ser Gln Lys Glu Met Asp Ile Asn Lys
                725                 730                 735

Phe Asn Glu Tyr Met Arg Asp Leu Lys Ser Asn Glu Lys Leu Arg Leu
            740                 745                 750

Lys Lys Val Glu Arg Phe His Ser Ile Asn Leu Ala Ala Lys Lys Gln
        755                 760                 765

Glu Ile Leu Asp Glu Ile Lys Tyr Ser Glu Glu Val Cys Asn Glu Gln
    770                 775                 780

Ile Asp Leu His Ile Leu Leu Asp Gly Ser Gly Ser Ile Gly His Ser
785                 790                 795                 800

Asn Trp Ile Ser His Val Ile Pro Met Leu Thr Thr Leu Val Asp Asn
                805                 810                 815

Leu Asn Ile Ser Arg Asp Glu Ile Asn Ile Ser Met Thr Leu Phe Ser
            820                 825                 830

Thr Tyr Ala Arg Glu Leu Val Arg Leu Lys Arg Tyr Gly Ser Thr Ser
        835                 840                 845

Lys Ala Ser Leu Arg Phe Ile Ile Ala Gln Leu Gln Asn Asn Tyr Ser
    850                 855                 860

Pro His Gly Thr Thr Asn Leu Thr Ser Ala Leu Leu Asn Val Asp Asn
865                 870                 875                 880

Leu Ile Gln Lys Lys Met Asn Arg Pro Asn Ala Ile Gln Leu Val Ile
                885                 890                 895

Ile Leu Thr Asp Gly Ile Pro Asn Asn Leu Lys Lys Ser Thr Thr Val
            900                 905                 910
```

Val Asn Gln Leu Lys Lys Lys Asp Val Asn Val Ala Ile Ile Gly Val
        915                 920                 925

Gly Ala Gly Val Asn Asn Met Phe Asn Arg Ile Leu Val Gly Cys Gly
    930                 935                 940

Lys Leu Gly Pro Cys Pro Tyr Tyr Ser Tyr Gly Ser Trp Asp Gln Ala
945                 950                 955                 960

Gln Thr Met Ile Lys Pro Phe Leu Ser Lys Val Cys Gln Glu Val Glu
                965                 970                 975

Lys Val Ala Leu Cys Gly Lys Trp Glu Glu Trp Ser Glu Cys Ser Thr
            980                 985                 990

Thr Cys Asp Asn Gly Thr Lys Ile  Arg Lys Arg Lys Val  Gly Ala Ser
        995                 1000                1005

Met Ser  His Leu Gln Cys Leu  Thr Ser Val Ala Gly  Leu Ser Ser
    1010                 1015                1020

Ile Val  Met Ser Met Phe Pro  Lys Leu Ile Ala Asn  Asn Pro Ser
    1025                 1030                1035

Leu Phe  Arg Pro Leu Leu Asn  Ile Ser Trp Gly Tyr  Leu Phe Gly
    1040                 1045                1050

Ser Thr  Val Trp Leu Cys Phe  Phe Ser Glu Ile Gly  Leu Val Arg
    1055                 1060                1065

Arg Ile  Asn Ala Pro Lys Arg  Lys Asn Leu Pro Glu  Asn Ala Glu
    1070                 1075                1080

Gln Ala  Lys Glu Gln Leu Lys  Glu Ile Lys Asn Asn  Glu Gly Asp
    1085                 1090                1095

Phe Asn  Arg Arg Asn Ile Asp  Phe Lys Tyr Phe Phe  Ser Leu Ser
    1100                 1105                1110

Thr Ile  Phe Ser Ser Ile Leu  Leu Leu Ser Thr Val  Lys Leu Ala
    1115                 1120                1125

Asn Asn  Asn Leu Gln Leu Arg  Ile Cys Ser Thr Ile  Val Ser Leu
    1130                 1135                1140

Ser Cys  Ile Leu Asn Asn Met  Tyr Phe Gln Asn Lys  Ile His Ser
    1145                 1150                1155

Leu Ala  Leu Lys Lys Glu Ser  Leu Phe Lys Asp Met  Ile Asp Arg
    1160                 1165                1170

Pro Lys  Asp Thr Thr Ile Leu  Val Asn Leu Lys Lys  Asn Lys Thr
    1175                 1180                1185

Asp Phe  His Ile His His Gly  Leu Ser Leu Leu Leu  Leu Tyr Ser
    1190                 1195                1200

Ser Phe  Phe Gly Leu Thr Pro  Tyr Ile Phe Thr
    1205                 1210

<210> SEQ ID NO 123
<211> LENGTH: 1044
<212> TYPE: DNA
<213> ORGANISM: Artificial Sequence
<220> FEATURE:
<223> OTHER INFORMATION: DNA sequence of Plasmodium berghei ANKA CSP

<400> SEQUENCE: 123
ggatccgcca ccatggccaa gaagtgtacc atactggtcg ttgcgtcact tctgttggtc      60
aattctctgc tcccaggcta tggacagaac aaatccattc aggcacagag gaacctcaac     120
gaactctgct acaatgaagg gaatgacaat aagctgtatc acgtgctgaa ttccaagaac     180
ggcaaaatct acaatcgcaa cacagtaaat cggttgcttg ccgatgcacc cgagggtaag     240

```
aagaatgaaa agaagaatga gaaaatcgag cgcaacaaca agcttaaaca gccaccgcct    300

cctcctaacc caaatgaccc accgccaccc aatccaaacg acccaccgcc tcccaaccct    360

aacgatcctc caccgcccaa ccctaatgac ccaccacctc ccaatgcaaa cgatccaccc    420

cctcctaacg ctaacgaccc tgctccaccc aacgctaacg atcccgcgcc ccccaatgcc    480

aacgaccccg caccacctaa tgccaacgat cccgccccgc ccaatgctaa tgatcctcca    540

ccacccaacc caaacgaccc tgcccctcct aatgctaacg atccaccacc tcccaatccg    600

aatgatcccg ctccacctca ggggaacaac aaccctcagc cccaacctag accacagccg    660

cagccccaac cccaacccca gccccagcct caaccccagc cccagccacg tccgcagcct    720

cagcctcaac ctggaggcaa caataacaac aagaataaca acaacgacga cagctacatt    780

ccaagtgccg agaaaattct ggagtttgtt aagcagatcc gagacagcat aaccgaagaa    840

tggtcacagt gtaacgtgac gtgtggatct ggcatcagag tgaggaaacg gaagggttcc    900

aataagaaag cagaggatct gactctggag gacattgata cagagatctg caaaatggac    960

aaatgcagct ctatcttcaa catcgtgagt aatagcctcg ggtttgtgat tctgctggtc   1020

ctggtgttct tcaattgact cgag                                          1044
```

<210> SEQ ID NO 124
<211> LENGTH: 341
<212> TYPE: PRT
<213> ORGANISM: Artificial Sequence
<220> FEATURE:
<223> OTHER INFORMATION: Amino acid sequence of Plasmodium berghei ANKA CSP

<400> SEQUENCE: 124

```
Met Ala Lys Lys Cys Thr Ile Leu Val Val Ala Ser Leu Leu Leu Val
1               5                   10                  15

Asn Ser Leu Leu Pro Gly Tyr Gly Gln Asn Lys Ser Ile Gln Ala Gln
            20                  25                  30

Arg Asn Leu Asn Glu Leu Cys Tyr Asn Glu Gly Asn Asp Asn Lys Leu
        35                  40                  45

Tyr His Val Leu Asn Ser Lys Asn Gly Lys Ile Tyr Asn Arg Asn Thr
    50                  55                  60

Val Asn Arg Leu Leu Ala Asp Ala Pro Glu Gly Lys Lys Asn Glu Lys
65                  70                  75                  80

Lys Asn Glu Lys Ile Glu Arg Asn Asn Lys Leu Lys Gln Pro Pro Pro
                85                  90                  95

Pro Pro Asn Pro Asn Asp Pro Pro Pro Pro Asn Pro Asn Asp Pro Pro
            100                 105                 110

Pro Pro Asn Pro Asn Asp Pro Pro Pro Pro Asn Pro Asn Asp Pro Pro
        115                 120                 125

Pro Pro Asn Ala Asn Asp Pro Pro Pro Pro Asn Ala Asn Asp Pro Ala
    130                 135                 140

Pro Pro Asn Ala Asn Asp Pro Ala Pro Pro Asn Ala Asn Asp Pro Ala
145                 150                 155                 160

Pro Pro Asn Ala Asn Asp Pro Ala Pro Pro Asn Ala Asn Asp Pro Pro
                165                 170                 175

Pro Pro Asn Pro Asn Asp Pro Ala Pro Pro Asn Ala Asn Asp Pro Pro
            180                 185                 190

Pro Pro Asn Pro Asn Asp Pro Ala Pro Pro Gln Gly Asn Asn Asn Pro
        195                 200                 205
```

-continued

```
Gln Pro Gln Pro Arg Pro Gln Pro Gln Pro Gln Pro Gln Pro Gln Pro
    210                 215                 220

Gln Pro Gln Pro Gln Pro Gln Pro Arg Pro Gln Pro Gln Pro Gln Pro
225                 230                 235                 240

Gly Gly Asn Asn Asn Asn Lys Asn Asn Asn Asn Asp Asp Ser Tyr Ile
                245                 250                 255

Pro Ser Ala Glu Lys Ile Leu Glu Phe Val Lys Gln Ile Arg Asp Ser
            260                 265                 270

Ile Thr Glu Glu Trp Ser Gln Cys Asn Val Thr Cys Gly Ser Gly Ile
        275                 280                 285

Arg Val Arg Lys Arg Lys Gly Ser Asn Lys Lys Ala Glu Asp Leu Thr
    290                 295                 300

Leu Glu Asp Ile Asp Thr Glu Ile Cys Lys Met Asp Lys Cys Ser Ser
305                 310                 315                 320

Ile Phe Asn Ile Val Ser Asn Ser Leu Gly Phe Val Ile Leu Leu Val
                325                 330                 335

Leu Val Phe Phe Asn
            340
```